US012698323B2

(12) United States Patent
Germaschewski et al.

(10) Patent No.: US 12,698,323 B2
(45) Date of Patent: Aug. 4, 2026

(54) ANTAGONISTS

(71) Applicant: Kymab Limited, Cambridge (GB)

(72) Inventors: Volker Germaschewski, Cambridge (GB); Igor Theurl, Cambridge (GB); Joana De Abreu Carvalho, Cambridge (GB); Morgane Marie Lecointre, Cambridge (GB); Jonathan Leslie Papworth, Cambridge (GB); Luke Thomas Bayliss, Cambridge (GB); Verena Petzer, Cambridge (GB)

(73) Assignee: Kymab Limited, Cambridge (GB)

( * ) Notice: Subject to any disclaimer, the term of this patent is extended or adjusted under 35 U.S.C. 154(b) by 1305 days.

(21) Appl. No.: 17/279,513

(22) PCT Filed: Aug. 15, 2019

(86) PCT No.: PCT/GB2019/052294
§ 371 (c)(1),
(2) Date: Mar. 24, 2021

(87) PCT Pub. No.: WO2020/065252
PCT Pub. Date: Apr. 2, 2020

(65) Prior Publication Data
US 2022/0073598 A1 Mar. 10, 2022

(30) Foreign Application Priority Data
Sep. 25, 2018 (GB) ...................................... 1815629

(51) Int. Cl.
| | |
|---|---|
| *C07K 16/22* | (2006.01) |
| *A61K 39/00* | (2006.01) |
| *A61K 39/395* | (2006.01) |
| *A61P 7/06* | (2006.01) |

(52) U.S. Cl.
CPC .......... *C07K 16/22* (2013.01); *A61K 39/3955* (2013.01); *A61P 7/06* (2018.01); *A61K 2039/505* (2013.01); *A61K 2039/545* (2013.01); *C07K 2317/31* (2013.01); *C07K 2317/33* (2013.01); *C07K 2317/52* (2013.01); *C07K 2317/55* (2013.01); *C07K 2317/56* (2013.01); *C07K 2317/565* (2013.01); *C07K 2317/76* (2013.01); *C07K 2317/92* (2013.01)

(58) Field of Classification Search
CPC ................ C07K 16/22; C07K 2317/31; C07K 2317/33; C07K 2317/52; C07K 2137/55; C07K 2317/56; C07K 2317/565; C07K 2317/76; C07K 2317/92; A61K 39/3955; A61K 2039/505; A61K 2039/545; A61P 7/06
USPC ........... 530/387.9, 387.3, 388.24; 424/130.1, 424/133.1, 139.1, 145.1
See application file for complete search history.

(56) References Cited

U.S. PATENT DOCUMENTS

| | | | |
|---|---|---|---|
| 4,675,187 A | 6/1987 | Konishi et al. |
| 8,318,167 B2 | 11/2012 | Lin et al. |
| 8,795,665 B2 | 8/2014 | Seo et al. |
| 8,980,582 B2 | 3/2015 | Seo et al. |
| 11,648,308 B2 | 5/2023 | Germaschewski et al. |
| 2005/0137329 A1 | 6/2005 | Holmes et al. |
| 2005/0272634 A1 | 12/2005 | Bahlmann et al. |
| 2010/0136015 A1 | 6/2010 | Lin et al. |
| 2013/0059783 A1 | 3/2013 | Flygare et al. |
| 2014/0086919 A1 | 3/2014 | Lin et al. |
| 2014/0199314 A1 | 7/2014 | Lin et al. |
| 2014/0309404 A1 | 10/2014 | Seo et al. |
| 2016/0176956 A1 | 6/2016 | Cong |
| 2017/0319689 A1 | 11/2017 | Germaschewski et al. |
| 2023/0233675 A1 | 7/2023 | Germaschewski et al. |

FOREIGN PATENT DOCUMENTS

| | | |
|---|---|---|
| JP | 2012508764 A | 4/2012 |
| JP | 2016501273 A | 1/2016 |
| WO | 2008003103 A2 | 1/2008 |
| WO | 2008003103 A3 | 4/2008 |
| WO | 2010056981 A2 | 5/2010 |
| WO | 2010056981 A3 | 9/2010 |
| WO | 2011004192 A1 | 1/2011 |
| WO | 2011158009 A1 | 12/2011 |
| WO | 2013061098 A2 | 5/2013 |
| WO | 2013061098 A3 | 5/2013 |
| WO | 2014099391 A1 | 6/2014 |
| WO | 2015040401 A1 | 3/2015 |
| WO | 2015103072 A1 | 7/2015 |
| WO | 2016098079 A2 | 6/2016 |
| WO | 2016098079 A3 | 8/2016 |
| WO | 2017191437 A1 | 11/2017 |
| WO | 2017216724 A1 | 12/2017 |
| WO | 2020065252 A1 | 4/2020 |

OTHER PUBLICATIONS

Vajdos et al. (2002) J. Mol. Biol., vol. 320, 415-428.*
Chen et al. (1992) J. Exp. Med., vol. 176, 855-866.*
Sela-Culang et al. (2013) Frontiers in Immunology, vol. 4, pp. 1-13.*
Amgen Inc. (Dec. 2013). "Epogen(R) (epoetin alfa) Injection, For Intravenous Or Subcutaneous Use," 27 pages.
Amgen Inc. (Jul. 2015). "ARANESP(R) (darbepoetin alfa) Injection, For Intravenous Or Subcutaneous Use," 25 pages.
Flight, M. (Oct. 2013). "AstraZeneca Bets on FibroGen's Anaemia Drug," Nature 12:730, 1 page.
Hayat, A. et al. (Jan. 1, 2008). "Erythropoietin Stimulating Agents in the Management of Anemia of Chronic Kidney Disease," Patient Preference and Adherence 2:195-200.
International Preliminary Report on Patentability, issued Nov. 6, 2018, for PCT Application No. PCT/GB2017/051208, filed Apr. 28, 2017, 6 pages.

(Continued)

*Primary Examiner* — Anne Marie S Wehbe
(74) *Attorney, Agent, or Firm* — MORRISON & FOERSTER LLP

(57) ABSTRACT
The invention relates to Bone Morphogenetic Protein 6 (BMP6) antagonists, such as antibodies and fragments, as well as methods, uses and combinations.

23 Claims, 39 Drawing Sheets
Specification includes a Sequence Listing.

(56) References Cited

OTHER PUBLICATIONS

International Search Report and Written Opinion, mailed Aug. 23, 2017, for PCT Application No. PCT/GB2017/051208, filed Apr. 28, 2017, 10 pages.

Kim, A. et al. (Feb. 20, 2014, e-pub. Dec. 19, 2013). "A Mouse Model Of Anemia Of Inflammation: Complex Pathogenesis With Partial Dependence On Hepcidin," Blood 123(8):1129-1136.

Kim, S.Y. et al. (Nov. 19, 2015). "Recent Advances in Developing Inhibitors for Hypoxia-Inducible Factor Prolyl Hydroxylases and Their Therapeutic Implications," Molecules 20:20551-20568.

Macció, A. et al. (Jan. 1, 2012). "Management of Anemia of Inflammation in the Elderly," Anemia 2012 (563251):1-20.

Nangaku, M. et al. (2007). "A Novel Class of Prolyl Hydroxylase Inhibitors Induces Angiogenesis and Exerts Organ Protection Against Ischemia," Arterioscler Thromb. Vasc. Biol. 27:2548-2554.

Poloznikov, A.A. et al. (Jan. 29, 2021). "HIF Prolyl Hydroxylase Inhibitors for COVID-19 Treatment: Pros and Cons," Frontiers in Pharmacology 11(621054):1-11.

Rivera, S. et al. (Oct. 2009). "Animal Models of Anemia of Inflammation," Semin Hematol. 46(4):351-357.

Selleck Chemical (2013). "HIF Inhibitors," Selleckchem.com, 4 pages.

Tegley, C.M. et al. (2008, e-pub. Jun. 13, 2008). "Discovery of Novel Hydroxy-Thiazoles as HIP-α Prolyl Hydroxylase Inhibitors: SAR, Synthesis, and Modeling Evaluation," Bioorganic & Medicinal Chemistry Letters 18:3925-3928.

Theurl, M. et al. (2014). "Hepcidin as a Predictive Factor and Therapeutic Target in Erythropoiesis-stimulating Agent Treatment for Anemia of Chronic Disease in Rats," Haematologica 99(9):1516-1524.

Thomas, D. W. et al. (2013). "Guideline for the Laboratory Diagnosis of Functional Iron Deficiency," British Journal of Haematology 161:639-648.

Warshakoon, N.C. et al. (2006). "Design and Synthesis of a Series of Novel Pyrazolopyridines as HIF 1-α Prolyl Hydroxylase Inhibitors," Bioorganic & Medicinal Chemistry Letters 16:5687-5690.

Yu, Z. et al. (May 31, 1993). "Recent Advances in Clinical hematology," Jinan University Press, pp. 83-84, With English Translation.

Changlin, M. et al. (Apr. 30, 2016). Physician Assessment and Training Standard Course—Nephrology Volume, pp. 210-212, Shanghai Science and Technology Press, Apr. 30, 2016. With English Translation, 10 pages.

Akchurin, O. et al. (2016, e-pub. Jul. 20, 2016). "Lack of Hepcidin Ameliorates Anemia and Improves Growth In An Adenine-Induced Mouse Model Of Chronic Kidney Disease," Am. J. Physiol. Ren. Physiol. 311:F877-F889.

Andriopoulos, B. Jr. et al. (Apr. 2009, e-pub. Mar. 1, 2009). "BMP-6 Is a Key Endogenous Regulator Of Hepcidin Expression and Iron Metabolism," Nature Genetics 41(4):482-487, 16 pages.

Berger, S.L. (1987). "Isolation of Cytoplamic RNA: Ribonucleoside-Vanadyl Complexes," Methods in Enzymology 152:227-234.

Casanovas, G. et al. (Jan. 2, 2014). "A Multi-Scale 25 Model of Hepcidin Promoter Regulation Reveals Factors Controlling Systemic Iron Homeostasis," PLoS Comput. Biol. 10(1):e1003421, 13 pages.

Chothia, C. et al. (1987). "Canonical Structures for the Hypervariable Regions of Immunoglobulins," J. Mol. Biol. 196:901-917.

Digiammarino, E. et al. (2012). "Design and Generation Of DVD-IgTM Molecules For Dual-Specific Targeting," Meth. Mo. Biol. 889:145-156.

Freshney, R.I. (2005). Culture of Animal Cells: A Manual of Basic Technique, 65th Edition, John Wiley & Sons, Inc. pp. 115-128. TOC, 12 pages.

Ganz, T. et al. (2011). "The Hepcidin-Ferroportin System as a Therapeutic Target in Anemias and Iron Overload Disorders," Hematology 2011:538-542.

International Preliminary Report on Patentability, issued Mar. 23, 2021, for PCT Application No. PCT/GB2019/052294, filed Aug. 15, 2019, 5 pages.

International Search Report and Written Opinion, mailed Nov. 22, 2019, for PCT Application No. PCT/GB2019/052294, filed Aug. 15, 2019, 9 pages.

Kabat, E.A. et al. (1971). "Attempts To Locate Complementarity-Determining Residues In The Variable Positions Of Light and Heavy Chains," Ann NY Acad Sci 190:382-391.

Kabat, E.A. et al. (1991). Sequences of Proteins of Immunological Interest, 5th Ed. Public Health Service, National Institutes of Health, Bethesda MD., Table of Contents, 21 pages.

Kautz, L. et al. (Oct. 16, 2014, e-pub. Sep. 5, 2014). "Erythroferrone Contributes To Recovery From Anemia Of Inflammation," Blood 124(16):2569-2574.

Kidney International Supplements (Aug. 2, 2012). "KDIGO Clinical Practice Guideline for Anemia in Chronic Kidney Disease," 2(4):1-64.

Latour, C. et al. (2016, e-pub. Nov. 12, 2015). "Differing Impact Of The Deletion Of Hemochromatosis-Associated Molecules HFE and Transferrin Receptor-2 On The Iron Phenotype Of Mice Lacking Bone Morphogenetic Protein 6 Or Hemojuvelin," Hepatology 63(1):126-137.

Lee, J.H. et al. (Sep. 25, 2015). "Antibodies to a Conformational Epitope On gp41 Neutralize HIV-1 By Destabilizing The Env Spike," Nature Communications 6:8167, 14 pages.

Lefranc, M.P. (Nov. 1, 1997). "Unique Database Numbering System For Immunogenetic Analysis," Immunol. Today 18(11):P509.

Mathis, G. (1995). "Probing Molecular Interactions With Homogeneous Techniques Based on Rare Earth Cryptates and Fluorescence Energy Transfer," Clinical Chemistry 41(9):1391-1397.

Mayeur, C. et al. (Apr. 3, 2014). "The Type I BMP Receptor Alk3 Is Required For The Induction Of Hepatic Hepcidin Gene Expression By Interleukin-6," Blood 123(14):2261-2268.

Nai, A. et al. (Feb. 12, 2015). "The Second Transferrin Receptor Regulates Red Blood Cell Production In Mice," Blood 125(7):1170-1179.

Niederfellner, G. et al. (Jul. 14, 2011). "Epitope Characterization and Crystal Structure Of GA101 Provide Insights Into The Molecular Basis For Type I/II Distinction Of CD20 Antibodies," Blood 118(2):358-367.

Paul, W.E. ed., Fundamental Immunology: Second Edition, Raven Press, New York at (1989) pp. 332-337.

Ramey, G. et al. (2010). "Hepcidin Targets Ferroportin For Degradation In Hepatocytes," Haematologica 95(3):501-504.

Rudikoff, S. et al. (Mar. 1982). "Single Amino Acid Substitution Altering Antigen-Binding Specificity," Proc. Natl. Acad. Sci. USA 79:1979-1983.

Sambrook, J. et al. (2012). Molecular Cloning: A Laboratory Manual (4 ed.), Cold Spring Harbor Laboratory Press, Cold Spring Harbor, N.Y., USA. TOC, 34 pages.

Schluessener, H.J. et al. (1995). "Immunolocalization of BMP-6, A Novel RGF-β-Related Cytokine, In Normal and Atherosclerotic Smooth Muscle Cells," Atherosclerosis 113:153-156.

Spiess, C. et al. (2015, e-pub. Jan. 27, 2015). "Alternative Molecular Formats and Therapeutic Applications For Bispecific Antibodies," Mol. Immunol. 67:95-106.

Steinbicker, A.U. et al. (Oct. 13, 2011, e-pub. Aug. 12, 2011). "Perturbation Of Hepcidin Expression By BMP Type I Receptor Deletion Induces Iron Overload In Mice," Blood 118(15):4224-4230.

Suckau, D. et al. (Dec. 1990). "Molecular Epitope Identification By Limited Proteolysis Of An Immobilized Antigen-Antibody Complex and Mass Spectrometric Peptide Mapping," Proceedings of the National Academy of Sciences 87:9848-9852.

The Human Protein Atlas (2021). Retrieved from internet www.proteinatlas.org/ENSG00000168509-5HFE2/cell#rna, last visited May 1, 2021, 1 page.

Theurl, I. et al. (Nov. 3, 2011, e-pub. Jul. 7, 2011). "Pharmacologic Inhibition Of Hepcidin Expression Reverses Anemia Of Chronic Inflammation In Rats," Blood 118(18):4977-4984, 16 pages.

(56)        References Cited

OTHER PUBLICATIONS

Wang, R.-H. et al. (Dec. 2005). "A Role Of SMAD4 In Iron Metabolism Through The Positive Regulation Of Hepcidin Expression," Cell Metabolism 2(6):399-409.

Xia, Y. et al. (May 15, 2008). "Hemojuvelin Regulates Hepcidin Expression Via A Selective Subset Of BMP Ligands and Receptors Independently Of Neogenin," Blood 111(10):5195-5204.

Xu, J.L. et al. (Jul. 2000). "Diversity in the CDR3 Region of VH Is Sufficient for Most Antibody Specificities," Immunity 13:37-45.

Yusa, K. et al. (Jan. 25, 2011). "A Hyperactive piggyBac Transposase For Mammalian Applications," Proc. Natl. Acad. Sci. U.S.A. 108(4):1531-1536.

Liberis, E. et al. (2018, e-pub. Apr. 16, 2018). "Parapred: Antibody Paratope Prediction Using Convolutional and Recurrent Neural Networks," Bioinformatics 34(17):2944-2950.

* cited by examiner

- Antibody B
- CL-58838
- Isotype
- Antibody A

- CL-58252
- CL-58851
- Isotype
- Antibody A

—■— CL-57931

··▲·· CL-58102

—●·· Isotype

—■— Antibody A

—▲— CL-57945

—●·· Isotype

-■- Antibody A

-●- Isotype

-★- CL-75539

·▼· CL-75714

-■- Antibody A

-●- Isotype

·▼· CL-75183

-★- CL-75500

- ⊞ - Antibody A

- ● - Isotype

——▼—— CL-75506

· ▲ · CL-75520

- ● - CL-75565

——▼—— CL-58835

- ⊞ - Antibody A

· ▲ · Antibody B

- ● - Isotype

··▼·  CL-58838 (0.3mg/kg)

────  CL-58838 (1mg/kg)

~■~  CL-58838 (3mg/kg)

~●·  Isotype (1mg/kg)

~■~  Antibody A (1mg/kg)

───  CL-58838 (1mg/kg)

~●·  Isotype (1mg/kg)

-▲- CL-58838 (0.3mg/kg)

··▼· CL-58838 (1mg/kg)

-■- CL-58838 (3mg/kg)

-●· Isotype(1mg/kg,iv)

-■- Antibody A (1mg/kg)

··▲· CL-58838 (1mg/kg)

-▼- Antibody B (1 mg/kg)

-●· Isotype (1mg/kg)

0.3 mg/kg CL-55838

1 mg/kg CL-58838

3 mg/kg CL-58838

1 mg/kg CL-58838

1 mg/kg Antibody A

·●· 0.3 mg/kg CL-55838

─■─ 1 mg/kg CL-58838

·▲· 3 mg/kg CL-58838

─■─ 1 mg/kg CL-58838

··●·· Naïve

–■– Isotype Control

–▲– CL-58838

–◆·· CL-58838 + EPO

··●·· Naïve

–■– Isotype Control

–▲– CL-58838

–◆·· CL-58838 + EPO

· •● · Naive

- ■· Isotype Control

—▲— CL-58838

- ◆ · CL-58838 + EPO

Time (h)

—●— 3 mg/kg CL-58838

·▲· 3 mg/kg Antibody B

·▦· 3 mg/kg Antibody A

Time (h)

·●· 1 mg/kg CL-58838

·▲· 3 mg/kg CL-58838

—✖— 10 mg/kg CL-58838

Hours

—■— 3 mg/kg CL-58838

··▲· 3 mg/kg Antibody B

-■- 3 mg/kg Antibody A

Hours

·●· 1 mg/kg CL-58838

-■· 3 mg/kg CL-58838

—▲— 10 mg/kg CL-58838

··•·· 1mg/kg CL-58838

—✖— 3mg/kg CL-58838

-▲- 10mg/kg CL-58838

—✖— 3 mg/kg CL-58838

··▼·· 3 mg/kg Antibody B

-•- 3 mg/kg Antibody A

SEQUENCE LISTING

<160> NUMBER OF SEQ ID NOS: 569

<210> SEQ ID NO 1
<211> LENGTH: 513
<212> TYPE: PRT
<213> ORGANISM: Homo Sapiens

<400> SEQUENCE: 1

```
Met Pro Gly Leu Gly Arg Arg Ala Gln Trp Leu Cys Trp Trp Trp Gly
1               5                   10                  15

Leu Leu Cys Ser Cys Cys Gly Pro Pro Pro Leu Arg Pro Pro Leu Pro
            20                  25                  30

Ala Ala Ala Ala Ala Ala Ala Gly Gly Gln Leu Leu Gly Asp Gly Gly
        35                  40                  45

Ser Pro Gly Arg Thr Glu Gln Pro Pro Pro Ser Pro Gln Ser Ser Ser
    50                  55                  60

Gly Phe Leu Tyr Arg Arg Leu Lys Thr Gln Glu Lys Arg Glu Met Gln
65                  70                  75                  80

Lys Glu Ile Leu Ser Val Leu Gly Leu Pro His Arg Pro Arg Pro Leu
                85                  90                  95

His Gly Leu Gln Gln Pro Gln Pro Pro Ala Leu Arg Gln Gln Glu Glu
            100                 105                 110

Gln Gln Gln Gln Gln Gln Leu Pro Arg Gly Glu Pro Pro Pro Gly Arg
            115                 120                 125

Leu Lys Ser Ala Pro Leu Phe Met Leu Asp Leu Tyr Asn Ala Leu Ser
    130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Ser Gln Arg Arg Gln Pro Pro Pro
            165                 170                 175

Gly Ala Ala His Pro Leu Asn Arg Lys Ser Leu Leu Ala Pro Gly Ser
            180                 185                 190

Gly Ser Gly Gly Ala Ser Pro Leu Thr Ser Ala Gln Asp Ser Ala Phe
            195                 200                 205

Leu Asn Asp Ala Asp Met Val Met Ser Phe Val Asn Leu Val Glu Tyr
    210                 215                 220

Asp Lys Glu Phe Ser Pro Arg Gln Arg His His Lys Glu Phe Lys Phe
225                 230                 235                 240

Asn Leu Ser Gln Ile Pro Glu Gly Glu Val Val Thr Ala Ala Glu Phe
            245                 250                 255

Arg Ile Tyr Lys Asp Cys Val Met Gly Ser Phe Lys Asn Gln Thr Phe
            260                 265                 270

Leu Ile Ser Ile Tyr Gln Val Leu Gln Glu His Gln His Arg Asp Ser
    275                 280                 285

Asp Leu Phe Leu Leu Asp Thr Arg Val Val Trp Ala Ser Glu Glu Gly
    290                 295                 300

Trp Leu Glu Phe Asp Ile Thr Ala Thr Ser Asn Leu Trp Val Val Thr
305                 310                 315                 320

Pro Gln His Asn Met Gly Leu Gln Leu Ser Val Val Thr Arg Asp Gly
            325                 330                 335

Val His Val His Pro Arg Ala Ala Gly Leu Val Gly Arg Asp Gly Pro
            340                 345                 350

Tyr Asp Lys Gln Pro Phe Met Val Ala Phe Phe Lys Val Ser Glu Val
    355                 360                 365
```

-continued

```
His Val Arg Thr Thr Arg Ser Ala Ser Ser Arg Arg Arg Gln Gln Ser
    370             375             380

Arg Asn Arg Ser Thr Gln Ser Gln Asp Val Ala Arg Val Ser Ser Ala
385             390             395             400

Ser Asp Tyr Asn Ser Ser Glu Leu Lys Thr Ala Cys Arg Lys His Glu
            405             410             415

Leu Tyr Val Ser Phe Gln Asp Leu Gly Trp Gln Asp Trp Ile Ile Ala
            420             425             430

Pro Lys Gly Tyr Ala Ala Asn Tyr Cys Asp Gly Glu Cys Ser Phe Pro
            435             440             445

Leu Asn Ala His Met Asn Ala Thr Asn His Ala Ile Val Gln Thr Leu
    450             455             460

Val His Leu Met Asn Pro Glu Tyr Val Pro Lys Pro Cys Cys Ala Pro
465             470             475             480

Thr Lys Leu Asn Ala Ile Ser Val Leu Tyr Phe Asp Asp Asn Ser Asn
            485             490             495

Val Ile Leu Lys Lys Tyr Arg Asn Met Val Val Arg Ala Cys Gly Cys
            500             505             510

His
```

```
<210> SEQ ID NO 2
<211> LENGTH: 117
<212> TYPE: PRT
<213> ORGANISM: Homo Sapiens

<400> SEQUENCE: 2

Val Ser Ser Ala Ser Asp Tyr Asn Ser Ser Glu Leu Lys Thr Ala Cys
1               5               10              15

Arg Lys His Glu Leu Tyr Val Ser Phe Gln Asp Leu Gly Trp Gln Asp
            20              25              30

Trp Ile Ile Ala Pro Lys Gly Tyr Ala Ala Asn Tyr Cys Asp Gly Glu
        35              40              45

Cys Ser Phe Pro Leu Asn Ala His Met Asn Ala Thr Asn His Ala Ile
    50              55              60

Val Gln Thr Leu Val His Leu Met Asn Pro Glu Tyr Val Pro Lys Pro
65              70              75              80

Cys Cys Ala Pro Thr Lys Leu Asn Ala Ile Ser Val Leu Tyr Phe Asp
            85              90              95

Asp Asn Ser Asn Val Ile Leu Lys Lys Tyr Arg Asn Met Val Val Arg
            100             105             110

Ala Cys Gly Cys His
        115
```

```
<210> SEQ ID NO 3
<211> LENGTH: 132
<212> TYPE: PRT
<213> ORGANISM: Homo Sapiens

<400> SEQUENCE: 3

Gln Gln Ser Arg Asn Arg Ser Thr Gln Ser Gln Asp Val Ala Arg Val
1               5               10              15

Ser Ser Ala Ser Asp Tyr Asn Ser Ser Glu Leu Lys Thr Ala Cys Arg
            20              25              30

Lys His Glu Leu Tyr Val Ser Phe Gln Asp Leu Gly Trp Gln Asp Trp
        35              40              45

Ile Ile Ala Pro Lys Gly Tyr Ala Ala Asn Tyr Cys Asp Gly Glu Cys
```

-continued

```
        50                  55                  60

Ser Phe Pro Leu Asn Ala His Met Asn Ala Thr Asn His Ala Ile Val
65                  70                  75                  80

Gln Thr Leu Val His Leu Met Asn Pro Glu Tyr Val Pro Lys Pro Cys
                85                  90                  95

Cys Ala Pro Thr Lys Leu Asn Ala Ile Ser Val Leu Tyr Phe Asp Asp
                100                 105                 110

Asn Ser Asn Val Ile Leu Lys Lys Tyr Arg Asn Met Val Val Arg Ala
            115                 120                 125

Cys Gly Cys His
    130

<210> SEQ ID NO 4
<211> LENGTH: 510
<212> TYPE: PRT
<213> ORGANISM: Mus Musculus

<400> SEQUENCE: 4

Met Pro Gly Leu Gly Arg Arg Ala Gln Trp Leu Cys Trp Trp Trp Gly
1               5                   10                  15

Leu Leu Cys Ser Cys Gly Pro Pro Leu Arg Pro Pro Leu Pro Val
                20                  25                  30

Ala Ala Ala Ala Ala Gly Gly Gln Leu Leu Gly Ala Gly Gly Ser Pro
            35                  40                  45

Val Arg Ala Glu Gln Pro Pro Pro Gln Ser Ser Ser Ser Gly Phe Leu
    50                  55                  60

Tyr Arg Arg Leu Lys Thr His Glu Lys Arg Glu Met Gln Lys Glu Ile
65                  70                  75                  80

Leu Ser Val Leu Gly Leu Pro His Arg Pro Arg Pro Leu His Gly Leu
                85                  90                  95

Gln Gln Pro Gln Pro Pro Val Leu Pro Pro Gln Gln Gln Gln Gln
                100                 105                 110

Gln Gln Gln Gln Thr Ala Arg Glu Glu Pro Pro Gly Arg Leu Lys
            115                 120                 125

Ser Ala Pro Leu Phe Met Leu Asp Leu Tyr Asn Ala Leu Ser Asn Asp
            130                 135                 140

Asp Glu Glu Asp Gly Ala Ser Glu Gly Val Gly Gln Glu Pro Gly Ser
145                 150                 155                 160

His Gly Gly Ala Ser Ser Ser Gln Leu Arg Gln Pro Ser Pro Gly Ala
                165                 170                 175

Ala His Ser Leu Asn Arg Lys Ser Leu Leu Ala Pro Gly Pro Gly Gly
            180                 185                 190

Gly Ala Ser Pro Leu Thr Ser Ala Gln Asp Ser Ala Phe Leu Asn Asp
            195                 200                 205

Ala Asp Met Val Met Ser Phe Val Asn Leu Val Glu Tyr Asp Lys Glu
    210                 215                 220

Phe Ser Pro His Gln Arg His His Lys Glu Phe Lys Phe Asn Leu Ser
225                 230                 235                 240

Gln Ile Pro Glu Gly Glu Ala Val Thr Ala Ala Glu Phe Arg Val Tyr
                245                 250                 255

Lys Asp Cys Val Val Gly Ser Phe Lys Asn Gln Thr Phe Leu Ile Ser
                260                 265                 270

Ile Tyr Gln Val Leu Gln Glu His Gln His Arg Asp Ser Asp Leu Phe
            275                 280                 285
```

-continued

```
Leu Leu Asp Thr Arg Val Val Trp Ala Ser Glu Glu Gly Trp Leu Glu
    290             295                 300

Phe Asp Ile Thr Ala Thr Ser Asn Leu Trp Val Val Thr Pro Gln His
305             310                 315                 320

Asn Met Gly Leu Gln Leu Ser Val Val Thr Arg Asp Gly Leu His Val
            325                 330                 335

Asn Pro Arg Ala Ala Gly Leu Val Gly Arg Asp Gly Pro Tyr Asp Lys
            340                 345                 350

Gln Pro Phe Met Val Ala Phe Phe Lys Val Ser Glu Val His Val Arg
            355                 360                 365

Thr Thr Arg Ser Ala Ser Ser Arg Arg Arg Gln Gln Ser Arg Asn Arg
    370                 375                 380

Ser Thr Gln Ser Gln Asp Val Ser Arg Gly Ser Gly Ser Ser Asp Tyr
385                 390                 395                 400

Asn Gly Ser Glu Leu Lys Thr Ala Cys Lys Lys His Glu Leu Tyr Val
            405                 410                 415

Ser Phe Gln Asp Leu Gly Trp Gln Asp Trp Ile Ile Ala Pro Lys Gly
            420                 425                 430

Tyr Ala Ala Asn Tyr Cys Asp Gly Glu Cys Ser Phe Pro Leu Asn Ala
            435                 440                 445

His Met Asn Ala Thr Asn His Ala Ile Val Gln Thr Leu Val His Leu
    450                 455                 460

Met Asn Pro Glu Tyr Val Pro Lys Pro Cys Cys Ala Pro Thr Lys Leu
465                 470                 475                 480

Asn Ala Ile Ser Val Leu Tyr Phe Asp Asp Asn Ser Asn Val Ile Leu
            485                 490                 495

Lys Lys Tyr Arg Asn Met Val Val Arg Ala Cys Gly Cys His
            500                 505                 510

<210> SEQ ID NO 5
<211> LENGTH: 139
<212> TYPE: PRT
<213> ORGANISM: Mus Musculus

<400> SEQUENCE: 5

Ser Ala Ser Ser Arg Arg Arg Gln Gln Ser Arg Asn Arg Ser Thr Gln
1               5                   10                  15

Ser Gln Asp Val Ser Arg Gly Ser Gly Ser Ser Asp Tyr Asn Gly Ser
            20                  25                  30

Glu Leu Lys Thr Ala Cys Lys Lys His Glu Leu Tyr Val Ser Phe Gln
            35                  40                  45

Asp Leu Gly Trp Gln Asp Trp Ile Ile Ala Pro Lys Gly Tyr Ala Ala
    50                  55                  60

Asn Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
            85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
            115                 120                 125

Arg Asn Met Val Val Arg Ala Cys Gly Cys His
    130                 135

<210> SEQ ID NO 6
```

-continued

```
<211> LENGTH: 44
<212> TYPE: DNA
<213> ORGANISM: Homo Sapiens

<400> SEQUENCE: 6
aaaaaaacta gtaaatggcc ccatgtggcc cccgccttgt ctgc                    44

<210> SEQ ID NO 7
<211> LENGTH: 46
<212> TYPE: DNA
<213> ORGANISM: Homo Sapiens

<400> SEQUENCE: 7 tttttctcg agctgtctgg ctgtcccact gctgggtctt gagctt                   46

<210> SEQ ID NO 8
<211> LENGTH: 11
<212> TYPE: PRT
<213> ORGANISM: Homo Sapiens

<400> SEQUENCE: 8

Thr Leu Val His Leu Met Asn Pro Glu Tyr Val
1               5                   10

<210> SEQ ID NO 9
<211> LENGTH: 7
<212> TYPE: PRT
<213> ORGANISM: Homo Sapiens

<400> SEQUENCE: 9

His Leu Met Asn Pro Glu Tyr
1               5

<210> SEQ ID NO 10
<211> LENGTH: 13
<212> TYPE: PRT
<213> ORGANISM: Homo Sapiens

<400> SEQUENCE: 10

Ser Ala Ser Asp Tyr Asn Ser Ser Glu Leu Lys Thr Ala
1               5                   10

<210> SEQ ID NO 11
<211> LENGTH: 13
<212> TYPE: PRT
<213> ORGANISM: Homo Sapiens

<400> SEQUENCE: 11

Glu Leu Lys Thr Ala Cys Arg Lys His Glu Leu Tyr Val
1               5                   10

<210> SEQ ID NO 12
<211> LENGTH: 13
<212> TYPE: PRT
<213> ORGANISM: Homo Sapiens

<400> SEQUENCE: 12

Gly Ser Ser Asp Tyr Asn Gly Ser Glu Leu Lys Thr Ala
1               5                   10

<210> SEQ ID NO 13
<211> LENGTH: 13
<212> TYPE: PRT
<213> ORGANISM: Homo Sapiens
```

-continued

<400> SEQUENCE: 13

Glu Leu Lys Thr Ala Cys Lys Lys His Glu Leu Tyr Val
1               5                   10

<210> SEQ ID NO 14
<211> LENGTH: 5
<212> TYPE: PRT
<213> ORGANISM: Homo Sapiens

<400> SEQUENCE: 14

Glu Leu Lys Thr Ala
1               5

<210> SEQ ID NO 15
<211> LENGTH: 7
<212> TYPE: PRT
<213> ORGANISM: Homo Sapiens

<400> SEQUENCE: 15

Gln Ser Gln Asp Val Ala Arg
1               5

<210> SEQ ID NO 16
<211> LENGTH: 7
<212> TYPE: PRT
<213> ORGANISM: Homo Sapiens

<400> SEQUENCE: 16

Gln Ser Gln Asp Val Ser Arg
1               5

<210> SEQ ID NO 17
<211> LENGTH: 30
<212> TYPE: PRT
<213> ORGANISM: Homo Sapiens

<400> SEQUENCE: 17

Gln Ser Arg Asn Arg Ser Thr Gln Ser Gln Asp Val Ala Arg Val Ser
1               5                   10                  15

Ser Ala Ser Asp Tyr Asn Ser Ser Glu Leu Lys Thr Ala Cys
            20                  25                  30

<210> SEQ ID NO 18
<211> LENGTH: 8
<212> TYPE: PRT
<213> ORGANISM: Homo Sapiens

<400> SEQUENCE: 18

Gly Tyr Thr Phe Thr Asn His Ala
1               5

<210> SEQ ID NO 19
<211> LENGTH: 8
<212> TYPE: PRT
<213> ORGANISM: Homo Sapiens

<400> SEQUENCE: 19

Ile Asn Ala Gly Asn Gly Lys Thr
1               5

<210> SEQ ID NO 20
<211> LENGTH: 11
<212> TYPE: PRT
<213> ORGANISM: Homo Sapiens -continued

<400> SEQUENCE: 20

Thr Arg Arg Val Tyr Gly Glu Ser Tyr Asp His
1               5                   10

<210> SEQ ID NO 21
<211> LENGTH: 5
<212> TYPE: PRT
<213> ORGANISM: Homo Sapiens

<400> SEQUENCE: 21

Asn His Ala Ile His
1               5

<210> SEQ ID NO 22
<211> LENGTH: 17
<212> TYPE: PRT
<213> ORGANISM: Homo Sapiens

<400> SEQUENCE: 22

Trp Ile Asn Ala Gly Asn Gly Lys Thr Asp Tyr Ser Gln Asn Phe Gln
1               5                   10                  15

Gly

<210> SEQ ID NO 23
<211> LENGTH: 9
<212> TYPE: PRT
<213> ORGANISM: Homo Sapiens

<400> SEQUENCE: 23

Arg Val Tyr Gly Glu Ser Tyr Asp His
1               5

<210> SEQ ID NO 24
<211> LENGTH: 118
<212> TYPE: PRT
<213> ORGANISM: Homo Sapiens

<400> SEQUENCE: 24

Gln Val Gln Phe Val Gln Ser Gly Ala Glu Val Lys Ser Pro Gly Ala
1               5                   10                  15

Ser Val Lys Val Ser Cys Lys Ala Ser Gly Tyr Thr Phe Thr Asn His
            20                  25                  30

Ala Ile His Trp Val Arg Gln Ala Pro Gly Gln Arg Leu Glu Trp Met
        35                  40                  45

Gly Trp Ile Asn Ala Gly Asn Gly Lys Thr Asp Tyr Ser Gln Asn Phe
    50                  55                  60

Gln Gly Arg Val Ile Ile Thr Arg Asp Thr Ser Ala Asn Thr Ala Tyr
65                  70                  75                  80

Met Ser Leu Ser Ser Leu Thr Ser Glu Asp Thr Ala Phe Tyr Tyr Cys
                85                  90                  95

Thr Arg Arg Val Tyr Gly Glu Ser Tyr Asp His Trp Gly Gln Gly Thr
            100                 105                 110

Leu Val Thr Val Ser Ser
        115

<210> SEQ ID NO 25
<211> LENGTH: 354
<212> TYPE: DNA
<213> ORGANISM: Homo Sapiens -continued

<400> SEQUENCE: 25
caggtccagt ttgtgcagtc tgggggctgag gtgaagagtc ctggggcctc tgtgaaggtt        60
tcctgcaagg cttctggata caccttcaca aatcatgcta tacattgggt gcgccaggcc       120
cccggacaaa ggcttgagtg gatgggatgg atcaacgctg gcaatggtaa aactgattat       180
tcacagaact tccagggcag agtcatcatt accagggaca catccgcgaa cacagcctac       240
atgtccctga gcagcctgac atctgaggac acggctttt attactgtac tagaagggtc       300
tacggtgaat cgtatgacca ctggggccag ggaaccctgg tcaccgtctc ctca           354

<210> SEQ ID NO 26
<211> LENGTH: 445
<212> TYPE: PRT
<213> ORGANISM: Homo Sapiens

<400> SEQUENCE: 26

Gln Val Gln Phe Val Gln Ser Gly Ala Glu Val Lys Ser Pro Gly Ala
1               5                   10                  15

Ser Val Lys Val Ser Cys Lys Ala Ser Gly Tyr Thr Phe Thr Asn His
                20                  25                  30

Ala Ile His Trp Val Arg Gln Ala Pro Gly Gln Arg Leu Glu Trp Met
            35                  40                  45

Gly Trp Ile Asn Ala Gly Asn Gly Lys Thr Asp Tyr Ser Gln Asn Phe
        50                  55                  60

Gln Gly Arg Val Ile Ile Thr Arg Asp Thr Ser Ala Asn Thr Ala Tyr
65                  70                  75                  80

Met Ser Leu Ser Ser Leu Thr Ser Glu Asp Thr Ala Phe Tyr Tyr Cys
                85                  90                  95

Thr Arg Arg Val Tyr Gly Glu Ser Tyr Asp His Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

-continued

```
Thr Val Leu His Gln Asp Trp Leu Asn Gly Lys Glu Tyr Lys Cys Lys
305             310             315             320

Val Ser Asn Lys Gly Leu Pro Ser Ser Ile Glu Lys Thr Ile Ser Lys
            325             330             335

Ala Lys Gly Gln Pro Arg Glu Pro Gln Val Tyr Thr Leu Pro Pro Ser
            340             345             350

Gln Glu Glu Met Thr Lys Asn Gln Val Ser Leu Thr Cys Leu Val Lys
            355             360             365

Gly Phe Tyr Pro Ser Asp Ile Ala Val Glu Trp Glu Ser Asn Gly Gln
            370             375             380

Pro Glu Asn Asn Tyr Lys Thr Thr Pro Pro Val Leu Asp Ser Asp Gly
385             390             395             400

Ser Phe Phe Leu Tyr Ser Arg Leu Thr Val Asp Lys Ser Arg Trp Gln
            405             410             415

Glu Gly Asn Val Phe Ser Cys Ser Val Met His Glu Ala Leu His Asn
            420             425             430

His Tyr Thr Gln Lys Ser Leu Ser Leu Ser Leu Gly Lys
            435             440             445

<210> SEQ ID NO 27
<211> LENGTH: 6
<212> TYPE: PRT
<213> ORGANISM: Homo Sapiens

<400> SEQUENCE: 27

Gln Gly Ile Arg Asn Asn
1               5

<210> SEQ ID NO 28
<211> LENGTH: 3
<212> TYPE: PRT
<213> ORGANISM: Homo Sapiens

<400> SEQUENCE: 28

Ala Ala Ser
1

<210> SEQ ID NO 29
<211> LENGTH: 9
<212> TYPE: PRT
<213> ORGANISM: Homo Sapiens

<400> SEQUENCE: 29

Leu Gln His Gln Ile Tyr Pro Trp Thr
1               5

<210> SEQ ID NO 30
<211> LENGTH: 11
<212> TYPE: PRT
<213> ORGANISM: Homo Sapiens

<400> SEQUENCE: 30

Arg Ala Ser Gln Gly Ile Arg Asn Asn Leu Gly
1               5               10

<210> SEQ ID NO 31
<211> LENGTH: 7
<212> TYPE: PRT
<213> ORGANISM: Homo Sapiens

<400> SEQUENCE: 31
```

```
Ala Ala Ser Ser Leu Gln Ser
1               5

<210> SEQ ID NO 32
<211> LENGTH: 9
<212> TYPE: PRT
<213> ORGANISM: Homo Sapiens

<400> SEQUENCE: 32

Leu Gln His Gln Ile Tyr Pro Trp Thr
1               5

<210> SEQ ID NO 33
<211> LENGTH: 107
<212> TYPE: PRT
<213> ORGANISM: Homo Sapiens

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
                20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Val Ala Ile Tyr Phe Cys Leu Gln His Gln Ile Tyr Pro Trp
                85                  90                  95

Thr Phe Gly Gln Gly Thr Lys Val Glu Thr Lys
            100                 105

<210> SEQ ID NO 34
<211> LENGTH: 321
<212> TYPE: DNA
<213> ORGANISM: Homo Sapiens

<400> SEQUENCE: 34
gacatccaga tgacccagtc tccatcctcc ctgtctgcat ctgtaggaga cagagtcacc      60
atcacttgcc gggcaagtca gggcattaga aataatttag ctggtatca gcagaaacca     120 gggaaagccc ctaagcgcct gatctatgct gcatccagtt tgcaaagtgg ggtcccatca     180
aggtttagcg gcagtggatc tgggacagaa ttcactctca caatcagcag cctgcagcct     240
gaagatgttg caatttattt ctgtctacaa catcaaattt acccgtggac gttcggccaa     300
gggaccaagg tggaaaccaa a                                               321

<210> SEQ ID NO 35
<211> LENGTH: 214
<212> TYPE: PRT
<213> ORGANISM: Homo Sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
                20                  25                  30

Leu Gly Trp Tyr Gln Gln Lys Pro Gly Lys Ala Pro Lys Arg Leu Ile
        35                  40                  45
```

```
Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Val Ala Ile Tyr Phe Cys Leu Gln His Gln Ile Tyr Pro Trp
                85                  90                  95

Thr Phe Gly Gln Gly Thr Lys Val Glu Thr Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 36
<211> LENGTH: 8
<212> TYPE: PRT
<213> ORGANISM: Homo Sapiens

<400> SEQUENCE: 36

Gly Tyr Thr Phe Thr Ser Tyr Ala
1               5
```

```
<210> SEQ ID NO 37
<211> LENGTH: 8
<212> TYPE: PRT
<213> ORGANISM: Homo Sapiens

<400> SEQUENCE: 37

Ile Ser Ala Ala Asn Gly Asn Thr
1               5
```

```
<210> SEQ ID NO 38
<211> LENGTH: 11
<212> TYPE: PRT
<213> ORGANISM: Homo Sapiens

<400> SEQUENCE: 38

Ala Arg Arg Lys Leu Trp Ser Pro Phe Asp Ile
1               5                   10
```

```
<210> SEQ ID NO 39
<211> LENGTH: 5
<212> TYPE: PRT
<213> ORGANISM: Homo Sapiens

<400> SEQUENCE: 39

Ser Tyr Ala Leu His
1               5
```

<210> SEQ ID NO 40
<211> LENGTH: 17
<212> TYPE: PRT
<213> ORGANISM: Homo Sapiens

<400> SEQUENCE: 40

Trp Ile Ser Ala Ala Asn Gly Asn Thr Asp Tyr Ser Trp Lys Phe Gln
1               5                   10                  15

Gly

<210> SEQ ID NO 41
<211> LENGTH: 9
<212> TYPE: PRT
<213> ORGANISM: Homo Sapiens

<400> SEQUENCE: 41

Arg Lys Leu Trp Ser Pro Phe Asp Ile
1               5

<210> SEQ ID NO 42
<211> LENGTH: 118
<212> TYPE: PRT
<213> ORGANISM: Homo Sapiens

<400> SEQUENCE: 42

Gln Val Gln Leu Val Gln Ser Gly Ala Glu Val Gln Lys Pro Gly Ala
1               5                   10                  15

Ser Val Lys Val Ser Cys Lys Ala Ser Gly Tyr Thr Phe Thr Ser Tyr
                20                  25                  30

Ala Leu His Trp Val Arg Gln Ala Pro Gly Gln Arg Leu Glu Trp Leu
            35                  40                  45

Gly Trp Ile Ser Ala Ala Asn Gly Asn Thr Asp Tyr Ser Trp Lys Phe
        50                  55                  60

Gln Gly Arg Val Thr Leu Thr Arg Asp Thr Ser Ala Asn Thr Val Tyr
65                  70                  75                  80

Met Glu Leu Asn Ser Leu Thr Ser Glu Asp Ser Ala Val Tyr Tyr Cys
                85                  90                  95

Ala Arg Arg Lys Leu Trp Ser Pro Phe Asp Ile Trp Gly Gln Gly Thr
            100                 105                 110

Leu Val Thr Val Ser Ser
        115

<210> SEQ ID NO 43
<211> LENGTH: 354
<212> TYPE: DNA
<213> ORGANISM: Homo Sapiens

<400> SEQUENCE: 43
caggtccaac ttgtgcagtc tgggggctgag gtgcagaagc ctggggcctc agtgaaggtt      60
tcctgcaagg cttctggata caccttcact tcatatgctt tgcattgggt gcgccaggcc     120
cccggacaaa ggcttgagtg gctgggatgg atcagcgctg ccaatggtaa cacagattat     180
tcatggaagt tccagggcag agtcacccctt accagggaca catccgcaaa cacagtctac     240
atggaactga acagtctgac atctgaggac tcggctgtgt attactgtgc gagaaggaaa     300
ctatggtctc cttttgatat ctggggccaa gggacattgg tcaccgtctc ttca            354

<210> SEQ ID NO 44
<211> LENGTH: 445
<212> TYPE: PRT

```
<213> ORGANISM: Homo Sapiens

<400> SEQUENCE: 44

Gln Val Gln Leu Val Gln Ser Gly Ala Glu Val Gln Lys Pro Gly Ala
1               5                   10                  15

Ser Val Lys Val Ser Cys Lys Ala Ser Gly Tyr Thr Phe Thr Ser Tyr
                20                  25                  30

Ala Leu His Trp Val Arg Gln Ala Pro Gly Gln Arg Leu Glu Trp Leu
            35                  40                  45

Gly Trp Ile Ser Ala Ala Asn Gly Asn Thr Asp Tyr Ser Trp Lys Phe
        50                  55                  60

Gln Gly Arg Val Thr Leu Thr Arg Asp Thr Ser Ala Asn Thr Val Tyr
65                  70                  75                  80

Met Glu Leu Asn Ser Leu Thr Ser Glu Asp Ser Ala Val Tyr Tyr Cys
                85                  90                  95

Ala Arg Arg Lys Leu Trp Ser Pro Phe Asp Ile Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400
```

-continued

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 45
<211> LENGTH: 7
<212> TYPE: PRT
<213> ORGANISM: Homo Sapiens

<400> SEQUENCE: 45

Gln Ser Leu Thr Asn Ser Phe
1               5

<210> SEQ ID NO 46
<211> LENGTH: 3
<212> TYPE: PRT
<213> ORGANISM: Homo Sapiens

<400> SEQUENCE: 46

Gly Ala Phe
1

<210> SEQ ID NO 47
<211> LENGTH: 9
<212> TYPE: PRT
<213> ORGANISM: Homo Sapiens

<400> SEQUENCE: 47

Gln Tyr Tyr Gly Thr Ser Pro Trp Thr
1               5

<210> SEQ ID NO 48
<211> LENGTH: 12
<212> TYPE: PRT
<213> ORGANISM: Homo Sapiens

<400> SEQUENCE: 48

Trp Ala Ser Gln Ser Leu Thr Asn Ser Phe Leu Ala
1               5                   10

<210> SEQ ID NO 49
<211> LENGTH: 7
<212> TYPE: PRT
<213> ORGANISM: Homo Sapiens

<400> SEQUENCE: 49

Gly Ala Phe Ser Arg Ala Thr
1               5

<210> SEQ ID NO 50
<211> LENGTH: 9
<212> TYPE: PRT
<213> ORGANISM: Homo Sapiens

<400> SEQUENCE: 50

Gln Tyr Tyr Gly Thr Ser Pro Trp Thr
1               5

<210> SEQ ID NO 51
<211> LENGTH: 108
<212> TYPE: PRT

<213> ORGANISM: Homo Sapiens

<400> SEQUENCE: 51

Glu Ile Val Leu Thr Gln Ser Pro Gly Thr Leu Ser Leu Ser Pro Gly
1               5                   10                  15

Glu Arg Ala Thr Leu Ser Cys Trp Ala Ser Gln Ser Leu Thr Asn Ser
            20                  25                  30

Phe Leu Ala Trp Tyr Arg Gln Lys Pro Gly Gln Ala Pro Arg Leu Leu
        35                  40                  45

Ile Ser Gly Ala Phe Ser Arg Ala Thr Asp Ile Pro Asp Arg Ile Ser
    50                  55                  60

Gly Ser Gly Ser Gly Thr Asp Phe Thr Leu Thr Ile Asn Arg Leu Glu
65                  70                  75                  80

Pro Glu Asp Phe Ala Val Tyr Tyr Cys Gln Tyr Tyr Gly Thr Ser Pro
                85                  90                  95

Trp Thr Phe Gly Gln Gly Thr Lys Val Glu Ile Lys
                100                 105

<210> SEQ ID NO 52
<211> LENGTH: 324
<212> TYPE: DNA
<213> ORGANISM: Homo Sapiens

<400> SEQUENCE: 52
gaaattgtgt tgacgcagtc tccaggcacc ctgtctttgt ctccagggga aagagccacc        60
ctctcctgtt gggccagtca aagtcttacc aacagtttct tagcctggta ccggcagaaa       120
cctggccagg ctcccaggct cctcatctct ggtgcattca gcagggccac tgacatccca       180
gacaggatca gtggcagtgg atctgggaca gacttcactc tcaccatcaa cagactggag       240
cctgaagatt ttgcagtgta ttactgtcag tactatggta cctcaccgtg gacgttcggc       300
caagggacca aggtggaaat caaa                                               324

<210> SEQ ID NO 53
<211> LENGTH: 215
<212> TYPE: PRT
<213> ORGANISM: Homo Sapiens

<400> SEQUENCE: 53

Glu Ile Val Leu Thr Gln Ser Pro Gly Thr Leu Ser Leu Ser Pro Gly
1               5                   10                  15

Glu Arg Ala Thr Leu Ser Cys Trp Ala Ser Gln Ser Leu Thr Asn Ser
            20                  25                  30

Phe Leu Ala Trp Tyr Arg Gln Lys Pro Gly Gln Ala Pro Arg Leu Leu
        35                  40                  45

Ile Ser Gly Ala Phe Ser Arg Ala Thr Asp Ile Pro Asp Arg Ile Ser
    50                  55                  60

Gly Ser Gly Ser Gly Thr Asp Phe Thr Leu Thr Ile Asn Arg Leu Glu
65                  70                  75                  80

Pro Glu Asp Phe Ala Val Tyr Tyr Cys Gln Tyr Tyr Gly Thr Ser Pro
                85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

-continued

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 54
<211> LENGTH: 8
<212> TYPE: PRT
<213> ORGANISM: Homo Sapiens

<400> SEQUENCE: 54

Gly Tyr Thr Phe Thr Thr Phe Ala
1               5

<210> SEQ ID NO 55
<211> LENGTH: 8
<212> TYPE: PRT
<213> ORGANISM: Homo Sapiens

<400> SEQUENCE: 55

Ile Asn Pro Gly Asn Val Lys Thr
1               5

<210> SEQ ID NO 56
<211> LENGTH: 11
<212> TYPE: PRT
<213> ORGANISM: Homo Sapiens

<400> SEQUENCE: 56

Ala Arg Arg Gln Leu Trp Leu Pro Phe Asp Tyr
1               5                   10

<210> SEQ ID NO 57
<211> LENGTH: 5
<212> TYPE: PRT
<213> ORGANISM: Homo Sapiens

<400> SEQUENCE: 57

Thr Phe Ala Ile His
1               5

<210> SEQ ID NO 58
<211> LENGTH: 17
<212> TYPE: PRT
<213> ORGANISM: Homo Sapiens

<400> SEQUENCE: 58

Trp Ile Asn Pro Gly Asn Val Lys Thr Asp Tyr Ser Gln Lys Phe Gln
1               5                   10                  15

Gly

<210> SEQ ID NO 59
<211> LENGTH: 9
<212> TYPE: PRT
<213> ORGANISM: Homo Sapiens
```

-continued

<400> SEQUENCE: 59

Arg Gln Leu Trp Leu Pro Phe Asp Tyr
1               5

<210> SEQ ID NO 60
<211> LENGTH: 118
<212> TYPE: PRT
<213> ORGANISM: Homo Sapiens

<400> SEQUENCE: 60

Gln Val His Leu Val Gln Ser Gly Ala Glu Val Lys Asn Pro Gly Ala
1               5                   10                  15

Ser Val Lys Val Ser Cys Lys Ala Ser Gly Tyr Thr Phe Thr Thr Phe
                20                  25                  30

Ala Ile His Trp Leu Arg Gln Ala Pro Gly Gln Arg Leu Glu Trp Met
            35                  40                  45

Gly Trp Ile Asn Pro Gly Asn Val Lys Thr Asp Tyr Ser Gln Lys Phe
        50                  55                  60

Gln Gly Arg Val Thr Ile Ser Arg Asp Thr Ser Ala Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gln Leu Trp Leu Pro Phe Asp Tyr Trp Gly Gln Gly Thr
                100                 105                 110

Leu Val Thr Val Ser Ser
        115

<210> SEQ ID NO 61
<211> LENGTH: 355
<212> TYPE: DNA
<213> ORGANISM: Homo Sapiens

<400> SEQUENCE: 61
caggtccacc ttgttcagtc aggggcagag gtgaagaacc ctggggcctc agtgaaggtc      60
tcctgcaagg cttctggata caccttcact acctttgcta ttcattggtt gcgccaggcc     120
cccggacaga ggcttgagtg gatgggatgg atcaaccctg gcaatgttaa gacagattat     180
tcgcagaagt tccagggcag agtcaccatt agcagggaca catccgcgac cactgcctac     240
atggagctga gcagcctgag atctgaagac acggctgttt attactgtgc gagaagacaa     300
ttatggttac cctttgacta ctggggccag ggaaccctgg tcaccgtctc ctcag          355

<210> SEQ ID NO 62
<211> LENGTH: 445
<212> TYPE: PRT
<213> ORGANISM: Homo Sapiens

<400> SEQUENCE: 62

Gln Val His Leu Val Gln Ser Gly Ala Glu Val Lys Asn Pro Gly Ala
1               5                   10                  15

Ser Val Lys Val Ser Cys Lys Ala Ser Gly Tyr Thr Phe Thr Thr Phe
                20                  25                  30

Ala Ile His Trp Leu Arg Gln Ala Pro Gly Gln Arg Leu Glu Trp Met
            35                  40                  45

Gly Trp Ile Asn Pro Gly Asn Val Lys Thr Asp Tyr Ser Gln Lys Phe
        50                  55                  60

Gln Gly Arg Val Thr Ile Ser Arg Asp Thr Ser Ala Thr Thr Ala Tyr
65                  70                  75                  80

```
Met Glu Leu Ser Ser Leu Arg Ser Glu Asp Thr Ala Val Tyr Tyr Cys
                  85              90                  95

Ala Arg Arg Gln Leu Trp Leu Pro Phe Asp Tyr Trp Gly Gln Gly Thr
             100             105             110

Leu Val Thr Val Ser Ser Ala Ser Thr Lys Gly Pro Ser Val Phe Pro
             115             120             125

Leu Ala Pro Cys Ser Arg Ser Thr Ser Glu Ser Thr Ala Ala Leu Gly
         130             135             140

Cys Leu Val Lys Asp Tyr Phe Pro Glu Pro Val Thr Val Ser Trp Asn
145             150             155             160

Ser Gly Ala Leu Thr Ser Gly Val His Thr Phe Pro Ala Val Leu Gln
             165             170             175

Ser Ser Gly Leu Tyr Ser Leu Ser Ser Val Val Thr Val Pro Ser Ser
             180             185             190

Ser Leu Gly Thr Lys Thr Tyr Thr Cys Asn Val Asp His Lys Pro Ser
             195             200             205

Asn Thr Lys Val Asp Lys Arg Val Glu Ser Lys Tyr Gly Pro Pro Cys
         210             215             220

Pro Pro Cys Pro Ala Pro Glu Phe Glu Gly Gly Pro Ser Val Phe Leu
225             230             235             240

Phe Pro Pro Lys Pro Lys Asp Thr Leu Met Ile Ser Arg Thr Pro Glu
             245             250             255

Val Thr Cys Val Val Val Asp Val Ser Gln Glu Asp Pro Glu Val Gln
             260             265             270

Phe Asn Trp Tyr Val Asp Gly Val Glu Val His Asn Ala Lys Thr Lys
             275             280             285

Pro Arg Glu Glu Gln Phe Asn Ser Thr Tyr Arg Val Val Ser Val Leu
         290             295             300

Thr Val Leu His Gln Asp Trp Leu Asn Gly Lys Glu Tyr Lys Cys Lys
305             310             315             320

Val Ser Asn Lys Gly Leu Pro Ser Ser Ile Glu Lys Thr Ile Ser Lys
             325             330             335

Ala Lys Gly Gln Pro Arg Glu Pro Gln Val Tyr Thr Leu Pro Pro Ser
             340             345             350

Gln Glu Glu Met Thr Lys Asn Gln Val Ser Leu Thr Cys Leu Val Lys
             355             360             365

Gly Phe Tyr Pro Ser Asp Ile Ala Val Glu Trp Glu Ser Asn Gly Gln
         370             375             380

Pro Glu Asn Asn Tyr Lys Thr Thr Pro Pro Val Leu Asp Ser Asp Gly
385             390             395             400

Ser Phe Phe Leu Tyr Ser Arg Leu Thr Val Asp Lys Ser Arg Trp Gln
             405             410             415

Glu Gly Asn Val Phe Ser Cys Ser Val Met His Glu Ala Leu His Asn
             420             425             430

His Tyr Thr Gln Lys Ser Leu Ser Leu Ser Leu Gly Lys
             435             440             445
```

<210> SEQ ID NO 63
<211> LENGTH: 7
<212> TYPE: PRT
<213> ORGANISM: Homo Sapiens

<400> SEQUENCE: 63

Gln Ser Ile Ser Asn Asn Phe

-continued

```
1               5

<210> SEQ ID NO 64
<211> LENGTH: 3
<212> TYPE: PRT
<213> ORGANISM: Homo Sapiens

<400> SEQUENCE: 64

Gly Ala Ser
1

<210> SEQ ID NO 65
<211> LENGTH: 9
<212> TYPE: PRT
<213> ORGANISM: Homo Sapiens

<400> SEQUENCE: 65

Gln His Tyr Gly Gly Ser Pro Trp Thr
1               5

<210> SEQ ID NO 66
<211> LENGTH: 12
<212> TYPE: PRT
<213> ORGANISM: Homo Sapiens

<400> SEQUENCE: 66

Arg Ala Ser Gln Ser Ile Ser Asn Asn Phe Leu Ala
1               5                   10

<210> SEQ ID NO 67
<211> LENGTH: 7
<212> TYPE: PRT
<213> ORGANISM: Homo Sapiens

<400> SEQUENCE: 67

Gly Ala Ser Ser Arg Ala Thr
1               5

<210> SEQ ID NO 68
<211> LENGTH: 9
<212> TYPE: PRT
<213> ORGANISM: Homo Sapiens

<400> SEQUENCE: 68

Gln His Tyr Gly Gly Ser Pro Trp Thr
1               5

<210> SEQ ID NO 69
<211> LENGTH: 108
<212> TYPE: PRT
<213> ORGANISM: Homo Sapiens

<400> SEQUENCE: 69

Glu Ile Val Leu Thr Gln Ser Pro Gly Thr Leu Ser Leu Ser Pro Gly
1               5                   10                  15

Glu Gly Ala Thr Leu Ser Cys Arg Ala Ser Gln Ser Ile Ser Asn Asn
                20                  25                  30

Phe Leu Ala Trp Tyr Gln Gln Lys Pro Gly Gln Ala Pro Arg Leu Leu
            35                  40                  45

Ile Phe Gly Ala Ser Ser Arg Ala Thr Ala Ile Pro Asp Arg Phe Val
        50                  55                  60

Gly Ser Gly Ser Gly Thr Asp Phe Thr Leu Thr Ile Thr Gly Leu Glu
65                  70                  75                  80
```

-continued

Pro Glu Asp Phe Ala Val Tyr His Cys Gln His Tyr Gly Gly Ser Pro
              85                  90                  95

Trp Thr Phe Gly Gln Gly Thr Lys Val Glu Ile Lys
            100                 105

<210> SEQ ID NO 70
<211> LENGTH: 324
<212> TYPE: DNA
<213> ORGANISM: Homo Sapiens

<400> SEQUENCE: 70
gaaattgtgt tgacgcagtc tccaggcacc ctgtctttgt ctccagggga gggagccacc      60
ctctcctgca gggccagtca gagtattagc aacaacttct tagcctggta ccaacagaaa     120
cctggccagg ctcccagact cctcatcttt ggtgcatcca gcagggccac tgccatccca     180
gacaggttcg ttggcagtgg gtctgggaca gacttcactc tcaccatcac cggactggag     240
cctgaagatt ttgcagtgta tcactgtcaa cactatggtg gttcaccttg gacgttcggc     300
caagggacca aggtggaaat caaa                                           324

<210> SEQ ID NO 71
<211> LENGTH: 215
<212> TYPE: PRT
<213> ORGANISM: Homo Sapiens

<400> SEQUENCE: 71

Glu Ile Val Leu Thr Gln Ser Pro Gly Thr Leu Ser Leu Ser Pro Gly
1               5                   10                  15

Glu Gly Ala Thr Leu Ser Cys Arg Ala Ser Gln Ser Ile Ser Asn Asn
              20                  25                  30

Phe Leu Ala Trp Tyr Gln Gln Lys Pro Gly Gln Ala Pro Arg Leu Leu
            35                  40                  45

Ile Phe Gly Ala Ser Ser Arg Ala Thr Ala Ile Pro Asp Arg Phe Val
          50                  55                  60

Gly Ser Gly Ser Gly Thr Asp Phe Thr Leu Thr Ile Thr Gly Leu Glu
65                  70                  75                  80

Pro Glu Asp Phe Ala Val Tyr His Cys Gln His Tyr Gly Gly Ser Pro
              85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
          115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
              165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
          195                 200                 205

Ser Phe Asn Arg Gly Glu Cys
          210                 215

<210> SEQ ID NO 72

-continued

```
<211> LENGTH: 8
<212> TYPE: PRT
<213> ORGANISM: Homo Sapiens

<400> SEQUENCE: 72

Gly Tyr Ser Phe Thr Asn Tyr Ala
1               5

<210> SEQ ID NO 73
<211> LENGTH: 8
<212> TYPE: PRT
<213> ORGANISM: Homo Sapiens

<400> SEQUENCE: 73

Ile His Ala Gly Asn Gly Lys Thr
1               5

<210> SEQ ID NO 74
<211> LENGTH: 11
<212> TYPE: PRT
<213> ORGANISM: Homo Sapiens

<400> SEQUENCE: 74

Ala Arg Arg Gln Leu Trp Leu Pro Phe Asp Tyr
1               5                   10

<210> SEQ ID NO 75
<211> LENGTH: 5
<212> TYPE: PRT
<213> ORGANISM: Homo Sapiens

<400> SEQUENCE: 75

Asn Tyr Ala Leu His
1               5

<210> SEQ ID NO 76
<211> LENGTH: 17
<212> TYPE: PRT
<213> ORGANISM: Homo Sapiens

<400> SEQUENCE: 76

Trp Ile His Ala Gly Asn Gly Lys Thr Glu Tyr Ala Gln Lys Phe Gln
1               5                   10                  15

Asp

<210> SEQ ID NO 77
<211> LENGTH: 9
<212> TYPE: PRT
<213> ORGANISM: Homo Sapiens

<400> SEQUENCE: 77

Arg Gln Leu Trp Leu Pro Phe Asp Tyr
1               5

<210> SEQ ID NO 78
<211> LENGTH: 118
<212> TYPE: PRT
<213> ORGANISM: Homo Sapiens

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
                20                  25                  30
```

```
Ala Leu His Trp Val Arg Gln Ala Pro Gly Gln Arg Leu Glu Trp Met
        35                  40                  45

Gly Trp Ile His Ala Gly Asn Gly Lys Thr Glu Tyr Ala Gln Lys Phe
    50                  55                  60

Gln Asp Arg Val Thr Ile Ser Arg Asp Ile Ser Ala Ile Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gln Leu Trp Leu Pro Phe Asp Tyr Trp Gly Gln Gly Thr
            100                 105                 110

Leu Val Thr Val Ser Ser
        115
```

```
<210> SEQ ID NO 79
<211> LENGTH: 354
<212> TYPE: DNA
<213> ORGANISM: Homo Sapiens

<400> SEQUENCE: 79
caggtccagc ttgtgcagtc tgggggctgag gtgaagaagc ctggggcctc agtgaaagtt      60
tcctgtaagg cttctgggta cagtttcact aactatgctt tacattgggt gcgccaggcc     120
cccggacaaa gacttgagtg gatgggatgg atccacgctg gtaatggtaa gacagaatat     180
gcacagaagt tccaggacag agtcaccatt agtagggaca tatccgcgat cacagtttac     240
atggaactga gcagcctgag atctgaagac acggctgttt attattgtgc gagaagacag     300
ttatggttac cctttgacta ctggggccag ggaaccctgg tcaccgtctc ctca          354
```

```
<210> SEQ ID NO 80
<211> LENGTH: 445
<212> TYPE: PRT
<213> ORGANISM: Homo Sapiens

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Ala Leu His Trp Val Arg Gln Ala Pro Gly Gln Arg Leu Glu Trp Met
        35                  40                  45

Gly Trp Ile His Ala Gly Asn Gly Lys Thr Glu Tyr Ala Gln Lys Phe
    50                  55                  60

Gln Asp Arg Val Thr Ile Ser Arg Asp Ile Ser Ala Ile Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gln Leu Trp Leu Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

-continued

```
Ser Ser Gly Leu Tyr Ser Leu Ser Ser Val Val Thr Val Pro Ser Ser
        180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
        260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
        435                 440                 445
```

```
<210> SEQ ID NO 81
<211> LENGTH: 7
<212> TYPE: PRT
<213> ORGANISM: Homo Sapiens

<400> SEQUENCE: 81

Gln Ile Ile Ile Asn Arg Gln
1               5

<210> SEQ ID NO 82
<211> LENGTH: 3
<212> TYPE: PRT
<213> ORGANISM: Homo Sapiens

<400> SEQUENCE: 82

Gly Ala Ser
1

<210> SEQ ID NO 83
<211> LENGTH: 9
<212> TYPE: PRT
<213> ORGANISM: Homo Sapiens
```

<400> SEQUENCE: 83

Gln His Tyr Gly Gly Ser Pro Trp Thr
1               5

<210> SEQ ID NO 84
<211> LENGTH: 12
<212> TYPE: PRT
<213> ORGANISM: Homo Sapiens

<400> SEQUENCE: 84

Arg Ala Gly Gln Ile Ile Ile Asn Arg Gln Leu Ala
1               5                   10

<210> SEQ ID NO 85
<211> LENGTH: 7
<212> TYPE: PRT
<213> ORGANISM: Homo Sapiens

<400> SEQUENCE: 85

Gly Ala Ser Asn Arg Val Thr
1               5

<210> SEQ ID NO 86
<211> LENGTH: 9
<212> TYPE: PRT
<213> ORGANISM: Homo Sapiens

<400> SEQUENCE: 86

Gln His Tyr Gly Gly Ser Pro Trp Thr
1               5

<210> SEQ ID NO 87
<211> LENGTH: 108
<212> TYPE: PRT
<213> ORGANISM: Homo Sapiens

<400> SEQUENCE: 87

Glu Ile Val Leu Thr Gln Ser Pro Asp Thr Leu Ser Leu Ser Pro Gly
1               5                   10                  15

Glu Thr Ala Ser Phe Ser Cys Arg Ala Gly Gln Ile Ile Ile Asn Arg
                20                  25                  30

Gln Leu Ala Trp Tyr Gln Arg Arg Pro Gly Gln Ala Pro Arg Leu Leu
            35                  40                  45

Ile Tyr Gly Ala Ser Asn Arg Val Thr Gly Ile Pro Asp Arg Phe Ser
        50                  55                  60

Gly Ser Gly Ser Gly Thr Asp Phe Thr Leu Thr Ile Asn Arg Leu Glu
65                  70                  75                  80

Pro Glu Asp Phe Ala Val Tyr Tyr Cys Gln His Tyr Gly Gly Ser Pro
                85                  90                  95

Trp Thr Phe Gly Gln Gly Thr Lys Val Glu Ile Lys
            100                 105

<210> SEQ ID NO 88
<211> LENGTH: 324
<212> TYPE: DNA
<213> ORGANISM: Homo Sapiens

<400> SEQUENCE: 88
gaaattgtgt tgacgcagtc tccagacacc ctctctttgt ctccagggga aacagccagt      60
ttctcctgca gggccggtca aattattatc aacagacagt tagcctggta ccagcggaga     120

-continued

```
cctggccagg ctcccccggct cctcatctat ggcgcgtcca ataggggtcac tggcatccca      180 gacaggttca gtggcagtgg gtctgggaca gacttcactc tcacgatcaa tagactggag      240
cctgaagatt ttgcagtgta ttactgtcag cactatggtg gctcaccttg gacgttcggc      300
caagggacca aggtggaaat caaa                                             324
```

```
<210> SEQ ID NO 89
<211> LENGTH: 215
<212> TYPE: PRT
<213> ORGANISM: Homo Sapiens

<400> SEQUENCE: 89

Glu Ile Val Leu Thr Gln Ser Pro Asp Thr Leu Ser Leu Ser Pro Gly
1               5                   10                  15

Glu Thr Ala Ser Phe Ser Cys Arg Ala Gly Gln Ile Ile Ile Asn Arg
            20                  25                  30

Gln Leu Ala Trp Tyr Gln Arg Arg Pro Gly Gln Ala Pro Arg Leu Leu
        35                  40                  45

Ile Tyr Gly Ala Ser Asn Arg Val Thr Gly Ile Pro Asp Arg Phe Ser
    50                  55                  60

Gly Ser Gly Ser Gly Thr Asp Phe Thr Leu Thr Ile Asn Arg Leu Glu
65                  70                  75                  80

Pro Glu Asp Phe Ala Val Tyr Tyr Cys Gln His Tyr Gly Gly Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

```
<210> SEQ ID NO 90
<211> LENGTH: 8
<212> TYPE: PRT
<213> ORGANISM: Homo Sapiens

<400> SEQUENCE: 90

Gly Tyr Thr Phe Thr Ser His Ala
1               5
```

```
<210> SEQ ID NO 91
<211> LENGTH: 8
<212> TYPE: PRT
<213> ORGANISM: Homo Sapiens

<400> SEQUENCE: 91

Ile Asn Ala Ala Asn Gly Lys Thr
```

-continued 1                           5

<210> SEQ ID NO 92
<211> LENGTH: 11
<212> TYPE: PRT
<213> ORGANISM: Homo Sapiens

<400> SEQUENCE: 92

Ala Arg Arg Pro Tyr Gly Gly Pro Phe Asp Tyr
1                           5                           10

<210> SEQ ID NO 93
<211> LENGTH: 5
<212> TYPE: PRT
<213> ORGANISM: Homo Sapiens

<400> SEQUENCE: 93

Ser His Ala Met His
1                           5

<210> SEQ ID NO 94
<211> LENGTH: 17
<212> TYPE: PRT
<213> ORGANISM: Homo Sapiens

<400> SEQUENCE: 94

Trp Ile Asn Ala Ala Asn Gly Lys Thr Asp Tyr Ser Gln Asn Phe Gln
1                           5                           10                          15

Gly

<210> SEQ ID NO 95
<211> LENGTH: 9
<212> TYPE: PRT
<213> ORGANISM: Homo Sapiens

<400> SEQUENCE: 95

Arg Pro Tyr Gly Gly Pro Phe Asp Tyr
1                           5

<210> SEQ ID NO 96
<211> LENGTH: 118
<212> TYPE: PRT
<213> ORGANISM: Homo Sapiens

<400> SEQUENCE: 96

Gln Val Gln Phe Val Gln Ser Gly Ala Glu Val Lys Lys Pro Gly Ala
1                           5                           10                          15

Ser Val Lys Val Ser Cys Lys Ala Ser Gly Tyr Thr Phe Thr Ser His
                20                          25                          30

Ala Met His Trp Val Arg Gln Ala Pro Gly Gln Arg Leu Glu Trp Met
                35                          40                          45

Gly Trp Ile Asn Ala Ala Asn Gly Lys Thr Asp Tyr Ser Gln Asn Phe
        50                          55                          60

Gln Gly Arg Val Thr Ile Thr Arg Asp Thr Tyr Ala Asn Thr Val Tyr
65                          70                          75                          80

Met Glu Leu Ser Ser Leu Arg Ser Glu Asp Thr Ala Val Tyr Tyr Cys
                85                          90                          95

Ala Arg Arg Pro Tyr Gly Gly Pro Phe Asp Tyr Trp Gly Gln Gly Thr
                100                         105                         110

Leu Val Thr Val Ser Ser
        115

-continued

<210> SEQ ID NO 97
<211> LENGTH: 354
<212> TYPE: DNA
<213> ORGANISM: Homo Sapiens

<400> SEQUENCE: 97
caggtccagt ttgtgcagtc tggggctgag gtgaagaagc ctgggggcctc agtgaaggtt      60 tcctgtaagg cttctggata caccttcact agccatgcta tgcattgggt gcgccaggcc     120
cccggacaaa ggcttgagtg gatgggatgg atcaacgctg ccaatggtaa aacagattat     180
tcacagaact ccagggcag agtcaccatt accaggggaca catacgcgaa cacagtctac     240
atggaactga gcagcctgag atctgaagac acggctgtgt attactgtgc gagacgccct     300
tacggtggtc cctttgacta ctggggccag ggaaccctgg tcaccgtctc ctca           354

<210> SEQ ID NO 98
<211> LENGTH: 445
<212> TYPE: PRT
<213> ORGANISM: Homo Sapiens

<400> SEQUENCE: 98

Gln Val Gln Phe Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Ala Met His Trp Val Arg Gln Ala Pro Gly Gln Arg Leu Glu Trp Met
        35                  40                  45

Gly Trp Ile Asn Ala Ala Asn Gly Lys Thr Asp Tyr Ser Gln Asn Phe
    50                  55                  60

Gln Gly Arg Val Thr Ile Thr Arg Asp Thr Tyr Ala Asn Thr Val Tyr
65                  70                  75                  80

Met Glu Leu Ser Ser Leu Arg Ser Glu Asp Thr Ala Val Tyr Tyr Cys
                85                  90                  95

Ala Arg Arg Pro Tyr Gly Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

-continued

```
Phe Asn Trp Tyr Val Asp Gly Val Glu Val His Asn Ala Lys Thr Lys
    275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
        435                 440                 445

<210> SEQ ID NO 99
<211> LENGTH: 6
<212> TYPE: PRT
<213> ORGANISM: Homo Sapiens

<400> SEQUENCE: 99

Gln Ser Ile Ser Ile Trp
1               5

<210> SEQ ID NO 100
<211> LENGTH: 3
<212> TYPE: PRT
<213> ORGANISM: Homo Sapiens

<400> SEQUENCE: 100

Lys Ala Ser
1

<210> SEQ ID NO 101
<211> LENGTH: 9
<212> TYPE: PRT
<213> ORGANISM: Homo Sapiens

<400> SEQUENCE: 101

Gln Gln Tyr Asn Leu Tyr Pro Trp Thr
1               5

<210> SEQ ID NO 102
<211> LENGTH: 11
<212> TYPE: PRT
<213> ORGANISM: Homo Sapiens

<400> SEQUENCE: 102

Arg Ala Ser Gln Ser Ile Ser Ile Trp Leu Ala
1               5                   10
```

-continued

```
<210> SEQ ID NO 103
<211> LENGTH: 7
<212> TYPE: PRT
<213> ORGANISM: Homo Sapiens

<400> SEQUENCE: 103

Lys Ala Ser Ser Leu Glu Ser
1               5

<210> SEQ ID NO 104
<211> LENGTH: 9
<212> TYPE: PRT
<213> ORGANISM: Homo Sapiens

<400> SEQUENCE: 104

Gln Gln Tyr Asn Leu Tyr Pro Trp Thr
1               5

<210> SEQ ID NO 105
<211> LENGTH: 107
<212> TYPE: PRT
<213> ORGANISM: Homo Sapiens

<400> SEQUENCE: 105

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ile Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Leu Tyr Pro Trp
                85                  90                  95

Thr Phe Gly Gln Gly Thr Lys Val Glu Ile Lys
                100                 105

<210> SEQ ID NO 106
<211> LENGTH: 321
<212> TYPE: DNA
<213> ORGANISM: Homo Sapiens

<400> SEQUENCE: 106
gacatccaga tgacccagtc tccttccacc ctgtctgcat ctgtaggaga cagagtcacc      60
atcacttgcc gggccagtca gagtattagt atctggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgtcaacag tataatcttt atccgtggac gttcggccaa     300
gggaccaagg tggaaatcaa a                                                321

<210> SEQ ID NO 107
<211> LENGTH: 214
<212> TYPE: PRT
<213> ORGANISM: Homo Sapiens

<400> SEQUENCE: 107

Asp Ile Gln Met Thr Gln Ser Pro Ser Thr Leu Ser Ala Ser Val Gly
```

-continued

```
1               5               10              15

Asp Arg Val Thr Ile Thr Cys Arg Ala Ser Gln Ser Ile Ser Ile Trp
            20              25              30

Leu Ala Trp Tyr Gln Gln Lys Pro Gly Lys Ala Pro Lys Leu Leu Ile
        35              40              45

Tyr Lys Ala Ser Ser Leu Glu Ser Gly Val Pro Ser Arg Phe Ser Gly
    50              55              60

Ser Gly Ser Gly Thr Glu Phe Thr Leu Thr Ile Ser Ser Leu Gln Pro
65              70              75              80

Asp Asp Phe Ala Thr Tyr Tyr Cys Gln Gln Tyr Asn Leu Tyr Pro Trp
            85              90              95

Thr Phe Gly Gln Gly Thr Lys Val Glu Ile Lys Arg Thr Val Ala Ala
        100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
        180             185             190

Ala Cys Glu Val Thr His Gln Gly Leu Ser Ser Pro Val Thr Lys Ser
        195             200             205

Phe Asn Arg Gly Glu Cys
    210
```

```
<210> SEQ ID NO 108
<211> LENGTH: 8
<212> TYPE: PRT
<213> ORGANISM: Homo Sapiens

<400> SEQUENCE: 108

Gly Phe Thr Phe Ser Asp Tyr Tyr
1               5

<210> SEQ ID NO 109
<211> LENGTH: 8
<212> TYPE: PRT
<213> ORGANISM: Homo Sapiens

<400> SEQUENCE: 109

Ile Ser Ile Ser Gly Ser Thr Ile
1               5

<210> SEQ ID NO 110
<211> LENGTH: 10
<212> TYPE: PRT
<213> ORGANISM: Homo Sapiens

<400> SEQUENCE: 110

Ala Arg Arg Ser Ser Gly Trp Tyr Asp Tyr
1               5               10

<210> SEQ ID NO 111
<211> LENGTH: 5
<212> TYPE: PRT
<213> ORGANISM: Homo Sapiens
```

-continued

```
<400> SEQUENCE: 111

Asp Tyr Tyr Met Ser
1               5

<210> SEQ ID NO 112
<211> LENGTH: 17
<212> TYPE: PRT
<213> ORGANISM: Homo Sapiens

<400> SEQUENCE: 112

Tyr Ile Ser Ile Ser Gly Ser Thr Ile Tyr Tyr Ala Asp Ser Val Lys
1               5                   10                  15

Gly

<210> SEQ ID NO 113
<211> LENGTH: 8
<212> TYPE: PRT
<213> ORGANISM: Homo Sapiens

<400> SEQUENCE: 113

Arg Ser Ser Gly Trp Tyr Asp Tyr
1               5

<210> SEQ ID NO 114
<211> LENGTH: 117
<212> TYPE: PRT
<213> ORGANISM: Homo Sapiens

<400> SEQUENCE: 114

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ile Ser Gly Ser Thr Ile Tyr Tyr Ala Asp Ser Val
    50                  55                  60

Lys Gly Arg Phe Thr Ile Ser Arg Asp Asn Ala Met Asp Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Ser Gly Trp Tyr Asp Tyr Trp Gly Gln Gly Thr Leu
            100                 105                 110

Val Thr Val Ser Ser
        115

<210> SEQ ID NO 115
<211> LENGTH: 351
<212> TYPE: DNA
<213> ORGANISM: Homo Sapiens

<400> SEQUENCE: 115
caggtgcaac tggtggagtc tggggggaggc ttggtcaagc ctggagggtc cctgagactc      60
tcctgtgcag cctctggatt caccttcagt gactactaca tgagttggat ccgccaggct     120
ccagggaagg ggctggagtg ggtttcatac attagtatta gtggtagtac catatactac     180
gcagactctg tgaagggccg attcaccatc tccagggaca cgccatgga ctcactgtat      240 ctgcaaatga acagcctgag agccgaggac acggccgtgt attactgtgc gagacggagc     300
```

-continued agtggctggt acgactactg gggccaggga accctggtca ccgtctcctc a                351

<210> SEQ ID NO 116
<211> LENGTH: 444
<212> TYPE: PRT
<213> ORGANISM: Homo Sapiens

<400> SEQUENCE: 116

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ile Ser Gly Ser Thr Ile Tyr Tyr Ala Asp Ser Val
    50                  55                  60

Lys Gly Arg Phe Thr Ile Ser Arg Asp Asn Ala Met Asp Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Ser Gly Trp Tyr Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
        210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

```
Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 117
<211> LENGTH: 7
<212> TYPE: PRT
<213> ORGANISM: Homo Sapiens

<400> SEQUENCE: 117

Gln Arg Val Val Tyr Arg Tyr
1               5

<210> SEQ ID NO 118
<211> LENGTH: 3
<212> TYPE: PRT
<213> ORGANISM: Homo Sapiens

<400> SEQUENCE: 118

Gly Ala Phe
1

<210> SEQ ID NO 119
<211> LENGTH: 9
<212> TYPE: PRT
<213> ORGANISM: Homo Sapiens

<400> SEQUENCE: 119

His Gln Tyr Gly Ser Ser Pro Pro Thr
1               5

<210> SEQ ID NO 120
<211> LENGTH: 12
<212> TYPE: PRT
<213> ORGANISM: Homo Sapiens

<400> SEQUENCE: 120

Trp Ala Ser Gln Arg Val Val Tyr Arg Tyr Leu Ala
1               5                   10

<210> SEQ ID NO 121
<211> LENGTH: 7
<212> TYPE: PRT
<213> ORGANISM: Homo Sapiens

<400> SEQUENCE: 121

Gly Ala Phe Asn Arg Ala Thr
1               5

<210> SEQ ID NO 122
<211> LENGTH: 9
<212> TYPE: PRT
<213> ORGANISM: Homo Sapiens

<400> SEQUENCE: 122
```

-continued

```
His Gln Tyr Gly Ser Ser Pro Pro Thr
1               5

<210> SEQ ID NO 123
<211> LENGTH: 108
<212> TYPE: PRT
<213> ORGANISM: Homo Sapiens

<400> SEQUENCE: 123

Glu Ile Val Leu Thr Gln Ser Pro Gly Thr Leu Ser Leu Ser Pro Gly
1               5                   10                  15

Glu Arg Ala Thr Leu Ser Cys Trp Ala Ser Gln Arg Val Val Tyr Arg
                20                  25                  30

Tyr Leu Ala Trp Tyr Gln Arg Lys Pro Gly Gln Ala Pro Arg Leu Leu
        35                  40                  45

Ile Tyr Gly Ala Phe Asn Arg Ala Thr Gly Ile Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys His Gln Tyr Gly Ser Ser Pro
                85                  90                  95

Pro Thr Phe Gly Gln Gly Thr Lys Val Glu Ile Lys
            100                 105

<210> SEQ ID NO 124
<211> LENGTH: 324
<212> TYPE: DNA
<213> ORGANISM: Homo Sapiens

<400> SEQUENCE: 124
gaaattgtgt tgacgcagtc tccaggcacc ctgtctttgt ctccagggga aagagccacc      60
ctctcttgtt gggccagtca gagggttgtt tacagatact tagcctggta ccagcggaaa     120
cctggccagg ctcccagact tctcatttat ggtgcattca cagggccac tggcatccca      180 gacaggttca gtggcagtgg gtctgggaca gacttcagtc tcactatcag tagactggag     240
cctgaggatt ttgcagttta ttactgtcac caatatggta gttcaccacc gacgttcggc     300
caagggacca aggtggaaat caaa                                            324

<210> SEQ ID NO 125
<211> LENGTH: 215
<212> TYPE: PRT
<213> ORGANISM: Homo Sapiens

<400> SEQUENCE: 125

Glu Ile Val Leu Thr Gln Ser Pro Gly Thr Leu Ser Leu Ser Pro Gly
1               5                   10                  15

Glu Arg Ala Thr Leu Ser Cys Trp Ala Ser Gln Arg Val Val Tyr Arg
                20                  25                  30

Tyr Leu Ala Trp Tyr Gln Arg Lys Pro Gly Gln Ala Pro Arg Leu Leu
        35                  40                  45

Ile Tyr Gly Ala Phe Asn Arg Ala Thr Gly Ile Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys His Gln Tyr Gly Ser Ser Pro
                85                  90                  95

Pro Thr Phe Gly Gln Gly Thr Lys Val Glu Ile Lys Arg Thr Val Ala
```

-continued

```
              100                 105                 110
Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
        210                 215

<210> SEQ ID NO 126
<211> LENGTH: 8
<212> TYPE: PRT
<213> ORGANISM: Homo Sapiens

<400> SEQUENCE: 126

Gly Phe Thr Phe Ile Thr Tyr Ala
1               5

<210> SEQ ID NO 127
<211> LENGTH: 8
<212> TYPE: PRT
<213> ORGANISM: Homo Sapiens

<400> SEQUENCE: 127

Ile Asn Val Gly Asn Gly Asn Arg
1               5

<210> SEQ ID NO 128
<211> LENGTH: 11
<212> TYPE: PRT
<213> ORGANISM: Homo Sapiens

<400> SEQUENCE: 128

Ala Arg Arg Pro Leu Trp Gly Pro Phe Asp Tyr
1               5                   10

<210> SEQ ID NO 129
<211> LENGTH: 5
<212> TYPE: PRT
<213> ORGANISM: Homo Sapiens

<400> SEQUENCE: 129

Thr Tyr Ala Phe His
1               5

<210> SEQ ID NO 130
<211> LENGTH: 17
<212> TYPE: PRT
<213> ORGANISM: Homo Sapiens

<400> SEQUENCE: 130

Trp Ile Asn Val Gly Asn Gly Asn Arg Glu Tyr Ser Gln Lys Phe Gln
1               5                   10                  15

Asp
```

```
<210> SEQ ID NO 131
<211> LENGTH: 9
<212> TYPE: PRT
<213> ORGANISM: Homo Sapiens

<400> SEQUENCE: 131

Arg Pro Leu Trp Gly Pro Phe Asp Tyr
1               5

<210> SEQ ID NO 132
<211> LENGTH: 118
<212> TYPE: PRT
<213> ORGANISM: Homo Sapiens

<400> SEQUENCE: 132

Gln Val Gln Leu Val Gln Ser Gly Ala Glu Val Lys Lys Pro Gly Ala
1               5                   10                  15

Ser Val Lys Val Ser Cys Lys Ala Thr Gly Phe Thr Phe Ile Thr Tyr
            20                  25                  30

Ala Phe His Trp Val Arg Gln Ala Pro Gly Gln Arg Phe Glu Trp Met
        35                  40                  45

Gly Trp Ile Asn Val Gly Asn Gly Asn Arg Glu Tyr Ser Gln Lys Phe
    50                  55                  60

Gln Asp Arg Val Thr Ile Thr Arg Asp Thr Ser Ala Thr Thr Val Tyr
65                  70                  75                  80

Met Glu Leu Asn Ser Leu Lys Ser Glu Asp Thr Ala Met Tyr Phe Cys
                85                  90                  95

Ala Arg Arg Pro Leu Trp Gly Pro Phe Asp Tyr Trp Gly Gln Gly Thr
            100                 105                 110

Leu Val Thr Val Ser Ser
        115

<210> SEQ ID NO 133
<211> LENGTH: 354
<212> TYPE: DNA
<213> ORGANISM: Homo Sapiens

<400> SEQUENCE: 133
caggtccaac ttgtgcagtc tgggggctgag gtgaagaagc ctgggggcctc agtgaaggtt      60 tcctgcaagg ctactggatt caccttcatt acctatgctt tccattgggt gcgccaggcc     120
cccggacaaa ggtttgagtg gatgggatgg atcaacgttg gcaatggtaa cagagaatat     180
tcacagaagt tccaggacag agtcaccatt accagggaca catccgcgac cacagtctac     240
atggaactga acagcctgaa atctgaagac acggctatgt atttctgtgc gagacgcccc     300
ctctggggtc cctttgacta ctggggccag ggaaccctgg tcaccgtctc ctca           354

<210> SEQ ID NO 134
<211> LENGTH: 445
<212> TYPE: PRT
<213> ORGANISM: Homo Sapiens

<400> SEQUENCE: 134

Gln Val Gln Leu Val Gln Ser Gly Ala Glu Val Lys Lys Pro Gly Ala
1               5                   10                  15

Ser Val Lys Val Ser Cys Lys Ala Thr Gly Phe Thr Phe Ile Thr Tyr
            20                  25                  30

Ala Phe His Trp Val Arg Gln Ala Pro Gly Gln Arg Phe Glu Trp Met
```

-continued

```
                35                    40                    45

Gly Trp Ile Asn Val Gly Asn Gly Asn Arg Glu Tyr Ser Gln Lys Phe
    50                    55                    60

Gln Asp Arg Val Thr Ile Thr Arg Asp Thr Ser Ala Thr Thr Val Tyr
65                    70                    75                    80

Met Glu Leu Asn Ser Leu Lys Ser Glu Asp Thr Ala Met Tyr Phe Cys
                85                    90                    95

Ala Arg Arg Pro Leu Trp Gly Pro Phe Asp Tyr Trp Gly Gln Gly Thr
            100                   105                   110

Leu Val Thr Val Ser Ser Ala Ser Thr Lys Gly Pro Ser Val Phe Pro
            115                   120                   125

Leu Ala Pro Cys Ser Arg Ser Thr Ser Glu Ser Thr Ala Ala Leu Gly
    130                   135                   140

Cys Leu Val Lys Asp Tyr Phe Pro Glu Pro Val Thr Val Ser Trp Asn
145                   150                   155                   160

Ser Gly Ala Leu Thr Ser Gly Val His Thr Phe Pro Ala Val Leu Gln
                165                   170                   175

Ser Ser Gly Leu Tyr Ser Leu Ser Ser Val Val Thr Val Pro Ser Ser
            180                   185                   190

Ser Leu Gly Thr Lys Thr Tyr Thr Cys Asn Val Asp His Lys Pro Ser
            195                   200                   205

Asn Thr Lys Val Asp Lys Arg Val Glu Ser Lys Tyr Gly Pro Pro Cys
    210                   215                   220

Pro Pro Cys Pro Ala Pro Glu Phe Glu Gly Gly Pro Ser Val Phe Leu
225                   230                   235                   240

Phe Pro Pro Lys Pro Lys Asp Thr Leu Met Ile Ser Arg Thr Pro Glu
                245                   250                   255

Val Thr Cys Val Val Val Asp Val Ser Gln Glu Asp Pro Glu Val Gln
            260                   265                   270

Phe Asn Trp Tyr Val Asp Gly Val Glu Val His Asn Ala Lys Thr Lys
            275                   280                   285

Pro Arg Glu Glu Gln Phe Asn Ser Thr Tyr Arg Val Val Ser Val Leu
    290                   295                   300

Thr Val Leu His Gln Asp Trp Leu Asn Gly Lys Glu Tyr Lys Cys Lys
305                   310                   315                   320

Val Ser Asn Lys Gly Leu Pro Ser Ser Ile Glu Lys Thr Ile Ser Lys
                325                   330                   335

Ala Lys Gly Gln Pro Arg Glu Pro Gln Val Tyr Thr Leu Pro Pro Ser
            340                   345                   350

Gln Glu Glu Met Thr Lys Asn Gln Val Ser Leu Thr Cys Leu Val Lys
            355                   360                   365

Gly Phe Tyr Pro Ser Asp Ile Ala Val Glu Trp Glu Ser Asn Gly Gln
    370                   375                   380

Pro Glu Asn Asn Tyr Lys Thr Thr Pro Pro Val Leu Asp Ser Asp Gly
385                   390                   395                   400

Ser Phe Phe Leu Tyr Ser Arg Leu Thr Val Asp Lys Ser Arg Trp Gln
                405                   410                   415

Glu Gly Asn Val Phe Ser Cys Ser Val Met His Glu Ala Leu His Asn
            420                   425                   430

His Tyr Thr Gln Lys Ser Leu Ser Leu Ser Leu Gly Lys
        435                   440                   445
```

<210> SEQ ID NO 135

```
<211> LENGTH: 7
<212> TYPE: PRT
<213> ORGANISM: Homo Sapiens

<400> SEQUENCE: 135

Gln Ile Phe Ser Asn Thr Phe
1               5

<210> SEQ ID NO 136
<211> LENGTH: 3
<212> TYPE: PRT
<213> ORGANISM: Homo Sapiens

<400> SEQUENCE: 136

Gly Ala Ser
1

<210> SEQ ID NO 137
<211> LENGTH: 9
<212> TYPE: PRT
<213> ORGANISM: Homo Sapiens

<400> SEQUENCE: 137

Gln His Tyr Gly Gly Ser Pro Trp Thr
1               5

<210> SEQ ID NO 138
<211> LENGTH: 12
<212> TYPE: PRT
<213> ORGANISM: Homo Sapiens

<400> SEQUENCE: 138

Arg Ala Ser Gln Ile Phe Ser Asn Thr Phe Leu Ala
1               5                   10

<210> SEQ ID NO 139
<211> LENGTH: 7
<212> TYPE: PRT
<213> ORGANISM: Homo Sapiens

<400> SEQUENCE: 139

Gly Ala Ser Lys Arg Ala Thr
1               5

<210> SEQ ID NO 140
<211> LENGTH: 9
<212> TYPE: PRT
<213> ORGANISM: Homo Sapiens

<400> SEQUENCE: 140

Gln His Tyr Gly Gly Ser Pro Trp Thr
1               5

<210> SEQ ID NO 141
<211> LENGTH: 108
<212> TYPE: PRT
<213> ORGANISM: Homo Sapiens

<400> SEQUENCE: 141

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ile Phe Ser Asn Thr
            20                  25                  30

Phe Leu Ala Trp Tyr Gln Gln Lys Pro Gly Gln Ala Pro Arg Leu Leu
```

-continued

```
          35               40               45
Val Tyr Gly Ala Ser Lys Arg Ala Thr Ala Ile Pro Asp Arg Phe Ser
    50               55               60

Gly Ser Gly Ser Gly Thr Asp Phe Ile Leu Thr Ile Asn Arg Leu Glu
65               70               75               80

Pro Glu Asp Phe Ala Val Tyr Tyr Cys Gln His Tyr Gly Gly Ser Pro
                85               90               95

Trp Thr Phe Gly Arg Gly Thr Lys Val Glu Ile Lys
            100              105
```

<210> SEQ ID NO 142
<211> LENGTH: 324
<212> TYPE: DNA
<213> ORGANISM: Homo Sapiens

<400> SEQUENCE: 142

```
gaaattgttt tgacacagtc tccaggcacc ctgtctttgt ctccagggga aagagccacc      60
ctctcctgca gggccagtca gattttagc aacaccttct tagcctggta ccagcagaaa      120
cctggccagg ctcccaggct cctcgtgtat ggtgcatcca agagggccac tgccatccca      180
gacaggttta gtggcagtgg gtctgggaca gacttcattc tcaccatcaa cagactggag      240
cctgaagatt ttgcagtata ttactgtcaa cactatggtg ggtcaccgtg gacgttcggc      300
cgagggacca aggtggaaat caaa                                            324
```

<210> SEQ ID NO 143
<211> LENGTH: 215
<212> TYPE: PRT
<213> ORGANISM: Homo Sapiens

<400> SEQUENCE: 143

```
Glu Ile Val Leu Thr Gln Ser Pro Gly Thr Leu Ser Leu Ser Pro Gly
1               5               10               15

Glu Arg Ala Thr Leu Ser Cys Arg Ala Ser Gln Ile Phe Ser Asn Thr
            20               25               30

Phe Leu Ala Trp Tyr Gln Gln Lys Pro Gly Gln Ala Pro Arg Leu Leu
        35               40               45

Val Tyr Gly Ala Ser Lys Arg Ala Thr Ala Ile Pro Asp Arg Phe Ser
    50               55               60

Gly Ser Gly Ser Gly Thr Asp Phe Ile Leu Thr Ile Asn Arg Leu Glu
65               70               75               80

Pro Glu Asp Phe Ala Val Tyr Tyr Cys Gln His Tyr Gly Gly Ser Pro
                85               90               95

Trp Thr Phe Gly Arg Gly Thr Lys Val Glu Ile Lys Arg Thr Val Ala
            100              105              110

Ala Pro Ser Val Phe Ile Phe Pro Pro Ser Asp Glu Gln Leu Lys Ser
        115              120              125

Gly Thr Ala Ser Val Val Cys Leu Leu Asn Asn Phe Tyr Pro Arg Glu
    130              135              140

Ala Lys Val Gln Trp Lys Val Asp Asn Ala Leu Gln Ser Gly Asn Ser
145              150              155              160

Gln Glu Ser Val Thr Glu Gln Asp Ser Lys Asp Ser Thr Tyr Ser Leu
                165              170              175

Ser Ser Thr Leu Thr Leu Ser Lys Ala Asp Tyr Glu Lys His Lys Val
            180              185              190

Tyr Ala Cys Glu Val Thr His Gln Gly Leu Ser Ser Pro Val Thr Lys
```

-continued

```
              195                 200                 205

Ser Phe Asn Arg Gly Glu Cys
    210                 215

<210> SEQ ID NO 144
<211> LENGTH: 8
<212> TYPE: PRT
<213> ORGANISM: Homo Sapiens

<400> SEQUENCE: 144

Gly Tyr Thr Phe Thr Ser His Ala
1               5

<210> SEQ ID NO 145
<211> LENGTH: 8
<212> TYPE: PRT
<213> ORGANISM: Homo Sapiens

<400> SEQUENCE: 145

Ile His Ala Gly Asn Gly Asn Ser
1               5

<210> SEQ ID NO 146
<211> LENGTH: 11
<212> TYPE: PRT
<213> ORGANISM: Homo Sapiens

<400> SEQUENCE: 146

Ala Arg Arg Ala Ile Met Ala Pro Phe Asp Leu
1               5                   10

<210> SEQ ID NO 147
<211> LENGTH: 5
<212> TYPE: PRT
<213> ORGANISM: Homo Sapiens

<400> SEQUENCE: 147

Ser His Ala Ile His
1               5

<210> SEQ ID NO 148
<211> LENGTH: 17
<212> TYPE: PRT
<213> ORGANISM: Homo Sapiens

<400> SEQUENCE: 148

Trp Ile His Ala Gly Asn Gly Asn Ser Lys Gln Ser Gln Asn Phe Gln
1               5                   10                  15

Asp

<210> SEQ ID NO 149
<211> LENGTH: 9
<212> TYPE: PRT
<213> ORGANISM: Homo Sapiens

<400> SEQUENCE: 149

Arg Ala Ile Met Ala Pro Phe Asp Leu
1               5

<210> SEQ ID NO 150
<211> LENGTH: 118
<212> TYPE: PRT
<213> ORGANISM: Homo Sapiens
```

-continued

```
<400> SEQUENCE: 150

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Ala Ile His Trp Val Arg Gln Ala Pro Gly Gln Arg Leu Glu Trp Met
        35                  40                  45

Gly Trp Ile His Ala Gly Asn Gly Asn Ser Lys Gln Ser Gln Asn Phe
    50                  55                  60

Gln Asp Arg Val Thr Ile Thr Arg Asp Thr Ser Ala Ser Ala Ala Tyr
65                  70                  75                  80

Met Glu Leu Ser Ser Leu Arg Ser Glu Asp Thr Ala Val Tyr Tyr Cys
                85                  90                  95

Ala Arg Arg Ala Ile Met Ala Pro Phe Asp Leu Trp Gly Gln Gly Thr
            100                 105                 110

Leu Val Thr Val Ser Ser
            115

<210> SEQ ID NO 151
<211> LENGTH: 354
<212> TYPE: DNA
<213> ORGANISM: Homo Sapiens

<400> SEQUENCE: 151
caggtccagc ttgtgcagtc tggggctgag gtgaagaagc ctggggcctc agtgaaggtt      60
tcctgcaagg cttctggata caccttcact agccatgcta tacattgggt gcgccaggcc     120
cccggacaac ggcttgagtg gatgggatgg atccacgctg gcaatggtaa ctcaaaacag     180
tcacagaact ccaggacag agtcaccatt accaggaca catccgcgag cgcagcctac       240
atggagctga gcagcctgag atctgaagac acggctgtat attactgtgc gagacgggcc     300
ataatggccc cgtttgacct ctggggccag ggaaccctgg tcaccgtctc ctca           354

<210> SEQ ID NO 152
<211> LENGTH: 445
<212> TYPE: PRT
<213> ORGANISM: Homo Sapiens

<400> SEQUENCE: 152

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Ala Ile His Trp Val Arg Gln Ala Pro Gly Gln Arg Leu Glu Trp Met
        35                  40                  45

Gly Trp Ile His Ala Gly Asn Gly Asn Ser Lys Gln Ser Gln Asn Phe
    50                  55                  60

Gln Asp Arg Val Thr Ile Thr Arg Asp Thr Ser Ala Ser Ala Ala Tyr
65                  70                  75                  80

Met Glu Leu Ser Ser Leu Arg Ser Glu Asp Thr Ala Val Tyr Tyr Cys
                85                  90                  95

Ala Arg Arg Ala Ile Met Ala Pro Phe Asp Leu Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
```

-continued

```
            130              135              140

Cys Leu Val Lys Asp Tyr Phe Pro Glu Pro Val Thr Val Ser Trp Asn
145              150              155              160

Ser Gly Ala Leu Thr Ser Gly Val His Thr Phe Pro Ala Val Leu Gln
                165              170              175

Ser Ser Gly Leu Tyr Ser Leu Ser Ser Val Val Thr Val Pro Ser Ser
                180              185              190

Ser Leu Gly Thr Lys Thr Tyr Thr Cys Asn Val Asp His Lys Pro Ser
                195              200              205

Asn Thr Lys Val Asp Lys Arg Val Glu Ser Lys Tyr Gly Pro Pro Cys
        210              215              220

Pro Pro Cys Pro Ala Pro Glu Phe Glu Gly Gly Pro Ser Val Phe Leu
225              230              235              240

Phe Pro Pro Lys Pro Lys Asp Thr Leu Met Ile Ser Arg Thr Pro Glu
                245              250              255

Val Thr Cys Val Val Val Asp Val Ser Gln Glu Asp Pro Glu Val Gln
                260              265              270

Phe Asn Trp Tyr Val Asp Gly Val Glu Val His Asn Ala Lys Thr Lys
        275              280              285

Pro Arg Glu Glu Gln Phe Asn Ser Thr Tyr Arg Val Val Ser Val Leu
        290              295              300

Thr Val Leu His Gln Asp Trp Leu Asn Gly Lys Glu Tyr Lys Cys Lys
305              310              315              320

Val Ser Asn Lys Gly Leu Pro Ser Ser Ile Glu Lys Thr Ile Ser Lys
                325              330              335

Ala Lys Gly Gln Pro Arg Glu Pro Gln Val Tyr Thr Leu Pro Pro Ser
                340              345              350

Gln Glu Glu Met Thr Lys Asn Gln Val Ser Leu Thr Cys Leu Val Lys
                355              360              365

Gly Phe Tyr Pro Ser Asp Ile Ala Val Glu Trp Glu Ser Asn Gly Gln
        370              375              380

Pro Glu Asn Asn Tyr Lys Thr Thr Pro Pro Val Leu Asp Ser Asp Gly
385              390              395              400

Ser Phe Phe Leu Tyr Ser Arg Leu Thr Val Asp Lys Ser Arg Trp Gln
                405              410              415

Glu Gly Asn Val Phe Ser Cys Ser Val Met His Glu Ala Leu His Asn
                420              425              430

His Tyr Thr Gln Lys Ser Leu Ser Leu Ser Leu Gly Lys
        435              440              445
```

```
<210> SEQ ID NO 153
<211> LENGTH: 6
<212> TYPE: PRT
<213> ORGANISM: Homo Sapiens

<400> SEQUENCE: 153

Gln Ser Ile Asn Asn Trp
1               5

<210> SEQ ID NO 154
<211> LENGTH: 3
<212> TYPE: PRT
<213> ORGANISM: Homo Sapiens

<400> SEQUENCE: 154

Lys Ala Ser
```

-continued

1

<210> SEQ ID NO 155
<211> LENGTH: 8
<212> TYPE: PRT
<213> ORGANISM: Homo Sapiens

<400> SEQUENCE: 155

Gln Gln Tyr Tyr Ser Ser Trp Thr
1               5

<210> SEQ ID NO 156
<211> LENGTH: 11
<212> TYPE: PRT
<213> ORGANISM: Homo Sapiens

<400> SEQUENCE: 156

Arg Ala Ser Gln Ser Ile Asn Asn Trp Leu Ala
1               5                   10

<210> SEQ ID NO 157
<211> LENGTH: 7
<212> TYPE: PRT
<213> ORGANISM: Homo Sapiens

<400> SEQUENCE: 157

Lys Ala Ser Ser Leu Glu Ser
1               5

<210> SEQ ID NO 158
<211> LENGTH: 8
<212> TYPE: PRT
<213> ORGANISM: Homo Sapiens

<400> SEQUENCE: 158

Gln Gln Tyr Tyr Ser Ser Trp Thr
1               5

<210> SEQ ID NO 159
<211> LENGTH: 106
<212> TYPE: PRT
<213> ORGANISM: Homo Sapiens

<400> SEQUENCE: 159

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Asn Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Gln Tyr Tyr Ser Ser Trp Thr
                85                  90                  95

Phe Gly Gln Gly Thr Lys Val Glu Ile Lys
            100                 105

<210> SEQ ID NO 160
<211> LENGTH: 318
<212> TYPE: DNA

-continued

<213> ORGANISM: Homo Sapiens

<400> SEQUENCE: 160
gacatccaga tgacccagtc tccttccacc ctgtctgcat ctgtaggaga cagagtcacc          60
atcacttgcc gggccagtca gagtattaat aactggttgg cctggtatca gcagaaacca         120
gggaaagccc ctaacctcct gatctataag gcgtctagtt tagaaagtgg ggtcccatca         180
aggttcagcg gcagtggatc tgggacagaa ttcactctca ccatcaacag cctgcagcct         240
gatgactttg caacttatta ctgccaacag tattatagtt cttggacgtt cggccaaggg         300
accaaggtgg aaatcaaa                                                        318

<210> SEQ ID NO 161
<211> LENGTH: 213
<212> TYPE: PRT
<213> ORGANISM: Homo Sapiens

<400> SEQUENCE: 161

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Asn Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Gln Tyr Tyr Ser Ser Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 162
<211> LENGTH: 8
<212> TYPE: PRT
<213> ORGANISM: Homo Sapiens

<400> SEQUENCE: 162

Gly Tyr Thr Phe Thr Ser Tyr Ala
1               5

<210> SEQ ID NO 163

-continued

```
<211> LENGTH: 8
<212> TYPE: PRT
<213> ORGANISM: Homo Sapiens

<400> SEQUENCE: 163

Ile Asn Ala Gly Asn Gly Asn Thr
1               5

<210> SEQ ID NO 164
<211> LENGTH: 11
<212> TYPE: PRT
<213> ORGANISM: Homo Sapiens

<400> SEQUENCE: 164

Ala Arg Arg Gly Phe Gly Glu Pro Phe Asp Tyr
1               5                   10

<210> SEQ ID NO 165
<211> LENGTH: 5
<212> TYPE: PRT
<213> ORGANISM: Homo Sapiens

<400> SEQUENCE: 165

Ser Tyr Ala Val His
1               5

<210> SEQ ID NO 166
<211> LENGTH: 17
<212> TYPE: PRT
<213> ORGANISM: Homo Sapiens

<400> SEQUENCE: 166

Trp Ile Asn Ala Gly Asn Gly Asn Thr Lys Phe Ser Gln Lys Phe Gln
1               5                   10                  15

Gly

<210> SEQ ID NO 167
<211> LENGTH: 9
<212> TYPE: PRT
<213> ORGANISM: Homo Sapiens

<400> SEQUENCE: 167

Arg Gly Phe Gly Glu Pro Phe Asp Tyr
1               5

<210> SEQ ID NO 168
<211> LENGTH: 118
<212> TYPE: PRT
<213> ORGANISM: Homo Sapiens

<400> SEQUENCE: 168

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Val His Trp Val Arg Gln Ala Pro Gly Gln Arg Leu Glu Trp Met
        35                  40                  45

Gly Trp Ile Asn Ala Gly Asn Gly Asn Thr Lys Phe Ser Gln Lys Phe
    50                  55                  60

Gln Gly Arg Ile Thr Ile Thr Arg Asp Thr Ser Ala Ser Thr Thr Tyr
65                  70                  75                  80

Met Glu Leu Asn Ser Leu Arg Ser Glu Asp Thr Ala Val Tyr Tyr Cys
```

-continued

```
                 85                  90                  95
Ala Arg Arg Gly Phe Gly Glu Pro Phe Asp Tyr Trp Gly Gln Gly Thr
                100                 105                 110

Leu Val Thr Val Ser Ser
        115

<210> SEQ ID NO 169
<211> LENGTH: 354
<212> TYPE: DNA
<213> ORGANISM: Homo Sapiens

<400> SEQUENCE: 169
caggtccagc ttgtgcagtc tgggggctgag gtgaagaagc ctggggcctc agtgaaggtt     60
tcctgcaagg cttctggata caccttcact agctatgctg tccattgggt gcgccaggcc    120
cccggacaaa ggcttgagtg gatgggatgg atcaacgctg gcaatggtaa cacaaaattt    180
tcacagaagt tccagggcag aatcaccatt accaggggaca catccgcgag cacaacctac    240
atggagttga atagtctgag atctgaagac acggctgtgt attattgtgc gagaaggggg    300
ttcggggagc catttgacta ctggggccag ggaaccctgg tcaccgtctc ctca         354

<210> SEQ ID NO 170
<211> LENGTH: 445
<212> TYPE: PRT
<213> ORGANISM: Homo Sapiens

<400> SEQUENCE: 170

Gln Val Gln Leu Val Gln Ser Gly Ala Glu Val Lys Lys Pro Gly Ala
1                5                  10                  15

Ser Val Lys Val Ser Cys Lys Ala Ser Gly Tyr Thr Phe Thr Ser Tyr
                20                  25                  30

Ala Val His Trp Val Arg Gln Ala Pro Gly Gln Arg Leu Glu Trp Met
        35                  40                  45

Gly Trp Ile Asn Ala Gly Asn Gly Asn Thr Lys Phe Ser Gln Lys Phe
    50                  55                  60

Gln Gly Arg Ile Thr Ile Thr Arg Asp Thr Ser Ala Ser Thr Thr Tyr
65                  70                  75                  80

Met Glu Leu Asn Ser Leu Arg Ser Glu Asp Thr Ala Val Tyr Tyr Cys
                85                  90                  95

Ala Arg Arg Gly Phe Gly Glu Pro Phe Asp Tyr Trp Gly Gln Gly Thr
                100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Lys Thr Tyr Thr Cys Asn Val Asp His Lys Pro Ser
                195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Glu Gly Gly Pro Ser Val Phe Leu
```

-continued

```
225              230              235              240

Phe Pro Pro Lys Pro Lys Asp Thr Leu Met Ile Ser Arg Thr Pro Glu
             245              250              255

Val Thr Cys Val Val Val Asp Val Ser Gln Glu Asp Pro Glu Val Gln
             260              265              270

Phe Asn Trp Tyr Val Asp Gly Val Glu Val His Asn Ala Lys Thr Lys
             275              280              285

Pro Arg Glu Glu Gln Phe Asn Ser Thr Tyr Arg Val Val Ser Val Leu
    290              295              300

Thr Val Leu His Gln Asp Trp Leu Asn Gly Lys Glu Tyr Lys Cys Lys
305              310              315              320

Val Ser Asn Lys Gly Leu Pro Ser Ser Ile Glu Lys Thr Ile Ser Lys
             325              330              335

Ala Lys Gly Gln Pro Arg Glu Pro Gln Val Tyr Thr Leu Pro Pro Ser
             340              345              350

Gln Glu Glu Met Thr Lys Asn Gln Val Ser Leu Thr Cys Leu Val Lys
             355              360              365

Gly Phe Tyr Pro Ser Asp Ile Ala Val Glu Trp Glu Ser Asn Gly Gln
             370              375              380

Pro Glu Asn Asn Tyr Lys Thr Thr Pro Pro Val Leu Asp Ser Asp Gly
385              390              395              400

Ser Phe Phe Leu Tyr Ser Arg Leu Thr Val Asp Lys Ser Arg Trp Gln
             405              410              415

Glu Gly Asn Val Phe Ser Cys Ser Val Met His Glu Ala Leu His Asn
             420              425              430

His Tyr Thr Gln Lys Ser Leu Ser Leu Ser Leu Gly Lys
             435              440              445

<210> SEQ ID NO 171
<211> LENGTH: 6
<212> TYPE: PRT
<213> ORGANISM: Homo Sapiens

<400> SEQUENCE: 171

Gln Ser Ile Ser Asn Asn
1               5

<210> SEQ ID NO 172
<211> LENGTH: 3
<212> TYPE: PRT
<213> ORGANISM: Homo Sapiens

<400> SEQUENCE: 172

Gly Thr Ser
1

<210> SEQ ID NO 173
<211> LENGTH: 9
<212> TYPE: PRT
<213> ORGANISM: Homo Sapiens

<400> SEQUENCE: 173

Gln Gln Tyr Asn Ile Trp Pro Phe Thr
1               5

<210> SEQ ID NO 174
<211> LENGTH: 11
<212> TYPE: PRT
<213> ORGANISM: Homo Sapiens
```

-continued

<400> SEQUENCE: 174

Arg Ala Ser Gln Ser Ile Ser Asn Asn Leu Ala
1               5                   10

<210> SEQ ID NO 175
<211> LENGTH: 7
<212> TYPE: PRT
<213> ORGANISM: Homo Sapiens

<400> SEQUENCE: 175

Gly Thr Ser Thr Arg Ala Thr
1               5

<210> SEQ ID NO 176
<211> LENGTH: 9
<212> TYPE: PRT
<213> ORGANISM: Homo Sapiens

<400> SEQUENCE: 176

Gln Gln Tyr Asn Ile Trp Pro Phe Thr
1               5

<210> SEQ ID NO 177
<211> LENGTH: 107
<212> TYPE: PRT
<213> ORGANISM: Homo Sapiens

<400> SEQUENCE: 177

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
                20                  25                  30

Leu Ala Trp Tyr Gln Gln Lys Pro Gly Gln Ala Pro Arg Leu Leu Ile
            35                  40                  45

Tyr Gly Thr Ser Thr Arg Ala Thr Gly Ile Pro Ala Arg Phe Ser Gly
        50                  55                  60

Ser Gly Ser Gly Thr Glu Phe Thr Leu Thr Ile Ser Thr Leu Gln Ser
65                  70                  75                  80

Glu Asp Phe Ala Val Tyr Tyr Cys Gln Gln Tyr Asn Ile Trp Pro Phe
                85                  90                  95

Thr Phe Gly Pro Gly Thr Lys Val Asp Ile Lys
            100                 105

<210> SEQ ID NO 178
<211> LENGTH: 321
<212> TYPE: DNA
<213> ORGANISM: Homo Sapiens

<400> SEQUENCE: 178
gaaatagtga tgacgcagtc tccagccacc ctgtctgtgt ctccagggga aagagccacc      60
ctctcctgca gggccagtca gagtattagt aacaacttag cctggtacca acagaaacct     120
ggccaggctc ccaggctcct catctatggt acatccacca gggccactgg tatcccagcc     180
aggttcagtg gcagtgggtc tgggacagag ttcactctca ccatcagcac cctgcagtct     240
gaagattttg cagtttatta ctgtcagcag tataatatct ggcctttcac tttcggccct     300
gggaccaaag tggatatcaa a                                               321

<210> SEQ ID NO 179

```
<211> LENGTH: 214
<212> TYPE: PRT
<213> ORGANISM: Homo Sapiens

<400> SEQUENCE: 179

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu Ala Trp Tyr Gln Gln Lys Pro Gly Gln Ala Pro Arg Leu Leu Ile
        35                  40                  45

Tyr Gly Thr Ser Thr Arg Ala Thr Gly Ile Pro Ala Arg Phe Ser Gly
    50                  55                  60

Ser Gly Ser Gly Thr Glu Phe Thr Leu Thr Ile Ser Thr Leu Gln Ser
65                  70                  75                  80

Glu Asp Phe Ala Val Tyr Tyr Cys Gln Gln Tyr Asn Ile Trp Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 180
<211> LENGTH: 8
<212> TYPE: PRT
<213> ORGANISM: Homo Sapiens

<400> SEQUENCE: 180

Gly Tyr Thr Phe Thr Ser Tyr Ala
1               5

<210> SEQ ID NO 181
<211> LENGTH: 8
<212> TYPE: PRT
<213> ORGANISM: Homo Sapiens

<400> SEQUENCE: 181

Ile Asn Pro Gly Asn Gly Asn Thr
1               5

<210> SEQ ID NO 182
<211> LENGTH: 11
<212> TYPE: PRT
<213> ORGANISM: Homo Sapiens

<400> SEQUENCE: 182

Ala Arg Arg Gly Phe Gly Glu Pro Phe Asp Tyr
```

-continued

```
1               5                    10
```

<210> SEQ ID NO 183
<211> LENGTH: 5
<212> TYPE: PRT
<213> ORGANISM: Homo Sapiens

<400> SEQUENCE: 183

Ser Tyr Ala Ile His
1               5

<210> SEQ ID NO 184
<211> LENGTH: 17
<212> TYPE: PRT
<213> ORGANISM: Homo Sapiens

<400> SEQUENCE: 184

Trp Ile Asn Pro Gly Asn Gly Asn Thr Lys Phe Ser Gln Lys Phe Gln
1               5                    10                   15

Gly

<210> SEQ ID NO 185
<211> LENGTH: 9
<212> TYPE: PRT
<213> ORGANISM: Homo Sapiens

<400> SEQUENCE: 185

Arg Gly Phe Gly Glu Pro Phe Asp Tyr
1               5

<210> SEQ ID NO 186
<211> LENGTH: 118
<212> TYPE: PRT
<213> ORGANISM: Homo Sapiens

<400> SEQUENCE: 186

Gln Val Gln Leu Val Gln Ser Gly Ala Glu Val Lys Lys Pro Gly Ala
1               5                    10                   15

Ser Val Lys Val Ser Cys Lys Ala Ser Gly Tyr Thr Phe Thr Ser Tyr
            20                   25                   30

Ala Ile His Trp Val Arg Gln Ala Pro Gly Gln Arg Leu Glu Trp Met
        35                   40                   45

Gly Trp Ile Asn Pro Gly Asn Gly Asn Thr Lys Phe Ser Gln Lys Phe
    50                   55                   60

Gln Gly Arg Ile Thr Ile Thr Arg Asp Thr Ser Ala Ser Thr Thr Tyr
65                   70                   75                   80

Met Glu Leu Asn Ser Leu Arg Ser Glu Asp Thr Ala Val Tyr Tyr Cys
                85                   90                   95

Ala Arg Arg Gly Phe Gly Glu Pro Phe Asp Tyr Trp Gly Gln Gly Thr
            100                  105                  110

Leu Val Thr Val Ser Ser
        115

<210> SEQ ID NO 187
<211> LENGTH: 354
<212> TYPE: DNA
<213> ORGANISM: Homo Sapiens

<400> SEQUENCE: 187
caggtccagc ttgtgcagtc tgggggctgag gtgaagaagc ctgggggcctc agtgaaggtt      60

-continued

```
tcctgcaagg cttctggata caccttcact agctatgcta tccattgggt gcgccaggcc      120
cccggacaaa ggcttgagtg gatgggatgg atcaaccctg gcaatggtaa cacaaaattt      180
tcacagaagt tccagggcag aatcaccatt accagggaca catccgcgag cacaacctac      240
atggagctga cagcctgag atctgaagac acggctgtgt attactgtgc gagaaggggg      300
ttcggggagc catttgacta ctggggccag ggaaccctgg tcaccgtctc ctca           354
```

```
<210> SEQ ID NO 188
<211> LENGTH: 445
<212> TYPE: PRT
<213> ORGANISM: Homo Sapiens

<400> SEQUENCE: 188

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Ile His Trp Val Arg Gln Ala Pro Gly Gln Arg Leu Glu Trp Met
            35                  40                  45

Gly Trp Ile Asn Pro Gly Asn Gly Asn Thr Lys Phe Ser Gln Lys Phe
        50                  55                  60

Gln Gly Arg Ile Thr Ile Thr Arg Asp Thr Ser Ala Ser Thr Thr Tyr
65                  70                  75                  80

Met Glu Leu Asn Ser Leu Arg Ser Glu Asp Thr Ala Val Tyr Tyr Cys
                85                  90                  95

Ala Arg Arg Gly Phe Gly Glu Pro Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
```

-continued

```
                325                     330                     335

Ala Lys Gly Gln Pro Arg Glu Pro Gln Val Tyr Thr Leu Pro Pro Ser
        340                     345                     350

Gln Glu Glu Met Thr Lys Asn Gln Val Ser Leu Thr Cys Leu Val Lys
        355                     360                     365

Gly Phe Tyr Pro Ser Asp Ile Ala Val Glu Trp Glu Ser Asn Gly Gln
    370                     375                     380

Pro Glu Asn Asn Tyr Lys Thr Thr Pro Pro Val Leu Asp Ser Asp Gly
385                     390                     395                     400

Ser Phe Phe Leu Tyr Ser Arg Leu Thr Val Asp Lys Ser Arg Trp Gln
                405                     410                     415

Glu Gly Asn Val Phe Ser Cys Ser Val Met His Glu Ala Leu His Asn
                420                     425                     430

His Tyr Thr Gln Lys Ser Leu Ser Leu Ser Leu Gly Lys
                435                     440                     445

<210> SEQ ID NO 189
<211> LENGTH: 6
<212> TYPE: PRT
<213> ORGANISM: Homo Sapiens

<400> SEQUENCE: 189

Gln Ser Ile Ser Ser Asn
1               5

<210> SEQ ID NO 190
<211> LENGTH: 3
<212> TYPE: PRT
<213> ORGANISM: Homo Sapiens

<400> SEQUENCE: 190

Gly Thr Ser
1

<210> SEQ ID NO 191
<211> LENGTH: 9
<212> TYPE: PRT
<213> ORGANISM: Homo Sapiens

<400> SEQUENCE: 191

Gln Gln Tyr Asn Ile Trp Pro Phe Thr
1               5

<210> SEQ ID NO 192
<211> LENGTH: 11
<212> TYPE: PRT
<213> ORGANISM: Homo Sapiens

<400> SEQUENCE: 192

Arg Ala Ser Gln Ser Ile Ser Ser Asn Leu Ala
1               5                   10

<210> SEQ ID NO 193
<211> LENGTH: 7
<212> TYPE: PRT
<213> ORGANISM: Homo Sapiens

<400> SEQUENCE: 193

Gly Thr Ser Thr Arg Ala Thr
1               5
```

<210> SEQ ID NO 194
<211> LENGTH: 9
<212> TYPE: PRT
<213> ORGANISM: Homo Sapiens

<400> SEQUENCE: 194

Gln Gln Tyr Asn Ile Trp Pro Phe Thr
1               5

<210> SEQ ID NO 195
<211> LENGTH: 107
<212> TYPE: PRT
<213> ORGANISM: Homo Sapiens

<400> SEQUENCE: 195

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Asn Pro Gly Gln Ala Pro Arg Leu Leu Ile
        35                  40                  45

Tyr Gly Thr Ser Thr Arg Ala Thr Gly Ile Pro Ala Arg Phe Ser Gly
    50                  55                  60

Ser Gly Ser Gly Thr Glu Phe Thr Leu Thr Ile Ser Thr Leu Gln Ser
65                  70                  75                  80

Glu Asp Phe Ala Val Tyr Tyr Cys Gln Gln Tyr Asn Ile Trp Pro Phe
                85                  90                  95

Thr Phe Gly Pro Gly Thr Lys Val Asp Ile Lys
            100                 105

<210> SEQ ID NO 196
<211> LENGTH: 322
<212> TYPE: DNA
<213> ORGANISM: Homo Sapiens

<400> SEQUENCE: 196
gaaatagtga tgacgcagtc tccagccacc ctgtctgtgt ctccagggga aagagccacc      60
ctctcctgca gggccagtca gagtattagc agcaacttag cctggtacca acagaaccct     120
ggccaggctc ccaggctcct catctatggt acatccacca gggccactgg tatcccagcc     180
aggttcagtg gcagtgggtc tgggacagag ttcactctca ccatcagcac cctgcagtct     240
gaagattttg cagtttatta ctgtcagcag tataatatct ggcctttcac tttcggccct     300
gggaccaaag tggatatcaa ac                                              322

<210> SEQ ID NO 197
<211> LENGTH: 214
<212> TYPE: PRT
<213> ORGANISM: Homo Sapiens

<400> SEQUENCE: 197

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Asn Pro Gly Gln Ala Pro Arg Leu Leu Ile
        35                  40                  45

Tyr Gly Thr Ser Thr Arg Ala Thr Gly Ile Pro Ala Arg Phe Ser Gly
    50                  55                  60

-continued

```
Ser Gly Ser Gly Thr Glu Phe Thr Leu Thr Ile Ser Thr Leu Gln Ser
65                  70                  75                  80

Glu Asp Phe Ala Val Tyr Tyr Cys Gln Gln Tyr Asn Ile Trp Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 198
<211> LENGTH: 8
<212> TYPE: PRT
<213> ORGANISM: Homo Sapiens

<400> SEQUENCE: 198

Gly Tyr Thr Phe Thr Ser Tyr Ala
1               5

<210> SEQ ID NO 199
<211> LENGTH: 8
<212> TYPE: PRT
<213> ORGANISM: Homo Sapiens

<400> SEQUENCE: 199

Ile Asn Ala Gly Asn Gly Tyr Thr
1               5

<210> SEQ ID NO 200
<211> LENGTH: 13
<212> TYPE: PRT
<213> ORGANISM: Homo Sapiens

<400> SEQUENCE: 200

Ala Arg Asp Arg Ile Thr Ile Ile Arg Pro Phe Asp Tyr
1               5                   10

<210> SEQ ID NO 201
<211> LENGTH: 5
<212> TYPE: PRT
<213> ORGANISM: Homo Sapiens

<400> SEQUENCE: 201

Ser Tyr Ala Met His
1               5

<210> SEQ ID NO 202
<211> LENGTH: 17
<212> TYPE: PRT
<213> ORGANISM: Homo Sapiens
```

-continued

<400> SEQUENCE: 202

```
Trp Ile Asn Ala Gly Asn Gly Tyr Thr Lys Tyr Ser Gln Lys Phe Gln
1               5                   10                  15

Asp
```

<210> SEQ ID NO 203
<211> LENGTH: 11
<212> TYPE: PRT
<213> ORGANISM: Homo Sapiens

<400> SEQUENCE: 203

```
Asp Arg Ile Thr Ile Ile Arg Pro Phe Asp Tyr
1               5                   10
```

<210> SEQ ID NO 204
<211> LENGTH: 120
<212> TYPE: PRT
<213> ORGANISM: Homo Sapiens

<400> SEQUENCE: 204

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly His Arg Leu Glu Trp Leu
            35                  40                  45

Gly Trp Ile Asn Ala Gly Asn Gly Tyr Thr Lys Tyr Ser Gln Lys Phe
        50                  55                  60

Gln Asp Arg Val Ala Ile Thr Arg Asp Thr Ser Ala Ser Thr Ala Phe
65                  70                  75                  80

Met Glu Leu Ser Ser Leu Arg Ser Glu Asp Thr Ala Val Tyr Tyr Cys
                85                  90                  95

Ala Arg Asp Arg Ile Thr Ile Ile Arg Pro Phe Asp Tyr Trp Gly Gln
            100                 105                 110

Gly Thr Leu Val Thr Val Ser Ser
        115                 120
```

<210> SEQ ID NO 205
<211> LENGTH: 360
<212> TYPE: DNA
<213> ORGANISM: Homo Sapiens

<400> SEQUENCE: 205

```
caggtccaac ttgtgcagtc tgggggctgag gtgaagaagc ctggggcctc agtgaaggtt      60
tcctgcaagg cttctggata caccttcact agctatgcta tgcattgggt gcgtcaggcc     120
cccggacaca ggcttgagtg gttgggatgg atcaacgctg gcaatggtta cacaaaatat     180
tcacagaaat tccaggacag agtcgccatt accaggggaca catccgcgag cacagccttc     240
atggagctga gcagcctgag atctgaagac acggctgtgt attactgtgc gagagatcgt     300
attactatta ttcggcccctt tgactactgg ggccagggaa ccctggtcac cgtctcctca     360
```

<210> SEQ ID NO 206
<211> LENGTH: 447
<212> TYPE: PRT
<213> ORGANISM: Homo Sapiens

<400> SEQUENCE: 206

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly His Arg Leu Glu Trp Leu
        35                  40                  45

Gly Trp Ile Asn Ala Gly Asn Gly Tyr Thr Lys Tyr Ser Gln Lys Phe
    50                  55                  60

Gln Asp Arg Val Ala Ile Thr Arg Asp Thr Ser Ala Ser Thr Ala Phe
65                  70                  75                  80

Met Glu Leu Ser Ser Leu Arg Ser Glu Asp Thr Ala Val Tyr Tyr Cys
                85                  90                  95

Ala Arg Asp Arg Ile Thr Ile Ile Arg Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
```

-continued

```
              420             425             430
His Asn His Tyr Thr Gln Lys Ser Leu Ser Leu Ser Leu Gly Lys
      435             440             445

<210> SEQ ID NO 207
<211> LENGTH: 7
<212> TYPE: PRT
<213> ORGANISM: Homo Sapiens

<400> SEQUENCE: 207

Gln Ser Ile Ser Ser Ser Tyr
1               5

<210> SEQ ID NO 208
<211> LENGTH: 3
<212> TYPE: PRT
<213> ORGANISM: Homo Sapiens

<400> SEQUENCE: 208

Gly Ala Ser
1

<210> SEQ ID NO 209
<211> LENGTH: 8
<212> TYPE: PRT
<213> ORGANISM: Homo Sapiens

<400> SEQUENCE: 209

Gln Leu Tyr Gly Ser Pro Phe Thr
1               5

<210> SEQ ID NO 210
<211> LENGTH: 12
<212> TYPE: PRT
<213> ORGANISM: Homo Sapiens

<400> SEQUENCE: 210

Arg Ala Ser Gln Ser Ile Ser Ser Ser Tyr Leu Ala
1               5                   10

<210> SEQ ID NO 211
<211> LENGTH: 7
<212> TYPE: PRT
<213> ORGANISM: Homo Sapiens

<400> SEQUENCE: 211

Gly Ala Ser Ser Arg Ala Thr
1               5

<210> SEQ ID NO 212
<211> LENGTH: 8
<212> TYPE: PRT
<213> ORGANISM: Homo Sapiens

<400> SEQUENCE: 212

Gln Leu Tyr Gly Ser Pro Phe Thr
1               5

<210> SEQ ID NO 213
<211> LENGTH: 107
<212> TYPE: PRT
<213> ORGANISM: Homo Sapiens

<400> SEQUENCE: 213
```

-continued

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Tyr Leu Ala Trp Phe Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Asn Gly Ser Gly Thr Asp Phe Thr Leu Thr Ile Ser Arg Leu Glu
65                  70                  75                  80

Pro Glu Asp Phe Ala Val Tyr Tyr Cys Gln Leu Tyr Gly Ser Pro Phe
                85                  90                  95

Thr Phe Gly Pro Gly Thr Lys Met Asp Ile Lys
            100                 105
```

<210> SEQ ID NO 214
<211> LENGTH: 322
<212> TYPE: DNA
<213> ORGANISM: Homo Sapiens

<400> SEQUENCE: 214

```
gaaattgtgt tgacgcagtc tccaggcacc ctgtctttgt ctccagggga aagagccacc      60
ctctcctgca gggccagtca gagtattagc agcagctact tagcctggtt ccagcaaaaa     120
cctggccagg ctcccaggct cctcatctat ggtgcatcca gcagggccac tggcatccca     180
gacaggttca gtggcaatgg gtctgggaca gacttcactc tcaccatcag cagactggag     240
cctgaagatt ttgcagtgta ttactgtcag ctgtatggta gcccattcac tttcggccct     300
gggaccaaaa tggatattaa ac                                              322
```

<210> SEQ ID NO 215
<211> LENGTH: 214
<212> TYPE: PRT
<213> ORGANISM: Homo Sapiens

<400> SEQUENCE: 215

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Tyr Leu Ala Trp Phe Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Asn Gly Ser Gly Thr Asp Phe Thr Leu Thr Ile Ser Arg Leu Glu
65                  70                  75                  80

Pro Glu Asp Phe Ala Val Tyr Tyr Cys Gln Leu Tyr Gly Ser Pro Phe
                85                  90                  95

Thr Phe Gly Pro Gly Thr Lys Met Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

-continued

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 216
<211> LENGTH: 8
<212> TYPE: PRT
<213> ORGANISM: Homo Sapiens

<400> SEQUENCE: 216

Gly Tyr Thr Phe Thr Ser Tyr Ala
1               5

<210> SEQ ID NO 217
<211> LENGTH: 8
<212> TYPE: PRT
<213> ORGANISM: Homo Sapiens

<400> SEQUENCE: 217

Ile Asn Val Gly Asn Gly Lys Thr
1               5

<210> SEQ ID NO 218
<211> LENGTH: 11
<212> TYPE: PRT
<213> ORGANISM: Homo Sapiens

<400> SEQUENCE: 218

Ala Arg Arg Gly Phe Gly Glu Pro Phe Asp Tyr
1               5                   10

<210> SEQ ID NO 219
<211> LENGTH: 5
<212> TYPE: PRT
<213> ORGANISM: Homo Sapiens

<400> SEQUENCE: 219

Ser Tyr Ala Ile His
1               5

<210> SEQ ID NO 220
<211> LENGTH: 17
<212> TYPE: PRT
<213> ORGANISM: Homo Sapiens

<400> SEQUENCE: 220

Trp Ile Asn Val Gly Asn Gly Lys Thr Lys Phe Ser Gln Lys Leu Gln
1               5                   10                  15

Gly

<210> SEQ ID NO 221
<211> LENGTH: 9
<212> TYPE: PRT
<213> ORGANISM: Homo Sapiens

<400> SEQUENCE: 221

Arg Gly Phe Gly Glu Pro Phe Asp Tyr
1               5
```

```
<210> SEQ ID NO 222
<211> LENGTH: 118
<212> TYPE: PRT
<213> ORGANISM: Homo Sapiens

<400> SEQUENCE: 222
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile His Trp Val Arg Gln Ala Pro Gly Gln Arg Leu Glu Trp Met
        35                  40                  45

Gly Trp Ile Asn Val Gly Asn Gly Lys Thr Lys Phe Ser Gln Lys Leu
    50                  55                  60

Gln Gly Arg Ile Thr Ile Thr Arg Asp Thr Ser Ala Ser Thr Thr Tyr
65                  70                  75                  80

Met Glu Leu Asn Ser Leu Arg Ser Glu Asp Thr Ala Val Phe Tyr Cys
                85                  90                  95

Ala Arg Arg Gly Phe Gly Glu Pro Phe Asp Tyr Trp Gly Gln Gly Thr
            100                 105                 110

Leu Val Thr Val Ser Ser
        115

```
<210> SEQ ID NO 223
<211> LENGTH: 354
<212> TYPE: DNA
<213> ORGANISM: Homo Sapiens

<400> SEQUENCE: 223
```
caggtccagc ttgtgcagtc tggggctgag gtgaagaagc ctggggcctc agtgaaagtt          60
tcctgcaagg cttctggata caccttcact agctatgcta tccattgggt gcgccaggcc         120
cccggacaaa ggcttgagtg gatgggatgg atcaacgttg gcaatggtaa aacaaaattt         180
tcacagaagt tacagggcag aatcaccatt accaggggaca catccgcgag cacaacctac        240
atggagctga acagcctgag atctgaagac acggctgtgt tttactgtgc gagaaggggg         300
ttcggggagc catttgacta ctggggccag ggaaccctgg tcaccgtctc ctca              354

```
<210> SEQ ID NO 224
<211> LENGTH: 445
<212> TYPE: PRT
<213> ORGANISM: Homo Sapiens

<400> SEQUENCE: 224
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile His Trp Val Arg Gln Ala Pro Gly Gln Arg Leu Glu Trp Met
        35                  40                  45

Gly Trp Ile Asn Val Gly Asn Gly Lys Thr Lys Phe Ser Gln Lys Leu
    50                  55                  60

Gln Gly Arg Ile Thr Ile Thr Arg Asp Thr Ser Ala Ser Thr Thr Tyr
65                  70                  75                  80

Met Glu Leu Asn Ser Leu Arg Ser Glu Asp Thr Ala Val Phe Tyr Cys
                85                  90                  95

-continued

Ala Arg Arg Gly Phe Gly Glu Pro Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
            210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 225
<211> LENGTH: 6
<212> TYPE: PRT
<213> ORGANISM: Homo Sapiens

<400> SEQUENCE: 225

Gln Ser Ile Ser Ser Asn
1               5

<210> SEQ ID NO 226

-continued

```
<211> LENGTH: 3
<212> TYPE: PRT
<213> ORGANISM: Homo Sapiens

<400> SEQUENCE: 226

Gly Thr Ser
1

<210> SEQ ID NO 227
<211> LENGTH: 9
<212> TYPE: PRT
<213> ORGANISM: Homo Sapiens

<400> SEQUENCE: 227

Gln Gln Tyr Asn Ile Trp Pro Phe Thr
1               5

<210> SEQ ID NO 228
<211> LENGTH: 11
<212> TYPE: PRT
<213> ORGANISM: Homo Sapiens

<400> SEQUENCE: 228

Arg Ala Ser Gln Ser Ile Ser Ser Asn Leu Ala
1               5                   10

<210> SEQ ID NO 229
<211> LENGTH: 7
<212> TYPE: PRT
<213> ORGANISM: Homo Sapiens

<400> SEQUENCE: 229

Gly Thr Ser Thr Arg Ala Thr
1               5

<210> SEQ ID NO 230
<211> LENGTH: 9
<212> TYPE: PRT
<213> ORGANISM: Homo Sapiens

<400> SEQUENCE: 230

Gln Gln Tyr Asn Ile Trp Pro Phe Thr
1               5

<210> SEQ ID NO 231
<211> LENGTH: 107
<212> TYPE: PRT
<213> ORGANISM: Homo Sapiens

<400> SEQUENCE: 231

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
            35                  40                  45

Tyr Gly Thr Ser Thr Arg Ala Thr Gly Ile Pro Ala Arg Phe Ser Gly
    50                  55                  60

Ser Gly Ser Gly Thr Glu Phe Thr Leu Thr Ile Ser Thr Leu Gln Ser
65                  70                  75                  80

Glu Asp Phe Ala Val Tyr Tyr Cys Gln Gln Tyr Asn Ile Trp Pro Phe
                85                  90                  95
```

-continued

```
Thr Phe Gly Pro Gly Thr Lys Val Asp Ile Lys
            100                 105
```

<210> SEQ ID NO 232
<211> LENGTH: 321
<212> TYPE: DNA
<213> ORGANISM: Homo Sapiens

<400> SEQUENCE: 232

```
gaaatagtga tgacgcagtc tccagccacc ctgtctgtgt ctccagggga aagagccacc      60
ctctcctgca gggccagtca gagtattagt agcaacttag cctggtacca acagaaacct     120
ggccaggctc ccaggctcct catctatggt acatccacca gggccactgg tatcccagcc     180
aggttcagtg gcagtgggtc tgggacagag ttcactctca ccatcagcac cctgcagtct     240
gaagattttg cagtttatta ctgtcagcag tataatatct ggcctttcac tttcggccct     300
gggaccaaag tggatatcaa a                                               321
```

<210> SEQ ID NO 233
<211> LENGTH: 214
<212> TYPE: PRT
<213> ORGANISM: Homo Sapiens

<400> SEQUENCE: 233

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
                20                  25                  30

Leu Ala Trp Tyr Gln Gln Lys Pro Gly Gln Ala Pro Arg Leu Leu Ile
            35                  40                  45

Tyr Gly Thr Ser Thr Arg Ala Thr Gly Ile Pro Ala Arg Phe Ser Gly
        50                  55                  60

Ser Gly Ser Gly Thr Glu Phe Thr Leu Thr Ile Ser Thr Leu Gln Ser
65                  70                  75                  80

Glu Asp Phe Ala Val Tyr Tyr Cys Gln Gln Tyr Asn Ile Trp Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 234
<211> LENGTH: 8
<212> TYPE: PRT
<213> ORGANISM: Homo Sapiens

```
<400> SEQUENCE: 234

Gly Tyr Thr Phe Thr Ser Tyr Ala
1               5

<210> SEQ ID NO 235
<211> LENGTH: 8
<212> TYPE: PRT
<213> ORGANISM: Homo Sapiens

<400> SEQUENCE: 235

Ile Asn Ala Gly Asn Gly Asn Thr
1               5

<210> SEQ ID NO 236
<211> LENGTH: 11
<212> TYPE: PRT
<213> ORGANISM: Homo Sapiens

<400> SEQUENCE: 236

Ala Arg Arg Gly Phe Gly Glu Pro Phe Asp Tyr
1               5                   10

<210> SEQ ID NO 237
<211> LENGTH: 5
<212> TYPE: PRT
<213> ORGANISM: Homo Sapiens

<400> SEQUENCE: 237

Ser Tyr Ala Ile His
1               5

<210> SEQ ID NO 238
<211> LENGTH: 17
<212> TYPE: PRT
<213> ORGANISM: Homo Sapiens

<400> SEQUENCE: 238

Trp Ile Asn Ala Gly Asn Gly Asn Thr Lys Tyr Ser Gln Lys Phe Gln
1               5                   10                  15

Gly

<210> SEQ ID NO 239
<211> LENGTH: 9
<212> TYPE: PRT
<213> ORGANISM: Homo Sapiens

<400> SEQUENCE: 239

Arg Gly Phe Gly Glu Pro Phe Asp Tyr
1               5

<210> SEQ ID NO 240
<211> LENGTH: 118
<212> TYPE: PRT
<213> ORGANISM: Homo Sapiens

<400> SEQUENCE: 240

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Ile His Trp Val Arg Gln Ala Pro Gly Gln Arg Leu Glu Trp Met
            35                  40                  45
```

-continued

```
Gly Trp Ile Asn Ala Gly Asn Gly Asn Thr Lys Tyr Ser Gln Lys Phe
50              55              60

Gln Gly Arg Ile Thr Ile Thr Arg Asp Thr Ser Ala Ser Thr Ala Tyr
65              70              75              80

Met Glu Leu Ser Ser Leu Arg Ser Glu Asp Thr Ala Val Tyr Tyr Cys
85              90              95

Ala Arg Arg Gly Phe Gly Glu Pro Phe Asp Tyr Trp Gly Gln Gly Thr
100             105             110

Leu Val Thr Val Ser Ser
115
```

<210> SEQ ID NO 241
<211> LENGTH: 354
<212> TYPE: DNA
<213> ORGANISM: Homo Sapiens

<400> SEQUENCE: 241

```
caggtccagc ttgtgcagtc tgggggctgag gtgaagaagc ctgggggcctc agtgaaggtt    60 tcctgcaagg cttctggata caccttcact agctatgcta tccattgggt gcgccaggcc   120
cccggacaaa ggcttgagtg gatgggatgg atcaacgctg gcaatggtaa cacaaaatat   180
tcacagaagt tccagggcag aatcaccatt accagggaca catccgcgag cacagcctac   240
atggagctga gcagcctgag atctgaagac acggctgtgt attactgtgc gagaaggggg   300
ttcggggagc catttgacta ctggggccag ggaaccctgg tcaccgtctc ctca          354
```

<210> SEQ ID NO 242
<211> LENGTH: 445
<212> TYPE: PRT
<213> ORGANISM: Homo Sapiens

<400> SEQUENCE: 242

```
Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Ser Tyr
20              25              30

Ala Ile His Trp Val Arg Gln Ala Pro Gly Gln Arg Leu Glu Trp Met
35              40              45

Gly Trp Ile Asn Ala Gly Asn Gly Asn Thr Lys Tyr Ser Gln Lys Phe
50              55              60

Gln Gly Arg Ile Thr Ile Thr Arg Asp Thr Ser Ala Ser Thr Ala Tyr
65              70              75              80

Met Glu Leu Ser Ser Leu Arg Ser Glu Asp Thr Ala Val Tyr Tyr Cys
85              90              95

Ala Arg Arg Gly Phe Gly Glu Pro Phe Asp Tyr Trp Gly Gln Gly Thr
100             105             110

Leu Val Thr Val Ser Ser Ala Ser Thr Lys Gly Pro Ser Val Phe Pro
115             120             125

Leu Ala Pro Cys Ser Arg Ser Thr Ser Glu Ser Thr Ala Ala Leu Gly
130             135             140

Cys Leu Val Lys Asp Tyr Phe Pro Glu Pro Val Thr Val Ser Trp Asn
145             150             155             160

Ser Gly Ala Leu Thr Ser Gly Val His Thr Phe Pro Ala Val Leu Gln
165             170             175

Ser Ser Gly Leu Tyr Ser Leu Ser Ser Val Val Thr Val Pro Ser Ser
180             185             190
```

-continued

```
Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
        340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
        435                 440                 445
```

<210> SEQ ID NO 243
<211> LENGTH: 6
<212> TYPE: PRT
<213> ORGANISM: Homo Sapiens

<400> SEQUENCE: 243

```
Gln Ser Ile Ser Ser Asn
1               5
```

<210> SEQ ID NO 244
<211> LENGTH: 3
<212> TYPE: PRT
<213> ORGANISM: Homo Sapiens

<400> SEQUENCE: 244

```
Gly Thr Ser
1
```

<210> SEQ ID NO 245
<211> LENGTH: 9
<212> TYPE: PRT
<213> ORGANISM: Homo Sapiens

<400> SEQUENCE: 245

```
Gln Gln Tyr Asn Ile Trp Pro Phe Thr
```

```
1               5
```

```
<210> SEQ ID NO 246
<211> LENGTH: 11
<212> TYPE: PRT
<213> ORGANISM: Homo Sapiens

<400> SEQUENCE: 246

Arg Ala Ser Gln Ser Ile Ser Ser Asn Leu Ala
1               5                   10

<210> SEQ ID NO 247
<211> LENGTH: 7
<212> TYPE: PRT
<213> ORGANISM: Homo Sapiens

<400> SEQUENCE: 247

Gly Thr Ser Thr Arg Ala Thr
1               5

<210> SEQ ID NO 248
<211> LENGTH: 9
<212> TYPE: PRT
<213> ORGANISM: Homo Sapiens

<400> SEQUENCE: 248

Gln Gln Tyr Asn Ile Trp Pro Phe Thr
1               5

<210> SEQ ID NO 249
<211> LENGTH: 107
<212> TYPE: PRT
<213> ORGANISM: Homo Sapiens

<400> SEQUENCE: 249

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
                20                  25                  30

Leu Ala Trp Tyr Gln Gln Lys Pro Gly Gln Ala Pro Arg Leu Leu Ile
            35                  40                  45

Tyr Gly Thr Ser Thr Arg Ala Thr Gly Ile Pro Ala Arg Phe Ser Gly
        50                  55                  60

Ser Gly Ser Gly Thr Glu Phe Thr Leu Thr Ile Ser Thr Leu Gln Ser
65                  70                  75                  80

Glu Asp Phe Ala Val Tyr Tyr Cys Gln Gln Tyr Asn Ile Trp Pro Phe
                85                  90                  95

Thr Phe Gly Pro Gly Thr Lys Val Asp Ile Lys
            100                 105

<210> SEQ ID NO 250
<211> LENGTH: 321
<212> TYPE: DNA
<213> ORGANISM: Homo Sapiens

<400> SEQUENCE: 250
gaaatagtga tgacgcagtc tccagccacc ctgtctgtgt ctccagggga aagagccacc      60
ctctcctgca gggccagtca gagtattagc agcaacttag cctggtacca acagaaacct     120
ggccaggctc ccaggctcct catctatggt acatccacca gggccactgg tatcccagcc     180
aggttcagtg gcagtgggtc tgggacagag ttcactctca ccatcagcac cctgcagtct     240
```
gaagattttg cagtttatta ctgtcagcag tataatatct ggcctttcac tttcggccct      300
gggaccaaag tggatatcaa a      321

<210> SEQ ID NO 251
<211> LENGTH: 214
<212> TYPE: PRT
<213> ORGANISM: Homo Sapiens

<400> SEQUENCE: 251

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
        35                  40                  45

Tyr Gly Thr Ser Thr Arg Ala Thr Gly Ile Pro Ala Arg Phe Ser Gly
    50                  55                  60

Ser Gly Ser Gly Thr Glu Phe Thr Leu Thr Ile Ser Thr Leu Gln Ser
65                  70                  75                  80

Glu Asp Phe Ala Val Tyr Tyr Cys Gln Gln Tyr Asn Ile Trp Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 252
<211> LENGTH: 8
<212> TYPE: PRT
<213> ORGANISM: Homo Sapiens

<400> SEQUENCE: 252

Gly Tyr Thr Phe Thr Thr Tyr Ala
1               5

<210> SEQ ID NO 253
<211> LENGTH: 8
<212> TYPE: PRT
<213> ORGANISM: Homo Sapiens

<400> SEQUENCE: 253

Ile Asn Ala Gly Asn Gly Arg Thr
1               5

<210> SEQ ID NO 254

-continued

<211> LENGTH: 11
<212> TYPE: PRT
<213> ORGANISM: Homo Sapiens

<400> SEQUENCE: 254

Ala Arg Arg Gly Phe Gly Glu Pro Phe Asp Gln
1               5                   10

<210> SEQ ID NO 255
<211> LENGTH: 5
<212> TYPE: PRT
<213> ORGANISM: Homo Sapiens

<400> SEQUENCE: 255

Thr Tyr Ala Ile His
1               5

<210> SEQ ID NO 256
<211> LENGTH: 17
<212> TYPE: PRT
<213> ORGANISM: Homo Sapiens

<400> SEQUENCE: 256

Trp Ile Asn Ala Gly Asn Gly Arg Thr Glu Tyr Ser Glu Lys Phe Gln
1               5                   10                  15

Gly

<210> SEQ ID NO 257
<211> LENGTH: 9
<212> TYPE: PRT
<213> ORGANISM: Homo Sapiens

<400> SEQUENCE: 257

Arg Gly Phe Gly Glu Pro Phe Asp Gln
1               5

<210> SEQ ID NO 258
<211> LENGTH: 118
<212> TYPE: PRT
<213> ORGANISM: Homo Sapiens

<400> SEQUENCE: 258

Gln Val His Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Thr Tyr
                20                  25                  30

Ala Ile His Trp Val Arg Gln Ala Pro Gly Gln Gly Leu Glu Trp Met
            35                  40                  45

Gly Trp Ile Asn Ala Gly Asn Gly Arg Thr Glu Tyr Ser Glu Lys Phe
        50                  55                  60

Gln Gly Arg Val Thr Ile Thr Arg Asp Thr Ser Ala Ser Thr Val Tyr
65                  70                  75                  80

Met Asp Leu Ser Ser Leu Arg Ser Gly Asp Thr Ala Val Tyr Tyr Cys
                85                  90                  95

Ala Arg Arg Gly Phe Gly Glu Pro Phe Asp Gln Trp Gly Gln Gly Thr
            100                 105                 110

Leu Val Thr Val Ser Ser
        115

<210> SEQ ID NO 259
<211> LENGTH: 354

```
<212> TYPE: DNA
<213> ORGANISM: Homo Sapiens

<400> SEQUENCE: 259
caggtccacc ttgtgcagtc tggggctgag gtgaagaagc ctggggcctc agtgaaggtg       60
tcctgcaaga cttctggata caccttcacc acctatgcta ttcattgggt gcgccaggcc      120
cccggacaag ggcttgagtg gatgggatgg atcaacgctg gcaatggtag aacagaatat      180
tcagagaagt ttcagggcag agtcaccatt accaggggaca cttccgcgag tacagtctac      240
atggacctga gcagcctgag atctggagac acggctgtgt attactgtgc gagaaggggga      300 ttcggggagc catttgacca atggggccag ggaaccctgg tcaccgtctc ctca           354

<210> SEQ ID NO 260
<211> LENGTH: 445
<212> TYPE: PRT
<213> ORGANISM: Homo Sapiens

<400> SEQUENCE: 260

Gln Val His Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Thr Tyr
            20                  25                  30

Ala Ile His Trp Val Arg Gln Ala Pro Gly Gln Gly Leu Glu Trp Met
        35                  40                  45

Gly Trp Ile Asn Ala Gly Asn Gly Arg Thr Glu Tyr Ser Glu Lys Phe
    50                  55                  60

Gln Gly Arg Val Thr Ile Thr Arg Asp Thr Ser Ala Ser Thr Val Tyr
65                  70                  75                  80

Met Asp Leu Ser Ser Leu Arg Ser Gly Asp Thr Ala Val Tyr Tyr Cys
                85                  90                  95

Ala Arg Arg Gly Phe Gly Glu Pro Phe Asp Gln Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285
```

-continued

```
Pro Arg Glu Glu Gln Phe Asn Ser Thr Tyr Arg Val Val Ser Val Leu
    290             295             300

Thr Val Leu His Gln Asp Trp Leu Asn Gly Lys Glu Tyr Lys Cys Lys
305             310             315             320

Val Ser Asn Lys Gly Leu Pro Ser Ser Ile Glu Lys Thr Ile Ser Lys
            325             330             335

Ala Lys Gly Gln Pro Arg Glu Pro Gln Val Tyr Thr Leu Pro Pro Ser
            340             345             350

Gln Glu Glu Met Thr Lys Asn Gln Val Ser Leu Thr Cys Leu Val Lys
        355             360             365

Gly Phe Tyr Pro Ser Asp Ile Ala Val Glu Trp Glu Ser Asn Gly Gln
    370             375             380

Pro Glu Asn Asn Tyr Lys Thr Thr Pro Pro Val Leu Asp Ser Asp Gly
385             390             395             400

Ser Phe Phe Leu Tyr Ser Arg Leu Thr Val Asp Lys Ser Arg Trp Gln
            405             410             415

Glu Gly Asn Val Phe Ser Cys Ser Val Met His Glu Ala Leu His Asn
            420             425             430

His Tyr Thr Gln Lys Ser Leu Ser Leu Ser Leu Gly Lys
        435             440             445
```

```
<210> SEQ ID NO 261
<211> LENGTH: 6
<212> TYPE: PRT
<213> ORGANISM: Homo Sapiens

<400> SEQUENCE: 261

Gln Ser Val Ser Ser Asn
1               5

<210> SEQ ID NO 262
<211> LENGTH: 3
<212> TYPE: PRT
<213> ORGANISM: Homo Sapiens

<400> SEQUENCE: 262

Gly Ala Ser
1

<210> SEQ ID NO 263
<211> LENGTH: 9
<212> TYPE: PRT
<213> ORGANISM: Homo Sapiens

<400> SEQUENCE: 263

Gln Gln Tyr Asn Asn Trp Pro Phe Ile
1               5

<210> SEQ ID NO 264
<211> LENGTH: 11
<212> TYPE: PRT
<213> ORGANISM: Homo Sapiens

<400> SEQUENCE: 264

Arg Ala Ser Gln Ser Val Ser Ser Asn Leu Ala
1               5               10

<210> SEQ ID NO 265
<211> LENGTH: 7
<212> TYPE: PRT
<213> ORGANISM: Homo Sapiens
```

<400> SEQUENCE: 265

Gly Ala Ser Thr Arg Ala Thr
1               5

<210> SEQ ID NO 266
<211> LENGTH: 9
<212> TYPE: PRT
<213> ORGANISM: Homo Sapiens

<400> SEQUENCE: 266

Gln Gln Tyr Asn Asn Trp Pro Phe Ile
1               5

<210> SEQ ID NO 267
<211> LENGTH: 107
<212> TYPE: PRT
<213> ORGANISM: Homo Sapiens

<400> SEQUENCE: 267

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln His Gln Pro Gly Gln Ala Pro Arg Leu Leu Ile
        35                  40                  45

Tyr Gly Ala Ser Thr Arg Ala Thr Gly Phe Pro Pro Arg Phe Ser Gly
    50                  55                  60

Ser Gly Ser Gly Thr Asp Phe Thr Leu Thr Ile Asn Ser Leu Gln Ser
65                  70                  75                  80

Glu Asp Phe Ala Val Tyr Tyr Cys Gln Gln Tyr Asn Asn Trp Pro Phe
                85                  90                  95

Ile Phe Gly Pro Gly Thr Lys Leu Asp Ile Thr
            100                 105

<210> SEQ ID NO 268
<211> LENGTH: 321
<212> TYPE: DNA
<213> ORGANISM: Homo Sapiens

<400> SEQUENCE: 268
gaaatagtga tgacgcagtc tccagccacc ctgtctgtgt ctccagggga aagagccacc      60
ctctcctgca gggccagtca gagtgttagc agcaacttag cctggtacca gcaccaacct     120
ggccaggctc ccaggctcct catctatggt gcatccacca gggccactgg tttcccaccc     180
aggttcagtg gcagtgggtc tgggacagac ttcactctca ccatcaacag cctgcagtct     240
gaagattttg cagtttatta ctgtcagcag tataataact ggcctttcat tttcggccct     300
gggaccaaac tggatatcac a                                              321

<210> SEQ ID NO 269
<211> LENGTH: 214
<212> TYPE: PRT
<213> ORGANISM: Homo Sapiens

<400> SEQUENCE: 269

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

```
Leu Ala Trp Tyr Gln His Gln Pro Gly Gln Ala Pro Arg Leu Leu Ile
        35                  40                  45

Tyr Gly Ala Ser Thr Arg Ala Thr Gly Phe Pro Pro Arg Phe Ser Gly
    50                  55                  60

Ser Gly Ser Gly Thr Asp Phe Thr Leu Thr Ile Asn Ser Leu Gln Ser
65                  70                  75                  80

Glu Asp Phe Ala Val Tyr Tyr Cys Gln Gln Tyr Asn Asn Trp Pro Phe
                85                  90                  95

Ile Phe Gly Pro Gly Thr Lys Leu Asp Ile Thr Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 270
<211> LENGTH: 8
<212> TYPE: PRT
<213> ORGANISM: Homo Sapiens

<400> SEQUENCE: 270

Gly Phe Thr Phe Ser Asp Tyr Tyr
1               5
```

```
<210> SEQ ID NO 271
<211> LENGTH: 8
<212> TYPE: PRT
<213> ORGANISM: Homo Sapiens

<400> SEQUENCE: 271

Ile Ser Ile Ser Gly Ser Thr Ile
1               5
```

```
<210> SEQ ID NO 272
<211> LENGTH: 10
<212> TYPE: PRT
<213> ORGANISM: Homo Sapiens

<400> SEQUENCE: 272

Ala Arg Arg Ser Ser Gly Trp Tyr Asp Tyr
1               5                   10
```

```
<210> SEQ ID NO 273
<211> LENGTH: 5
<212> TYPE: PRT
<213> ORGANISM: Homo Sapiens

<400> SEQUENCE: 273

Asp Tyr Tyr Met Ser
```

-continued

```
1               5
```

```
<210> SEQ ID NO 274
<211> LENGTH: 17
<212> TYPE: PRT
<213> ORGANISM: Homo Sapiens

<400> SEQUENCE: 274

Tyr Ile Ser Ile Ser Gly Ser Thr Ile Tyr Tyr Ala Asp Ser Val Lys
1               5                   10                  15

Gly

<210> SEQ ID NO 275
<211> LENGTH: 8
<212> TYPE: PRT
<213> ORGANISM: Homo Sapiens

<400> SEQUENCE: 275

Arg Ser Ser Gly Trp Tyr Asp Tyr
1               5

<210> SEQ ID NO 276
<211> LENGTH: 117
<212> TYPE: PRT
<213> ORGANISM: Homo Sapiens

<400> SEQUENCE: 276

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ile Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Arg Ser Ser Gly Trp Tyr Asp Tyr Trp Gly Gln Gly Thr Leu
            100                 105                 110

Val Thr Val Ser Ser
        115

<210> SEQ ID NO 277
<211> LENGTH: 351
<212> TYPE: DNA
<213> ORGANISM: Homo Sapiens

<400> SEQUENCE: 277
caggtgcaac tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtatta gtggtagtac catatactac     180
gcagactctg tgaagggccg attcaccatc tccagggaca cgccaagaa ctcactgttt      240 ctgcaaatga acagcctgag agccgaggac acggccgtgt attactgtgc gagaagaagc     300
agtggctggt acgactactg gggccaggga accctggtca ccgtctcctc a              351
```

-continued

```
<210> SEQ ID NO 278
<211> LENGTH: 444
<212> TYPE: PRT
<213> ORGANISM: Homo Sapiens

<400> SEQUENCE: 278

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ile Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Arg Ser Ser Gly Trp Tyr Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380
```

-continued

```
Glu Asn Asn Tyr Lys Thr Thr Pro Pro Val Leu Asp Ser Asp Gly Ser
385                 390             395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
        435                 440

<210> SEQ ID NO 279
<211> LENGTH: 7
<212> TYPE: PRT
<213> ORGANISM: Homo Sapiens

<400> SEQUENCE: 279

Gln Ser Val Ser Ser Asn Tyr
1               5

<210> SEQ ID NO 280
<211> LENGTH: 3
<212> TYPE: PRT
<213> ORGANISM: Homo Sapiens

<400> SEQUENCE: 280

Gly Ala Ser
1

<210> SEQ ID NO 281
<211> LENGTH: 9
<212> TYPE: PRT
<213> ORGANISM: Homo Sapiens

<400> SEQUENCE: 281

His Gln Tyr Gly Ser Ser Pro Pro Thr
1               5

<210> SEQ ID NO 282
<211> LENGTH: 12
<212> TYPE: PRT
<213> ORGANISM: Homo Sapiens

<400> SEQUENCE: 282

Arg Ala Ser Gln Ser Val Ser Ser Asn Tyr Leu Ala
1               5                   10

<210> SEQ ID NO 283
<211> LENGTH: 7
<212> TYPE: PRT
<213> ORGANISM: Homo Sapiens

<400> SEQUENCE: 283

Gly Ala Ser Ile Arg Ala Thr
1               5

<210> SEQ ID NO 284
<211> LENGTH: 9
<212> TYPE: PRT
<213> ORGANISM: Homo Sapiens

<400> SEQUENCE: 284

His Gln Tyr Gly Ser Ser Pro Pro Thr
1               5
```

-continued

---

<210> SEQ ID NO 285
<211> LENGTH: 108
<212> TYPE: PRT
<213> ORGANISM: Homo Sapiens

<400> SEQUENCE: 285

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Ser Cys His Gln Tyr Gly Ser Ser Pro
                85                  90                  95

Pro Thr Phe Gly Gln Gly Thr Lys Val Glu Ile Lys
            100                 105
```

<210> SEQ ID NO 286
<211> LENGTH: 325
<212> TYPE: DNA
<213> ORGANISM: Homo Sapiens

<400> SEQUENCE: 286

```
gaaattgtgt tgacgcagtc tccaggcacc ctgtctttgt ctccagggga aagagccacc      60
ctctcctgca gggccagtca gagtgttagc agcaactact tagcctggta ccagcagaaa     120
cctggccagg ctcccaggct cctcatctat ggtgcatcca tcagggccac tggcatccca     180
gacaggttca gtggcagtgg gtctgggaca gacttcactc tcaccatcag cagactggag     240
cctgaagatt ttgcagtgta ttcctgtcac cagtatggta gctcacctcc gacgttcggc     300
caagggacca aggtggaaat caaac                                           325
```

<210> SEQ ID NO 287
<211> LENGTH: 215
<212> TYPE: PRT
<213> ORGANISM: Homo Sapiens

<400> SEQUENCE: 287

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Ser Cys His Gln Tyr Gly Ser Ser Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125
```

```
Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 288
<211> LENGTH: 8
<212> TYPE: PRT
<213> ORGANISM: Homo Sapiens

<400> SEQUENCE: 288

Gly Phe Thr Phe Ser Asp Tyr Tyr
1               5

<210> SEQ ID NO 289
<211> LENGTH: 8
<212> TYPE: PRT
<213> ORGANISM: Homo Sapiens

<400> SEQUENCE: 289

Ile Ser Ile Ser Gly Thr Thr Ile
1               5

<210> SEQ ID NO 290
<211> LENGTH: 10
<212> TYPE: PRT
<213> ORGANISM: Homo Sapiens

<400> SEQUENCE: 290

Ala Arg Arg Ser Ser Gly Trp Tyr Asp Tyr
1               5                   10

<210> SEQ ID NO 291
<211> LENGTH: 5
<212> TYPE: PRT
<213> ORGANISM: Homo Sapiens

<400> SEQUENCE: 291

Asp Tyr Tyr Met Ser
1               5

<210> SEQ ID NO 292
<211> LENGTH: 17
<212> TYPE: PRT
<213> ORGANISM: Homo Sapiens

<400> SEQUENCE: 292

Tyr Ile Ser Ile Ser Gly Thr Thr Ile Tyr Tyr Ala Asp Ser Val Lys
1               5                   10                  15

Gly

<210> SEQ ID NO 293
<211> LENGTH: 8
```

<212> TYPE: PRT
<213> ORGANISM: Homo Sapiens

<400> SEQUENCE: 293

Arg Ser Ser Gly Trp Tyr Asp Tyr
1               5

<210> SEQ ID NO 294
<211> LENGTH: 117
<212> TYPE: PRT
<213> ORGANISM: Homo Sapiens

<400> SEQUENCE: 294

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ile Ser Gly Thr Thr Ile Tyr Tyr Ala Asp Ser Val
    50                  55                  60

Lys Gly Arg Phe Thr Ile Ser Arg Asp Asn Ala Met Asp Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Ser Gly Trp Tyr Asp Tyr Trp Gly Gln Gly Thr Leu
            100                 105                 110

Val Thr Val Ser Ser
        115

<210> SEQ ID NO 295
<211> LENGTH: 351
<212> TYPE: DNA
<213> ORGANISM: Homo Sapiens

<400> SEQUENCE: 295
caggtgcaac tggtggagtc tgggggaggc ttggtcaagc ctggagggtc cctgagactc      60
tcctgtgcag cctctggatt caccttcagt gactactaca tgagttggat ccgccaggct     120
ccagggaagg ggctggagtg ggtttcatac attagtatta gtggtactac catatactac     180
gcagactctg tgaagggccg attcaccatc tccagggaca cgccatgga ctcactgtat      240 ctgcaaatga acagcctgag agccgaggac acggccgtgt attactgtgc gagacggagc     300
agtggctggt acgactactg gggccaggga accctggtca ccgtctcctc a              351

<210> SEQ ID NO 296
<211> LENGTH: 444
<212> TYPE: PRT
<213> ORGANISM: Homo Sapiens

<400> SEQUENCE: 296

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ile Ser Gly Thr Thr Ile Tyr Tyr Ala Asp Ser Val
    50                  55                  60

-continued

```
Lys Gly Arg Phe Thr Ile Ser Arg Asp Asn Ala Met Asp Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Ser Gly Trp Tyr Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
                195                 200                 205

Thr Lys Val Asp Lys Arg Val Glu Ser Lys Tyr Gly Pro Pro Cys Pro
        210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
            435                 440
```

```
<210> SEQ ID NO 297
<211> LENGTH: 7
<212> TYPE: PRT
<213> ORGANISM: Homo Sapiens
```

-continued

```
<400> SEQUENCE: 297

Gln Arg Val Val Tyr Arg Tyr
1               5

<210> SEQ ID NO 298
<211> LENGTH: 3
<212> TYPE: PRT
<213> ORGANISM: Homo Sapiens

<400> SEQUENCE: 298

Gly Ala Phe
1

<210> SEQ ID NO 299
<211> LENGTH: 9
<212> TYPE: PRT
<213> ORGANISM: Homo Sapiens

<400> SEQUENCE: 299

His Gln Tyr Gly Ser Ser Pro Pro Thr
1               5

<210> SEQ ID NO 300
<211> LENGTH: 12
<212> TYPE: PRT
<213> ORGANISM: Homo Sapiens

<400> SEQUENCE: 300

Trp Ala Ser Gln Arg Val Val Tyr Arg Tyr Leu Ala
1               5                   10

<210> SEQ ID NO 301
<211> LENGTH: 7
<212> TYPE: PRT
<213> ORGANISM: Homo Sapiens

<400> SEQUENCE: 301

Gly Ala Phe Asn Arg Ala Thr
1               5

<210> SEQ ID NO 302
<211> LENGTH: 9
<212> TYPE: PRT
<213> ORGANISM: Homo Sapiens

<400> SEQUENCE: 302

His Gln Tyr Gly Ser Ser Pro Pro Thr
1               5

<210> SEQ ID NO 303
<211> LENGTH: 108
<212> TYPE: PRT
<213> ORGANISM: Homo Sapiens

<400> SEQUENCE: 303

Glu Ile Val Leu Thr Gln Ser Pro Gly Thr Leu Ser Leu Ser Pro Gly
1               5                   10                  15

Glu Arg Ala Thr Leu Ser Cys Trp Ala Ser Gln Arg Val Val Tyr Arg
            20                  25                  30

Tyr Leu Ala Trp Tyr Gln Arg Lys Pro Gly Gln Ala Pro Arg Leu Leu
        35                  40                  45

Ile Tyr Gly Ala Phe Asn Arg Ala Thr Gly Ile Pro Asp Arg Phe Ser
    50                  55                  60
```

```
Gly Ser Gly Ser Gly Thr Asp Phe Ser Leu Thr Ile Ser Arg Leu Glu
65                  70                  75                  80

Pro Glu Asp Phe Ala Val Tyr Tyr Cys His Gln Tyr Gly Ser Ser Pro
                85                  90                  95

Pro Thr Phe Gly Gln Gly Thr Lys Val Glu Ile Lys
            100                 105
```

```
<210> SEQ ID NO 304
<211> LENGTH: 324
<212> TYPE: DNA
<213> ORGANISM: Homo Sapiens

<400> SEQUENCE: 304
gaaattgtgt tgacgcagtc tccaggcacc ctgtctttgt ctccagggga aagagccacc      60
ctctcttgtt gggccagtca gagggttgtt tacagatact tagcctggta ccagcggaaa     120
cctggccagg ctcccagact tctcatttat ggtgcattca acagggccac tggcatccca     180
gacaggttca gtggcagtgg gtctgggaca gacttcagtc tcactatcag tagactggag     240
cctgaggatt ttgcagttta ttactgtcac caatatggta gttccaccac gacgttcggc     300
caagggacca aggtggaaat caaa                                            324
```

```
<210> SEQ ID NO 305
<211> LENGTH: 215
<212> TYPE: PRT
<213> ORGANISM: Homo Sapiens

<400> SEQUENCE: 305

Glu Ile Val Leu Thr Gln Ser Pro Gly Thr Leu Ser Leu Ser Pro Gly
1               5                   10                  15

Glu Arg Ala Thr Leu Ser Cys Trp Ala Ser Gln Arg Val Val Tyr Arg
                20                  25                  30

Tyr Leu Ala Trp Tyr Gln Arg Lys Pro Gly Gln Ala Pro Arg Leu Leu
            35                  40                  45

Ile Tyr Gly Ala Phe Asn Arg Ala Thr Gly Ile Pro Asp Arg Phe Ser
        50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys His Gln Tyr Gly Ser Ser Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

```
<210> SEQ ID NO 306
<211> LENGTH: 8
<212> TYPE: PRT
<213> ORGANISM: Homo Sapiens

<400> SEQUENCE: 306

Gly Phe Thr Phe Ser Asp Tyr Tyr
1               5

<210> SEQ ID NO 307
<211> LENGTH: 8
<212> TYPE: PRT
<213> ORGANISM: Homo Sapiens

<400> SEQUENCE: 307

Ile Ser Ile Ser Gly Ser Thr Ile
1               5

<210> SEQ ID NO 308
<211> LENGTH: 10
<212> TYPE: PRT
<213> ORGANISM: Homo Sapiens

<400> SEQUENCE: 308

Ala Arg Arg Ser Ser Gly Trp Tyr Asp Tyr
1               5               10

<210> SEQ ID NO 309
<211> LENGTH: 5
<212> TYPE: PRT
<213> ORGANISM: Homo Sapiens

<400> SEQUENCE: 309

Asp Tyr Tyr Met Ser
1               5

<210> SEQ ID NO 310
<211> LENGTH: 17
<212> TYPE: PRT
<213> ORGANISM: Homo Sapiens

<400> SEQUENCE: 310

Tyr Ile Ser Ile Ser Gly Ser Thr Ile Tyr Tyr Ala Asp Ser Val Lys
1               5               10              15

Gly

<210> SEQ ID NO 311
<211> LENGTH: 8
<212> TYPE: PRT
<213> ORGANISM: Homo Sapiens

<400> SEQUENCE: 311

Arg Ser Ser Gly Trp Tyr Asp Tyr
1               5

<210> SEQ ID NO 312
<211> LENGTH: 117
<212> TYPE: PRT
<213> ORGANISM: Homo Sapiens

<400> SEQUENCE: 312

Gln Val Gln Leu Val Glu Ser Gly Gly Gly Leu Val Lys Pro Gly Gly
1               5               10              15
```

-continued

---

```
Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ile Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Ser Gly Trp Tyr Asp Tyr Trp Gly Gln Gly Thr Leu
            100                 105                 110

Val Thr Val Ser Ser
        115

<210> SEQ ID NO 313
<211> LENGTH: 351
<212> TYPE: DNA
<213> ORGANISM: Homo Sapiens

<400> SEQUENCE: 313
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtatta gtggtagtac catatactac     180
gcagactctg tgaagggccg attcaccatc tccagggaca cgccaagaa ctcactgtat      240 ctgcaaatga acagcctgag agccgaggac acggccgtgt attactgtgc gagaagaagc      300
agtggctggt acgactactg gggccaggga accctggtca ccgtctcctc a               351

<210> SEQ ID NO 314
<211> LENGTH: 444
<212> TYPE: PRT
<213> ORGANISM: Homo Sapiens

<400> SEQUENCE: 314

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ile Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Ser Gly Trp Tyr Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160
```

-continued

```
Gly Ala Leu Thr Ser Gly Val His Thr Phe Pro Ala Val Leu Gln Ser
            165             170             175

Ser Gly Leu Tyr Ser Leu Ser Ser Val Val Thr Val Pro Ser Ser Ser
            180             185             190

Leu Gly Thr Lys Thr Tyr Thr Cys Asn Val Asp His Lys Pro Ser Asn
            195             200             205

Thr Lys Val Asp Lys Arg Val Glu Ser Lys Tyr Gly Pro Pro Cys Pro
    210             215             220

Pro Cys Pro Ala Pro Glu Phe Glu Gly Gly Pro Ser Val Phe Leu Phe
225             230             235             240

Pro Pro Lys Pro Lys Asp Thr Leu Met Ile Ser Arg Thr Pro Glu Val
            245             250             255

Thr Cys Val Val Val Asp Val Ser Gln Glu Asp Pro Glu Val Gln Phe
            260             265             270

Asn Trp Tyr Val Asp Gly Val Glu Val His Asn Ala Lys Thr Lys Pro
            275             280             285

Arg Glu Glu Gln Phe Asn Ser Thr Tyr Arg Val Val Ser Val Leu Thr
    290             295             300

Val Leu His Gln Asp Trp Leu Asn Gly Lys Glu Tyr Lys Cys Lys Val
305             310             315             320

Ser Asn Lys Gly Leu Pro Ser Ser Ile Glu Lys Thr Ile Ser Lys Ala
            325             330             335

Lys Gly Gln Pro Arg Glu Pro Gln Val Tyr Thr Leu Pro Pro Ser Gln
            340             345             350

Glu Glu Met Thr Lys Asn Gln Val Ser Leu Thr Cys Leu Val Lys Gly
            355             360             365

Phe Tyr Pro Ser Asp Ile Ala Val Glu Trp Glu Ser Asn Gly Gln Pro
    370             375             380

Glu Asn Asn Tyr Lys Thr Thr Pro Pro Val Leu Asp Ser Asp Gly Ser
385             390             395             400

Phe Phe Leu Tyr Ser Arg Leu Thr Val Asp Lys Ser Arg Trp Gln Glu
            405             410             415

Gly Asn Val Phe Ser Cys Ser Val Met His Glu Ala Leu His Asn His
            420             425             430

Tyr Thr Gln Lys Ser Leu Ser Leu Ser Leu Gly Lys
            435             440

<210> SEQ ID NO 315
<211> LENGTH: 7
<212> TYPE: PRT
<213> ORGANISM: Homo Sapiens

<400> SEQUENCE: 315

Gln Ser Val Ser Ser Asn Tyr
1               5

<210> SEQ ID NO 316
<211> LENGTH: 3
<212> TYPE: PRT
<213> ORGANISM: Homo Sapiens

<400> SEQUENCE: 316

Gly Ala Ser
1

<210> SEQ ID NO 317
```

-continued

```
<211> LENGTH: 9
<212> TYPE: PRT
<213> ORGANISM: Homo Sapiens

<400> SEQUENCE: 317

His Gln Tyr Gly Ser Ser Pro Pro Thr
1               5

<210> SEQ ID NO 318
<211> LENGTH: 12
<212> TYPE: PRT
<213> ORGANISM: Homo Sapiens

<400> SEQUENCE: 318

Arg Ala Ser Gln Ser Val Ser Ser Asn Tyr Leu Ala
1               5                   10

<210> SEQ ID NO 319
<211> LENGTH: 7
<212> TYPE: PRT
<213> ORGANISM: Homo Sapiens

<400> SEQUENCE: 319

Gly Ala Ser Ile Arg Ala Thr
1               5

<210> SEQ ID NO 320
<211> LENGTH: 9
<212> TYPE: PRT
<213> ORGANISM: Homo Sapiens

<400> SEQUENCE: 320

His Gln Tyr Gly Ser Ser Pro Pro Thr
1               5

<210> SEQ ID NO 321
<211> LENGTH: 108
<212> TYPE: PRT
<213> ORGANISM: Homo Sapiens

<400> SEQUENCE: 321

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Cys Cys His Gln Tyr Gly Ser Ser Pro
                85                  90                  95

Pro Thr Phe Gly Gln Gly Thr Lys Val Glu Ile Lys
            100                 105

<210> SEQ ID NO 322
<211> LENGTH: 324
<212> TYPE: DNA
<213> ORGANISM: Homo Sapiens

<400> SEQUENCE: 322
```

```
gaaattgtgt tgacgcagtc tccaggcacc ctgtctttgt ctccagggga aagagccacc        60
ctctcctgca gggccagtca gagtgttagc agcaactact tagcctggta ccagcagaaa       120
cctggccagg ctcccaggct cctcatctat ggtgcatcca tcagggccac tggcatccca       180
gacaggttca gtggcagtgg gtctgggaca gacttcactc tcaccatcag cagactggag       240
cctgaagatt ttgcagtgta ttgctgtcac cagtatggta gctcacctcc gacgttcggc       300
caagggacca aggtggaaat caaa                                               324
```

```
<210> SEQ ID NO 323
<211> LENGTH: 215
<212> TYPE: PRT
<213> ORGANISM: Homo Sapiens

<400> SEQUENCE: 323

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
                20                  25                  30

Tyr Leu Ala Trp Tyr Gln Gln Lys Pro Gly Gln Ala Pro Arg Leu Leu
            35                  40                  45

Ile Tyr Gly Ala Ser Ile Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Cys Cys His Gln Tyr Gly Ser Ser Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
        210                 215
```

```
<210> SEQ ID NO 324
<211> LENGTH: 8
<212> TYPE: PRT
<213> ORGANISM: Homo Sapiens

<400> SEQUENCE: 324

Gly Phe Thr Phe Ser Asp Tyr Phe
1               5
```

```
<210> SEQ ID NO 325
<211> LENGTH: 8
<212> TYPE: PRT
<213> ORGANISM: Homo Sapiens
```

```
<400> SEQUENCE: 325

Ile Ser Ile Ser Gly Ser Thr Ile
1               5

<210> SEQ ID NO 326
<211> LENGTH: 10
<212> TYPE: PRT
<213> ORGANISM: Homo Sapiens

<400> SEQUENCE: 326

Ala Arg Arg Thr Ser Gly Trp Tyr Asp Phe
1               5               10

<210> SEQ ID NO 327
<211> LENGTH: 5
<212> TYPE: PRT
<213> ORGANISM: Homo Sapiens

<400> SEQUENCE: 327

Asp Tyr Phe Met Ser
1               5

<210> SEQ ID NO 328
<211> LENGTH: 17
<212> TYPE: PRT
<213> ORGANISM: Homo Sapiens

<400> SEQUENCE: 328

Tyr Ile Ser Ile Ser Gly Ser Thr Ile Tyr Tyr Ala Asp Ser Val Lys
1               5               10              15

Gly

<210> SEQ ID NO 329
<211> LENGTH: 8
<212> TYPE: PRT
<213> ORGANISM: Homo Sapiens

<400> SEQUENCE: 329

Arg Thr Ser Gly Trp Tyr Asp Phe
1               5

<210> SEQ ID NO 330
<211> LENGTH: 117
<212> TYPE: PRT
<213> ORGANISM: Homo Sapiens

<400> SEQUENCE: 330

Gln Val Gln Leu Val Glu Ser Gly Gly Gly Leu Val Lys Pro Gly Gly
1               5               10              15

Ser Leu Arg Leu Ser Cys Ala Ala Ser Gly Phe Thr Phe Ser Asp Tyr
            20              25              30

Phe Met Ser Trp Ile Arg Gln Ala Pro Gly Lys Gly Leu Glu Trp Val
            35              40              45

Ser Tyr Ile Ser Ile Ser Gly Ser Thr Ile Tyr Tyr Ala Asp Ser Val
        50              55              60

Lys Gly Arg Phe Thr Ile Ser Arg Asp Asn Ala Arg Asn Ser Leu Phe
65              70              75              80

Leu Gln Met Asn Ser Leu Arg Ala Glu Asp Thr Ala Ile Tyr Tyr Cys
                85              90              95

Ala Arg Arg Thr Ser Gly Trp Tyr Asp Phe Trp Gly Gln Gly Thr Leu
            100             105             110
```

Val Thr Val Ser Ser
        115

<210> SEQ ID NO 331
<211> LENGTH: 351
<212> TYPE: DNA
<213> ORGANISM: Homo Sapiens

<400> SEQUENCE: 331
caggtgcagc tggtggagtc tggggggaggc ttggtcaagc ctggagggtc cctgcgactc      60
tcctgtgcag cctctggatt caccttcagt gactacttca tgagctggat ccgccaggct     120
ccagggaagg ggctggagtg ggtttcgtac attagtatta gtggtagtac catatactac     180
gcagactctg tgaagggccg attcaccatc tccagggaca cgccaggaa ctcactgttt       240 ctgcaaatga acagcctgag agccgaggac acggccatct attactgtgc gagaagaacc     300
agtggctggt acgacttctg gggccaggga accctggtca ccgtctcctc a              351

<210> SEQ ID NO 332
<211> LENGTH: 444
<212> TYPE: PRT
<213> ORGANISM: Homo Sapiens

<400> SEQUENCE: 332

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Phe Met Ser Trp Ile Arg Gln Ala Pro Gly Lys Gly Leu Glu Trp Val
        35                  40                  45

Ser Tyr Ile Ser Ile Ser Gly Ser Thr Ile Tyr Tyr Ala Asp Ser Val
    50                  55                  60

Lys Gly Arg Phe Thr Ile Ser Arg Asp Asn Ala Arg Asn Ser Leu Phe
65                  70                  75                  80

Leu Gln Met Asn Ser Leu Arg Ala Glu Asp Thr Ala Ile Tyr Tyr Cys
                85                  90                  95

Ala Arg Arg Thr Ser Gly Trp Tyr Asp Phe Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
        210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

-continued

```
Thr Cys Val Val Val Asp Val Ser Gln Glu Asp Pro Glu Val Gln Phe
          260             265             270

Asn Trp Tyr Val Asp Gly Val Glu Val His Asn Ala Lys Thr Lys Pro
          275             280             285

Arg Glu Glu Gln Phe Asn Ser Thr Tyr Arg Val Val Ser Val Leu Thr
          290             295             300

Val Leu His Gln Asp Trp Leu Asn Gly Lys Glu Tyr Lys Cys Lys Val
305             310             315             320

Ser Asn Lys Gly Leu Pro Ser Ser Ile Glu Lys Thr Ile Ser Lys Ala
          325             330             335

Lys Gly Gln Pro Arg Glu Pro Gln Val Tyr Thr Leu Pro Pro Ser Gln
          340             345             350

Glu Glu Met Thr Lys Asn Gln Val Ser Leu Thr Cys Leu Val Lys Gly
          355             360             365

Phe Tyr Pro Ser Asp Ile Ala Val Glu Trp Glu Ser Asn Gly Gln Pro
          370             375             380

Glu Asn Asn Tyr Lys Thr Thr Pro Pro Val Leu Asp Ser Asp Gly Ser
385             390             395             400

Phe Phe Leu Tyr Ser Arg Leu Thr Val Asp Lys Ser Arg Trp Gln Glu
          405             410             415

Gly Asn Val Phe Ser Cys Ser Val Met His Glu Ala Leu His Asn His
          420             425             430

Tyr Thr Gln Lys Ser Leu Ser Leu Ser Leu Gly Lys
          435             440
```

```
<210> SEQ ID NO 333
<211> LENGTH: 7
<212> TYPE: PRT
<213> ORGANISM: Homo Sapiens

<400> SEQUENCE: 333

Gln Ser Val Ser Tyr Ser Tyr
1               5
```

```
<210> SEQ ID NO 334
<211> LENGTH: 3
<212> TYPE: PRT
<213> ORGANISM: Homo Sapiens

<400> SEQUENCE: 334

Gly Ala Ser
1
```

```
<210> SEQ ID NO 335
<211> LENGTH: 9
<212> TYPE: PRT
<213> ORGANISM: Homo Sapiens

<400> SEQUENCE: 335

His Gln Tyr Gly Ser Ser Pro Pro Thr
1               5
```

```
<210> SEQ ID NO 336
<211> LENGTH: 12
<212> TYPE: PRT
<213> ORGANISM: Homo Sapiens

<400> SEQUENCE: 336

Arg Ala Ser Gln Ser Val Ser Tyr Ser Tyr Leu Ala
```

-continued

```
1              5              10
```

<210> SEQ ID NO 337
<211> LENGTH: 7
<212> TYPE: PRT
<213> ORGANISM: Homo Sapiens

<400> SEQUENCE: 337

```
Gly Ala Ser Ser Arg Ala Thr
1               5
```

<210> SEQ ID NO 338
<211> LENGTH: 9
<212> TYPE: PRT
<213> ORGANISM: Homo Sapiens

<400> SEQUENCE: 338

```
His Gln Tyr Gly Ser Ser Pro Pro Thr
1               5
```

<210> SEQ ID NO 339
<211> LENGTH: 108
<212> TYPE: PRT
<213> ORGANISM: Homo Sapiens

<400> SEQUENCE: 339

```
Glu Ile Val Leu Thr Gln Ser Pro Gly Thr Leu Ser Leu Ser Pro Gly
1               5               10              15

Glu Arg Ala Thr Leu Ser Cys Arg Ala Ser Gln Ser Val Ser Tyr Ser
            20              25              30

Tyr Leu Ala Trp Tyr Gln Gln Lys Pro Gly Gln Ala Pro Arg Leu Leu
        35              40              45

Ile Tyr Gly Ala Ser Ser Arg Ala Thr Gly Ile Pro Asp Arg Phe Ser
    50              55              60

Gly Ser Gly Ser Gly Thr Asp Phe Thr Leu Thr Ile Ser Arg Leu Glu
65              70              75              80

Pro Glu Asp Phe Ala Val Tyr Cys Cys His Gln Tyr Gly Ser Ser Pro
            85              90              95

Pro Thr Phe Gly Gln Gly Thr Lys Val Glu Ile Lys
        100             105
```

<210> SEQ ID NO 340
<211> LENGTH: 324
<212> TYPE: DNA
<213> ORGANISM: Homo Sapiens

<400> SEQUENCE: 340

```
gaaattgtgt tgacgcagtc tccaggcacc ctgtctttgt ctccagggga aagagccacc      60
ctctcctgca gggccagtca gagtgttagc tacagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttgttgtcac cagtatggta gttcacctcc gacgttcggc     300
caagggacca aggtggaaat caaa                                           324
```

<210> SEQ ID NO 341
<211> LENGTH: 215
<212> TYPE: PRT
<213> ORGANISM: Homo Sapiens -continued

```
<400> SEQUENCE: 341

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Tyr Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Cys Cys His Gln Tyr Gly Ser Ser Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 342
<211> LENGTH: 8
<212> TYPE: PRT
<213> ORGANISM: Homo Sapiens

<400> SEQUENCE: 342

Gly Phe Thr Phe Ser Asp Phe Tyr
1               5

<210> SEQ ID NO 343
<211> LENGTH: 8
<212> TYPE: PRT
<213> ORGANISM: Homo Sapiens

<400> SEQUENCE: 343

Ile Ser Ile Ser Gly Thr Thr Ile
1               5

<210> SEQ ID NO 344
<211> LENGTH: 10
<212> TYPE: PRT
<213> ORGANISM: Homo Sapiens

<400> SEQUENCE: 344

Ala Arg Arg Thr Ser Gly Trp Tyr Asp Phe
1               5                   10

<210> SEQ ID NO 345
```

<211> LENGTH: 5
<212> TYPE: PRT
<213> ORGANISM: Homo Sapiens

<400> SEQUENCE: 345

Asp Phe Tyr Met Ser
1               5

<210> SEQ ID NO 346
<211> LENGTH: 17
<212> TYPE: PRT
<213> ORGANISM: Homo Sapiens

<400> SEQUENCE: 346

Tyr Ile Ser Ile Ser Gly Thr Thr Ile Tyr Tyr Ala Asp Ser Val Lys
1               5                   10                  15

Gly

<210> SEQ ID NO 347
<211> LENGTH: 8
<212> TYPE: PRT
<213> ORGANISM: Homo Sapiens

<400> SEQUENCE: 347

Arg Thr Ser Gly Trp Tyr Asp Phe
1               5

<210> SEQ ID NO 348
<211> LENGTH: 117
<212> TYPE: PRT
<213> ORGANISM: Homo Sapiens

<400> SEQUENCE: 348

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Phe
            20                  25                  30

Tyr Met Ser Trp Ile Arg Gln Ala Pro Gly Arg Gly Leu Glu Trp Val
        35                  40                  45

Ser Tyr Ile Ser Ile Ser Gly Thr Thr Ile Tyr Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Ser Gly Trp Tyr Asp Phe Trp Gly Gln Gly Thr Leu
            100                 105                 110

Val Thr Val Ser Ser
        115

<210> SEQ ID NO 349
<211> LENGTH: 351
<212> TYPE: DNA
<213> ORGANISM: Homo Sapiens

<400> SEQUENCE: 349
caggtgcagc tggtggagtc tgggggaggc ttggtcaagc ctggagggtc ccttagactc      60
tcctgtgcag cctctggatt caccttcagt gacttctaca tgagctggat ccgccaggct     120
ccagggaggg ggctggagtg ggtttcgtac attagtatta gtggtactac catatactac     180

-continued

```
gcagactctg tgaagggccg attcaccatc tccagggaca acgccaggaa ctcactgtat      240
ctgcaaatga acagcctgag agccgaggac acggccgtgt attactgtgc gagaagaacc      300
agtggctggt acgacttctg gggccaggga accctggtca ccgtctcctc a              351

<210> SEQ ID NO 350
<211> LENGTH: 444
<212> TYPE: PRT
<213> ORGANISM: Homo Sapiens

<400> SEQUENCE: 350

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Phe
            20                  25                  30

Tyr Met Ser Trp Ile Arg Gln Ala Pro Gly Arg Gly Leu Glu Trp Val
        35                  40                  45

Ser Tyr Ile Ser Ile Ser Gly Thr Thr Ile Tyr Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Ser Gly Trp Tyr Asp Phe Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350
```

-continued

```
Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
        435                 440
```

```
<210> SEQ ID NO 351
<211> LENGTH: 7
<212> TYPE: PRT
<213> ORGANISM: Homo Sapiens

<400> SEQUENCE: 351

Gln Ser Val Ser Tyr Ser Tyr
1               5
```

```
<210> SEQ ID NO 352
<211> LENGTH: 3
<212> TYPE: PRT
<213> ORGANISM: Homo Sapiens

<400> SEQUENCE: 352

Gly Ala Ser
1
```

```
<210> SEQ ID NO 353
<211> LENGTH: 9
<212> TYPE: PRT
<213> ORGANISM: Homo Sapiens

<400> SEQUENCE: 353

His Gln Tyr Gly Ser Ser Pro Pro Thr
1               5
```

```
<210> SEQ ID NO 354
<211> LENGTH: 12
<212> TYPE: PRT
<213> ORGANISM: Homo Sapiens

<400> SEQUENCE: 354

Arg Ala Ser Gln Ser Val Ser Tyr Ser Tyr Leu Ala
1               5                   10
```

```
<210> SEQ ID NO 355
<211> LENGTH: 7
<212> TYPE: PRT
<213> ORGANISM: Homo Sapiens

<400> SEQUENCE: 355

Gly Ala Ser Ser Arg Ala Thr
1               5
```

```
<210> SEQ ID NO 356
<211> LENGTH: 9
<212> TYPE: PRT
<213> ORGANISM: Homo Sapiens
```

<400> SEQUENCE: 356

His Gln Tyr Gly Ser Ser Pro Pro Thr
1               5

<210> SEQ ID NO 357
<211> LENGTH: 108
<212> TYPE: PRT
<213> ORGANISM: Homo Sapiens

<400> SEQUENCE: 357

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Tyr Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Cys Cys His Gln Tyr Gly Ser Ser Pro
                85                  90                  95

Pro Thr Phe Gly Gln Gly Thr Lys Val Glu Met Lys
            100                 105

<210> SEQ ID NO 358
<211> LENGTH: 324
<212> TYPE: DNA
<213> ORGANISM: Homo Sapiens

<400> SEQUENCE: 358
gaaattgtgt tgacgcagtc tccaggcacc ctgtctttgt ctccagggga aagagccacc      60
ctctcctgca gggccagtca gagtgttagc tacagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttgctgtcac cagtatggta gttcacctcc gacgttcggc     300
caagggacca aggtggaaat gaaa                                            324

<210> SEQ ID NO 359
<211> LENGTH: 215
<212> TYPE: PRT
<213> ORGANISM: Homo Sapiens

<400> SEQUENCE: 359

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Tyr Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Cys Cys His Gln Tyr Gly Ser Ser Pro

-continued

```
                          85                  90                  95

Pro Thr Phe Gly Gln Gly Thr Lys Val Glu Met Lys Arg Thr Val Ala
                100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 360
<211> LENGTH: 8
<212> TYPE: PRT
<213> ORGANISM: Homo Sapiens

<400> SEQUENCE: 360

Gly Phe Thr Phe Ser Asp Tyr Tyr
1               5

<210> SEQ ID NO 361
<211> LENGTH: 8
<212> TYPE: PRT
<213> ORGANISM: Homo Sapiens

<400> SEQUENCE: 361

Ile Ser Ile Ser Gly Ser Thr Ile
1               5

<210> SEQ ID NO 362
<211> LENGTH: 10
<212> TYPE: PRT
<213> ORGANISM: Homo Sapiens

<400> SEQUENCE: 362

Ala Arg Arg Thr Ser Gly Trp Tyr Asp Phe
1               5                   10

<210> SEQ ID NO 363
<211> LENGTH: 5
<212> TYPE: PRT
<213> ORGANISM: Homo Sapiens

<400> SEQUENCE: 363

Asp Tyr Tyr Met Ser
1               5

<210> SEQ ID NO 364
<211> LENGTH: 17
<212> TYPE: PRT
<213> ORGANISM: Homo Sapiens

<400> SEQUENCE: 364

Tyr Ile Ser Ile Ser Gly Ser Thr Ile Tyr Tyr Ala Asp Ser Val Lys
```

-continued

```
1               5                10               15

Gly

<210> SEQ ID NO 365
<211> LENGTH: 8
<212> TYPE: PRT
<213> ORGANISM: Homo Sapiens

<400> SEQUENCE: 365

Arg Thr Ser Gly Trp Tyr Asp Phe
1               5

<210> SEQ ID NO 366
<211> LENGTH: 117
<212> TYPE: PRT
<213> ORGANISM: Homo Sapiens

<400> SEQUENCE: 366

Gln Val Gln Leu Val Glu Ser Gly Gly Gly Leu Val Arg Pro Gly Gly
1               5                10               15

Ser Leu Arg Leu Ser Cys Ala Ala Ser Gly Phe Thr Phe Ser Asp Tyr
            20               25               30

Tyr Met Ser Trp Ile Arg Gln Ala Pro Gly Lys Gly Leu Glu Trp Val
            35               40               45

Ser Tyr Ile Ser Ile Ser Gly Ser Thr Ile Tyr Tyr Ala Asp Ser Val
        50               55               60

Lys Gly Arg Phe Thr Ile Ser Arg Asp Asn Ala Arg Asp Ser Leu Tyr
65               70               75               80

Leu Gln Met Asn Ser Leu Arg Ala Glu Asp Thr Ala Val Tyr Tyr Cys
            85               90               95

Ala Arg Arg Thr Ser Gly Trp Tyr Asp Phe Trp Gly Gln Gly Thr Leu
            100              105              110

Val Thr Val Ser Ser
        115

<210> SEQ ID NO 367
<211> LENGTH: 351
<212> TYPE: DNA
<213> ORGANISM: Homo Sapiens

<400> SEQUENCE: 367
caggtgcagc tggtggagtc tgggggaggc ttggtcaggc ctggagggtc cctgagactc      60
tcctgtgcag cctctggatt caccttcagt gactactaca tgagctggat ccgccaggct     120
ccagggaagg ggctggagtg ggtttcgtac attagtatta gtggtagtac catatactac     180
gcagactctg tgaagggccg attcaccatc tccagggaca cgccaggga ctcactttat      240 ctgcaaatga acagcctgag agccgaggac acggccgtgt attactgtgc gagaagaacc     300
agtggctggt acgacttctg gggccaggga accctggtca ccgtctcctc a              351

<210> SEQ ID NO 368
<211> LENGTH: 444
<212> TYPE: PRT
<213> ORGANISM: Homo Sapiens

<400> SEQUENCE: 368

Gln Val Gln Leu Val Glu Ser Gly Gly Gly Leu Val Arg Pro Gly Gly
1               5                10               15

Ser Leu Arg Leu Ser Cys Ala Ala Ser Gly Phe Thr Phe Ser Asp Tyr
```

-continued

```
                20              25              30
Tyr Met Ser Trp Ile Arg Gln Ala Pro Gly Lys Gly Leu Glu Trp Val
        35              40              45
Ser Tyr Ile Ser Ile Ser Gly Ser Thr Ile Tyr Tyr Ala Asp Ser Val
    50              55              60
Lys Gly Arg Phe Thr Ile Ser Arg Asp Asn Ala Arg Asp Ser Leu Tyr
65              70              75              80
Leu Gln Met Asn Ser Leu Arg Ala Glu Asp Thr Ala Val Tyr Tyr Cys
                85              90              95
Ala Arg Arg Thr Ser Gly Trp Tyr Asp Phe Trp Gly Gln Gly Thr Leu
            100             105             110
Val Thr Val Ser Ser Ala Ser Thr Lys Gly Pro Ser Val Phe Pro Leu
            115             120             125
Ala Pro Cys Ser Arg Ser Thr Ser Glu Ser Thr Ala Ala Leu Gly Cys
        130             135             140
Leu Val Lys Asp Tyr Phe Pro Glu Pro Val Thr Val Ser Trp Asn Ser
145             150             155             160
Gly Ala Leu Thr Ser Gly Val His Thr Phe Pro Ala Val Leu Gln Ser
            165             170             175
Ser Gly Leu Tyr Ser Leu Ser Ser Val Val Thr Val Pro Ser Ser Ser
            180             185             190
Leu Gly Thr Lys Thr Tyr Thr Cys Asn Val Asp His Lys Pro Ser Asn
        195             200             205
Thr Lys Val Asp Lys Arg Val Glu Ser Lys Tyr Gly Pro Pro Cys Pro
        210             215             220
Pro Cys Pro Ala Pro Glu Phe Glu Gly Gly Pro Ser Val Phe Leu Phe
225             230             235             240
Pro Pro Lys Pro Lys Asp Thr Leu Met Ile Ser Arg Thr Pro Glu Val
            245             250             255
Thr Cys Val Val Val Asp Val Ser Gln Glu Asp Pro Glu Val Gln Phe
            260             265             270
Asn Trp Tyr Val Asp Gly Val Glu Val His Asn Ala Lys Thr Lys Pro
        275             280             285
Arg Glu Glu Gln Phe Asn Ser Thr Tyr Arg Val Val Ser Val Leu Thr
    290             295             300
Val Leu His Gln Asp Trp Leu Asn Gly Lys Glu Tyr Lys Cys Lys Val
305             310             315             320
Ser Asn Lys Gly Leu Pro Ser Ser Ile Glu Lys Thr Ile Ser Lys Ala
            325             330             335
Lys Gly Gln Pro Arg Glu Pro Gln Val Tyr Thr Leu Pro Pro Ser Gln
            340             345             350
Glu Glu Met Thr Lys Asn Gln Val Ser Leu Thr Cys Leu Val Lys Gly
        355             360             365
Phe Tyr Pro Ser Asp Ile Ala Val Glu Trp Glu Ser Asn Gly Gln Pro
    370             375             380
Glu Asn Asn Tyr Lys Thr Thr Pro Pro Val Leu Asp Ser Asp Gly Ser
385             390             395             400
Phe Phe Leu Tyr Ser Arg Leu Thr Val Asp Lys Ser Arg Trp Gln Glu
            405             410             415
Gly Asn Val Phe Ser Cys Ser Val Met His Glu Ala Leu His Asn His
            420             425             430
Tyr Thr Gln Lys Ser Leu Ser Leu Ser Leu Gly Lys
        435             440
```

```
<210> SEQ ID NO 369
<211> LENGTH: 7
<212> TYPE: PRT
<213> ORGANISM: Homo Sapiens

<400> SEQUENCE: 369

Gln Ser Val Ser Tyr Arg Tyr
1               5

<210> SEQ ID NO 370
<211> LENGTH: 3
<212> TYPE: PRT
<213> ORGANISM: Homo Sapiens

<400> SEQUENCE: 370

Gly Ala Ser
1

<210> SEQ ID NO 371
<211> LENGTH: 9
<212> TYPE: PRT
<213> ORGANISM: Homo Sapiens

<400> SEQUENCE: 371

His Gln Tyr Gly Ser Ser Pro Pro Thr
1               5

<210> SEQ ID NO 372
<211> LENGTH: 12
<212> TYPE: PRT
<213> ORGANISM: Homo Sapiens

<400> SEQUENCE: 372

Arg Ala Ser Gln Ser Val Ser Tyr Arg Tyr Leu Ala
1               5                   10

<210> SEQ ID NO 373
<211> LENGTH: 7
<212> TYPE: PRT
<213> ORGANISM: Homo Sapiens

<400> SEQUENCE: 373

Gly Ala Ser Ser Arg Ala Thr
1               5

<210> SEQ ID NO 374
<211> LENGTH: 9
<212> TYPE: PRT
<213> ORGANISM: Homo Sapiens

<400> SEQUENCE: 374

His Gln Tyr Gly Ser Ser Pro Pro Thr
1               5

<210> SEQ ID NO 375
<211> LENGTH: 108
<212> TYPE: PRT
<213> ORGANISM: Homo Sapiens

<400> SEQUENCE: 375

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Tyr Arg
```

-continued

```
                20                    25                    30

Tyr Leu Ala Trp Tyr Gln Gln Lys Pro Gly Gln Ala Pro Arg Leu Leu
        35                    40                    45

Ile Tyr Gly Ala Ser Ser Arg Ala Thr Gly Ile Pro Asp Arg Phe Ser
    50                    55                    60

Gly Ser Gly Ser Gly Thr Asp Phe Thr Leu Thr Ile Ser Arg Leu Glu
65                    70                    75                    80

Pro Glu Asp Phe Ala Val Tyr Cys Cys His Gln Tyr Gly Ser Ser Pro
                85                    90                    95

Pro Thr Phe Gly Gln Gly Thr Lys Val Glu Ile Lys
            100                   105
```

```
<210> SEQ ID NO 376
<211> LENGTH: 324
<212> TYPE: DNA
<213> ORGANISM: Homo Sapiens

<400> SEQUENCE: 376
gaaattgtgt tgacgcagtc tccaggcacc ctgtctttgt ctccagggga aagagccacc        60
ctctcctgta gggccagtca gagtgttagc tacaggtact tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt ttgcagtgta ttgctgtcac cagtatggta gttcacctcc gacgttcggc       300
caagggacca aggtggaaat caaa                                               324
```

```
<210> SEQ ID NO 377
<211> LENGTH: 215
<212> TYPE: PRT
<213> ORGANISM: Homo Sapiens

<400> SEQUENCE: 377

Glu Ile Val Leu Thr Gln Ser Pro Gly Thr Leu Ser Leu Ser Pro Gly
1               5                    10                    15

Glu Arg Ala Thr Leu Ser Cys Arg Ala Ser Gln Ser Val Ser Tyr Arg
            20                    25                    30

Tyr Leu Ala Trp Tyr Gln Gln Lys Pro Gly Gln Ala Pro Arg Leu Leu
        35                    40                    45

Ile Tyr Gly Ala Ser Ser Arg Ala Thr Gly Ile Pro Asp Arg Phe Ser
    50                    55                    60

Gly Ser Gly Ser Gly Thr Asp Phe Thr Leu Thr Ile Ser Arg Leu Glu
65                    70                    75                    80

Pro Glu Asp Phe Ala Val Tyr Cys Cys His Gln Tyr Gly Ser Ser Pro
                85                    90                    95

Pro Thr Phe Gly Gln Gly Thr Lys Val Glu Ile Lys Arg Thr Val Ala
            100                   105                   110

Ala Pro Ser Val Phe Ile Phe Pro Pro Ser Asp Glu Gln Leu Lys Ser
        115                   120                   125

Gly Thr Ala Ser Val Val Cys Leu Leu Asn Asn Phe Tyr Pro Arg Glu
    130                   135                   140

Ala Lys Val Gln Trp Lys Val Asp Asn Ala Leu Gln Ser Gly Asn Ser
145                   150                   155                   160

Gln Glu Ser Val Thr Glu Gln Asp Ser Lys Asp Ser Thr Tyr Ser Leu
                165                   170                   175

Ser Ser Thr Leu Thr Leu Ser Lys Ala Asp Tyr Glu Lys His Lys Val
```

-continued

```
                180              185              190

Tyr Ala Cys Glu Val Thr His Gln Gly Leu Ser Ser Pro Val Thr Lys
        195              200              205

Ser Phe Asn Arg Gly Glu Cys
    210              215

<210> SEQ ID NO 378
<211> LENGTH: 8
<212> TYPE: PRT
<213> ORGANISM: Homo Sapiens

<400> SEQUENCE: 378

Gly Phe Thr Phe Ser Asp Tyr Tyr
1               5

<210> SEQ ID NO 379
<211> LENGTH: 8
<212> TYPE: PRT
<213> ORGANISM: Homo Sapiens

<400> SEQUENCE: 379

Ile Ser Ile Ser Gly Ile Thr Ile
1               5

<210> SEQ ID NO 380
<211> LENGTH: 10
<212> TYPE: PRT
<213> ORGANISM: Homo Sapiens

<400> SEQUENCE: 380

Ala Arg Arg Ser Ser Gly Trp Tyr Asp Tyr
1               5                   10

<210> SEQ ID NO 381
<211> LENGTH: 5
<212> TYPE: PRT
<213> ORGANISM: Homo Sapiens

<400> SEQUENCE: 381

Asp Tyr Tyr Met Ser
1               5

<210> SEQ ID NO 382
<211> LENGTH: 17
<212> TYPE: PRT
<213> ORGANISM: Homo Sapiens

<400> SEQUENCE: 382

Tyr Ile Ser Ile Ser Gly Ile Thr Ile Tyr Tyr Ala Asp Ser Val Lys
1               5                   10                  15

Gly

<210> SEQ ID NO 383
<211> LENGTH: 8
<212> TYPE: PRT
<213> ORGANISM: Homo Sapiens

<400> SEQUENCE: 383

Arg Ser Ser Gly Trp Tyr Asp Tyr
1               5

<210> SEQ ID NO 384
<211> LENGTH: 117
```

```
<212> TYPE: PRT
<213> ORGANISM: Homo Sapiens

<400> SEQUENCE: 384

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ile Ser Gly Ile Thr Ile Tyr Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Ser Gly Trp Tyr Asp Tyr Trp Gly Gln Gly Thr Leu
            100                 105                 110

Val Thr Val Ser Ser
        115

<210> SEQ ID NO 385
<211> LENGTH: 351
<212> TYPE: DNA
<213> ORGANISM: Homo Sapiens

<400> SEQUENCE: 385
caagttcagt tggttgagtc tggcggcgga ctggttaagc ctggcggatc tctgagactg        60
tcttgtgccg cctctggctt caccttctcc gactactaca tgtcctggat cagacaggcc       120
cctggcaaag gcctggaatg ggtgtcctac atctccatct ccggcatcac catctactac       180
gccgactccg tgaagggcag attcaccatc tccagagaca cgcccgaa ctccctgtac        240 ctgcagatga actctctgag agccgaggac accgccgtgt actactgcgc ccgtagatcc       300
tctggatggt acgactattg gggccagggc accctggtca cagtttctag t                351

<210> SEQ ID NO 386
<211> LENGTH: 444
<212> TYPE: PRT
<213> ORGANISM: Homo Sapiens

<400> SEQUENCE: 386

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ile Ser Gly Ile Thr Ile Tyr Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Ser Gly Trp Tyr Asp Tyr Trp Gly Gln Gly Thr Leu
            100                 105                 110

Val Thr Val Ser Ser Ala Ser Thr Lys Gly Pro Ser Val Phe Pro Leu
```

-continued

```
             115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
                195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
                435                 440
```

<210> SEQ ID NO 387
<211> LENGTH: 7
<212> TYPE: PRT
<213> ORGANISM: Homo Sapiens

<400> SEQUENCE: 387

```
Gln Ser Val Ser Tyr Asn Tyr
1               5
```

<210> SEQ ID NO 388
<211> LENGTH: 3
<212> TYPE: PRT
<213> ORGANISM: Homo Sapiens -continued

<400> SEQUENCE: 388

Gly Ala Ser
1

<210> SEQ ID NO 389
<211> LENGTH: 9
<212> TYPE: PRT
<213> ORGANISM: Homo Sapiens

<400> SEQUENCE: 389

His Gln Tyr Gly Ser Ser Pro Pro Thr
1               5

<210> SEQ ID NO 390
<211> LENGTH: 12
<212> TYPE: PRT
<213> ORGANISM: Homo Sapiens

<400> SEQUENCE: 390

Arg Ala Ser Gln Ser Val Ser Tyr Asn Tyr Leu Ala
1               5                   10

<210> SEQ ID NO 391
<211> LENGTH: 7
<212> TYPE: PRT
<213> ORGANISM: Homo Sapiens

<400> SEQUENCE: 391

Gly Ala Ser Ile Arg Ala Thr
1               5

<210> SEQ ID NO 392
<211> LENGTH: 9
<212> TYPE: PRT
<213> ORGANISM: Homo Sapiens

<400> SEQUENCE: 392

His Gln Tyr Gly Ser Ser Pro Pro Thr
1               5

<210> SEQ ID NO 393
<211> LENGTH: 108
<212> TYPE: PRT
<213> ORGANISM: Homo Sapiens

<400> SEQUENCE: 393

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Tyr Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Cys Cys His Gln Tyr Gly Ser Ser Pro
                85                  90                  95

Pro Thr Phe Gly Gln Gly Thr Lys Val Glu Ile Lys
            100                 105

-continued

```
<210> SEQ ID NO 394
<211> LENGTH: 324
<212> TYPE: DNA
<213> ORGANISM: Homo Sapiens

<400> SEQUENCE: 394
gaaattgtgc tgactcagtc ccctggcaca ctgtctttga gccctggcga gagagctacc      60
ctgtcctgta gagcctctca gtccgtgtcc tacaactacc tggcctggta tcagcagaag     120
cccggccagg ctcctagact gttgatctac ggcgcctcca tcagagccac aggcatccct     180
gatagattct ccggctctgg ctctggcacc gacttcaccc tgaccatctc cagactggaa     240
cccgaggact tcgccgtgta ctgctgtcac cagtacggct ctagccctcc tacctttgga     300
cagggcacca aggtggaaat caaa                                             324

<210> SEQ ID NO 395
<211> LENGTH: 215
<212> TYPE: PRT
<213> ORGANISM: Homo Sapiens

<400> SEQUENCE: 395

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Tyr Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Cys Cys His Gln Tyr Gly Ser Ser Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 396
<211> LENGTH: 8
<212> TYPE: PRT
<213> ORGANISM: Homo Sapiens

<400> SEQUENCE: 396

Gly Tyr Thr Phe Thr Ser Tyr Ala
1               5
```

-continued

```
<210> SEQ ID NO 397
<211> LENGTH: 8
<212> TYPE: PRT
<213> ORGANISM: Homo Sapiens

<400> SEQUENCE: 397

Ile Asn Pro Tyr Asn Arg Gly Thr
1               5

<210> SEQ ID NO 398
<211> LENGTH: 11
<212> TYPE: PRT
<213> ORGANISM: Homo Sapiens

<400> SEQUENCE: 398

Ala Arg Arg Pro Phe Gly Asn Ala Met Asp Ile
1               5                   10

<210> SEQ ID NO 399
<211> LENGTH: 5
<212> TYPE: PRT
<213> ORGANISM: Homo Sapiens

<400> SEQUENCE: 399

Ser Tyr Ala Met His
1               5

<210> SEQ ID NO 400
<211> LENGTH: 17
<212> TYPE: PRT
<213> ORGANISM: Homo Sapiens

<400> SEQUENCE: 400

Tyr Ile Asn Pro Tyr Asn Arg Gly Thr Lys Tyr Asn Glu Asn Phe Lys
1               5                   10                  15

Gly

<210> SEQ ID NO 401
<211> LENGTH: 9
<212> TYPE: PRT
<213> ORGANISM: Homo Sapiens

<400> SEQUENCE: 401

Arg Pro Phe Gly Asn Ala Met Asp Ile
1               5

<210> SEQ ID NO 402
<211> LENGTH: 118
<212> TYPE: PRT
<213> ORGANISM: Homo Sapiens

<400> SEQUENCE: 402

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Gly Leu Glu Trp Met
            35                  40                  45

Gly Tyr Ile Asn Pro Tyr Asn Asp Gly Thr Lys Tyr Asn Glu Asn Phe
        50                  55                  60

Lys Gly Arg Val Thr Ile Thr Ala Asp Glu Ser Thr Ser Thr Ala Tyr
```

-continued

```
65                  70                  75                  80

Met Glu Leu Ser Ser Leu Arg Ser Glu Asp Thr Ala Val Tyr Tyr Cys
                85                  90                  95

Ala Arg Arg Pro Phe Gly Asn Ala Met Asp Ile Trp Gly Gln Gly Thr
            100                 105                 110

Leu Val Thr Val Ser Ser
        115

<210> SEQ ID NO 403
<211> LENGTH: 445
<212> TYPE: PRT
<213> ORGANISM: Homo Sapiens

<400> SEQUENCE: 403

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Gly Leu Glu Trp Met
        35                  40                  45

Gly Tyr Ile Asn Pro Tyr Asn Asp Gly Thr Lys Tyr Asn Glu Asn Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Pro Phe Gly Asn Ala Met Asp Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320
```

-continued

```
Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 404
<211> LENGTH: 6
<212> TYPE: PRT
<213> ORGANISM: Homo Sapiens

<400> SEQUENCE: 404

Glu Asn Ile Tyr Arg Asn
1               5

<210> SEQ ID NO 405
<211> LENGTH: 3
<212> TYPE: PRT
<213> ORGANISM: Homo Sapiens

<400> SEQUENCE: 405

Ala Ala Thr
1

<210> SEQ ID NO 406
<211> LENGTH: 9
<212> TYPE: PRT
<213> ORGANISM: Homo Sapiens

<400> SEQUENCE: 406

Gln Gly Ile Trp Gly Thr Pro Leu Thr
1               5

<210> SEQ ID NO 407
<211> LENGTH: 11
<212> TYPE: PRT
<213> ORGANISM: Homo Sapiens

<400> SEQUENCE: 407

Arg Ser Ser Glu Asn Ile Tyr Arg Asn Leu Ala
1               5                   10

<210> SEQ ID NO 408
<211> LENGTH: 7
<212> TYPE: PRT
<213> ORGANISM: Homo Sapiens

<400> SEQUENCE: 408

Ala Ala Thr Asn Leu Ala Asp
1               5
```

-continued

```
<210> SEQ ID NO 409
<211> LENGTH: 9
<212> TYPE: PRT
<213> ORGANISM: Homo Sapiens

<400> SEQUENCE: 409

Gln Gly Ile Trp Gly Thr Pro Leu Thr
1               5

<210> SEQ ID NO 410
<211> LENGTH: 107
<212> TYPE: PRT
<213> ORGANISM: Homo Sapiens

<400> SEQUENCE: 410

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Asn Ile Tyr Arg Asn
                20                  25                  30

Leu Ala Trp Tyr Gln Gln Lys Pro Gly Lys Ala Pro Lys Leu Leu Ile
            35                  40                  45

Tyr Ala Ala Thr Asn Leu Ala Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ile Trp Gly Thr Pro Leu
                85                  90                  95

Thr Phe Gly Gly Gly Thr Lys Val Glu Ile Lys
            100                 105

<210> SEQ ID NO 411
<211> LENGTH: 214
<212> TYPE: PRT
<213> ORGANISM: Homo Sapiens

<400> SEQUENCE: 411

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Asn Ile Tyr Arg Asn
                20                  25                  30

Leu Ala Trp Tyr Gln Gln Lys Pro Gly Lys Ala Pro Lys Leu Leu Ile
            35                  40                  45

Tyr Ala Ala Thr Asn Leu Ala Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ile Trp Gly Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

-continued

```
                165             170             175
Ser Thr Leu Thr Leu Ser Lys Ala Asp Tyr Glu Lys His Lys Val Tyr
            180             185             190
Ala Cys Glu Val Thr His Gln Gly Leu Ser Ser Pro Val Thr Lys Ser
        195             200             205
Phe Asn Arg Gly Glu Cys
    210

<210> SEQ ID NO 412
<211> LENGTH: 8
<212> TYPE: PRT
<213> ORGANISM: Homo Sapiens

<400> SEQUENCE: 412

Gly Phe Thr Phe Ser Ser Tyr Val
1               5

<210> SEQ ID NO 413
<211> LENGTH: 10
<212> TYPE: PRT
<213> ORGANISM: Homo Sapiens

<400> SEQUENCE: 413

Ile Arg Leu Glu Thr His Gly Tyr Ala Ala
1               5               10

<210> SEQ ID NO 414
<211> LENGTH: 12
<212> TYPE: PRT
<213> ORGANISM: Homo Sapiens

<400> SEQUENCE: 414

Ala Arg Val Glu Arg Ser Lys Ser Gly Phe Asp Asn
1               5               10

<210> SEQ ID NO 415
<211> LENGTH: 5
<212> TYPE: PRT
<213> ORGANISM: Homo Sapiens

<400> SEQUENCE: 415

Ser Tyr Val Val His
1               5

<210> SEQ ID NO 416
<211> LENGTH: 19
<212> TYPE: PRT
<213> ORGANISM: Homo Sapiens

<400> SEQUENCE: 416

Arg Ile Arg Leu Glu Thr His Gly Tyr Ala Ala Glu Tyr Ala Ala Ser
1               5               10              15

Val Lys Gly

<210> SEQ ID NO 417
<211> LENGTH: 10
<212> TYPE: PRT
<213> ORGANISM: Homo Sapiens

<400> SEQUENCE: 417

Val Glu Arg Ser Lys Ser Gly Phe Asp Asn
1               5               10
```

```
<210> SEQ ID NO 418
<211> LENGTH: 121
<212> TYPE: PRT
<213> ORGANISM: Homo Sapiens

<400> SEQUENCE: 418

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Val Val His Trp Val Arg Gln Ala Pro Gly Lys Gly Leu Glu Trp Val
        35                  40                  45

Gly Arg Ile Arg Leu Glu Thr His Gly Tyr Ala Ala Glu Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Val Glu Arg Ser Lys Ser Gly Phe Asp Asn Trp Gly
            100                 105                 110

Gln Gly Thr Leu Val Thr Val Ser Ser
        115                 120

<210> SEQ ID NO 419
<211> LENGTH: 451
<212> TYPE: PRT
<213> ORGANISM: Homo Sapiens

<400> SEQUENCE: 419

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Val Val His Trp Val Arg Gln Ala Pro Gly Lys Gly Leu Glu Trp Val
        35                  40                  45

Gly Arg Ile Arg Leu Glu Thr His Gly Tyr Ala Ala Glu Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Val Glu Arg Ser Lys Ser Gly Phe Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asn Thr Lys Val Asp Lys Arg Val Glu Pro Lys Ser Cys
    210             215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
    450
```

```
<210> SEQ ID NO 420
<211> LENGTH: 9
<212> TYPE: PRT
<213> ORGANISM: Homo Sapiens

<400> SEQUENCE: 420

Ser Ser Asn Ile Gly Ala Gly Tyr Ser
1               5
```

```
<210> SEQ ID NO 421
<211> LENGTH: 3
<212> TYPE: PRT
<213> ORGANISM: Homo Sapiens

<400> SEQUENCE: 421

Gly Gln Ser
1
```

```
<210> SEQ ID NO 422
<211> LENGTH: 11
<212> TYPE: PRT
<213> ORGANISM: Homo Sapiens

<400> SEQUENCE: 422

Gln Ser Trp Asp Ser Ser Gln Thr Leu Val Val
```

```
1               5                    10
```

```
<210> SEQ ID NO 423
<211> LENGTH: 14
<212> TYPE: PRT
<213> ORGANISM: Homo Sapiens

<400> SEQUENCE: 423

Thr Gly Ser Ser Ser Asn Ile Gly Ala Gly Tyr Ser Val His
1               5                    10

<210> SEQ ID NO 424
<211> LENGTH: 7
<212> TYPE: PRT
<213> ORGANISM: Homo Sapiens

<400> SEQUENCE: 424

Gly Gln Ser Glu Arg Pro Ser
1               5

<210> SEQ ID NO 425
<211> LENGTH: 11
<212> TYPE: PRT
<213> ORGANISM: Homo Sapiens

<400> SEQUENCE: 425

Gln Ser Trp Asp Ser Ser Gln Thr Leu Val Val
1               5                    10

<210> SEQ ID NO 426
<211> LENGTH: 111
<212> TYPE: PRT
<213> ORGANISM: Homo Sapiens

<400> SEQUENCE: 426

Gln Ser Val Leu Thr Gln Pro Pro Ser Val Ser Gly Ala Pro Gly Gln
1               5                    10                  15

Arg Val Thr Ile Ser Cys Thr Gly Ser Ser Ser Asn Ile Gly Ala Gly
                20                  25                  30

Tyr Ser Val His Trp Tyr Gln Gln Leu Pro Gly Thr Ala Pro Lys Leu
            35                  40                  45

Leu Ile Tyr Gly Gln Ser Glu Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Trp Asp Ser Ser
                85                  90                  95

Gln Thr Leu Val Val Phe Gly Gly Gly Thr Lys Leu Thr Val Leu
            100                 105                 110

<210> SEQ ID NO 427
<211> LENGTH: 217
<212> TYPE: PRT
<213> ORGANISM: Homo Sapiens

<400> SEQUENCE: 427

Gln Ser Val Leu Thr Gln Pro Pro Ser Val Ser Gly Ala Pro Gly Gln
1               5                    10                  15

Arg Val Thr Ile Ser Cys Thr Gly Ser Ser Ser Asn Ile Gly Ala Gly
                20                  25                  30

Tyr Ser Val His Trp Tyr Gln Gln Leu Pro Gly Thr Ala Pro Lys Leu
```

-continued

```
            35                40                45

Leu Ile Tyr Gly Gln Ser Glu Arg Pro Ser Gly Val Pro Asp Arg Phe
    50                55                60

Ser Gly Ser Lys Ser Gly Thr Ser Ala Ser Leu Ala Ile Thr Gly Leu
65                70                75                80

Gln Ala Glu Asp Glu Ala Asp Tyr Tyr Cys Gln Ser Trp Asp Ser Ser
                85                90                95

Gln Thr Leu Val Val Phe Gly Gly Gly Thr Lys Leu Thr Val Leu Gly
            100               105               110

Gln Pro Lys Ala Ala Pro Ser Val Thr Leu Phe Pro Pro Ser Ser Glu
        115               120               125

Glu Leu Gln Ala Asn Lys Ala Thr Leu Val Cys Leu Ile Ser Asp Phe
    130               135               140

Tyr Pro Gly Ala Val Thr Val Ala Trp Lys Ala Asp Ser Ser Pro Val
145               150               155               160

Lys Ala Gly Val Glu Thr Thr Thr Pro Ser Lys Gln Ser Asn Asn Lys
            165               170               175

Tyr Ala Ala Ser Ser Tyr Leu Ser Leu Thr Pro Glu Gln Trp Lys Ser
            180               185               190

His Arg Ser Tyr Ser Cys Gln Val Thr His Glu Gly Ser Thr Val Glu
        195               200               205

Lys Thr Val Ala Pro Thr Glu Cys Ser
    210               215
```

```
<210> SEQ ID NO 428
<211> LENGTH: 990
<212> TYPE: DNA
<213> ORGANISM: Homo Sapiens

<400> SEQUENCE: 428
gcctccacca agggcccatc ggtcttcccc ctggcaccct cctccaagag cacctctggg     60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctggggggga    360 ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gggtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag gcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990
```

```
<210> SEQ ID NO 429
```

```
<211> LENGTH: 330
<212> TYPE: PRT
<213> ORGANISM: Homo Sapiens

<400> SEQUENCE: 429

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 430
<211> LENGTH: 990
<212> TYPE: DNA
<213> ORGANISM: Homo Sapiens

<400> SEQUENCE: 430
gcctccacca agggcccatc ggtcttcccc ctggcaccct cctccaagag cacctctggg      60
```

-continued

```
ggcacagcgg ccctgggctg cctggtcaag gactacttcc ccgaaccggt gacggtgtcg      120
tggaactcag gcgccctgac cagcggcgtg cacaccttcc cggctgtcct acagtcctca      180
ggactctact ccctcagcag cgtggtgacc gtgccctcca gcagcttggg cacccagacc      240
tacatctgca acgtgaatca caagcccagc aacaccaagg tggacaagaa agttgagccc      300
aaatcttgtg acaaaactca cacatgccca ccgtgcccag cacctgaact cctggggggga      360 ccgtcagtct tcctcttccc cccaaaaccc aaggacaccc tcatgatctc ccggacccct      420
gaggtcacat gcgtggtggt ggacgtgagc cacgaagacc ctgaggtcaa gttcaactgg      480
tacgtggacg gcgtggaggt gcataatgcc aagacaaagc cgcgggagga gcagtacaac      540
agcacgtacc gtgtggtcag cgtcctcacc gtcctgcacc aggactggct gaatggcaag      600
gagtacaagt gcaaggtctc caacaaagcc ctcccagccc ccatcgagaa aaccatctcc      660
aaagccaaag ggcagccccg agaaccacag gtgtacaccc tgccccacatc ccgggatgag      720 ctgaccaaga accaggtcag cctgacctgc ctggtcaaag gcttctatcc cagcgacatc      780
gccgtggagt gggagagcaa tgggcagccg gagaacaact acaagaccac gcctcccgtg      840
ctggactccg acggctcctt cttcctctac agcaagctca ccgtggacaa gagcaggtgg      900
cagcagggga acgtcttctc atgctccgtg atgcatgagg ctctgcacaa ccactacacg      960
cagaagagcc tctccctgtc tccgggtaaa      990
```

<210> SEQ ID NO 431
<211> LENGTH: 330
<212> TYPE: PRT
<213> ORGANISM: Homo Sapiens

<400> SEQUENCE: 431

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205
```

-continued

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 432
<211> LENGTH: 990
<212> TYPE: DNA
<213> ORGANISM: Homo Sapiens

<400> SEQUENCE: 432
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctggggggga     360 ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc ccggggtaaa                                     990
```

```
<210> SEQ ID NO 433
<211> LENGTH: 330
<212> TYPE: PRT
<213> ORGANISM: Homo Sapiens

<400> SEQUENCE: 433

Ala Ser Thr Lys Gly Pro Ser Val Phe Pro Leu Ala Pro Ser Ser Lys
1                 5                  10                  15

Ser Thr Ser Gly Gly Thr Ala Ala Leu Gly Cys Leu Val Lys Asp Tyr
            20                  25                  30
```

-continued

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 434
<211> LENGTH: 990
<212> TYPE: DNA
<213> ORGANISM: Homo Sapiens

<400> SEQUENCE: 434
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctggggggga     360 ccgtcagtct tcctcttccc cccaaaaccc aaggacaccc tcatgatctc ccggacccct     420
```

```
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acatcttctc atgctccgtg atgcatgagg ctctgcacaa ccactacacg    960
cagaagagcc tctccctgtc tccgggtaaa                                      990

<210> SEQ ID NO 435
<211> LENGTH: 330
<212> TYPE: PRT
<213> ORGANISM: Homo Sapiens

<400> SEQUENCE: 435

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270
```

-continued

```
Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
    290                 295                 300

Ile Phe Ser Cys Ser Val Met His Glu Ala Leu His Asn His Tyr Thr
305                 310                 315                 320

Gln Lys Ser Leu Ser Leu Ser Pro Gly Lys
                325             330
```

```
<210> SEQ ID NO 436
<211> LENGTH: 990
<212> TYPE: DNA
<213> ORGANISM: Homo Sapiens

<400> SEQUENCE: 436
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agtggagccc     300
aaatcttgtg acaaaactca cacatgccca ccgtgcccag cacctgaact cgcggggggca     360 ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                       990
```

```
<210> SEQ ID NO 437
<211> LENGTH: 330
<212> TYPE: PRT
<213> ORGANISM: Homo Sapiens

<400> SEQUENCE: 437

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

-continued

```
                85                   90                   95

Lys Val Glu Pro Lys Ser Cys Asp Lys Thr His Thr Cys Pro Pro Cys
            100                 105                 110

Pro Ala Pro Glu Leu Ala Gly Ala Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

<210> SEQ ID NO 438
<211> LENGTH: 978
<212> TYPE: DNA
<213> ORGANISM: Homo Sapiens

<400> SEQUENCE: 438

```
gcctccacca agggcccatc ggtcttcccc ctggcgccct gctccaggag cacctccgag      60
agcacagccg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggacccctga ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagccccc atcgagaaaa ccatctccaa aaccaaaggg     660
cagccccgag aaccacaggt gtacaccctg cccccatccc gggaggagat gaccaagaac     720
```

-continued

```
caggtcagcc tgacctgcct ggtcaaaggc ttctacccca gcgacatcgc cgtggagtgg     780
gagagcaatg ggcagccgga gaacaactac aagaccacac ctcccatgct ggactccgac     840
ggctccttct tcctctacag caagctcacc gtggacaaga gcaggtggca gcaggggaac     900
gtcttctcat gctccgtgat gcatgaggct ctgcacaacc actacacgca gaagagcctc     960
tccctgtctc cgggtaaa                                                    978
```

```
<210> SEQ ID NO 439
<211> LENGTH: 326
<212> TYPE: PRT
<213> ORGANISM: Homo Sapiens

<400> SEQUENCE: 439

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
```

-continued

```
          325

<210> SEQ ID NO 440
<211> LENGTH: 326
<212> TYPE: PRT
<213> ORGANISM: Homo Sapiens

<400> SEQUENCE: 440

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 441
<211> LENGTH: 978
<212> TYPE: DNA
<213> ORGANISM: Homo Sapiens
```

-continued

```
<400> SEQUENCE: 441
gcctccacca agggcccatc ggtcttcccc ctggcgccct gctccaggag cacctccgag        60
agcacagcgg ccctgggctg cctggtcaag gactacttcc ccgaaccggt gacggtgtcg       120
tggaactcag gcgctctgac cagcggcgtg cacaccttcc cagctgtcct acagtcctca       180
ggactctact ccctcagcag cgtggtgacc gtgccctcca gcagcttggg cacccagacc       240
tacacctgca acgtagatca caagcccagc aacaccaagg tggacaagac agttgagcgc       300
aaatgttgtg tcgagtgccc accgtgccca gcaccacctg tggcaggacc gtcagtcttc       360
ctcttccccc caaaacccaa ggacaccctc atgatctccc ggacccctga ggtcacgtgc       420
gtggtggtgg acgtgagcca cgaagacccc gaggtccagt tcaactggta cgtggacggc       480
gtggaggtgc ataatgccaa gacaaagcca cgggaggagc agttcaacag cacgttccgt       540
gtggtcagcg tcctcaccgt tgtgcaccag gactggctga acggcaagga gtacaagtgc       600
aaggtctcca acaaaggcct cccagccccc atcgagaaaa ccatctccaa aaccaaaggg       660
cagccccgag aaccacaggt gtacaccctg cccccatccc gggaggagat gaccaagaac       720
caggtcagcc tgacctgcct ggtcaaaggc ttctacccca gcgacatcgc cgtggagtgg       780
gagagcaatg ggcagccgga gaacaactac aagaccacgc tcccatgct ggactccgac       840 ggctccttct tcctctacag caagctcacc gtggacaaga gcaggtggca gcaggggaac       900
gtcttctcat gctccgtgat gcatgaggct ctgcacaacc actacacgca gaagagcctc       960
tccctgtctc cgggtaaa                                                      978

<210> SEQ ID NO 442
<211> LENGTH: 326
<212> TYPE: PRT
<213> ORGANISM: Homo Sapiens

<400> SEQUENCE: 442

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190
```

-continued

```
Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 443
<211> LENGTH: 978
<212> TYPE: DNA
<213> ORGANISM: Homo Sapiens

<400> SEQUENCE: 443
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cggctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggacccctga ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt cgtgcaccag gactggctga acggcaagga gtacaagtgc     600
aaggtctcca acaaaggcct cccagccccc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctacccca gcgacatctc cgtggagtgg     780
gagagcaatg ggcagccgga gaacaactac aagaccacac tcccatgct ggactccgac     840 ggctccttct tcctctacag caagctcacc gtggacaaga gcaggtggca gcaggggaac     900
gtcttctcat gctccgtgat gcatgaggct ctgcacaacc actacacaca gaagagcctc     960
tccctgtctc cgggtaaa                                                    978

<210> SEQ ID NO 444
<211> LENGTH: 326
<212> TYPE: PRT
<213> ORGANISM: Homo Sapiens

<400> SEQUENCE: 444

Ala Ser Thr Lys Gly Pro Ser Val Phe Pro Leu Ala Pro Cys Ser Arg
```

-continued

```
1               5               10              15

Ser Thr Ser Glu Ser Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
    50              55              60

Leu Ser Ser Val Val Thr Val Pro Ser Ser Asn Phe Gly Thr Gln Thr
65              70              75              80

Tyr Thr Cys Asn Val Asp His Lys Pro Ser Asn Thr Lys Val Asp Lys
            85              90              95

Thr Val Glu Arg Lys Cys Cys Val Glu Cys Pro Pro Cys Pro Ala Pro
            100             105             110

Pro Val Ala Gly Pro Ser Val Phe Leu Phe Pro Pro Lys Pro Lys Asp
            115             120             125

Thr Leu Met Ile Ser Arg Thr Pro Glu Val Thr Cys Val Val Val Asp
    130             135             140

Val Ser His Glu Asp Pro Glu Val Gln Phe Asn Trp Tyr Val Asp Gly
145             150             155             160

Val Glu Val His Asn Ala Lys Thr Lys Pro Arg Glu Glu Gln Phe Asn
            165             170             175

Ser Thr Phe Arg Val Val Ser Val Leu Thr Val Val His Gln Asp Trp
            180             185             190

Leu Asn Gly Lys Glu Tyr Lys Cys Lys Val Ser Asn Lys Gly Leu Pro
            195             200             205

Ala Pro Ile Glu Lys Thr Ile Ser Lys Thr Lys Gly Gln Pro Arg Glu
    210             215             220

Pro Gln Val Tyr Thr Leu Pro Pro Ser Arg Glu Glu Met Thr Lys Asn
225             230             235             240

Gln Val Ser Leu Thr Cys Leu Val Lys Gly Phe Tyr Pro Ser Asp Ile
            245             250             255

Ser Val Glu Trp Glu Ser Asn Gly Gln Pro Glu Asn Asn Tyr Lys Thr
            260             265             270

Thr Pro Pro Met Leu Asp Ser Asp Gly Ser Phe Phe Leu Tyr Ser Lys
            275             280             285

Leu Thr Val Asp Lys Ser Arg Trp Gln Gln Gly Asn Val Phe Ser Cys
    290             295             300

Ser Val Met His Glu Ala Leu His Asn His Tyr Thr Gln Lys Ser Leu
305             310             315             320

Ser Leu Ser Pro Gly Lys
            325
```

<210> SEQ ID NO 445
<211> LENGTH: 981
<212> TYPE: DNA
<213> ORGANISM: Homo Sapiens

<400> SEQUENCE: 445

```
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
```

-continued

```
aaatatggtc cccatgccc atcatgccca gcacctgagt tcctggggggg accatcagtc      360 ttcctgttcc ccccaaaacc caaggacact ctcatgatct cccggacccc tgaggtcacg      420
tgcgtggtgg tggacgtgag ccaggaagac cccgaggtcc agttcaactg gtacgtggat      480
ggcgtggagg tgcataatgc caagacaaag ccgcgggagg agcagttcaa cagcacgtac      540
cgtgtggtca gcgtcctcac cgtcctgcac caggactggc tgaacggcaa ggagtacaag      600
tgcaaggtct ccaacaaagg cctcccgtcc tccatcgaga aaaccatctc caaagccaaa      660
gggcagcccc gagagccaca ggtgtacacc ctgcccccat cccaggagga gatgaccaag      720
aaccaggtca gcctgacctg cctggtcaaa ggcttctacc ccagcgacat cgccgtggag      780
tgggagagca atgggcagcc ggagaacaac tacaagacca cgcctcccgt gctggactcc      840
gacggctcct tcttcctcta cagcaggcta accgtggaca gagcaggtg gcaggagggg      900 aatgtcttct catgctccgt gatgcatgag gctctgcaca accactacac acagaagagc      960
ctctccctgt ctctgggtaa a                                                981
```

<210> SEQ ID NO 446
<211> LENGTH: 327
<212> TYPE: PRT
<213> ORGANISM: Homo Sapiens

<400> SEQUENCE: 446

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
```

-continued

```
                        245               250               255
Ile Ala Val Glu Trp Glu Ser Asn Gly Gln Pro Glu Asn Asn Tyr Lys
              260               265               270

Thr Thr Pro Pro Val Leu Asp Ser Asp Gly Ser Phe Phe Leu Tyr Ser
          275               280               285

Arg Leu Thr Val Asp Lys Ser Arg Trp Gln Glu Gly Asn Val Phe Ser
      290               295               300

Cys Ser Val Met His Glu Ala Leu His Asn His Tyr Thr Gln Lys Ser
305               310               315               320

Leu Ser Leu Ser Leu Gly Lys
                  325

<210> SEQ ID NO 447
<211> LENGTH: 981
<212> TYPE: DNA
<213> ORGANISM: Homo Sapiens

<400> SEQUENCE: 447
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccgtgccc atcatgccca gcacctgagt tcctgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcgtgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga tgaccaag      720 aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggcta accgtggaca gagcaggtg gcaggagggg      900 aatgtcttct catgctccgt gatgcatgag gctctgcaca accactacac gcagaagagc     960
ctctccctgt ctctgggtaa a                                              981

<210> SEQ ID NO 448
<211> LENGTH: 327
<212> TYPE: PRT
<213> ORGANISM: Homo Sapiens

<400> SEQUENCE: 448

Ala Ser Thr Lys Gly Pro Ser Val Phe Pro Leu Ala Pro Cys Ser Arg
1               5               10                 15

Ser Thr Ser Glu Ser Thr Ala Ala Leu Gly Cys Leu Val Lys Asp Tyr
              20               25               30

Phe Pro Glu Pro Val Thr Val Ser Trp Asn Ser Gly Ala Leu Thr Ser
          35               40               45

Gly Val His Thr Phe Pro Ala Val Leu Gln Ser Ser Gly Leu Tyr Ser
      50               55               60
```

```
Leu Ser Ser Val Val Thr Val Pro Ser Ser Ser Leu Gly Thr Lys Thr
65              70              75              80

Tyr Thr Cys Asn Val Asp His Lys Pro Ser Asn Thr Lys Val Asp Lys
            85              90              95

Arg Val Glu Ser Lys Tyr Gly Pro Pro Cys Pro Ser Cys Pro Ala Pro
            100             105             110

Glu Phe Leu Gly Gly Pro Ser Val Phe Leu Phe Pro Pro Lys Pro Lys
        115             120             125

Asp Thr Leu Met Ile Ser Arg Thr Pro Glu Val Thr Cys Val Val Val
    130             135             140

Asp Val Ser Gln Glu Asp Pro Glu Val Gln Phe Asn Trp Tyr Val Asp
145             150             155             160

Gly Val Glu Val His Asn Ala Lys Thr Lys Pro Arg Glu Glu Gln Phe
            165             170             175

Asn Ser Thr Tyr Arg Val Val Ser Val Leu Thr Val Val His Gln Asp
        180             185             190

Trp Leu Asn Gly Lys Glu Tyr Lys Cys Lys Val Ser Asn Lys Gly Leu
        195             200             205

Pro Ser Ser Ile Glu Lys Thr Ile Ser Lys Ala Lys Gly Gln Pro Arg
    210             215             220

Glu Pro Gln Val Tyr Thr Leu Pro Pro Ser Gln Glu Glu Met Thr Lys
225             230             235             240

Asn Gln Val Ser Leu Thr Cys Leu Val Lys Gly Phe Tyr Pro Ser Asp
            245             250             255

Ile Ala Val Glu Trp Glu Ser Asn Gly Gln Pro Glu Asn Asn Tyr Lys
        260             265             270

Thr Thr Pro Pro Val Leu Asp Ser Asp Gly Ser Phe Phe Leu Tyr Ser
        275             280             285

Arg Leu Thr Val Asp Lys Ser Arg Trp Gln Glu Gly Asn Val Phe Ser
    290             295             300

Cys Ser Val Met His Glu Ala Leu His Asn His Tyr Thr Gln Lys Ser
305             310             315             320

Leu Ser Leu Ser Leu Gly Lys
            325
```

```
<210> SEQ ID NO 449
<211> LENGTH: 981
<212> TYPE: DNA
<213> ORGANISM: Homo Sapiens

<400> SEQUENCE: 449
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc atcatgccca gcacctgagt tcctggggggg accatcagtc     360 ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
```

-continued

```
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaagctc accgtggaca agagcaggtg gcaggagggg     900
aacgtcttct catgctccgt gatgcatgag gctctgcaca accactacac gcagaagagc     960
ctctccctgt ctctgggtaa a                                                981

<210> SEQ ID NO 450
<211> LENGTH: 327
<212> TYPE: PRT
<213> ORGANISM: Homo Sapiens

<400> SEQUENCE: 450

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                    85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                    165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                    245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Lys Leu Thr Val Asp Lys Ser Arg Trp Gln Glu Gly Asn Val Phe Ser
            290                 295                 300
```

-continued

```
Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 451
<211> LENGTH: 981
<212> TYPE: DNA
<213> ORGANISM: Homo Sapiens

<400> SEQUENCE: 451
gcctccacca agggcccatc cgtcttcccc ctggcgccct gctccaggag cacctccgag      60
agcacggccg ccctgggctg cctggtcaag gactacttcc ccgaaccagt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc accatgccca gcgcctgaat ttgaggggg accatcagtc     360 ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtca tcgatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggatcct tcttcctcta cagcaggcta accgtggaca agagcaggtg gcaggagggg     900
aatgtcttct catgctccgt gatgcatgag gctctgcaca accactacac acagaagagc     960
ctctccctgt ctctgggtaa a                                               981

<210> SEQ ID NO 452
<211> LENGTH: 981
<212> TYPE: DNA
<213> ORGANISM: Homo Sapiens

<400> SEQUENCE: 452
gcctccacca agggacctag cgtgttccct ctcgcccct gttccaggtc cacaagcgag       60
tccaccgctg ccctcggctg tctggtgaaa gactactttc ccgagcccgt gaccgtctcc      120
tggaatagcg gagccctgac ctccggcgtg cacacatttc ccgccgtgct gcagagcagc      180
ggactgtata gcctgagcag cgtggtgacc gtgcccagct ccagcctcgg caccaaaacc      240
tacacctgca acgtggacca caagccctcc aacaccaagg tggacaagcg ggtggagagc      300
aagtacggcc ccccttgccc tccttgtcct gcccctgagt cgagggagg accctccgtg       360 ttcctgtttc cccccaaaacc caaggacacc ctgatgatct cccggacacc cgaggtgacc      420
tgtgtggtcg tggacgtcag ccaggaggac cccgaggtgc agttcaactg gtatgtggac      480
ggcgtggagg tgcacaatgc caaaaccaag cccagggagg agcagttcaa ttccacctac      540 aggtggtga gcgtgctgac cgtcctgcat caggattggc tgaacggcaa ggagtacaag      600
tgcaaggtgt ccaacaaggg actgcccagc tccatcgaga agaccatcag caaggctaag      660
ggccagccga gggagcccca ggtgtatacc ctgcctccta gccaggaaga gatgaccaag      720
```

-continued

```
aaccaagtgt ccctgacctg cctggtgaag ggattctacc cctccgacat cgccgtggag      780
tgggagagca atggccagcc cgagaacaac tacaaaacaa cccctcccgt gctcgatagc      840
gacggcagct tctttctcta cagccggctg acagtggaca agagcaggtg gcaggagggc      900
aacgtgttct cctgttccgt gatgcacgag gccctgcaca tcactacac ccagaagagc      960 ctctccctgt ccctgggcaa g      981
```

<210> SEQ ID NO 453
<211> LENGTH: 981
<212> TYPE: DNA
<213> ORGANISM: Homo Sapiens

<400> SEQUENCE: 453

```
gccagcacca agggcccttc cgtgttcccc ctggcccctt gcagcaggag cacctccgaa       60
tccacagctg ccctgggctg tctggtgaag gactactttc ccgagcccgt gaccgtgagc      120
tggaacagcg gcgctctgac atccggcgtc cacacctttc ctgccgtcct gcagtcctcc      180
ggcctctact ccctgtcctc cgtggtgacc gtgcctagct cctccctcgg caccaagacc      240
tacacctgta acgtggacca caaaccctcc aacaccaagg tggacaaacg ggtcgagagc      300
aagtacggcc ctcctgccc tccttgtcct gcccccgagt cgaaggcgg acccagcgtg      360 ttcctgttcc ctcctaagcc caaggacacc ctcatgatca gccggacacc cgaggtgacc      420
tgcgtggtgg tggatgtgag ccaggaggac cctgaggtcc agttcaactg gtatgtggat      480
ggcgtggagg tgcacaacgc caagacaaag ccccgggaag agcagttcaa ctccacctac      540
agggtggtca gcgtgctgac cgtgctgcat caggactggc tgaacggcaa ggagtacaag      600
tgcaaggtca gcaataaggg actgcccagc agcatcgaga agaccatctc caaggctaaa      660
ggccagcccc gggaacctca ggtgtacacc ctgcctccca gccaggagga gatgaccaag      720
aaccaggtga gcctgacctg cctggtgaag ggattctacc cttccgacat cgccgtggag      780
tgggagtcca acggccagcc cgagaacaat tataagacca cccctcccgt cctcgacagc      840
gacggatcct tctttctgta ctccaggctg accgtggata gtccaggtg gcaggaaggc      900 aacgtgttca gctgctccgt gatgcacgag gccctgcaca tcactacac ccagaagtcc      960 ctgagcctgt ccctgggaaa g      981
```

<210> SEQ ID NO 454
<211> LENGTH: 327
<212> TYPE: PRT
<213> ORGANISM: Homo Sapiens

<400> SEQUENCE: 454

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95
```

-continued

```
Arg Val Glu Ser Lys Tyr Gly Pro Pro Cys Pro Pro Cys Pro Ala Pro
                100                 105                 110

Glu Phe Glu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 455
<211> LENGTH: 981
<212> TYPE: DNA
<213> ORGANISM: Homo Sapiens

<400> SEQUENCE: 455

```
gcctccacca agggcccatc cgtcttcccc ctggcgccct gctccaggag cacctccgag      60
agcacggccg ccctgggctg cctggtcaag gactacttcc ccgaaccagt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc accatgccca gcgcctccag ttgcgggggg accatcagtc     360
ttcctgttcc cccaaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtca tcgatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
```

-continued

```
tgggagagca atgggcagcc ggagaacaac tacaagacca cgcctcccgt gctggactcc      840
gacggatcct tcttcctcta cagcaggcta accgtggaca agagcaggtg gcaggagggg      900
aatgtcttct catgctccgt gatgcatgag gctctgcaca accactacac acagaagagc      960
ctctccctgt ctctgggtaa a                                                981
```

```
<210> SEQ ID NO 456
<211> LENGTH: 327
<212> TYPE: PRT
<213> ORGANISM: Homo Sapiens

<400> SEQUENCE: 456

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 457
<211> LENGTH: 321
<212> TYPE: DNA
<213> ORGANISM: Homo Sapiens

<400> SEQUENCE: 457
cgtacggtgg ccgctccctc cgtgttcatc ttcccacctt ccgacgagca gctgaagtcc        60
ggcaccgctt ctgtcgtgtg cctgctgaac aacttctacc cccgcgaggc caaggtgcag       120
tggaaggtgg acaacgccct gcagtccggc aactcccagg aatccgtgac cgagcaggac       180
tccaaggaca gcacctactc cctgtcctcc accctgaccc tgtccaaggc cgactacgag       240
aagcacaagg tgtacgcctg cgaagtgacc caccagggcc tgtctagccc cgtgaccaag       300
tctttcaacc ggggcgagtg t                                                 321

<210> SEQ ID NO 458
<211> LENGTH: 107
<212> TYPE: PRT
<213> ORGANISM: Homo Sapiens

<400> SEQUENCE: 458

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 459
<211> LENGTH: 321
<212> TYPE: DNA
<213> ORGANISM: Homo Sapiens

<400> SEQUENCE: 459
cgaactgtgg ctgcaccatc tgtcttcatc ttcccgccat ctgatgagca gttgaaatct        60
ggaactgcct ctgttgtgtg cctgctgaat aacttctatc ccagagaggc caaagtacag       120
tggaaggtgg ataacgccct ccaatcgggt aactcccagg agagtgtcac agagcaggag       180
agcaaggaca gcacctacag cctcagcagc accctgacgc tgagcaaagc agactacgag       240
aaacacaaag tctacgccgg cgaagtcacc catcagggcc tgagctcgcc cgtcacaaag       300
agcttcaaca ggggagagtg t                                                 321

<210> SEQ ID NO 460
<211> LENGTH: 107
<212> TYPE: PRT
<213> ORGANISM: Homo Sapiens

<400> SEQUENCE: 460

Arg Thr Val Ala Ala Pro Ser Val Phe Ile Phe Pro Pro Ser Asp Glu
1               5                   10                  15

-continued

```
Gln Leu Lys Ser Gly Thr Ala Ser Val Val Cys Leu Leu Asn Asn Phe
        20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Glu Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Gly Glu Val Thr His Gln Gly Leu Ser Ser
                    85                  90                  95

Pro Val Thr Lys Ser Phe Asn Arg Gly Glu Cys
            100                 105
```

```
<210> SEQ ID NO 461
<211> LENGTH: 321
<212> TYPE: DNA
<213> ORGANISM: Homo Sapiens

<400> SEQUENCE: 461
cgaactgtgg ctgcaccatc tgtcttcatc ttcccgccat ctgatgagca gttgaaatct        60
ggaactgcct ctgttgtgtg cctgctgaat aacttctatc ccagagaggc caaagtacag       120
cggaaggtgg ataacgccct ccaatcgggt aactcccagg agagtgtcac agagcaggag       180
agcaaggaca gcacctacag cctcagcagc accctgacgc tgagcaaagc agactacgag       240
aaacacaaag tctacgcctg cgaagtcacc catcagggcc tgagctcgcc cgtcacaaag       300
agcttcaaca ggggagagtg t                                                 321
```

```
<210> SEQ ID NO 462
<211> LENGTH: 107
<212> TYPE: PRT
<213> ORGANISM: Homo Sapiens

<400> SEQUENCE: 462

Arg Thr Val Ala Ala Pro Ser Val Phe Ile Phe Pro Pro Ser Asp Glu
1                   5                   10                  15

Gln Leu Lys Ser Gly Thr Ala Ser Val Val Cys Leu Leu Asn Asn Phe
        20                  25                  30

Tyr Pro Arg Glu Ala Lys Val Gln Arg Lys Val Asp Asn Ala Leu Gln
        35                  40                  45

Ser Gly Asn Ser Gln Glu Ser Val Thr Glu Gln Glu Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                    85                  90                  95

Pro Val Thr Lys Ser Phe Asn Arg Gly Glu Cys
            100                 105
```

```
<210> SEQ ID NO 463
<211> LENGTH: 321
<212> TYPE: DNA
<213> ORGANISM: Homo Sapiens

<400> SEQUENCE: 463
cgaactgtgg ctgcaccatc tgtcttcatc ttcccgccat ctgatgagca gttgaaatct        60
ggaactgcct ctgttgtgtg cctgctgaat aacttctatc ccagagaggc caaagtacag       120
```

-continued

```
tggaaggtgg ataacgccct ccaatcgggt aactcccagg agagtgtcac agagcaggac      180
agcaaggaca gcacctacag cctcagcagc accctgacgc tgagcaaagc agactacgag      240
aaacacaaac tctacgcctg cgaagtcacc catcagggcc tgagctcgcc cgtcacaaag      300
agcttcaaca ggggagagtg t                                                321
```

```
<210> SEQ ID NO 464
<211> LENGTH: 107
<212> TYPE: PRT
<213> ORGANISM: Homo Sapiens

<400> SEQUENCE: 464

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 465
<211> LENGTH: 321
<212> TYPE: DNA
<213> ORGANISM: Homo Sapiens

<400> SEQUENCE: 465
cgaactgtgg ctgcaccatc tgtcttcatc ttcccgccat ctgatgagca gttgaaatct       60
ggaactgcct ctgttgtgtg cctgctgaat aacttctatc ccagagaggc caaagtacag      120
tggaaggtgg ataacgccct ccaatcgggt aactcccagg agagtgtcac agagcaggac      180
agcaaggaca gcacctacag cctcagcaac accctgacgc tgagcaaagc agactacgag      240
aaacacaaag tctacgcctg cgaagtcacc catcagggcc tgagctcgcc cgtcacaaag      300
agcttcaaca ggggagagtg c                                                321
```

```
<210> SEQ ID NO 466
<211> LENGTH: 107
<212> TYPE: PRT
<213> ORGANISM: Homo Sapiens

<400> SEQUENCE: 466

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Asn Thr Leu Thr Leu Ser Lys Ala Asp Tyr Glu
```

-continued

```
65              70              75              80

Lys His Lys Val Tyr Ala Cys Glu Val Thr His Gln Gly Leu Ser Ser
                85              90              95

Pro Val Thr Lys Ser Phe Asn Arg Gly Glu Cys
            100             105

<210> SEQ ID NO 467
<211> LENGTH: 312
<212> TYPE: DNA
<213> ORGANISM: Homo Sapiens

<400> SEQUENCE: 467
cccaaggcca accccacggt cactctgttc ccgccctcct ctgaggagct ccaagccaac      60
aaggccacac tagtgtgtct gatcagtgac ttctacccgg gagctgtgac agtggcttgg     120
aaggcagatg gcagccccgt caaggcggga gtggagacga ccaaaccctc caaacagagc     180
aacaacaagt acgcggccag cagctacctg agcctgacgc ccgagcagtg gaagtcccac     240
agaagctaca gctgccaggt cacgcatgaa gggagcaccg tggagaagac agtggcccct     300
acagaatgtt ca                                                         312

<210> SEQ ID NO 468
<211> LENGTH: 104
<212> TYPE: PRT
<213> ORGANISM: Homo Sapiens

<400> SEQUENCE: 468

Pro Lys Ala Asn Pro Thr Val Thr Leu Phe Pro Pro Ser Ser Glu Glu
1               5               10              15

Leu Gln Ala Asn Lys Ala Thr Leu Val Cys Leu Ile Ser Asp Phe Tyr
                20              25              30

Pro Gly Ala Val Thr Val Ala Trp Lys Ala Asp Gly Ser Pro Val Lys
            35              40              45

Ala Gly Val Glu Thr Thr Lys Pro Ser Lys Gln Ser Asn Asn Lys Tyr
        50              55              60

Ala Ala Ser Ser Tyr Leu Ser Leu Thr Pro Glu Gln Trp Lys Ser His
65              70              75              80

Arg Ser Tyr Ser Cys Gln Val Thr His Glu Gly Ser Thr Val Glu Lys
                85              90              95

Thr Val Ala Pro Thr Glu Cys Ser
            100

<210> SEQ ID NO 469
<211> LENGTH: 318
<212> TYPE: DNA
<213> ORGANISM: Homo Sapiens

<400> SEQUENCE: 469
ggtcagccca aggccaaccc cactgtcact ctgttcccgc cctcctctga ggagctccaa      60
gccaacaagg ccacactagt gtgtctgatc agtgacttct acccgggagc tgtgacagtg     120
gcctggaagg cagatggcag ccccgtcaag gcgggagtgg agaccaccaa accctccaaa     180
cagagcaaca caagtacgc ggccagcagc tacctgagcc tgacgcccga gcagtggaag      240
tcccacagaa gctacagctg ccaggtcacg catgaaggga gcaccgtgga agacagtg       300 gcccctacag aatgttca                                                   318

<210> SEQ ID NO 470
```

```
<211> LENGTH: 318
<212> TYPE: DNA
<213> ORGANISM: Homo Sapiens

<400> SEQUENCE: 470
ggtcagccca aggccaaccc cactgtcact ctgttcccgc cctcctctga ggagctccaa      60
gccaacaagg ccacactagt gtgtctgatc agtgacttct acccgggagc tgtgacagtg     120
gcctggaagg cagatggcag ccccgtcaag gcgggagtgg agaccaccaa accctccaaa     180
cagagcaaca acaagtacgc ggccagcagc tacctgagcc tgacgcccga gcagtggaag     240
tcccacagaa gctacagctg ccaggtcacg catgaaggga gcaccgtgga aagacagtg     300 gcccctacag aatgttca                                                   318

<210> SEQ ID NO 471
<211> LENGTH: 106
<212> TYPE: PRT
<213> ORGANISM: Homo Sapiens

<400> SEQUENCE: 471

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Gly Ser Pro
            35                  40                  45

Val Lys Ala Gly Val Glu Thr Thr Lys Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 472
<211> LENGTH: 318
<212> TYPE: DNA
<213> ORGANISM: Homo Sapiens

<400> SEQUENCE: 472
ggccagccta aggccgctcc ttctgtgacc ctgttccccc catcctccga ggaactgcag      60
gctaacaagg ccaccctcgt gtgcctgatc agcgacttct accctggcgc cgtgaccgtg     120
gcctggaagg ctgatagctc tcctgtgaag gccggcgtgg aaaccaccac cccttccaag     180
cagtccaaca caaatacgc cgcctcctcc tacctgtccc tgacccctga gcagtggaag     240
tcccaccggt cctacagctg ccaagtgacc cacgagggct ccaccgtgga aaagaccgtg     300
gctcctaccg agtgctcc                                                   318

<210> SEQ ID NO 473
<211> LENGTH: 318
<212> TYPE: DNA
<213> ORGANISM: Homo Sapiens

<400> SEQUENCE: 473
ggccagccta aagctgcccc cagcgtcacc ctgtttcctc cctccagcga ggagctccag      60
gccaacaagg ccaccctcgt gtgcctgatc tccgacttct atcccggcgc tgtgaccgtg     120
```

-continued

```
gcttggaaag ccgactccag ccctgtcaaa gccggcgtgg agaccaccac accctccaag      180
cagtccaaca acaagtacgc cgcctccagc tatctctccc tgacccctga gcagtggaag      240
tcccaccggt cctactcctg tcaggtgacc cacgagggct ccaccgtgga aaagaccgtc      300
gcccccaccg agtgctcc                                                    318
```

```
<210> SEQ ID NO 474
<211> LENGTH: 106
<212> TYPE: PRT
<213> ORGANISM: Homo Sapiens

<400> SEQUENCE: 474

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

```
<210> SEQ ID NO 475
<211> LENGTH: 318
<212> TYPE: DNA
<213> ORGANISM: Homo Sapiens

<400> SEQUENCE: 475
ggtcagccca aggctgcccc ctcggtcact ctgttcccgc cctcctctga ggagcttcaa       60
gccaacaagg ccacactggt gtgtctcata agtgacttct acccgggagc cgtgacagtg      120
gcctggaagg cagatagcag ccccgtcaag gcgggagtgg agaccaccac accctccaaa      180
caaagcaaca acaagtacgc ggccagcagc tatctgagcc tgacgcctga gcagtggaag      240
tcccacagaa gctacagctg ccaggtcacg catgaaggga gcaccgtgga agacagtg        300 gcccctacag aatgttca                                                    318
```

```
<210> SEQ ID NO 476
<211> LENGTH: 106
<212> TYPE: PRT
<213> ORGANISM: Homo Sapiens

<400> SEQUENCE: 476

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80
```

-continued

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 477
<211> LENGTH: 312
<212> TYPE: DNA
<213> ORGANISM: Homo Sapiens

<400> SEQUENCE: 477
cccaaggctg ccccctcggt cactctgttc ccacccctcct ctgaggagct tcaagccaac      60
aaggccacac tggtgtgtct cataagtgac ttctacccgg gagccgtgac agttgcctgg     120
aaggcagata gcagccccgt caaggcgggg gtggagacca ccacaccctc caaacaaagc     180
aacaacaagt acgcggccag cagctacctg agcctgacgc ctgagcagtg gaagtcccac     240
aaaagctaca gctgccaggt cacgcatgaa gggagcaccg tggagaagac agttgcccct     300
acggaatgtt ca                                                        312

<210> SEQ ID NO 478
<211> LENGTH: 104
<212> TYPE: PRT
<213> ORGANISM: Homo Sapiens

<400> SEQUENCE: 478

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
                20                  25                  30

Pro Gly Ala Val Thr Val Ala Trp Lys Ala Asp Ser Ser Pro Val Lys
            35                  40                  45

Ala Gly Val Glu Thr Thr Thr Pro Ser Lys Gln Ser Asn Asn Lys Tyr
        50                  55                  60

Ala Ala Ser Ser Tyr Leu Ser Leu Thr Pro Glu Gln Trp Lys Ser His
65                  70                  75                  80

Lys Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 479
<211> LENGTH: 318
<212> TYPE: DNA
<213> ORGANISM: Homo Sapiens

<400> SEQUENCE: 479
ggtcagccca aggctgcccc ctcggtcact ctgttcccac cctcctctga ggagcttcaa      60
gccaacaagg ccacactggt gtgtctcata agtgacttct acccgggggcc agtgacagtt     120 gcctggaagg cagatagcag ccccgtcaag gcggggggtgg agaccaccac accctccaaa     180
caaagcaaca caagtacgc ggccagcagc tacctgagcc tgacgcctga gcagtggaag      240
tcccacaaaa gctacagctg ccaggtcacg catgaaggga gcaccgtgga aagacagtg      300 gcccctacgg aatgttca                                                   318

<210> SEQ ID NO 480
<211> LENGTH: 106

```
<212> TYPE: PRT
<213> ORGANISM: Homo Sapiens

<400> SEQUENCE: 480

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Pro Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 481
<211> LENGTH: 318
<212> TYPE: DNA
<213> ORGANISM: Homo Sapiens

<400> SEQUENCE: 481
ggtcagccca aggctgcccc ctcggtcact ctgttcccac cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca caagtacgc ggccagcagc tacctgagcc tgacgcctga gcagtggaag     240
tcccacaaaa gctacagctg ccaggtcacg catgaaggga gcaccgtgga aagacagtg     300 gcccctacag aatgttca                                                  318

<210> SEQ ID NO 482
<211> LENGTH: 106
<212> TYPE: PRT
<213> ORGANISM: Homo Sapiens

<400> SEQUENCE: 482

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 483
<211> LENGTH: 318
<212> TYPE: DNA
```

<213> ORGANISM: Homo Sapiens

<400> SEQUENCE: 483

```
ggtcagccca aggctgcccc ctcggtcact ctgttcccgc cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca caagtacgc ggccagcagc tacctgagcc tgacgcctga gcagtggaag     240
tcccacagaa gctacagctg ccaggtcacg catgaaggga gcaccgtgga aagacagtg     300 gcccctacag aatgttca                                                  318
```

<210> SEQ ID NO 484
<211> LENGTH: 106
<212> TYPE: PRT
<213> ORGANISM: Homo Sapiens

<400> SEQUENCE: 484

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 485
<211> LENGTH: 318
<212> TYPE: DNA
<213> ORGANISM: Homo Sapiens

<400> SEQUENCE: 485

```
ggtcagccca aggctgcccc atcggtcact ctgttcccgc cctcctctga ggagcttcaa      60
gccaacaagg ccacactggt gtgcctgatc agtgacttct acccgggagc tgtgaaagtg     120
gcctggaagg cagatggcag ccccgtcaac acgggagtgg agaccaccac accctccaaa     180
cagagcaaca caagtacgc ggccagcagc tacctgagcc tgacgcctga gcagtggaag     240
tcccacagaa gctacagctg ccaggtcacg catgaaggga gcaccgtgga aagacagtg     300 gcccctgcag aatgttca                                                  318
```

<210> SEQ ID NO 486
<211> LENGTH: 106
<212> TYPE: PRT
<213> ORGANISM: Homo Sapiens

<400> SEQUENCE: 486

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30
```

-continued

```
Phe Tyr Pro Gly Ala Val Lys Val Ala Trp Lys Ala Asp Gly Ser Pro
        35              40              45
Val Asn Thr Gly Val Glu Thr Thr Thr Pro Ser Lys Gln Ser Asn Asn
    50              55              60
Lys Tyr Ala Ala Ser Ser Tyr Leu Ser Leu Thr Pro Glu Gln Trp Lys
65              70              75              80
Ser His Arg Ser Tyr Ser Cys Gln Val Thr His Glu Gly Ser Thr Val
                85              90              95
Glu Lys Thr Val Ala Pro Ala Glu Cys Ser
            100             105
```

```
<210> SEQ ID NO 487
<211> LENGTH: 318
<212> TYPE: DNA
<213> ORGANISM: Homo Sapiens

<400> SEQUENCE: 487
ggtcagccca aggctgcccc atcggtcact ctgttcccac cctcctctga ggagcttcaa      60
gccaacaagg ccacactggt gtgtctcgta agtgacttct acccgggagc cgtgacagtg     120
gcctggaagg cagatggcag ccccgtcaag gtgggagtgg agaccaccaa accctccaaa     180
caaagcaaca acaagtatgc ggccagcagc tacctgagcc tgacgcccga gcagtggaag     240
tcccacagaa gctacagctg ccgggtcacg catgaaggga caccgtggaa gaagacagtg     300 gccctgcag aatgctct                                                    318
```

```
<210> SEQ ID NO 488
<211> LENGTH: 106
<212> TYPE: PRT
<213> ORGANISM: Homo Sapiens

<400> SEQUENCE: 488
```

```
Gly Gln Pro Lys Ala Ala Pro Ser Val Thr Leu Phe Pro Pro Ser Ser
1               5               10              15
Glu Glu Leu Gln Ala Asn Lys Ala Thr Leu Val Cys Leu Val Ser Asp
            20              25              30
Phe Tyr Pro Gly Ala Val Thr Val Ala Trp Lys Ala Asp Gly Ser Pro
        35              40              45
Val Lys Val Gly Val Glu Thr Thr Lys Pro Ser Lys Gln Ser Asn Asn
    50              55              60
Lys Tyr Ala Ala Ser Ser Tyr Leu Ser Leu Thr Pro Glu Gln Trp Lys
65              70              75              80
Ser His Arg Ser Tyr Ser Cys Arg Val Thr His Glu Gly Ser Thr Val
                85              90              95
Glu Lys Thr Val Ala Pro Ala Glu Cys Ser
            100             105
```

```
<210> SEQ ID NO 489
<211> LENGTH: 318
<212> TYPE: DNA
<213> ORGANISM: Homo Sapiens

<400> SEQUENCE: 489
ggtcagccca aggctgcccc ctcggtcact ctgttcccac cctcctctga ggagcttcaa      60
gccaacaagg ccacactggt gtgtctcgta agtgacttca cccgggagc cgtgacagtg     120 gcctggaagg cagatggcag ccccgtcaag gtgggagtgg agaccaccaa accctccaaa     180
caaagcaaca acaagtatgc ggccagcagc tacctgagcc tgacgcccga gcagtggaag     240
```

-continued

```
tcccacagaa gctacagctg ccgggtcacg catgaaggga gcaccgtgga gaagacagtg     300
gcccctgcag aatgctct                                                  318
```

```
<210> SEQ ID NO 490
<211> LENGTH: 106
<212> TYPE: PRT
<213> ORGANISM: Homo Sapiens

<400> SEQUENCE: 490

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Asn Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105

<210> SEQ ID NO 491
<211> LENGTH: 506
<212> TYPE: PRT
<213> ORGANISM: Rattus rattus

<400> SEQUENCE: 491

Met Pro Gly Leu Gly Arg Arg Ala Gln Trp Leu Cys Trp Trp Trp Gly
1               5                   10                  15

Leu Leu Cys Ser Cys Gly Pro Pro Leu Arg Pro Pro Leu Pro Val
            20                  25                  30

Ala Ala Ala Ala Ala Gly Gly Gln Leu Leu Gly Ala Gly Gly Ser Pro
            35                  40                  45

Val Arg Ala Glu Gln Pro Pro Pro Gln Ser Ser Ser Ser Gly Phe Leu
    50                  55                  60

Tyr Arg Arg Leu Lys Thr His Glu Lys Arg Glu Met Gln Lys Glu Ile
65                  70                  75                  80

Leu Ser Val Leu Gly Leu Pro His Arg Pro Arg Pro Leu His Gly Leu
                85                  90                  95

Gln Gln Pro Gln Ser Pro Val Leu Pro Gln Gln Gln Ser Gln Gln
            100                 105                 110

Thr Ala Arg Glu Glu Pro Pro Pro Gly Arg Leu Lys Ser Ala Pro Leu
        115                 120                 125

Phe Met Leu Asp Leu Tyr Asn Ser Leu Ser Lys Asp Asp Glu Glu Asp
        130                 135                 140

Gly Val Ser Glu Gly Glu Gly Leu Glu Pro Glu Ser His Gly Arg Ala
145                 150                 155                 160

Ser Ser Ser Gln Leu Lys Gln Pro Ser Pro Gly Ala Ala His Ser Leu
                165                 170                 175

Asn Arg Lys Ser Leu Leu Ala Pro Gly Pro Gly Gly Ser Ala Ser Pro
            180                 185                 190

Leu Thr Ser Ala Gln Asp Ser Ala Phe Leu Asn Asp Ala Asp Met Val
```

-continued

```
                195                 200                 205

Met Ser Phe Val Asn Leu Val Glu Tyr Asp Lys Glu Phe Ser Pro Arg
    210                 215                 220

Gln Arg His His Lys Glu Phe Lys Phe Asn Leu Ser Gln Ile Pro Glu
225                 230                 235                 240

Gly Glu Ala Val Thr Ala Ala Glu Phe Arg Val Tyr Lys Asp Cys Val
                245                 250                 255

Val Gly Ser Phe Lys Asn Gln Thr Phe Leu Ile Ser Ile Tyr Gln Val
                260                 265                 270

Leu Gln Glu His Gln His Arg Asp Ser Asp Leu Phe Leu Leu Asp Thr
                275                 280                 285

Arg Val Val Trp Ala Ser Glu Glu Gly Trp Leu Glu Phe Asp Ile Thr
    290                 295                 300

Ala Thr Ser Asn Leu Trp Val Val Thr Pro Gln His Asn Met Gly Leu
305                 310                 315                 320

Gln Leu Ser Val Val Thr Arg Asp Gly Leu His Ile Asn Pro Arg Ala
                325                 330                 335

Ala Gly Leu Val Gly Arg Asp Gly Pro Tyr Asp Lys Gln Pro Phe Met
                340                 345                 350

Val Ala Phe Phe Lys Val Ser Glu Val His Val Arg Thr Thr Arg Ser
                355                 360                 365

Ala Ser Ser Arg Arg Arg Gln Gln Ser Arg Asn Arg Ser Thr Gln Ser
    370                 375                 380

Gln Asp Val Ser Arg Gly Ser Ser Ala Ser Asp Tyr Asn Ser Ser Glu
385                 390                 395                 400

Leu Lys Thr Ala Cys Lys Lys His Glu Leu Tyr Val Ser Phe Gln Asp
                405                 410                 415

Leu Gly Trp Gln Asp Trp Ile Ile Ala Pro Lys Gly Tyr Ala Ala Asn
                420                 425                 430

Tyr Cys Asp Gly Glu Cys Ser Phe Pro Leu Asn Ala His Met Asn Ala
                435                 440                 445

Thr Asn His Ala Ile Val Gln Thr Leu Val His Leu Met Asn Pro Glu
    450                 455                 460

Tyr Val Pro Lys Pro Cys Cys Ala Pro Thr Lys Leu Asn Ala Ile Ser
465                 470                 475                 480

Val Leu Tyr Phe Asp Asp Asn Ser Asn Val Ile Leu Lys Lys Tyr Arg
                485                 490                 495

Asn Met Val Val Arg Ala Cys Gly Cys His
            500                 505
```

<210> SEQ ID NO 492
<211> LENGTH: 509
<212> TYPE: PRT
<213> ORGANISM: Macaca fascicularis

<400> SEQUENCE: 492

```
Met Pro Gly Leu Gly Arg Arg Ala Gln Trp Leu Cys Trp Trp Trp Gly
1                   5                   10                  15

Leu Leu Cys Ser Cys Cys Gly Pro Pro Arg Pro Leu Pro Ala Ala
            20                  25                  30

Ala Ala Ala Ala Ala Gly Gly Gln Leu Leu Gly Asp Gly Gly Ser Pro
            35                  40                  45

Gly Arg Thr Glu Gln Pro Pro Pro Ser Pro Gln Ser Ser Ser Gly Phe
    50                  55                  60
```

-continued

```
Leu Tyr Arg Arg Leu Lys Thr His Glu Lys Arg Glu Met Gln Lys Glu
65              70              75              80

Ile Leu Ser Val Leu Gly Leu Pro His Arg Pro Arg Pro Leu His Gly
                85              90              95

Leu Gln Gln Pro Gln Pro Pro Ala Leu Pro Gln Gln Gln Gln Gln Gln
            100             105             110

Gln Gln Pro Pro Arg Gly Glu Pro Pro Gly Arg Leu Lys Ser Ala
            115             120             125

Pro Leu Phe Met Leu Asp Leu Tyr Asn Ala Leu Ser Ala Asp Asp Glu
    130             135             140

Glu Asp Gly Ala Ser Glu Gly Glu Arg Gln Gln Pro Trp Pro His Glu
145             150             155             160

Gly Ala Ser Ser Ser Gln Pro Arg Gln Pro Ala Pro Gly Ala Ala His
                165             170             175

Pro Leu Asn Arg Lys Ser Leu Leu Ala Pro Gly Pro Gly Ser Gly Gly
            180             185             190

Ala Ser Pro Leu Thr Ser Ala Gln Asp Ser Ala Phe Leu Asn Asp Ala
            195             200             205

Asp Met Val Met Ser Phe Val Asn Leu Val Glu Tyr Asp Lys Glu Phe
    210             215             220

Ser Pro Arg Gln Arg His His Lys Glu Phe Lys Phe Asn Leu Ser Gln
225             230             235             240

Ile Pro Glu Gly Glu Ala Val Thr Ala Ala Glu Phe Arg Ile Tyr Lys
                245             250             255

Asp Cys Val Met Gly Ser Phe Lys Asn Gln Thr Phe Leu Ile Ser Ile
            260             265             270

Tyr Gln Val Leu Gln Glu His Gln His Arg Asp Ser Asp Leu Phe Leu
            275             280             285

Leu Asp Thr Arg Val Val Trp Ala Ser Glu Glu Gly Trp Leu Glu Phe
    290             295             300

Asp Ile Thr Ala Thr Ser Asn Leu Trp Val Val Thr Pro Gln His Asn
305             310             315             320

Met Gly Leu Gln Leu Ser Val Val Thr Arg Asp Gly Val His Ile His
                325             330             335

Pro Arg Ala Ala Gly Leu Val Gly Arg Asp Gly Pro Tyr Asp Lys Gln
            340             345             350

Pro Phe Met Val Ala Phe Phe Lys Val Ser Glu Val His Val Arg Thr
            355             360             365

Thr Arg Ser Ala Ser Gly Arg Arg Arg Gln Gln Ser Arg Asn Arg Ser
    370             375             380

Thr Gln Ser Gln Asp Val Ala Arg Val Ser Ser Ala Ser Asp Tyr Asn
385             390             395             400

Ser Ser Glu Leu Lys Thr Ala Cys Arg Lys His Glu Leu Tyr Val Ser
                405             410             415

Phe Gln Asp Leu Gly Trp Gln Asp Trp Ile Ile Ala Pro Lys Gly Tyr
            420             425             430

Ala Ala Asn Tyr Cys Asp Gly Glu Cys Ser Phe Pro Leu Asn Ala His
            435             440             445

Met Asn Ala Thr Asn His Ala Ile Val Gln Thr Leu Val His Leu Met
    450             455             460

Asn Pro Glu Tyr Val Pro Lys Pro Cys Cys Ala Pro Thr Lys Leu Asn
465             470             475             480

Ala Ile Ser Val Leu Tyr Phe Asp Asp Asn Ser Asn Val Ile Leu Lys
```

-continued

```
                    485              490              495
Lys Tyr Arg Asn Met Val Val Arg Ala Cys Gly Cys His
        500              505

<210> SEQ ID NO 493
<211> LENGTH: 114
<212> TYPE: PRT
<213> ORGANISM: Homo Sapiens

<400> SEQUENCE: 493

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg

<210> SEQ ID NO 494
<211> LENGTH: 116
<212> TYPE: PRT
<213> ORGANISM: Homo Sapiens

<400> SEQUENCE: 494

Ser Pro Lys His His Ser Gln Arg Ala Arg Lys Lys Asn Lys Asn Cys
1               5                   10                  15

Arg Arg His Ser Leu Tyr Val Asp Phe Ser Asp Val Gly Trp Asn Asp
            20                  25                  30

Trp Ile Val Ala Pro Pro Gly Tyr Gln Ala Phe Tyr Cys His Gly Asp
        35                  40                  45

Cys Pro Phe Pro Leu Ala Asp His Leu Asn Ser Thr Asn His Ala Ile
    50                  55                  60

Val Gln Thr Leu Val Asn Ser Val Asn Ser Ser Ile Pro Lys Ala Cys
65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
            100                 105                 110

Cys Gly Cys Arg
        115

<210> SEQ ID NO 495
<211> LENGTH: 138
<212> TYPE: PRT
<213> ORGANISM: Homo Sapiens

<400> SEQUENCE: 495

Ala Ala Asn Lys Arg Lys Asn Gln Asn Arg Asn Lys Ser Ser Ser His
1               5                   10                  15
```

Gln Asp Ser Ser Arg Met Ser Ser Val Gly Asp Tyr Asn Thr Ser Glu
        20                  25                  30

Gln Lys Gln Ala Cys Lys Lys His Glu Leu Tyr Val Ser Phe Arg Asp
        35                  40                  45

Leu Gly Trp Gln Asp Trp Ile Ile Ala Pro Glu Gly Tyr Ala Ala Phe
        50                  55                  60

Tyr Cys Asp Gly Glu Cys Ser Phe Pro Leu Asn Ala His Met Asn Ala
65                  70                  75                  80

Thr Asn His Ala Ile Val Gln Thr Leu Val His Leu Met Phe Pro Asp
                85                  90                  95

His Val Pro Lys Pro Cys Cys Ala Pro Thr Lys Leu Asn Ala Ile Ser
                100                 105                 110

Val Leu Tyr Phe Asp Asp Ser Ser Asn Val Ile Leu Lys Lys Tyr Arg
            115                 120                 125

Asn Met Val Val Arg Ser Cys Gly Cys His
    130                 135

<210> SEQ ID NO 496
<211> LENGTH: 139
<212> TYPE: PRT
<213> ORGANISM: Homo Sapiens

<400> SEQUENCE: 496

Ser Thr Gly Ser Lys Gln Arg Ser Gln Asn Arg Ser Lys Thr Pro Lys
1                   5                   10                  15

Asn Gln Glu Ala Leu Arg Met Ala Asn Val Ala Glu Asn Ser Ser Ser
        20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
        50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
                100                 105                 110

Ser Val Leu Tyr Phe Asp Asp Ser Ser Asn Val Ile Leu Lys Lys Tyr
            115                 120                 125

Arg Asn Met Val Val Arg Ala Cys Gly Cys His
    130                 135

<210> SEQ ID NO 497
<211> LENGTH: 110
<212> TYPE: PRT
<213> ORGANISM: Homo Sapiens

<400> SEQUENCE: 497

Ser Ala Gly Ala Gly Ser His Cys Gln Lys Thr Ser Leu Arg Val Asn
1                   5                   10                  15

Phe Glu Asp Ile Gly Trp Asp Ser Trp Ile Ile Ala Pro Lys Glu Tyr
        20                  25                  30

Glu Ala Tyr Glu Cys Lys Gly Gly Cys Phe Phe Pro Leu Ala Asp Asp
        35                  40                  45

Val Thr Pro Thr Lys His Ala Ile Val Gln Thr Leu Val His Leu Lys
    50                  55                  60

-continued

```
Phe Pro Thr Lys Val Gly Lys Ala Cys Cys Val Pro Thr Lys Leu Ser
65                  70                  75                  80

Pro Ile Ser Val Leu Tyr Lys Asp Asp Met Gly Val Pro Thr Leu Lys
                85                  90                  95

Tyr His Tyr Glu Gly Met Ser Val Ala Glu Cys Gly Cys Arg
                100                 105                 110

<210> SEQ ID NO 498
<211> LENGTH: 1335
<212> TYPE: DNA
<213> ORGANISM: Homo Sapiens

<400> SEQUENCE: 498
caggtccagt ttgtgcagtc tggggctgag gtgaagagtc ctggggcctc tgtgaaggtt    60
tcctgcaagg cttctggata caccttcaca aatcatgcta tacattgggt gcgccaggcc    120
cccggacaaa ggcttgagtg gatgggatgg atcaacgctg gcaatggtaa aactgattat    180
tcacagaact ccagggcag agtcatcatt accaggggaca catccgcgaa cacagcctac    240
atgtccctga gcagcctgac atctgaggac acggctttt attactgtac tagaagggtc    300
tacggtgaat cgtatgacca ctggggccag ggaaccctgg tcaccgtctc ctcagccagc    360
accaagggcc cttccgtgtt cccctggcc ccttgcagca ggagcacctc cgaatccaca    420
gctgccctgg gctgtctggt gaaggactac tttcccgagc ccgtgaccgt gagctggaac    480
agcggcgctc tgacatccgg cgtccacacc tttcctgccg tcctgcagtc ctccggcctc    540
tactccctgt cctccgtggt gaccgtgcct agctcctccc tcggcaccaa gacctacacc    600
tgtaacgtgg accacaaacc ctccaacacc aaggtggaca acgggtcga gagcaagtac    660 ggccctccct gcctccttg tcctgccccc gagttcgaag gcggacccag cgtgttcctg    720
ttccctccta gcccaagga caccctcatg atcagccgga cacccgaggt gacctgcgtg    780
gtggtggatg tgagccagga ggaccctgag gtccagttca ctggtatgt ggatggcgtg    840 gaggtgcaca cgccaagac aaagccccgg gaagagcagt tcaactccac ctacagggtg    900
gtcagcgtgc tgaccgtgct gcatcaggac tggctgaacg gcaaggagta caagtgcaag    960
gtcagcaata agggactgcc cagcagcatc gagaagacca tctccaaggc taaaggccag    1020
ccccgggaac ctcaggtgta caccctgcct cccagccagg aggagatgac caagaaccag    1080
gtgagcctga cctgcctggt gaagggattc taccttccg acatcgccgt ggagtgggag    1140
tccaacggcc agcccgagaa caattataag accacccctc ccgtcctcga cagcgacgga    1200
tccttctttc tgtactccag gctgaccgtg dataagtcca ggtggcagga aggcaacgtg    1260
ttcagctgct ccgtgatgca cgaggccctg cacaatcact acacccagaa gtccctgagc    1320
ctgtccctgg aaag                                                        1335

<210> SEQ ID NO 499
<211> LENGTH: 642
<212> TYPE: DNA
<213> ORGANISM: Homo Sapiens

<400> SEQUENCE: 499
gacatccaga tgacccagtc tccatcctcc ctgtctgcat ctgtaggaga cagagtcacc    60
atcacttgcc gggcaagtca gggcattaga aataatttag ctggtatca gcagaaacca    120 gggaaagccc ctaagcgcct gatctatgct gcatccagtt tgcaaagtgg ggtcccatca    180
aggtttagcg gcagtggatc tgggacagaa ttcactctca caatcagcag cctgcagcct    240
```

-continued

```
gaagatgttg caatttattt ctgtctacaa catcaaattt acccgtggac gttcggccaa        300
gggaccaagg tggaaaccaa acgtacggtg gccgctccct ccgtgttcat cttcccacct        360
tccgacgagc agctgaagtc cggcaccgct tctgtcgtgt gcctgctgaa caacttctac        420
ccccgcgagg ccaaggtgca gtggaaggtg acaacgcccc tgcagtccgg caactcccag        480
gaatccgtga ccgagcagga ctccaaggac agcacctact ccctgtcctc caccctgacc        540
ctgtccaagg ccgactacga gaagcacaag gtgtacgcct cgcaagtgac ccaccagggc        600
ctgtctagcc ccgtgaccaa gtctttcaac cggggcgagt gt                          642
```

```
<210> SEQ ID NO 500
<211> LENGTH: 1335
<212> TYPE: DNA
<213> ORGANISM: Homo Sapiens

<400> SEQUENCE: 500
caggtccaac ttgtgcagtc tgggggctgag gtgcagaagc ctgggggcctc agtgaaggtt        60 tcctgcaagg cttctggata caccttcact tcatatgctt tgcattgggt gcgccaggcc        120
cccggacaaa ggcttgagtg gctgggatgg atcagcgctg ccaatggtaa cacagattat        180
tcatggaagt tccagggcag agtcacccctt accagggaca catccgcaaa cacagtctac        240
atggaactga acagtctgac atctgaggac tcggctgtgt attactgtgc gagaaggaaa        300
ctatggtctc cttttgatat ctggggccaa gggacattgg tcaccgtctc ttcagccagc        360
accaagggcc cttccgtgtt cccctggcc ccttgcagca ggagcacctc cgaatccaca        420
gctgccctgg gctgtctggt gaaggactac tttcccgagc ccgtgaccgt gagctggaac        480
agcggcgctc tgacatccgg cgtccacacc tttcctgccg tcctgcagtc ctccggcctc        540
tactccctgt cctccgtggt gaccgtgcct agctcctccc tcggcaccaa gacctacacc        600
tgtaacgtgg accacaaacc ctccaacacc aaggtggaca acgggtcga gagcaagtac        660 ggcccctccct gccctccttg tcctgccccc gagttcgaag gcggacccag cgtgttcctg        720
ttccctccta gcccaagga caccctcatg atcagccgga cacccgaggt gacctgcgtg        780
gtggtggatg tgagccagga ggaccctgag gtccagttca actggtatgt ggatggcgtg        840
gaggtgcaca acgccaagac aaagccccgg gaagagcagt tcaactccac ctacagggtg        900
gtcagcgtgc tgaccgtgct gcatcaggac tggctgaacg gcaaggagta caagtgcaag        960
gtcagcaata agggactgcc cagcagcatc gagaagacca tctccaaggc taaaggccag       1020
ccccgggaac ctcaggtgta caccctgcct cccagccagg aggagatgac caagaaccag       1080
gtgagcctga cctgcctggt gaagggattc taccccttccg acatcgccgt ggagtgggag       1140
tccaacggcc agcccgagaa caattataag accaccccctc ccgtcctcga cagcgacgga       1200
tccttctttc tgtactccag gctgaccgtg gataagtcca ggtggcagga aggcaacgtg       1260
ttcagctgct ccgtgatgca cgaggccctg cacaatcact acacccagaa gtccctgagc       1320
ctgtccctgg gaaag                                                        1335
```

```
<210> SEQ ID NO 501
<211> LENGTH: 645
<212> TYPE: DNA
<213> ORGANISM: Homo Sapiens

<400> SEQUENCE: 501
gaaattgtgt tgacgcagtc tccaggcacc ctgtctttgt ctccagggga aagagccacc         60
ctctcctgtt gggccagtca aagtcttacc aacagtttct tagcctggta ccggcagaaa        120
```

-continued

```
cctggccagg ctcccaggct cctcatctct ggtgcattca gcagggccac tgacatccca      180
gacaggatca gtggcagtgg atctgggaca gacttcactc tcaccatcaa cagactggag      240
cctgaagatt ttgcagtgta ttactgtcag tactatggta cctcaccgtg gacgttcggc      300
caagggacca aggtggaaat caaacgtacg gtggccgctc cctccgtgtt catcttccca      360
ccttccgacg agcagctgaa gtccggcacc gcttctgtcg tgtgcctgct gaacaacttc      420
tacccccgcg aggccaaggt gcagtggaag gtggacaacg ccctgcagtc cggcaactcc      480
caggaatccg tgaccgagca ggactccaag gacagcacct actccctgtc ctccaccctg      540
accctgtcca aggccgacta cgagaagcac aaggtgtacg cctgcgaagt gacccaccag      600
ggcctgtcta gccccgtgac caagtctttc aaccggggcg agtgt                     645
```

<210> SEQ ID NO 502
<211> LENGTH: 1335
<212> TYPE: DNA
<213> ORGANISM: Homo Sapiens

<400> SEQUENCE: 502

```
caggtccacc ttgttcagtc aggggcagag gtgaagaacc ctggggcctc agtgaaggtc       60
tcctgcaagg cttctggata caccttcact acctttgcta ttcattggtt gcgccaggcc      120
cccggacaga ggcttgagtg gatgggatgg atcaaccctg gcaatgttaa gacagagttat      180 tcgcagaagt tccagggcag agtcaccatt agcagggaca catccgcgac cactgcctac      240
atggagctga gcagcctgag gtctgaagac acggctgttt attactgtgc gagaagacaa      300
ttatggttac cctttgacta ctggggccag ggaaccctgg tcaccgtctc ctcagccagc      360
accaagggcc cttccgtgtt ccccctggcc ccttgcagca ggagcacctc cgaatccaca      420
gctgccctgg gctgtctggt gaaggactac tttcccgagc ccgtgaccgt gagctggaac      480
agcggcgctc tgacatccgg cgtccacacc tttcctgccg tcctgcagtc ctccggcctc      540
tactccctgt cctccgtggt gaccgtgcct agctcctccc tcggcaccaa gacctacacc      600
tgtaacgtgg accacaaacc ctccaacacc aaggtggaca aacgggtcga gagcaagtac      660
ggccctccct gccctccttg tcctgccccc gagttcgaag cggacccag cgtgttcctg       720 ttccctccta gcccaagga caccctcatg atcagccgga cacccgaggt gacctgcgtg       780
gtggtggatg tgagccagga ggaccctgag gtccagttca actggtatgt ggatggcgtg      840
gaggtgcaca cgccaagac aaagccccgg gaagagcagt tcaactccac ctacagggtg       900
gtcagcgtgc tgaccgtgct gcatcaggac tggctgaacg gcaaggagta caagtgcaag      960
gtcagcaata agggactgcc cagcagcatc gagaagacca tctccaaggc taaaggccag     1020 cccgggaac ctcaggtgta caccctgcct cccagccagg aggagatgac caagaaccag      1080
gtgagcctga cctgcctggt gaagggattc taccttccg acatcgccgt ggagtgggag      1140
tccaacggcc agcccgagaa caattataag accaccctc ccgtcctcga cagcgacgga      1200
tccttctttc tgtactccag gctgaccgtg gataagtcca ggtggcagga aggcaacgtg      1260
ttcagctgct ccgtgatgca cgaggccctg cacaatcact acacccagaa gtccctgagc      1320
ctgtccctgg gaaag                                                       1335
```

<210> SEQ ID NO 503
<211> LENGTH: 645
<212> TYPE: DNA
<213> ORGANISM: Homo Sapiens

```
<400> SEQUENCE: 503
gaaattgtgt tgacgcagtc tccaggcacc ctgtctttgt ctccagggga gggagccacc      60
ctctcctgca gggccagtca gagtattagc aacaacttct tagcctggta ccaacagaaa     120
cctggccagg ctcccagact cctcatcttt ggtgcatcca gcagggccac tgccatccca     180
gacaggttcg ttggcagtgg gtctgggaca gacttcactc tcaccatcac cggactggag     240
cctgaagatt ttgcagtgta tcactgtcaa cactatggtg gttcaccttg gacgttcggc     300
caagggacca aggtggaaat caaacgtacg gtggccgctc cctccgtgtt catcttccca     360
ccttccgacg agcagctgaa gtccggcacc gcttctgtcg tgtgcctgct gaacaacttc     420 taccccgcg aggccaaggt gcagtggaag gtggacaacg ccctgcagtc cggcaactcc     480
caggaatccg tgaccgagca ggactccaag gacagcacct actccctgtc ctccaccctg     540
accctgtcca aggccgacta cgagaagcac aaggtgtacg cctgcgaagt gacccaccag     600
ggcctgtcta gccccgtgac caagtctttc aaccggggcg agtgt               645

<210> SEQ ID NO 504
<211> LENGTH: 1335
<212> TYPE: DNA
<213> ORGANISM: Homo Sapiens

<400> SEQUENCE: 504
caggtccacc ttgttcagtc aggggcagag gtgaagaacc ctggggcctc agtgaaggtc      60
tcctgcaagg cttctggata caccttcact acctttgcta ttcattggtt gcgccaggcc     120
cccggacaga ggcttgagtg gatgggatgg atcaaccctg gcaatgttaa gacagattat     180
tcgcagaagt tccagggcag agtcaccatt agcagggaca catccgcgac cactgcctac     240
atggagctga gcagcctgag atctgaagac acggctgttt attactgtgc gagaagacaa     300
ttatggttac cctttgacta ctggggccag ggaaccctgg tcaccgtctc ctcagccagc     360
accaagggcc cttccgtgtt ccccctggcc ccttgcagca ggagcacctc cgaatccaca     420
gctgccctgg gctgtctggt gaaggactac tttcccgagc ccgtgaccgt gagctggaac     480
agcggcgctc tgacatccgg cgtccacacc tttcctgccg tcctgcagtc ctccggcctc     540
tactccctgt cctccgtggt gaccgtgcct agctcctccc tcggcaccaa gacctacacc     600
tgtaacgtgg accacaaacc ctccaacacc aaggtggaca acggtcga gagcaagtac     660 ggccctccct gccctccttg tcctgccccc gagttcgaag gcggacccag cgtgttcctg     720
ttccctccta gcccaaggga caccctcatg atcagccgga cacccgaggt gacctgcgtg     780
gtggtggatg tgagccagga ggaccctgag gtccagttca ctggtatgt ggatggcgtg     840 gaggtgcaca cgccaagac aaagccccgg gaagagcagt tcaactccac ctacaggGtg     900
gtcagcgtgc tgaccgtgct gcatcaggac tggctgaacg gcaaggagta caagtgcaag     960
gtcagcaata agggactgcc cagcagcatc gagaagacca tctccaaggc taaaggccag    1020 cccgggaac ctcaggtgta caccctgcct cccagccagg aggagatgac caagaaccag    1080
gtgagcctga cctgcctggt gaagggattc taccCttccg acatcgccgt ggagtgggag    1140
tccaacggcc agcccgagaa caattataag accaccCctc ccgtcctcga cagcgacgga    1200 tccttcttc tgtactccag gctgaccgtg ataagtcca ggtggcagga aggcaacgtg    1260
ttcagctgct ccgtgatgca cgaggccctg cacaatcact acacccagaa gtccctgagc    1320
ctgtccctgg gaaag                                                     1335
```

```
<210> SEQ ID NO 505
<211> LENGTH: 645
<212> TYPE: DNA
<213> ORGANISM: Homo Sapiens

<400> SEQUENCE: 505
gaaattgtgt tgacgcagtc tccaggcacc ctgtctttgt ctccagggga gggagccacc      60
ctctcctgca gggccagtca gagtattagc aacaacttct tagcctggta ccaacagaaa     120
cctggccagg ctcccagact cctcatcttt ggtgcatcca gcagggccac tgccatccca     180
gacaggttcg ttggcagtgg gtctgggaca gacttcactc tcaccatcac cggactggag     240
cctgaagatt ttgcagtgta tcactgtcaa cactatggtg gttcaccttg gacgttcggc     300
caagggacca aggtggaaat caaacgtacg gtggccgctc cctccgtgtt catcttccca     360
ccttccgacg agcagctgaa gtccggcacc gcttctgtcg tgtgcctgct gaacaacttc     420 taccccgcg aggccaaggt gcagtggaag gtggacaacg ccctgcagtc cggcaactcc      480
caggaatccg tgaccgagca ggactccaag gacagcacct actccctgtc ctccaccctg     540
accctgtcca aggccgacta cgagaagcac aaggtgtacg cctgcgaagt gacccaccag     600
ggcctgtcta gccccgtgac caagtctttc aaccggggcg agtgt                     645

<210> SEQ ID NO 506
<211> LENGTH: 1335
<212> TYPE: DNA
<213> ORGANISM: Homo Sapiens

<400> SEQUENCE: 506
caggtccagc ttgtgcagtc tggggctgag gtgaagaagc ctggggcctc agtgaaagtt      60
tcctgtaagg cttctgggta cagtttcact aactatgctt tacattgggt gcgccaggcc     120
cccggacaaa gacttgagtg gatgggatgg atccacgctg gtaatggtaa cacagaatat     180
gcacagaagt ccaggacag agtcaccatt agtagggaca tatccgcgat cacagtttac     240
atggaactga gcagcctgag atctgaagac acggctgttt attattgtgc gagaagacag     300
ttatggttac cctttgacta ctggggccag ggaaccctgg tcaccgtctc ctcagccagc     360
accaagggcc cttccgtgtt cccccctggcc ccttgcagca ggagcacctc cgaatccaca     420
gctgccctgg gctgtctggt gaaggactac tttcccgagc ccgtgaccgt gagctggaac     480
agcggcgctc tgacatccgg cgtccacacc tttcctgccg tcctgcagtc ctccggcctc     540
tactccctgt cctccgtggt gaccgtgcct agctcctccc tcggcaccaa gacctacacc     600
tgtaacgtgg accacaaacc ctccaacacc aaggtggaca acgggtcga gagcaagtac      660 ggccctccct gcctccttg tcctgccccc gagttcgaag cggaccagc cgtgttcctg       720 ttccctccta gcccaagga caccctcatg atcagccgga cacccgaggt gacctgcgtg     780
gtggtggatg tgagccagga ggaccctgag gtccagttca actggtatgt ggatggcgtg     840
gaggtgcaca cgccaagac aaagccccgg gaagagcagt tcaactccac ctacagggtg     900
gtcagcgtgc tgaccgtgct gcatcaggac tggctgaacg gcaaggagta caagtgcaag     960
gtcagcaata agggactgcc cagcagcatc gagaagacca tctccaaggc taaaggccag    1020 cccgggaac tcaggtgta caccctgcct cccagccagg aggagatgac caagaaccag     1080
gtgagcctga cctgcctggt gaagggattc taccctccg acatcgccgt ggagtgggag     1140
tccaacggcc agcccgagaa caattataag accacccctc ccgtcctcga cagcgacgga    1200
tccttctttc tgtactccag gctgaccgtg gataagtcca ggtggcagga aggcaacgtg    1260
```

-continued

```
ttcagctgct ccgtgatgca cgaggccctg cacaatcact acacccagaa gtccctgagc      1320
ctgtccctgg gaaag                                                        1335

<210> SEQ ID NO 507
<211> LENGTH: 645
<212> TYPE: DNA
<213> ORGANISM: Homo Sapiens

<400> SEQUENCE: 507
gaaattgtgt tgacgcagtc tccagacacc ctctctttgt ctccagggga aacagccagt        60
ttctcctgca gggccggtca aattattatc aacagacagt tagcctggta ccagcggaga       120
cctggccagg ctccccggct cctcatctat ggcgcgtcca atagggtcac tggcatccca       180
gacaggttca gtggcagtgg gtctgggaca gacttcactc tcacgatcaa tagactggag       240
cctgaagatt ttgcagtgta ttactgtcag cactatggtg gctcaccttg gacgttcggc       300
caagggacca aggtggaaat caaacgtacg gtggccgctc cctccgtgtt catcttccca       360
ccttccgacg agcagctgaa gtccggcacc gcttctgtcg tgtgcctgct gaacaacttc       420 taccccgcg aggccaaggt gcagtggaag gtggacaacg ccctgcagtc cggcaactcc        480
caggaatccg tgaccgagca ggactccaag gacagcacct actccctgtc ctccaccctg       540
accctgtcca aggccgacta cgagaagcac aaggtgtacg cctgcgaagt gacccaccag       600
ggcctgtcta gccccgtgac caagtctttc aaccggggcg agtgt                       645

<210> SEQ ID NO 508
<211> LENGTH: 1335
<212> TYPE: DNA
<213> ORGANISM: Homo Sapiens

<400> SEQUENCE: 508
caggtccagt tgtgcagtc tggggctgag gtgaagaagc ctggggcctc agtgaaggtt         60
tcctgtaagg cttctggata caccttcact agccatgcta tgcattgggt gcgccaggcc       120
cccggacaaa ggcttgagtg gatgggatgg atcaacgctg ccaatggtaa aacagattat       180
tcacagaact tccagggcag agtcaccatt accaggggaca catacgcgaa cacagtctac      240
atggaactga gcagcctgag atctgaagac acggctgtgt attactgtgc gagacgccct       300
tacggtggtc cctttgacta ctggggccag ggaaccctgg tcaccgtctc ctcagccagc       360
accaagggcc cttccgtgtt ccccctggcc ccttgcagca ggagcacctc cgaatccaca       420
gctgccctgg ctgtctggt gaaggactac tttcccgagc ccgtgaccgt gagctggaac        480
agcggcgctc tgacatccgg cgtccacacc tttcctgccg tcctgcagtc ctccggcctc       540
tactccctgt cctccgtggt gaccgtgcct agctcctccc tcggcaccaa gacctacacc       600
tgtaacgtgg accacaaacc ctccaacacc aaggtggaca acgggtcga gagcaagtac        660 ggccctccct gccctccttg tcctgccccc gagttcgaag cggacccag cgtgttcctg        720 ttccctccta gcccaagga caccctcatg atcagccgga cacccgaggt gacctgcgtg        780
gtggtggatg tgagccagga ggaccctgag gtccagttca actggtatgt ggatggcgtg       840
gaggtgcaca cgccaagac aaagcccgg gaagagcagt tcaactccac ctacagggtg         900
gtcagcgtgc tgaccgtgct gcatcaggac tggctgaacg gcaaggagta caagtgcaag       960
gtcagcaata agggactgcc cagcagcatc gagaagacca tctccaaggc taaaggccag      1020
cccccggaac tcaggtgta cacccctgcct ccagcccagg aggagatgac caagaaccag      1080
gtgagcctga cctgcctggt gaaggggattc tacccttccg acatcgccgt ggagtgggag     1140
```

-continued

```
tccaacggcc agcccgagaa caattataag accacccctc ccgtcctcga cagcgacgga      1200
tccttctttc tgtactccag gctgaccgtg gataagtcca ggtggcagga aggcaacgtg      1260
ttcagctgct ccgtgatgca cgaggccctg cacaatcact acacccagaa gtccctgagc      1320
ctgtccctgg gaaag                                                        1335

<210> SEQ ID NO 509
<211> LENGTH: 642
<212> TYPE: DNA
<213> ORGANISM: Homo Sapiens

<400> SEQUENCE: 509
gacatccaga tgacccagtc tccttccacc ctgtctgcat ctgtaggaga cagagtcacc        60
atcacttgcc gggccagtca gagtattagt atctggttgg cctggtatca gcagaaacca       120
gggaaagccc ctaagctcct gatctataag gcgtctagtt tagaaagtgg ggtcccatca       180
aggttcagcg gcagtggatc tgggacagaa ttcactctca ccatcagcag cctgcagcct       240
gatgattttg caacttatta ctgtcaacag tataatcttt atccgtggac gttcggccaa       300
gggaccaagg tggaaatcaa acgtacggtg gccgctccct ccgtgttcat cttcccacct       360
tccgacgagc agctgaagtc cggcaccgct tctgtcgtgt gcctgctgaa caacttctac       420
ccccgcgagg ccaaggtgca gtggaaggtg gacaacgccc tgcagtccgg caactcccag       480
gaatccgtga ccgagcagga ctccaaggac agcacctact ccctgtcctc caccctgacc       540
ctgtccaagg ccgactacga gaagcacaag gtgtacgcct gcgaagtgac ccaccagggc       600
ctgtctagcc ccgtgaccaa gtctttcaac cggggcgagt gt                          642

<210> SEQ ID NO 510
<211> LENGTH: 1335
<212> TYPE: DNA
<213> ORGANISM: Homo Sapiens

<400> SEQUENCE: 510
caggtccagt ttgtgcagtc tgggggctgag gtgaagaagc ctgggggcctc agtgaaggtt        60 tcctgtaagg cttctggata caccttcact agccatgcta tgcattgggt gcgccaggcc       120
cccggacaaa ggcttgagtg gatgggatgg atcaacgctg ccaatggtaa aacagattat       180
tcacagaact tccagggcag agtcaccatt accagggaca catacgcgaa cacagtctac       240
atggaactga gcagcctgag atctgaagac acggctgtgt attactgtgc gagacgccct       300
tacggtggtc cctttgacta ctggggccag ggaaccctgg tcaccgtctc ctcagccagc       360
accaagggcc cttccgtgtt ccccctggcc ccttgcagca ggagcacctc cgaatccaca       420
gctgccctgg gctgtctggt gaaggactac tttcccgagc ccgtgaccgt gagctggaac       480
agcggcgctc tgacatccgg cgtccacacc tttcctgccg tcctgcagtc ctccggcctc       540
tactccctgt cctccgtggt gaccgtgcct agctcctccc tcggcaccaa gacctacacc       600
tgtaacgtgg accacaaacc ctccaacacc aaggtggaca acgggtcga gagcaagtac        660 ggccctccct gccctccttg tcctgccccc gagttcgaag cggacccag cgtgttcctg        720 ttccctccta gcccaagga caccctcatg atcagccgga cacccgaggt gacctgcgtg        780
gtggtggatg tgagccagga ggaccctgag gtccagttca actggtatgt ggatggcgtg        840
gaggtgcaca cgccaagac aaagccccgg gaagagcagt tcaactccac ctacagggtg        900
gtcagcgtgc tgaccgtgct gcatcaggac tggctgaacg gcaaggagta caagtgcaag       960
```

```
gtcagcaata agggactgcc cagcagcatc gagaagacca tctccaaggc taaaggccag      1020
ccccgggaac ctcaggtgta caccctgcct cccagccagg aggagatgac caagaaccag      1080
gtgagcctga cctgcctggt gaagggattc taccttccg acatcgccgt ggagtgggag       1140
tccaacggcc agcccgagaa caattataag accacccctc ccgtcctcga cagcgacgga      1200 tccttcttc tgtactccag gctgaccgtg gataagtcca ggtggcagga aggcaacgtg       1260
ttcagctgct ccgtgatgca cgaggccctg cacaatcact acacccagaa gtccctgagc      1320
ctgtccctgg gaaag                                                       1335
```

<210> SEQ ID NO 511
<211> LENGTH: 642
<212> TYPE: DNA
<213> ORGANISM: Homo Sapiens

<400> SEQUENCE: 511

```
gacatccaga tgacccagtc tccttccacc ctgtctgcat ctgtaggaga cagagtcacc        60
atcacttgcc gggccagtca gagtattagt atctggttgg cctggtatca gcagaaacca       120
gggaaagccc ctaagctcct gatctataag gcgtctagtt tagaaagtgg ggtcccatca       180
aggttcagcg gcagtggatc tgggacagaa ttcactctca ccatcagcag cctgcagcct       240
gatgattttg caacttatta ctgtcaacag tataatcttt atccgtggac gttcggccaa       300
gggaccaagg tggaaatcaa acgtacggtg gccgctccct ccgtgttcat cttcccacct       360
tccgacgagc agctgaagtc cggcaccgct tctgtcgtgt gcctgctgaa caacttctac       420
ccccgcgagg ccaaggtgca gtggaaggtg gacaacgccc tgcagtccgg caactcccag       480
gaatccgtga ccgagcagga ctccaaggac agcacctact ccctgtcctc caccctgacc       540
ctgtccaagg ccgactacga gaagcacaag gtgtacgcct gcgaagtgac ccaccagggc       600
ctgtctagcc ccgtgaccaa gtctttcaac cggggcgagt gt                         642
```

<210> SEQ ID NO 512
<211> LENGTH: 1332
<212> TYPE: DNA
<213> ORGANISM: Homo Sapiens

<400> SEQUENCE: 512

```
caggtgcaac tggtggagtc tgggggaggc ttggtcaagc ctggagggtc cctgagactc        60
tcctgtgcag cctctggatt caccttcagt gactactaca tgagttggat ccgccaggct       120
ccagggaagg ggctggagtg ggtttcatac attagtatta gtggtagtac catatactac       180
gcagactctg tgaagggccg attcaccatc tccagggaca cgccatggga ctcactgtat       240
ctgcaaatga acagcctgag agccgaggac acggccgtgt attactgtgc gagacggagc       300
agtggctggt acgactactg gggccaggga accctggtca ccgtctcctc agccagcacc       360
aagggccctt ccgtgttccc cctggcccct tgcagcagga gcacctccga atccacagct       420
gccctgggct gtctggtgaa ggactacttt cccgagcccg tgaccgtgag ctggaacagc       480
ggcgctctga catccggcgt ccacaccttt cctgccgtcc tgcagtcctc cggcctctac       540
tccctgtcct ccgtggtgac cgtgcctagc tcctccctcg gcaccaagac ctacacctgt       600
aacgtggacc acaaaccctc caacaccaag gtggacaaac gggtcgagag caagtacggc       660 cctcctgcc ctccttgtcc tgcccccgag ttcgaaggcg acccagcgt gttcctgttc        720 cctcctaagc ccaaggacac cctcatgatc agccggacac ccgaggtgac ctgcgtggtg       780
gtggatgtga gccaggagga ccctgaggtc cagttcaact ggtatgtgga tggcgtggag       840
```

-continued

```
gtgcacaacg ccaagacaaa gccccgggaa gagcagttca actccaccta cagggtggtc      900
agcgtgctga ccgtgctgca tcaggactgg ctgaacggca aggagtacaa gtgcaaggtc      960
agcaataagg gactgcccag cagcatcgag aagaccatct ccaaggctaa aggccagccc     1020
cgggaacctc aggtgtacac cctgcctccc agccaggagg agatgaccaa gaaccaggtg     1080
agcctgacct gcctggtgaa gggattctac ccttccgaca tcgccgtgga gtgggagtcc     1140
aacggccagc ccgagaacaa ttataagacc acccctcccg tcctcgacag cgacggatcc     1200
ttctttctgt actccaggct gaccgtggat aagtccaggt ggcaggaagg caacgtgttc     1260
agctgctccg tgatgcacga ggccctgcac aatcactaca cccagaagtc cctgagcctg     1320
tccctgggaa ag                                                          1332
```

<210> SEQ ID NO 513
<211> LENGTH: 645
<212> TYPE: DNA
<213> ORGANISM: Homo Sapiens

<400> SEQUENCE: 513

```
gaaattgtgt tgacgcagtc tccaggcacc ctgtctttgt ctccagggga aagagccacc       60
ctctcttgtt gggccagtca gagggttgtt tacagatact tagcctggta ccagcggaaa      120
cctggccagg ctcccagact tctcatttat ggtgcattca acaggggccac tggcatccca      180 gacaggttca gtggcagtgg gtctgggaca gacttcagtc tcactatcag tagactggag      240
cctgaggatt ttgcagtttta ttactgtcac caatatggta gttcaccacc gacgttcggc      300
caagggacca aggtggaaat caaacgtacg gtggccgctc cctccgtgtt catcttccca      360
ccttccgacg agcagctgaa gtccggcacc gcttctgtcg tgtgcctgct gaacaacttc      420
tacccccgcg aggccaaggt gcagtggaag gtggacaacg ccctgcagtc cggcaactcc      480
caggaatccg tgaccgagca ggactccaag gacagcacct actccctgtc ctccaccctg      540
accctgtcca aggccgacta cgagaagcac aaggtgtacg cctgcgaagt gacccaccag      600
ggcctgtcta gccccgtgac caagtctttc aaccggggcg agtgt                      645
```

<210> SEQ ID NO 514
<211> LENGTH: 1332
<212> TYPE: DNA
<213> ORGANISM: Homo Sapiens

<400> SEQUENCE: 514

```
caagttcagt tggttgagtc tggcggcgga ctggttaagc ctggcggatc tctgagactg       60
tcttgtgccg cctctggctt caccttctcc gactactaca tgtcctggat cagacaggcc      120
cctggcaaag gctggaatg ggtgtcctac atctccatct ccggctccac catctactac      180
gccgactccg tgaagggcag attcaccatc tccagagaca cgccatgga ctccctgtac      240 ctgcagatga actccctgag agccgaggac accgccgtgt actactgcgc ccgtagatcc      300
tctggatggt acgactattg gggccagggc accctggtca cagtgtcctc tgccagcacc      360
aagggccctt ccgtgttccc cctggcccct tgcagcagga gcacctccga atccacagct      420
gccctgggct gtctggtgaa ggactacttt cccgagcccg tgaccgtgag ctggaacagc      480
ggcgctctga catccggcgt ccacaccttt cctgccgtcc tgcagtcctc cggcctctac      540
tccctgtcct ccgtggtgac cgtgcctagc tcctccctcg gcaccaagac ctacacctgt      600
aacgtggacc acaaaccctc caacaccaag gtggacaaac gggtcgagag caagtacggc      660
```

```
                                                   -continued
```

```
cctccctgcc ctccttgtcc tgcccccgag ttcgaaggcg acccagcgt gttcctgttc      720 cctcctaagc ccaaggacac cctcatgatc agccggacac ccgaggtgac ctgcgtggtg      780
gtggatgtga gccaggagga ccctgaggtc cagttcaact ggtatgtgga tggcgtggag      840
gtgcacaacg ccaagacaaa gccccgggaa gagcagttca actccaccta cagggtggtc      900
agcgtgctga ccgtgctgca tcaggactgg ctgaacggca aggagtacaa gtgcaaggtc      960
agcaataagg gactgcccag cagcatcgag aagaccatct ccaaggctaa aggccagccc     1020
cgggaacctc aggtgtacac cctgcctccc agccaggagg agatgaccaa gaaccaggtg     1080
agcctgacct gcctggtgaa gggattctac ccttccgaca tcgccgtgga gtgggagtcc     1140
aacggccagc ccgagaacaa ttataagacc acccctcccg tcctcgacag cgacggatcc     1200
ttctttctgt actccaggct gaccgtggat aagtccaggt ggcaggaagg caacgtgttc     1260
agctgctccg tgatgcacga ggccctgcac aatcactaca cccagaagtc cctgagcctg     1320
tccctgggaa ag                                                         1332
```

```
<210> SEQ ID NO 515
<211> LENGTH: 645
<212> TYPE: DNA
<213> ORGANISM: Homo Sapiens

<400> SEQUENCE: 515
gaaattgtgc tgactcagtc ccctggcaca ctgtctttga gccctggcga gagagctacc       60
ctgtcttgtt gggcctctca gagagtggtg tacagatacc tggcttggta tcagcggaag      120
cccggccagg ctcctagact gttgatctac ggcgccttca acagagccac aggcatccct      180
gacagattct ccggctctgg ctctggcacc gacttctccc tgactatctc tcggctggaa      240
cccgaggact tcgccgtgta ctactgtcac cagtacggca gcagccctcc tacctttggc      300
cagggcacta aggtggaaat caaacgtacg gtggccgctc cctccgtgtt catcttccca      360
ccttccgacg agcagctgaa gtccggcacc gcttctgtcg tgtgcctgct gaacaacttc      420 taccccccgcg aggccaaggt gcagtggaag gtggacaacg ccctgcagtc cggcaactcc      480
caggaatccg tgaccgagca ggactccaag acagcacct actccctgtc ctccaccctg       540
accctgtcca aggccgacta cgagaagcac aaggtgtacg cctgcgaagt gacccaccag      600
ggcctgtcta gccccgtgac caagtctttc aaccggggcg agtgt                      645
```

```
<210> SEQ ID NO 516
<211> LENGTH: 1332
<212> TYPE: DNA
<213> ORGANISM: Homo Sapiens

<400> SEQUENCE: 516
caggttcagc tggttgaatc tggcggcgga ctggttaagc ctggcggatc tctgagactg       60
tcttgtgccg cctctggctt caccttctcc gactactaca tgtcctggat cagacaggcc      120
cctggcaaag cctggaatg ggtgtcctac atctccatct ccggctccac catctactac       180
gccgactccg tgaagggcag attcaccatc tccagagaca cgccatgga ctccctgtac       240 ctgcagatga ctcccctgag agccgaggac accgccgtgt actactgcgc ccgtagatcc      300
tctggatggt acgactattg gggccagggc accctggtca cagtgtcctc tgcttctacc      360
aagggaccca gcgtgttccc tctggctcct tgctccagat ccacctccga gtctacagct      420
gctctgggct gcctggtcaa ggactacttt cctgagcctg tgaccgtgtc ctggaactct      480
ggcgctctga catctggcgt gcacacctt ccagctgtgc tgcagtcctc cggcctgtac      540
```

-continued

```
tctctgtcct ctgtcgtgac cgtgccttcc tctagcctgg gcaccaagac ctacacctgt        600
aatgtggacc acaagccttc caacaccaag gtggacaagc gcgtggaatc taagtacggc        660
cctccttgtc ctccatgtcc tgctccagag tttgaaggcg gcccttccgt gtttctgttc        720
cctccaaagc ctaaggacac cctgatgatc tctcggaccc ctgaagtgac ctgcgtggtg        780
gtggatgtgt cccaagagga ccctgaggtg cagttcaatt ggtacgtgga cggcgtggaa        840
gtgcacaacg ccaagaccaa gcctagagag gaacagttca actccaccta cagagtggtg        900
tccgtgctga ccgtgctgca ccaggattgg ctgaacggca agagtacaa gtgcaaggtg        960 tccaacaagg gcctgcctag ctccatcgaa aagaccatca gcaaggccaa gggccagcct      1020
cgagaacccc aggtttacac cctgcctcca agccaagagg aaatgaccaa gaaccaggtg      1080
tccctgacct gcctcgtgaa gggattctac ccctccgata tcgccgtgga atgggagtct      1140
aatggccagc cagagaacaa ctacaagaca acccctcctg tgctggactc cgacggctcc      1200
ttctttctgt attcccgcct gaccgtggac aagtccagat ggcaagaggg caacgtgttc      1260
tcctgcagcg tgatgcacga ggccctgcac aatcactaca cccagaagtc cctgtctctg      1320
tccctgggca ag                                                          1332
```

```
<210> SEQ ID NO 517
<211> LENGTH: 645
<212> TYPE: DNA
<213> ORGANISM: Homo Sapiens

<400> SEQUENCE: 517
gagatcgtgc tgacccagtc tcctggcaca ctgtcactgt ctccaggcga gagagctacc         60
ctgtcttgtt gggcctctca gagagtggtg tacagatacc tggcttggta tcagcggaag        120
cccggccagg ctcctagact gttgatctac ggcgccttca cagagccac aggcatccct        180 gacagattct ccggctctgg ctctggcacc gacttctccc tgactatctc tcggctggaa        240
cccgaggact tcgccgtgta ctactgtcac cagtacggca gcagccctcc tacctttggc        300
cagggcacaa aggtggaaat caagcgtacg gtggccgctc ccagcgtgtt catcttcccc        360
ccaagcgacg agcagctgaa gagcggcacc gccagcgtgg tgtgtctgct gaacaacttc        420
taccccaggg aggccaaggt gcagtggaag gtggacaacg ccctgcagag cggcaacagc        480
caggagagcg tcaccgagca ggacagcaag gactccacct acagcctgag cagcaccctg        540
accctgagca aggccgacta cgagaagcac aaggtgtacg cctgtgaggt gacccaccag        600
ggcctgtcca gccccgtgac caagagcttc aacaggggcg agtgc                       645
```

```
<210> SEQ ID NO 518
<211> LENGTH: 1332
<212> TYPE: DNA
<213> ORGANISM: Homo Sapiens

<400> SEQUENCE: 518
caggtgcaac tggtggagtc tgggggaggc ttggtcaagc ctggagggtc cctgagactc         60
tcctgtgcag cctctggatt caccttcagt gactactaca tgagttggat ccgccaggct        120
ccagggaagg ggctggagtg ggtttcatac attagtatta gtggtagtac catatactac        180
gcagactctg tgaagggccg attcaccatc tccagggaca cgccatgga ctcactgtat        240 ctgcaaatga acagcctgag agccgaggac acggccgtgt attactgtgc gagacggagc        300
agtggctggt acgactactg gggccaggga accctggtca ccgtctcctc agcctccacc        360
```

-continued

```
aagggcccat ccgtcttccc cctggcgccc tgctccagga gcacctccga gagcacggcc      420
gccctgggct gcctggtcaa ggactacttc cccgaaccag tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacgaagac ctacacctgc      600
aacgtagatc acaagcccag caacaccaag gtggacaaga gagttgagtc caaatatggt      660
cccccatgcc caccatgccc agcgcctgaa tttgaggggg gaccatcagt cttcctgttc      720
cccccaaaac ccaaggacac tctcatgatc tcccggaccc ctgaggtcac gtgcgtggtg      780
gtggacgtga gccaggaaga cccccgaggtc cagttcaact ggtacgtgga tggcgtggag      840
gtgcataatg ccaagacaaa gccgcgggag gagcagttca cagcacgta ccgtgtggtc      900 agcgtcctca ccgtcctgca ccaggactgg ctgaacggca aggagtacaa gtgcaaggtc      960
tccaacaaag gcctcccgtc atcgatcgag aaaaccatct ccaaagccaa agggcagccc     1020
cgagagccac aggtgtacac cctgcccccca tcccaggagg agatgaccaa gaaccaggtc     1080
agcctgacct gcctggtcaa aggcttctac cccagcgaca tcgccgtgga gtgggagagc     1140
aatgggcagc cggagaacaa ctacaagacc acgcctcccg tgctggactc cgacggatcc     1200
ttcttcctct acagcaggct aaccgtggac aagagcaggt ggcaggaggg gaatgtcttc     1260
tcatgctccg tgatgcatga ggctctgcac aaccactaca cacagaagag cctctccctg     1320
tctctgggta aa                                                          1332
```

<210> SEQ ID NO 519
<211> LENGTH: 1332
<212> TYPE: DNA
<213> ORGANISM: Homo Sapiens

<400> SEQUENCE: 519

```
caggtgcaac tggtggagtc tggggggaggc ttggtcaagc ctggagggtc cctgagactc       60
tcctgtgcag cctctggatt caccttcagt gactactaca tgagttggat ccgccaggct      120
ccagggaagg ggctggagtg ggtttcatac attagtatta gtggtagtac catatactac      180
gcagactctg tgaagggccg attcaccatc tccagggaca cgccatgga ctcactgtat      240 ctgcaaatga acagcctgag agccgaggac acggccgtgt attactgtgc gagacggagc      300
agtggctggt acgactactg gggccaggga accctggtca ccgtctcctc agcctccacc      360
aagggaccta cggtgttccc tctcgccccc tgttccaggt ccacaagcga gtccaccgct      420
gccctcggct gtctggtgaa agactacttt cccgagcccg tgaccgtctc ctggaatagc      480
ggagccctga cctccggcgt gcacacattt cccgccgtgc tgcagagcag cggactgtat      540
agcctgagca gcgtggtgac cgtgcccagc tccagcctcg gcaccaaaac ctacacctgc      600
aacgtggacc acaagccctc caacaccaag gtggacaagc gggtggagag caagtacggc      660
cccccttgcc ctccttgtcc tgccctgag ttcgagggag accctccgt gttcctgttt      720 cccccccaaac ccaaggacac cctgatgatc tcccggacac ccgaggtgac ctgtgtggtc      780
gtggacgtca gccaggagga cccccgaggtg cagttcaact ggtatgtgga cggcgtggag      840
gtgcacaatg ccaaaaccaa gccacaggag gagcagttca attccaccta caggtggtg      900 agcgtgctga ccgtcctgca tcaggattgg ctgaacggca aggagtacaa gtgcaaggtg      960
tccaacaagg gactgcccag ctccatcgag aagaccatca gcaaggctaa gggccagccg     1020
agggagcccc aggtgtatac cctgcctcct agccaggaag agatgaccaa gaaccaagtg     1080
tccctgacct gcctggtgaa gggattctac ccctccgaca tcgccgtgga gtgggagagc     1140
```

```
aatggccagc ccgagaacaa ctacaaaaca acccctcccg tgctcgatag cgacggcagc      1200
ttctttctct acagccggct gacagtggac aagagcaggt ggcaggaggg caacgtgttc      1260
tcctgttccg tgatgcacga ggccctgcac aatcactaca cccagaagag cctctccctg      1320
tccctgggca ag                                                          1332

<210> SEQ ID NO 520
<211> LENGTH: 351
<212> TYPE: DNA
<213> ORGANISM: Homo Sapiens

<400> SEQUENCE: 520
caggttcagc tggttgaatc tggcggcgga ctggttaagc ctggcggatc tctgagactg        60
tcttgtgccg cctctggctt caccttctcc gactactaca tgtcctggat cagacaggcc       120
cctggcaaag gcctggaatg ggtgtcctac atctccatct ccggctccac catctactac       180
gccgactccg tgaagggcag attcaccatc tccagagaca cgccatgga ctccctgtac        240 ctgcagatga actccctgag agccgaggac accgccgtgt actactgcgc ccgtagatcc       300
tctggatggt acgactattg gggccagggc accctggtca cagtgtcctc t               351

<210> SEQ ID NO 521
<211> LENGTH: 351
<212> TYPE: DNA
<213> ORGANISM: Homo Sapiens

<400> SEQUENCE: 521
caagttcagt tggttgagtc tggcggcgga ctggttaagc ctggcggatc tctgagactg        60
tcttgtgccg cctctggctt caccttctcc gactactaca tgtcctggat cagacaggcc       120
cctggcaaag gcctggaatg ggtgtcctac atctccatct ccggctccac catctactac       180
gccgactccg tgaagggcag attcaccatc tccagagaca cgccatgga ctccctgtac        240 ctgcagatga actccctgag agccgaggac accgccgtgt actactgcgc ccgtagatcc       300
tctggatggt acgactattg gggccagggc accctggtca cagtgtcctc t               351

<210> SEQ ID NO 522
<211> LENGTH: 324
<212> TYPE: DNA
<213> ORGANISM: Homo Sapiens

<400> SEQUENCE: 522
gagatcgtgc tgacccagtc tcctggcaca ctgtcactgt ctccaggcga gagagctacc        60
ctgtcttgtt gggcctctca gagagtggtg tacagatacc tggcttggta tcagcggaag       120
cccggccagg ctcctagact gttgatctac ggcgccttca acagagccac aggcatccct       180
gacagattct ccggctctgg ctctggcacc gacttctccc tgactatctc tcggctggaa       240
cccgaggact tcgccgtgta ctactgtcac cagtacggca gcagccctcc tacctttggc       300
cagggcacaa aggtggaaat caag                                             324

<210> SEQ ID NO 523
<211> LENGTH: 324
<212> TYPE: DNA
<213> ORGANISM: Homo Sapiens

<400> SEQUENCE: 523
gaaattgtgc tgactcagtc ccctggcaca ctgtctttga gccctggcga gagagctacc        60
```

-continued

```
ctgtcttgtt gggcctctca gagagtggtg tacagatacc tggcttggta tcagcggaag      120
cccggccagg ctcctagact gttgatctac ggcgccttca acagagccac aggcatccct      180
gacagattct ccggctctgg ctctggcacc gacttctccc tgactatctc tcggctggaa      240
cccgaggact cgccgtgta ctactgtcac cagtacggca gcagccctcc tacctttggc      300
cagggcacta aggtggaaat caaa                                             324

<210> SEQ ID NO 524
<211> LENGTH: 1335
<212> TYPE: DNA
<213> ORGANISM: Homo Sapiens

<400> SEQUENCE: 524
caggtccaac ttgtgcagtc tggggctgag gtgaagaagc ctggggcctc agtgaaggtt       60
tcctgcaagg ctactggatt caccttcatt acctatgctt tccattgggt gcgccaggcc      120
cccggacaaa ggtttgagtg gatgggatgg atcaacgttg gcaatggtaa cagagaatat      180
tcacagaagt tccaggacag agtcaccatt accaggaca catccgcgac cacagtctac       240
atggaactga acagcctgaa atctgaagac acggctatgt atttctgtgc gagacgcccc      300
ctctggggtc cctttgacta ctggggccag ggaaccctgg tcaccgtctc ctcagccagc      360
accaagggcc cttccgtgtt ccccctggcc ccttgcagca ggagcacctc cgaatccaca      420
gctgccctgg ctgtctggt gaaggactac tttcccgagc ccgtgaccgt gagctggaac       480
agcggcgctc tgacatccgg cgtccacacc tttcctgccg tcctgcagtc ctccggcctc      540
tactccctgt cctccgtggt gaccgtgcct agctcctccc tcggcaccaa gacctacacc      600
tgtaacgtgg accacaaacc ctccaacacc aaggtggaca acgggtcga gagcaagtac       660 ggccctccct gcctccttg tcctgcccc gagttcgaag gcggaccag cgtgttcctg         720 ttccctccta gcccaagga caccctcatg atcagccgga cacccgaggt gacctgcgtg       780
gtggtggatg tgagccagga ggaccctgag gtccagttca actggtatgt ggatggcgtg      840
gaggtgcaca cgccaagac aaagccccgg gaagagcagt tcaactccac ctacagggtg       900
gtcagcgtgc tgaccgtgct gcatcaggac tggctgaacg gcaaggagta caagtgcaag      960
gtcagcaata agggactgcc cagcagcatc gagaagacca tctccaaggc taaaggccag     1020
ccccgggaac ctcaggtgta caccctgcct cccagccagg aggagatgac caagaaccag     1080
gtgagcctga cctgcctggt gaagggattc taccccttccg acatcgccgt ggagtgggag    1140
tccaacggcc agcccgagaa caattataag accaccctc ccgtcctcga cagcgacgga     1200 tccttcttc tgtactccag gctgaccgtg gataagtcca ggtggcagga aggcaacgtg      1260
ttcagctgct ccgtgatgca cgaggccctg cacaatcact acacccagaa gtccctgagc     1320
ctgtccctgg gaaag                                                     1335

<210> SEQ ID NO 525
<211> LENGTH: 645
<212> TYPE: DNA
<213> ORGANISM: Homo Sapiens

<400> SEQUENCE: 525
gaaattgttt tgacacagtc tccaggcacc ctgtctttgt ctccagggga aagagccacc       60
ctctcctgca gggccagtca gattttagc aacaccttct tagcctggta ccagcagaaa      120
cctggccagg ctcccaggct cctcgtgtat ggtgcatcca gagggccac tgccatccca       180 gacaggttta gtggcagtgg gtctgggaca gacttcattc tcaccatcaa cagactggag     240
```

-continued

```
cctgaagatt ttgcagtata ttactgtcaa cactatggtg ggtcaccgtg gacgttcggc      300
cgagggacca aggtggaaat caaacgtacg gtggccgctc cctccgtgtt catcttccca      360
ccttccgacg agcagctgaa gtccggcacc gcttctgtcg tgtgcctgct gaacaacttc      420
tacccccgcg aggccaaggt gcagtggaag gtggacaacg ccctgcagtc cggcaactcc      480
caggaatccg tgaccgagca ggactccaag gacagcacct actccctgtc ctccaccctg      540
accctgtcca aggccgacta cgagaagcac aaggtgtacg cctgcgaagt gacccaccag      600
ggcctgtcta gccccgtgac caagtctttc aaccggggcg agtgt                      645

<210> SEQ ID NO 526
<211> LENGTH: 1335
<212> TYPE: DNA
<213> ORGANISM: Homo Sapiens

<400> SEQUENCE: 526
caggtccaac ttgtgcagtc tgggggctgag gtgaagaagc ctgggggcctc agtgaaggtt       60 tcctgcaagg ctactggatt caccttcatt acctatgctt ccattgggt gcgccaggcc       120 cccggacaaa ggtttgagtg gatgggatgg atcaacgttg gcaatggtaa cagagaatat      180
tcacagaagt tccaggacag agtcaccatt accagggaca catccgcgac cacagtctac      240
atggaactga cagcctgaa atctgaagac acggctatgt atttctgtgc gagacgcccc      300
ctctggggtc cctttgacta ctggggccag ggaaccctgg tcaccgtctc ctcagccagc      360
accaagggcc cttccgtgtt ccccctggcc ccttgcagca ggagcacctc cgaatccaca      420
gctgccctgg gctgtctggt gaaggactac tttcccgagc ccgtgaccgt gagctggaac      480
agcggcgctc tgacatccgg cgtccacacc tttcctgccg tcctgcagtc ctccggcctc      540
tactccctgt cctccgtggt gaccgtgcct agctcctccc tcggcaccaa gacctacacc      600
tgtaacgtgg accacaaacc ctccaacacc aaggtggaca aacgggtcga gagcaagtac      660
ggccctccct gccctccttg tcctgcccc gagttcgaag cggacccag cgtgttcctg      720 ttccctccta gcccaagga caccctcatg atcagccgga cacccgaggt gacctgcgtg      780
gtggtggatg tgagccagga ggaccctgag gtccagttca actggtatgt ggatggcgtg      840
gaggtgcaca cgccaagac aaagccccgg gaagagcagt tcaactccac ctacagggtg      900
gtcagcgtgc tgaccgtgct gcatcaggac tggctgaacg gcaaggagta caagtgcaag      960
gtcagcaata agggactgcc cagcagcatc gagaagacca tctccaaggc taaaggccag     1020 cccgggaac ctcaggtgta cacctgcct cccagccagg aggagatgac caagaaccag     1080
gtgagcctga cctgcctggt gaagggattc taccttccg acatcgccgt ggagtgggag     1140
tccaacggcc agccgagaa caattataag accacccctc ccgtcctcga cagcgacgga     1200
tccttctttc tgtactccag gctgaccgtg gataagtcca ggtggcagga aggcaacgtg     1260
ttcagctgct ccgtgatgca cgaggccctg cacaatcact acacccagaa gtccctgagc     1320
ctgtccctgg gaaag                                                      1335

<210> SEQ ID NO 527
<211> LENGTH: 645
<212> TYPE: DNA
<213> ORGANISM: Homo Sapiens

<400> SEQUENCE: 527
gaaattgttt tgacacagtc tccaggcacc ctgtctttgt ctccagggga aagagccacc       60
```

```
ctctcctgca gggccagtca gatttttagc aacaccttct tagcctggta ccagcagaaa      120
cctggccagg ctcccaggct cctcgtgtat ggtgcatcca agagggccac tgccatccca      180
gacaggttta gtggcagtgg gtctgggaca gacttcattc tcaccatcaa cagactggag      240
cctgaagatt ttgcagtata ttactgtcaa cactatggtg ggtcaccgtg gacgttcggc      300
cgagggacca aggtggaaat caaacgtacg gtggccgctc cctccgtgtt catcttccca      360
ccttccgacg agcagctgaa gtccggcacc gcttctgtcg tgtgcctgct gaacaacttc      420
tacccccgcg aggccaaggt gcagtggaag gtggacaacg ccctgcagtc cggcaactcc      480
caggaatccg tgaccgagca ggactccaag gacagcacct actccctgtc ctccaccctg      540
accctgtcca aggccgacta cgagaagcac aaggtgtacg cctgcgaagt gacccaccag      600
ggcctgtcta gccccgtgac caagtctttc aaccggggcg agtgt                      645
```

<210> SEQ ID NO 528
<211> LENGTH: 1335
<212> TYPE: DNA
<213> ORGANISM: Homo Sapiens

<400> SEQUENCE: 528

```
caggtccagc ttgtgcagtc tggggctgag gtgaagaagc ctggggcctc agtgaaggtt       60
tcctgcaagg cttctggata caccttcact agccatgcta tacattgggt gcgccaggcc      120
cccggacaac ggcttgagtg gatgggatgg atccacgctg gcaatggtaa ctcaaaacag      180
tcacagaact tccaggacag agtcaccatt accagggaca catccgcgag cgcagcctac      240
atggagctga gcagcctgag atctgaagac acggctgtat attactgtgc gagacgggcc      300
ataatggccc cgtttgacct ctggggccag ggaaccctgg tcaccgtctc ctcagccagc      360
accaagggcc cttccgtgtt ccccctggcc ccttgcagca ggagcacctc cgaatccaca      420
gctgccctgg gctgtctggt gaaggactac tttcccgagc ccgtgaccgt gagctggaac      480
agcggcgctc tgacatccgg cgtccacacc tttcctgccg tcctgcagtc ctccggcctc      540
tactccctgt cctccgtggt gaccgtgcct agctcctccc tcggcaccaa gacctacacc      600
tgtaacgtgg accacaaacc ctccaacacc aaggtggaca acgggtcga gagcaagtac      660 ggccctccct gccctccttg tcctgccccc gagttcgaag gcggacccag cgtgttcctg      720
ttccctccta gcccaagga caccctcatg atcagccgga cacccgaggt gacctgcgtg      780
gtggtggatg tgagccagga ggaccctgag gtccagttca ctggtatgt ggatggcgtg      840 gaggtgcaca cgccaagac aaagccccgg gaagagcagt tcaactccac ctacagggtg      900
gtcagcgtgc tgaccgtgct gcatcaggac tggctgaacg gcaaggagta caagtgcaag      960
gtcagcaata agggactgcc cagcagcatc gagaagacca tctccaaggc taaaggccag     1020 cccgggaac ctcaggtgta caccctgcct cccagccagg aggagatgac caagaaccag     1080
gtgagcctga cctgcctggt gaagggattc taccttccg acatcgccgt ggagtgggag     1140
tccaacggcc agcccgagaa caattataag accacccctc ccgtcctcga cagcgacgga     1200 tccttcttc tgtactccag gctgaccgtg gataagtcca ggtggcagga aggcaacgtg     1260
ttcagctgct ccgtgatgca cgaggccctg cacaatcact acacccagaa gtccctgagc     1320
ctgtccctgg gaaag                                                      1335
```

<210> SEQ ID NO 529
<211> LENGTH: 639
<212> TYPE: DNA
<213> ORGANISM: Homo Sapiens -continued

<400> SEQUENCE: 529
gacatccaga tgacccagtc tccttccacc ctgtctgcat ctgtaggaga cagagtcacc          60
atcacttgcc gggccagtca gagtattaat aactggttgg cctggtatca gcagaaacca         120
gggaaagccc ctaacctcct gatctataag gcgtctagtt tagaaagtgg ggtcccatca         180
aggttcagcg gcagtggatc tgggacagaa ttcactctca ccatcaacag cctgcagcct         240
gatgactttg caacttatta ctgccaacag tattatagtt cttggacgtt cggccaaggg         300
accaaggtgg aaatcaaacg tacggtggcc gctccctccg tgttcatctt cccaccttcc         360
gacgagcagc tgaagtccgg caccgcttct gtcgtgtgcc tgctgaacaa cttctacccc         420
cgcgaggcca aggtgcagtg gaaggtggac aacgccctgc agtccggcaa ctcccaggaa         480
tccgtgaccg agcaggactc caaggacagc acctactccc tgtcctccac cctgaccctg         540
tccaaggccg actacgagaa gcacaaggtg tacgcctgcg aagtgaccca ccagggcctg         600
tctagccccg tgaccaagtc tttcaaccgg ggcgagtgt                               639

<210> SEQ ID NO 530
<211> LENGTH: 1335
<212> TYPE: DNA
<213> ORGANISM: Homo Sapiens

<400> SEQUENCE: 530
caggtccagc ttgtgcagtc tggggctgag gtgaagaagc ctggggcctc agtgaaggtt          60
tcctgcaagg cttctggata caccttcact agctatgctg tccattgggt gcgccaggcc         120
cccggacaaa ggcttgagtg gatgggatgg atcaacgctg gcaatggtaa cacaaaattt         180
tcacagaagt tccagggcag aatcaccatt accagggaca tccgcgag cacaacctac          240 atggagttga atagtctgag atctgaagac acggctgtgt attattgtgc gagaagggg          300 ttcggggagc catttgacta ctggggccag ggaaccctgg tcaccgtctc ctcagccagc         360
accaagggcc cttccgtgtt cccctggcc ccttgcagca ggagcacctc cgaatccaca         420
gctgccctgg gctgtctggt gaaggactac tttcccgagc ccgtgaccgt gagctggaac         480
agcggcgctc tgacatccgg cgtccacacc tttcctgccg tcctgcagtc ctccggcctc         540
tactccctgt cctccgtggt gaccgtgcct agctcctccc tcggcaccaa gacctacacc         600
tgtaacgtgg accacaaacc ctccaacacc aaggtggaca acgggtcga gagcaagtac         660 ggccctccct gcctccttg tcctgccccc gagttcgaag cggacccag cgtgttcctg          720 ttccctccta gcccaagga caccctcatg atcagccgga cacccgaggt gacctgcgtg         780
gtggtggatg tgagccagga ggaccctgag gtccagttca actggtatgt ggatggcgtg         840
gaggtgcaca cgccaagac aaagccccgg gaagagcagt tcaactccac ctacaggtg          900 gtcagcgtgc tgaccgtgct gcatcaggac tggctgaacg gcaaggagta caagtgcaag         960
gtcagcaata agggactgcc cagcagcatc gagaagacca tctccaaggc taaaggccag        1020 cccgggaac ctcaggtgta caccctgcct cccagccagg aggagatgac caagaaccag        1080
gtgagcctga cctgcctggt gaagggattc taccttccg acatcgccgt ggagtgggag         1140
tccaacggcc agcccgagaa caattataag accaccctc ccgtcctcga cagcgacgga        1200
tccttctttc tgtactccag gctgaccgtg gataagtcca ggtggcagga aggcaacgtg        1260
ttcagctgct ccgtgatgca cgaggccctg cacaatcact acacccagaa gtccctgagc        1320
ctgtccctgg gaaag                                                        1335

<210> SEQ ID NO 531
<211> LENGTH: 642
<212> TYPE: DNA
<213> ORGANISM: Homo Sapiens

<400> SEQUENCE: 531
gaaatagtga tgacgcagtc tccagccacc ctgtctgtgt ctccagggga aagagccacc          60
ctctcctgca gggccagtca gagtattagt aacaacttag cctggtacca acagaaacct         120
ggccaggctc ccaggctcct catctatggt acatccacca gggccactgg tatcccagcc         180
aggttcagtg gcagtgggtc tgggacagag ttcactctca ccatcagcac cctgcagtct         240
gaagattttg cagtttatta ctgtcagcag tataatatct ggcctttcac tttcggccct         300
gggaccaaag tggatatcaa acgtacggtg gccgctccct ccgtgttcat cttcccacct         360
tccgacgagc agctgaagtc cggcaccgct tctgtcgtgt gcctgctgaa caacttctac         420
ccccgcgagg ccaaggtgca gtggaaggtg gacaacgccc tgcagtccgg caactcccag         480
gaatccgtga ccgagcagga ctccaaggac agcacctact ccctgtcctc caccctgacc         540
ctgtccaagg ccgactacga gaagcacaag gtgtacgcct gcgaagtgac ccaccagggc         600
ctgtctagcc ccgtgaccaa gtctttcaac cggggcgagt gt                            642

<210> SEQ ID NO 532
<211> LENGTH: 1335
<212> TYPE: DNA
<213> ORGANISM: Homo Sapiens

<400> SEQUENCE: 532
caggtccagc ttgtgcagtc tggggctgag gtgaagaagc ctggggcctc agtgaaggtt          60
tcctgcaagg cttctggata caccttcact agctatgcta tccattgggt gcgccaggcc         120
cccggacaaa ggcttgagtg gatgggatgg atcaaccctg caatggtaa cacaaaattt         180 tcacagaagt tccagggcag aatcaccatt accagggaca catccgcgag cacaacctac         240
atggagctga acagcctgag atctgaagac acggctgtgt attactgtgc gagaagggggg        300 ttcgggggagc catttgacta ctggggccag ggaaccctgg tcaccgtctc ctcagccagc         360
accaagggcc cttccgtgtt cccctggcc ccttgcagca ggagcacctc cgaatccaca          420
gctgccctgg ctgtctggt gaaggactac tttcccgagc ccgtgaccgt gagctggaac          480
agcggcgctc tgacatccgg cgtccacacc tttcctgccg tcctgcagtc ctccggcctc         540
tactccctgt cctccgtggt gaccgtgcct agctcctccc tcggcaccaa gacctacacc         600
tgtaacgtgg accacaaacc ctccaacacc aaggtggaca acgggtcga gagcaagtac          660 ggccctccct gcctccttg tcctgcccccc gagttcgaag gcggacccag cgtgttcctg         720
ttccctccta agcccaagga caccctcatg atcagccgga cacccgaggt gacctgcgtg          780
gtggtggatg tgagccagga ggaccctgag gtccagttca actggtatgt ggatggcgtg          840
gaggtgcaca cgccaagac aaagccccgg gaagagcagt tcaactccac ctacagggtg          900
gtcagcgtgc tgaccgtgct gcatcaggac tggctgaacg gcaaggagta caagtgcaag          960
gtcagcaata agggactgcc cagcagcatc gagaagacca tctccaaggc taaaggccag        1020
ccccgggaac ctcaggtgta caccctgcct cccagccagg aggagatgac caagaaccag        1080
gtgagcctga cctgcctggt gaagggattc taccttccg acatcgccgt ggagtgggag         1140
tccaacggcc agcccgagaa caattataag accacccctc ccgtcctcga cagcgacgga        1200
tccttctttc tgtactccag gctgaccgtg gataagtcca ggtggcagga aggcaacgtg        1260

-continued

```
ttcagctgct ccgtgatgca cgaggccctg cacaatcact acacccagaa gtccctgagc      1320
ctgtccctgg gaaag                                                       1335

<210> SEQ ID NO 533
<211> LENGTH: 642
<212> TYPE: DNA
<213> ORGANISM: Homo Sapiens

<400> SEQUENCE: 533
gaaatagtga tgacgcagtc tccagccacc ctgtctgtgt ctccagggga aagagccacc        60
ctctcctgca gggccagtca gagtattagc agcaacttag cctggtacca acagaaccct       120
ggccaggctc ccaggctcct catctatggt acatccacca gggccactgg tatcccagcc       180
aggttcagtg gcagtgggtc tgggacagag ttcactctca ccatcagcac cctgcagtct       240
gaagattttg cagtttatta ctgtcagcag tataatatct ggcctttcac tttcggccct       300
gggaccaaag tggatatcaa acgtacggtg gccgctccct ccgtgttcat cttcccacct       360
tccgacgagc agctgaagtc cggcaccgct tctgtcgtgt gcctgctgaa caacttctac       420
ccccgcgagg ccaaggtgca gtggaaggtg gacaacgccc tgcagtccgg caactcccag       480
gaatccgtga ccgagcagga ctccaaggac agcacctact ccctgtcctc caccctgacc       540
ctgtccaagg ccgactacga gaagcacaag gtgtacgcct gcgaagtgac ccaccagggc       600
ctgtctagcc ccgtgaccaa gtctttcaac cggggcgagt gt                         642

<210> SEQ ID NO 534
<211> LENGTH: 1341
<212> TYPE: DNA
<213> ORGANISM: Homo Sapiens

<400> SEQUENCE: 534
caggtccaac ttgtgcagtc tggggctgag gtgaagaagc ctgggggcctc agtgaaggtt        60 tcctgcaagg cttctggata caccttcact agctatgcta tgcattgggt gcgtcaggcc       120
cccggacaca ggcttgagtg gttgggatgg atcaacgctg gcaatggtta cacaaaatat       180
tcacagaaat ccaggacag agtcgccatt accaggacca catccgcgag cacagccttc        240
atggagctga gcagcctgag atctgaagac acggctgtgt attactgtgc gagagatcgt       300
attactatta ttcggccctt tgactactgg ggccaggga ccctggtcac cgtctcctca        360
gccagcacca agggcccttc cgtgttcccc ctggcccctt gcagcaggag cacctccgaa       420
tccacagctg ccctgggctg tctggtgaag gactactttc ccgagcccgt gaccgtgagc       480
tggaacagcg gcgctctgac atccggcgtc cacacctttc ctgccgtcct gcagtcctcc       540
ggcctctact ccctgtcctc cgtggtgacc gtgcctagct cctccctcgg caccaagacc       600
tacacctgta acgtggacca caaaccctcc aacaccaagg tggacaaacg ggtcgagagc       660
aagtacggcc ctcctgccc tccttgtcct gcccccgagt cgaaggcggc acccagcgtg       720
ttcctgttcc ctcctaagcc caaggacacc ctcatgatca gccggacacc cgaggtgacc       780
tgcgtggtgg tggatgtgag ccaggaggac cctgaggtcc agttcaactg gtatgtggat       840
ggcgtggagg tgcacaacgc caagacaaag ccccgggaag agcagttcaa ctccacctac       900
agggtggtca gcgtgctgac cgtgctgcat caggactggc tgaacggcaa ggagtacaag       960
tgcaaggtca gcaataaggg actgcccagc agcatcgaga gaaccatctc caaggctaaa      1020
ggccagcccc gggaacctca ggtgtacacc ctgcctccca gccaggagga gatgaccaag      1080
```

```
aaccaggtga gcctgacctg cctggtgaag ggattctacc cttccgacat cgccgtggag    1140
tgggagtcca acggccagcc cgagaacaat tataagacca cccctcccgt cctcgacagc    1200
gacggatcct tctttctgta ctccaggctg accgtggata agtccaggtg gcaggaaggc    1260
aacgtgttca gctgctccgt gatgcacgag gccctgcaca atcactacac ccagaagtcc    1320
ctgagcctgt ccctgggaaa g                                               1341
```

```
<210> SEQ ID NO 535
<211> LENGTH: 642
<212> TYPE: DNA
<213> ORGANISM: Homo Sapiens

<400> SEQUENCE: 535
gaaattgtgt tgacgcagtc tccaggcacc ctgtctttgt ctccagggga aagagccacc     60
ctctcctgca gggccagtca gagtattagc agcagctact tagcctggtt ccagcaaaaa    120
cctggccagg ctcccaggct cctcatctat ggtgcatcca gcagggccac tggcatccca    180
gacaggttca gtggcaatgg gtctgggaca gacttcactc tcaccatcag cagactggag    240
cctgaagatt ttgcagtgta ttactgtcag ctgtatggta gcccattcac tttcggccct    300
gggaccaaaa tggatattaa acgtacggtg gccgctccct ccgtgttcat cttcccacct    360
tccgacgagc agctgaagtc cggcaccgct tctgtcgtgt gcctgctgaa caacttctac    420
ccccgcgagg ccaaggtgca gtggaaggtg gacaacgccc tgcagtccgg caactcccag    480
gaatccgtga ccgagcagga ctccaaggac agcacctact ccctgtcctc caccctgacc    540
ctgtccaagg ccgactacga gaagcacaag gtgtacgcct gcgaagtgac ccaccagggc    600
ctgtctagcc ccgtgaccaa gtctttcaac cggggcgagt gt                        642
```

```
<210> SEQ ID NO 536
<211> LENGTH: 1335
<212> TYPE: DNA
<213> ORGANISM: Homo Sapiens

<400> SEQUENCE: 536
caggtccagc ttgtgcagtc tggggctgag gtgaagaagc ctgggggcctc agtgaaagtt     60 tcctgcaagg cttctggata caccttcact agctatgcta tccattgggt gcgccaggcc    120
cccggacaaa ggcttgagtg gatgggatgg atcaacgttg gcaatggtaa aacaaaattt    180
tcacagaagt tacagggcag aatcaccatt accagggaca catccgcgag cacaacctac    240
atggagctga cagcctgag atctgaagac acggctgtgt tttactgtgc gagaaggggg    300
ttcggggagc catttgacta ctggggccag ggaaccctgg tcaccgtctc ctcagccagc    360
accaagggcc cttccgtgtt ccccctggcc ccttgcagca ggagcacctc cgaatccaca    420
gctgccctgg gctgtctggt gaaggactac tttcccgagc ccgtgaccgt gagctggaac    480
agcggcgctc tgacatccgg cgtccacacc tttcctgccg tcctgcagtc ctccggcctc    540
tactccctgt cctccgtggt gaccgtgcct agctcctccc tcggcaccaa gacctacacc    600
tgtaacgtgg accacaaacc ctccaacacc aaggtggaca acgggtcga gagcaagtac    660 ggccctccct gcctcccttg tcctgccccc gagttcgaag cggacccag cgtgttcctg    720 ttccctccta gccccaagga caccctcatg atcagccgga cacccgaggt gacctgcgtg    780
gtggtggatg tgagccagga ggaccctgag gtccagttca actggtatgt ggatggcgtg    840
gaggtgcaca acgccaagac aaagccccgg gaagagcagt tcaactccac ctacagggtg    900
gtcagcgtgc tgaccgtgct gcatcaggac tggctgaacg gcaaggagta caagtgcaag    960
```

-continued

```
gtcagcaata agggactgcc cagcagcatc gagaagacca tctccaaggc taaaggccag      1020
ccccgggaac ctcaggtgta caccctgcct cccagccagg aggagatgac caagaaccag      1080
gtgagcctga cctgcctggt gaagggattc tacccttccg acatcgccgt ggagtgggag      1140
tccaacggcc agcccgagaa caattataag accacccctc ccgtcctcga cagcgacgga      1200
tccttctttc tgtactccag gctgaccgtg gataagtcca ggtggcagga aggcaacgtg      1260
ttcagctgct ccgtgatgca cgaggccctg cacaatcact acacccagaa gtccctgagc      1320
ctgtccctgg gaaag                                                        1335
```

<210> SEQ ID NO 537
<211> LENGTH: 642
<212> TYPE: DNA
<213> ORGANISM: Homo Sapiens

<400> SEQUENCE: 537

```
gaaatagtga tgacgcagtc tccagccacc ctgtctgtgt ctccagggga aagagccacc        60
ctctcctgca gggccagtca gagtattagt agcaacttag cctggtacca acagaaacct       120
ggccaggctc ccaggctcct catctatggt acatccacca gggccactgg tatcccagcc       180
aggttcagtg gcagtgggtc tgggacagag ttcactctca ccatcagcac cctgcagtct       240
gaagattttg cagtttatta ctgtcagcag tataatatct ggcctttcac tttcggccct       300
gggaccaaag tggatatcaa acgtacggtg gccgctccct ccgtgttcat cttcccacct       360
tccgacgagc agctgaagtc cggcaccgct tctgtcgtgt gcctgctgaa caacttctac       420
ccccgcgagg ccaaggtgca gtggaaggtg gacaacgccc tgcagtccgg caactcccag       480
gaatccgtga ccgagcagga ctccaaggac agcacctact ccctgtcctc cacccctgacc      540 ctgtccaagg ccgactacga gaagcacaag gtgtacgcct gcgaagtgac ccaccagggc       600
ctgtctagcc ccgtgaccaa gtctttcaac cggggcgagt gt                          642
```

<210> SEQ ID NO 538
<211> LENGTH: 1335
<212> TYPE: DNA
<213> ORGANISM: Homo Sapiens

<400> SEQUENCE: 538

```
caggtccagc ttgtgcagtc tggggctgag gtgaagaagc ctgggggcctc agtgaaggtt        60 tcctgcaagg cttctggata caccttcact agctatgcta tccattgggt gcgccaggcc       120
cccggacaaa ggcttgagtg gatgggatgg atcaacgctg gcaatggtaa cacaaaatat       180
tcacagaagt tccagggcag aatcaccatt accagggaca catccgcgag cacagcctac       240
atggagctga gcagcctgag atctgaagac acggctgtgt attactgtgc gagaaggggg       300
ttcggggagc catttgacta ctggggccag ggaaccctgg tcaccgtctc ctcagccagc       360
accaagggcc cttccgtgtt ccccctggcc ccttgcagca ggagcacctc cgaatccaca       420
gctgccctgg gctgtctggt gaaggactac tttcccgagc ccgtgaccgt gagctggaac       480
agcggcgctc tgacatccgg cgtccacacc tttcctgccg tcctgcagtc ctccggcctc       540
tactccctgt cctccgtggt gaccgtgcct agctcctccc tcggcaccaa gacctacacc       600
tgtaacgtgg accacaaacc ctccaacacc aaggtggaca acgggtcgga gagcaagtac       660
ggccctccct gcctcctctg tcctgccccc gagttcgaag cggaccccag cgtgttcctg       720
ttccctccta agcccaagga cacctcatg atcagccgga cacccgaggt gacctgcgtg       780
```

-continued

```
gtggtggatg tgagccagga ggaccctgag gtccagttca actggtatgt ggatggcgtg      840
gaggtgcaca acgccaagac aaagccccgg gaagagcagt tcaactccac ctacagggtg      900
gtcagcgtgc tgaccgtgct gcatcaggac tggctgaacg gcaaggagta caagtgcaag      960
gtcagcaata agggactgcc cagcagcatc gagaagacca tctccaaggc taaaggccag     1020
ccccgggaac ctcaggtgta caccctgcct cccagccagg aggagatgac caagaaccag     1080
gtgagcctga cctgcctggt gaagggattc tacccttccg acatcgccgt gggagtgggag   1140 tccaacggcc agcccgagaa caattataag accacccctc ccgtcctcga cagcgacgga    1200 tccttcttc tgtactccag gctgaccgtg gataagtcca ggtggcagga aggcaacgtg      1260
ttcagctgct ccgtgatgca cgaggccctg cacaatcact acacccagaa gtccctgagc     1320
ctgtccctgg gaaag                                                       1335
```

```
<210> SEQ ID NO 539
<211> LENGTH: 642
<212> TYPE: DNA
<213> ORGANISM: Homo Sapiens

<400> SEQUENCE: 539
gaaatagtga tgacgcagtc tccagccacc ctgtctgtgt ctccagggga aagagccacc       60
ctctcctgca gggccagtca gagtattagc agcaacttag cctggtacca acagaaacct      120
ggccaggctc ccaggctcct catctatggt acatccacca gggccactgg tatcccagcc      180
aggttcagtg gcagtgggtc tgggacagag ttcactctca ccatcagcac cctgcagtct      240
gaagattttg cagtttatta ctgtcagcag tataatatct ggcctttcac tttcggccct      300
gggaccaaag tggatatcaa acgtacggtg gccgctccct ccgtgttcat cttcccacct      360
tccgacgagc agctgaagtc cggcaccgct tctgtcgtgt gcctgctgaa caacttctac      420
ccccgcgagg ccaaggtgca gtggaaggtg gacaacgccc tgcagtccgg caactcccag      480
gaatccgtga ccgagcagga ctccaaggac agcacctact ccctgtcctc caccctgacc      540
ctgtccaagg ccgactacga gaagcacaag gtgtacgcct gcgaagtgac ccaccagggc      600
ctgtctagcc ccgtgaccaa gtctttcaac cggggcgagt gt                         642
```

```
<210> SEQ ID NO 540
<211> LENGTH: 1335
<212> TYPE: DNA
<213> ORGANISM: Homo Sapiens

<400> SEQUENCE: 540
caggtccacc ttgtgcagtc tggggctgag gtgaagaagc ctggggcctc agtgaaggtg       60
tcctgcaaga cttctggata caccttcacc acctatgcta ttcattgggt gcgccaggcc      120
cccggacaag ggcttgagtg gatgggatgg atcaacgctg gcaatggtag aacagaatat      180
tcagagaagt ttcagggcag agtcaccatt accagggaca cttccgcgag tacagtctac      240
atggacctga gcagcctgag atctggagac acggctgtgt attactgtgc gagaagggga      300
ttcggggagc catttgacca atggggccag ggaaccctgg tcaccgtctc ctcagccagc      360
accaagggcc cttccgtgtt ccccctggcc ccttgcagca ggagcacctc cgaatccaca      420
gctgccctgg gctgtctggt gaaggactac tttcccgagc ccgtgaccgt gagctggaac      480
agcggcgctc tgacatccgg cgtccacacc tttcctgccg tcctgcagtc ctccggcctc      540
tactccctgt cctccgtggt gaccgtgcct agctcctccc tcggcaccaa gacctacacc      600
tgtaacgtgg accacaaacc ctccaacacc aaggtggaca acgggtcga gagcaagtac       660
```

-continued

```
ggccctccct gccctccttg tcctgccccc gagttcgaag gcggacccag cgtgttcctg      720
ttccctccta agcccaagga caccctcatg atcagccgga cacccgaggt gacctgcgtg      780
gtggtggatg tgagccagga ggaccctgag gtccagttca actggtatgt ggatggcgtg      840
gaggtgcaca acgccaagac aaagccccgg gaagagcagt tcaactccac ctacagggtg      900
gtcagcgtgc tgaccgtgct gcatcaggac tggctgaacg gcaaggagta caagtgcaag      960
gtcagcaata agggactgcc cagcagcatc gagaagacca tctccaaggc taaaggccag     1020
ccccgggaac tcaggtgta cacccctgcct cccagccagg aggagatgac caagaaccag     1080
gtgagcctga cctgcctggt gaagggattc taccctttccg catcgccgt ggagtgggag     1140 tccaacggcc agcccgagaa caattataag accaccccctc ccgtcctcga cagcgacgga     1200
tccttctttc tgtactccag gctgaccgtg ataagtcca ggtggcagga aggcaacgtg     1260
ttcagctgct ccgtgatgca cgaggccctg cacaatcact acacccagaa gtccctgagc     1320
ctgtccctgg aaag                                                          1335
```

<210> SEQ ID NO 541
<211> LENGTH: 642
<212> TYPE: DNA
<213> ORGANISM: Homo Sapiens

<400> SEQUENCE: 541

```
gaaatagtga tgacgcagtc tccagccacc ctgtctgtgt ctccagggga aagagccacc       60
ctctcctgca gggccagtca gagtgttagc agcaacttag cctggtacca gcaccaacct      120
ggccaggctc ccaggctcct catctatggt gcatccacca gggccactgg tttcccaccc      180
aggttcagtg gcagtgggtc tgggacagac ttcactctca ccatcaacag cctgcagtct      240
gaagattttg cagtttatta ctgtcagcag tataataact ggcctttcat tttcggccct      300
gggaccaaac tggatatcac acgtacggtg gccgctccct ccgtgttcat cttcccacct      360
tccgacgagc agctgaagtc cggcaccgct tctgtcgtgt gcctgctgaa caacttctac      420
ccccgcgagg ccaaggtgca gtggaaggtg acaacgccc tgcagtccgg caactcccag      480
gaatccgtga ccgagcagga ctccaaggac agcacctact ccctgtcctc caccctgacc      540
ctgtccaagg ccgactacga gaagcacaag gtgtacgcct gcgaagtgac ccaccagggc      600
ctgtctagcc ccgtgaccaa gtctttcaac cggggcgagt gt                          642
```

<210> SEQ ID NO 542
<211> LENGTH: 1332
<212> TYPE: DNA
<213> ORGANISM: Homo Sapiens

<400> SEQUENCE: 542

```
caggtgcaac tggtggagtc tggggggaggc ttggtcaagc ctggagggtc cctgagactc       60
tcctgtgcag cctctggatt caccttcagt gactactaca tgagctggat ccgccaggct      120
ccagggaagg ggctggagtg ggtttcatac attagtatta gtggtagtac catatactac      180
gcagactctg tgaagggccg attcaccatc tccagggaca cgccaagaa ctcactgttt      240 ctgcaaatga acagcctgag agccgaggac acggccgtgt attactgtgc gagaagaagc      300
agtggctggt acgactactg gggccaggga accctggtca ccgtctcctc agccagcacc      360
aagggccctt ccgtgttccc cctggcccct tgcagcagga gcacctccga atccacagct      420
gccctgggct gtctggtgaa ggactacttt cccgagcccg tgaccgtgag ctggaacagc      480
```

-continued

```
ggcgctctga catccggcgt ccacaccttt cctgccgtcc tgcagtcctc cggcctctac          540
tccctgtcct ccgtggtgac cgtgcctagc tcctccctcg gcaccaagac ctacacctgt          600
aacgtggacc acaaaccctc caacaccaag gtggacaaac gggtcgagag caagtacggc          660 cctcctgcc  ctccttgtcc tgcccccgag ttcgaaggcg acccagccgt gttcctgttc          720
cctcctaagc ccaaggacac cctcatgatc agccggacac ccgaggtgac ctgcgtggtg          780
gtggatgtga gccaggagga ccctgaggtc cagttcaact ggtatgtgga tggcgtggag          840
gtgcacaacg ccaagacaaa gccccgggaa gagcagttca actccaccta cagggtggtc          900
agcgtgctga ccgtgctgca tcaggactgg ctgaacggca aggagtacaa gtgcaaggtc          960
agcaataagg gactgcccag cagcatcgag aagaccatct ccaaggctaa aggccagccc         1020
cgggaacctc aggtgtacac cctgcctccc agccaggagg agatgaccaa gaaccaggtg         1080
agcctgacct gcctggtgaa gggattctac ccttccgaca tcgccgtgga gtgggagtcc         1140
aacggccagc ccgagaacaa ttataagacc acccctcccg tcctcgacag cgacggatcc         1200
ttctttctgt actccaggct gaccgtggat aagtccaggt ggcaggaagg caacgtgttc         1260
agctgctccg tgatgcacga ggccctgcac aatcactaca cccagaagtc cctgagcctg         1320
tccctgggaa ag                                                            1332
```

<210> SEQ ID NO 543
<211> LENGTH: 645
<212> TYPE: DNA
<213> ORGANISM: Homo Sapiens

<400> SEQUENCE: 543

```
gaaattgtgt tgacgcagtc tccaggcacc ctgtctttgt ctccagggga aagagccacc           60
ctctcctgca gggccagtca gagtgttagc agcaactact tagcctggta ccagcagaaa          120
cctggccagg ctcccaggct cctcatctat ggtgcatcca tcagggccac tggcatccca          180
gacaggttca gtggcagtgg gtctgggaca gacttcactc tcaccatcag cagactggag          240
cctgaagatt ttgcagtgta ttcctgtcac cagtatggta gctcacctcc gacgttcggc          300
caagggacca aggtggaaat caaacgtacg gtggccgctc cctccgtgtt catcttccca          360
ccttccgacg agcagctgaa gtccggcacc gcttctgtcg tgtgcctgct gaacaacttc          420 taccccgcg aggccaaggt gcagtggaag gtggacaacg ccctgcagtc cggcaactcc          480
caggaatccg tgaccgagca ggactccaag gacagcacct actccctgtc ctccaccctg          540
accctgtcca aggccgacta cgagaagcac aaggtgtacg cctgcgaagt gacccaccag          600
ggcctgtcta gccccgtgac caagtctttc aaccggggcg agtgt                         645
```

<210> SEQ ID NO 544
<211> LENGTH: 1332
<212> TYPE: DNA
<213> ORGANISM: Homo Sapiens

<400> SEQUENCE: 544

```
caagttcagt tggttgagtc tggcggcgga ctggttaagc ctggcggatc tctgagactg           60
tcttgtgccg cctctggctt caccttctcc gactactaca tgtcctggat cagacaggcc          120
cctggcaaag cctggaatg  ggtgtcctac atctccatct ccggctccac catctactac          180
gccgactccg tgaagggcag attcaccatc tccagagaca cgccaagaa ctccctgttc          240 ctgcagatga acagcctgag agccgaggac accgccgtgt actactgcgc ccgtagatcc          300
tctggatggt acgactattg gggccagggc accctggtca cagtttctag tgccagcacc          360
```

```
aagggccctt ccgtgttccc cctggcccct tgcagcagga gcacctccga atccacagct      420
gccctgggct gtctggtgaa ggactacttt cccgagcccg tgaccgtgag ctggaacagc      480
ggcgctctga catccggcgt ccacaccttt cctgccgtcc tgcagtcctc cggcctctac      540
tccctgtcct ccgtggtgac cgtgcctagc tcctccctcg gcaccaagac ctacacctgt      600
aacgtggacc acaaaccctc caacaccaag gtggacaaac gggtcgagag caagtacggc      660
cctccctgcc ctccttgtcc tgcccccgag ttcgaaggcg acccagcgt gttcctgttc       720 cctcctaagc ccaaggacac cctcatgatc agccggacac ccgaggtgac ctgcgtggtg      780
gtggatgtga gccaggagga ccctgaggtc cagttcaact ggtatgtgga tggcgtggag      840
gtgcacaacg ccaagacaaa gccccgggaa gagcagttca actccaccta cagggtggtc      900
agcgtgctga ccgtgctgca tcaggactgg ctgaacggca aggagtacaa gtgcaaggtc      960
agcaataagg gactgcccag cagcatcgag aagaccatct ccaaggctaa aggccagccc     1020
cgggaacctc aggtgtacac cctgcctccc agccaggagg agatgaccaa gaaccaggtg     1080
agcctgacct gcctggtgaa gggattctac ccttccgaca tcgccgtgga gtgggagtcc     1140
aacggccagc ccgagaacaa ttataagacc acccctcccg tcctcgacag cgacggatcc     1200
ttctttctgt actccaggct gaccgtggat aagtccaggt ggcaggaagg caacgtgttc     1260
agctgctccg tgatgcacga ggccctgcac aatcactaca cccagaagtc cctgagcctg     1320
tccctgggaa ag                                                        1332

<210> SEQ ID NO 545
<211> LENGTH: 645
<212> TYPE: DNA
<213> ORGANISM: Homo Sapiens

<400> SEQUENCE: 545
gaaattgtgc tgactcagtc ccctggcaca ctgtctttga gccctggcga gagagctacc       60
ctgtcctgta gagcctctca gtccgtgtcc tccaactacc tggcctggta tcagcagaag      120
cctggacagg ctcccccggct gttgatctac ggcgcttcta tcagagccac aggcatccct      180
gaccggttct ccggatctgg ctctggcacc gatttcaccc tgaccatctc tcggctggaa      240
cccgaggatt tcgccgtgta ctcttgccac cagtacggct ctagccctcc tacctttgga      300
cagggcacca agtggaaat caaacgtacg gtggccgctc cctccgtgtt catcttccca       360
ccttccgacg agcagctgaa gtccggcacc gcttctgtcg tgtgcctgct gaacaacttc      420
tacccccgcg aggccaaggt gcagtggaag gtggacaacg ccctgcagtc cggcaactcc      480
caggaatccg tgaccgagca ggactccaag gacagcacct actccctgtc ctccaccctg      540
accctgtcca aggccgacta cgagaagcac aaggtgtacg cctgcgaagt gacccaccag      600
ggcctgtcta gccccgtgac caagtctttc aaccggggcg agtgt                      645

<210> SEQ ID NO 546
<211> LENGTH: 1332
<212> TYPE: DNA
<213> ORGANISM: Homo Sapiens

<400> SEQUENCE: 546
caggtgcaac tggtggagtc tgggggaggc ttggtcaagc ctggagggtc cctgagactc       60
tcctgtgcag cctctggatt caccttcagt gactactaca tgagttggat ccgccaggct      120
ccagggaagg ggctggagtg ggtttcatac attagtatta gtggtactac catatactac      180
```

-continued

```
gcagactctg tgaagggccg attcaccatc tccagggaca acgccatgga ctcactgtat      240
ctgcaaatga acagcctgag agccgaggac acggccgtgt attactgtgc gagacggagc      300
agtggctggt acgactactg gggccaggga accctggtca ccgtctcctc agccagcacc      360 aagggccct t ccgtgttccc cctggcccct tgcagcagga gcacctccga atccacagct      420
gccctgggct gtctggtgaa ggactacttt cccgagcccg tgaccgtgag ctggaacagc      480
ggcgctctga catccggcgt ccacacctt t cctgccgtcc tgcagtcctc cggcctctac      540
tccctgtcct ccgtggtgac cgtgcctagc tcctccctcg gcaccaagac ctacacctgt      600
aacgtggacc acaaaccctc caacaccaag gtggacaaac gggtcgagag caagtacggc      660
cctccctgcc ctccttgtcc tgcccccgag ttcgaaggcg acccagcgt gttcctgttc      720 cctcctaagc ccaaggacac cctcatgatc agccggacac ccgaggtgac ctgcgtggtg      780
gtggatgtga gccaggagga ccctgaggtc cagttcaact ggtatgtgga tggcgtggag      840
gtgcacaacg ccaagacaaa gccccgggaa gagcagttca actccaccta caggtggtc      900 agcgtgctga ccgtgctgca tcaggactgg ctgaacggca aggagtacaa gtgcaaggtc      960
agcaataagg gactgcccag cagcatcgag aagaccatct ccaaggctaa aggccagccc     1020
cgggaacctc aggtgtacac cctgcctccc agccaggagg agatgaccaa gaaccaggtg     1080
agcctgacct gcctggtgaa gggattctac ccttccgaca tcgccgtgga gtgggagtcc     1140
aacggccagc ccgagaacaa ttataagacc acccctcccg tcctcgacag cgacggatcc     1200
ttctttctgt actccaggct gaccgtggat aagtccaggt ggcaggaagg caacgtgttc     1260
agctgctccg tgatgcacga ggccctgcac aatcactaca cccagaagtc cctgagcctg     1320
tccctgggaa ag                                                         1332
```

```
<210> SEQ ID NO 547
<211> LENGTH: 645
<212> TYPE: DNA
<213> ORGANISM: Homo Sapiens

<400> SEQUENCE: 547
gaaattgtgt tgacgcagtc tccaggcacc ctgtctttgt ctccagggga aagagccacc       60
ctctcttgtt gggccagtca gagggttgtt tacagatact tagcctggta ccagcggaaa      120
cctggccagg ctcccagact tctcatttat ggtgcattca acaggccac tggcatccca       180 gacaggttca gtggcagtgg gtctgggaca gacttcagtc tcactatcag tagactggag      240
cctgaggatt ttgcagtttt a ttactgtcac caatatggta gttcaccacc gacgttcggc      300
caagggacca aggtggaaat caaacgtacg gtggccgctc cctccgtgtt catcttccca      360
ccttccgacg agcagctgaa gtccggcacc gcttctgtcg tgtgcctgct gaacaacttc      420 taccccgcg aggccaaggt gcagtggaag gtggacaacg ccctgcagtc cggcaactcc      480
caggaatccg tgaccgagca ggactccaag gacagcacct actccctgtc ctccaccctg      540
accctgtcca aggccgacta cgagaagcac aaggtgtacg cctgcgaagt gacccaccag      600
ggcctgtcta gccccgtgac caagtctttc aaccggggcg agtgt                      645
```

```
<210> SEQ ID NO 548
<211> LENGTH: 1332
<212> TYPE: DNA
<213> ORGANISM: Homo Sapiens

<400> SEQUENCE: 548
caagttcagt tggttgagtc tggcggcgga ctggttaagc ctggcggatc tctgagactg       60
```

-continued

```
tcttgtgccg cctctggctt caccttctcc gactactaca tgtcctggat cagacaggcc        120
cctggcaaag gcctggaatg ggtgtcctac atctccatct ccggcaccac catctactac        180
gccgactccg tgaagggcag attcaccatc tccagagaca acgccatgga ctccctgtac        240
ctgcagatga actccctgag agccgaggac accgccgtgt actactgcgc ccgtagatcc        300
tctggatggt acgactattg gggccagggc accctggtca cagtttctag tgccagcacc        360
aagggccctt ccgtgttccc cctggcccct tgcagcagga gcacctccga atccacagct        420
gccctgggct gtctggtgaa ggactacttt cccgagcccg tgaccgtgag ctggaacagc        480
ggcgctctga catccggcgt ccacaccttt cctgccgtcc tgcagtcctc cggcctctac        540
tccctgtcct ccgtggtgac cgtgcctagc tcctccctcg gcaccaagac ctacacctgt        600
aacgtggacc acaaaccctc caacaccaag gtggacaaac gggtcgagag caagtacggc        660
cctccctgcc ctccttgtcc tgcccccgag ttcgaaggcg gacccagcgt gttcctgttc        720
cctcctaagc ccaaggacac cctcatgatc agccggacac ccgaggtgac ctgcgtggtg        780
gtggatgtga gccaggagga ccctgaggtc cagttcaact ggtatgtgga tggcgtggag        840
gtgcacaacg ccaagacaaa gccccgggaa gagcagttca actccaccta cagggtggtc        900
agcgtgctga ccgtgctgca tcaggactgg ctgaacggca aggagtacaa gtgcaaggtc        960
agcaataagg gactgcccag cagcatcgag aagaccatct ccaaggctaa aggccagccc       1020
cgggaacctc aggtgtacac cctgcctccc agccaggagg agatgaccaa gaaccaggtg       1080
agcctgacct gcctggtgaa gggattctac ccttccgaca tcgccgtgga gtgggagtcc       1140
aacggccagc ccgagaacaa ttataagacc acccctcccg tcctcgacag cgacggatcc       1200
ttctttctgt actccaggct gaccgtggat aagtccaggt ggcaggaagg caacgtgttc       1260
agctgctccg tgatgcacga ggccctgcac aatcactaca cccagaagtc cctgagcctg       1320
tccctgggaa ag                                                            1332
```

```
<210> SEQ ID NO 549
<211> LENGTH: 645
<212> TYPE: DNA
<213> ORGANISM: Homo Sapiens

<400> SEQUENCE: 549
gaaattgtgc tgactcagtc ccctggcaca ctgtctttga gccctggcga gagagctacc         60
ctgtcttgtt gggcctctca gagagtggtg tacagatacc tggcttggta tcagcggaag        120
cccggccagg ctcctagact gttgatctac ggcgccttca cagagccac aggcatccct         180 gacagattct ccggctctgg ctctggcacc gacttctccc tgactatctc tcggctggaa        240
cccgaggact cgccgtgta ctactgtcac cagtacggca gcagccctcc tacctttggc         300
cagggcacta aggtggaaat caaacgtacg gtggccgctc cctccgtgtt catcttccca        360
ccttccgacg agcagctgaa gtccggcacc gcttctgtcg tgtgcctgct gaacaacttc        420
tacccccgcg aggccaaggt gcagtggaag gtggacaacg ccctgcagtc cggcaactcc        480
caggaatccg tgaccgagca ggactccaag gacagcacct actccctgtc ctccaccctg        540
accctgtcca aggccgacta cgagaagcac aaggtgtacg cctgcgaagt gacccaccag        600
ggcctgtcta gccccgtgac caagtctttc aaccggggcg agtgt                        645
```

```
<210> SEQ ID NO 550
<211> LENGTH: 1332
<212> TYPE: DNA
```

-continued

<213> ORGANISM: Homo Sapiens

<400> SEQUENCE: 550

```
caggtgcagc tggtggagtc tggggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtatta gtggtagtac catatactac     180
gcagactctg tgaagggccg attcaccatc tccagggaca cgccaagaa ctcactgtat      240 ctgcaaatga acagcctgag agccgaggac acggccgtgt attactgtgc gagaagaagc     300
agtggctggt acgactactg gggccaggga accctggtca ccgtctcctc agccagcacc     360
aagggccctt ccgtgttccc cctggcccct tgcagcagga gcacctccga atccacagct     420
gccctgggct gtctggtgaa ggactacttt cccgagcccg tgaccgtgag ctggaacagc     480
ggcgctctga catccggcgt ccacaccttt cctgccgtcc tgcagtcctc cggcctctac     540
tccctgtcct ccgtggtgac cgtgcctagc tcctccctcg gcaccaagac ctacacctgt     600
aacgtggacc acaaaccctc caacaccaag gtggacaaac gggtcgagag caagtacggc     660 cctcctgcc ctccttgtcc tgcccccgag ttcgaaggcg acccagcgt gttcctgttc       720 cctcctaagc ccaaggacac cctcatgatc agccggacac ccgaggtgac ctgcgtggtg     780
gtggatgtga gccaggagga ccctgaggtc cagttcaact ggtatgtgga tggcgtggag     840
gtgcacaacg ccaagacaaa gccccgggaa gagcagttca actccaccta cagggtggtc     900
agcgtgctga ccgtgctgca tcaggactgg ctgaacggca aggagtacaa gtgcaaggtc     960
agcaataagg gactgcccag cagcatcgag aagaccatct ccaaggctaa aggccagccc    1020
cgggaacctc aggtgtacac cctgcctccc agccaggagg agatgaccaa gaaccaggtg    1080
agcctgacct gcctggtgaa gggattctac ccttccgaca tcgccgtgga gtgggagtcc    1140
aacggccagc ccgagaacaa ttataagacc acccctcccg tcctcgacag cgacggatcc    1200
ttctttctgt actccaggct gaccgtggat aagtccaggt ggcaggaagg caacgtgttc    1260
agctgctccg tgatgcacga ggccctgcac aatcactaca cccagaagtc cctgagcctg    1320
tccctgggaa ag                                                        1332
```

<210> SEQ ID NO 551
<211> LENGTH: 645
<212> TYPE: DNA
<213> ORGANISM: Homo Sapiens

<400> SEQUENCE: 551

```
gaaattgtgt tgacgcagtc tccaggcacc ctgtctttgt ctccaggggga aagagccacc      60 ctctcctgca gggccagtca gagtgttagc agcaactact tagcctggta ccagcagaaa     120
cctggccagg ctcccaggct cctcatctat ggtgcatcca tcagggccac tggcatccca     180
gacaggttca gtggcagtgg gtctgggaca gacttcactc tcaccatcag cagactggag     240
cctgaagatt ttgcagtgta ttgctgtcac cagtatggta gctcacctcc gacgttcggc     300
caagggacca aggtggaaat caaacgtacg gtggccgctc cctccgtgtt catcttccca     360
ccttccgacg agcagctgaa gtccggcacc gcttctgtcg tgtgcctgct gaacaacttc     420
tacccccgcg aggccaaggt gcagtggaag gtggacaacg ccctgcagtc cggcaactcc     480
caggaatccg tgaccgagca ggactccaag gacagcacct actccctgtc ctccaccctg     540
accctgtcca aggccgacta cgagaagcac aaggtgtacg cctgcgaagt gacccaccag     600
ggcctgtcta gccccgtgac caagtctttc aaccggggcg agtgt                     645
```

-continued

```
<210> SEQ ID NO 552
<211> LENGTH: 1332
<212> TYPE: DNA
<213> ORGANISM: Homo Sapiens

<400> SEQUENCE: 552
caagttcagt tggttgagtc tggcggcgga ctggttaagc ctggcggatc tctgagactg      60
tcttgtgccg cctctggctt caccttctcc gactactaca tgtcctggat cagacaggcc     120
cctggcaaag gcctggaatg ggtgtcctac atctccatct ccggctccac catctactac     180
gccgactccg tgaagggcag attcaccatc tccagagaca cgccaagaa ctccctgtac     240 ctgcagatga acagcctgag agccgaggac accgccgtgt actactgcgc ccgtagatcc     300
tctggatggt acgactattg gggccagggc accctggtca cagtttctag tgccagcacc     360
aagggccctt ccgtgttccc cctggcccct tgcagcagga gcacctccga atccacagct     420
gccctgggct gtctggtgaa ggactacttt cccgagcccg tgaccgtgag ctggaacagc     480
ggcgctctga catccggcgt ccacaccttt cctgccgtcc tgcagtcctc cggcctctac     540
tccctgtcct ccgtggtgac cgtgcctagc tcctccctcg gcaccaagac ctacacctgt     600
aacgtggacc acaaaccctc caacaccaag gtggacaaac gggtcgagag caagtacggc     660
cctccctgcc ctccttgtcc tgccccgag ttcgaaggcg gacccagcgt gttcctgttc     720
cctcctaagc ccaaggacac cctcatgatc agccggacac ccgaggtgac ctgcgtggtg     780
gtggatgtga gccaggagga ccctgaggtc cagttcaact ggtatgtgga tggcgtggag     840
gtgcacaacg ccaagacaaa gccccgggaa gagcagttca actccaccta cagggtggtc     900
agcgtgctga ccgtgctgca tcaggactgg ctgaacggca aggagtacaa gtgcaaggtc     960
agcaataagg gactgcccag cagcatcgag aagaccatct ccaaggctaa aggccagccc    1020
cgggaacctc aggtgtacac cctgcctccc agccaggagg atgaccaa gaaccaggtg    1080 agcctgacct gcctggtgaa gggattctac ccttccgaca tcgccgtgga gtgggagtcc    1140
aacggccagc ccgagaacaa ttataagacc acccctcccg tcctgacag cgacggatcc    1200 ttctttctgt actccaggct gaccgtggat aagtccaggt ggcaggaagg caacgtgttc    1260
agctgctccg tgatgcacga ggccctgcac aatcactaca cccagaagtc cctgagcctg    1320
tccctgggaa ag                                                        1332

<210> SEQ ID NO 553
<211> LENGTH: 645
<212> TYPE: DNA
<213> ORGANISM: Homo Sapiens

<400> SEQUENCE: 553
gaaattgtgc tgactcagtc ccctggcaca ctgtctttga gccctggcga gagagctacc      60
ctgtcctgta gagcctctca gtccgtgtcc tccaactacc tggcctggta tcagcagaag     120
cctggacagg ctcccggct gttgatctac ggcgcttcta tcagagccac aggcatccct     180
gaccggttct ccggatctgg ctctggcacc gatttcaccc tgaccatctc tcggctggaa     240
cccgaggatt tcgccgtgta ctgctgtcac cagtacggct ctagccctcc tacctttgga     300
cagggcacca aggtggaaat caaacgtacg gtggccgctc cctccgtgtt catcttccca     360
ccttccgacg agcagctgaa gtccggcacc gcttctgtcg tgtgcctgct gaacaacttc     420
tacccccgcg aggccaaggt gcagtggaag gtggacaacg ccctgcagtc cggcaactcc     480
```

-continued

```
caggaatccg tgaccgagca ggactccaag gacagcacct actccctgtc ctccaccctg        540
accctgtcca aggccgacta cgagaagcac aaggtgtacg cctgcgaagt gacccaccag        600
ggcctgtcta gccccgtgac caagtctttc aaccggggcg agtgt                        645

<210> SEQ ID NO 554
<211> LENGTH: 1332
<212> TYPE: DNA
<213> ORGANISM: Homo Sapiens

<400> SEQUENCE: 554
caggtgcagc tggtggagtc tgggggaggc ttggtcaagc ctggagggtc cctgcgactc         60
tcctgtgcag cctctggatt caccttcagt gactacttca tgagctggat ccgccaggct        120
ccagggaagg ggctggagtg ggtttcgtac attagtatta gtggtagtac catatactac        180
gcagactctg tgaagggccg attcaccatc tccagggaca cgccaggaa ctcactgttt         240 ctgcaaatga acagcctgag agccgaggac acggccatct attactgtgc gagaagaacc        300
agtggctggt acgacttctg gggccaggga accctggtca ccgtctcctc agccagcacc        360
aagggccctt ccgtgttccc cctggcccct gcagcagga gcacctccga atccacagct        420
gccctgggct gtctggtgaa ggactacttt cccgagcccg tgaccgtgag ctggaacagc        480
ggcgctctga catccggcgt ccacaccttt cctgccgtcc tgcagtcctc cggcctctac        540
tccctgtcct ccgtggtgac cgtgcctagc tcctccctcg gcaccaagac ctacacctgt        600
aacgtggacc acaaaccctc caacaccaag gtggacaaac gggtcgagag caagtacggc        660 cctcctgcc ctccttgtcc tgcccccgag ttcgaaggcg acccagcgt gttcctgttc         720 cctcctaagc ccaaggacac cctcatgatc agccggacac ccgaggtgac ctgcgtggtg        780
gtggatgtga gccaggagga ccctgaggtc cagttcaact ggtatgtgga tggcgtggag        840
gtgcacaacg ccaagacaaa gccccgggaa gagcagttca actccaccta caggtggtc        900 agcgtgctga ccgtgctgca tcaggactgg ctgaacggca aggagtacaa gtgcaaggtc        960
agcaataagg gactgcccag cagcatcgag aagaccatct ccaaggctaa aggccagccc       1020
cgggaacctc aggtgtacac cctgcctccc agccaggagg agatgaccaa gaaccaggtg       1080
agcctgacct gcctggtgaa gggattctac ccttccgaca tcgccgtgga gtgggagtcc       1140
aacggccagc ccgagaacaa ttataagacc acccctcccg tcctgacag cgacggatcc       1200 ttctttctgt actccaggct gaccgtggat aagtccaggt ggcaggaagg caacgtgttc       1260
agctgctccg tgatgcacga ggccctgcac aatcactaca cccagaagtc cctgagcctg       1320
tccctgggaa ag                                                           1332

<210> SEQ ID NO 555
<211> LENGTH: 645
<212> TYPE: DNA
<213> ORGANISM: Homo Sapiens

<400> SEQUENCE: 555
gaaattgtgt tgacgcagtc tccaggcacc ctgtctttgt ctccagggga aagagccacc         60
ctctcctgca gggccagtca gagtgttagc tacagctact agcctggta ccagcagaaa        120 cctggccagg ctcccaggct cctcatctat ggtgcatcca gcagggccac tggcatccca        180
gacaggttca gtggcagtgg gtctgggaca gacttcactc tcaccatcag cagactggag        240
cctgaagatt ttgcagtgta ttgttgtcac cagtatggta gttcacctcc gacgttcggc        300
caagggacca aggtggaaat caaacgtacg gtggccgctc cctccgtgtt catcttccca        360
```

```
ccttccgacg agcagctgaa gtccggcacc gcttctgtcg tgtgcctgct gaacaacttc      420 taccccccgcg aggccaaggt gcagtggaag gtggacaacg ccctgcagtc cggcaactcc      480
caggaatccg tgaccgagca ggactccaag gacagcacct actccctgtc ctccaccctg      540
accctgtcca aggccgacta cgagaagcac aaggtgtacg cctgcgaagt gacccaccag      600
ggcctgtcta gccccgtgac caagtctttc aaccggggcg agtgt                       645

<210> SEQ ID NO 556
<211> LENGTH: 1332
<212> TYPE: DNA
<213> ORGANISM: Homo Sapiens

<400> SEQUENCE: 556
caggtgcagc tggtggagtc tggggggaggc ttggtcaagc ctggagggtc ccttagactc      60
tcctgtgcag cctctggatt caccttcagt gacttctaca tgagctggat ccgccaggct      120
ccagggaggg ggctggagtg ggtttcgtac attagtatta gtggtactac catatactac      180
gcagactctg tgaagggccg attcaccatc tccagggaca cgccaggaa ctcactgtat        240 ctgcaaatga acagcctgag agccgaggac acggccgtgt attactgtgc gagaagaacc      300
agtggctggt acgacttctg gggccaggga accctggtca ccgtctcctc agccagcacc      360 aagggcccctt ccgtgttccc cctggcccct gcagcagga gcacctccga atccacagct       420
gccctgggct gtctggtgaa ggactacttt cccgagcccg tgaccgtgag ctggaacagc      480
ggcgctctga catccggcgt ccacacctttt cctgccgtcc tgcagtcctc cggcctctac      540
tccctgtcct ccgtggtgac cgtgcctagc tcctccctcg gcaccaagac ctacacctgt      600
aacgtggacc acaaaccctc caacaccaag gtggacaaac gggtcgagag caagtacggc      660 cctcctgcc ctccttgtcc tgcccccgag ttcgaaggcg acccagcgt gttcctgttc        720 cctcctaagc ccaaggacac cctcatgatc agccggacac ccgaggtgac ctgcgtggtg      780
gtggatgtga gccaggagga ccctgaggtc cagttcaact ggtatgtgga tggcgtggag      840
gtgcacaacg ccaagacaaa gccccgggaa gagcagttca actccaccta caggtggtc       900 agcgtgctga ccgtgctgca tcaggactgg ctgaacggca aggagtacaa gtgcaaggtc      960
agcaataagg gactgcccag cagcatcgag aagaccatct ccaaggctaa aggccagccc      1020
cgggaacctc aggtgtacac cctgcctccc agccaggagg atgaccaa gaaccaggtg        1080 agcctgacct gcctggtgaa gggattctac ccttccgaca tcgccgtgga gtgggagtcc      1140
aacggccagc ccgagaacaa ttataagacc accctcccg tcctcgacag cgacggatcc       1200
ttctttctgt actccaggct gaccgtggat aagtccaggt ggcaggaagg caacgtgttc      1260
agctgctccg tgatgcacga ggccctgcac aatcactaca cccagaagtc cctgagcctg      1320
tccctgggaa ag                                                          1332

<210> SEQ ID NO 557
<211> LENGTH: 645
<212> TYPE: DNA
<213> ORGANISM: Homo Sapiens

<400> SEQUENCE: 557
gaaattgtgt tgacgcagtc tccaggcacc ctgtctttgt ctccaggggga aagagccacc      60 ctctcctgca gggccagtca gagtgttagc tacagctact tagcctggta ccagcagaaa      120
cctggccagg ctcccaggct cctcatctat ggtgcatcca gcagggccac tggcatccca      180
```

-continued

```
gacaggttca gtggcagtgg gtctgggaca gacttcactc tcaccatcag cagactggag        240
cctgaagatt ttgcagtgta ttgctgtcac cagtatggta gttcacctcc gacgttcggc        300
caagggacca aggtggaaat gaaacgtacg gtggccgctc cctccgtgtt catcttccca        360
ccttccgacg agcagctgaa gtccggcacc gcttctgtcg tgtgcctgct gaacaacttc        420 taccccgcg aggccaaggt gcagtggaag gtggacaacg ccctgcagtc cggcaactcc         480
caggaatccg tgaccgagca ggactccaag gacagcacct actccctgtc ctccaccctg        540
accctgtcca aggccgacta cgagaagcac aaggtgtacg cctgcgaagt gacccaccag        600
ggcctgtcta gccccgtgac caagtctttc aaccggggcg agtgt                        645
```

<210> SEQ ID NO 558
<211> LENGTH: 1332
<212> TYPE: DNA
<213> ORGANISM: Homo Sapiens

<400> SEQUENCE: 558

```
caggtgcagc tggtggagtc tgggggaggc ttggtcaggc ctggagggtc cctgagactc         60
tcctgtgcag cctctggatt caccttcagt gactactaca tgagctggat ccgccaggct        120
ccagggaagg ggctggagtg ggtttcgtac attagtatta gtggtagtac catatactac        180
gcagactctg tgaagggccg attcaccatc tccagggaca cgccaggga ctcactttat          240 ctgcaaatga acagcctgag agccgaggac acggccgtgt attactgtgc gagaagaacc        300
agtggctggt acgacttctg gggccaggga accctggtca ccgtctcctc agccagcacc        360
aagggccctt ccgtgttccc cctggcccct gcagcagga gcacctccga atccacagct          420
gccctgggct gtctggtgaa ggactacttt cccgagcccg tgaccgtgag ctggaacagc        480
ggcgctctga catccggcgt ccacaccttt cctgccgtcc tgcagtcctc cggcctctac        540
tccctgtcct ccgtggtgac cgtgcctagc tcctccctcg gcaccaagac ctacacctgt        600
aacgtggacc acaaaccctc caacaccaag gtggacaaac gggtcgagag caagtacggc        660 cctcctgcc ctccttgtcc tgcccccgag ttcgaaggcg gacccagcgt gttcctgttc          720
cctcctaagc ccaaggacac cctcatgatc agccggacac ccgaggtgac ctgcgtggtg        780
gtggatgtga gccaggagga ccctgaggtc cagttcaact ggtatgtgga tggcgtggag        840
gtgcacaacg ccaagacaaa gccccgggaa gagcagttca actccaccta caggtggtc          900 agcgtgctga ccgtgctgca tcaggactgg ctgaacggca aggagtacaa gtgcaaggtc        960
agcaataagg gactgcccag cagcatcgag aagaccatct ccaaggctaa aggccagccc       1020
cgggaacctc aggtgtacac cctgcctccc agccaggagg agatgaccaa gaaccaggtg       1080
agcctgacct gcctggtgaa gggattctac ccttccgaca tcgccgtgga gtgggagtcc       1140
aacggccagc ccgagaacaa ttataagacc acccctcccg tcctcgacag cgacggatcc       1200
ttctttctgt actccaggct gaccgtggat aagtccaggt ggcaggaagg caacgtgttc       1260
agctgctccg tgatgcacga ggccctgcac aatcactaca cccagaagtc cctgagcctg       1320
tccctgggaa ag                                                          1332
```

<210> SEQ ID NO 559
<211> LENGTH: 645
<212> TYPE: DNA
<213> ORGANISM: Homo Sapiens

<400> SEQUENCE: 559

```
gaaattgtgt tgacgcagtc tccaggcacc ctgtctttgt ctccagggga aagagccacc         60
```

```
ctctcctgta gggccagtca gagtgttagc tacaggtact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttgctgtcac cagtatggta gttcacctcc gacgttcggc     300
caagggacca aggtggaaat caaacgtacg gtggccgctc cctccgtgtt catcttccca     360
ccttccgacg agcagctgaa gtccggcacc gcttctgtcg tgtgcctgct gaacaacttc     420 taccccgcg aggccaaggt gcagtggaag gtggacaacg ccctgcagtc cggcaactcc     480
caggaatccg tgaccgagca ggactccaag gacagcacct actccctgtc ctccaccctg     540
accctgtcca aggccgacta cgagaagcac aaggtgtacg cctgcgaagt gacccaccag     600
ggcctgtcta gccccgtgac caagtctttc aaccggggcg agtgt              645

<210> SEQ ID NO 560
<211> LENGTH: 1332
<212> TYPE: DNA
<213> ORGANISM: Homo Sapiens

<400> SEQUENCE: 560
caagttcagt tggttgagtc tggcggcgga ctggttaagc ctggcggatc tctgagactg      60
tcttgtgccg cctctggctt caccttctcc gactactaca tgtcctggat cagacaggcc     120
cctggcaaag gcctggaatg ggtgtcctac atctccatct ccggcatcac catctactac     180
gccgactccg tgaagggcag attcaccatc tccagagaca cgccccggaa ctccctgtac     240
ctgcagatga actctctgag agccgaggac accgccgtgt actactgcgc ccgtagatcc     300
tctggatggt acgactattg gggccagggc accctggtca cagtttctag tgccagcacc     360 aagggcccctt ccgtgttccc cctggcccct tgcagcagga gcacctccga atccacagct     420
gccctgggct gtctggtgaa ggactacttt cccgagcccg tgaccgtgag ctggaacagc     480
ggcgctctga catccggcgt ccacaccttt cctgccgtcc tgcagtcctc cggcctctac     540
tccctgtcct ccgtggtgac cgtgcctagc tcctccctcg gcaccaagac ctacacctgt     600
aacgtggacc acaaaccctc caacaccaag gtggacaaac gggtcgagag caagtacggc     660
cctccctgcc ctccttgtcc tgcccccgag ttcgaaggcg gacccagcgt gttcctgttc     720
cctcctaagc ccaaggacac cctcatgatc agccggacac ccgaggtgac ctgcgtggtg     780
gtggatgtga gccaggagga ccctgaggtc cagttcaact ggtatgtgga tggcgtggag     840
gtgcacaacg ccaagacaaa gccccgggaa gagcagttca actccaccta cagggtggtc     900
agcgtgctga ccgtgctgca tcaggactgg ctgaacggca aggagtacaa gtgcaaggtc     960
agcaataagg gactgcccag cagcatcgag aagaccatct ccaaggctaa aggccagccc    1020
cgggaacctc aggtgtacac cctgcctccc agccaggagg agatgaccaa gaaccaggtg    1080
agcctgacct gcctggtgaa gggattctac ccttccgaca tcgccgtgga gtgggagtcc    1140
aacggccagc ccgagaacaa ttataagacc acccctcccg tcctcgacag cgacggatcc    1200
ttctttctgt actccaggct gaccgtggat aagtccaggt ggcaggaagg caacgtgttc    1260
agctgctccg tgatgcacga ggccctgcac aatcactaca cccagaagtc cctgagcctg    1320
tccctgggaa ag                                                       1332

<210> SEQ ID NO 561
<211> LENGTH: 645
<212> TYPE: DNA
```

-continued

```
<213> ORGANISM: Homo Sapiens

<400> SEQUENCE: 561
gaaattgtgc tgactcagtc ccctggcaca ctgtctttga gccctggcga gagagctacc        60
ctgtcctgta gagcctctca gtccgtgtcc tacaactacc tggcctggta tcagcagaag       120
cccggccagg ctcctagact gttgatctac ggcgcctcca tcagagccac aggcatccct       180
gatagattct ccggctctgg ctctggcacc gacttcaccc tgaccatctc cagactggaa       240
cccgaggact tcgccgtgta ctgctgtcac cagtacggct ctagccctcc tacctttgga       300
cagggcacca aggtggaaat caaacgtacg gtggccgctc cctccgtgtt catcttccca       360
ccttccgacg agcagctgaa gtccggcacc gcttctgtcg tgtgcctgct gaacaacttc       420
tacccccgcg aggccaaggt gcagtggaag gtggacaacg ccctgcagtc cggcaactcc       480
caggaatccg tgaccgagca ggactccaag gacagcacct actccctgtc ctccaccctg       540
accctgtcca aggccgacta cgagaagcac aaggtgtacg cctgcgaagt gacccaccag       600
ggcctgtcta gccccgtgac caagtctttc aaccggggcg agtgt                       645

<210> SEQ ID NO 562
<211> LENGTH: 139
<212> TYPE: PRT
<213> ORGANISM: Homo Sapiens

<400> SEQUENCE: 562

Ser Ala Ser Ser Arg Arg Arg Gln Gln Ser Arg Asn Arg Ser Thr Gln
1               5                   10                  15

Ser Gln Asp Val Ala Arg Val Ser Ser Ala Ser Asp Tyr Asn Ser Ser
            20                  25                  30

Glu Leu Lys Thr Ala Cys Arg Lys His Glu Leu Tyr Val Ser Phe Gln
        35                  40                  45

Asp Leu Gly Trp Gln Asp Trp Ile Ile Ala Pro Lys Gly Tyr Ala Ala
    50                  55                  60

Asn Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
        115                 120                 125

Arg Asn Met Val Val Arg Ala Cys Gly Cys His
    130                 135

<210> SEQ ID NO 563
<211> LENGTH: 139
<212> TYPE: PRT
<213> ORGANISM: Rattus rattus

<400> SEQUENCE: 563

Ser Ala Ser Ser Arg Arg Arg Gln Gln Ser Arg Asn Arg Ser Thr Gln
1               5                   10                  15

Ser Gln Asp Val Ser Arg Gly Ser Ser Ala Ser Asp Tyr Asn Ser Ser
            20                  25                  30

Glu Leu Lys Thr Ala Cys Lys Lys His Glu Leu Tyr Val Ser Phe Gln
        35                  40                  45

Asp Leu Gly Trp Gln Asp Trp Ile Ile Ala Pro Lys Gly Tyr Ala Ala
```

-continued

```
          50                  55                  60

Asn Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
               100                 105                 110

Ser Val Leu Tyr Phe Asp Asp Asn Ser Asn Val Ile Leu Lys Lys Tyr
           115                 120                 125

Arg Asn Met Val Val Arg Ala Cys Gly Cys His
      130                 135

<210> SEQ ID NO 564
<211> LENGTH: 139
<212> TYPE: PRT
<213> ORGANISM: Macaca fascicularis

<400> SEQUENCE: 564

Ser Ala Ser Gly Arg Arg Arg Gln Gln Ser Arg Asn Arg Ser Thr Gln
1               5                   10                  15

Ser Gln Asp Val Ala Arg Val Ser Ser Ala Ser Asp Tyr Asn Ser Ser
                20                  25                  30

Glu Leu Lys Thr Ala Cys Arg Lys His Glu Leu Tyr Val Ser Phe Gln
           35                  40                  45

Asp Leu Gly Trp Gln Asp Trp Ile Ile Ala Pro Lys Gly Tyr Ala Ala
      50                  55                  60

Asn Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
               100                 105                 110

Ser Val Leu Tyr Phe Asp Asp Asn Ser Asn Val Ile Leu Lys Lys Tyr
           115                 120                 125

Arg Asn Met Val Val Arg Ala Cys Gly Cys His
      130                 135

<210> SEQ ID NO 565
<211> LENGTH: 118
<212> TYPE: PRT
<213> ORGANISM: Homo Sapiens

<400> SEQUENCE: 565

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Gly Leu Glu Trp Met
           35                  40                  45

Gly Tyr Ile Asn Pro Tyr Asn Arg Gly Thr Lys Tyr Asn Glu Asn Phe
      50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Pro Phe Gly Asn Ala Met Asp Ile Trp Gly Gln Gly Thr
```

-continued

```
                100             105             110
Leu Val Thr Val Ser Ser
        115

<210> SEQ ID NO 566
<211> LENGTH: 445
<212> TYPE: PRT
<213> ORGANISM: Homo Sapiens

<400> SEQUENCE: 566

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Gly Leu Glu Trp Met
        35                  40                  45

Gly Tyr Ile Asn Pro Tyr Asn Arg Gly Thr Lys Tyr Asn Glu Asn Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Pro Phe Gly Asn Ala Met Asp Ile Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

```
Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
        435                 440                 445
```

<210> SEQ ID NO 567
<211> LENGTH: 978
<212> TYPE: DNA
<213> ORGANISM: Homo Sapiens

<400> SEQUENCE: 567

```
gcctccacca agggcccatc ggtcttcccc ctggcgccct gctccaggag cacctccgag    60
agcacagcgg ccctgggctg cctggtcaag gactacttcc ccgaaccggt gacggtgtcg   120
tggaactcag gcgctctgac cagcggcgtg cacaccttcc cggctgtcct acagtcctca   180
ggactctact ccctcagcag cgtggtgacc gtgacctcca gcaacttcgg cacccagacc   240
tacacctgca acgtagatca caagcccagc aacaccaagg tggacaagac agttgagcgc   300
aaatgttgtg tcgagtgccc accgtgccca gcaccacctg tggcaggacc gtcagtcttc   360
ctcttccccc caaaacccaa ggacaccctc atgatctccc ggacccctga ggtcacgtgc   420
gtggtggtgg acgtgagcca cgaagacccc gaggtccagt tcaactggta cgtggacggc   480
atggaggtgc ataatgccaa gacaaagcca cgggaggagc agttcaacag cacgttccgt   540
gtggtcagcg tcctcaccgt cgtgcaccag gactggctga cggcaagga gtacaagtgc   600 aaggtctcca acaaaggcct cccagccccc atcgagaaaa ccatctccaa aaccaaaggg   660
cagccccgag aaccacaggt gtacaccctg cccccatccc gggaggagat gaccaagaac   720
caggtcagcc tgacctgcct ggtcaaaggc ttctacccca gcgacatcgc cgtggagtgg   780
gagagcaatg ggcagccgga gaacaactac aagaccacac ctcccatgct ggactccgac   840
ggctccttct tcctctacag caagctcacc gtggacaaga gcaggtggca gcaggggaac   900
gtcttctcat gctccgtgat gcatgaggct ctgcacaacc actacacaca gaagagcctc   960
tccctgtctc cgggtaaa                                                  978
```

<210> SEQ ID NO 568
<211> LENGTH: 98
<212> TYPE: PRT
<213> ORGANISM: Homo sapiens

<400> SEQUENCE: 568

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60
```

-continued

```
Lys Gly Arg Phe Thr Ile Ser Arg Asp Asn Ala Lys Asn Ser Leu Tyr
65              70              75              80

Leu Gln Met Asn Ser Leu Arg Ala Glu Asp Thr Ala Val Tyr Tyr Cys
                85              90              95

Ala Arg

<210> SEQ ID NO 569
<211> LENGTH: 97
<212> TYPE: PRT
<213> ORGANISM: Homo sapiens

<400> SEQUENCE: 569

Glu Ile Val Leu Thr Gln Ser Pro Gly Thr Leu Ser Leu Ser Pro Gly
1               5               10              15

Glu Arg Ala Thr Leu Ser Cys Arg Ala Ser Gln Ser Val Ser Ser Ser
                20              25              30

Tyr Leu Ala Trp Tyr Gln Gln Lys Pro Gly Gln Ala Pro Arg Leu Leu
        35              40              45

Ile Tyr Gly Ala Ser Ser Arg Ala Thr Gly Ile Pro Asp Arg Phe Ser
        50              55              60

Gly Ser Gly Ser Gly Thr Asp Phe Thr Leu Thr Ile Ser Arg Leu Glu
65              70              75              80

Pro Glu Asp Phe Ala Val Tyr Tyr Cys Gln Gln Tyr Gly Ser Ser Pro
                85              90              95

Pro
```

ANTAGONISTS

CROSS REFERENCE TO RELATED APPLICATIONS

This application is a national stage application under 35 U.S.C. § 371 of International Application No. PCT/GB2019/052294, filed internationally on Aug. 15, 2019, which claims priority benefit to United Kingdom Application No. 1815629.9, filed Sep. 25, 2018, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 165062000400SEQLIST.TXT, date recorded: Mar. 24, 2021, size: 448 KB).

FIELD OF THE INVENTION

The invention relates to Bone Morphogenetic Protein 6 (BMP6) antagonists, such as antibodies and fragments, as well as methods, uses and combinations.

BACKGROUND

Bone Morphogenetic Protein 6 (BMP6) is the key regulator of hepcidin, the small peptide secreted by the liver which is the major regulator of iron metabolism in mammals. Anti-BMP6 antagonists, such as antibodies, are being developed for use in a method of treating or preventing anaemia (see, eg, WO2016098079, US20160176956A1). See also WO2017191437 which discloses combinations of anti-BMP6 antagonists with erythropoietin stimulating agents (ESAs).

Anaemia is a major disease impacting 25% of the global population, or more than 1.7 billion people, particularly pregnant women, neonates and children. More than 40% of anaemia reflect a malfunction in the homeostatic control of iron uptake, storage and recycling. This dysregulation is a consequence of a variety of chronic diseases including infection (e.g. HIV, hepatitis), inflammation (e.g. rheumatoid arthritis), cancer and kidney disease. The enormous impact of diseases causing dysregulation of iron homeostasis can be seen in the USA where, of 40 million adults of >65 years of age, 10% suffer from anaemia and ⅓ of these are caused by chronic disorders.

Standards of care focus on blood transfusions and treatments with ESAs such as EPO or Aranesp® (Amgen, Inc).

The hamp gene encodes hepcidin, a 25 amino acid peptide hormone produced by the liver. Hepcidin works principally by controlling iron flux out of cells by regulating the amount of the iron transporter ferroportin present on the cell surface of cells involved in iron trafficking. Hepcidin interacts with ferroportin, primarily expressed on macrophages and duodenal enterocytes, causing internalisation and degradation of ferroportin (Ganz and Nemeth, 2011; Ramey et al., 2010). BMP6 triggers hepcidin expression in a mechanism involving several receptors and co-factors. These include BMP class I and class II receptors which are essential for triggering hamp expression and members of the repulsive guidance molecule family RGM such as RGMc (hemojuvelin, HJV) and RGMb (DRAGON), matriptase-2, neogenin, HFE and transferrin receptors 1 and 2. The SMAD pathway is presumably triggered by the initial interaction of BMP6 with class I BMP receptors possibly also involving HJV. This causes an association with the auto-phosphorylated BMPR II and activation of phosphorylation of BMPRI thus triggering of the SMAD cascade. Phosphorylated SMAD1, 5 and 8 and eventually SMAD4 translocate to the nucleus to interact with BMP responsive elements in the hamp gene control region to trigger expression of hepcidin. In mice, liver specific disruption of the SMAD4 signalling molecule or the type I receptors Alk2 and ALk3 decrease hepcidin expression similar to a BMP6 knock out confirming that these factors are also part of the relevant pathway (Steinbicker et al., 2011; Wang et al., 2005).

Ganz, T., Nemeth, E., 2011. The Hepcidin-Ferroportin System as a Therapeutic Target in Anemias and Iron Overload Disorders. Hematology 2011, 538-542.

Ramey, G., Deschemin, J. C., Durel, B., Canonne-Hergaux, F., Nicolas, G., Vaulont, S., 2010. Hepcidin targets ferroportin for degradation in hepatocytes. Haematologica 95, 501-504.

Steinbicker, A. U., Bartnikas, T. B., Lohmeyer, L. K., Leyton, P., Mayeur, C., Kao, S. M., Pappas, A. E., Peterson, R. T., Bloch, D. B., Yu, P. B., Fleming, M. D., Bloch, K. D., 2011. Perturbation of hepcidin expression by BMP type I receptor deletion induces iron overload in mice. Blood 118, 4224-4230.

Wang, R.-H., Li, C., Xu, X., Zheng, Y., Xiao, C., Zerfas, P., Cooperman, S., Eckhaus, M., Rouault, T., Mishra, L., 2005. A role of SMAD4 in iron metabolism through the positive regulation of hepcidin expression. Cell Metab. 2, 399-409.

STATEMENT OF INVENTION

The invention provides the following:—

An antibody or fragment comprising a binding site which specifically binds to Bone Morphogenetic Protein 6 (BMP6), wherein the binding site comprises a VH domain, wherein the VH domain comprises a CDRH3 sequence of a VH domain comprising SEQ ID NO: 114.

An antibody or fragment comprising a binding site which specifically binds to BMP6, wherein the binding site comprises a VH domain that comprises SEQ ID NO: 114, or an amino acid that is at least 70% identical thereto.

An antibody or fragment comprising a binding site which specifically binds to BMP6, wherein the binding site comprises a VL domain, wherein the VL domain comprises a CDRL3 sequence of a VL domain comprising SEQ ID NO: 123.

An antibody or fragment comprising a binding site which specifically binds to BMP6, wherein the binding site comprises a VL domain that comprises SEQ ID NO: 123, or an amino acid that is at least 70% identical thereto.

An antibody or fragment which specifically binds to Bone Morphogenetic Protein 6 (BMP6) and comprises (i) a heavy chain amino acid sequence comprising SEQ ID NO: 116 or an amino acid that is at least 70% identical thereto; and/or (ii) a light chain sequence comprising SEQ ID NO: 125 or an amino acid that is at least 70% identical thereto.

An antibody or fragment which (i) specifically binds to a human BMP6 epitope that is identical to an epitope to which the antibody of the invention binds; and/or (ii) competes for binding to human BMP6 with the antibody of the invention. The Invention Also Provides the Following Configurations. In a First Configuration the Invention Provides:

An antibody or fragment comprising a binding site which specifically binds to Bone Morphogenetic Protein 6 (BMP6), wherein the binding site comprises a VH domain that is encoded by a nucleotide sequence that is derived from the recombination of a human VH gene segment, DH gene segment and JH gene segment, wherein the VH gene segment is selected from IGHV3-11 and IGHV1-3.

In a Second Configuration the Invention Provides:

An antibody or fragment which specifically binds to BMP6 and comprises the CDRH3 sequence of an anti-BMP6 antibody according to the invention, or said CDRH3 sequence comprising 3, 2 or 1 amino acid substitution(s).

In a Third Configuration the Invention Provides:

An antibody or fragment which specifically binds to BMP6 and comprises a VH domain which comprises a CDRH3 sequence of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or said sequence comprising 3, 2 or 1 amino acid substitution(s).

In a Fourth Configuration the Invention Provides:

An antibody or fragment comprising a binding site which specifically binds to BMP6, wherein the binding site comprises a VH domain that comprises the amino acid sequence of a VH domain of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or an amino acid that is at least 70% identical thereto.

In a Fifth Configuration the Invention Provides:

An antibody or fragment comprising a binding site which specifically binds to BMP6, wherein the binding site comprises a VL domain that is encoded by a nucleotide sequence that is derived from the recombination of a human VL gene segment and JL gene segment, wherein the VL gene segment is selected from IGKV3-20, IGKV1-5 and IGKV3-15.

In a Sixth Configuration the Invention Provides:

An antibody or fragment which specifically binds to BMP6 and comprises the CDRL3 sequence of an anti-BMP6 antibody of the invention, said CDRL3 sequence comprising 3, 2 or 1 amino acid substitution(s).

In a Seventh Configuration the Invention Provides:

An antibody or fragment which specifically binds to BMP6 and comprises a VL domain which comprises a CDRL3 (and optionally a CDRH3) sequence of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or said sequence(s) each comprising 3, 2 or 1 amino acid substitution(s).

In a Eighth Configuration the Invention Provides:

An antibody or fragment comprising a binding site which specifically binds to BMP6, wherein the binding site comprises a VL domain that comprises the amino acid sequence of a VL domain of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or an amino acid that is at least 70% identical thereto.

In a Ninth Configuration the Invention Provides:

An antibody or fragment which specifically binds to BMP6 and comprises the heavy chain amino acid sequence of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or an amino acid that is at least 70% identical thereto.

In a Tenth Configuration the Invention Provides:

An antibody or fragment which specifically binds to BMP6 and comprises the light chain amino acid sequence of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or an amino acid that is at least 70% identical thereto.

In a Eleventh Configuration the Invention Provides:

An antibody or fragment which specifically binds to a human BMP6 epitope that is identical to an epitope to which the antibody of the invention (eg, CL-58838) binds.

In a Twelfth Configuration the Invention Provides:

An antibody or fragment which competes for binding to human BMP6 with the antibody of the invention.

In a Thirteenth Configuration the Invention Provides:

An anti-BMP6 antibody or fragment of the invention for treating or preventing a BMP6-mediated disease or condition (optionally anaemia) in a subject.

In a Fourteenth Configuration the Invention Provides:

A combination of an amount of an anti-BMP6 antibody or fragment and an amount of an ESA (optionally comprising multiple doses of said antibody and/or ESA), wherein the antibody or fragment is according to the invention.

In a Fifteenth Configuration the Invention Provides:

Use of the antibody, fragment or combination of the invention in the manufacture of a medicament for administration to a subject for treating or preventing a BMP6-mediated disease or condition, optionally anaemia.

In a Sixteenth Configuration the Invention Provides:

A method of treating or preventing a BMP6-mediated disease or condition in a subject (optionally anaemia), the method comprising administering to said subject a therapeutically effective amount of an antibody, fragment or combination of the invention, wherein the BMP6-mediated disease or condition is thereby treated or prevented.

In a Seventeenth Configuration the Invention Provides:

A pharmaceutical composition comprising an antibody, fragment or combination of the invention and a pharmaceutically acceptable excipient, diluent or carrier.

In a Eighteenth Configuration the Invention Provides:

A nucleic acid that encodes a VH domain and/or a VL domain of an antibody or fragment of the invention In a Nineteenth Configuration the Invention Provides:

A nucleic acid that encodes a VH domain comprising the amino acid sequence of a VH domain of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or an amino acid that is at least 70% identical thereto.

In a Twentieth Configuration the Invention Provides:

A nucleic acid (eg, in a host cell, eg, a CHO or HEK293 or Cos cell) comprising (a) a nucleotide sequence that is at least 70% identical to the sequence of SEQ ID NO: 115, 520 or 521; and/or (b) a nucleotide sequence that is at least 70% identical to the sequence of SEQ ID NO: 124, 522 or 523.

A nucleic acid (eg, in a host cell, eg, a CHO or HEK293 or Cos cell) comprising (a) a nucleotide sequence that is at least 70% identical to the sequence of SEQ ID NO: 115; and/or (b) a nucleotide sequence that is at least 70% identical to the sequence of SEQ ID NO: 124.

A nucleic acid (eg, in a host cell, eg, a CHO or HEK293 or Cos cell) comprising (a) a nucleotide sequence that is at least 70% identical to the sequence of SEQ ID NO: 520; and/or (b) a nucleotide sequence that is at least 70% identical to the sequence of SEQ ID NO: 522.

A nucleic acid (eg, in a host cell, eg, a CHO or HEK293 or Cos cell) comprising (a) a nucleotide sequence that is at least 70% identical to the sequence of SEQ ID NO: 521; and/or (b) a nucleotide sequence that is at least 70% identical to the sequence of SEQ ID NO: 523.

In a Twenty-First Configuration the Invention Provides:

A combination of first and second nucleic acids (eg, in a host cell, eg, a CHO or HEK293 or Cos cell) respectively comprising (a) a nucleotide sequence that is at least 70% identical to the sequence of SEQ ID NO: 115, 520 or 521; and/or (b) a nucleotide sequence that is at least 70% identical to the sequence of SEQ ID NO: 124, 522 or 523.

A combination of first and second nucleic acids (eg, in a host cell, eg, a CHO or HEK293 or Cos cell) respectively comprising (a) a nucleotide sequence that is at least 70% identical to the sequence of SEQ ID NO: 115; and/or (b) a nucleotide sequence that is at least 70% identical to the sequence of SEQ ID NO: 124.

A combination of first and second nucleic acids (eg, in a host cell, eg, a CHO or HEK293 or Cos cell) respectively comprising (a) a nucleotide sequence that is at least 70% identical to the sequence of SEQ ID NO: 520; and/or (b) a nucleotide sequence that is at least 70% identical to the sequence of SEQ ID NO: 522.

A combination of first and second nucleic acids (eg, in a host cell, eg, a CHO or HEK293 or Cos cell) respectively comprising (a) a nucleotide sequence that is at least 70% identical to the sequence of SEQ ID NO: 521; and/or (b) a nucleotide sequence that is at least 70% identical to the sequence of SEQ ID NO: 523.

In a Twenty-Second Configuration the Invention Provides:

A nucleic acid that encodes a heavy chain and/or a light chain of an antibody or fragment of the invention.

In a Twenty-Third Configuration the Invention Provides:

A nucleic acid that encodes a heavy chain comprising an amino acid sequence that is at least 70% identical to SEQ ID NO: 116.

In a Twenty-Fourth Configuration the Invention Provides:

A nucleic acid that encodes a light chain comprising an amino acid sequence that is at least 70% identical to SEQ ID NO: 125.

In a Twenty-Fifth Configuration the Invention Provides:

A nucleic acid (eg, in a host cell, eg, a CHO or HEK293 or Cos cell) comprising (a) a nucleotide sequence that is at least 70% identical to a heavy chain sequence selected of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; and/or (b) a nucleotide sequence that is at least 70% identical to a sequence selected of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713.

A nucleic acid (eg, in a host cell, eg, a CHO or HEK293 or Cos cell) comprising (a) a nucleotide sequence that is at least 70% identical to a sequence selected from SEQ ID NO: 512, 514, 516, 518 and 519; and/or (b) a nucleotide sequence that is at least 70% identical to a sequence selected from SEQ ID NO: 513, 515 and 517.

A nucleic acid (eg, in a host cell, eg, a CHO or HEK293 or Cos cell) comprising (a) a nucleotide sequence that is at least 70% identical SEQ ID NO: 512; and/or (b) a nucleotide sequence that is at least 70% identical to SEQ ID NO: 513.

A nucleic acid (eg, in a host cell, eg, a CHO or HEK293 or Cos cell) comprising (a) a nucleotide sequence that is at least 70% identical SEQ ID NO: 516; and/or (b) a nucleotide sequence that is at least 70% identical to SEQ ID NO: 517.

A nucleic acid (eg, in a host cell, eg, a CHO or HEK293 or Cos cell) comprising (a) a nucleotide sequence that is at least 70% identical SEQ ID NO: 518; and/or (b) a nucleotide sequence that is at least 70% identical to SEQ ID NO: 513.

A nucleic acid (eg, in a host cell, eg, a CHO or HEK293 or Cos cell) comprising (a) a nucleotide sequence that is at least 70% identical SEQ ID NO: 519; and/or (b) a nucleotide sequence that is at least 70% identical to SEQ ID NO: 513.

A nucleic acid (eg, in a host cell, eg, a CHO or HEK293 or Cos cell) comprising (a) a nucleotide sequence that is at least 70% identical SEQ ID NO: 518; and/or (b) a nucleotide sequence that is at least 70% identical to SEQ ID NO: 517.

A nucleic acid (eg, in a host cell, eg, a CHO or HEK293 or Cos cell) comprising (a) a nucleotide sequence that is at least 70% identical SEQ ID NO: 519; and/or (b) a nucleotide sequence that is at least 70% identical to SEQ ID NO: 517.

A nucleic acid (eg, in a host cell, eg, a CHO or HEK293 or Cos cell) comprising (a) a nucleotide sequence that is at least 70% identical SEQ ID NO: 514; and/or (b) a nucleotide sequence that is at least 70% identical to SEQ ID NO: 515.

A nucleic acid (eg, in a host cell, eg, a CHO or HEK293 or Cos cell) comprising (a) a nucleotide sequence that is at least 70% identical SEQ ID NO: 516; and/or (b) a nucleotide sequence that is at least 70% identical to SEQ ID NO: 517.

A nucleic acid (eg, in a host cell, eg, a CHO or HEK293 or Cos cell) comprising (a) a nucleotide sequence that is at least 70% identical SEQ ID NO: 518; and/or (b) a nucleotide sequence that is at least 70% identical to SEQ ID NO: 513, 515 or 517.

A nucleic acid (eg, in a host cell, eg, a CHO or HEK293 or Cos cell) comprising (a) a nucleotide sequence that is at least 70% identical SEQ ID NO: 519; and/or (b) a nucleotide sequence that is at least 70% identical to SEQ ID NO: 513, 515 or 517.

In a Twenty-Sixth Configuration the Invention Provides:

A vector comprising the nucleic acid(s); optionally wherein the vector is a CHO or HEK293 vector.

In a Twenty-Seventh Configuration the Invention Provides:

A host cell comprising the nucleic acid(s) or the vector.

In a Twenty-Eighth Configuration the Invention Provides:

An antibody, fragment, combination, vector, host cell, use or method as herein described.

In a Twenty-Ninth Configuration the Invention Provides:

An antibody or fragment that specifically binds to a bone morphogenetic protein (BMP) for use in a method of treating or preventing a disease or condition caused by haemojuvelin (HJV)-deficient BMP-BMP receptor (BMPR) complexes in a human or animal subject, wherein the method comprises administering the antibody or fragment to the subject for inhibiting formation of said complexes and/or inhibiting triggering of intracellular signalling by such complexes in the subject, whereby a HJV-independent BMP-BMPR mediated disease or condition is treated or prevented.

An antibody or fragment that specifically binds to a bone morphogenetic protein (BMP) for use in a method of treating or preventing HJV-independent anaemia or osteoporosis in a human or animal subject, wherein the method comprises administering the antibody or fragment to the subject for inhibiting formation of haemojuvelin (HJV)-deficient BMP-BMP receptor (BMPR) complexes and/or inhibiting triggering of intracellular signalling by such complexes in the subject, whereby HJV-independent anaemia or osteoporosis is treated or prevented.

An antibody or fragment that specifically binds to a bone morphogenetic protein (BMP) for use in a method of treating or preventing haemojuvelin (HJV)-independent anaemia or osteoporosis in a human or animal subject, wherein the method comprises administering the antibody to the subject, whereby HJV-independent anaemia or osteoporosis is treated or prevented.

The invention also provides such methods for treating a disease or condition, eg, anaemia or osteoporosis.

Figure 1A:
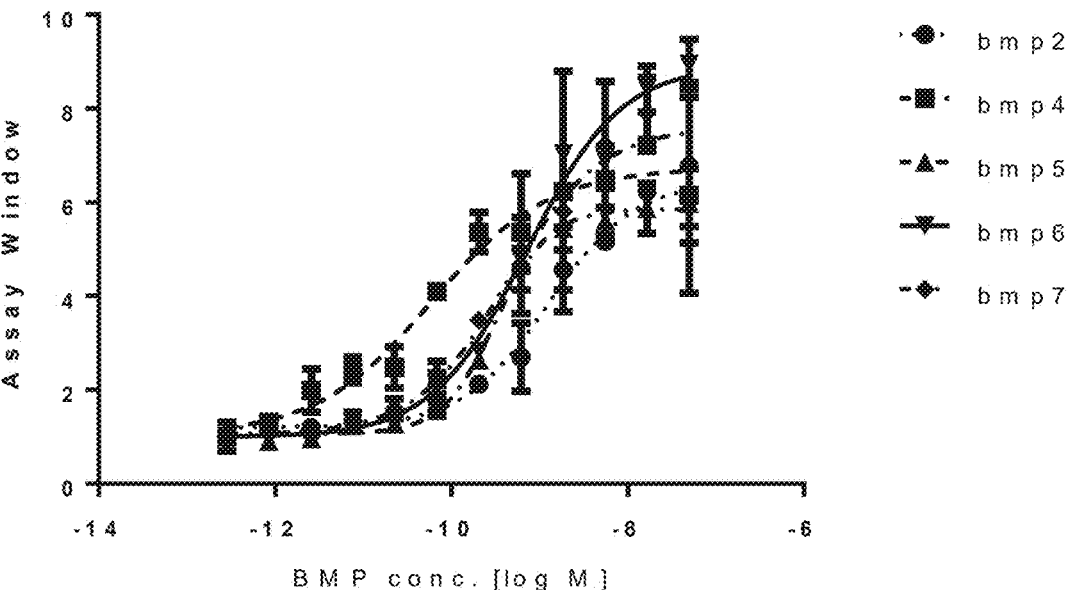
FIGS. 1A-1B.
Figure 1B:
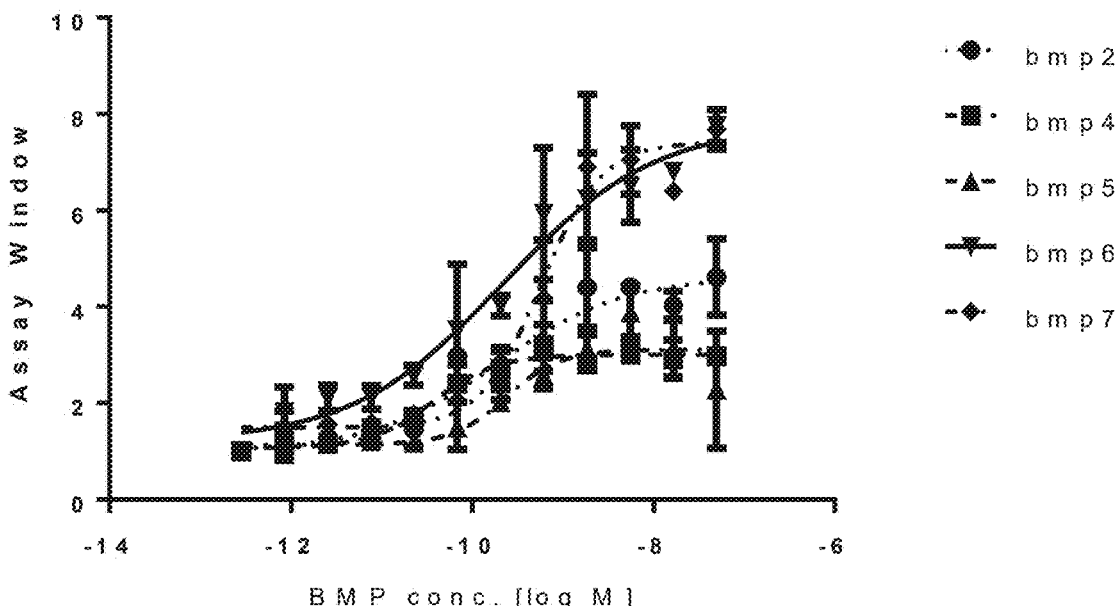

Establishing of the assay window using a HepG2 hamp luciferase reporter gene cell line and various human BMP ligands as stimulating agents. Red Firefly luciferase gene under control of the human hepcidin promoter regulatory element in HepG2 cells was tested for function by stimulating the cells with various human BMP proteins (R&D Systems or Peprotech) added at increasing concentrations. The performance of the assay was tested in two different culture media settings, MEM containing 1% FBS (FIG. 1A) and Hybridoma Media containing 25% MEM (FIG. 1B; details see Example 1).

FIG. 2:

HepG2 hamp luciferase reporter gene cell assay window assessed using various human or mouse BMP6 ligands as stimulating agents (R&D Systems or Peprotech) added at increasing concentrations. BMP6 was diluted in MEM containing 1% FBS. Total assay volume was 60 μl using 25% HMM (for more details and reagents used see Example 1).

FIGS. 3A-3B:

HepG2 hamp luciferase reporter gene cell assay window assessed using a fixed concentration of human (Peprotech) or mouse BMP6 (R&D Systems) at 1 nM in MEM containing 1% FBS and commercial mouse anti-BMP6 monoclonal antibodies MAB507 (FIG. 3A) and MAB2365 (FIG. 3B) from R&D Systems diluted in hybridoma maintenance medium (HMM); (for more details and reagents see Example 1).

FIG. 4:

Serum titer determination of immunisation regime KM089 using five bmp6 –/– Kymice by a reverse DEL-FIA® assay (Perkin Elmer) where IgG antibody contained in the serum added at various serial dilutions was captured with anti-mouse IgG (goat anti-mouse IgG; Southern Biotech 1030-01) via the Fc-domain and then incubated with biotinylated BMP6 and detected using DELFIA Eu-N1 Europium-labelled streptavidin (Perkin Elmer). The cut-off (any signal below this value was judged as negative) was defined as the negative control average of all replicates+3× standard deviation. KMBM codes in legend refer to individual Kymouse™ bmp6 –/– animals.

FIG. 5:

2 μg/lane purified human BMP6 (Peprotech) separated by SDS-PAGE and stained with Coomassie blue (A) under reducing (R) and non-reducing (NR) conditions and Western blots from such gels blotted onto membranes and then probed with purified human anti-BMP6 antibodies as labelled. Bound antibody was detected with anti-human kappa light chain-horse radish peroxidase (HRP) and peroxidase by Enhanced Chemiluminescence (CL-58838 & Antibody A) or with anti-human Fc-alkaline phosphatase (AP) and phosphatase 5-bromo-4-chloro-3-indolyl-phosphate (BCIP) and nitro blue tetrazolium (NBT) colorimetric substrate conversion (Antibody B).

Figure 6A:
Figure 6A:
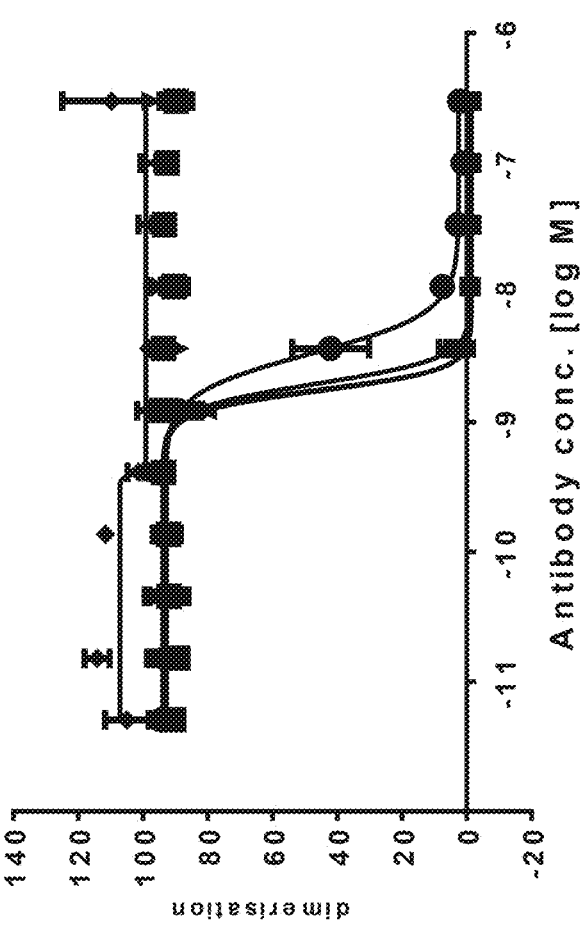
Figure 6B:
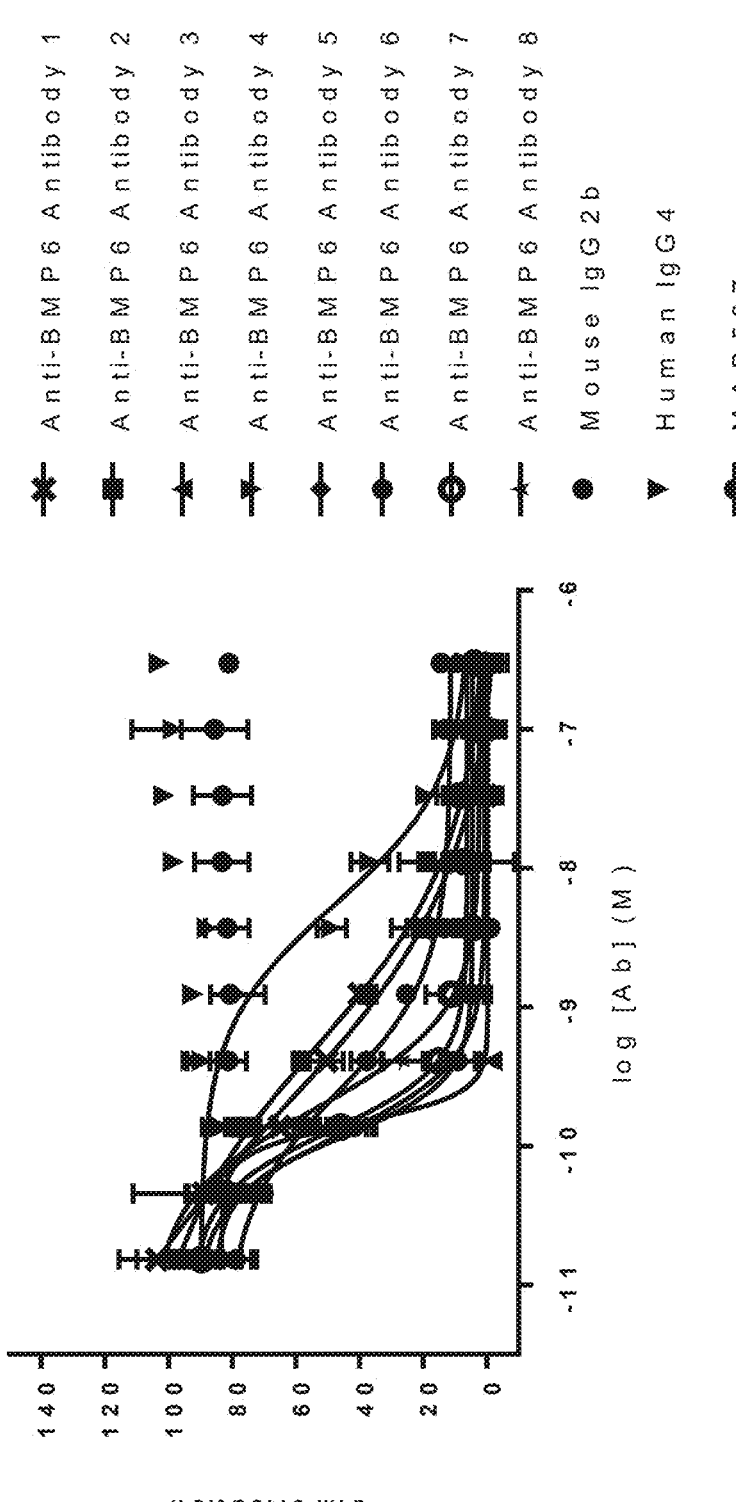

FIGS. 6A-6B:

Receptor dimerization assay based on U20S cells transfected with either BMPRIA (ALK3, CD292) and BMPRII (T-ALK; FIG. 6A) or BMPRIA (ALK6) and BMPRII (T-ALK; FIG. 6B). Ligand driven dimerization with BMP6 (Peprotech 120-06 SEQ ID NO: 2) generated a chemiluminescent signal. Human anti-BMP6 IgG4 antibody CL-58838 and anti-BMP6 Antibodies A, B (FIG. 6A), human anti-BMP6 IgG4 antibodies 1-8 (FIG. 6B) and murine monoclonal antibody MAB507 (R&D Systems; FIGS. 6A and B) were added at increasing concentrations (11-point dilutions). Representative data of two experiments in each case. Appropriate isotype control IgG were used in both experiments.

Figure 7A:
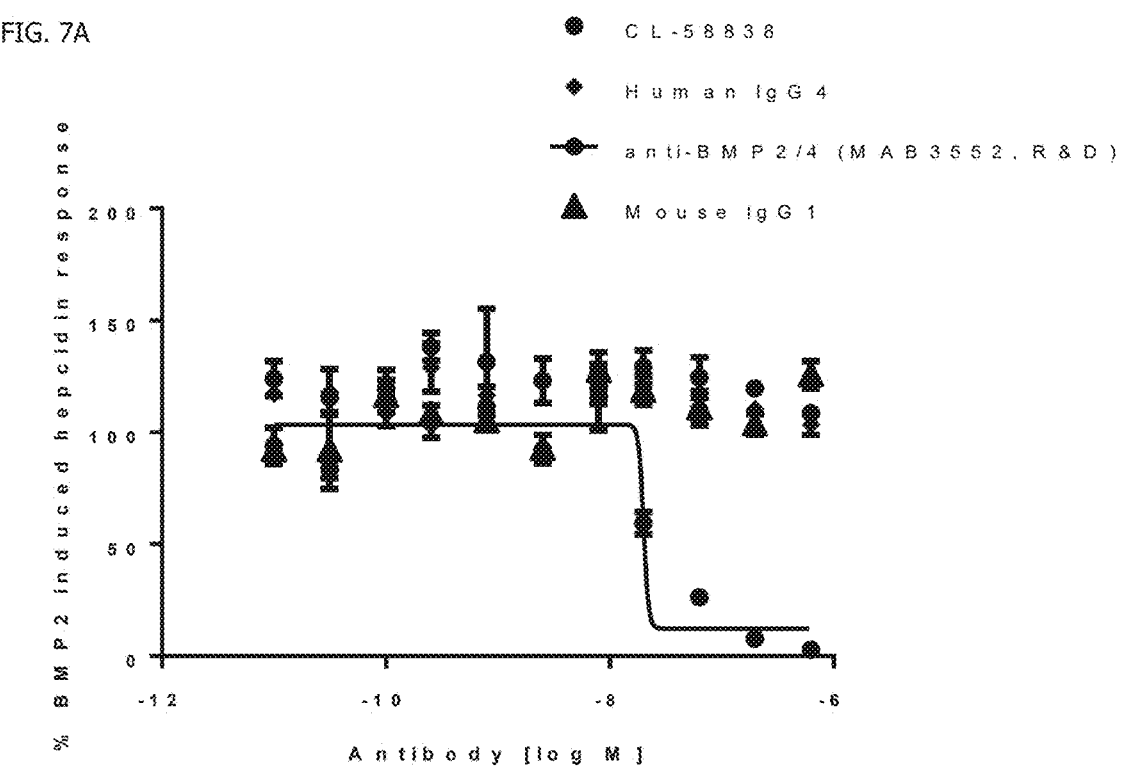
Figure 7B:
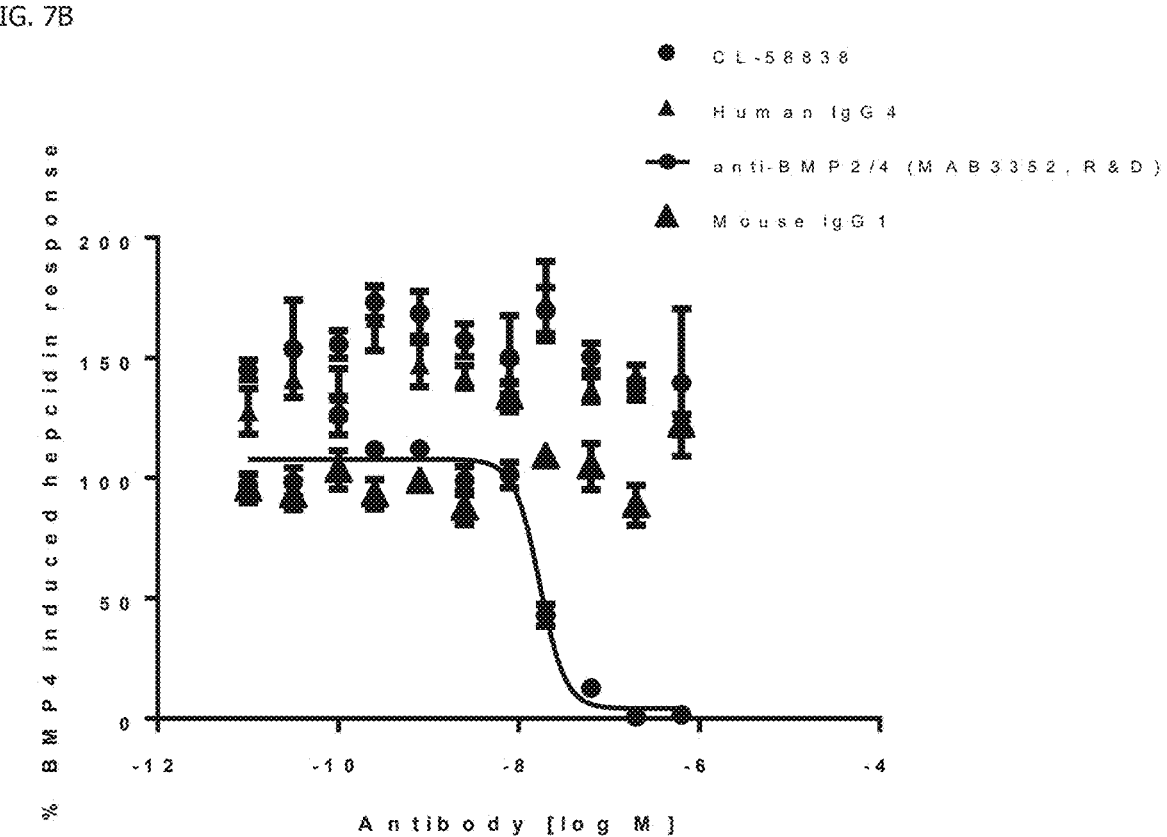
Figure 7C:
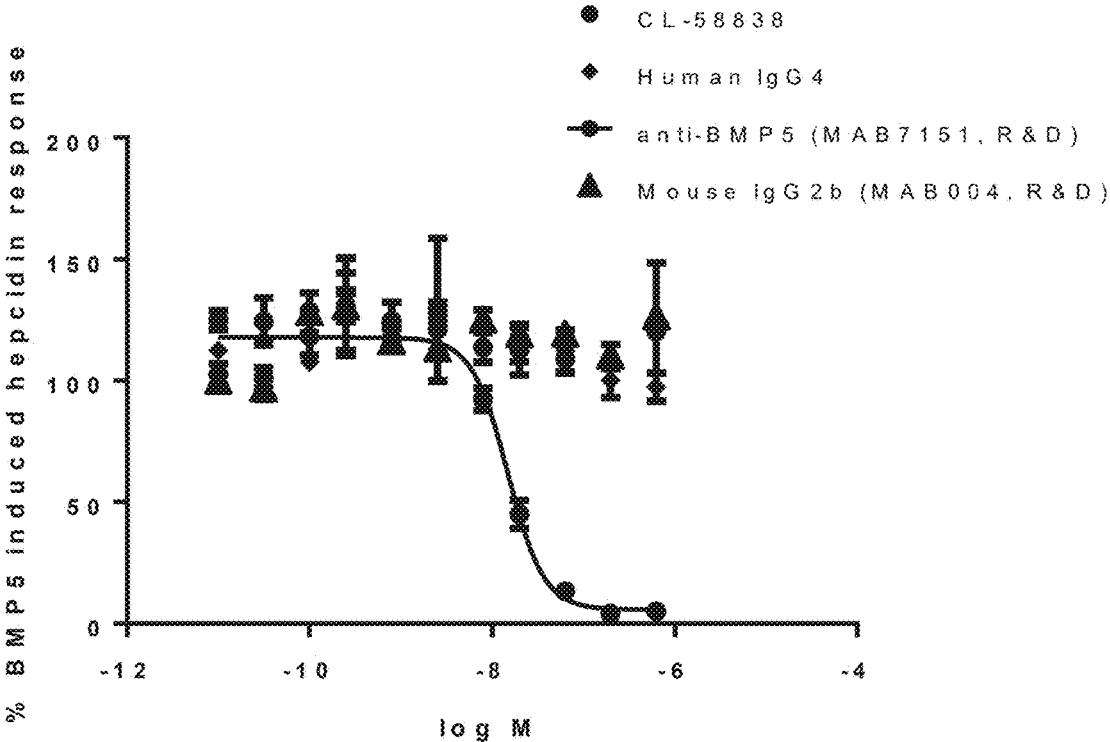
Figure 7D:
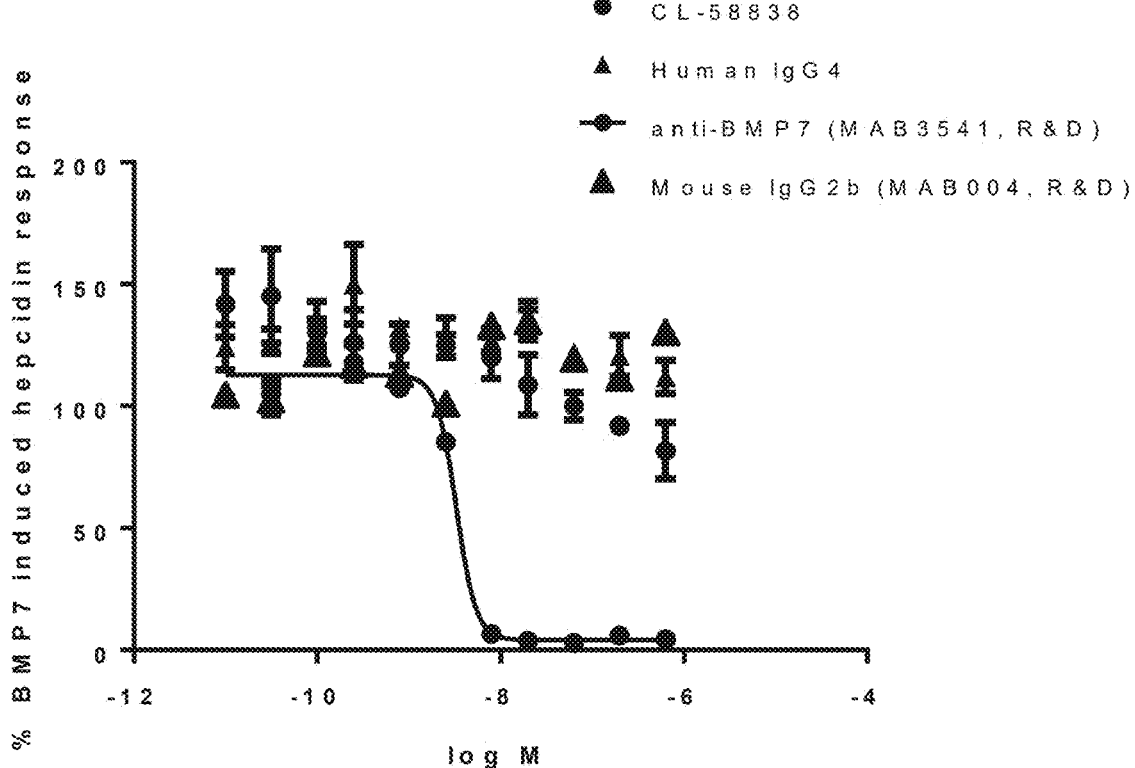
Figure 7E:
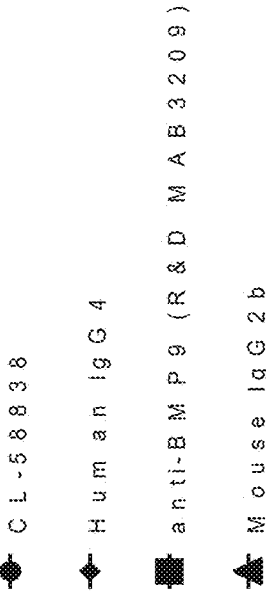
Figure 7E:
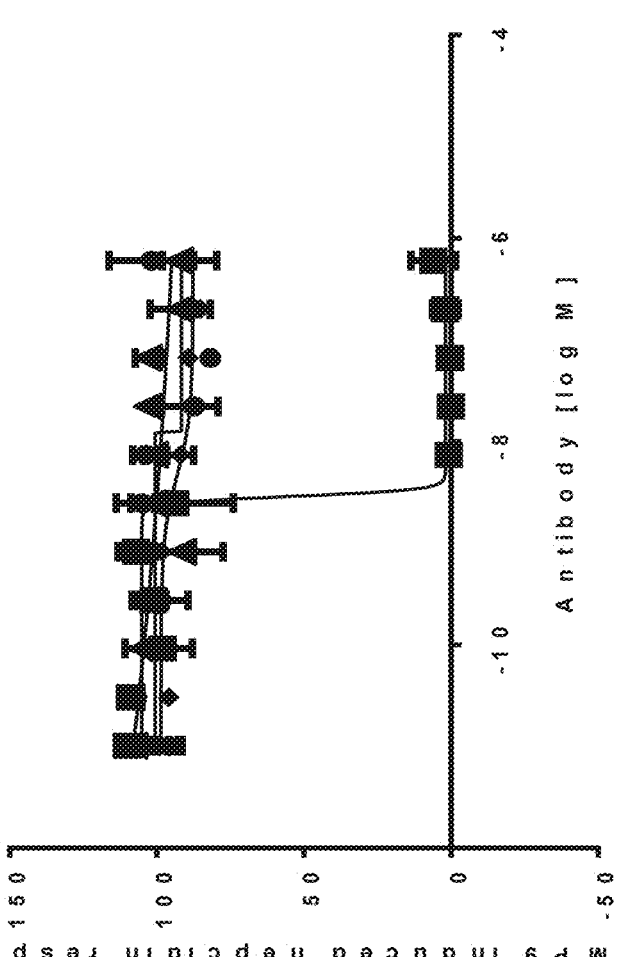

FIGS. 7A-7E:

Cross-reactivity profile of purified CL-58838 IgG4 (SEQ ID NO: 116 and SEQ ID NO: 125) with human BMP2 (FIG. 7A), BMP4 (FIG. 7B), BMP5 (FIG. 7C), BMP7 (FIG. 7D) and BMP9 (FIG. 7E; details described in Example 7). The effects of anti-BMP6 antibody CL-58838 on the BMP-driven activation of the hamp luciferase reporter gene in HepG2 cells was studied by adding increasing amounts of CL-58838. As a positive control, relevant BMP specific antibodies (all R&D Systems) were added to interfere with the relevant BMP activation.

FIGS. 8A-8I:

Plotted transferrin saturation in % (TSAT) in normal rats plotted from Table 12 (for FIGS. 8 A-8D), Table 13 (for FIGS. 8 E-8G) and Table 14 (for FIGS. 8 H and 8I) following a single iv injection of anti-BMP-6 or isotype IgG control antibodies.

Figure 9A:
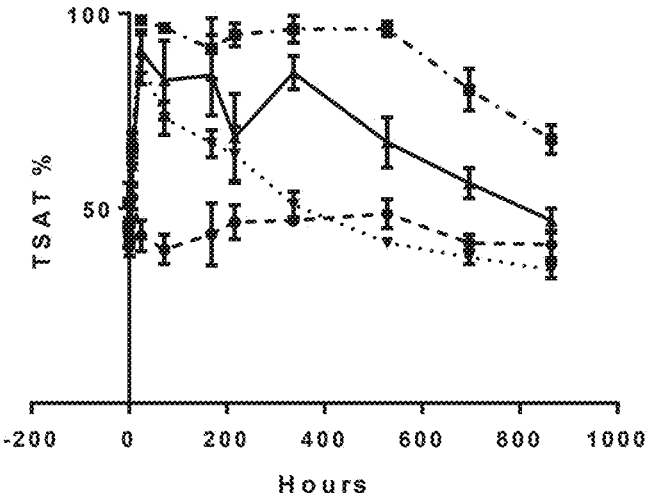
Figure 9B:
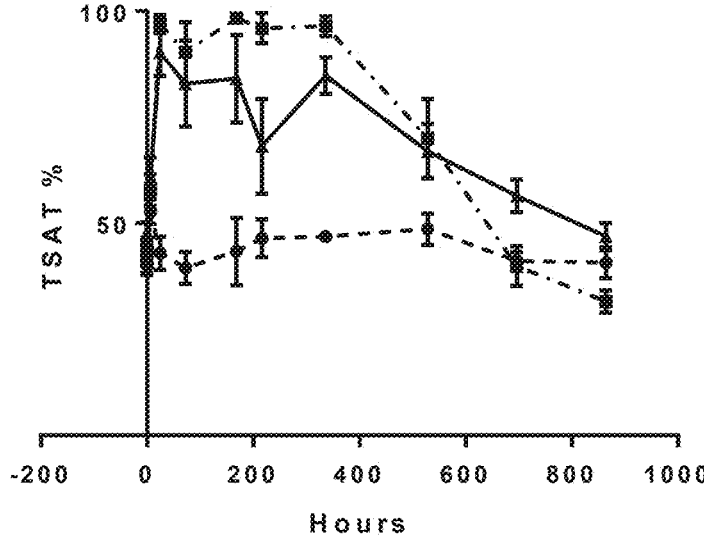

FIGS. 9A-9B:

Results for transferrin saturation in % (TSAT) in normal rats following a single iv injection of CL-58838 at various doses (FIG. 9A) or CL-58838 and Antibody A at 1 mg/kg (FIG. 9B; Table 15).

Figure 10A:
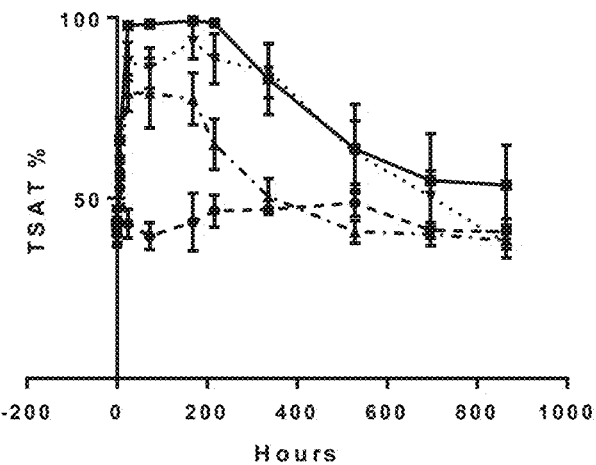
Figure 10B:
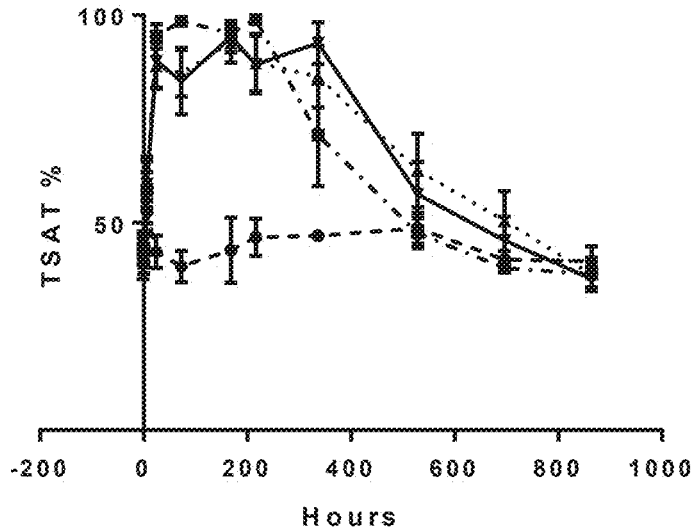

FIGS. 10A-10B:

Results for transferrin saturation in % (TSAT); in normal rats following a single sc injection of CL-58838 at various doses (FIG. 10A) or CL-58838 and Antibody A and B at 1 mg/kg (FIG. 10B; Table 16).

FIGS. 11A-11D:

Pharmacokinetic (PK) profile for human anti-BMP6 IgG4 antibody CL-58838 following a single iv injection at various doses (FIG. 11A) or comparison with Antibody A (FIG. 11B) at 1 mg/kg dose. PK profile following a single subcutaneous (sc) injection of CL-58838 at various doses (FIG. 11C) or Antibodies A and B at 1 mg/kg dose (FIG. 11D). Results plotted as IgG [ng/ml] IgG over time [h].

FIGS. 12A-12F:

Results of the rat PG-PS model of ACD. Transferrin saturation TSAT (FIG. 12A), Haemoglobin [g/dL](FIG. 12B), MCH [pg](FIG. 12C), and serum hepcidin levels [ng/mL] at week 0 (FIG. 12D), week 1 (FIG. 12E) and week 2 (FIG. 12F) after start of treatment (* $p<0.05$,  $p<0.01$, *$p<0.001$).

Figure 13A:
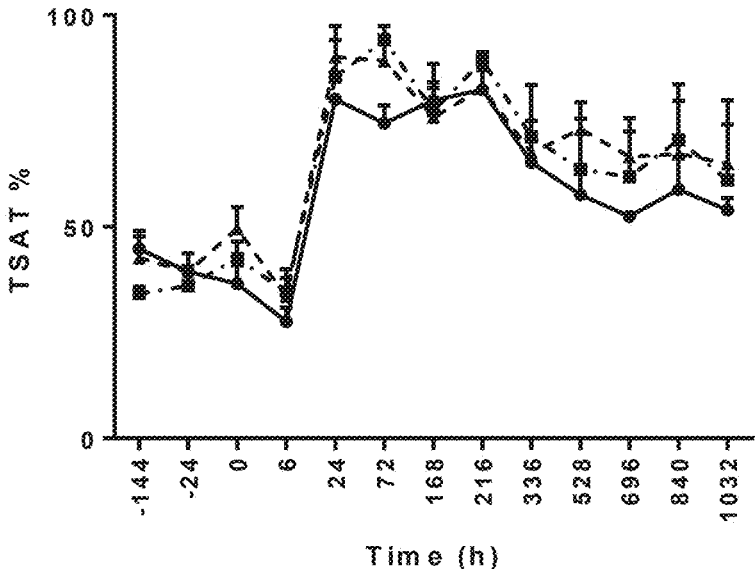
Figure 13B:
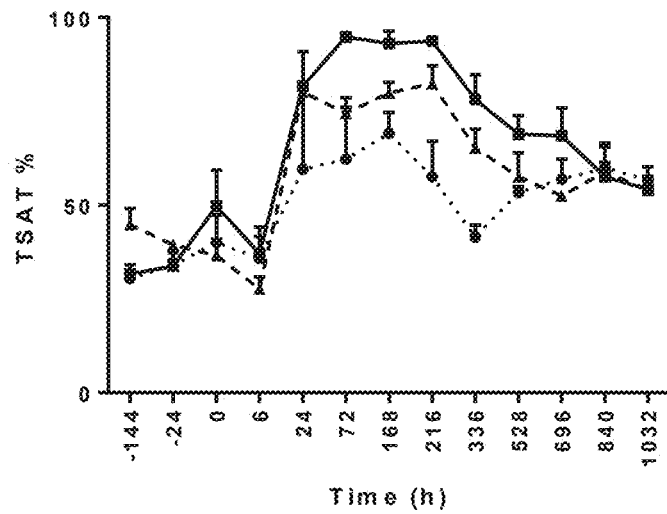
Figure 13C:
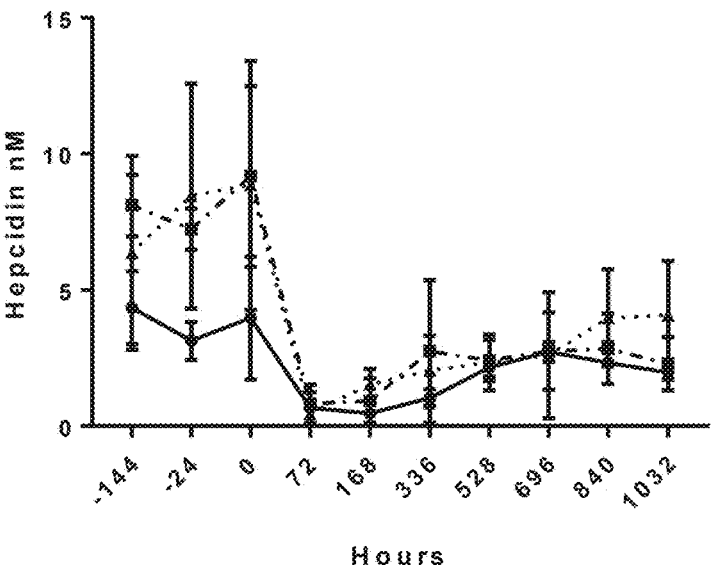
Figure 13D:
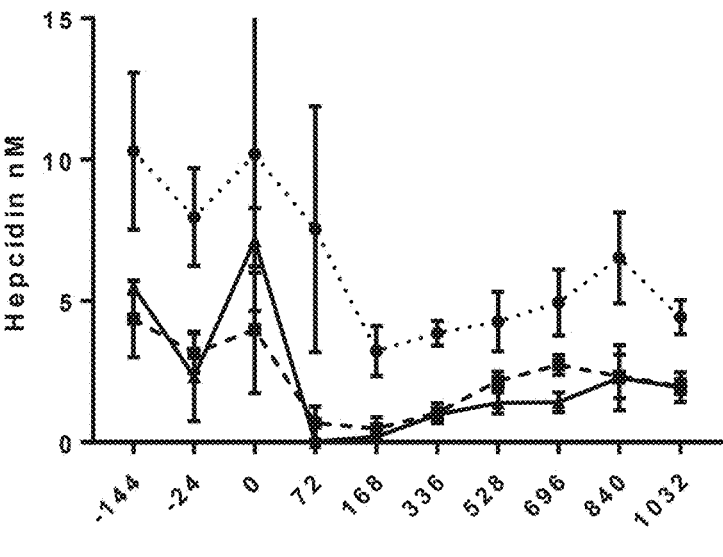

FIGS. 13A-13D:

Transferrin saturation in % (TSAT) following a single iv administration of CL-58838 and Antibody A and B at 3 mg/kg in cynomolgus monkeys (FIG. 13A) and CL-58838 at various doses (FIG. 13B) and plasma hepcidin levels following a single iv administration of CL-58838 and Antibody A and B at 3 mg/kg in cynomolgus monkeys (FIG. 13C) and CL-58838 at various doses (FIG. 13D).

FIGS. 14A-14B:

PK profile of CL-58838 following a single iv injection in cynomolgus monkeys at various doses (A) and PK profile comparison of CL-58838 with Antibody A and B at 3 mg/kg (B).

FIG. 15:

Amino acid sequence alignment of antibody Vh and Vk sequences highly related to CL-58838 based on V-region usage and CDRH3 (Table 6). Top line shows the germline sequence of IMGT V-region genes IGHV3-11 and IGKV3-20 as encoded in bmp6 –/– Kymouse used in this invention. Amino acid positions that differed from the germline V-region sequences in the selected antibody sequences below are boxed. Antibodies selected for in vivo assessment are shown in bold (Table 6).

FIG. 16:

Homogeneous time resolved FRET (HTRF) assay showing the ability of antibodies highly related to CL-58838 based on V-region usage and CDRH antibodies identified by NGS sequence (Table 6) to compete with labelled CL-58838 (10 nM) for binding to human BMP6 present at 32 nM. Competing antibodies were added as a range of concentrations in an 11-point dilution range starting at 3 μM final concentration.

Figure 17A:
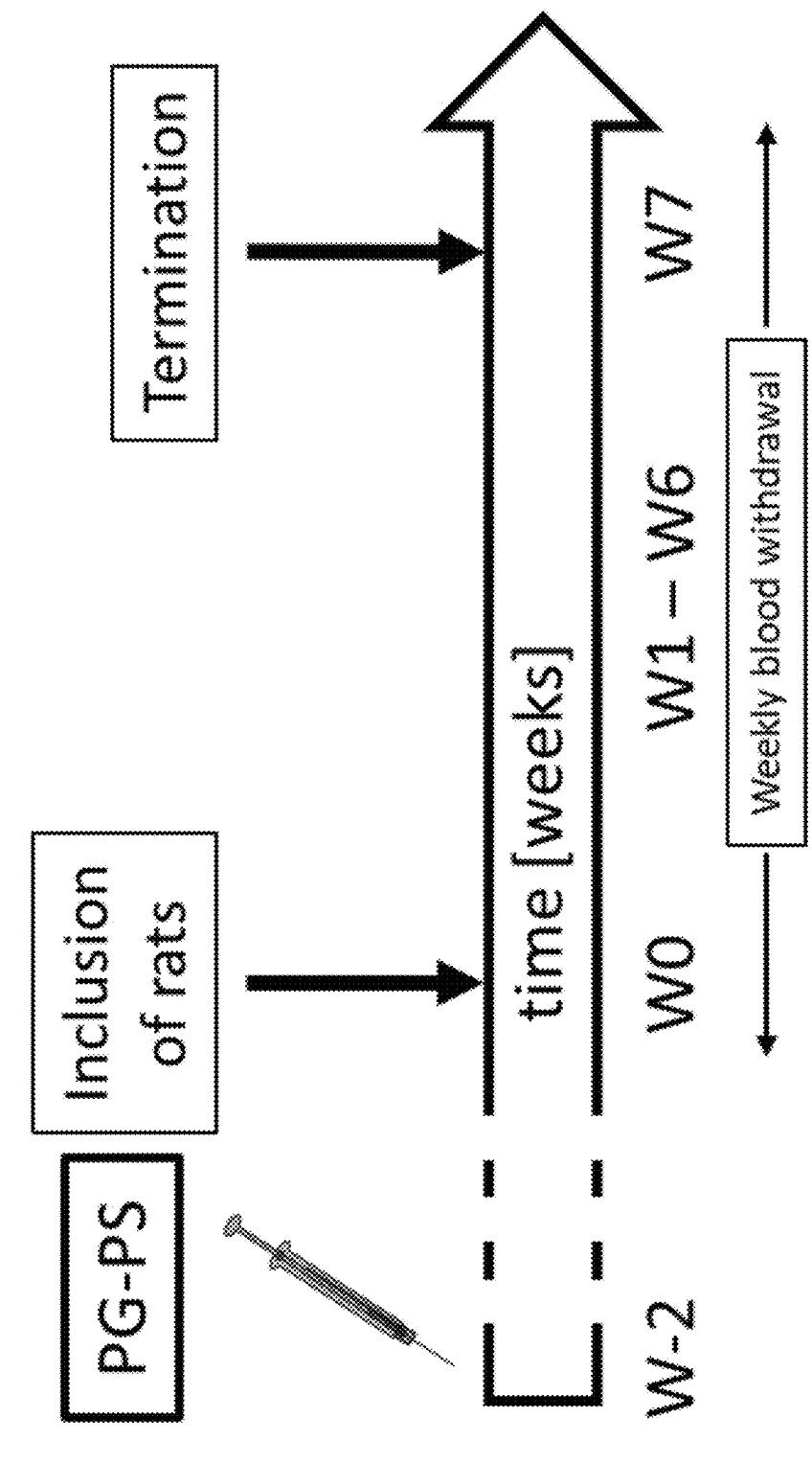
Figure 17B:
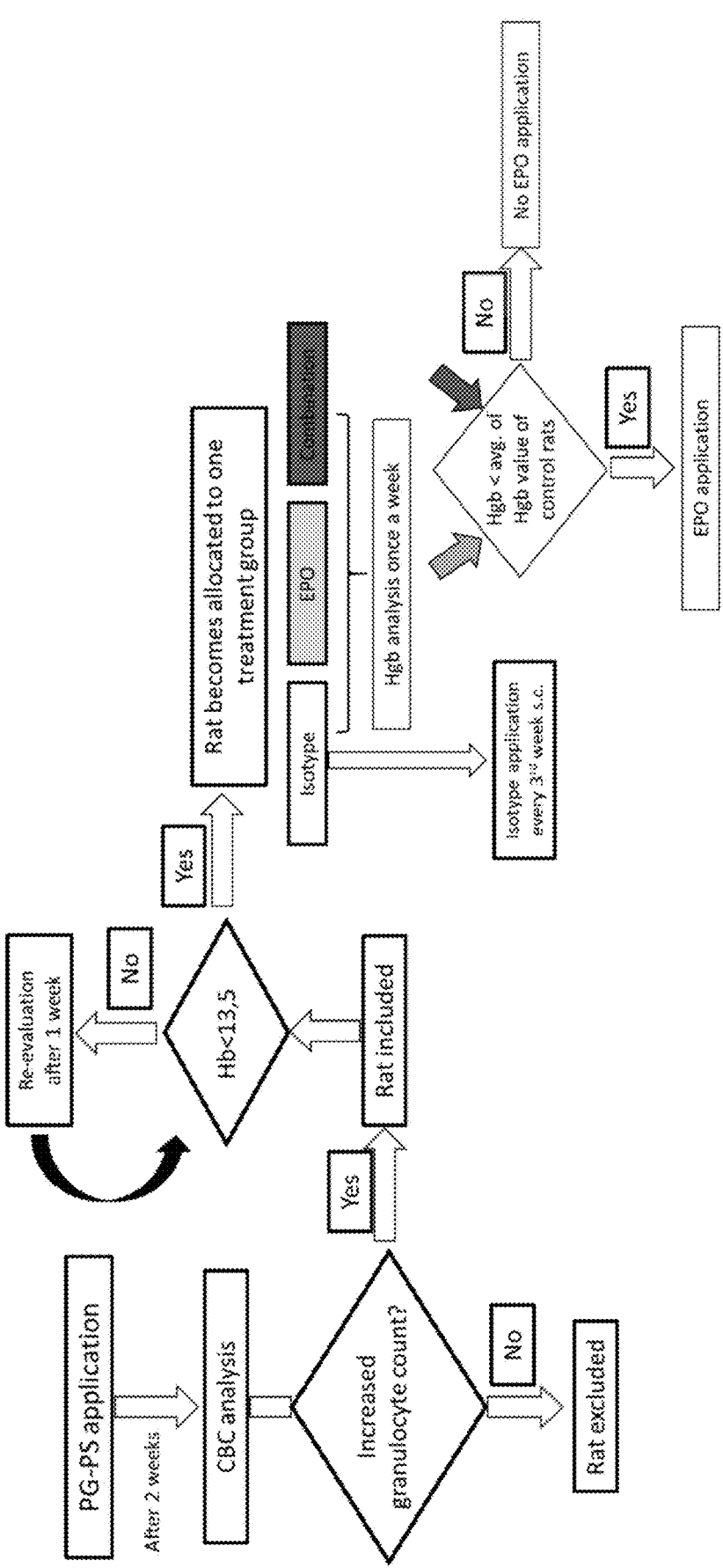
Figure 17C:
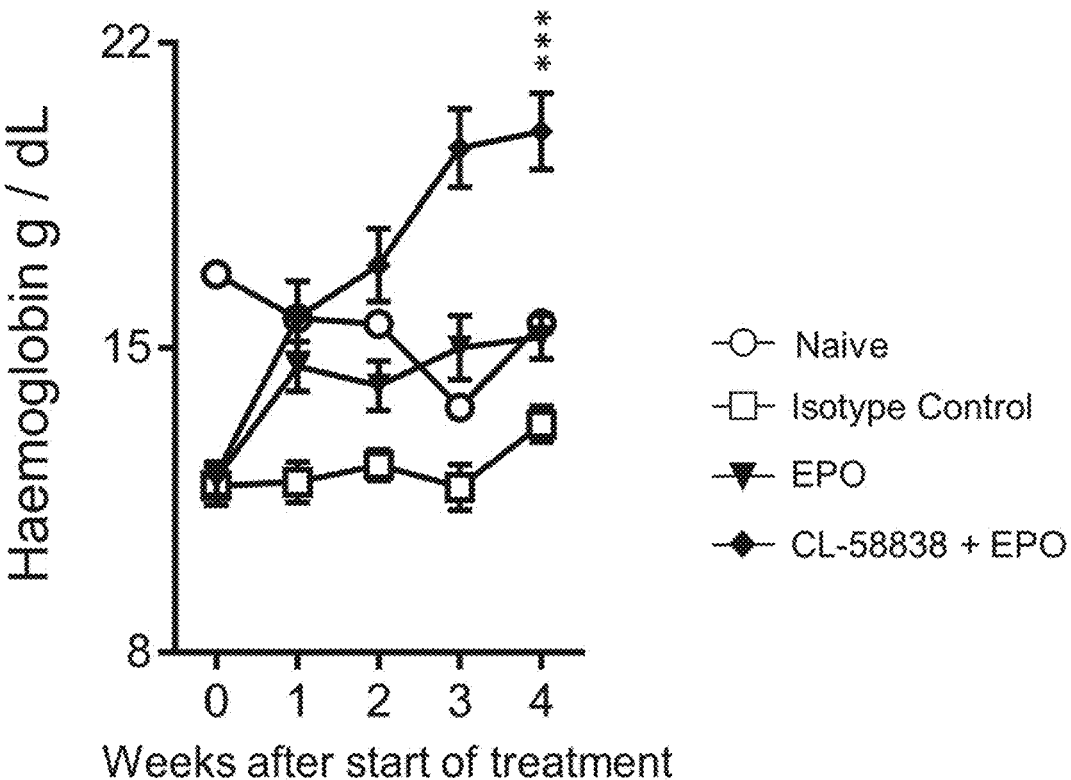
Figure 17D:
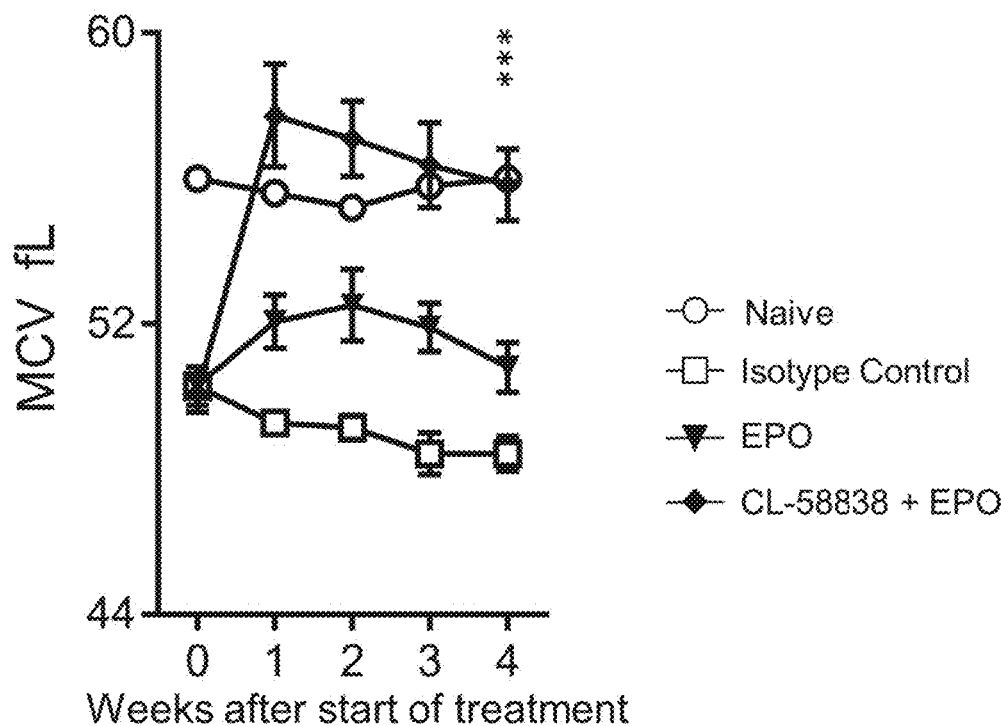
Figure 17E:
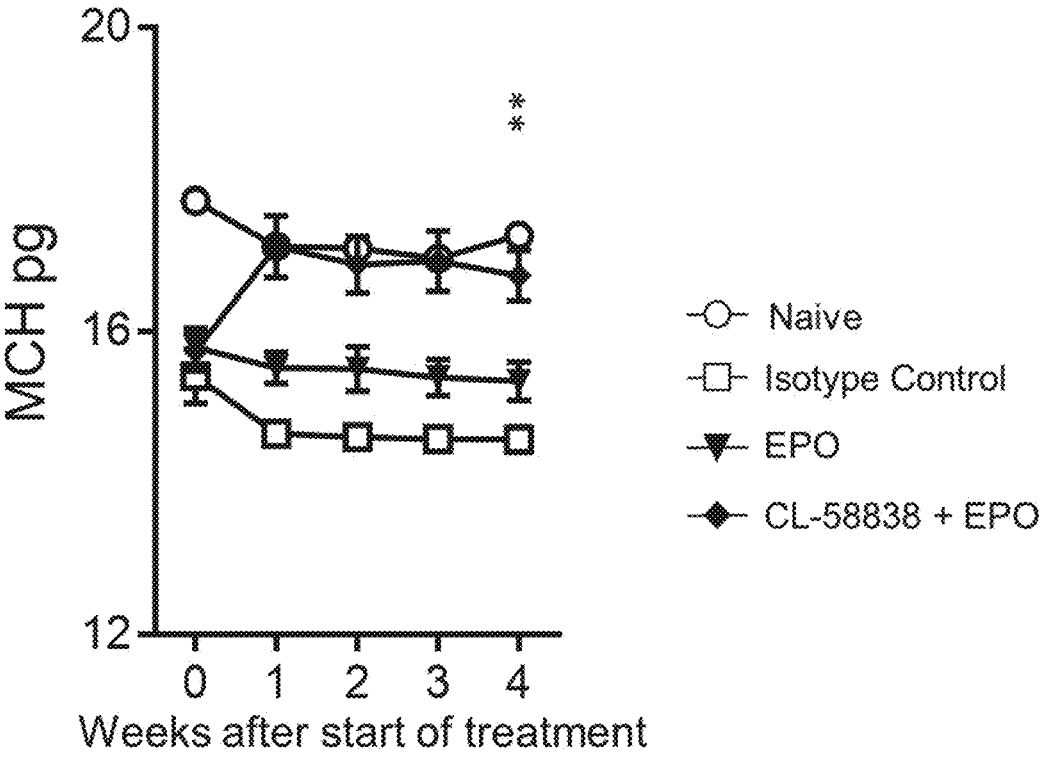
Figure 17F:
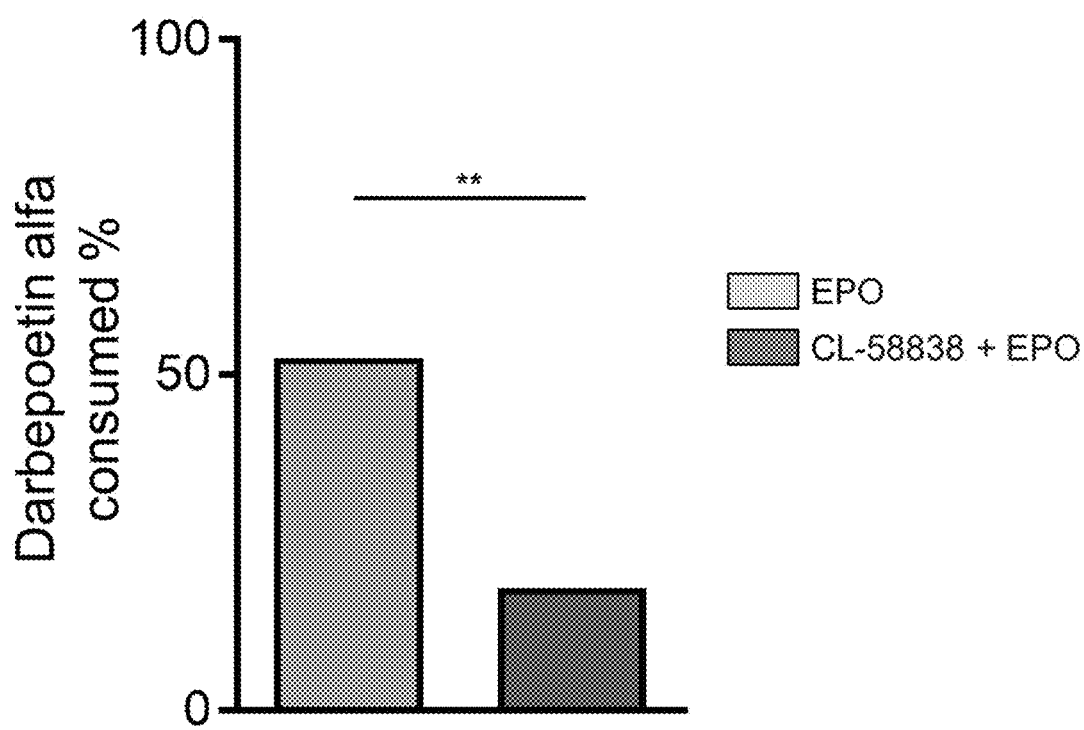

FIGS. 17A-17F:

Experimental setup and results obtained from Example 17. Graphical illustration of experimental time course (FIG. 17A) decision diagram for inclusion of rats and application of EPO (FIG. 17B), Haemoglobin [g/dL](FIG. 17C), MCV [fL](FIG. 17D), MCH [pg](FIG. 17E) and applied EPO doses [%](FIG. 17F). ANCOVA analysis on change from baseline at week 4 with baseline as a covariate (FIGS. 17C-17E) and Fishers exact test (FIG. 17F) were used. Data are shown as mean±SEM (* $p<0.05$,  $p<0.01$, *$p<0.001$).

Figure 18A:
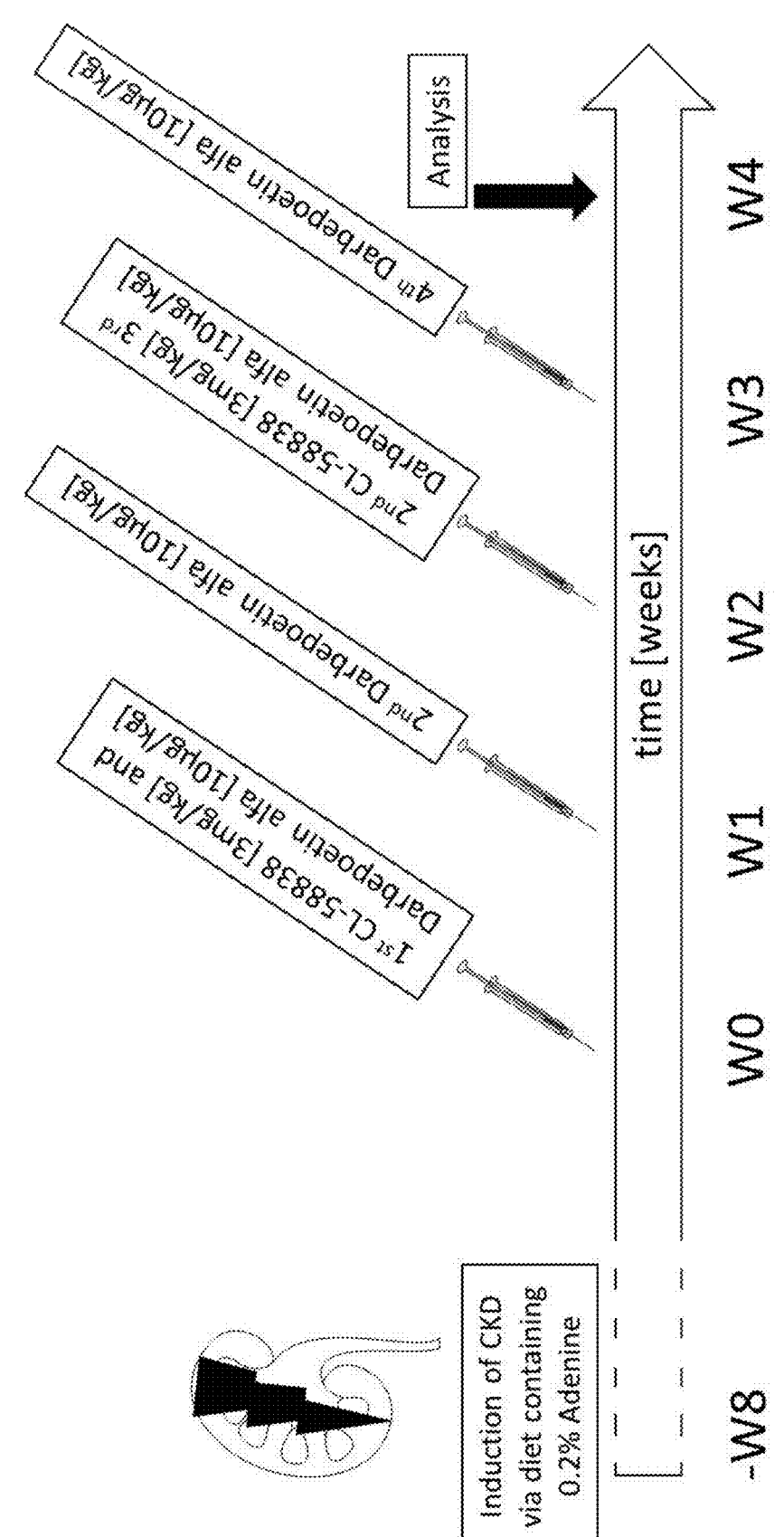
Figure 18B:
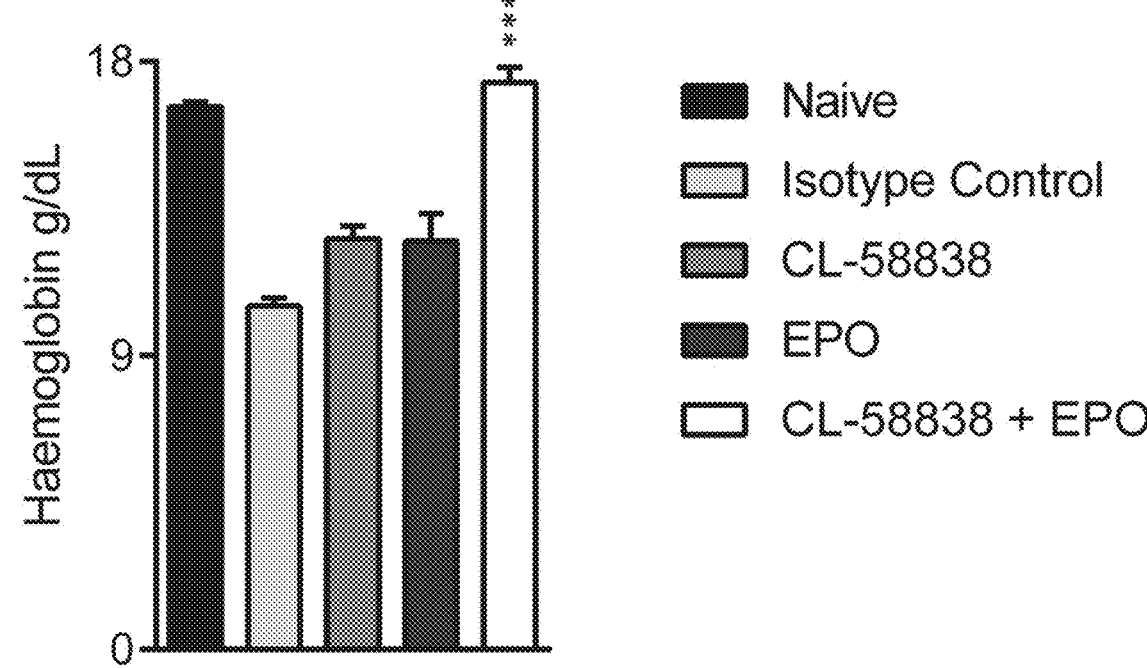
Figure 18C:
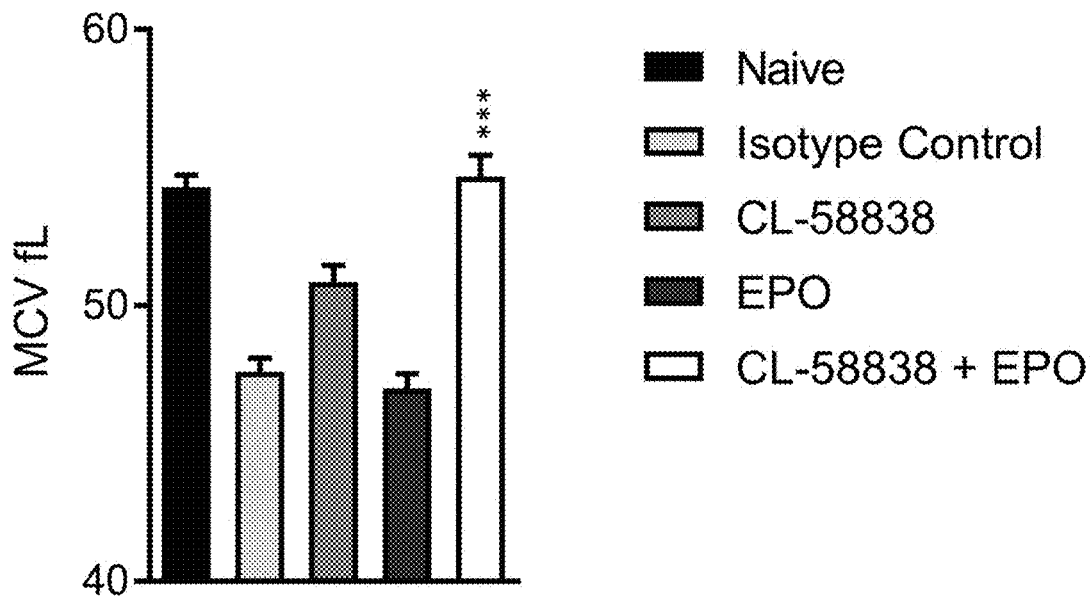
Figure 18D:
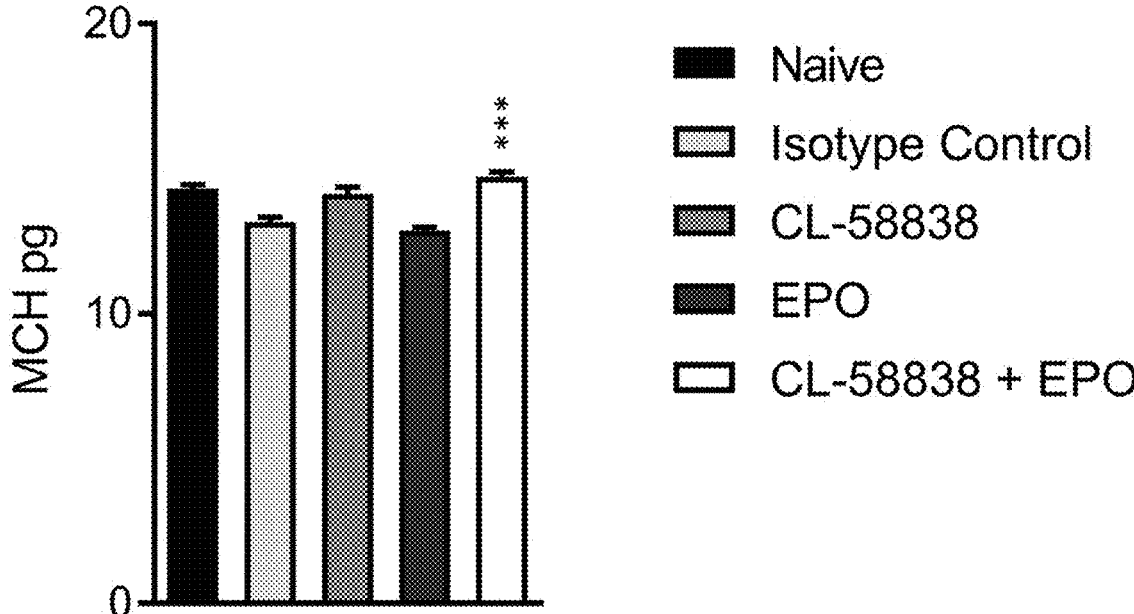
Figure 18E:
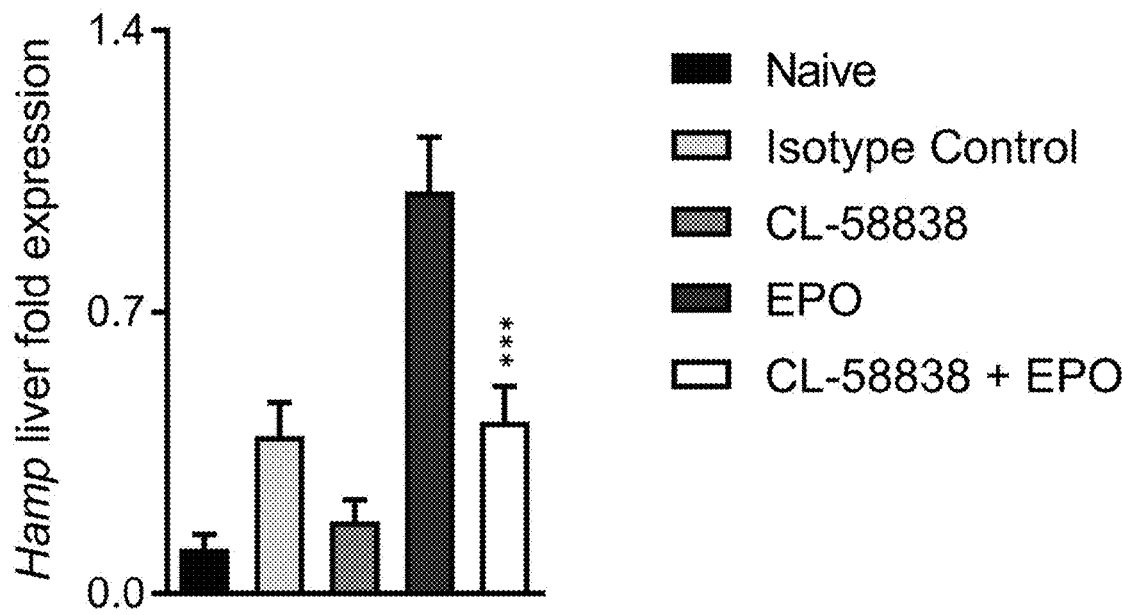
Figure 18F:
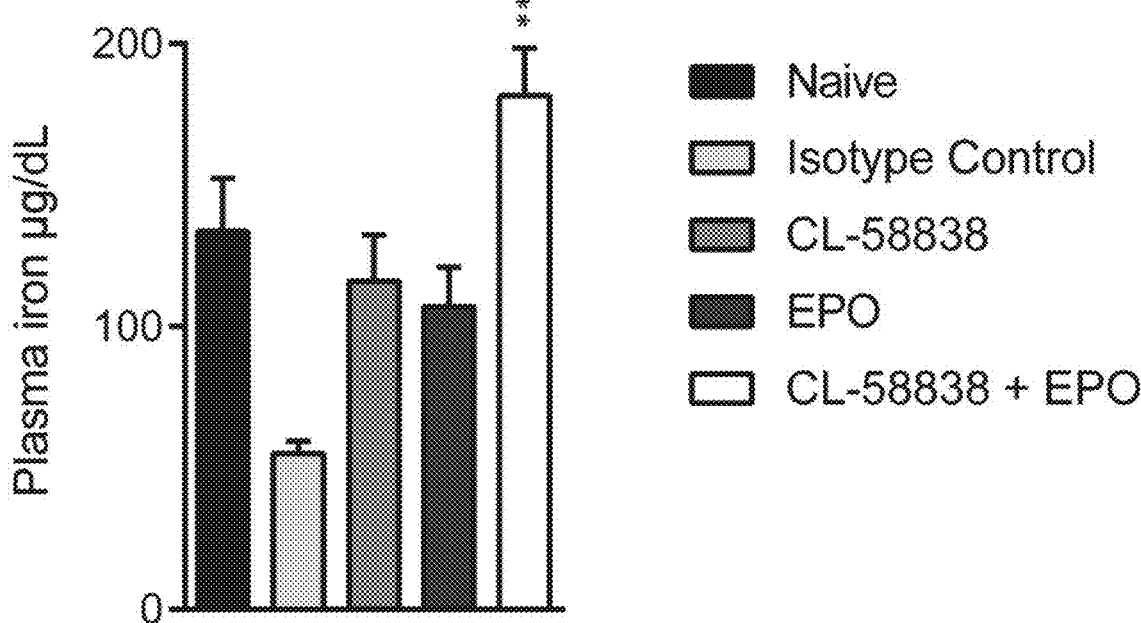
Figure 18G:
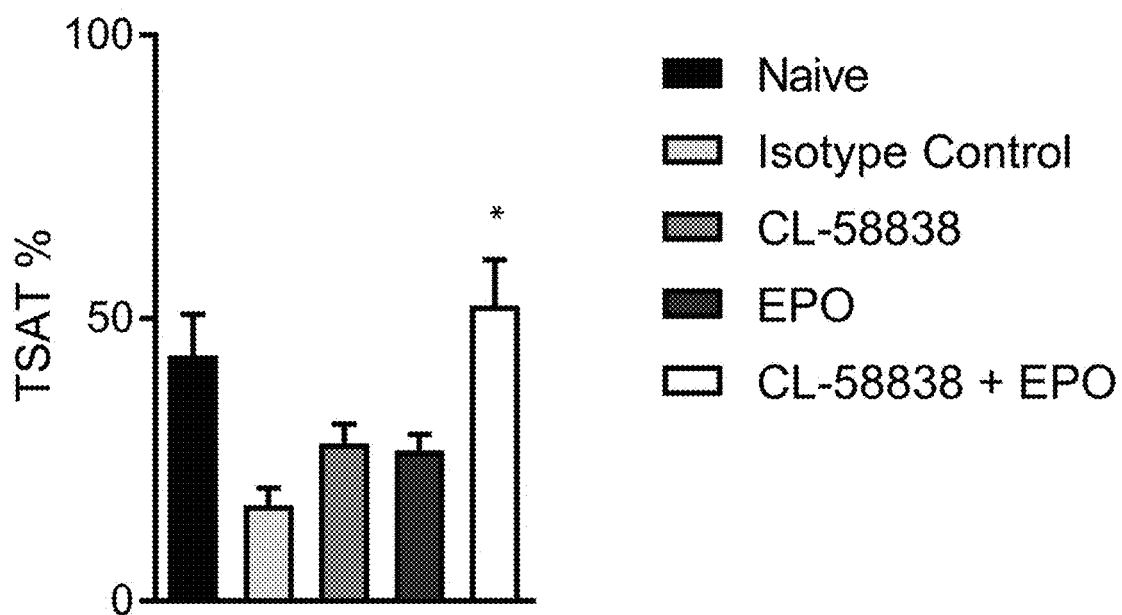

FIGS. 18A-18G:

Experimental setup and results for Example 18. Graphical illustration of experimental time course (FIG. 18A), Haemoglobin [g/dL](FIG. 18B), MCV [fL](FIG. 18C), MCH [pg](FIG. 18D), hepatic Hamp mRNA levels [fold expression], Plasma iron levels [μg/dL](FIG. 18F) and TSAT values [%]. Analysis of variance with Dunnett's correction for multiple comparisons vs. EPO was applied. Results for comparison of EPO vs. EPO+CL-58838 are indicated. Data are shown as mean±SEM (* $p<0.05$,  $p<0.01$, *$p<0.001$).

Figure 19A:
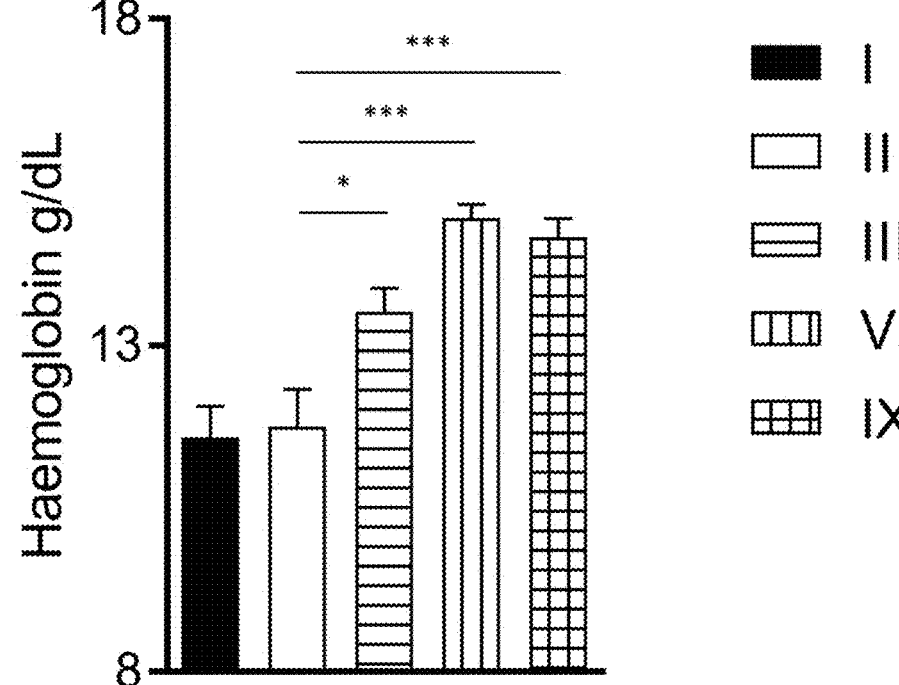
Figure 19B:
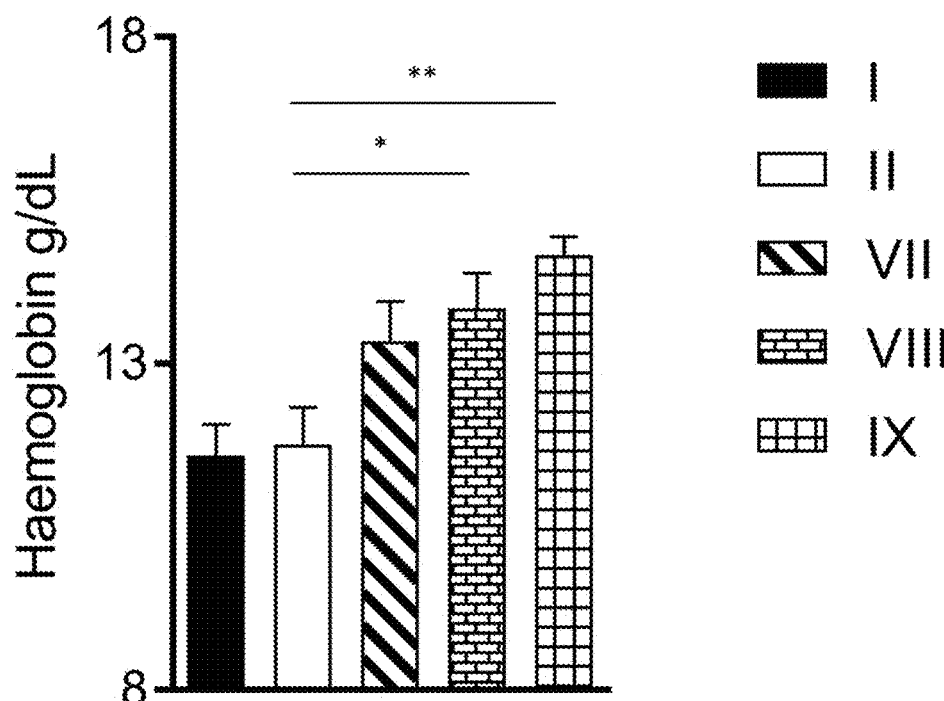
Figure 19C:
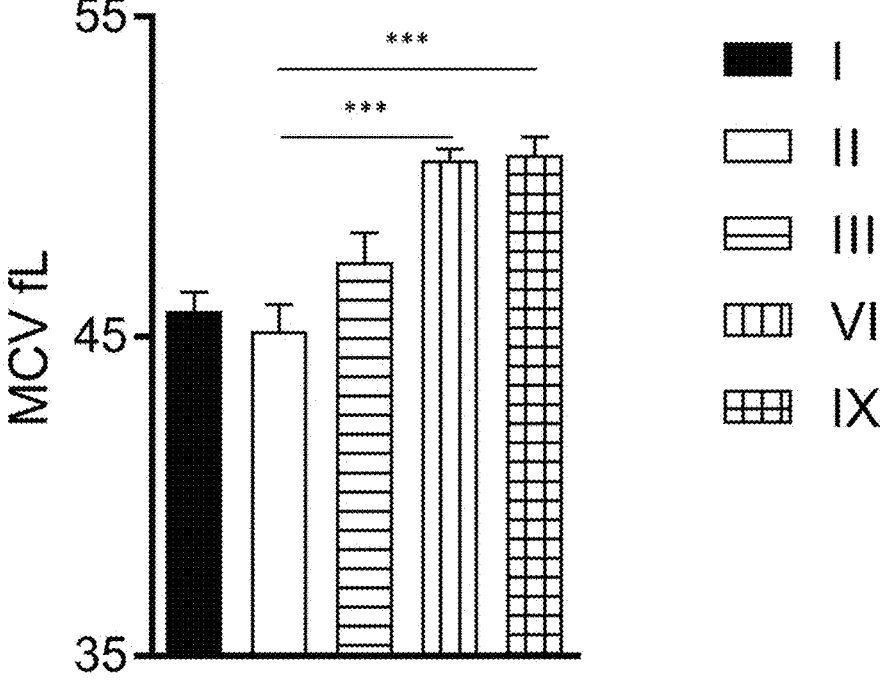
Figure 19D:
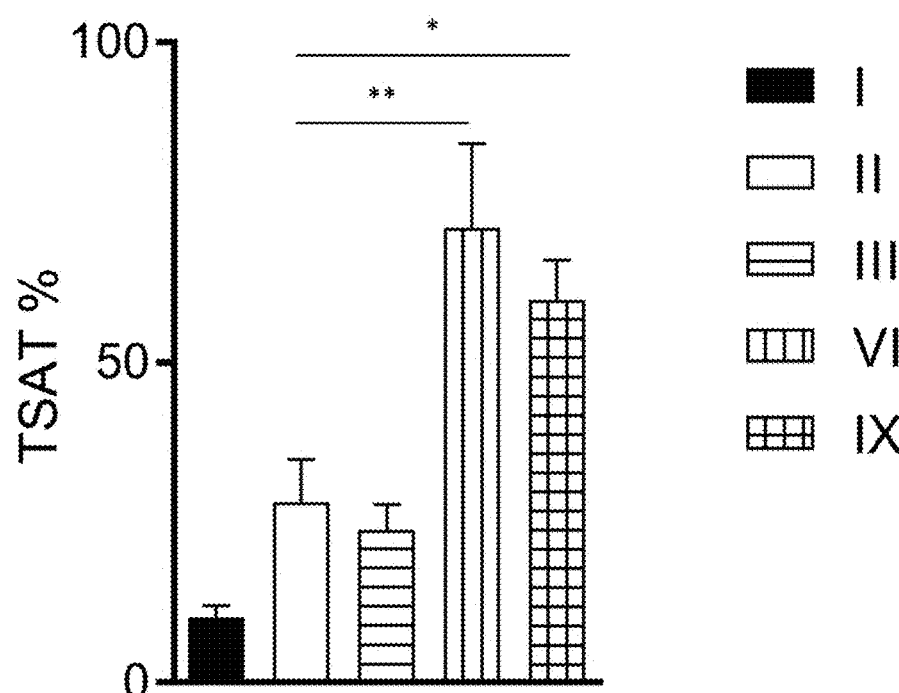
Figure 19E:
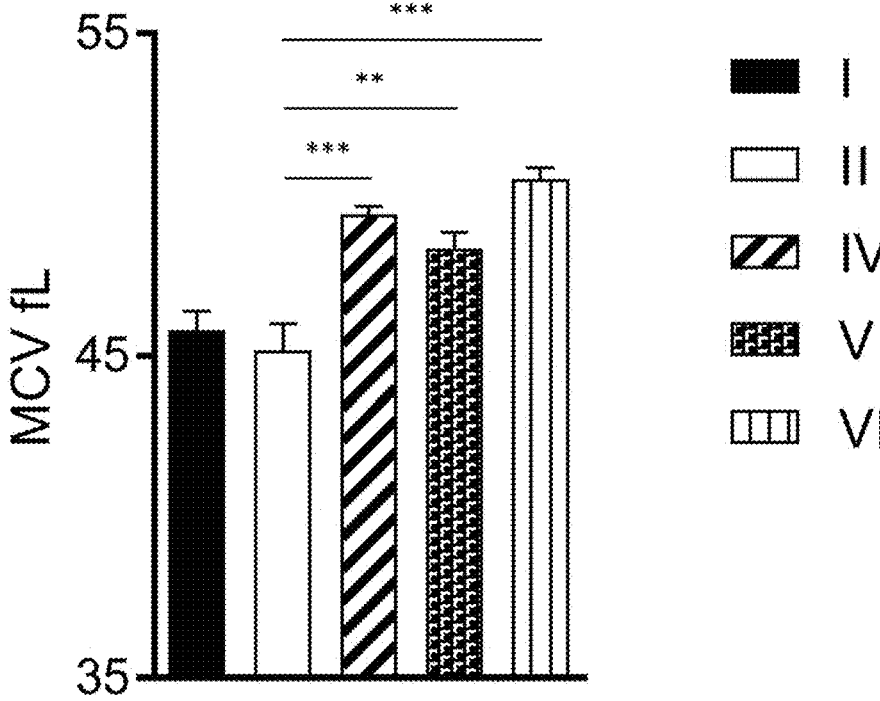
Figure 19F:
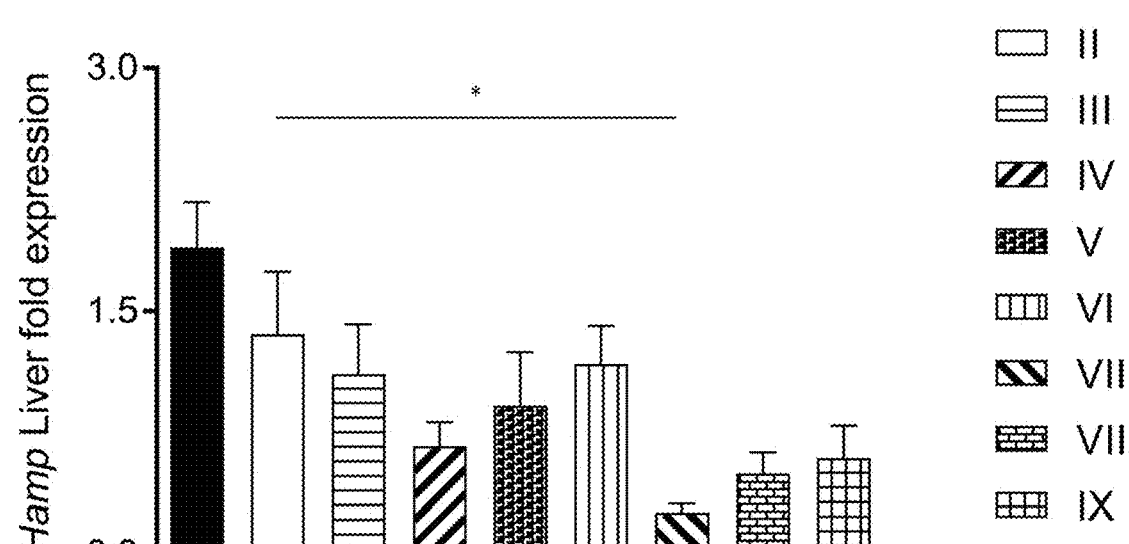

FIGS. 19A-19F:

Results obtained from Example 19. Haemoglobin values [g/dL] comparing treatment groups after administration of 1 μg/kg EPO in combination with different CL-58838 concentrations (FIG. 19A), Haemoglobin values [g/dL] after administration of 10 mg/kg CL-58838 in combination with different EPO doses (FIG. 19B), MCV values [fL](FIG. 19C) and TSAT [%](FIG. 19D) of mice after administration of 1 μg/kg EPO in combination with different CL-58838 concentrations, MCV values [fL] of mice after administration of 1 mg/kg CL-58838 in combination with different EPO doses (FIG. 19E), hepatic Hamp mRNA levels [fold expression] among all treatment groups (FIG. 19F). Analysis of variance with Dunnett's correction for multiple comparisons vs. Group II was applied. Data are shown as mean±SEM (* $p<0.05$,  $p<0.01$, *$p<0.001$).

DETAILED DESCRIPTION

Definitions

Unless otherwise defined herein, scientific and technical terms shall have the meanings that are commonly understood by those of ordinary skill in the art. Further, unless otherwise required by context, singular terms shall include pluralities and plural terms shall include the singular. The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia and is used herein to indicate a non-limiting example. Thus, the abbreviation "e.g." is synonymous with the term "for example." In the specification and claims, the term "about" is used to modify, for example, the quantity of an ingredient in a composition, concentration, volume, process temperature, process time, yield, flow rate, pressure, and like values, and ranges thereof, employed in describing the embodiments of the disclosure. The term "about" refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

As used herein, "administer" or "administration" refers to the act of injecting or otherwise physically delivering a substance as it exists outside the body (eg, an anti-hBMP6 antibody provided herein) into a patient, such as by mucosal, intradermal, intravenous, intramuscular delivery and/or any other method of physical delivery described herein or known in the art. When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof.

The term "antibody", "immunoglobulin" or "Ig" may be used interchangeably herein and means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific antibodies (including dual binding antibodies), chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. The term "antibody" can also refer to a Y-shaped glycoprotein with a molecular weight of approximately 150 kDa that is made up of four polypeptide chains: two light (L) chains and two heavy (H) chains. There are five types of mammalian Ig heavy chain isotypes denoted by the Greek letters alpha ($\alpha$), delta ($\delta$), epsilon ($\varepsilon$), gamma ($\gamma$), and mu ($\mu$). The type of heavy chain defines the class of antibody, i.e., IgA, IgD, IgE, IgG, and IgM, respectively. The $\gamma$ and $\alpha$ classes are further divided into subclasses on the basis of differences in the constant domain sequence and function, eg, IgG1, hIgG2, mIgG2A, mIgG2B, IgG3, IgG4, IgA1 and IgA2. In mammals, there are two types of immunoglobulin light chains, $\lambda$ and $\kappa$. The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites. An example of antibodies are heavy chain-only (ie, H2) antibodies that comprise a dimer of a heavy chain (5'-VH-(optional Hinge)-CH2-CH3-3') and are devoid of a light chain.

The antibodies described herein may be oligoclonal, polyclonal, monoclonal (including full-length monoclonal antibodies), camelised, chimeric, CDR-grafted, multi-specific, bi-specific (including dual-binding antibodies), catalytic, chimeric, humanized, fully human, anti-idiotypic, including antibodies that can be labelled in soluble or bound form as well as fragments, variants or derivatives thereof, either alone or in combination with other amino acid sequences provided by known techniques. An antibody may be from any species. Antibodies described herein can be naked or conjugated to other molecules such as toxins, radioisotopes, etc.

The term "antigen binding site," "antigen binding domain," "antigen binding region," "antigen binding fragment," and similar terms refer to that portion of an antibody which comprises the amino acid residues that interact with an antigen and confer on the binding agent its specificity and affinity for the antigen (e.g. the complementarity determining regions (CDRs)). The antigen binding region can be derived from any animal species, such as rodents (e.g. rabbit, rat or hamster) and humans. Preferably, the antigen binding region will be of human origin.

Antigen binding fragments described herein can include single-chain Fvs (scFv), single-chain antibodies, single domain antibodies, domain antibodies, Fv fragments, Fab fragments, F(ab') fragments, F(ab')$_2$ fragments, antibody fragments that exhibit the desired biological activity, disulfide-stabilised variable region (dsFv), dimeric variable region (diabody), anti-idiotypic (anti-Id) antibodies (including, e.g. anti-Id antibodies to antibodies), intrabodies, linear antibodies, single-chain antibody molecules and multispecific antibodies formed from antibody fragments and epitope-binding fragments of any of the above. In particular, antibodies and antibody fragments described herein can include immunoglobulin molecules and immunologically active fragments of immunoglobulin molecules, i.e., molecules that contain an antigen-binding site. Digestion of antibodies with the enzyme, papain, results in two identical antigen-binding fragments, known also as "Fab" fragments, and a "Fc" fragment, having no antigen-binding activity but having the ability to crystallize. "Fab" when used herein refers to a fragment of an antibody that includes one constant and one variable domain of each of the heavy and light chains. The term "Fc region" herein is used to define a C-terminal region of an immunoglobulin heavy chain, including native-sequence Fc regions and variant Fc regions. The "Fc fragment" refers to the carboxy-terminal portions of both H chains held together by disulfides. The effector functions of antibodies are determined by sequences in the Fc region, the region which is also recognized by Fc receptors (FcR) found on certain types of cells. Digestion of antibodies with the enzyme, pepsin, results in a F(ab')$_2$ fragment in which the two arms of the antibody molecule remain linked and comprise two-antigen binding sites. The F(ab')$_2$ fragment has the ability to crosslink antigen.

The term "derived from the recombination of" in relation to gene segments will be readily apparent to the skilled person, who will understand that B-cells recombine their variable region gene segments to produce coding sequence for variable domains. For example "derived from the recombination of a human VH gene segment, DH gene segment and JH gene segment" relates to the recombination of one human VH gene segment, with one DH gene segment and one JH gene segment together to form a rearranged VDJ sequence encoding a heavy chain antibody variable domain. Junctional and somatic hypermutation may also be features of the process, whereby the resulting recombined VDJ sequence includes one or more nucleotide additions, substitutions or deletions (eg, p-additions and/or n-additions) that are not comprised by the germline V, D and J sequences. The equivalent will be said of $V_\kappa$ and $J_\kappa$ gene segments for a kappa light chain variable domain, and of V$\lambda$ and J$\lambda$ for a lambda light chain variable domain. It is intended that any post-translational modifications may additionally encompassed in variable domains.

"Fv" when used herein refers to the minimum fragment of an antibody that retains both antigen-recognition and antigen-binding sites. This region consists of a dimer of one heavy and one light chain variable domain in tight, noncovalent or covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The term "monoclonal antibody" as used herein refers to an antibody obtained from a population of substantially homogeneous antibodies, i.e. the individual antibodies comprising the population are identical except for possible naturally occurring mutations and/or post-translation modifications (e.g. isomerizations, amidations) that may be present in minor amounts. Monoclonal antibodies are highly specific and are directed against a single antigentic determinant or epitope. In contrast, polyclonal antibody preparations typically include different antibodies directed against different antigenic determinants (or epitopes). The term "monoclonal antibody" as used herein encompasses both intact and full-length monoclonal antibodies as well as antibody fragments (such as Fab, Fab', F(ab')$_2$, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, hybridoma, phage selection, recombinant expression, and transgenic animals.

The monoclonal antibodies herein can include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies that exhibit the desired biological activity.

The term "humanised antibody" refers to a subset of chimeric antibodies in which a "hypervariable region" from a non-human immunoglobulin (the donor antibody) replaces residues from a hypervariable region in a human immunoglobulin (recipient antibody). In general, a humanized antibody will include substantially all of at least one, and typically two, variable domains, in which all or substantially all of the hypervariable loops correspond to those of a non-human immunoglobulin sequence, and all or substantially all of the framework regions are those of a human immunoglobulin sequence, although the framework regions may include one or more substitutions that improve antibody performance, such as binding affinity, isomerization, immunogenicity, etc.

The term "bispecific antibody" means an antibody which comprises specificity for two target molecules, and includes, but is not limited to, formats such as DVD-Ig (see DiGiammarino et al., "Design and generation of DVD-Ig™ molecules for dual-specific targeting", Meth. Mo. Biol., 2012, 889, 145-156), mAb$^2$ (see WO2008/003103, the description of the mAb$^2$ format is incorporated herein by reference), FIT-Ig (see WO2015/103072, the description of the FIT-Ig scaffold is incorporated herein by reference), mAb-dAb, dock and lock, Fab-arm exchange, SEEDbody, Triomab, LUZ-Y, Fcab, Kh-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, Triple body, Miniantibody, minibody, TriBi minibody, scFv-CH3 KIH, scFv-CH-CL-scFv, F(ab')2-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)—IgG, IgG(L)-V, V(L)-IgG, KIH IgG-scFab, 2scFv-IgG, IgG-2scFv, scFv4-Ig and zybody. For a review of bispecific formats, see Spiess, C., et al., Mol. Immunol. (2015). In another embodiment, the bispecific molecule comprises an antibody which is fused to another non-Ig format, for example a T-cell receptor binding domain; an immunoglobulin superfamily domain; an agnathan variable lymphocyte receptor; a fibronectin domain (e.g. an Adnectin™); an antibody constant domain (e.g. a CH$_3$ domain, e.g., a CH$_2$ and/or CH$_3$ of an Fcab™) wherein the constant domain is not a functional CH$_1$ domain; an scFv; an (scFv)$_2$; an sc-diabody; an scFab; a centyrin and an epitope binding domain derived from a scaffold selected from CTLA-4 (Evibody™); a lipocalin domain; Protein A such as Z-domain of Protein A (e.g. an Affibody™ or SpA); an A-domain (e.g. an Avimer™ or Maxibody™); a heat shock protein (such as and epitope binding domain derived from GroEI and GroES); a transferrin domain (e.g. a trans-body); ankyrin repeat protein (e.g. a DARPin™); peptide aptamer; C-type lectin domain (e.g. Tetranectin™); human γ-crystallin or human ubiquitin (an affilin); a PDZ domain; scorpion toxin; and a kunitz type domain of a human protease inhibitor.

In one embodiment, the bispecific antibody is a mAb$^2$. A mAb$^2$ comprises a $V_H$ and VL domain from an intact antibody, fused to a modified constant region, which has been engineered to form an antigen-binding site, known as an "Fcab". The technology behind the Fcab/mAb$^2$ format is described in more detail in WO2008/003103, and the description of the mAb$^2$ format is incorporated herein by reference.

In another embodiment, the bispecific antibody is a "dual binding antibody". As used herein, the term "dual binding antibody" is a bispecific antibody wherein both antigen-binding domains are formed by a $V_H$/$V_L$ pair, and includes FIT-Ig (see WO2015/103072, incorporated herein by reference), mAb-dAb, dock and lock, Fab-arm exchange, SEEDbody, Triomab, LUZ-Y, Fcab, Kh-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, Triple body, Miniantibody, minibody, scFv-CH$_3$ KIH, scFv-CH-CL-scFv, F(ab')$_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)—IgG, IgG(L)-V, V(L)-IgG, KIH IgG-scFab, 2scFv-IgG, IgG-2scFv and scFv4-Ig.

The term "hypervariable region", "CDR region" or "CDR" refers to the regions of an antibody variable domain which are hypervariable in sequence and/or form structurally defined loops. Generally, antigen binding sites of an antibody include six hypervariable regions: three in the $V_H$ (CDRH1, CDRH2, CDRH3), and three in the VL (CDRL1, CDRL2, CDRL3). These regions of the heavy and light chains of an antibody confer antigen-binding specificity to the antibody. CDRs may be defined according to the Kabat system (see Kabat, E. A. et al., 1991, "Sequences of Proteins of Immunological Interest", 5$^{th}$ edit., NIH Publication no. 91-3242, U.S. Department of Health and Human Services). Other systems may be used to define CDRs, which as the system devised by Chothia et al (see Chothia, C. & Lesk, A. M., 1987, "Canonical structures for the hypervariable regions of immunoglobulins", J. Mol. Biol., 196, 901-917) and the IMGT system (see Lefranc, M. P., 1997, "Unique database numbering system for immunogenetic analysis", Immunol. Today, 18, 50). An antibody typically contains 3 heavy chain CDRs and 3 light chain CDRs. The term CDR or CDRs is used here to indicate one or several of these regions. A person skilled in the art is able to readily compare the different systems of nomenclature and determine whether a particular sequence may be defined as a CDR.

A "human antibody" is an antibody that possesses an amino-acid sequence corresponding to that of an antibody produced by a human and/or has been made using any of the techniques for making human antibodies and specifically excludes a humanized antibody comprising non-human antigen-binding residues. The term "specifically binds to" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g. by a radioimmunoassay (RIA).

An antibody or a fragment thereof that specifically binds to a hBMP6 antigen may be cross-reactive with related antigens. Preferably, an antibody or a fragment thereof that specifically binds to a hBMP6 antigen does not cross-react with other antigens (but may optionally cross-react with BMP6 of a different species, e.g. rhesus, or murine). An antibody or a fragment thereof that specifically binds to a hBMP6 antigen can be identified, for example, by immunoassays, BIAcore™, or other techniques known to those of skill in the art. An antibody or a fragment thereof binds specifically to a BMP6 antigen when it binds to a hBMP6 antigen with higher affinity than to any cross-reactive antigen as determined using experimental techniques, such as radioimmunoassays (RIA) and enzyme-linked immunosorbent assays (ELISAs). Typically, a specific or selective reaction will be at least twice background signal or noise and more typically more than 10 times (such as more than 15 times, more than 20 times, more than 50 times or more than 100 times) background. See, e.g. Paul, ed., 1989, Fundamental Immunology Second Edition, Raven Press, New York at pages 332-336 for a discussion regarding antibody specificity.

The term "aliphatic amino acid" means that the amino acid R groups are nonpolar and hydrophobic. Hydrophobicity increases with increasing number of C atoms in the hydrocarbon chain. Glycine, Alanine, Valine, Leucine and Isoleucine are aliphatic amino acids.

The term "aromatic amino acid" means that the amino acid R groups contain an aromatic ring system. Phenylalanine, Tyrosine and Tryptophan are aromatic amino acids.

The term "hydroxyl-containing amino acid" means that the amino acid R groups contain a hydroxyl group and are hydrophilic. Serine, Cysteine, Threonine and Methionine are hydroxyl-containing amino acids.

The term "basic amino acid" means that the amino acid R groups are nitrogen containing and are basic at neutral pH. Histidine, Lysine and Arginine are basic amino acids.

The term "cyclic amino acid" means that the amino acid R groups have an aliphatic cyclic structure. Proline is the only cyclic aliphatic amino acid.

The term "acidic amino acid" means that the amino acid R groups are polar and are negatively charged at physiological pH. Aspartate and Glutamate are acidic amino acids.

The term "amide amino acid" means that the amino acid R groups contain an amide group. Asparagine and Glutamine are amide amino acids.

As used herein, "authorization number" or "marketing authorization number" refers to a number issued by a regulatory agency upon that agency determining that a particular medical product and/or composition may be marketed and/or offered for sale in the area under the agency's jurisdiction. As used herein "regulatory agency" refers to one of the agencies responsible for evaluating, e.g. the safety and efficacy of a medical product and/or composition and controlling the sales/marketing of such products and/or compositions in a given area. The Food and Drug Administration (FDA) in the US and the European Medicines Agency (EPA) in Europe are but two examples of such regulatory agencies. Other non-limiting examples can include SDA, MPA, MHPRA, IMA, ANMAT, Hong Kong Department of Health-Drug Office, CDSCO, Medsafe, and KFDA.

As used herein, a "buffer" refers to a chemical agent that is able to absorb a certain quantity of acid or base without undergoing a strong variation in pH.

As used herein, the term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

The term "chemotherapeutic agent" or "chemotherapy" refers to a therapeutic agent whose primary purpose is to destroy cancer cells, typically by interfering with the tumour cell's ability to grow or multiply. There are many different types of chemotherapeutic agents, with more than 50 approved chemotherapy drugs available. Chemotherapeutic drugs can be classified based on how they work. Alkylating drugs kill cancer cells by directly attacking DNA, the genetic material of the genes. Cyclophosphamide is an alkylating drug. Antimetabolites interfere with the production of DNA and keep cells from growing and multiplying. An example of an antimetabolite is 5-fluorouracil (5-FU). Anti-tumour antibiotics are made from natural substances such as fungi in the soil. They interfere with important cell functions, including production of DNA and cell proteins. Doxorubicin and bleomycin belong to this group of chemotherapy drugs. Plant alkaloids prevent cells from dividing normally. Vinblastine and vincristine are plant alkaloids obtained from the periwinkle plant. Steroid hormones slow the growth of some cancers that depend on hormones. For example, tamoxifen is used to treat breast cancers that depend on the hormone estrogen for growth. DNA damage response (DDR) inhibitors, such as PARP inhibitors, block DNA repair mechanisms following single or double stranded breaks.

Examples of chemotherapeutic agents include Adriamycin, Doxorubicin, 5-Fluorouracil, Cytosine arabinoside (Ara-C), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see, U.S. Pat. No. 4,675,187), Melphalan, and other related nitrogen mustards. Suitable toxins and chemotherapeutic agents are described in Remington's Pharmaceutical Sciences, 19th Ed. (Mack Publishing Co. 1995), and in Goodman and Gilman's The Pharmacological Basis of Therapeutics, $7^{th}$ Ed. (MacMillan Publishing Co. 1985). Another example of chemotherapeutic agents is the class of antibody-conjugated toxins, including, but not limited to pyrrolobenzodiazepiness, maytansanoids, calicheamicin, etc. Other suitable toxins and/or chemotherapeutic agents are known to those of skill in the art.

As used herein, the term "composition" is intended to encompass a product containing the specified ingredients (e.g. an antibody of the invention) in, optionally, the specified amounts, as well as any product which results, directly or indirectly, from combination of the specified ingredients in, optionally, the specified amounts.

As used herein the term "comprising" or "comprises" is used with reference to antibodies, fragments, uses, compositions, methods, and respective component(s) thereof, that are essential to the method or composition, yet open to the inclusion of unspecified elements, whether essential or not.

The term "consisting of" refers to antibodies, fragments, uses, compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

In the context of a polypeptide, the term "derivative" as used herein includes a polypeptide that comprises an amino acid sequence of a hBMP6 polypeptide, a fragment of a hBMP6 polypeptide, or an antibody or fragment that specifically binds to a hBMP6 polypeptide which has been altered by the introduction of amino acid residue substitutions, deletions or additions. The term "derivative" as used herein also includes a hBMP6 polypeptide, a fragment of a hBMP6 polypeptide, or an antibody that specifically binds to a hBMP6 polypeptide which has been chemically modified, e.g. by the covalent attachment of any type of molecule to the polypeptide. For example, but not by way of limitation, a hBMP6 polypeptide, a fragment of a hBMP6 polypeptide, or a hBMP6 antibody may be chemically modified, e.g. by glycosylation, acetylation, pegylation, phosphorylation, amidation, derivatization by known protecting/blocking groups, proteolytic cleavage, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. A derivative of a hBMP6 polypeptide, a fragment of a hBMP6 polypeptide, or a hBMP6 antibody may be chemically modified by chemical modifications using techniques known to those of skill in the art, including, but not limited to specific chemical cleavage, acetylation, formulation, metabolic synthesis of tunicamycin, etc. Further, a derivative of a hBMP6 polypeptide, a fragment of a hBMP6 polypeptide, or a hBMP6 antibody may contain one or more non-classical amino acids. A polypeptide derivative possesses a similar or identical function as a hBMP6 polypeptide, a fragment of a hBMP6 polypeptide, or a hBMP6 antibody described herein.

The term "effector function" (or "effector-enabled") as used herein refers to one or more of antibody dependant cell mediated cytotoxic activity (ADCC), complement-dependant cytotoxic activity (CDC) mediated responses, Fc-mediated phagocytosis or antibody dependant cellular phagocytosis (ADCP) and antibody recycling via the FcRn receptor.

An "effective amount" refers to an amount effective, at dosages and for periods of time necessary, to achieve the desired effect, including a therapeutic or prophylactic result. A "therapeutically effective amount" refers to the minimum concentration required to effect a measurable improvement or prevention of a particular disorder. A therapeutically effective amount herein may vary according to factors such as the disease state, age, sex, and weight of the patient, and the ability of the antibody to elicit a desired response in the individual. A therapeutically effective amount is also one in which toxic or detrimental effects of the antibody are outweighed by the therapeutically beneficial effects. A "prophylactically effective amount" refers to an amount effective, at the dosages and for periods of time necessary, to achieve the desired prophylactic result. In some embodiments, the effective amount of an antibody of the invention is from about 0.1 mg/kg (mg of antibody per kg weight of the subject) to about 100 mg/kg. In certain embodiments, an effective amount of an antibody provided therein is about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg about 90 mg/kg or about 100 mg/kg (or a range therein). In some embodiments, "effective amount" as used herein also refers to the amount of an antibody of the invention to achieve a specified result (e.g. inhibition of a hBMP6 biological activity of a cell).

The term "epitope" as used herein refers to a localized region on the surface of an antigen, such as hBMP6 polypeptide or hBMP6 polypeptide fragment, that is capable of being bound to one or more antigen binding regions of an antibody, and that has antigenic or immunogenic activity in an animal, preferably a mammal, and most preferably in a human, that is capable of eliciting an immune response. An epitope having immunogenic activity is a portion of a polypeptide that elicits an antibody response in an animal. An epitope having antigenic activity is a portion of a polypeptide to which an antibody specifically binds as determined by any method well known in the art, for example, by the immunoassays described herein. Antigenic epitopes need not necessarily be immunogenic. Epitopes usually consist of chemically active surface groupings of molecules such as amino acids or sugar side chains and have specific three-dimensional structural characteristics as well as specific charge characteristics. A region of a polypeptide contributing to an epitope may be contiguous amino acids of the polypeptide or the epitope may come together from two or more non-contiguous regions of the polypeptide. The epitope may or may not be a three-dimensional surface feature of the antigen. In certain embodiments, a hBMP6 epitope is a three-dimensional surface feature of a hBMP6 polypeptide (e.g. in a trimeric form of a hBMP6 polypeptide). In other embodiments, a hBMP6 epitope is linear feature of a hBMP6 polypeptide (e.g. in a trimeric form or monomeric form of the hBMP6 polypeptide). Antibodies provided herein may specifically bind to an epitope of the monomeric (denatured) form of hBMP6, an epitope of the trimeric (native) form of hBMP6, or both the monomeric (denatured) form and the trimeric (native) form of hBMP6. In specific embodiments, the antibodies provided herein specifically bind to an epitope of the trimeric form of hBMP6 but do not specifically bind the monomeric form of hBMP6.

The term "excipients" as used herein refers to inert substances which are commonly used as a diluent, vehicle, preservatives, binders, or stabilizing agent for drugs and includes, but not limited to, proteins (e.g. serum albumin, etc.), amino acids (e.g. aspartic acid, glutamic acid, lysine, arginine, glycine, histidine, etc.), fatty acids and phospholipids (e.g. alkyl sulfonates, caprylate, etc.), surfactants (e.g. SDS, polysorbate, nonionic surfactant, etc.), saccharides (e.g. sucrose, maltose, trehalose, etc.) and polyols (e.g. mannitol, sorbitol, etc.). See, also, Remington's Pharmaceutical Sciences (1990) Mack Publishing Co., Easton, Pa., which is hereby incorporated by reference in its entirety.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, BMP6 fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a hBMP6 polypeptide or an antibody that specifically binds to a hBMP6 polypeptide. In a specific embodiment, a fragment of a hBMP6 polypeptide or an antibody that specifically binds to a hBMP6 antigen retains at least 1, at least 2, or at least 3 functions of the polypeptide or antibody.

The term "free" can refer to a polypeptide, for example, BMP6 or fragments and variants thereof, that is combined with a buffer, wherein the polypeptide is not associated with a cell surface or cell membrane. As such, the term "free" can refer to a polypeptide that is capable of surface expression (i.e. includes one or more transmembrane domains or membrane association domains), but that is not, in its present state, expressed on the surface of a cell or bound to a protein that is expressed on the surface of a cell. A free polypeptide can also refer to a free recombinant or native or unbound polypeptide. In the context of phage display, a free antigen can be selected in solution (referred to herein as a "soluble selection") or adsorbed to a surface, for example, adsorbed to the surface of a 96-well plate (referred to herein as "biopanning selection").

The term "fusion protein" as used herein refers to a polypeptide that comprises an amino acid sequence of an antibody and an amino acid sequence of a heterologous polypeptide or protein (i.e. a polypeptide or protein not normally a part of the antibody (e.g. a non-anti-BMP6 antigen antibody)). The term "fusion" when used in relation to BMP6 or to an anti-BMP6 antibody refers to the joining of a peptide or polypeptide, or fragment, variant and/or derivative thereof, with a heterologous peptide or polypeptide. Preferably, the fusion protein retains the biological activity of the BMP6 or anti-BMP6 antibody. In certain embodiments, the fusion protein comprises a BMP6 antibody VH domain, VL domain, VH CDR (one, two or three VH CDRs), and/or VL CDR (one, two or three VL CDRs), wherein the fusion protein specifically binds to a BMP6 epitope.

The term "heavy chain" when used with reference to an antibody refers to five distinct types, called alpha ($\alpha$), delta ($\delta$), epsilon ($\epsilon$), gamma ($\gamma$) and mu ($\mu$), based on the amino acid sequence of the heavy chain constant domain. These distinct types of heavy chains are well known and give rise to five classes of antibodies, IgA, IgD, IgE, IgG and IgM, respectively, including four subclasses of IgG, namely IgG1, IgG2, IgG3 and IgG4. Preferably the heavy chain is a human heavy chain. In the human population, multiple heavy chain constant region alleles, of each immunoglobulin or immunoglobulin subclass, exist. The nucleotide and amino acid sequences of these allelic variants are accessible on publicly available databases such as IMGT, ENSEMBL Swiss-Prot and Uniprot. Allelic variants may also be identified in various genome sequencing projects. In one embodiment, the antibodies and antibody fragments disclosed herein comprise a heavy chain encoded by a IgG1 constant region allele, which includes, but is not limited to, human IGHG1*01 (Seq ID Nos:340, 341 & 537), IGHG1*02 (Seq ID Nos:340, 341 &537), IGHG1*03 (Seq ID Nos:523 & 524), IGHG1*04 (Seq ID Nos:525 & 526) and IGHG1*05 (Seq ID Nos:340, 341 & 537). In one embodiment, the antibodies and antibody fragments disclosed herein comprise a protein encoded by a IgG2 constant region allele, which includes, but is not limited to, human IGHG2*01 (Seq ID Nos:527 & 528), IGHG2*02 (Seq ID Nos:529 & 530), IGHG2*03 (Seq ID Nos:527 & 528), IGHG2*04 (Seq ID Nos:531 & 532), IGHG2*05 (Seq ID Nos:527 & 528) and IGHG2*06 (Seq ID Nos:533 & 534). In one embodiment, the antibodies or antibody fragments disclosed herein comprise a protein encoded by a IgG3 constant region allele, which includes but is not limited to human IGHG3*01, IGHG3*02, IGHG3*03, IGHG3*04, IGHG3*05, IGHG3*06, IGHG3*07, IGHG3*08, IGHG3*09, IGHG3*10, IGHG3*11, IGHG3*12, IGHG3*13, IGHG3*14, IGHG3*15, IGHG3*16, IGHG3*17, IGHG3*18 and IGHG3*19. In one embodiment, the antibodies or antibody fragments disclosed herein comprise a protein encoded by a IgG4 constant region allele, which includes but is not limited to human IGHG4*01 (see, eg, the sequence table herein), IGHG4*02 (see, eg, the sequence table herein), IGHG4*03 (see, eg, the sequence table herein) and IGHG4*04 (see, eg, the sequence table herein). In another example, the heavy chain is a disabled IgG isotype, e.g. a disabled IgG4. In certain embodiments, the antibodies of the invention comprise a human gamma 4 constant region. In another embodiment, the heavy chain constant region does not bind Fc-$\gamma$ receptors, and e.g. comprises a Leu235Glu mutation. In another embodiment, the heavy chain constant region comprises a Ser228Pro mutation to increase stability. In another embodiment, the heavy chain constant region is IgG4-PE (see, eg, the sequence table herein). In another embodiment, the antibodies and antibody fragments disclosed herein comprise a heavy chain constant region encoded by a murine IgG1 constant region allele, which includes but is not limited to mouse IGHG1*01 or IGHG1*02. In one embodiment, the antibodies and antibody fragments disclosed herein comprise a heavy chain constant region encoded by a murine IgG2 constant region allele, which includes, but is not limited to, mouse IGHG2A*01, IGHG2A*02, IGHG2B*01, IGHG2B*02, IGHG2C*01, IGHG2C*02 or IGHG2C*03. In one embodiment, the antibodies or antibody fragments disclosed herein comprise a protein encoded by a murine IgG3 constant region allele, which includes but is not limited to mouse IGHG3*01.

The term "host" as used herein refers to an animal, preferably a mammal, and most preferably a human.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "in combination" in the context of the administration of other therapies refers to the use of more than one therapy. The use of the term "in combination" does not restrict the order in which therapies are administered to a subject with a disease. A first therapy can be administered before (e.g. 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g. 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject which had, has, or is susceptible to a BMP6-mediated disease. Any additional therapy can be administered in any order with the other additional therapies. In certain embodiments, the antibodies of the invention can be administered in combination with one or more therapies (e.g. therapies that are not the antibodies of the invention that are currently administered to prevent, treat, manage, and/or ameliorate a BMP6-mediated disease. Non-limiting examples of therapies that can be administered in combination with an antibody of the invention include analgesic agents, anaesthetic agents, antibiotics, or immunomodulatory agents or any other agent listed in the U.S. Pharmacopoeia and/or Physician's Desk Reference.

As used herein, "injection device" refers to a device that is designed for carrying out injections, an injection including the steps of temporarily fluidically coupling the injection device to a person's tissue, typically the subcutaneous tissue. An injection further includes administering an amount of liquid drug into the tissue and decoupling or removing the injection device from the tissue. In some embodiments, an injection device can be an intravenous device or IV device, which is a type of injection device used when the target tissue is the blood within the circulatory system, e.g. the blood in a vein. A common, but non-limiting example of an injection device is a needle and syringe.

As used herein, "instructions" refers to a display of written, printed or graphic matter on the immediate con-tainer of an article, for example the written material displayed on a vial containing a pharmaceutically active agent, or details on the composition and use of a product of interest included in a kit containing a composition of interest. Instructions set forth the method of the treatment as contemplated to be administered or performed.

An "isolated" or "purified" antibody or protein is one that has been identified, separated and/or recovered from a component of its production environment (e.g. natural or recombinant). For example, the antibody or protein is substantially free of cellular material or other contaminating proteins from the cell or tissue source from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). When the antibody is recombinantly produced, it is also preferably substantially free of culture medium, i.e. culture medium represents less than about 20%, 10%, or 5% of the volume of the protein preparation. When the antibody is produced by chemical synthesis, it is preferably substantially free of chemical precursors or other chemicals, i.e., it is separated from chemical precursors or other chemicals which are involved in the synthesis of the protein. Accordingly, such preparations of the antibody have less than about 30%, 20%, 10%, 5% (by dry weight) of chemical precursors or compounds other than the antibody of interest. In a preferred embodiment, antibodies of the invention are isolated or purified.

The terms "Kabat numbering," and like terms are recognized in the art and refer to a system of numbering amino acid residues which are more variable (i.e. hypervariable) than other amino acid residues in the heavy chain variable regions of an antibody, or an antigen binding portion thereof (Kabat et al., (1971) Ann. NY Acad. Sci., 190:382-391 and, Kabat et al. (1991) Sequences of Proteins of Immunological Interest, Fifth Edition, U.S. Department of Health and Human Services, NIH Publication No. 91-3242). For the heavy chain variable region, the hypervariable region typically ranges from amino acid positions 31 to 35 for CDR1, amino acid positions 50 to 65 for CDR2, and amino acid positions 95 to 102 for CDR3.

"Label" or "labelled" as used herein refers to the addition of a detectable moiety to a polypeptide, for example, a radiolabel, fluorescent label, enzymatic label, chemiluminescent label or a biotinyl group or gold. Radioisotopes or radionuclides may include $^3$H, $^{14}$C, $^{15}$N, $^{35}$S, $^{90}$Y, $^{99}$Tc, $^{115}$In, $^{125}$1$^{31}$1, fluorescent labels may include rhodamine, lanthanide phosphors or FITC and enzymatic labels may include horseradish peroxidase, p3-galactosidase, luciferase, alkaline phosphatase. Additional labels include, by way of illustration and not limitation: enzymes, such as glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase; dyes (e.g. cyanine dyes, e.g. Cy5™, Cy5.5™. or Cy7™); additional fluorescent labels or fluorescers include, such as fluorescein and its derivatives, fluorochrome, GFP (GFP for "Green Fluorescent Protein"), other fluorescent proteins (e.g. mCherry, mTomato), dansyl, umbelliferone, phycoerythrin, phycocyanin, allophycocyanin, o-phthaldehyde, and fiuorescamine; fluorophores such as lanthanide cryptates and chelates e.g. Europium etc (Perkin Elmer and Cisbio Assays); chemoluminescent labels or chemiluminescers, such as isoluminol, luminol and the dioxetanes; sensitisers; coenzymes; enzyme substrates; particles, such as latex or carbon particles; metal sol; crystallite; liposomes; cells, etc., which may be further labelled with a dye, catalyst or other detectable group; molecules such as biotin, digoxygenin or 5-bromodeoxyuridine; toxin moieties, such as for example a toxin moiety selected from a group of *Pseudomonas* exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

The term "light chain" when used in reference to an antibody refers to the immunoglobulin light chains, of which there are two types in mammals, lambda (λ) and kappa (κ). Preferably, the light chain is a human light chain. Preferably the light chain constant region is a human constant region. In the human population, multiple light chain constant region alleles exist. The nucleotide and amino acid sequences of these allelic variants are accessible on publicly available databases such as IMGT, ENSEMBL, Swiss-Prot and Uniprot. In one embodiment, the antibodies or antibody fragments disclosed herein comprise a protein encoded by a human λ constant region allele, which includes, but is not limited to, IGKC*01 (see, eg, the sequence table herein), IGKC*02 (see, eg, the sequence table herein), IGKC*03 (see, eg, the sequence table herein), IGKC*04 (see, eg, the sequence table herein) and IGKC*05 (see, eg, the sequence table herein). In one embodiment, the antibodies or antibody fragments disclosed herein comprise a protein encoded by a human A constant region allele, which includes but is not limited to IGLC1*01 (see, eg, the sequence table herein), IGLC1*02 (see, eg, the sequence table herein), IGLC2*01 (see, eg, the sequence table herein), IGLC2*02 (see, eg, the sequence table herein), IGLC2*03 (see, eg, the sequence table herein), IGLC3*01 (see, eg, the sequence table herein), IGLC3*02 (see, eg, the sequence table herein), IGLC3*03 (see, eg, the sequence table herein), IGLC3*04 (see, eg, the sequence table herein), IGLC6*01 (see, eg, the sequence table herein), IGLC7*01 (see, eg, the sequence table herein), IGLC7*02 (see, eg, the sequence table herein), IGLC7*03 (see, eg, the sequence table herein). In another embodiment, the antibodies and antibody fragments disclosed herein comprise a light chain constant region encoded by a mouse K constant region allele, which includes, but is not limited to, IGKC*01, IGKC*03 or IGKC*03. In another embodiment, the antibodies and antibody fragments disclosed herein comprise a light chain constant region encoded by a mouse A constant region allele, which includes, but is not limited to, IGLC1*01, IGLC2*01 or IGLC3*01.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEG ALIGN™ (DNASTAR) software. In one embodiment, the % homology is about 70%. In one embodiment, the % homology is about 75%. In one embodiment, the % homology is about 80%. In one embodiment, the % homology is about 85%. In one embodiment, the % homology is about 90%. In one embodiment, the % homology is about 92%. In one embodiment, the % homology is about 95%. In one embodiment, the % homology is about 97%. In one embodiment, the % homology is about 98%. In one embodiment, the % homology is about 99%. In one embodiment, the % homology is 100%.

The term "naturally occurring" or "native" when used in connection with biological materials such as nucleic acid molecules, polypeptides, host cells, and the like, refers to those which are found in nature and not manipulated by a human being.

As used herein, "packaging" refers to how the components are organized and/or restrained into a unit fit for distribution and/or use. Packaging can include, e.g. boxes, bags, syringes, ampoules, vials, tubes, clamshell packaging, barriers and/or containers to maintain sterility, labelling, etc.

The term "pharmaceutically acceptable" as used herein means being approved by a regulatory agency of the Federal or a state government, or listed in the U.S. Pharmacopeia, European Pharmacopeia or other generally recognized Pharmacopeia for use in animals, and more particularly in humans.

As used herein, the term "polynucleotide," "nucleotide," nucleic acid" "nucleic acid molecule" and other similar terms are used interchangeable and include DNA, RNA, mRNA and the like.

As used herein, the terms "prevent", "preventing", and "prevention" refer to the total or partial inhibition of the development, recurrence, onset or spread of a hBMP6-mediated disease and/or symptom related thereto, resulting from the administration of a therapy or combination of therapies provided herein (e.g. a combination of prophylactic or therapeutic agents, such as an antibody of the invention).

The term "soluble" refers to a polypeptide, such as BMP6 and variants or fragments thereof, that is lacking one or more transmembrane or cytoplasmic domains found in the native or membrane-associated form. In one embodiment, the "soluble" form of BMP6 lacks both the transmembrane domain and the cytoplasmic domain.

The term "subject" or "patient" refers to any animal, including, but not limited to, mammals. As used herein, the term "mammal" refers to any vertebrate animal that suckle their young and either give birth to living young (eutharian or placental mammals) or are egg-laying (metatharian or nonplacental mammals). Examples of mammalian species include, but are not limited to, humans and other primates, including non-human primates such as chimpanzees and other apes and monkey species; farm animals such as cattle, sheep, pigs, goats and horses; domestic mammals such as dogs and cats; laboratory animals including rodents such as mice, rats (including cotton rats) and guinea pigs; birds, including domestic, wild and game birds such as chickens, turkeys and other gallinaceous birds, ducks, geese, and the like.

As used herein "substantially all" refers to refers to at least about 60%, at least about 70%, at least about 75%, at least about 80%, at least about 85%, at least about 90%, at least about 95%, at least about 98%, at least about 99%, or about 100%.

As used herein, the term "therapeutic agent" refers to any agent that can be used in the treatment, management or amelioration of a BMP6-mediated disease and/or a symptom related thereto. In certain embodiments, the term "therapeutic agent" refers to an antibody of the invention. In certain other embodiments, the term "therapeutic agent" refers to an agent other than an antibody of the invention. Preferably, a therapeutic agent is an agent which is known to be useful for, or has been or is currently being used for the treatment, management or amelioration of a BMP6-mediated disease or one or more symptoms related thereto. In specific embodiments, the therapeutic agent is a fully human anti-BMP6 antibody, such as a fully human anti-BMP6 monoclonal antibody.

As used herein, the term "therapy" refers to any protocol, method and/or agent that can be used in the prevention, management, treatment and/or amelioration of a BMP6-mediated disease (e.g. cancer). In certain embodiments, the terms "therapies" and "therapy" refer to a biological therapy, supportive therapy, and/or other therapies useful in the prevention, management, treatment and/or amelioration of a BMP6-mediated disease known to one of skill in the art such as medical personnel.

The terms "treat", "treatment" and "treating" refer to the reduction or amelioration of the progression, severity, and/or duration of a hBMP6-mediated disease (e.g. cancer) resulting from the administration of one or more therapies (including, but not limited to, the administration of one or more prophylactic or therapeutic agents, such as an antibody of the invention). In specific embodiments, such terms refer to the reduction or inhibition of the binding of hBMP6 to a BMP receptor or HJV, and/or the inhibition or reduction of one or more symptoms associated with a BMP6-mediated disease, such as anaemia.

The term "variable region" or "variable domain" refers to a portion of the light and heavy chains, typically about the amino-terminal 120 to 130 amino acids in the heavy chain and about 100 to 110 amino acids in the light chain, which differ extensively in sequence among antibodies and are used in the binding and specificity of each particular antibody for its particular antigen. The variability in sequence is concentrated in those regions called complimentarily determining regions (CDRs) while the more highly conserved regions in the variable domain are called framework regions (FR). The CDRs of the BMP6 and heavy chains are primarily responsible for the interaction of the antibody with antigen. Numbering of amino acid positions used herein is according to the EU Index, as in Kabat et al. (1991) Sequences of proteins of immunological interest. (U.S. Department of Health and Human Services, Washington, D.C.) 5$^{th}$ ed. ("Kabat et al."). In preferred embodiments, the variable region is a human variable region.

Definitions of common terms in cell biology and molecular biology can be found in "The Merck Manual of Diagnosis and Therapy", 19$^{th}$ Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (Eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et al., ed., John Wiley and Sons, Inc.), Current Protocols in Cell Biology (CPCB) (Juan S. Bonifacino et al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

BMP6 & Iron

Since iron is fundamental to all forms of life and has to be sourced from the environment, the availability and usage in the body is tightly controlled. A key regulator of iron homeostasis is a 25 amino acid peptide hormone called hepcidin. Hepcidin is produced by the liver and causes the main iron uptake and storage compartments, the duodenal enterocytes and macrophages, to retain iron by means of controlling expression of the iron transporter molecule ferroportin. Hepcidin itself is regulated by iron levels through a homeostatic control mechanism, following activation of the immune system during infection and/or inflammation as well as by erythropoiesis. Importantly, hepcidin levels are elevated in chronic inflammatory situations, infections and also certain cancers. Elevated hepcidin levels sequester iron in enterocytes, macrophages and hepatocytes thereby suppressing haemoglobin synthesis and erythropoiesis. This leads to anaemia despite the fact that iron storage levels are normal. Hepcidin gene expression is controlled by a soluble factor called BMP6 (bone morphogenetic protein 6). BMP6 is considered the master regulator, since in the absence of BMP6, cytokines alone (or other BMPs) are not able to overcome the deficit of a BMP6 signal. The inventors thus focused on BMP6 is a key drug target for controlling aberrant dysregulation of iron homeostasis in anaemia, eg, in anaemia of chronic disease (ACD).

BMP6 is a highly conserved soluble protein factor that is considered the "master" regulator of hepcidin production in mice and humans. Hence, administration of BMP6 to mice increases hepcidin levels and decreases blood and serum iron, while inhibitors of BMP6 do the opposite. In addition, knock-out of the mouse BMP6 gene or human mutations within the BMP6 pathway support a central role for BMP6 in controlling hepcidin and blood and serum iron levels. Furthermore, pre-clinical and clinical validation for targeting BMP6 comes from increasing available iron levels by administering an anti-BMP6 antibody to rodents or cynomolgus monkeys or BMP6 neutralization using HJV-Fc (FMX-8, Ferrumax Inc) in a Phase I study, respectively. Reference is made to Andriopoulos Jr. B, Corradini E, Xia Y, Faasse S A, Chen S, Grgurevic L, Knutson M D, Pietrangelo A, Vukicevic S, Lin HY and Babitt. 2009. BMP-6 is a key endogenous regulator of hepcidin expression and iron metabolism. Nat. Genet. 41(4), 482-487; WO2016098079 and U.S. Pat. No. 8,980,582.

Anti-BMP6 Antibodies & Fragments

The invention provides various anti-BMP6 antibodies and fragments (such as Fab or scFv fragments), uses, methods and combinations (eg, with ESA). Examples are set out in the following numbered Clauses.

1. An antibody or fragment comprising a binding site which specifically binds to Bone Morphogenetic Protein 6 (BMP6), wherein the binding site comprises a VH domain that is encoded by a nucleotide sequence that is derived from the recombination of a human VH gene segment, DH gene segment and JH gene segment, wherein the VH gene segment is selected from IGHV3-11 and IGHV1-3.

For example, the VH gene segment is IGHV3-11 and the DH gene segment and JH gene segments are human gene segments. For example, the VH gene segment is IGHV1-3 and the DH gene segment and JH gene segments are human gene segments. Optionally, the VH segment is a human IGHV3-11*01 gene segment. Alternatively, optionally the VH segment is a human IGHV1-3*01 gene segment.

In an example, specific binding is with a KD, $K_{off}$ and/or $K_{on}$ as described further below. In an example, specific binding is with a KD from 1 pM to 5 nM.

The skilled person is familiar with databases and other sources for human and other species of antibody gene segments. For example, the IMGT database (world wide web.IMGT.org) is a suitable source, eg, the version as at 1 Sep. 2018.

Reference is made to Tables 7 and 8, showing antibodies that are based on IGHV1-3. Surprisingly, this human VH gene segment produces anti-BMP6 antibodies which have desirable anti-BMP6 properties, such as those described in, eg, in the Examples.

Reference is made to Table 9, showing antibodies that are based on IGHV3-11. Surprisingly, this human VH gene segment produces anti-BMP6 antibodies which have desirable anti-BMP6 properties, such as those described in, eg, in the Examples. Thus, for example, the antibody or fragment comprises a CDRH3 sequence selected from SEQ ID NO: 110, 113, 290, 293, 308, 311, 272 and 275. For example, the antibody or fragment comprises a CDRL3 sequence selected from SEQ ID NO: 119, 122, 299, 302, 317, 320, 281 and 284. For example, the antibody or fragment comprises a CDRH3 sequence selected from SEQ ID NO: 110, 113, 290, 293, 308, 311, 272 and 275 and respectively a CDRL3 sequence selected from SEQ ID NO: 119, 122, 299, 302, 317, 320, 281 and 284.

For example, the antibody or fragment comprises a CDRH3 sequence selected from SEQ ID NO: 110 and 113; and a CDRL3 sequence selected from SEQ ID NO: 119 and 122. For example, the antibody or fragment comprises an anti-BMP6 binding site, wherein the binding site comprises a VH domain comprising SEQ ID NO: 110 paired with a VL domain comprising SEQ ID NO: 119. For example, the antibody or fragment comprises an anti-BMP6 binding site, wherein the binding site comprises a VH domain comprising SEQ ID NO: 113 paired with a VL domain comprising SEQ ID NO: 122.

For example, the antibody or fragment comprises a CDRH3 sequence of an antibody selected from CL-58838, CL-58835, CL-58756 and CL-58722 and optionally a CDRL3 of said selected antibody. For example, the antibody or fragment comprises a CDRH1 and CDRH3 sequence of an antibody selected from CL-58838, CL-58835, CL-58756 and CL-58722 and optionally a CDRL2 of said selected antibody. For example, the antibody or fragment comprises a CDRH1 and CDRH2 sequence of an antibody selected from CL-58838, CL-58835, CL-58756 and CL-58722. For example, the antibody or fragment comprises a CDRH2 and CDRH3 sequence of an antibody selected from CL-58838, CL-58835, CL-58756 and CL-58722. For example, the antibody or fragment comprises an anti-BMP6 binding site, wherein the binding site comprises a VH domain comprising the CDRH3 sequence of CL-58838 paired with a VL domain of CL-58838.

For example, the antibody or fragment comprises an anti-BMP6 binding site, wherein the binding site comprises a VH domain comprising SEQ ID NO: 114, 294, 312 or 276 optionally paired with a VL domain comprising respectively SEQ ID NO: 123, 303, 321 or 285. For example, the antibody or fragment comprises an anti-BMP6 binding site, wherein the binding site comprises a VH domain comprising SEQ ID NO: 114 paired with a VL domain comprising SEQ ID NO: 123.

For example, the antibody or fragment comprises an anti-BMP6 binding site, wherein the binding site comprises a VH domain of an antibody selected from CL-58838, CL-58835, CL-58756 and CL-58722, optionally paired with a VL domain of the selected antibody. For example, the antibody or fragment comprises an anti-BMP6 binding site, wherein the binding site comprises a VH domain of CL-58838 paired with a VL domain of CL-58838.

2. The antibody or fragment according to Clause 1, wherein the DH gene segment is a human gene segment selected from IGHD3-10, IGHD6-19, IGHD7-27, IGHD4-23, IGHD5-18, IGHD3-22 and IGHD3-16.

Optionally, the DH gene segment is selected from IGHD3-10*01, IGHD6-19*01, IGHD7-27*02, IGHD4-23*01, IGHD5-18*01, IGHD3-22*01 and IGHD3-16*02.

3. The antibody or fragment according to Clause 1 or 2, wherein the JH gene segment is a human gene segment selected from IGHJ3, IGHJ4 and IGHJ5.

Optionally, the JH gene segment is selected from IGHJ3*02, IGHJ4*02 and IGHJ5*02.

4. An antibody or fragment which specifically binds to Bone Morphogenetic Protein 6 (BMP6) and comprises the CDRH3 sequence of an anti-BMP6 antibody according to any preceding Clause.

5. An antibody or fragment which specifically binds to Bone Morphogenetic Protein 6 (BMP6) and comprises a VH domain which comprises the CDRH3 sequence of any anti-BMP6 antibody disclosed herein (eg, any antibody selected from an antibody or fragment listed in any of Tables 4 to 11 herein), or said CDRH3 sequence comprising 3, 2 or 1 amino acid substitution(s).

6. An antibody or fragment (optionally according to any preceding Clause) which specifically binds to Bone Morphogenetic Protein 6 (BMP6) and comprises a VH domain which comprises a CDRH3 sequence of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or said sequence comprising 3, 2 or 1 amino acid substitution(s).

Optionally, the VH domain comprises a CDRH3 sequence selected from SEQ ID NO: 110 or 113, or said selected sequence comprising 3, 2 or 1 amino acid substitution(s).

7. The antibody or fragment according to Clause 6, wherein the VH domain comprises (i) a CDRH3 sequence of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or said CDRH3 sequence comprising 3, 2 or 1 amino acid substitution(s); and (ii) a CDRH1 sequence of said selected antibody; or said CDRH1 sequence comprising 3, 2 or 1 amino acid substitution(s).

Optionally, the VH domain of the antibody or fragment comprises (a) the CDRH3 sequence of SEQ ID NO: 110 or 113; or said CDRH3 sequence comprising 3, 2 or 1 amino acid substitution(s); and (b) the CDRH1 sequence of SEQ ID NO: 108 or 111, or said CDRH1 sequence comprising 3, 2 or 1 amino acid substitution(s).

8. The antibody or fragment according to Clause 6 or 7, wherein the VH domain comprises (iii) a CDRH3 sequence of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or said CDRH3 sequence comprising 3, 2 or 1 amino acid substitution(s); and (iv) a CDRH2 sequence of said selected antibody; or said CDRH2 sequence comprising 3, 2 or 1 amino acid substitution(s).

Optionally, the VH domain of the antibody or fragment comprises (c) the CDRH3 sequence of SEQ ID NO: 110 or 113; or said CDRH3 sequence comprising 3, 2 or 1 amino acid substitution(s); and (d) the CDRH2 sequence of SEQ ID NO: 109 or 112, or said CDRH2 sequence comprising 3, 2 or 1 amino acid substitution(s).

Optionally, the VH domain of the antibody or fragment comprises (e) the CDRH3 sequence of SEQ ID NO: 110 or 113; or said CDRH3 sequence comprising 3, 2 or 1 amino acid substitution(s); (f) the CDRH1 sequence of SEQ ID NO: 108 or 111, or said CDRH1 sequence comprising 3, 2 or 1 amino acid substitution(s); and (g) the CDRH2 sequence of SEQ ID NO: 109 or 112, or said CDRH2 sequence comprising 3, 2 or 1 amino acid substitution(s).

9. An antibody or fragment (optionally according to any preceding Clause) comprising a binding site which specifically binds to Bone Morphogenetic Protein 6 (BMP6), wherein the binding site comprises a VH domain that comprises the amino acid sequence of a VH domain of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or an amino acid that is at least 70, 80, 85, 90, 95, 96, 97, 98 or 99% identical thereto.

For example, the identity is at least 85%. For example, the identity is at least 90%. For example, the identity is at least 95%.

Optionally the VH domain of the antibody or fragment of comprises the amino acid sequence of SEQ ID NO: 114, or a heavy chain variable domain amino acid sequence that is at least 70, 80, 85, 90, 95, 96, 97, 98 or 99% identical to SEQ ID NO: 114. For example, the identity is at least 85%. For example, the identity is at least 90%. For example, the identity is at least 95%.

10. The antibody or fragment according to any preceding Clause comprising first and second copies of said VH domain.

In an example, the antibody or fragment comprises a binding site comprising a VH domain of the invention paired with a VL domain of the invention, wherein the binding site is capable of specifically binding to BMP6 (eg, mature BMP6, eg human and/or cynomolgus monkey BMP6). For example, the antibody or fragment comprise two of such binding sites.

11. An antibody or fragment (optionally according to any preceding Clause) comprising a binding site which specifically binds to Bone Morphogenetic Protein 6 (BMP6), wherein the binding site comprises a VL domain that is encoded by a nucleotide sequence that is derived from the recombination of a human VL gene segment and JL gene segment, wherein the VL gene segment is selected from IGKV3-20, IGKV1-5 and IGKV3-15.

For example, the VL gene segment is IGKV3-20, eg, IGKV3-20*01. For example, the VL gene segment is IGKV1-5, eg, IGKV1-5 *03. For example, the VL gene segment is IGKV3-15, eg, IGKV3-15*01.

12. The antibody or fragment according to Clause 11, wherein the VL is a VK and the JL gene segment is a human gene segment selected from IGKJ1 and IGKJ3.

Optionally, the JL gene segment is selected from IGKJ1*01 and IGKJ3*01.

13. An antibody or fragment which specifically binds to Bone Morphogenetic Protein 6 (BMP6) and comprises the CDRL3 sequence of an anti-BMP6 antibody according to Clause 11 or 12.

14. An antibody or fragment (optionally according to any preceding Clause) which specifically binds to Bone Morphogenetic Protein 6 (BMP6) and comprises a VL domain which comprises the CDRL3 sequence of any anti-BMP6 antibody disclosed herein (eg, any antibody selected from an antibody or fragment listed in any of Tables 4 to 11 herein) or said selected CDRL3 sequence comprising 3, 2 or 1 amino acid substitution(s).

15. The antibody or fragment of Clause 14, comprising a VH domain which comprises the CDRH3 sequence of said selected antibody.

16. An antibody or fragment (optionally according to any preceding Clause) which specifically binds to Bone Morphogenetic Protein 6 (BMP6) and comprises a VL domain which comprises a CDRL3 sequence selected from SEQ ID NO: 119 or 122, or said selected CDRL3 sequence comprising 3, 2 or 1 amino acid substitution(s).

17. An antibody or fragment (optionally according to any preceding Clause) which specifically binds to Bone Morphogenetic Protein 6 (BMP6) and comprises a VL domain which comprises a CDRL3 (and optionally a CDRH3) sequence of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or said sequence(s) each comprising 3, 2 or 1 amino acid substitution(s).

Optionally, the VL domain comprises a CDRL3 sequence selected from SEQ ID NO: 119 or 122, or said selected sequence comprising 3, 2 or 1 amino acid substitution(s) and/or optionally, the VH domain comprises a CDRH3 sequence selected from SEQ ID NO: 119 or 122, or said selected sequence comprising 3, 2 or 1 amino acid substitution(s).

18. The antibody or fragment according to Clause 17, wherein the VL domain comprises (i) a CDRL3 sequence (and optionally a CDRH3) of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or said CDR3 sequence(s) each comprising 3, 2 or 1 amino acid substitution(s); and (ii) a CDRL1 (and optionally a CDRH1) sequence of said selected antibody; or said CDR1 sequence(s) each comprising 3, 2 or 1 amino acid substitution(s).

Optionally, the VL domain of the antibody or fragment comprises (a) the CDRL3 sequence of SEQ ID NO: 119 or 122; or said CDRL3 sequence comprising 3, 2 or 1 amino acid substitution(s); and (b) the CDRL1 sequence of SEQ ID NO: 117 or 120, or said CDRL1 sequence comprising 3, 2 or 1 amino acid substitution(s).

19. The antibody or fragment according to Clause 17 or 18, wherein the VL domain comprises (iii) a CDRL3 (and optionally a CDRH3) sequence of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or said CDR3 sequence(s) each comprising 3, 2 or 1 amino acid substitution(s); and (iv) a CDRL2 (and optionally a CDRH2) sequence of said selected antibody; or said CDR2 sequence(s) each comprising 3, 2 or 1 amino acid substitution(s).

Optionally, the VL domain of the antibody or fragment comprises (c) the CDRL3 sequence of SEQ ID NO: 119 or 122; or said CDRL3 sequence comprising 3, 2 or 1 amino acid substitution(s); and (d) the CDRL2 sequence of SEQ ID NO: 118 or 121, or said CDRL2 sequence comprising 3, 2 or 1 amino acid substitution(s).

Optionally, the VL domain of the antibody or fragment comprises (e) the CDRL3 sequence of SEQ ID NO: 119 or 122; or said CDRL3 sequence comprising 3, 2 or 1 amino acid substitution(s); (f) the CDRL1 sequence of SEQ ID NO: 117 or 120, or said CDRL1 sequence comprising 3, 2 or 1 amino acid substitution(s); and (g) the CDRL2 sequence of SEQ ID NO: 118 or 121, or said CDRL2 sequence comprising 3, 2 or 1 amino acid substitution(s).

20. An antibody or fragment (optionally according to any preceding Clause) comprising a binding site which specifically binds to Bone Morphogenetic Protein 6 (BMP6), wherein the binding site comprises a VL domain that comprises the amino acid sequence of a VL domain of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or an amino acid that is at least 70, 80, 85, 90, 95, 96, 97, 98 or 99% identical thereto.

For example, the identity is at least 85%. For example, the identity is at least 90%. For example, the identity is at least 95%.

Optionally the VL domain of the antibody or fragment comprises the amino acid sequence of SEQ ID NO: 123, or a heavy chain variable domain amino acid sequence that is at least 70, 80, 85, 90, 95, 96, 97, 98 or 99% identical to SEQ ID NO: 123. For example, the identity is at least 85%. For example, the identity is at least 90%. For example, the identity is at least 95%.

21. The antibody or fragment according to any preceding Clause comprising first and second copies of said VL domain.

In an example, the antibody or fragment comprises a binding site comprising a VL domain of the invention paired with a VH domain, wherein the binding site is capable of specifically binding to BMP6 (eg, mature BMP6, eg human and/or cynomolgus monkey BMP6). For example, the antibody or fragment comprise two of such binding sites.

22. An antibody or fragment (optionally according to any preceding Clause) which specifically binds to Bone Morphogenetic Protein 6 (BMP6) and comprises the heavy chain amino acid sequence of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or an amino acid that is at least 70, 80, 85, 90, 95, 96, 97, 98 or 99% identical thereto.

For example, the identity is at least 85%. For example, the identity is at least 90%. For example, the identity is at least 95%.

23. An antibody or fragment (optionally according to any preceding Clause) which specifically binds to Bone Morphogenetic Protein 6 (BMP6) and comprises the light chain amino acid sequence of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or an amino acid that is at least 70, 80, 85, 90, 95, 96, 97, 98 or 99% identical thereto.

For example, the identity is at least 85%. For example, the identity is at least 90%. For example, the identity is at least 95%.

24. The antibody or fragment of Clause 23, comprising the light chain amino acid sequence of said selected antibody; or an amino acid that is at least 70, 80, 85, 90, 95, 96, 97, 98 or 99% identical thereto.

For example, the identity is at least 85%. For example, the identity is at least 90%. For example, the identity is at least 95%.

25. An antibody or fragment (optionally according to any preceding Clause) which specifically binds to a human BMP6 epitope that is identical to an epitope to which the antibody of any preceding Clause binds.

26. The antibody or fragment according to Clause 25, wherein the epitope is identified by unrelated amino acid scanning, or by X-ray crystallography.

Contact amino acid residues involved in the interaction of antibody and antigen may be determined by various known methods to those skilled in the art.

In one embodiment, sequential replacement of the amino acids of the antigen sequence (using standard molecular biology techniques to mutate the DNA of the coding sequence of the antigen), in this case BMP6 with Alanine (a.k.a Alanine scan), or another unrelated amino acid, may provide residues whose mutation would reduce or ablate the ability of the antibody to recognise the antigen in question. Binding may be assessed using standard techniques, such as, but not limited to, SPR, HTRF, ELISA (which are described elsewhere herein). Other substitutions could be made to enhance the disruption of binding such as changing the charge on the side chain of antigen sequence amino acids (e.g. Lysine change to glutamic acid), switching polar and non-polar residues (e.g. Serine change to leucine). The alanine scan or other amino substitution method may be carried out either with recombinant soluble antigen, or where the target is a cell membrane target, directly on cells using transient or stable expression of the mutated versions.

In one embodiment, protein crystallography may be used to determine contact residues between antibody and antigen (i.e. to determine the epitope to which the antibody binds), crystallography allows the direct visualisation of contact residues involved in the antibody-antigen interaction. As well as standard X-ray crystallography, cryo-electro microscopy has been used to determine contact residues between antibodies and HIV capsid protein (see Lee, Jeong Hyun, et al. "Antibodies to a conformational epitope on gp41 neutralize HIV-1 by destabilizing the Env spike.", Nature communications, 6, (2015)).

In one embodiment, if the antibody recognises a linear epitope, short peptides based on the antigen sequence can be produced and binding of the antibody to these peptides can be assessed using standard techniques, such as, but not limited to, SPR, HTRF, ELISA (which are described elsewhere herein). Further investigation of the epitope could be provided by performing an Alanine scan on any peptides that show binding. Alternative to linear peptides, conformational scans could be carried out using Pepscan technology (world wide web.pepscan.com) using their chemical linkage of peptides onto scaffolds, which has been used to determine discontinuous epitopes on CD20 targeting antibodies (Niederfellner, Gerhard, et al. "Epitope characterization and crystal structure of GA101 provide insights into the molecular basis for type I/II distinction of CD20 antibodies.", Blood, 118.2, (2011), 358-367).

In one embodiment, limited proteolytic digestion and mass spectrophotometry can be used to identify binding epitopes. The antibody-antigen complex is digested by a protease, such as, but not limited to, trypsin. The digested complex peptides are compared to antibody-alone and antigen-alone digestion mass spectrophotometry to determine if a particular epitope is protected by the complexation. Further work involving amino acid substitution, competition binding, may then be employed to narrow down to individual amino acid residues involved in the interaction (see, for example, Suckau, Detlev, et al. "Molecular epitope identification by limited proteolysis of an immobilized antigen-antibody complex and mass spectrometric peptide mapping.", Proceedings of the National Academy of Sciences, 87.24, (1990), 9848-9852).

Thus, in one embodiment, the contact residues of the epitope are identified with an unrelated amino acid scan (e.g. alanine scan). In another embodiment, an unrelated amino acid scan (e.g. alanine scan) is carried out using a technique selected from SPR, HTRF, ELISA, X-ray crystallography, cryo-electro microscopy and a combination of limited proteolytic digestion and mass spectrometry. In one embodiment, the unrelated amino acid scan (e.g. alanine scan) is carried out using HTRF. In one embodiment, the unrelated amino acid scan (e.g. alanine scan) is carried out using ELISA.

When the alanine scan is carried out with either ELISA or HTRF, an amino acid residue is identified as contributing to the epitope if the reduction in signal is at least 25%. In one embodiment, the reduction in signal is at least 30%. In one embodiment, the reduction in signal is at least 35%. In one embodiment, the reduction in signal is at least 40%. In one embodiment, the reduction in signal is at least 45%. In one embodiment, the reduction in signal is at least 50%. In one embodiment, the reduction in signal is at least 55%. In one embodiment, the reduction in signal is at least 60%. In one embodiment, the reduction in signal is at least 70%. In one embodiment, the reduction in signal is at least 75%. In one embodiment, the reduction in signal is at least 80%. In one embodiment, the reduction in signal is at least 85%. In one embodiment, the reduction in signal is at least 90%.

When the alanine scan is carried out with SPR, an amino acid residue is identified as contributing to the epitope if there is at least a 10-fold reduction in affinity. In one embodiment, the reduction in affinity is at least 15-fold. In one embodiment, the reduction in affinity is at least 20-fold. In one embodiment, the reduction in affinity is at least 30-fold. In one embodiment, the reduction in affinity is at least 40-fold. In one embodiment, the reduction in affinity is at least 50-fold. In one embodiment, the reduction in affinity is at least 100-fold.

In one embodiment, the contact residues of the epitope are identified by X-ray crystallography. In one embodiment, the contact residues of the epitope are identified by cryo-electro microscopy. In one embodiment, the contact residues of the epitope are identified by a combination of limited proteolytic digestion and mass spectrometry.

27. The antibody or fragment according to Clause 26, wherein the contact residues of the epitope are defined by a reduction in affinity of at least 10-fold in an unrelated amino acid scan, e.g. an alanine scan as determined by SPR.

In one embodiment, the reduction in affinity is at least 15-fold. In one embodiment, the reduction in affinity is at least 20-fold. In one embodiment, the reduction in affinity is at least 30-fold. In one embodiment, the reduction in affinity is at least 40-fold. In one embodiment, the reduction in affinity is at least 50-fold. In one embodiment, the reduction in affinity is at least 100-fold. SPR may be carried out as described herein.

28. An antibody or fragment (optionally according to any preceding Clause) which competes for binding to human BMP6 with the antibody of any preceding Clause.

Optionally, competition is determined by surface plasmon resonance (SPR) or ELISA. The skilled person will be familiar with these techniques and standard conditions, for example.

In one embodiment, the antibody or fragment competes (e.g. in a dose-dependent manner) with hBMP6 (or a fusion protein thereof) for binding to cell surface-expressed hBMP6. In one embodiment, the antibody or fragment competes (e.g. in a dose-dependent manner) with hBMP6 (or a fusion protein thereof) for binding to soluble hBMP6.

Optionally, the competition for binding to hBMP6 is conducted using SPR. SPR may be carried out as described herein.

29. The antibody or fragment according to any preceding Clause which specifically binds to human BMP6 comprising SEQ ID NO: 562; and/or a cynomolgus BMP6 comprising SEQ ID NO: 564; and/or a rat BMP6 comprising SEQ ID NO: 563.

Optionally, the antibody or fragment of the invention specifically binds to the amino acid sequence of SEQ ID NO: 562. Optionally, the antibody or fragment of the invention specifically binds to the amino acid sequence of SEQ ID NO: 563. Optionally, the antibody or fragment of the invention specifically binds to the amino acid sequence of SEQ ID NO: 564.

In an example, BMP6 herein is a human, mouse or cynomolgus monkey BMP6.

In one embodiment, the antibody or fragment binds to cynomolgus BMP6 with an affinity of less than 1 nM (e.g. from 1 nM to 0.01 pM or from 1 nM to 0.1 pM, or from 1 nM to 1 pM). In one embodiment, the antibody or fragment binds to cynomolgus BMP6 with an affinity of less than 10 nM (e.g. from 10 nM to 0.01 pM or from 10 nM to 0.1 pM, or from 10 nM to 1 pM). In one embodiment, the antibody or fragment binds to cynomolgus BMP6 with an affinity of less than 0.1 nM (e.g. from 0.1 nM to 0.01 pM or from 0.1 nM to 0.1 pM, or from 0.1 nM to 1 pM). In one embodiment, the antibody or fragment binds to cynomolgus BMP6 with an affinity of less than 0.01 nM (e.g. from 0.011 nM to 0.01 pM or from 0.01 nM to 0.1 pM).

In one embodiment, the antibody or fragment binds to cynomolgus BMP6 with an affinity of within 2-fold of the affinity to hBMP6. In one embodiment, the antibody or fragment binds to cynomolgus BMP6 with an affinity of within 4-fold of the affinity to hBMP6. In one embodiment, the antibody or fragment binds to cynomolgus BMP6 with an affinity of within 5-fold of the affinity to hBMP6. In one embodiment, the antibody or fragment binds to cynomolgus BMP6 with an affinity of within 6-fold of the affinity to hBMP6. In one embodiment, the antibody or fragment binds to cynomolgus BMP6 with an affinity of within 8-fold of the affinity to hBMP6. In one embodiment, the antibody or fragment binds to cynomolgus BMP6 with an affinity of within 10-fold of the affinity to hBMP6.

"hBMP6" herein is a human BMP6, eg, a human BMP6 disclosed herein, eg, comprising SEQ ID NO: 562.

In one embodiment, the antibody or fragment does not detectably bind to cynomolgus BMP6. In one embodiment, the antibody or fragment does not detectably bind to murine (eg, mouse and/or rat) BMP6.

In one embodiment, the antibody or fragment binds to murine (eg, mouse and/or rat) BMP6 with an affinity of less than 1 nM (e.g. from 1 nM to 0.01 pM or from 1 nM to 0.1 pM, or from 1 nM to 1 pM). In one embodiment, the antibody or fragment binds to murine BMP6 with an affinity of less than 10 nM (e.g. from 10 nM to 0.01 pM or from 10 nM to 0.1 pM, or from 10 nM to 1 pM). In one embodiment, the antibody or fragment binds to murine BMP6 with an affinity of less than 0.1 nM (e.g. from 0.1 nM to 0.01 pM or from 0.1 nM to 0.1 pM, or from 0.1 nM to 1 pM). In one embodiment, the antibody or fragment binds to murine BMP6 with an affinity of less than 0.01 nM (e.g. from 0.011 nM to 0.01 pM or from 0.01 nM to 0.1 pM).

Optionally, the antibody or fragment comprises an effector-enabled or effector-disabled constant region, such as a human constant region, for example an effector-null human constant region, e.g. an IgG4 constant region or an IgG1 constant region, optionally wherein the constant region is IgG4-PE, or a disabled IgG1. Optionally, the antibody or fragment comprises a murine (eg, mouse and/or rat) constant region. Optionally, the antibody or fragment comprises any of the heavy chain constant region sequences described herein.

Optionally, the constant region has CDC and/or ADCC activity.

30. The antibody or fragment according to any preceding Clause, wherein the antibody or fragment comprises a human constant region, e.g. an IgG4 constant region or an IgG1 constant region.

For example, the constant region comprises a heavy chain constant region, the heavy chain constant region comprising the amino acid sequence of SEQ ID NO: 429, 431, 433, 435, 437, 439, 440, 442, 444, 446, 448, 450, 454 or 456. Optionally, the heavy chain C region is a IGHG1 C region comprising the amino acid sequence of SEQ ID NO: 429, 431, 433, 435 or 437. Optionally, the heavy chain C region is a IGHG2 C region comprising the amino acid sequence of SEQ ID NO: 439, 440, 442 or 444.

Optionally, the heavy chain C region is a IGHG4 C region comprising the amino acid sequence of SEQ ID NO: 446, 448, 450, 454 or 456, preferably SEQ ID NO: 454, preferably SEQ ID NO: 456. In an example, the heavy chain C region is encoded by a nucleic acid comprising SEQ ID NO: 451, 452 or 453.

In an example (optionally in addition to the heavy chain region as per the paragraph immediately above), the constant region comprises a light chain constant region, the light chain constant region comprising the amino acid sequence of SEQ ID NO: 458, 460, 462, 464, 466, 468, 470, 473, 476, 478, 480, 482, 484, 486, 488 or 490. Optionally, the light chain C region is a IGKC C region comprising the amino acid sequence of SEQ ID NO: 458, 460, 462, 464 or 466, preferably SEQ ID NO: 458.

Optionally, the light chain C region is a IGLC C region comprising the amino acid sequence of SEQ ID NO: 468, 470, 473, 476, 478, 480, 482, 484, 486, 488 or 490.

31. The antibody or fragment according to Clause 30, wherein the constant region is an IgG4-PE constant region.

Optionally, the antibody or fragment comprises a heavy chain constant region, wherein the constant region comprises the amino acid sequence of SEQ ID NO: 454.

The anti-BMP6 antibody or fragment according to the invention may comprise a constant region, such as a human constant region, for example an effector-null human constant region, e.g. an IgG4 constant region or an IgG1 constant region, optionally wherein the constant region is IgG4-PE, or a disabled IgG1 as defined in the sequence table herein.

In other embodiments, the antibody or fragment is any of the isotypes or constant regions as defined herein. In one embodiment, the constant region is wild-type human IgG1. For example, the constant region is an effector-enabled IgG1 constant region, optionally having ADCC and/or CDC activity. In one embodiment, the constant region is engineered for enhanced ADCC and/or CDC and/or ADCP. In another embodiment, the constant region is engineered for enhanced effector function.

The IgG4 constant region may be any of the IgG4 constant region amino acid sequences or encoded by any of the nucleic acid sequences of the sequence table herein. A heavy chain constant region may be an IgG4 comprising both the Leu235Glu mutation and the Ser228Pro mutation. This "IgG4-PE" heavy chain constant region (see the sequence table for an example) is effector null.

An alternative effector null human constant region is a disabled IgG1 being an IgG1*01 allele comprising the L235A and/or G237A mutations (e.g. LAGA, see the sequence table). In one embodiment, the antibodies or antibody fragments disclosed herein comprise an IgG1 heavy chain constant region, wherein the sequence contains alanine at position 235 and/or 237 (EU index numbering).

The potency of Fc-mediated effects may be enhanced by engineering the Fc domain by any of the techniques as will be apparent to the skilled person. In another embodiment, the antibodies and fragments disclosed herein may comprise a triple mutation (M252Y/S254T/T256E) which enhances binding to FcRn.

32. The antibody or fragment according to any preceding Clause (eg, a bispecific antibody), further comprising an antigen-binding site that specifically binds another target antigen (eg, human hemojuvelin, transferrin receptor (eg, TFR2) or a BMP receptor (eg, BMPRI or BMPRII) or binds BMP6 and another BMP (eg, BMP2, 4, 7 or 9).

For example, the bispecific antibody specifically binds to BMP6 and BMP2. For example, the bispecific antibody specifically binds to BMP6 and HJV. For example, the bispecific antibody specifically binds to BMP6 and BMPRI (ie, BMPR1, eg, BMPR1A or BMPR1B). For example, the bispecific antibody specifically binds to BMP6 and BMPRII. For example, the bispecific antibody specifically binds to BMP6 and 2. For example the bispecific antibody specifically binds to BMP6 and 4. For example the bispecific antibody specifically binds to BMP6 and 9. For example the bispecific antibody specifically binds to BMP6 and 7. For example the bispecific antibody specifically binds to BMP6 and TFR2.

In an example, the further binding site is an agonist binding site for said another antigen. In an example, the further binding site is an antagonist binding site for said another antigen.

In an example, the further binding site is an antibody binding site comprising a VH and a VL; a binding site comprised by a constant domain of the antibody (eg, an Fcab binding site) or a non-immunoglobulin binding site (eg, a fibronectin domain). Optionally, the antigen-binding site is any antigen-binding site disclosed herein.

For example, the antibody or fragment is a bispecific antibody or fragment. For example, the antibody or fragment is a dual binding antibody or fragment, or a fusion protein comprising an antibody or fragment thereof as defined in any preceding Clause. A dual binding antibody has the meaning as set out above.

In an example, the antibody, fragment or fusion protein of Clause 24 or 24a comprises a bispecific format selected from DVD-Ig, $mAb^2$, FIT-Ig, mAb-dAb, dock and lock, SEED-body, scDiabody-Fc, diabody-Fc, tandem scFv-Fc, Fab-scFv-Fc, Fab-scFv, intrabody, BiTE, diabody, DART, TandAb, scDiabody, scDiabody-$CH_3$, Diabody-$CH_3$, mini-body, knobs-in-holes, knobs-in-holes with common light chain, knobs-in-holes with common light chain and charge pairs, charge pairs, charge pairs with common light chain, in particular $mAb^2$, knob-in-holes, knob-in-holes with common light chain, knobs-in-holes with common light chain and charge pairs and FIT-Ig, e.g. $mAb^2$ and FIT-Ig.

In one embodiment, the bispecific format is selected from DVD-Ig, $mAb^2$, FIT-Ig, mAb-dAb, dock and lock, Fab-arm exchange, SEEDbody, Triomab, LUZ-Y, Fcab, KA-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-$CH_3$, Diabody-$CH_3$, Triple body, Miniantibody, minibody, TriBi minibody, scFv-$CH_3$ KIH, scFv-CH-CL-scFv, F(ab')$_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG (L,H)-Fv, IgG(H)-V, V(H)—IgG, IgG(L)-V, V(L)-IgG, KIH IgG-scFab, 2scFv-IgG, IgG-2scFv, scFv4-Ig and zybody.

In one embodiment, the bispecific format is selected from DVD-Ig, FIT-Ig, mAb-dAb, dock and lock, Fab-arm exchange, SEEDbody, Triomab, LUZ-Y, Fcab, KA-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-$CH_3$, Diabody-$CH_3$, Triple body, Miniantibody, minibody, TriBi minibody, scFv-$CH_3$ KIH, scFv-CH-CL-scFv, F(ab')$_2$-scFv, scFv-KIH, FabscFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG (L,H)-Fv, IgG(H)-V, V(H)—IgG, IgG(L)-V, V(L)-IgG, KIH IgG-scFab, 2scFv-IgG, IgG-2scFv, scFv4-Ig and zybody, for example DVD-Ig, FIT-Ig, mAb-dAb, dock and lock, SEED-body, scDiabody-Fc, diabody-Fc, tandem scFv-Fc, Fab-scFv-Fc, Fab-scFv, intrabody, BiTE, diabody, DART, TandAb, scDiabody, scDiabody-$CH_3$, Diabody-$CH_3$, mini-body, knobs-in-holes, knobs-in-holes with common light chain, knobs-in-holes with common light chain and charge pairs, charge pairs, charge pairs with common light chain, in particular knob-in-holes, knob-in-holes with common light chain, knobs-in-holes with common light chain and charge pairs and FIT-Ig, e.g. FIT-Ig.

In one embodiment, the bispecific format is selected from DVD-Ig, $mAb^2$, mAb-dAb, dock and lock, Fab-arm exchange, SEEDbody, Triomab, LUZ-Y, Fcab, Kh-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-$CH_3$, Diabody-$CH_3$, Triple body, Miniantibody, minibody, TriBi minibody, scFv-$CH_3$ KIH, scFv-CH-CL-scFv, F(ab')$_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG (L,H)-Fv, IgG(H)-V, V(H)—IgG, IgG(L)-V, V(L)-IgG, KIH IgG-scFab, 2scFv-IgG, IgG-2scFv, scFv4-Ig and zybody, for example DVD-Ig, $mAb^2$, mAb-dAb, dock and lock, SEED-body, scDiabody-Fc, diabody-Fc, tandem scFv-Fc, Fab-scFv-Fc, Fab-scFv, intrabody, BiTE, diabody, DART, TandAb, scDiabody, scDiabody-$CH_3$, Diabody-$CH_3$, mini-body, knobs-in-holes, knobs-in-holes with common light chain, knobs-in-holes with common light chain and charge pairs, charge pairs, charge pairs with common light chain, in particular $mAb^2$, knob-in-holes, knobs-in-holes with common light chain and charge pairs, and knob-in-holes with common light chain, e.g. $mAb^2$.

In one embodiment, the bispecific format is selected from DVD-Ig, mAb-dAb, dock and lock, Fab-arm exchange, SEEDbody, Triomab, LUZ-Y, Fcab, Kh-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-$CH_3$, Diabody-$CH_3$, Triple body, Miniantibody, minibody, TriBi minibody, scFv-$CH_3$ KIH, scFv-CH-CL-scFv, F(ab')$_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)—IgG, IgG(L)-V, V(L)-IgG, KIH IgG-scFab, 2scFv-IgG, IgG-2scFv, scFv4-Ig and zybody, for example DVD-Ig, mAb-dAb, dock and lock, SEEDbody, scDiabody-Fc, diabody-Fc, tandem scFv-Fc, Fab-scFv-Fc, Fab-scFv, intrabody, BiTE, diabody, DART, TandAb, scDiabody, scDiabody-$CH_3$, Diabody-$CH_3$, minibody, knobs-in-holes, knobs-in-holes with common light chain, knobs-in-holes with common light chain and charge pairs, charge pairs, charge pairs with common light chain, in particular knob-in-holes, knobs-in-holes with common light chain and charge pairs, and knob-in-holes with common light chain.

33. An anti-BMP6 antibody or fragment as defined in any preceding Clause for treating or preventing a BMP6-mediated disease or condition (eg, anaemia) in a subject.

In an example, the subject is a human. In an alternative, the subject is a non-human animal. In an example, the subject is an adult human. In an example, the subject is a paediatric human. In an example, the subject is a human CKD patient on dialysis treatment. In an example, the subject is a human having end-stage renal disease.

In an example, the antibody or fragment herein is for treating or preventing a disease or condition in a subject (eg, a human) selected from anaemia, pulmonary arterial hypertension (PAH) (eg, primary PAH or secondary PAH), Cerebral Cavernous Malformation (CCM) (eg, familial CCM or sporadic CCM), Restless Legs Syndrome (RLS), cancer (eg, breast cancer, pancreatic cancer, colorectal cancer, salivary gland cancer, oesophageal cancer or melanoma), cancer mestasis, systemic sclerosis, Sjögren's Syndrome, Endothelial to Mesenchymal Transformation (EndoMT), cardiovascular disease, atherosclerosis, Systemic Sclerosis-associated pulmonary fibrosis and cardiac fibrosis.

Examples of a disease or condition mediated by EndoMT are cardiovascular disease, atherosclerosis, Systemic Sclerosis-associated pulmonary fibrosis, cardiac fibrosis, PAH, tumour formation, tumour invasion, tumour mestasis, fibrotic disease and the generation of Carcinoma-Associated Fibroblasts (eg, in pancreatic cancer).

In an example, the disease or condition is in a human. In an example, the disease or condition is in an animal.

In an example, the antibody or fragment of the invention is for treating or preventing a TIGIT mediated disease or condition in a human, e.g. selected from neoplastic or non-neoplastic disease, chronic viral infections, and malignant tumours, such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease and diffuse large B-cell lymphoma (for example melanoma, Merkel cell carcinoma, non-small cell lung cancer (squamous and non-squamous), renal cell cancer, bladder cancer, head and neck squamous cell carcinoma and mesothelioma or for example virally induced cancers (such as cervical cancer and nasopharyngeal cancer) and soft tissue sarcomas).

In an example, the BMP6-mediated disease or condition is a neurodegenerative disease, disorder or condition, e.g. selected from Alzheimer's disease, amyotrophic lateral sclerosis, Parkinson's disease, Huntington's disease, primary progressive multiple sclerosis, secondary progressive multiple sclerosis, corticobasal degeneration, Rett syndrome, a retinal degeneration disorder selected from age-related macular degeneration and retinitis pigmentosa; anterior ischemic optic neuropathy, glaucoma, uveitis, depression, trauma-associated stress or post-traumatic stress disorder, frontotemporal dementia, Lewy body dementias, mild cognitive impairments, posterior cortical atrophy, primary progressive aphasia and progressive supranuclear palsy or aged-related dementia, in particular, the neurodegenerative disease, disorder or condition is selected from Alzheimer's disease, amyotrophic lateral sclerosis, Parkinson's disease and Huntington's disease, for example, Alzheimer's disease.

In an example, the antibody, fragment, combination of the invention is administered intravenously to the subject; or is for administration intravenously to the subject. In an example, the antibody, fragment, combination of the invention is administered subcutaneously to the subject; or is for administration subcutaneously to the subject.

34. The antibody or fragment of Clause 33, wherein the antibody or fragment is administered to the subject simultaneously or sequentially with an erythropoietin stimulating agent (ESA).

35. A combination of an amount of an anti-BMP6 antibody or fragment and an amount of an ESA (eg, comprising multiple doses of said antibody and/or ESA), wherein the antibody or fragment is according to any one of Clauses 1 to 34.

There is also provided: A medical kit comprising the combination, a first sterile container comprising said amount of antibody or fragment, and a second sterile container comprising said amount of ESA, and optionally instructions for using the combination to treat anaemia in a subject.

In an example, the combination is for treating or preventing anaemia in a subject, wherein over a 4 consecutive week period a total dose of the antibody and total dose of ESA are administered to said subject in a ratio of X:Y, wherein X is from 10 to $2 \times 10^6$ and Y=4, eg, X is from 10 to $2 \times 10^6$ micrograms and Y=4 micrograms.

In an example the treatment increases (or is for increasing) in the subject one, more or all of Hb concentration, mean corpuscular haemoglobin (MCH) and transferrin saturation. The skilled addressee will be familiar with these parameters and how to determine them, eg, using one or more serum samples of the subject. For example, transferrin saturation, measured as a percentage, is the value of serum iron divided by the total iron-binding capacity.

In an example, said subject at the start of treatment suffers from anaemia of chronic disease (ACD) and optionally wherein the anaemia is associated with chronic inflammation (eg, the subject suffers from arthritis) or a bacterial infection (eg, *Streptococcus* infection), or wherein the subject is a chronic kidney disease (CKD) patient.

36. The antibody, fragment or combination according to any one of Clauses 1 to 34 for use in a method of:

(a) preventing the blood haemoglobin level of a subject from decreasing to less than 10 g/dL, the method comprising administering the antibody or fragment and an erythropoiesis stimulating agent (ESA) to the subject;

(b) raising blood haemoglobin to a level of at least 10 g/dL in a subject suffering from anaemia, the method comprising administering the antibody or fragment and an erythropoiesis stimulating agent (ESA) to the subject, wherein said anaemia is treated;

(c) treating or preventing anaemia in a subject suffering from an inflammatory disease or condition, the method comprising administering the antibody or fragment and an erythropoiesis stimulating agent (ESA) to the subject, wherein said anaemia is treated or prevented;

(d) eliminating or reducing the need to administer iron or blood transfusion to a subject suffering from anaemia, the method comprising administering the antibody or fragment and an erythropoiesis stimulating agent (ESA) to the subject, wherein said need is eliminated or reduced;

(e) treating or preventing anaemia in a subject suffering from a microbial infection, the method comprising administering an anti-BMP6 antagonist and an erythropoiesis stimulating agent (ESA) to the subject;

(f) reducing administration of an erythropoiesis stimulating agent (ESA) to a subject suffering from anaemia for treating anaemia, the method comprising administering the antibody or fragment and said ESA, wherein anaemia is treated in the subject; or (g) treating or reducing the risk of anaemia in a subject suffering from or at risk of anaemia, the method comprising administering the antibody or fragment and a low dose of an erythropoiesis stimulating agent (ESA) to the subject, wherein anaemia is treated or the risk of anaemia is reduced in the subject.

37. The antibody, fragment or combination of any one of Clauses 1 to 34 and 36, wherein the ESA is a. Epoetin alfa and is administered at a weekly dose of less than 1000, 1500, 2500, 5000, 11000, 18000, 34000 or 90000 units, optionally wherein the subject has previously received a weekly epoetin alfa treatment of <1500, 1500 to 2499, 2500 to 4999, 5000 to 10999, 11000 to 17999, 18000 to 33999, 34000 to 89999 or 90000 units respectively;

b. darbepoetin alfa or Aranesp® and is administered at a weekly dose of less than 6.25, 10, 12.5, 20, 25, 40, 60, 100 or 200 mcg, optionally wherein the subject has previously received a weekly darbepoetin alfa or Aranesp® treatment of 6.25, 10, 12.5, 20, 25, 40, 60, 100 or 200 mcg respectively; or c. darbepoetin alfa or Aranesp® and is administered at a weekly dose of less than 6.25, 10, 20, 40, 60, 100 or 200 mcg, optionally wherein the subject has previously received a weekly Epoetin alfa treatment of 1500 to 2499, 2500 to 4999, 5000 to 10999, 11000 to 17999, 18000 to 33999, 34000 to 89999 or >90,000 units respectively.

38. The antibody, fragment or combination of any one of Clauses 1 to 34, 36 and 37 for maintaining or raising blood haemoglobin level to at least 10 g/dL in the subject at least 13 or 14 days after the subject has received the anti-BMP6 antibody or fragment and ESA.

39. Use of the antibody, fragment or combination as defined in any preceding Clause in the manufacture of a medicament for administration to a subject for treating or preventing a BMP6-mediated disease or condition, e.g. anaemia.

40. A method of treating or preventing a BMP6-mediated disease or condition in a subject (e.g. anaemia), the method comprising administering to said subject a therapeutically effective amount of an antibody, fragment or combination as defined in any one of Clauses 1 to 38, wherein the BMP6-mediated disease or condition is thereby treated or prevented.

The disease or condition can be any disclosed herein.

41. The use according to Clause 39 or the method according to Clause 40, wherein the BMP6-mediated disease or condition is anaemia.

42. The antibody, fragment, combination, use or the method according to any one of Clauses 33 to 41, further comprising administering to the subject a further therapy, for example a further therapeutic agent, optionally wherein the further therapeutic agent is selected from the group consisting of:

(a) Intravenous iron;

(b) An ESA (eg, an EPO);

(c) An ActRIIa inhibitor;

(d) An ActRIIb inhibitor;

(e) An IL-6 or IL-6 receptor inhibitor (eg, an anti-IL-6 or IL-6 receptor antibody);

(f) ATNF-alpha or TNF-alpha receptor inhibitor (eg, an anti-TNF-alpha or TNF-alpha receptor antibody);

(g) A HJV inhibitor (eg, an anti-HJV antibody);

(h) A BMP inhibitor (eg, a further anti-BMP antibody or fragment), eg, wherein the BMP is BMP2, 4, 5, 6, 7 or 9;

(i) A matriptase-2 (MTP2) agonist (eg, a matriptase-2 (MTP2) agonist antibody);

(j) A HIF-PH inhibitor;

(k) A transferrin receptor 2 (TFR2) inhibitor;

(l) A HFE inhibitor;

(m) A NRf2 inhibitor;

(n) A transforming growth factor-beta superfamily type I activin receptor-like kinase (ALK) receptor inhibitor;

(o) An activin receptor inhibitor (eg, an activin receptor Fc fusion);

(p) A GDF11 inhibitor; and (q) A myostatin inhibitor.

Optionally, the further agent is Luspatercept™ or Sotatercept™. Optionally, the further agent is a TGF-β Superfamily inhibitor. In an example, the further agent is a transforming growth factor-beta superfamily type I activin receptor-like kinase (ALK) receptor inhibitor; ALK 2 inhibitor, ALK3 inhibitor; ALK4 inhibitor; ALK5 inhibitor; or ALK7 inhibitor.

In an example the further agent is an IL-6 or IL-6R inhibitor, eg, Sarilumab, Vobarilizumab or tocilizumab (eg, Kevzara® or Actemra®).

In an example the further agent is a TNF-alpha or TNF-alpha receptor inhibitor, eg, adalimumab, HUMIRA®, REMICADE® or ENBREL®, SIMPONI®.

In an embodiment, the NRf2 inhibitor improves efficacy of anti-BMP6 antibody or fragment by breaking the feedback loop of more iron inducing more BMP6 expression in the subject being treated.

The disclosure includes generic versions of the branded drugs instead and the disclosure of these generic drugs is included by reference herein for possible use in the invention, eg, as part of a combination.

In an example, the combination comprises inhibitors of BMP6 and HJV; or BMP6 and HFE; or BMP6 and TFR2; or BMP6 and BMP2; or BMP6 and BMP4; or BMP6 and ALK2, wherein the BMP6 inhibitor comprises the antibody or fragment of the invention.

43. A pharmaceutical composition comprising an antibody, fragment or combination as defined in any one of Clauses 1 to 38 and 42 and a pharmaceutically acceptable excipient, diluent or carrier and optionally in combination with a further therapeutic agent selected from those mentioned above (eg, in Clause 42).

44. The pharmaceutical composition according to Clause 43 for treating and/or preventing a BMP6-mediated condition or disease, e.g. anaemia.

Suitable diseases and conditions include anaemia, pulmonary arterial hypertension (PAH) (eg, primary PAH or secondary PAH), Cerebral Cavernous Malformation (CCM) (eg, familial CCM or sporadic CCM), Restless Legs Syndrome (RLS), cancer (eg, breast cancer, pancreatic cancer, colorectal cancer, salivary gland cancer, oesophageal cancer or melanoma), cancer mestasis, systemic sclerosis, Sjögren's Syndrome, Endothelial to Mesenchymal Transformation (EndoMT), cardiovascular disease, atherosclerosis, Systemic Sclerosis-associated pulmonary fibrosis and cardiac fibrosis.

Examples of a disease or condition mediated by EndoMT are cardiovascular disease, atherosclerosis, Systemic Sclerosis-associated pulmonary fibrosis, cardiac fibrosis, PAH, tumour formation, tumour invasion, tumour mestasis, fibrotic disease and the generation of Carcinoma-Associated Fibroblasts (eg, in pancreatic cancer).

45. The pharmaceutical composition according to Clause 43 or 44 in combination with a label or instructions for use to treat and/or prevent said disease or condition in a human; optionally wherein the label or instructions comprise a marketing authorisation number (e.g., an FDA or EMA authorisation number); optionally wherein the kit comprises an IV or injection device that comprises the antibody or fragment.

46. A nucleic acid that encodes a VH domain and/or a VL domain of an antibody or fragment as defined in any one of Clauses 1 to 32.

47. A nucleic acid that encodes a VH domain comprising the amino acid sequence of a VH domain of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or an amino acid that is at least 70, 80, 85, 90, 95, 96, 97, 98 or 99% identical thereto.

For example, the identity is at least 85%. For example, the identity is at least 90%. For example, the identity is at least 95%.

Optionally, there is provided a nucleic acid that encodes a VH domain comprising the amino acid sequence of SEQ ID NO: 114, or an amino acid that is at least 70, 80, 85, 90, 95, 96, 97, 98 or 99% identical thereto. For example, the identity is at least 85%. For example, the identity is at least 90%.

For example, the identity is at least 95%.

48. A nucleic acid that encodes a VL domain comprising the amino acid sequence of a VL domain of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; or an amino acid that is at least 70, 80, 85, 90, 95, 96, 97, 98 or 99% identical thereto.

Optionally, the nucleic acid also encodes a VH domain comprising the amino acid sequence of a VH domain of the selected antibody; or an amino acid that is at least 70, 80, 85, 90, 95, 96, 97, 98 or 99% identical thereto. For example, the identity is at least 85%. For example, the identity is at least 90%. For example, the identity is at least 95%.

Optionally, there is provided a nucleic acid that encodes a VL domain comprising the amino acid sequence of SEQ ID NO: 123, or an amino acid that is at least 70, 80, 85, 90, 95, 96, 97, 98 or 99% identical thereto. For example, the identity is at least 85%. For example, the identity is at least 90%.

For example, the identity is at least 95%.

49. A nucleic acid (eg, in a host cell, eg, a CHO or HEK293 or Cos cell) comprising
(a) a nucleotide sequence that is at least 70, 80, 85, 90, 95, 96, 97, 98 or 99% identical to the sequence of SEQ ID NO: 115, 520 or 521; and/or
(b) a nucleotide sequence that is at least 70, 80, 85, 90, 95, 96, 97, 98 or 99% identical to the sequence of SEQ ID NO: 124, 522 or 523.

In an alternative, there is provided:
A nucleic acid (eg, in a host cell, eg, a CHO or HEK293 or Cos cell) comprising
(a) a nucleotide sequence that is at least 70, 80, 85, 90, 95, 96, 97, 98 or 99% identical to the sequence of SEQ ID NO: 115; and/or
(b) a nucleotide sequence that is at least 70, 80, 85, 90, 95, 96, 97, 98 or 99% identical to the sequence of SEQ ID NO: 124.

A nucleic acid (eg, in a host cell, eg, a CHO or HEK293 or Cos cell) comprising
(a) a nucleotide sequence that is at least 70, 80, 85, 90, 95, 96, 97, 98 or 99% identical to the sequence of SEQ ID NO: 520; and/or
(b) a nucleotide sequence that is at least 70, 80, 85, 90, 95, 96, 97, 98 or 99% identical to the sequence of SEQ ID NO: 522.

A nucleic acid (eg, in a host cell, eg, a CHO or HEK293 or Cos cell) comprising
(a) a nucleotide sequence that is at least 70, 80, 85, 90, 95, 96, 97, 98 or 99% identical to the sequence of SEQ ID NO: 521; and/or
(b) a nucleotide sequence that is at least 70, 80, 85, 90, 95, 96, 97, 98 or 99% identical to the sequence of SEQ ID NO: 523.

A combination of first and second nucleic acids (eg, in a host cell, eg, a CHO or HEK293 or Cos cell) respectively comprising
(a) a nucleotide sequence that is at least 70, 80, 85, 90, 95, 96, 97, 98 or 99% identical to the sequence of SEQ ID NO: 115, 520 or 521; and/or
(b) a nucleotide sequence that is at least 70, 80, 85, 90, 95, 96, 97, 98 or 99% identical to the sequence of SEQ ID NO: 124, 522 or 523.

A combination of first and second nucleic acids (eg, in a host cell, eg, a CHO or HEK293 or Cos cell) respectively comprising
(a) a nucleotide sequence that is at least 70, 80, 85, 90, 95, 96, 97, 98 or 99% identical to the sequence of SEQ ID NO: 115; and/or
(b) a nucleotide sequence that is at least 70, 80, 85, 90, 95, 96, 97, 98 or 99% identical to the sequence of SEQ ID NO: 124.

A combination of first and second nucleic acids (eg, in a host cell, eg, a CHO or HEK293 or Cos cell) respectively comprising
(a) a nucleotide sequence that is at least 70, 80, 85, 90, 95, 96, 97, 98 or 99% identical to the sequence of SEQ ID NO: 520; and/or
(b) a nucleotide sequence that is at least 70, 80, 85, 90, 95, 96, 97, 98 or 99% identical to the sequence of SEQ ID NO: 522.

A combination of first and second nucleic acids (eg, in a host cell, eg, a CHO or HEK293 or Cos cell) respectively comprising
(a) a nucleotide sequence that is at least 70, 80, 85, 90, 95, 96, 97, 98 or 99% identical to the sequence of SEQ ID NO: 521; and/or
(b) a nucleotide sequence that is at least 70, 80, 85, 90, 95, 96, 97, 98 or 99% identical to the sequence of SEQ ID NO: 523.

For example, for (a) the identity is at least 85%. For example, the identity is at least 90%. For example, the identity is at least 95%.

For example, for (b) the identity is at least 85%. For example, the identity is at least 90%. For example, the identity is at least 95%.

Herein in any instance where % identity is mentioned, in an example there is 100% identity.

50. A nucleic acid that encodes a heavy chain and/or a light chain of an antibody or fragment as defined in any one of Clauses 1 to 32.

51. A nucleic acid that encodes a heavy chain comprising an amino acid sequence that is at least 70, 80, 85, 90, 95, 96, 97, 98 or 99% identical to SEQ ID NO: 116.

For example, the identity is at least 85%. For example, the identity is at least 90%. For example, the identity is at least 95%.

52. A nucleic acid that encodes a light chain comprising an amino acid sequence that is at least 70, 80, 85, 90, 95, 96, 97, 98 or 99% identical to SEQ ID NO: 125.

For example, the identity is at least 85%. For example, the identity is at least 90%. For example, the identity is at least 95%.

53. A nucleic acid (eg, in a host cell, eg, a CHO or HEK293 or Cos cell) comprising
  (a) a nucleotide sequence that is at least 70, 80, 85, 90, 95, 96, 97, 98 or 99% identical to a heavy chain sequence selected of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713; and/or
  (b) a nucleotide sequence that is at least 70, 80, 85, 90, 95, 96, 97, 98 or 99% identical to a sequence selected of an antibody selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713.

Preferably, the selected antibody in (a) and (b) is the same antibody, eg, CL-58838. In a alternative, a first nucleic acid comprises (a) and a second nucleic acid comprises (b), eg, in a host cell, eg, a CHO or HEK293 or Cos cell.

All of the nucleic acids of the invention herein are expressible in a host cell, eg, a CHO or HEK293 or Cos cell, such as for expressing a variable domain or chain of an antibody or fragment of the invention.

For example, there is provided:

A nucleic acid (eg, in a host cell, eg, a CHO or HEK293 or Cos cell) comprising
  (a) a nucleotide sequence that is at least 70, 80, 85, 90, 95, 96, 97, 98 or 99% identical to a sequence selected from SEQ ID NO: 512, 514, 516, 518 and 519; and/or
  (b) a nucleotide sequence that is at least 70, 80, 85, 90, 95, 96, 97, 98 or 99% identical to a sequence selected from SEQ ID NO: 513, 515 and 517.

A nucleic acid (eg, in a host cell, eg, a CHO or HEK293 or Cos cell) comprising
  (a) a nucleotide sequence that is at least 70, 80, 85, 90, 95, 96, 97, 98 or 99% identical SEQ ID NO: 512; and/or
  (b) a nucleotide sequence that is at least 70, 80, 85, 90, 95, 96, 97, 98 or 99% identical to SEQ ID NO: 513.

A nucleic acid (eg, in a host cell, eg, a CHO or HEK293 or Cos cell) comprising
  (a) a nucleotide sequence that is at least 70, 80, 85, 90, 95, 96, 97, 98 or 99% identical SEQ ID NO: 514; and/or
  (b) a nucleotide sequence that is at least 70, 80, 85, 90, 95, 96, 97, 98 or 99% identical to SEQ ID NO: 515.

A nucleic acid (eg, in a host cell, eg, a CHO or HEK293 or Cos cell) comprising
  (a) a nucleotide sequence that is at least 70, 80, 85, 90, 95, 96, 97, 98 or 99% identical SEQ ID NO: 516; and/or
  (b) a nucleotide sequence that is at least 70, 80, 85, 90, 95, 96, 97, 98 or 99% identical to SEQ ID NO: 517.

A nucleic acid (eg, in a host cell, eg, a CHO or HEK293 or Cos cell) comprising
  (a) a nucleotide sequence that is at least 70, 80, 85, 90, 95, 96, 97, 98 or 99% identical SEQ ID NO: 518; and/or
  (b) a nucleotide sequence that is at least 70, 80, 85, 90, 95, 96, 97, 98 or 99% identical to SEQ ID NO: 513, 515 or 517.

A nucleic acid (eg, in a host cell, eg, a CHO or HEK293 or Cos cell) comprising
  (a) a nucleotide sequence that is at least 70, 80, 85, 90, 95, 96, 97, 98 or 99% identical SEQ ID NO: 519; and/or
  (b) a nucleotide sequence that is at least 70, 80, 85, 90, 95, 96, 97, 98 or 99% identical to SEQ ID NO: 513, 515 or 517.

For example, for (a) the identity is at least 85%. For example, the identity is at least 90%. For example, the identity is at least 95%.

For example, for (b) the identity is at least 85%. For example, the identity is at least 90%. For example, the identity is at least 95%.

54. A vector comprising the nucleic acid(s) (eg, the nucleic acid(s) of any one of Clauses 46 to 53); optionally wherein the vector is a CHO or HEK293 vector.

55. A host cell comprising the nucleic acid(s) (eg, the nucleic acid(s) of any one of Clauses 46 to 53) or the vector of Clause 54.

Optionally, the VH gene segment is selected from IGHV1-3*01 and IGHV3-11*01. Optionally, the VL gene segment is selected from IGKV1-5*03, IGKV3-20*01 and IGKV3-15*01.

In an example, the VH, DH and JH are IGHV1-3, IGHD3-10 and IGHJ4 (eg, IGHV1-3*01, IGHD3-10*01 and IGHJ4*02).

In an example, the VH, DH and JH are IGHV1-3, IGHD3-10 and IGHJ3, eg, IGHV1-3*01, IGHD3-10*01 and IGHJ3*02.

In an example, the VH, DH and JH are IGHV3-11, IGHD6-19 and IGHJ4, eg, IGHV3-11*01, IGHD6-19*01 and IGHJ4*02.

In an example, the VH, DH and JH are IGHV1-3, IGHD7-27 and IGHJ4, eg, IGHV1-3*01, IGHD7-27*02 and IGHJ4*02.

In an example, the VH, DH and JH are IGHV1-3, IGHD4-23 and IGHJ4, eg, IGHV1-3*01, IGHD4-23*01 and IGHJ4*02.

In an example, the VH, DH and JH are IGHV1-3, IGHD5-18 and IGHJ4, eg, IGHV1-3*01, IGHD5-18*01 and IGHJ4*02.

In an example, the VL and JL are IGKV1-5 and IGKJ1, eg, IGKV1-5*03 and IGKJ1*01.

In an example, the VL and JL are IGKV3-20 and IGKJ1, eg, IGKV3-20*01 and IGKJ1*01.

In an example, the VL and JL are IGKV3-15 and IGKJ3, eg, IGKV3-15*01 and IGKJ3*01.

In an example, the VL and JL are IGKV3-20 and IGKJ3, eg, IGKV3-20*01 and IGKJ3*01.

In an example, the antibody or fragment comprises a HCDR3 length of 9, 10, 11 or 12 residues, eg, 10, eg, 11. In an example, the antibody or fragment comprises a LCDR3 length of 7, 8 or 9 residues, eg, 8, eg, 9. In an example, each VH domain of the antibody or fragment comprises from 1-11 non-germline residues, eg, 1, 2, 3, 4, 5, 6, 7, 8, 9, 10 or 11 non-germline residues. In an example, each VL domain of the antibody or fragment comprises from 3-8 non-germline residues, eg, 3, 4, 5, 6, 7 or 8 non-germline residues.

In an embodiment, a CDR sequence herein is determined according to Kabat. In an alternative, the CDR sequence is determined according to IMGT.

In an example, the selected antibody is CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 or CL-58713. In an example, the selected antibody is CL-58838.

In an example, the selected antibody comprises the heavy chain of CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 or CL-58713. In an example, the selected antibody comprises the heavy chain of CL-58838.

In an example, the heavy chain of the antibody or fragment of the invention is a human gamma-1, gamma-2, gamma-3, gamma-4, mu, delta, epsilon or alpha isotype, preferably a gamma isotype (eg, an IgG4 isotype). In an example, the light chain of the antibody or fragment of the invention comprises a human kappa constant region. Alternatively, in an example, the light chain of the antibody or fragment of the invention comprises a human lambda constant region.

Optionally, the antibody is a 4-chain antibody comprising a dimer of a heavy chain associated with a dimer of a light chain. In an example, the heavy chain comprises one or heavy chain CDRs or a CDR combination as disclosed herein and/or the light chain comprises one or heavy chain CDRs or a CDR combinations as disclosed herein, such as from the same selected antibody. In an example, the heavy chain comprises a VH domain as disclosed herein and/or the light chain comprises a VL as disclosed herein, such as from the same selected antibody. In an example, the heavy chain and the light chain are from the same selected antibody, eg, any antibody disclosed in the sequence table herein or the tables in the Examples herein.

In an example, the selected antibody comprises the light chain of CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 or CL-58713. In an example, the selected antibody comprises the light chain of CL-58838.

In an example, the selected antibody comprises the variable domains of CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 or CL-58713. In an example, the selected antibody comprises the variable domains of CL-58838.

In an example, the selected antibody comprises the VH domains of CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 or CL-58713. In an example, the selected antibody comprises the VH domains of CL-58838.

In an example, the selected antibody comprises the VH and VL domains of CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 or CL-58713. In an example, the selected antibody comprises the VH and VL domains of CL-58838.

Optionally, the VH segment is a human IGHV3-11 gene segment, eg, the VH is encoded by a nucleotide sequence that is derived from the recombination of a human IGHV3-11 and IGHJ4 (eg, human gene segments IGHV3-11*01 and IGHJ4*02; IGHV3-11, IGHD6-19, IGHJ4; or IGHV3-11*01, IGHD6-19*01 and IGHJ4*02). Optionally, the JH is a IGHJ4*02. Optionally, the VL is encoded by a nucleotide sequence that is derived from the recombination of a human VL gene segment and JL gene segment, wherein the VL gene segment is selected from IGKV1-5, IGKV3-20 and IGKV3-15. Optionally, the VL is a human IGKV3-20 (eg, IGKV3-20*01). Optionally, the JL is a IGKJ1 (eg, IGKJ1*01). For example, the VL is encoded by a nucleotide sequence that is derived from the recombination of a human IGKV3-20 (eg, IGKV3-20*01) and a human IGKJ1 (eg, IGKJ1*01).

In an example, the binding site comprises a VH/VL pair that specifically binds to human BMP6 (eg, a human BMP6 comprising or consisting of the bold sequence of SEQ ID NO: 1 in the sequence table herein). In an example, the antibody or fragment comprises 2 (eg, 2 and no more than 2) copies of the binding site.

In an example, the antibody or fragment comprises a HCDR3 length of 9-12 residues and/or the antibody or fragment comprises a LCDR3 length of 7-9 residues. In an example, the antibody or fragment comprises a HCDR3 length of 9, 10, 11 or 12 residues, eg, 10, eg, 11. In an example, the antibody or fragment comprises a LCDR3 length of 7, 8 or 9 residues, eg, 8, eg, 9. In an example, each VH domain of the antibody or fragment comprises from 1-11 non-germline residues, eg, 1, 2, 3, 4, 5, 6, 7, 8, 9, 10 or 11 non-germline residues. In an example, each VL domain of the antibody or fragment comprises from 3-8 non-germline residues, eg, 3, 4, 5, 6, 7 or 8 non-germline residues.

Optionally, the antibody or fragment competes with CL-58838 (eg, CL-58838 in IgG format, eg, IgG-PE) for binding to BMP6 (eg, human BMP6, eg, mature human BMP6, eg, BMP6 comprising or consisting of the sequence of mature BMP6 disclosed in the sequence table herein, ie, the bold sequence of SEQ ID NO: 1) as determined by SPR.

Optionally, the amino acid substitutions are conservative amino acid substitutions, optionally wherein each conservative substitution is from group (1) to (6):

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Any SPR herein is, for example, surface plasmon resonance (SPR) at 37° C. and pH 7.6.

Optionally, any BMP6 herein is (for example, in in vitro testing) human BMP6, eg, hBMP6 (Peprotech 120-06).

In an example, the antibody or fragment of the invention binds to human BMP6 with a Ka of eg, $5 \times 10^6$ $M^{-1} \times s^{-1}$; or about $5 \times 10^6$ $M^{-1} \times s^{-1}$. In an example, the antibody or fragment of the invention binds to human BMP6 with a Kd of eg, 4 or 5 $s^{-1}$; or about 4 or 5 $s^{-1}$. In an example, the antibody or fragment of the invention binds to human BMP6 with a KD of eg, 0.07 or 0.14 nM; or about 0.07 or 0.14 nM. In an embodiment, the fragment is a Fab fragment. In an embodiment, the fragment is a scFv.

In an example, the antibody comprises heavy chains, wherein each heavy chain comprises or consists of the amino acid sequence of SEQ ID NO: 116; and light chains each comprising or consisting of the amino acid sequence of SEQ ID NO: 125.

In an example, the antibody or fragment comprises heavy chain VH domains, wherein each VH comprises or consists of the amino acid sequence of SEQ ID NO: 418; and light chain VL domains each comprising or consisting of the amino acid sequence of SEQ ID NO:426.

Alternative Antibody or Fragment:

The invention, in any of its configurations, may relate to an antibody or fragment (Alternative Antibody or Fragment) as follows.

Optionally (Option 1), the antibody or fragment comprises a. Heavy chains each comprising or consisting of the amino acid sequence of SEQ ID NO: 403 or 566, and light chains each comprising or consisting of the amino acid sequence of SEQ ID NO: 411; or b. Heavy chains each comprising or consisting of the amino acid sequence of SEQ ID NO: 419 and light chains each comprising or consisting of the amino acid sequence of SEQ ID NO: 427.

Optionally (Option 2), the antibody or fragment comprises a. Heavy chains each comprising the VH domain amino acid sequence of SEQ ID NO: 402 or 565, and light chains each comprising the VL domain amino acid sequence of SEQ ID NO: 410; or b. Heavy chains each comprising the VH domain amino acid sequence of SEQ ID NO: 418 and light chains each comprising the VH domain amino acid sequence of SEQ ID NO: 426; and c. Optionally the heavy chains comprise a human gamma-1 (eg, IGHG1*01) or gamma-4 (eg, IGHG4*01 or IGHG4*01-PE) constant region, or the amino acid sequence of SEQ ID NO: 429, 437, 446, 454 or 456.

Optionally, the antibody or fragment competes with a reference antibody for binding BMP6, wherein the reference antibody is mAb507 (R&D Systems) or an Alternative Antibody (eg, an Option 1 or Option 2 antibody as herein defined). Competition can be by SPR or ELISA, for example, or in a functional assay such as an assay described herein (eg, in the Examples). The BMP6 can be human BMP6 (eg, mature BMP6 comprising the sequence of SEQ ID NO: 562), a rat BMP6 (eg, mature BMP6 comprising the sequence of SEQ ID NO: 56 or cynomolgus monkey BMP6 (eg, mature BMP6 comprising the sequence of SEQ ID NO: 564).

Human IgG heavy chain genes naturally encode a C-terminal lysine. This residue is mostly missing in antibodies isolated from serum and is present at low but variable levels on therapeutic antibodies expressed in mammalian cell culture systems. Since C-terminal lysine clipping occurs naturally in serum and is not known to affect overall antibody function it can be removed from the heavy chain coding sequence to provide homogeneous "lysine-clipped" heavy chains and therefore homogeneous drug product. Thus, any IgG antibody, constant region or heavy chain herein shown terminating at its C-terminus with a G can alternatively be provided in a form that ends with a GK (ie, a lysine bonded at the C-terminal side of the G shown).

Examples of Option 1 and 2 are:—

Option 1a: In an example, the antibody comprises heavy chains, wherein each heavy chain comprises or consists of the amino acid sequence of SEQ ID NO: 403; and light chains each comprising or consisting of the amino acid sequence of SEQ ID NO: 411.

Option 1b: In an example, the antibody comprises heavy chains, wherein each heavy chain comprises or consists of the amino acid sequence of SEQ ID NO: 566 and light chains each comprising or consisting of the amino acid sequence of SEQ ID NO: 411.

Option 1c: In an example, the antibody comprises heavy chains, wherein each heavy chain comprises or consists of the amino acid sequence of SEQ ID NO: 419; and light chains each comprising or consisting of the amino acid sequence of SEQ ID NO: 427.

Option 2a: In an example, the antibody or fragment comprises heavy chain VH domains, wherein each VH comprises or consists of the amino acid sequence of SEQ ID NO: 402; and light chain VL domains each comprising or consisting of the amino acid sequence of SEQ ID NO: 410.

Option 2b: In an example, the antibody or fragment comprises heavy chain VH domains, wherein each VH comprises or consists of the amino acid sequence of SEQ ID NO: 565, and light chain VL domains each comprising or consisting of the amino acid sequence of SEQ ID NO: 410.

In an example, the antibody or fragment comprises heavy chain VH domains, wherein each VH comprises or consists of the amino acid sequence of SEQ ID NO: 114; and light chain VL domains each comprising or consisting of the amino acid sequence of SEQ ID NO: 123.

Optionally, the antibody or fragment competes with said reference antibody for binding to the amino acid sequence of SEQ ID NO: 1. Additionally or alternatively, optionally, the antibody or fragment competes with said reference antibody for binding to the amino acid sequence of SEQ ID NO: 492. Additionally or alternatively, optionally, the antibody or fragment competes with said reference antibody for binding to the amino acid sequence of SEQ ID NO: 491. Additionally or alternatively, optionally, the antibody or fragment competes with said reference antibody for binding the amino acid sequence of SEQ ID NO: 4. Additionally or alternatively, the antibody or fragment competes with said reference antibody for binding to the mature version of any one or more of these.

Optionally, the antibody or fragment competitively inhibits the binding of soluble haemojuvelin (HJV) to BMP6. Optionally, HJV herein is human HJV.

Optionally, the antibody or fragment does not competitively inhibit the binding of soluble haemojuvelin (HJV) to BMP6.

As used herein, "inhibits", "inhibition", "inhibiting" and the like, as used herein refers to the ability of an antagonist (e.g. an antibody or fragment thereof) to bind to an epitope (eg, of hBMP6) which either partially or completely prevents the binding of another antigen If the epitope to which the antagonist binds completely blocks the binding site of the ligand, then ligand binding is completely prevented (which may be a physical blocking—in the case of overlapping epitopes—or steric blocking—where the antagonist is large such that it prevents the ligand binding to its distinct epitope), and the ligand is not removed from circulation. The concentration of circulating ligand may therefore appear to be increased. If the epitope to which the antagonist binds partially blocks the binding site of the ligand, the ligand may be able to bind, but only weakly (in the case of partial inhibition), or in a different orientation to the natural binding interaction. In this case, some of the ligand may be removed from circulation, but not as much as when the ligand binding site is completely free and available for binding. Inhibition thus refers to the physical interaction of ligand and receptor. Inhibition can be measured by HTRF, which is described in more detail elsewhere herein and in Mathis (1995) Clinical Chemistry 41(9), 1391-1397. Inhibition can also be measured by flow cytometry, where receptor is expressed on cells, or by ELISA, where receptor is adsorbed onto plates.

Optionally, the antibody comprises VH domains encoded by a VDJ region sequence, wherein the VDJ is derived from the recombination of a VH gene segment, D gene segment and JH gene segment, wherein the VH is a human germline (i) VH1-3, (ii) VH2-5 or (iii) VH3-15 gene segment. Additionally or alternatively, optionally the antibody comprises VL domains encoded by a VJ region sequence, wherein the VJ is derived from the recombination of a VL gene segment and JL gene segment, wherein the VL is a human germline (iv) Vκ3-20, (v) Vκ3-1, (vi) Vκ1-17 or (vii) Vλ1-40.

Optionally, the antibody or fragment binds to BMP6 with a stronger affinity (lower KD determined by SPR) than binding to BMP7; and/or optionally binds to BMP6 with a stronger affinity than to BMP5.

For example, (a) the antibody or fragment binds to BMP6 with a stronger affinity (lower KD determined by SPR) than binding to BMP7; and optionally binds to BMP6 with a stronger affinity than to BMP5; and (b) the antibody or fragment competes with a reference antibody for binding BMP6, wherein the reference antibody is mAb507 (R&D Systems) or an Alternative Antibody (eg, an Option 1 antibody or an Option 2 antibody).

Optionally, the antibody of the invention has an affinity (KD) for binding BMP6 of from 1 pM to 5 nM, optionally wherein binding is determined by SPR using a Fab of said antibody at 37° C. at pH 7.6.

Optionally, the antibody has off-rate ($K_{off}$) for binding BMP6 of from $1\times10^{-5}$ to $1\times10^{-3}S^{-1}$, optionally wherein binding is determined by SPR using a Fab of said antibody at 37° C. at pH 7.6.

Optionally, the antibody has on-rate (K.,) for binding BMP6 of from $1\times10^5$ to $1\times10^7$ M$^{-1}$S$^{-1}$, optionally wherein binding is determined by SPR using a Fab of said antibody at 37° C. at pH 7.6.

In an example, the antibody (eg, as a Fab) or fragment has an affinity (KD) for binding BMP6 (eg, human BMP6) of (a) from 2, 3, 4, 5 or 10 pM to 3, 4 or 5 nM;
(b) from 1-10 pM to 5 nM;
(c) from 10 pM to 3, 4 or 5 nM;
(d) from 50 or 80 pM to 200 nM;
(e) from 50 or 80 pM to 150 nM; or
(f) from 50 or 80 pM to 100 nM.

In an example, the KD is (or is about) 5-15 pM (eg, 10 pM). In an example, the KD is (or is about) 2-5 nM (eg, 3 nM). In an example, the KD is (or is about) 100-400 pM (eg, 140 or 390 pM).

In an example, the antibody (eg, as a Fab) or fragment has an off-rate ($K_{off}$) for binding BMP6 (eg, human BMP6) of (a) from $1\times10^{-5}$ to $5\times10^{-4}$ S$^{-1}$;
(b) from $1\times10^{-5}$ to $6\times10^{-4}$ S$^{-1}$;
(c) from $1\times10^{-5}$ to $7\times10^{-4}$ S$^{-1}$;
(d) from $1\times10^{-5}$ to $8\times10^{-4}$ S$^{-1}$;
(e) from $2\times10^{-5}$ to $1\times10^{-4}$ S$^{-1}$;
(f) from $2\times10^{-5}$ to $5\times10^{-4}$ S$^{-1}$;
(g) from $2\times10^{-5}$ to $6\times10^{-4}$ S$^{-1}$;
(h) from $2\times10^{-5}$ to $7\times10^{-4}$S$^{-1}$; or
(i) from $2\times10^{-5}$ to $8\times10^{-4}$S$^{-1}$.

In an example, the $K_{off}$ is (or is about) $5\times10^{-4}$S$^{-1}$ (eg, when the KD is (or is about) from 2 nM to 400 pM; when the KD is (or is about) 2-5 nM (eg, 3 nM); or when the KD is (or is about) 100-400 pM (eg, 140 or 390 pM)). In an example, the $K_{off}$ is (or is about) $3\times10^{-5}$ S$^{-1}$ (eg, when the KD is (or is about) from 5-15 pM (eg, 10 pM)).

In an example, the antibody (eg, as a Fab) or fragment has an on-rate ($K_{on}$) for binding BMP6 (eg, human BMP6) of (a) from $1\times10^1$ to $1\times10^6$ M$^{-1}$S$^{-1}$;
(b) from $1\times10^5$ to $2\times10^6$ M$^{-1}$S$^{-1}$;
(c) from $1\times10^5$ to $3\times10^6$ M$^{-1}$S$^{-1}$;
(d) from $1\times10^5$ to $4\times10^6$ M$^{-1}$S$^{-1}$;
(e) from $1\times10^5$ to $5\times10^6$ M$^{-1}$S$^{-1}$;
(f) from $2\times10^5$ to $5\times10^6$ M$^{-1}$S$^{-1}$;
(g) from $3\times10^5$ to $5\times10^6$ M$^{-1}$S$^{-1}$;
(h) from $4\times10^5$ to $5\times10^6$ M$^{-1}$S$^{-1}$;
(i) from $5\times10^5$ to $5\times10^6$ M$^{-1}$S$^{-1}$; or
(j) from $6\times10^5$ to $5\times10^6$ M$^{-1}$S$^{-1}$.

In an example, the $K_{on}$ is (or is about) 1 or $2\times10^{-5}$ M$^{-1}$S$^{-1}$ (eg, when the KD is 2-5 nM (eg, 3 nM)). In an example, the $K_{on}$ is (or is about) 1-4, 1, 2, 3 or $4\times10^{-6}$ M$^{-1}$S$^{-1}$ (eg, when the KD is (or is about) from 5-400 pM (eg, 140 or 390 pM) or 5-15 pM (eg, 10 pM)).

As provided in the Clauses or other aspects herein, an anti-BMP6 antibody or fragment may bind to BMP6, e.g. human BMP6 with a $K_D$ of less than 50 nM, less than 40 nM, less than 30 nM as determined by surface plasmon resonance. Another embodiment, anti-BMP6 antibody or fragment may bind to BMP6, e.g. human BMP6 with a $K_D$ of less than 20 nM, less than 15 nM, less than 10 nM as determined by surface plasmon resonance. The anti-BMP6 antibody or fragment may bind to BMP6, e.g. human BMP6 with a $K_D$ of less than 8 nM, less than 5 nM, less than 4 nM, less than 3 nM, less than 2 nM or less than 1 nM as determined by surface plasmon resonance. The $K_D$ may be 0.9 nM or less, 0.8 nM or less, 0.7 nM or less, 0.6 nM or less, 0.5 nM or less, 0.4 nM or less, 0.3 nM or less, 0.2 nM or less, or 0.1 nM or less.

In another embodiment, the $K_D$ is within a range of 0.01 to 1 nM, or a range of 0.05 to 2 nM, or a range of 0.05 to 1 nM. The $K_D$ may be with regard to hBMP6, cynomolgus monkey (ie, "cyno") BMP6 and/or mouse BMP6.

In another embodiment, the anti-BMP6 antibodies described herein have a $K_{ON}$ rate (e.g. as measured by SPR, e.g. at 25° C. or at 37° C.) of approximately 0.5 to 10 μM, for example approximately 1 to 8 μM or approximately 1 to 7 μM. In another embodiment, the $K_{ON}$ rate is approximately 1 to 5 μM, e.g. approximately 1 μM, approximately 1.5 μM, approximately 2 μM, approximately 2.5 μM or approximately 3 μM. In another embodiment, the $K_{ON}$ rate is approximately 3.5 μM, approximately 4 μM, approximately 4.5 μM, approximately 5 μM or approximately 5.5 μM.

In another embodiment, the anti-BMP6 antibodies described herein have a $K_{OFF}$ rate (e.g. as measured by SPR, e.g. at 25° C. or at 37° C.) of approximately 0.01 to 100 mM, for example approximately 0.1 to 50 mM or approximately 0.5 to 50 mM. In another embodiment, the $K_{OFF}$ rate is approximately 0.5 to 10 mM, or approximately 0.5 to 10 mM, e.g. approximately 1 mM, approximately 2 mM, approximately 3 mM, approximately 4 mM or approximately 5 mM. In another embodiment, the $K_{OFF}$ rate is approximately 0.6 mM, approximately 0.7 mM, approximately 0.8 mM or approximately 0.9 mM.

The invention also provides the following method (or the antibody or fragment of the invention for use in such a method):—

A method of treating anaemia in a subject, the method comprising (a) on an initial day ($D_0$) administering to the subject the anti-BMP6 antibody or fragment; and (b) in a period of at least 3 consecutive weeks, said period starting on $D_0$, administering a plurality of doses of an erythropoietin stimulating agent (ESA) wherein blood haemoglobin (Hb) concentration in said subject is elevated from a baseline concentration on $D_0$ for the entire duration of said period, (c) such that for the entire duration of said period:—

(i) Hb concentration is no lower than 100% of baseline Hb concentration; and during said period Hb concentration reaches at least 120% of baseline; and/or (ii) Hb concentration is increased over baseline by at least 1 g/dl.

Optionally, the antibody, fragment or combination inhibits iron release by human liver cells, eg, in an in vitro assay or in a human. The skilled addressee will be aware of standard assays, such as those mentioned in the Examples herein.

Optionally, the antibody, fragment or combination is for treating or preventing a BMP6-mediated disease or condition as disclosed herein in a human by inhibiting iron release by human liver cells in the human. Optionally, the antibody, fragment or combination is for treating or preventing anaemia, PAH or fibrosis in a human by inhibiting iron release by human liver cells in the human.

Optionally, the antibody, fragment or combination is for treating or preventing a BMP6-mediated disease or condition as disclosed herein in a human by inhibiting hamp gene expression in human liver cells in the human. Optionally, the antibody, fragment or combination is for treating or preventing anaemia, PAH or fibrosis in a human by inhibiting hamp gene expression in human liver cells in the human.

Optionally, the antibody, fragment or combination is for treating or preventing a BMP6-mediated disease or condition as disclosed herein in a human by inhibiting hepcidin or expression thereof in human liver cells in the human. Optionally, the antibody, fragment or combination is for treating or preventing anaemia, PAH or fibrosis in a human by inhibiting hepcidin or expression thereof in human liver cells in the human.

Optionally, the antibody, fragment or combination is for treating or preventing a BMP6-mediated disease or condition as disclosed herein in a human by inhibiting BMP6 activation of hamp gene expression in the human (eg, in liver cells thereof). Optionally, the antibody, fragment or combination is for treating or preventing anaemia, PAH or fibrosis in a human by inhibiting BMP6 activation of hamp gene expression in the human (eg, in liver cells thereof).

Optionally, the antibody, fragment or combination is for treating or preventing a BMP6-mediated disease or condition as disclosed herein in a human by inhibiting HJV-mediated activation of hamp gene expression in the human (eg, in liver cells thereof). Optionally, the antibody, fragment or combination is for treating or preventing anaemia, PAH or fibrosis in a human by inhibiting HJV-mediated activation of hamp gene expression in the human (eg, in liver cells thereof). In an example, the antibody or fragment competitively inhibits HJV binding to BMP6 in vitro and/or in the human. In vitro competition may be determined by standard SPR or ELISA, for example.

In an example, the antibody or fragment inhibits human BMP6 induced luciferase expression in HepG2 cells under control of a hamp regulatory region in vitro.

Optionally, the antibody, fragment or combination is for treating or preventing a BMP6-mediated disease or condition as disclosed herein in a human by inhibiting BMP binding in the human (eg, in liver cells thereof). Optionally, the antibody, fragment or combination is for treating or preventing anaemia, PAH or fibrosis in a human by inhibiting BMP binding in the human (eg, in liver cells thereof). In an example, the antibody or fragment binds to an epitope where HJV contacts BMP6 to form a HJV-BMP6 complex which is capable of activating hamp gene expression in human liver cells.

In an example, the human cells are HepG2 cells in vitro. More details are provided in the examples herein. In an example, the inhibition is inhibition in a HepG2 cell assay in vitro, eg, as determined by inhibition of a reporter gene under control of one or more human hamp regulatory elements in vitro. For example the regulatory elements comprise response elements to pSMAD (BMP) and pSTAT (IL6). In an example, the assay is carried out using human BMP6, cynomolgus monkey BMP6, rat BMP6 or mouse BMP6; and/or the assay is carried out using human HJV, cynomolgus monkey HJV, rat HJV or mouse HJV. In an example the reporter is a luciferase gene. In an example, the antibody or fragment neutralises BMP activation of the reporter gene expression in the assay, eg, the neutralisation is at least 20, 30, 40, 50, 60, 70, 80, 90 or 95% or is complete neutralisation.

In an example, the antibody or fragment competes with a reference antibody for binding to BMP6, eg as determined by SPR, ELISA or in a HepG2 assay (eg, a HepG2 assay as described herein), eg, determined in vitro using a labelled reference antibody. In an example, competition reduces said binding by at least 20, 30, 40, 50, 60, 70, 80, 90 or 95% or is complete inhibition of the binding. For example the reference antibody is MAb507 or MAb2365; for example the reference antibody is an Alternative Antibody (eg, an Option 1 or Option 2 antibody).

In an example a or the BMP6 herein is human BMP6 (Peprotech #120-06) (SEQ ID NO: 2). In an example a or the BMP6 herein is any other human BMP6 disclosed herein.

In an example the antibody or fragment binds to human BMP6 with an off-rate of $1 \times 10^{-4}$ S$^{-1}$ or lower as determined by surface plasmon resonance (SPR), eg, at room temperature or rtp. See Examples.

In an example, the antibody competes for binding to human BMP6 with a reference antibody selected from CL-66833, CL-57890, CL-57931, CL-58838, CL-58851, CL-58252, CL-58102, CL-57859, CL-58832, CL-57945, CL-75714, CL-75605, CL-75565, CL-75539, CL-75520, CL-75519, CL-75511, CL-75506, CL-75500, CL-75496, CL-75194, CL-75183, CL-58722, CL-58713, CL-58680, CL-58679, CL-58921, CL-58676, CL-58835, CL-58650 and CL-58756; eg, selected from CL-66833, CL-57931, CL-58838, CL-58851, CL-58252, CL-58102 and CL-57945; eg, selected from CL-58722, CL-58713, CL-58680, CL-58679, CL-58921, CL-58676, CL-58835, CL-58650 and CL-58756.

In an alternative, the reference antibody herein is selected from CL-58838, CL-66833, CL-57931, CL-57945, CL-58102, CL-58252, CL-58851, CL-75183, CL-75500, CL-75506, CL-75520, CL-75539, CL-75565, CL-75714, CL-58722, CL-58835, CL-58756, CL-58650, CL-58679, CL-58680 and CL-58713.

Optionally, the reference antibody is CL-58838.

In an example, the antibody competes for binding to human BMP6 with a reference antibody, the reference antibody comprising a VH amino acid sequence selected from SEQ ID Nos: 24, 42, 114, 132, 96, 78, 60, 258, 240, 222, 204, 186, 168, 150, 276, 384, 366, 348, 294, 330 and 312 C; eg, selected from SEQ ID Nos: 24, 42, 114, 132, 96, 78 and 60; eg, selected from SEQ ID Nos: 276, 384, 366, 348, 294, 330 and 312; and/or the reference antibody comprising (eg, respectively comprising) a VL amino acid sequence selected from SEQ ID Nos: 33, 51, 123, 141, 105, 87, 69, 267, 249, 231, 213 195, 177, 159, 285, 393, 375, 357, 303, 339 and 321; eg, selected from SEQ ID Nos: 33, 51, 123, 141, 105, 87 and 69; eg, selected from SEQ ID Nos: 285, 393, 375, 357, 303, 339 and 321. In an example, the reference antibody is an IgG4 (eg, IgG4-PE) antibody. In an example, the reference antibody is an IgG1 antibody. In an example, the antibody of the invention is an IgG4 (eg, IgG4-PE) antibody. In an example, the antibody of the invention is an IgG1 antibody. In an example, the antibody of the invention binds preferentially to human BMP6 than to human BMP5 and/or human BMP7. Binding or competition may be determined, for example, by SPR or ELISA, as will be known by the skilled addressee.

In an example, the antibody competes for binding to human BMP6 with a reference antibody, the reference antibody comprising a VH amino acid sequence of a VH of an antibody selected from the sequence table herein; or selected from the tables in the Examples; or selected from CL-66833, CL-57890, 42 CL-57931, 114 CL-58838, 132 CL-58851, 96 CL-58252, 78 CL-58102, CL-57859, CL-58832, 60 CL-57945, 258 CL-75714, CL-75605, 240 CL-75565, 222 CL-75539, 204 CL-75520, CL-75519, CL-75511, 186 CL-75506, 168 CL-75500, CL-75496, CL-75194, 150 CL-75183, 276 CL-58722, 384 CL-58713, 366 CL-58680, 348 CL-58679, CL-58921, CL-58676, 294 CL-58835, 330 CL-58650 and 312 CL-58756; and/or the reference antibody comprising a VL amino acid sequence of a VH of the selected antibody. In an example, the reference antibody is an IgG4 (eg, IgG4-PE) antibody. In an example, the reference antibody is an IgG1 antibody. In an example, the antibody of the invention is an IgG4 (eg, IgG4-PE) antibody. In an example, the antibody of the invention is an IgG1 antibody. In an example, the antibody of the invention binds preferentially to human BMP6 than to human BMP5 and/or human BMP7. Binding or competition may be determined, for example, by SPR or ELISA, as will be known by the skilled addressee.

In an example, the invention antibody or fragment comprises the VH and VL domains of CL-66833, CL-57890, CL-57931, CL-58838, CL-58851, CL-58252, CL-58102, CL-57859, CL-58832, CL-57945, CL-75714, CL-75605, CL-75565, CL-75539, CL-75520, CL-75519, CL-75511, CL-75506, CL-75500, CL-75496, CL-75194, CL-75183, CL-58722, CL-58713, CL-58680, CL-58679, CL-58921, CL-58676, CL-58835, CL-58650 or CL-58756.

In an example, the invention antibody or fragment comprises the VH and VL domains of CL-66833.

In an example, the invention antibody or fragment comprises the VH and VL domains of CL-57931.

In an example, the invention antibody or fragment comprises the VH and VL domains of CL-58838.

In an example, the invention antibody or fragment comprises the VH and VL domains of CL-58851.

In an example, the invention antibody or fragment comprises the VH and VL domains of CL-58252.

In an example, the invention antibody or fragment comprises the VH and VL domains of CL-58102.

In an example, the invention antibody or fragment comprises the VH and VL domains of CL-57945.

In an example, the selected antibody is CL-66833, CL-57931, CL-58838, CL-58851, CL-58252 or CL-58102. In an example, the selected antibody is CL-66833. In an example, the selected antibody is CL-58838.

In an example, the selected antibody comprises the variable domains of CL-66833, CL-57931, CL-58838, CL-58851, CL-58252 or CL-58102. In an example, the selected antibody comprises the variable domains of CL-66833. In an example, the selected antibody comprises the variable domains of CL-58838.

In an example, the selected antibody comprises the VH domains of CL-66833, CL-57931, CL-58838, CL-58851, CL-58252 or CL-58102. In an example, the selected antibody comprises the VH domains of CL-66833. In an example, the selected antibody comprises the VH domains of CL-58838.

In an example, the selected antibody comprises the VH and VL domains of CL-66833, CL-57931, CL-58838, CL-58851, CL-58252 or CL-58102. In an example, the selected antibody comprises the VH and VL domains of CL-66833. In an example, the selected antibody comprises the VH and VL domains of CL-58838.

In an example, the antibody or fragment of the invention comprises VH domains encoded by a nucleotide sequence that is a recombinant of human gene segments IGHV3-11 and IGHJ4 (eg, human gene segments IGHV3-11*01 and IGHJ4*02; IGHV3-11, IGHD6-19, IGHJ4; or IGHV3-11*01, IGHD6-19*01 and IGHJ4*02). Additionally or alternatively, optionally the antibody or fragment of the invention comprises VL domains encoded by a nucleotide sequence that is a recombinant of human gene segments IGKV3-20 and IGKJ1 (eg, IGKV3-20*01 and IGKJ1*01). Additionally or alternatively, optionally the antibody or fragment of the invention comprises the HCDR3 of CL-58835.

Optionally, the antibody or fragment of the invention comprises the HCDR3 of an antibody selected from CL-66833, CL-57890, CL-57931, CL-58838, CL-58851, CL-58252, CL-58102, CL-57859, CL-58832, CL-57945, CL-75714, CL-75605, CL-75565, CL-75539, CL-75520, CL-75519, CL-75511, CL-75506, CL-75500, CL-75496, CL-75194, CL-75183, CL-58722, CL-58713, CL-58680, CL-58679, CL-58921, CL-58676, CL-58835, CL-58650 and CL-58756; eg, selected from CL-66833, CL-57931, CL-58838, CL-58851, CL-58252, CL-58102 and CL-57945. Optionally, the antibody or fragment of the invention comprises the HCDR1 and/or HCDR2 of said selected antibody.

Optionally the antibody or fragment of the invention comprises the HCDR1 of an antibody selected from CL-66833, CL-57890, CL-57931, CL-58838, CL-58851, CL-58252, CL-58102, CL-57859, CL-58832, CL-57945, CL-75714, CL-75605, CL-75565, CL-75539, CL-75520, CL-75519, CL-75511, CL-75506, CL-75500, CL-75496, CL-75194, CL-75183, CL-58722, CL-58713, CL-58680, CL-58679, CL-58921, CL-58676, CL-58835, CL-58650 and CL-58756; eg, selected from CL-66833, CL-57931, CL-58838, CL-58851, CL-58252, CL-58102 and CL-57945. Optionally, the antibody or fragment of the invention comprises the HCDR2 and/or HCDR3 of said selected antibody.

Optionally the antibody or fragment of the invention comprises the HCDR2 of an antibody selected from CL-66833, CL-57890, CL-57931, CL-58838, CL-58851, CL-58252, CL-58102, CL-57859, CL-58832, CL-57945, CL-75714, CL-75605, CL-75565, CL-75539, CL-75520, CL-75519, CL-75511, CL-75506, CL-75500, CL-75496, CL-75194, CL-75183, CL-58722, CL-58713, CL-58680, CL-58679, CL-58921, CL-58676, CL-58835, CL-58650 and CL-58756; eg, selected from CL-66833, CL-57931, CL-58838, CL-58851, CL-58252, CL-58102 and CL-57945. Optionally, the antibody or fragment of the invention comprises the HCDR1 and/or HCDR3 of said selected antibody.

Optionally, the antibody or fragment of the invention comprises the VH of an antibody selected from CL-66833, CL-57890, CL-57931, CL-58838, CL-58851, CL-58252, CL-58102, CL-57859, CL-58832, CL-57945, CL-75714, CL-75605, CL-75565, CL-75539, CL-75520, CL-75519, CL-75511, CL-75506, CL-75500, CL-75496, CL-75194, CL-75183, CL-58722, CL-58713, CL-58680, CL-58679, CL-58921, CL-58676, CL-58835, CL-58650 and CL-58756; eg, selected from CL-66833, CL-57931, CL-58838, CL-58851, CL-58252, CL-58102 and CL-57945; eg, selected from CL-58722, CL-58713, CL-58680, CL-58679, CL-58921, CL-58676, CL-58835, CL-58650 and CL-58756. Optionally, the antibody or fragment of the invention comprises the VL of said selected antibody.

Optionally, the antibody or fragment of the invention comprises the VL of an antibody selected from CL-66833, CL-57890, CL-57931, CL-58838, CL-58851, CL-58252, CL-58102, CL-57859, CL-58832, CL-57945, CL-75714, CL-75605, CL-75565, CL-75539, CL-75520, CL-75519, CL-75511, CL-75506, CL-75500, CL-75496, CL-75194, CL-75183, CL-58722, CL-58713, CL-58680, CL-58679, CL-58921, CL-58676, CL-58835, CL-58650 and CL-58756; eg, selected from CL-66833, CL-57931, CL-58838, CL-58851, CL-58252, CL-58102 and CL-57945; eg, selected from CL-58722, CL-58713, CL-58680, CL-58679, CL-58921, CL-58676, CL-58835, CL-58650 and CL-58756. Optionally, the antibody or fragment of the invention comprises the VH of said selected antibody.

Optionally, the antibody or fragment of the invention comprises the heavy chain of an antibody selected from CL-66833, CL-57890, CL-57931, CL-58838, CL-58851, CL-58252, CL-58102, CL-57859, CL-58832, CL-57945, CL-75714, CL-75605, CL-75565, CL-75539, CL-75520, CL-75519, CL-75511, CL-75506, CL-75500, CL-75496, CL-75194, CL-75183, CL-58722, CL-58713, CL-58680, CL-58679, CL-58921, CL-58676, CL-58835, CL-58650 and CL-58756; eg, selected from CL-66833, CL-57931, CL-58838, CL-58851, CL-58252, CL-58102 and CL-57945; eg, selected from CL-58722, CL-58713, CL-58680, CL-58679, CL-58921, CL-58676, CL-58835, CL-58650 and CL-58756. Optionally, the antibody or fragment of the invention comprises the light chain of said selected antibody.

Optionally, the antibody or fragment of the invention comprises the light chain of an antibody selected from CL-66833, CL-57890, CL-57931, CL-58838, CL-58851, CL-58252, CL-58102, CL-57859, CL-58832, CL-57945, CL-75714, CL-75605, CL-75565, CL-75539, CL-75520, CL-75519, CL-75511, CL-75506, CL-75500, CL-75496, CL-75194, CL-75183, CL-58722, CL-58713, CL-58680, CL-58679, CL-58921, CL-58676, CL-58835, CL-58650 and CL-58756; eg, selected from CL-66833, CL-57931, CL-58838, CL-58851, CL-58252, CL-58102 and CL-57945; eg, selected from CL-58722, CL-58713, CL-58680, CL-58679, CL-58921, CL-58676, CL-58835, CL-58650 and CL-58756. Optionally, the antibody or fragment of the invention comprises the heavy chain of said selected antibody.

In an example, the selected antibody is CL-58835.

Optionally, the antibody of the invention comprises a human IgG4 constant region.

Preferably, an antibody or a fragment thereof that specifically binds to a hBMP6 does not cross-react with other antigens (but may optionally cross-react with different BMP6 species, e.g., rhesus, cynomolgus, or murine; and or may optionally cross-react with different BMPs, e.g., BMP2, 4 or 9). An antibody or a fragment thereof that specifically binds to a BMP6 antigen can be identified, for example, by immunoassays, BIAcore™, or other techniques known to those of skill in the art. An antibody or a fragment thereof binds specifically to a hBMP6 antigen when it binds to a hBMP6 antigen with higher affinity than to any cross-reactive antigen as determined using experimental techniques, such as radioimmunoassays (RIA) and enzyme-linked immunosorbent assays (ELISAs).

Typically, a specific or selective reaction will be at least twice background signal or noise and more typically more than 10 times background. See, e.g. Paul, ed., 1989, Fundamental Immunology Second Edition, Raven Press, New York at pages 332-336 for a discussion regarding antibody specificity.

Contact amino acid residues involved in the interaction of antibody and antigen, such as BMP6, may be determined by various known methods to those skilled in the art.

In one embodiment, if the antibody recognises a linear epitope, short peptides based on the antigen sequence can be produced and binding of the antibody to these peptides can be assessed using standard techniques.

In one embodiment, limited proteolytic digestion and mass spectrophotometry can be used to identify binding epitopes.

In one embodiment, the contact residues of the epitope are identified by X-ray crystallography. In one embodiment, the contact residues of the epitope are identified by cryo-electro microscopy. In one embodiment, the contact residues of the epitope are identified by a combination of limited proteolytic digestion and mass spectrometry.

In another embodiment, the anti-BMP6 antibodies (and fragments) described in herein provide improved transient expression levels over other anti-BMP6 antibodies and fragments. Thus, in one embodiment, the anti-BMP6 antibody (or fragment) is expressed in a HEK293 cell, e.g. a HEK293T cell, at an expression level of approximately 100 μg/mL, or in a range of approximately 100 to 350 μg/mL. In another embodiment, the expression level is above approximately 350 μg/mL.

In another embodiment, the anti-BMP6 antibody (or fragment) is expressed in a CHO cell, e.g. an Expi-CHO cell, at an expression level of approximately 100 μg/mL, or in a range of approximately 100 to 350 μg/mL. In another embodiment, the expression level is above approximately 350 μg/mL.

In another embodiment, the anti-BMP6 antibody (or fragment) is expressed in a CHO cell, e.g. an Expi-CHO cell or a CHO-E7 EBNA cell, at an expression level of approximately 100 μg/mL, or in a range of approximately 100 to 350 μg/mL. In another embodiment, the expression level is above approximately 350 μg/mL. The antibody for example, comprises the VH and VL domains of any one of CL-58838, formatted as a human IgG1 or human IgG4 (eg, IgG4-PE).

In any of these expression systems, the expression is carried out of a scale of between approximately 0.5 mL and 3 mL, for example between approximately 0.5 mL and 2 mL. In any of these expression systems, the anti-BMP6 antibody (or fragment) may be expressed from a pTT5 vector. In any of these expression systems, the anti-BMP6 antibody (or fragment) may be expressed in conjunction with a lipid transfection reagent, and may optionally be expressed in a CHO cell, e.g. an Expi-CHO cell. In any of these expression systems, the anti-BMP6 antibody (or fragment) may be expressed in conjunction with a PEI transfection reagent, and may optionally be expressed in a CHO cell, e.g. an CHO-E7 EBNA cell. In any of these expression systems, the anti-BMP6 antibody (or fragment) may be expressed in conjunction with a helper plasmid (e.g. an AKT helper plasmid), and may optionally be expressed in a CHO cell, e.g. an CHO-E7 EBNA cell.

In any of these expression systems, the expression level is between approximately 100 µg/mL and approximately 1500 µg/mL, for example between approximately 100 µg/mL and approximately 1000 µg/mL, or between approximately 200 µg/mL and approximately 1000 µg/mL, or between approximately 350 µg/mL and approximately 1000 µg/mL. In any of these expression systems, the lower limit of expression may be approximately 100 µg/mL, approximately 200 µg/mL, approximately 300 µg/mL, or approximately 400 µg/mL. In another embodiment, the lower limit of expression may be approximately 500 µg/mL, approximately 600 µg/mL, approximately 700 µg/mL, or approximately 800 µg/mL. In any of these expression systems, the upper limit of expression may be approximately 2000 µg/mL, approximately 1800 µg/mL, approximately 1600 µg/mL, or approximately 1500 µg/mL. In another embodiment, the upper limit of expression may be approximately 1250 µg/mL, approximately 1000 µg/mL, approximately 900 µg/mL, or approximately 800 µg/mL.

In another embodiment, the expression system is a Lonza expression system, e.g. Lonza X-Ceed® system. In the Lonza expression system, the expression may be carried out at a scale of approximately 30 mL to 2 L, for example 50 mL to 1 L, or 1 L tp 2 L. In the Lonza expression system, the anti-BMP6 antibody (or fragment) may be expressed in conjunction with electroporation, and optionally without any helper plasmids. In the Lonza expression system, the anti-BMP6 antibody (or fragment) may be expressed at a level of approximately 1 g/L, or approximately 900 mg/L, or approximately 800 mg/L, or approximately 700 mg/L. In another embodiment, In the Lonza expression system, the anti-BMP6 antibody (or fragment) may be expressed at a level of approximately 600 mg/L or approximately 500 mg/L or approximately 400 mg/L. In the Lonza expression system, the anti-BMP6 antibody (or fragment) may be expressed at a level of between approximately 400 mg/L and approximately 2 g/L, for example between approximately 500 mg/L and approximately 1.5 g/L, or between approximately 500 mg/L and approximately 1 g/L. In another embodiment, the expression level is above 1 g/L. In another embodiment, the anti-BMP6 antibodies provide improved half-life over other anti-BMP6 antibodies.

In one embodiment, the antibody or fragment is a human antibody or fragment. In one embodiment, the antibody or fragment is a fully human antibody or fragment. In one embodiment, the antibody or fragment is a fully human monoclonal antibody or fragment.

in one embodiment, the antibody or fragment is a humanised antibody or fragment. In one embodiment, the antibody or fragment is a humanised monoclonal antibody or fragment.

Contact amino acid residues involved in the interaction of antibody and antigen may be determined by various known methods to those skilled in the art, such as alanine scanning, protein crystallography, mass spectrophotometry or any other technique as will be apparent to the skilled addressee.

In one embodiment, the recited CDR comprises one amino acid substitution, which may be a conservative amino acid substitution. In one embodiment, the recited CDR comprises two amino acid substitutions, which may be conservative amino acid substitutions. In one embodiment, the recited CDR comprises three amino acid substitutions, which may be conservative amino acid substitutions. In one embodiment, the recited CDR comprises four amino acid substitutions, which may be conservative amino acid substitutions. In one embodiment, the recited CDR comprises five amino acid substitutions, which may be conservative amino acid substitutions. In one embodiment, the recited CDR comprises six amino acid substitutions, which may be conservative amino acid substitutions.

Amino acid substitutions include alterations in which an amino acid is replaced with a different naturally-occurring amino acid residue. Such substitutions may be classified as "conservative", in which case an amino acid residue contained in a polypeptide is replaced with another naturally occurring amino acid of similar character either in relation to polarity, side chain functionality or size.

Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g. substituting a charged or hydrophobic amino; acid with alanine), or alternatively, in which a naturally-occurring amino acid is substituted with a non-conventional amino acid.

In one embodiment, the conservative amino acid substitutions are as described herein. For example, the substitution may be of Y with F, T with S or K, P with A, E with D or Q, N with D or G, R with K, G with N or A, T with S or K, D with N or E, I with L or V, F with Y, S with T or A, R with K, G with N or A, K with R, A with S, K or P. In another embodiment, the conservative amino acid substitutions may be wherein Y is substituted with F, T with A or S, I with L or V, W with Y, M with L, N with D, G with A, T with A or S, D with N, I with L or V, F with Y or L, S with A or T and A with S, G, T or V.

Combinations

The antibody or fragment of the invention may be comprised by a combination therapy with an ESA for treating or preventing anaemia, particularly moderate to severe anaemia (ie, indicated by a blood haemoglobin of less than 9.5 g/dL). Such combination may be efficacious for treating anaemia such as ACD (Anaemia of Chronic Disease), inflammation or infection and the combination therapy may produce maintenance and elevation of blood haemoglobin concentration that is statistically significant versus use of an anti-BMP6 antibody alone. Furthermore, such effects may be durable over weeks (even after a single dose of administered anti-BMP6 antibody). Additionally, the combination therapy of the invention is useful for ESA sparing anaemia therapy, ie, enabling ESA treatment with lower than standard doses of ESA. This is useful in view of potentially harmful side-effects of ESAs. The invention also may be useful for anaemia therapy in subjects that are refractory to ESAs or have poor response to standard ESA therapy. The invention usefully can maintain blood haemoglobin outside a moderate to severe anaemia range and/or prevent decrease of blood haemoglobin to such a range. The invention, thus, is useful for reducing the need for iron or blood transfusion therapy.

The invention is useful for anaemia therapy in inflammatory disease settings and microbial infection settings.

To this end, the invention provides the following configurations 1-13:—

1. A method of maintaining a blood haemoglobin level of at least 10 g/dL in a subject, the method comprising administering an anti-BMP6 antagonist and an erythropoiesis stimulating agent (ESA) to the subject.

2. A method of preventing the blood haemoglobin level of a subject from decreasing to less than 10 g/dL, the method comprising administering an anti-BMP6 antagonist and an erythropoiesis stimulating agent (ESA) to the subject.

3. A method of raising blood haemoglobin to a level of at least 10 g/dL in a subject suffering from anaemia, the method comprising administering an anti-BMP6 antagonist and an erythropoiesis stimulating agent (ESA) to the subject, wherein said anaemia is treated.

4. A method of treating or preventing moderate or severe anaemia in a subject, the method comprising administering an anti-BMP6 antagonist and an erythropoiesis stimulating agent (ESA) to the subject, wherein said anaemia is treated or prevented.

5. A method of treating or preventing anaemia in a subject suffering from an inflammatory disease or condition, the method comprising administering an anti-BMP6 antagonist and an erythropoiesis stimulating agent (ESA) to the subject, wherein said anaemia is treated or prevented.

6. A method of eliminating or reducing the need to administer iron or blood transfusion to a subject suffering from anaemia, the method comprising administering an anti-BMP6 antagonist and an erythropoiesis stimulating agent (ESA) to the subject, wherein said need is eliminated or reduced.

In an example, one, more or all of labile plasma iron (LPI), enhanced LPI (eLPI) and non-transferrin bound iron (NTBI) are reduced in the subject. In an example, one, more or all of labile plasma iron (LPI), enhanced LPI (eLPI) and non-transferrin bound iron (NTBI) are reduced in the subject.

7. A method of treating or preventing anaemia in a subject suffering from a microbial infection, the method comprising administering an anti-BMP6 antagonist and an erythropoiesis stimulating agent (ESA) to the subject.

8. A method of reducing administration of an erythropoiesis stimulating agent (ESA) to a subject suffering from anaemia for treating anaemia, the method comprising administering an anti-BMP6 antagonist and said ESA, wherein anaemia is treated in the subject.

9. A method of treating or reducing the risk of anaemia in a subject suffering from or at risk of anaemia, the method comprising administering an anti-BMP6 antagonist and a low dose of an erythropoiesis stimulating agent (ESA) to the subject, wherein anaemia is treated or the risk of anaemia is reduced in the subject.

10. A therapeutic regimen for treating or preventing anaemia in a subject suffering from or at risk of anaemia, the regimen comprising simultaneously or sequentially administering an anti-BMP6 antagonist and an ESA to the subject, wherein a. On day zero the antagonist is administered to the subject; and no later than day 7 (eg, on day 1) the ESA is administered to the subject; or b. On day zero the ESA is administered to the subject; and no later than day 7 (eg, on day 1) the antagonist is administered to the subject; or c. On day zero the antagonist and the ESA are simultaneously administered to the subject; or d. On day zero the subject has already received the ESA and on day zero the antagonist is administered to the subject; or e. On day zero the subject has already received the antagonist and on day zero the ESA is administered to the subject;

whereby at day 14 or later the blood haemoglobin level is at least 10 g/dL in the subject, wherein said anaemia is treated or prevented.

11. A combination therapy for use in a method or regimen of any preceding claim for treating or preventing anaemia in a subject, the combination comprising a. An anti-BMP6 antagonist;

b. An ESA; and c. Optionally instructions for use in the method or regimen.

12. An anti-BMP6 antagonist for use in in a method or regimen of any preceding configuration for treating or preventing anaemia in a subject.

13. An anti-Bone Morphogenetic Protein 6 (BMP6) antagonist for use in a method of treating or preventing anaemia in a subject, the method comprising administering said anti-BMP6 antagonist and an erythropoiesis stimulating agent (ESA) to the subject, wherein said anaemia is treated or prevented.

When an "anti-BMP6 antagonist" is mentioned herein, the antagonist may be any anti-BMP6 antibody or fragment disclosed herein, such as Alternative Antibody or fragment (as described elsewhere herein) or any antibody or fragment as claimed or in the statement of invention or mentioned in the Examples, such as in Tables 4 to 11.

In an aspect, the antagonist comprises or consists of an anti-BMP6 antibody or fragment, the method comprising (a) on an initial day ($D_0$) administering to the subject the anti-BMP6 antibody or fragment; and (b) in a period of at least 3 consecutive weeks, said period starting on $D_0$, administering a plurality of doses of an ESA wherein blood Hb concentration in said subject is elevated from a baseline concentration on Do for the entire duration of said period, such that:—

(i) for the entire duration of said period Hb concentration is no lower than 100% of baseline Hb concentration; and during said period Hb concentration reaches at least 120% of baseline; and/or (ii) for the entire duration of said period Hb concentration is increased over baseline by at least 1 g/dl.

Aspects of the invention are as follows, and these aspects (and any un-numbered paragraphs) are combinable with any other configuration, example, feature, aspect or Clause of the invention as described herein; an antagonist (eg, anti-BMP6 antibody or fragment) or ESA of the invention can be provided for use in (or can be used in) a method in the following aspects:—

1. A method of maintaining a blood haemoglobin level of at least 10, 10.5, 11, 11.5, 12, 12.5 or 13 g/dL in a subject, the method comprising administering an anti-BMP6 antagonist and an erythropoiesis stimulating agent (ESA) to the subject.

In an example, Hb level is no more than 11, 11.5 or 12 g/dl in the subject.

2. A method of preventing the blood haemoglobin level of a subject from decreasing to less than 10, 10.5, 11, 11.5, 12, 12.5 or 13/dL, the method comprising administering an anti-BMP6 antagonist and an erythropoiesis stimulating agent (ESA) to the subject.

3. A method of raising blood haemoglobin to a level of at least 10, 10.5, 11, 11.5, 12, 12.5 or 13 g/dL in a subject suffering from anaemia, the method comprising administering an anti-BMP6 antagonist and an erythropoiesis stimulating agent (ESA) to the subject, wherein said anaemia is treated.

In an example of any aspect, the subject is suffering from moderate or severe anaemia prior to administration of the BMP6 antagonist. An outcome of the method is, in one embodiment, that the subject does not have anaemia or has mild (and not moderate or severe) anaemia.

4. A method of treating or preventing moderate or severe anaemia in a subject, the method comprising administering an anti-BMP6 antagonist and an erythropoiesis stimulating agent (ESA) to the subject, wherein said anaemia is treated or prevented.

5. A method of treating or preventing anaemia in a subject suffering from an inflammatory disease or condition, the method comprising administering an anti-BMP6 antagonist and an erythropoiesis stimulating agent (ESA) to the subject, wherein said anaemia is treated or prevented.

In an example, the inflammatory disease or condition is selected from the group consisting of inflammation of microbial infection (eg, a bacterial infection) or rheumatoid arthritis. In an example, the anaemia is anaemia of inflammation (also known as anaemia of chronic disease, ACD).

6. A method of eliminating or reducing the need to administer iron or blood transfusion to a subject suffering from anaemia, the method comprising administering an anti-BMP6 antagonist and an erythropoiesis stimulating agent (ESA) to the subject, wherein said need is eliminated or reduced.

In an embodiment, the method reduces the dose (eg, weekly, fortnightly or monthly dose) or dosing frequency of iron.

7. A method of treating or preventing anaemia in a subject suffering from a microbial (eg, bacterial) infection, the method comprising administering an anti-BMP6 antagonist and an erythropoiesis stimulating agent (ESA) to the subject.

8. A method of reducing administration of an erythropoiesis stimulating agent (ESA) to a subject suffering from anaemia for treating anaemia, the method comprising administering an anti-BMP6 antagonist and said ESA, wherein anaemia is treated in the subject.

9. A method of treating or reducing the risk of anaemia in a subject suffering from or at risk of anaemia, the method comprising administering an anti-BMP6 antagonist and a low dose of an erythropoiesis stimulating agent (ESA) to the subject, wherein anaemia is treated or the risk of anaemia is reduced in the subject.

The dose is lower than a standard dose typically used to treat or reduce anaemia in a subject, eg, a human or adult human, such as a male or female. A typical dose for treatment or prophylaxis will be readily apparent to the skilled addressee. For example, see aspect 10.

Epogen is typically formulated in vials in multiple formulations. Single-dose vials, formulated with an isotonic sodium chloride/sodium citrate-buffered solution, are supplied in multiple strengths. Each 1 mL vial contains 2000, 3000, 4000, or 10,000 Units of epoetin alfa, Albumin (Human) (2.5 mg), citric acid (0.06 mg), sodium chloride (5.9 mg), and sodium citrate (5.8 mg) in Water for Injection, USP (pH 6.9±0.3). Single-dose 1 mL vials formulated with an isotonic sodium chloride/sodium phosphate buffer contain 40,000 Units of epoetin alfa albumin (human) (2.5 mg),citric acid (0.0068 mg), sodium chloride (5.8 mg), sodium citrate (0.7 mg), sodium phosphate dibasic anhydrate (1.8 mg), and sodium phosphate monobasic monohydrate (1.2 mg) in Water for Injection, USP (pH 6.9±0.3). Multidose, 2 mL vials contain 10,000 Units epoetin alfa, albumin (human) (2.5 mg), benzyl alcohol (1%), sodium chloride (8.2 mg), and sodium citrate (1.3 mg) per 1 mL Water for Injection, USP (pH 6.1±0.3). Multidose 1 mL vials contain 20,000 Units epoetin alfa, albumin (human) (2.5 mg), benzyl alcohol (1%), sodium chloride (8.2 mg), citric acid (0.11 mg), and sodium citrate (1.3 mg), per 1 mL in Water for Injection, USP (pH 6.1±0.3). In an example of the invention, the ESA is administered as one of these formulations.

10. The method of any preceding aspect, wherein the ESA is a. Epoetin alfa and is administered at a weekly dose of less than 1000, 1500, 2500, 5000, 11000, 18000, 34000 or 90000 units, optionally wherein the subject has previously received a weekly epoetin alfa treatment of <1500, 1500 to 2499, 2500 to 4999, 5000 to 10999, 11000 to 17999, 18000 to 33999, 34000 to 89999 or 90000 units respectively;

b. darbepoetin alfa or Aranesp® and is administered at a weekly dose of less than 6.25, 10, 12.5, 20, 25, 40, 60, 100 or 200 mcg, optionally wherein the subject has previously received a weekly darbepoetin alfa or Aranesp® treatment of 6.25, 10, 12.5, 20, 25, 40, 60, 100 or 200 mcg respectively; or c. darbepoetin alfa or Aranesp® and is administered at a weekly dose of less than 6.25, 10, 20, 40, 60, 100 or 200 mcg, optionally wherein the subject has previously received a weekly Epoetin alfa treatment of 1500 to 2499, 2500 to 4999, 5000 to 10999, 11000 to 17999, 18000 to 33999, 34000 to 89999 or 90,000 units respectively.

11. The method of any preceding aspect, wherein the anti-BMP6 antagonist is an antibody and is administered at a total dose of no more than 30 mg/kg (eg, 0.1 to 30 mg/kg) such as every 1, 2 or 3 weeks, or every month, 2 months or 3 months. Administration can be IV or subcutaneous, eg, and the subject is a human such as a human adult.

12. A therapeutic regimen for treating or preventing anaemia in a subject suffering from or at risk of anaemia, the regimen comprising simultaneously or sequentially administering an anti-BMP6 antagonist and an ESA to the subject, wherein a. On day zero the antagonist is administered to the subject; and no later than day 56, 28, 14 or 7 (eg, on day 1, 6 or 7) the ESA is administered to the subject; or b. On day zero the ESA is administered to the subject; and no later than day 56, 28, 14 or 7 (eg, on day 1, 6 or 7) the antagonist is administered to the subject; or c. On day zero the antagonist and the ESA are simultaneously administered to the subject; or d. On day zero the subject has already received the ESA and on day zero the antagonist is administered to the subject; or e. On day zero the subject has already received the antagonist and on day zero the ESA is administered to the subject;

whereby at day 14 or later (eg, at day 28, 56 or 70) the blood haemoglobin level is at least 10, 10.5, 11, 11.5, 12, 12.5 or 13 g/dL in the subject, wherein said anaemia is treated or prevented.

Optionally the antagonist is administered for a second time no later than day 7 (eg, the antagonist is administered on day 6).

13. The method or regimen of any preceding aspect, wherein the anti-BMP6 antagonist and ESA are administered to the subject no more than 7 days apart.

14. The method or regimen of any one of any preceding aspect, wherein the method or regimen maintains blood haemoglobin level in the subject at more than 10 g/dL in the subject.

15. The method or regimen of any preceding aspect, wherein the method or regimen maintains or raises blood haemoglobin level to at least 10 g/dL in the subject at least 13 or 14 days after the subject has received the anti-BMP6 antagonist and ESA.

16. The method or regimen of aspect 14 or 15, wherein the anti-BMP6 antagonist and ESA are administered to the subject no more than 1 day apart.

17. The method or regimen of any preceding aspect, wherein the anti-BMP6 antagonist and ESA are administered to the subject simultaneously.

18. The method or regimen of any preceding aspect, wherein the blood haemoglobin level of the subject is prevented from decreasing to less than 10, 10.5, 11, 11.5, 12, 12.5 or 13 g/dL (eg, at day 14).

19. The method or regimen of any preceding aspect, wherein the blood haemoglobin of the subject is raised to a level of at least 10, 10.5, 11, 11.5, 12, 12.5 or 13 g/dL (eg, at day 14).

20. The method or regimen of any preceding aspect, wherein moderate or severe anaemia is prevented in the subject (eg, at day 14).

21. The method or regimen of any preceding aspect, wherein the subject is suffering from
   a. an inflammatory disease or condition; or
   b. an infection;
   c. kidney disease;
   d. HIV or undergoing HIV treatment; or
   e. cancer; and
   anaemia is treated or prevented in the subject.

In an example, the subject is suffering from HIV infection is HIV, hepatitis, rheumatoid arthritis, chronic kidney disease or end stage renal disease. For example, the infection is a gram-negative bacterial infection. For example, the infection is a gram-positive bacterial infection.

HIV-infected humans treated with anti-HIV therapies may develop anaemia. Thus, the invention may be useful for treating or preventing anaemia in such patients. In an example, the method or regimen treats or prevents anaemia in a HIV-infected human administered with an anti-HIV therapy, eg, administered with <4200 mg/week zidovudine.

Cancer patients treated with anti-cancer chemotherapy (eg, immunotherapy, eg, by administering an immune checkpoint inhibitor to the subject, eg, an anti-CTLA4, anti-PD-L1, anti-TIGIT, anti-ICOS or anti-PD1 antibody) may develop anaemia. Thus, the invention may be useful for treating or preventing anaemia in such patients. In an example, the method or regimen treats or prevents anaemia in a human suffering from a cancer. In the art, ESAs such as erythropoietin are typically administered to such patients at a dose of 150 units/kg IV or SC 3 times weekly initially; alternatively, 40,000 units SC once weekly until completion of chemotherapy course. In an example, the invention treats or prevents anaemia in a human cancer patient, wherein the ESA is administered to the human at less than 150 units/kg intravenously or subcutaneously 3 times weekly; or a total weekly dose of less than 450 units/kg; or less than 40,000 units subcutaneously weekly.

ESA treatment is used in the art for the reduction of need for red blood cell (RBC) transfusions in patients, eg, in patients undergoing surgery. Thus, ESA treatment is used, for example, in human patients with perioperative haemoglobin >10 g/dL but 13 g/dL who are at high risk for perioperative blood loss from surgery, such as elective, noncardiac, nonvascular surgery. ESA is administered at 300 units/kg SC once daily for 15 consecutive days (10 days preceding surgery, day of surgery, 4 days following surgery); alternatively, 600 units/kg SC in 4 doses administered 21, 14, and 7 days before surgery and on day of surgery. In an example, the invention treats or prevents anaemia in a human surgery patient, wherein the ESA is administered to the human at less than 300 units/kg once daily for 15 consecutive days (10 days preceding surgery, day of surgery, 4 days following surgery); or less than a total 15 day dose of 4500 units/kg; or less than 600 units/kg in 3-5 or 4 doses, eg, administered 21, 14, and 7 days before surgery and on day of surgery.

22. The method of aspect 21, wherein moderate or severe anaemia is treated or prevented in the subject.

23. The method or regimen of any preceding aspect, wherein the subject is a mammal.

24. A combination therapy for use in a method or regimen of any preceding aspect for treating or preventing anaemia in a subject, the combination comprising
   a. An anti-BMP6 antagonist;
   b. An ESA; and
   c. Optionally instructions for use in the method or regimen.

25. An anti-BMP6 antagonist for use in a method or regimen of any preceding aspect for treating or preventing anaemia in a subject.

26. The combination of aspect 24 or the antagonist of aspect 25, for treating or preventing moderate or severe anaemia.

27. The combination of antagonist of any one of aspects 24 to 26 in combination with an anti-inflammatory agent.

28. The method, regimen, combination or antagonist of any preceding aspect, wherein the antagonist comprises an anti-BMP6 antibody binding site, eg, wherein the antagonist is an antibody or anti-BMP6 trap.
   In an example, the trap comprises a human BMP6 receptor domain fused to a human antibody Fc region. In an embodiment, the Fc comprises a human gamma-1 or -4 heavy chain constant region.

29. The method, regimen, combination or antagonist of any preceding aspect, wherein the ESA is an erythropoietin.

30. The method or regimen of any one of aspects 1 to 23, 28 and 29 wherein an anti-inflammatory agent is administered to the subject.

In an example, the invention uses an anti-BMP6 monoclonal antibody (mAb) for mobilizing endogenous iron stores and increasing haemoglobin synthesis and optionally also erythropoiesis. The invention, in one aspect, may reduce the need for simultaneous and prevalent use of intravenous iron or blood transfusions in ACD patients. Additionally or alternatively, the invention may reduce the dose for the underlying standard of care treatment with ESA (eg, EPO) or render ESA (eg, EPO)-non responsive patients (or those with low response) responsive to ESA co-administration with an anti-BMP6 antagonist. Additionally or alternatively, the invention may treat or prevent anaemia in patients whose anaemia is refractory or non-responsive to ESA standard of care. ESAs may be contraindicated in patients that have uncontrolled high blood pressure, or have had pure red cell aplasia (PRCA, a type of anaemia) caused by receiving an ESA (eg, darbepoetin alfa, such as Aranesp®, or eg, epoetin alfa, such as Epogen® or Procrit®.

Thus, in one embodiment of the invention the subject (eg, a human) is i. Refractory or non-responsive to an ESA (eg, darbepoetin alfa or epoetin alfa);

ii. Suffers from or has suffered from high blood pressure (eg, uncontrolled high blood pressure); or iii. Suffers from or has suffered from pure red cell aplasia (eg, caused by receiving an ESA, such as darbepoetin alfa or epoetin alfa).

"Refractory" in relation to drug treatment, such as ESA treatment will be readily apparent to the skilled addressee, and for example means that the subject is ESA-resistant or a low responder to the ESA (ie, has a less than average response) and is not effectively treated for anaemia by the standard of care using an ESA.

ESAs are typically used to maintain haemoglobin at the lowest level that both minimises transfusions and best meets a patient's needs. As explained above, the invention in its various configurations, aspects, examples and embodiments is useful for ESA sparing anaemia therapy, ie, enabling ESA treatment with lower than standard doses of ESA. This is useful in view of potentially harmful side-effects of ESAs. Tables A-D provide relevant information in this respect.

TABLE A

| Aranesp ® dosing information |
| --- |
| Usual Adult Dose of Aranesp for Anaemia Associated with Chronic Renal Failure: |
| Chronic Kidney Disease (CKD) Patients Not on Dialysis:<br>Initial dose: 0.45 mcg/kg IV or subcutaneously once every 4 weeks as appropriate<br>Comments:<br>Initiate treatment only when haemoglobin is less than 10 g/dL, rate of haemoglobin decline indicates likelihood of requiring RBC transfusion, and reducing risk of alloimmunisation and/or other RBC transfusion-related risks is a goal.<br>CKD Patients on Dialysis:<br>Initial dose: 0.45 mcg/kg IV or subcutaneously once a week or 0.75 mcg/kg once every 2 weeks as appropriate<br>Comments:<br>Initiate treatment when haemoglobin is less than 10 g/dL.<br>IV route is recommended for patients on hemodialysis.<br>Usual Adult Dose of Aranesp for Anaemia Associated with Chemotherapy: |
| Initial dose: 2.25 mcg/kg subcutaneously once a week or 500 mcg subcutaneously once every 3 weeks<br>Duration of therapy: Until completion of chemotherapy course<br>Comments:<br>Initiate treatment if haemoglobin is less than 10 g/dL and a minimum of 2 additional months of chemotherapy is planned.<br>Use the lowest dose necessary to avoid RBC transfusions.<br>Use: Treatment of anaemia in patients with non-myeloid malignancies where anaemia is due to the effect of concomitant myelosuppressive chemotherapy.<br>Usual Pediatric Dose of Aranesp for Anaemia Associated with Chronic Renal Failure:<br>Less than 18 Years:<br>Initial dose:<br>Chronic Kidney Disease (CKD) Patients Not on Dialysis: 0.45 mcg/kg IV or subcutaneously once a week or 0.75 mcg/kg once every 2 weeks<br>CKD Patients on Dialysis: 0.45 mcg/kg IV or subcutaneously once a week<br>Comments:<br>Initiate treatment when haemoglobin is less than 10 g/dL.<br>mcg = micrograms |

In an example, the subject is a Chronic Kidney Disease (CKD) patient not on dialysis. In an example, the subject is a Chronic Kidney Disease (CKD) patient on dialysis. In an example, the subject is a chemotherapy patient (eg, receiving or having received chemotherapy treatment for cancer). [Table B follows]

TABLE B

| Aranesp ® Side Effects |
| --- |
| In addition to its needed effects, some unwanted effects may be caused by darbepoetin alfa (the active ingredient contained in Aranesp).<br>More common |
| Abdominal or stomach pain<br>accumulation of pus<br>arm, back, or jaw pain<br>blurred vision<br>breathing problems (irregular, noisy, or trouble when resting)<br>chest pain, discomfort, tightness, or heaviness<br>chills |

TABLE B-continued

Aranesp ® Side Effects confusion
cough producing mucus
decrease in the amount of urine
diarrhea
dilated neck veins
dizziness, fainting, or lightheadedness
dry mouth
fast, slow, or irregular heartbeat
fatigue or tiredness (extreme or unusual)
fever
headache
nausea
pain, tenderness, swelling, or warmth over injection site
pounding in the ears
rapid breathing
rapid or pounding pulse
shortness of breath
skin discoloration at the injection site
sunken eyes
sweating
swelling of the ankles, face, fingers, feet, hands, or lower legs
thirst
trouble with breathing
unconsciousness
vomiting
weight gain
wheezing
wrinkled skin
Less common Anxiety
convulsions
difficulty with speaking (slow speech or unable to speak)
double vision
trouble with thinking
trouble with walking
unable to move the arms, legs, or face muscles (including numbness and tingling)
Rare Fever and sore throat
hives
itching
pale skin
skin rash
unusual tiredness or weakness
Some of the side effects that can occur with darbepoetin alfa may not need medical attention. As your body adjusts to the medicine during treatment these side effects may go away. Your health care professional may also be able to tell you about ways to reduce or prevent some of these side effects. If any of the following side effects continue, are bothersome or if you have any questions about them, check with your health care professional:
More common Constipation
general feeling of discomfort or illness
lack or loss of strength
loss of appetite
itching
pale skin
skin rash
unusual tiredness or weakness
Applies to darbepoetin alfa: injectable solution General
The most common adverse reactions in patients with chronic kidney disease (CKD) were hypertension, dyspnea, peripheral edema, cough, and procedural hypotension. The most common adverse reactions in cancer patients receiving chemotherapy were abdominal pain, edema, and thrombovascular events.
Gastrointestinal
Very common (10% or more): Nausea (up to 38%), vomiting (up to 27%), diarrhea (up to 20%), constipation (up to 19%), abdominal pain (up to 16%)
Common (1% to 10%): Dyspepsia
Other
Very common (10% or more): Fatigue (up to 32%), fever (up to 19%), peripheral edema (up to 17%), asthenia (up to 16%), edema (up to 12.8%), procedural hypotension (10%), chest pain (up to 10%)
Common (1% to 10%): Death, influenza-like symptoms, fluid overload, fall, contusion, pain, arteriovenous graft thrombosis
Cardiovascular TABLE B-continued Aranesp ® Side Effects Very common (10% or more): Hypertension (up to 31%), hypotension (up to 22%)
Common (1% to 10%): Myocardial infarction, thrombotic events, angina pectoris
Frequency not reported: Arrhythmia, thromboembolism, thrombosis, thrombophlebitis
Musculoskeletal
Very common (10% or more): Myalgia (up to 20%), back pain (14%), arthralgia (up to 13%), limb
pain (up to 11%)
Common (1% to 10%): Skeletal pain
Respiratory
Very common (10% or more): Dyspnea (up to 20%), upper respiratory infection (up to 14%),
cough (up to 12%), nasopharyngitis (11%)
Common (1% to 10%): Bronchitis, sinusitis, sore throat, pulmonary embolism
Nervous system
Very common (10% or more): Headache (up to 16%), dizziness (up to 14%)
Common (1% to 10%): Cerebrovascular accident/transient ischemic attack, convulsions,
paresthesia, hypoesthesia, cerebrovascular disorders, stroke
Frequency not reported: Somnolence
Genitourinary
Very common (10% or more): Urinary tract infection (15%)
Renal
Very common (10% or more): Chronic renal failure (15%)
Metabolic
Very common (10% or more): Hypoglycemia (14%)
Psychiatric
Very common (10% or more): Insomnia (11%)
Common (1% to 10%): Depression, anxiety
Dermatologic
Common (1% to 10%): Pruritus, cellulitis, rash, skin ulcer, alopecia
Frequency not reported: Angioedema, urticaria
Local
Common (1% to 10%): Injection site pain, access hemorrhage, access infection, vascular access
thrombosis, vascular access complications
Hematologic
Common (1% to 10%): Granulocytopenia
Frequency not reported: Anaemia , pure red cell aplasia associated with neutralizing antibodies to
erythropoietin
Oncologic
Common (1% to 10%): Metastatic neoplasm
Immunologic
Frequency not reported: Serious allergic reaction, hypersensitivity reaction, anaphylactic reaction
References:
1. Cerner Multum, Inc. "Australian Product Information.";
2. "Product Information. Aranesp (darbepoetin alfa)." Amgen, Thousand Oaks, CA;
3. Cerner Multum, Inc. "UK Summary of Product Characteristics."

In an embodiment, the treatment or prophylaxis of the invention reduces in the subject the incidence or risk of one or more side effects listed in Table B, eg, one or more of the 'common', "more common" or "very common" side effects.

effects) is reduced. In an example, the therapy is anaemia treatment. In an example, the therapy is anaemia prophylaxis. In an example, the anaemia is moderate or severe anaemia.

TABLE C

Aranesp ® US Boxed Warnings

CANCER: ESAs shortened overall survival and/or increased the risk of tumor progression or recurrence in clinical studies of patients with breast, non-small cell lung, head and neck, lymphoid, and cervical cancers. Because of these risks, prescribers and hospitals must enroll in and comply with the ESA APPRISE Oncology Program to prescribe and/or dispense this drug to patients with cancer. To enroll in the ESA APPRISE Oncology Program, visit world wide web.esa.apprise.com or call 1-866-284-8089 for further assistance. To decrease these risks, as well as the risk of serious cardiovascular and thromboembolic reactions, use the lowest dose needed to avoid RBC transfusions. Use ESAs only for anaemia from myelosuppressive chemotherapy. ESAs are not indicated for patients receiving myelosuppressive chemotherapy when the anticipated outcome is cure. Discontinue following the completion of a chemotherapy course.

In an aspect, the invention provides a method of reduced side-effect ESA therapy of a subject suffering from or at risk of anaemia, the method comprising administering an anti-BMP6 antagonist and an erythropoiesis stimulating agent (ESA) to the subject, wherein said anaemia is treated or prevented. Optionally, the incidence or risk of one or more ESA side effects listed in Table B (eg, one or more of the "common", "more common" or "very common" side In an embodiment, the treatment or prophylaxis of the invention reduces in the subject the incidence or risk of one or more side effects listed in Table C, eg, shortened overall survival and/or increased risk of tumour progression or recurrence wherein the subject is a breast, non-small cell lung, head and neck, lymphoid, and cervical cancer patient; or a cardiovascular or thromboembolic reaction, such as stroke.

In an aspect, the invention provides a method of reduced side-effect ESA therapy of a subject suffering from or at risk of anaemia, the method comprising administering an anti-BMP6 antagonist and an erythropoiesis stimulating agent (ESA) to the subject, wherein said anaemia is treated or prevented. Optionally, the incidence or risk of one or more ESA side effects listed in Table C (eg, shortened overall survival and/or increased risk of tumour progression or recurrence wherein the subject is a breast, non-small cell lung, head and neck, lymphoid, and cervical cancer patient; or a cardiovascular or thromboembolic reaction, such as stroke) is reduced. In an example, the therapy is anaemia treatment. In an example, the therapy is anaemia prophylaxis. In an example, the anaemia is moderate anaemia. In an example, the anaemia is moderate to severe anaemia. In an example, the anaemia is severe anaemia. In an example, the anaemia in the invention is anaemia from myelosuppressive chemotherapy.

TABLE D

Estimated Aranesp Starting Doses (mcg/week) for Patients with CKD on Dialysis Based on Previous Epoetin alfa Dose (Units/week)

| Previous Weekly Epoetin alfa Dose (Units/week) | Aranesp Dose (mcg/week) | |
|---|---|---|
| | Adult | Paediatric |
| <1,500 | 6.25 | * |
| 1,500 to 2,499 | 6.25 | 6.25 |
| 2,500 to 4,999 | 12.5 | 10 |
| 5,000 to 10,999 | 25 | 20 |
| 11,000 to 17,999 | 40 | 40 |
| 18,000 to 33,999 | 60 | 60 |
| 34,000 to 89,999 | 100 | 100 |
| ≥90,000 | 200 | 200 |

*For paediatric patients receiving a weekly epoetin alfa dose of <1,500 Units/week, the available data are insufficient to determine an Aranesp conversion dose.

Aspects of the Invention Provide (i) and (ii)
  (i) A method of reducing administration of an erythropoiesis stimulating agent (ESA) to a subject suffering from anaemia for treating anaemia, the method comprising administering an anti-BMP6 antagonist and said ESA, wherein anaemia is treated in the subject.
  (ii) A method of treating or reducing the risk of anaemia in a subject suffering from or at risk of anaemia, the method comprising administering an anti-BMP6 antagonist and a low dose of an erythropoiesis stimulating agent (ESA) to the subject, wherein anaemia is treated or the risk of anaemia is reduced in the subject.
  In examples of these aspects the ESA is
  a. Epoetin alfa and is administered at a weekly dose of less than 1000, 1500, 2500, 5000, 11000, 18000, 34000 or 90000 units, optionally wherein the subject has previously received a weekly epoetin alfa treatment of <1500, 1500 to 2499, 2500 to 4999, 5000 to 10999, 11000 to 17999, 18000 to 33999, 34000 to 89999 or 90000 units respectively;
  b. darbepoetin alfa or Aranesp® and is administered at a weekly dose of less than 6.25, 10, 12.5, 20, 25, 40, 60, 100 or 200 mcg, optionally wherein the subject has previously received a weekly darbepoetin alfa or Aranesp® treatment of 6.25, 10, 12.5, 20, 25, 40, 60, 100 or 200 mcg respectively; or
  c. darbepoetin alfa or Aranesp® and is administered at a weekly dose of less than 6.25, 10, 20, 40, 60, 100 or 200 mcg, optionally wherein the subject has previously received a weekly Epoetin alfa treatment of 1500 to 2499, 2500 to 4999, 5000 to 10999, 11000 to 17999, 18000 to 33999, 34000 to 89999 or >90,000 units respectively.

In examples the ESA is
  (i) Epoetin alfa and is administered at a weekly dose in the range from 3000 to 30000 units; or
  (ii) darbepoetin alfa or Aranesp® and is administered at a weekly dose in the range from 15 to 100 mcg; and
  wherein the subject is a human, eg, an adult human.

In an example, the blood haemoglobin is raised to or maintained at a level of more than 10 g/dL.

In an example, the subject is an adult human. In an example, the subject is a paediatric human. In an example, the subject is a human CKD patient on dialysis treatment. In an example, the subject is a human having end-stage renal disease.

A therapeutically or prophylactically effective amount of the antagonist and ESA are administered to the subject in the methods of the invention. In an example, the anti-BMP6 antagonist and ESA are administered to the subject no more than 10, 14, 21 or 28 days apart. For example, the anti-BMP6 antagonist and ESA are administered to the subject no more than 1 or 2 months apart.

Examples of Erythropoiesis-Stimulating Agents (ESAs) are epoetin alfa, Epogen®, Dynepo®, Eprex®, erythropoietin, Darbepoetin alfa, Aranesp®, Epoetin beta, NeoRecormon®, methoxy polyethylene glycol-epoetin beta, Mircera® and Procrit®. In an embodiment, the ESA of the invention is any one of these or a combination of two or more of these.

In an example, the ESA comprises or consists of recombinant erythropoietin, eg, selected from the following table. Erythropoietin has a variety of glycosylation patterns giving rise to alpha, beta, delta, and omega forms:

TABLE E

Example Erythropoietins

| | |
|---|---|
| epoetin alfa: | epoetin zeta (biosimilar |
| Darbepoetin (Aranesp ™) | forms for epoetin alpha): |
| Epocept ™ (Lupin pharma) | Silapo ™ (from Stada) |
| Nanokine ™ (Nanogen | Retacrit ™ (from Hospira) |
| Pharmaceutical biotechnology, | Miscellaneous: |
| Vietnam) | Epocept ™, made by Lupin |
| Epofit ™ (Intas pharma) | Pharmaceuticals |
| Epogen ™, made by Amgen | EPOTrust ™, made by |
| Epogin ™ | Panacea Biotec Ltd |
| Eprex ™, made by Janssen-Cilag | Erypro Safe ™, made by |
| Binocrit ™, made by Sandoz | Biocon Ltd. |
| Procrit ™ | Repoitin ™, made by Serum |
| epoetin beta: | Institute of india Limited |
| epoetin beta: | Vintor ™, made by Emcure |
| NeoRecormon ™, made | Pharmaceuticals |
| by Hoffmann-La Roche | Epofit ™, made by Intas |
| Recormon ™ | pharma |
| Methoxy polyethylene glycol- | Erykine ™, made by Intas |
| epoetin beta (Mircera ™) by Roche | Biopharmaceutica |
| epoetin delta: | Wepox ™, made by |
| Dynepo ™ trademark name for an | Wockhardt Biotech |
| erythropoiesis stimulating protein, | Espogen ™, made by LG life |
| byShire plc | sciences. |
| epoetin omega: | ReliPoietin ™, made by |
| Epomax ™ | Reliance Life Sciences |
| | Shanpoietin ™, made by |
| | Shantha Biotechnics Ltd |
| | Zyrop ™, made by Cadila |
| | Healthcare Ltd. |
| | EPIAO ™ (rHuEPO), made by |
| | Shenyang Sunshine |
| | Pharmaceutical Co.. LTD. |
| | China |
| | Cinnapoietin ™, made by |
| | CinnaGen biopharmaceutical |
| | Iran. |

In an example, the ESA of the invention is selected from the group consisting of an alpha, beta, delta, zeta and omega form.

In an example, the ESA is a hypoxia-inducible factor prolyl-hydroxylase (HIF-PH) inhibitor, eg, roxadustat or FG-4592. HIF is the primary regulator of the production of red blood cells (RBCs) in the body and a potentially novel mechanism of treating anaemia. This novel mechanism of action is referred to as hypoxia inducible factor-prolyl hydroxylase (HIF-PH) inhibitors. HIF-PH inhibitors act by simulating the body's natural response to anaemia. This allows a controlled, adaptive stimulation of the erythropoietic system in the body. This activation of the whole system results in both increased red blood cell (RBC) production and improved stabilization of the bone marrow's iron supply, which ensures the proper incorporation of iron into haemoglobin necessary for such RBC production. This adaptive simulation is very similar to the natural response that is induced when a person ascends in altitude. At higher altitudes, low levels of oxygen circulating in the bloodstream lead to reduced HIF-PH activity in relevant cells in the kidney and liver. The reduced HIF-PH activity stabilizes and increases intracellular levels of proteins HIF1α and HIF2α (referred to as HIFα collectively). For most cells the stabilization of HIF2α is greater than that of HIF1α, which ultimately leads to an increase in erythropoietin (EPO) secretion and a subsequent increase in RBC production. HIF-PH inhibitors work by blocking the effect of the prolyl hydroxylase enzymes, which promote the breakdown of HIFα proteins. As the breakdown is inhibited, the level of these HIFα proteins increases in cells. These HIFs are the primary protein mediators that enable the body and all of its individual cells to adapt to changes in levels of oxygen. Both HIFα proteins are consistently produced and their levels in cells are adjusted by the activity of the HIF-PH enzymes, which target the HIFα proteins for degradation. HIF1α helps cells survive under very low oxygen conditions, whereas HIF2α helps cells and the body to adapt to modest changes in oxygen, such that would occur with a change in altitude from sea level to up to 7500 feet. When HIFα is stabilized, it travels to the nucleus of the cell, where it binds to the protein HIFβ. When bound together, they induce the genetic signal for the production of EPO and several other proteins. The HIF-PH inhibitors increase HIFα levels much in the same way that a reduction in oxygen increases HIFα levels by inhibiting the HIF-PH enzymes in the body. With continued stabilisation of HIFα (either by staying at higher altitude or by daily dosing of the HIF-PH inhibitor), the level of haemoglobin and RBCs will rise in order to increase the amount of oxygen circulating in the blood.

An example of an anti-BMP6 antibody is MAB507, that is commercially available from R&D Systems (Monoclonal Mouse IgG2B, Clone #74219). Other suitable antibodies are disclosed in U.S. Pat. No. 8,980,582, WO2016098079 and US20160176956A1 the disclosure of which (and explicitly the sequences of antibodies, variable regions and CDRs therein) are incorporated herein by reference for possible use in the present invention.

In an embodiment, the antagonist comprises or consists of an antibody, or antigen-binding fragment thereof, that binds to human BMP-6 (SEQ ID NO: 1), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide of SEQ ID NO: 2, the LCDR2 is the polypeptide of SEQ ID NO: 3, the LCDR3 is the polypeptide of SEQ ID NO: 4, the HCDR1 is the polypeptide of SEQ ID NO: 5, the HCDR2 is the polypeptide of SEQ ID NO: 6 or SEQ ID NO: 7, and the HCDR3 is the polypeptide of SEQ ID NO: 8. The SEQ ID NOs in this paragraph are those disclosed in U.S. Pat. No. 8,980,582, and these sequences are explicitly incorporated herein by reference for possible use in the present invention and for possible inclusion in one or more claims herein.

In an embodiment, the antagonist comprises or consists of an antibody, or antigen-binding fragment thereof, that binds to human BMP-6 (SEQ ID NO: 1), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide of SEQ ID NO: 2, the LCDR2 is the polypeptide of SEQ ID NO: 3, the LCDR3 is the polypeptide of SEQ ID NO: 4, the HCDR1 is the polypeptide of SEQ ID NO: 5, the HCDR2 is the polypeptide of SEQ ID NO: 6, and the HCDR3 is the polypeptide of SEQ ID NO: 8. The SEQ ID NOs in this paragraph are those disclosed in U.S. Pat. No. 8,980,582, and these sequences are explicitly incorporated herein by reference for possible use in the present invention and for possible inclusion in one or more claims herein.

In an embodiment, the antagonist comprises or consists of an antibody, or antigen-binding fragment thereof, that binds to human BMP-6 (SEQ ID NO: 1), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide of SEQ ID NO: 2, the LCDR2 is the polypeptide of SEQ ID NO: 3, the LCDR3 is the polypeptide of SEQ ID NO: 4, the HCDR1 is the polypeptide of SEQ ID NO: 5, the HCDR2 is the polypeptide of SEQ ID NO: 7, and the HCDR3 is the polypeptide of SEQ ID NO: 8. The SEQ ID NOs in this paragraph are those disclosed in U.S. Pat. No. 8,980,582, and these sequences are explicitly incorporated herein by reference for possible use in the present invention and for possible inclusion in one or more claims herein.

In an embodiment, the antagonist comprises or consists of an antibody, or antigen-binding fragment thereof, that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 10 or SEQ ID NO: 11. In a further embodiment, the antagonist comprises or consists of an antibody, or antigen-binding fragment thereof, that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 10. In another embodiment, the antagonist comprises or consists of an antibody, or antigen-binding fragment thereof, that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 11. The SEQ ID NOs in this paragraph are those disclosed in U.S. Pat. No. 8,980,582, and these sequences are explicitly incorporated herein by reference for possible use in the present invention and for possible inclusion in one or more claims herein.

In an embodiment, the antagonist comprises or consists of an antibody that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 10 or SEQ ID NO: 11. In a further embodiment, the present invention provides an antibody that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 10. In another embodiment, the antagonist comprises or consists of an antibody that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 11. The SEQ ID NOs in this paragraph are those disclosed in U.S. Pat. No. 8,980,582, and these sequences are explicitly incorporated herein by reference for possible use in the present invention and for possible inclusion in one or more claims herein.

In an embodiment, the antagonist comprises or consists of an antibody that binds to human BMP-6 (SEQ ID NO: 1), comprising a light chain (LC) and a heavy chain (HC), wherein the LC is the polypeptide of SEQ ID NO: 12, and the HC is the polypeptide of SEQ ID NO: 13 or SEQ ID NO: 14. In a further embodiment, the antagonist comprises or consists of an antibody that binds to human BMP-6 (SEQ ID NO: 1), comprising a LC and a HC, wherein the LC is the polypeptide of SEQ ID NO: 12, and the HC is the polypeptide of SEQ ID NO: 13. In another embodiment, the antagonist comprises or consists of an antibody that binds to human BMP-6 (SEQ ID NO: 1), comprising a LC and a HC, wherein the LC is the polypeptide of SEQ ID NO: 12, and the HC is the polypeptide of SEQ ID NO: 14. The SEQ ID NOs in this paragraph are those disclosed in U.S. Pat. No. 8,980,582, and these sequences are explicitly incorporated herein by reference for possible use in the present invention and for possible inclusion in one or more claims herein.

In an embodiment, the antagonist comprises or consists of an antibody that binds to human BMP-6 (SEQ ID NO: 1), comprising two light chains and two heavy chains, wherein each light chain is the polypeptide of SEQ ID NO: 12, and each heavy chain is the polypeptide of SEQ ID NO: 13. In an embodiment, the antagonist comprises or consists of an antibody that binds to human BMP-6 (SEQ ID NO: 1), comprising two light chains and two heavy chains, wherein each light chain is the polypeptide of SEQ ID NO: 12, and each heavy chain is the polypeptide of SEQ ID NO: 14. The SEQ ID NOs in this paragraph are those disclosed in U.S. Pat. No. 8,980,582, and these sequences are explicitly incorporated herein by reference for possible use in the present invention and for possible inclusion in one or more claims herein.

In an embodiment, the present invention provides a pharmaceutical composition comprising an anti-BMP6 antagonist (eg, an antibody, or BMP6-binding fragment thereof) of the present invention, and an acceptable carrier, diluent, or excipient. More particularly, the compositions of the present invention further comprise one or more additional therapeutic agents, eg, an ESA and/or an anti-inflammatory agent. Suitable anti-inflammatory agents can be antibodies or antibody fragments, eg, an anti-TNF alpha antibody (eg, adalimumab, Humira®, infliximab, Remicade®, golimumab, Simponi®, or trap (eg, etanercept or Enbrel®); or anti-TNFR antibody or antibody fragment, or an anti-IL6R antibody (eg, sarilumab, tocilizumab or Actemra®).

In an example, the anti-BMP6 antagonist, antibody or fragment binds to BMP6 with a KD of less than about $1\times10^{-8}$ M, preferably, less than about $1\times10^{-9}$ M as determined by common methods known in the art, eg, by use of a surface plasmon resonance (SPR) biosensor at 37° C.

"Effective amount" means the amount of an antagonist (eg, antibody) or ESA of the present invention or pharmaceutical composition of the present invention that will elicit the biological or medical response or desired therapeutic effect on a subject, mammal or human that is being sought by the researcher, medical doctor, or other clinician. An effective amount may vary according to factors such as the disease state, age, sex, and weight of the individual, and the ability of the antibody and/or ESA to elicit a desired response in the individual. An effective amount is also one in which any toxic or detrimental effect is outweighed by the therapeutically beneficial effects.

The terms "treatment," "treat," "treating," and the like, are meant to include slowing or reversing the progression of a disorder, such as anaemia, moderate anaemia, severe anaemia or blood haemoglobin decrease. These terms also include alleviating, ameliorating, attenuating, eliminating, or reducing one or more symptoms of a disorder or condition (such as anaemia, moderate anaemia, severe anaemia or blood haemoglobin decrease), even if the disorder or condition is not actually completely eliminated. A subject or patient refers to a mammal, preferably a human with a disease, disorder or condition (eg, anaemia or at risk of anaemia) that would benefit from inhibition of BMP-6 activity. The term "preventing" is for example reducing the risk of a disease or condition, such as anaemia.

An ESA, anti-BMP6 antagonist antibody, or antigen-binding fragment thereof, of the present invention, combination or pharmaceutical composition comprising the same, may be administered by parenteral routes (eg, subcutaneous, intravenous, intraperitoneal, intramuscular, or transdermal). Administration may be to a subject alone or in combination with a pharmaceutically acceptable carrier and/or diluent in single or multiple doses. Pharmaceutical compositions, combinations or antagonists of the present invention can be prepared by methods well known in the art (e.g., *Remington: The Science and Practice of Pharmacy,* 19^{th} ed. (1995), A. Gennaro et al., Mack Publishing Co.) and may comprise or be combined with one or more pharmaceutically acceptable carriers, diluents, or excipients.

In an example, the subject is suffering from moderate or severe anaemia prior to administration of the BMP6 antagonist and the moderate or severe anaemia is treated. In an embodiment, the subject is suffering from moderate anaemia prior to administration and after the treatment the subject has mild or no anaemia. In an embodiment, the subject is suffering from severe anaemia prior to administration and after the treatment the subject has mild, moderate or no anaemia. In an embodiment, after the treatment the subject has mild or no anaemia, and not moderate or severe anaemia. In another embodiment, after the treatment the subject does not have anaemia. In an embodiment, the subject has a blood haemoglobin level of less than 9.5 g/dL prior to administration and after the treatment the subject has a blood haemoglobin level of at least 10, 11, 12, 13 or 14 g/dL.

Anaemia is generally considered when haemoglobin concentrations fall below 11 g/dL for pregnant women, 12 g/dL for non-pregnant women, and 13 g/dL for men.

The severity of anaemia is categorized by the following haemoglobin concentration ranges:

Mild anaemia is considered when haemoglobin is between 9.5-13.0 g/dL

Moderate anaemia is considered when haemoglobin is between 8.0-9.5 g/dL

Severe anaemia is considered for haemoglobin concentrations below 8.0 g/dL

In an example, the level of haemoglobin is at or equivalent to a measurement at sea level.

In an embodiment, the subject is a human male, eg, an adult or infant. In an embodiment, the subject is a human female, eg, an adult or infant, eg, a non-pregnant female or pregnant female. I an example, the human is a dialysis patient. The infant may be a human that is >1 month old.

In an example, the method is a method of eliminating or reducing the need to administer iron or blood transfusion to a subject suffering from anaemia, Eg, for reducing the dose or dosing frequency of iron to the subject.

The invention may comprise simultaneously or sequentially administering the anti-BMP6 antagonist and ESA. In an example, antagonist and ESA are administered no more than 1 month, 4 weeks, 3 weeks, 2 weeks, 1 week, 10 days, 9 days, 8 days, 7 days, 6 days, 5 days, 4 days, 3 days, 2 days or 1 day apart. As exemplified herein, administration of the antagonist and ESA can be effective if no more than 7 days (eg, no more than one day) apart. In an example, the anti-BMP6 antagonist and ESA are administered to the subject no more than 10, 14, 21 or 28 days apart.

In an example, the ESA is administered 2, 3 or 4 times weekly. In an example, the ESA is administered 1, 2, 3 or 4 times monthly or in a 8 week period. In an example, the ESA (eg, epoetin alfa) is administered at a total dose of <3000, 2900, 2800, 2700, 2600, <2500, 2500, 2400, 2300, 2200, 2100, <2000, 2000, 1900, 1800, 1700, 1600, 1500, 1400, 1300, 1200, 1100 or 1000 units/kg per week. In another example, the ESA is administered 1, 2, 3 or 4 times monthly or in a 8 week period. In an example, the ESA (eg, darbepoetin alfa) is administered at a total dose of <15, <30, 12, 11, 10, 9, 8, 7, 6 or 5 mcg/kg per week.

In an example, the ESA and/or antagonist is administered to the subject intravenously or subcutaneously.

In an example, the anaemia is in a subject receiving or having received zidovudine treatment.

Optionally, any configuration of the invention is also for one or more of:—

(a) increasing or maintaining increased blood iron, eg, for treating or reducing the risk of anaemia;

(b) treating iron deficiency;

(c) treating or reducing the risk of Anaemia of Chronic inflammation (ACD);

(d) treating or reducing the risk of Anaemia of Chronic Disease (ACD);

(e) treating or reducing the risk of anaemia associated with cancer, a kidney condition or GvHD;

(f) increasing blood or serum iron level;

(g) increasing reticulocyte count;

(h) increasing red blood cell count;

(i) increasing haemoglobin; and (j) increasing haematocrit in the subject (eg, in a human).

In an embodiment, the invention is for regulating (eg, increasing) erythropoiesis in the subject.

In an embodiment, the subject is a human comprising BMP6 gene SNP rs111588693. This may be correlated with increased propensity for anaemia.

In an example, the anaemia is anaemia of chronic disease (ACD), such as anaemia of cancer, or anaemia of chronic kidney disease (CKD). Certain chronic diseases, such as cancer, kidney disease, and autoimmune disorders, can lead to ACD when overactive inflammatory cytokines cause dysregulation of iron homeostasis, reduction of erythropoiesis, and a decrease in the life span of red blood cells. Hepcidin has been identified as a key hormone involved in iron homeostasis; high levels of hepcidin have been associated with the iron restricted erythropoiesis seen in ACD. BMP-6 has been shown to increase hepcidin expression. In an example, the invention is for reducing or maintaining reduced hepcidin level in the subject.

Anaemia of CKD is anaemia that is an early and common complication in patients suffering with CKD. Anaemia of cancer is anaemia caused by haematological malignancies and some solid tumours; whereas, chemotherapy-induced (eg, immunotherapy-induced) anaemia is anaemia caused by the treatment of cancer patients with chemotherapeutic agents. Anaemia in CKD exacerbates diabetic neuropathy, cardiovascular disease, and retinopathy, among other conditions. Cancer-related anaemia is associated with an increased relative risk of death. Current treatment options for cancer-related anaemia are limited to blood transfusions, as erythropoiesis-stimulating agents are only indicated for chemotherapy-induced anaemia.

In an example, the subject is suffering from a chronic disease, such as cancer (eg, a haematological malignancy or a solid tumour), kidney disease, an autoimmune disorder or chemotherapy-induced anaemia. In an example, the subject (eg, human) is suffering from CKD and one or more of diabetic neuropathy, cardiovascular disease and retinopathy.

In an example, the anaemia is hepcidin related iron restricted anaemia. In an example, the anaemia is iron refractory iron deficiency anaemia (IRIDA). In an embodiment, the IRIDA is caused by a defect in the TMPRSS6 gene of the subject, eg, wherein IRIDA is caused by a TMPRSS6 gene mutation (eg, a SNP, such as rs855791; rs2543519; rs2235324; or rs1421312).

In an example, the method is a method of treating or preventing Sjögren's syndrome in addition to or instead of treating or preventing anaemia.

In an example, the invention is for increasing blood iron level, serum iron level, reticulocyte count, red blood cell count, haemoglobin, and/or haematocrit in the subject (eg, in a human).

In an embodiment, the present invention provides the use of an anti-BMP6 antagonist and an ESA for the manufacture of a medicament. In a further embodiment, the present invention provides the use of an anti-BMP6 antagonist and an ESA for the manufacture of a medicament for the treatment or prevention of anaemia, eg, moderate to severe anaemia. In another embodiment, the present invention provides the use of an anti-BMP6 antagonist and an ESA for the manufacture of a medicament for the treatment of anaemia of chronic disease. In another embodiment, the present invention provides the use of an anti-BMP6 antagonist and an ESA for the manufacture of a medicament for the treatment of anaemia of chronic kidney disease. In another embodiment, the present invention provides the use of an anti-BMP6 antagonist and an ESA for the manufacture of a medicament for the treatment of anaemia of cancer. In an embodiment, the present invention provides the use of an anti-BMP6 antagonist and an ESA for the manufacture of a medicament for the treatment of IRIDA. In a further embodiment, the present invention provides the use of an anti-BMP6 antagonist and an ESA for the manufacture of a medicament for the treatment of IRIDA, wherein IRIDA is caused by a TMPRSS6 gene mutation (eg, a SNP, such as rs855791; rs2543519; rs2235324; or rs1421312). In an embodiment, the present invention provides the use of an anti-BMP6 antagonist and an ESA for the manufacture of a medicament for the treatment of Sjogren's syndrome.

EMBODIMENTS

Embodiments of the invention are as follows, and these Embodiments (and any un-numbered paragraphs) are combinable with any other configuration, Clause, paragraph, example, feature or aspect of the invention as described herein; an antagonist (eg, anti-BMP6 antibody or fragment) or ESA of the invention can be provided for use in (or can be used in) an method in the following Embodiments:—

1. An anti-Bone Morphogenetic Protein 6 (BMP6) antagonist for use in a method of treating or preventing anaemia in a subject, the method comprising administering said anti-BMP6 antagonist and an erythropoiesis stimulating agent (ESA) to the subject, wherein said anaemia is treated or prevented.

In an embodiment, the method is for treating anaemia in the subject, wherein said anaemia is treated.

In an example, the antagonist comprises or consists of an anti-BMP6 antibody or fragment, eg, a human, humanised or chimaeric antibody. In an alternative to an antibody or fragment, a different BMP6 antagonist is contemplated by the invention, eg, an anti-BMP6 trap or a HJV-Fc.

2. An antagonist according to Embodiment 1, wherein the antagonist comprises or consists of an anti-BMP6 antibody or fragment, the method comprising (a) on an initial day ($D_0$) administering to the subject the anti-BMP6 antibody or fragment; and (b) in a period of at least 3 consecutive weeks, said period starting on $D_0$, administering a plurality of doses of an ESA wherein blood Hb concentration in said subject is elevated from a baseline concentration on $D_0$ for the entire duration of said period, such that:—

(i) for the entire duration of said period Hb concentration is no lower than 100% of baseline Hb concentration; and during said period Hb concentration reaches at least 120% of baseline; and/or (ii) for the entire duration of said period Hb concentration is increased over baseline by at least 1 g/dl.

In any Embodiment herein, in an example for the entire duration of said period Hb concentration is increased over baseline by at least 1 g/dl, eg, by at least 1.5, 2 or 2.5 g/dl. In an example, Hb concentration is no more than 11. 11.5 or 12 g/dl in the subject, eg, an adult male or female human.

Hb concentrations and MCH (see below) may be determined using one or more blood samples obtained from the subject. For example, as determined using a blood sample taken at the end of each week of said period (and the baseline determined using a sample taken at $D_0$).

3. A combination of an amount of anti-BMP6 antibody or fragment and an amount of an ESA (eg, comprising multiple doses of said ESA) for use in a method of treating anaemia, wherein the antibody, fragment and method are according to Embodiment 2.

4. The combination of Embodiment 3, wherein the method comprises obtaining a single dose from said amount of antibody or fragment, wherein the single dose is administered to the subject on $D_0$, and obtaining a plurality of doses of said ESA, wherein at least one dose is administered weekly from $D_0$.

In any Embodiment herein, in an example the first dose of ESA is administered on $D_0$ 5. The combination of Embodiment 3 or 4, wherein the antibody or fragment is comprised by a pharmaceutical composition, wherein the antibody or fragment is mixed with a dose of the ESA for administration to said subject on $D_0$.

6. A medical kit comprising the combination of any one of Embodiments 3 to 5, a first sterile container comprising said amount of antibody or fragment, and a second sterile container comprising said amount of ESA, and optionally instructions for carrying out said method.

7. An antagonist according to Embodiment 1, wherein the antagonist comprises or consists of an erythropoietin stimulating agent (ESA) (eg, comprised by multiple doses of said ESA), the method comprising (a) on an initial day ($D_0$) administering to the subject an anti-BMP6 antibody or fragment; and (b) in a period of at least 3 consecutive weeks, said period starting on $D_0$, administering a plurality of doses of said ESA wherein blood haemoglobin (Hb) concentration in said subject is elevated from a baseline concentration on $D_0$ for the entire duration of said period, such:—

(i) for the entire duration of said period Hb concentration is no lower than 100% of baseline Hb concentration; and during said period Hb concentration reaches at least 120% of baseline; and/or (ii) for the entire duration of said period Hb concentration is increased over baseline by at least 1 g/dl.

8. The antagonist, combination or kit of any one of Embodiments 2 to 7, wherein (iii) the Hb concentration on the last day of said consecutive week period is at least 120% of the Hb concentration on the $7^{th}$ day immediately preceding said last day.

9. The antagonist, combination or kit of any one of Embodiments 2 to 8, wherein ESA is administered to the subject within 24 hours of administration of the anti-BMP6 antibody or fragment.

10. The antagonist, combination or kit of any one of Embodiments 2 to 9, wherein said consecutive week period consists of a period of 3 or 4 consecutive weeks.

11. The antagonist, combination or kit of any one of Embodiments 2 to 10 (eg, Embodiment 10), wherein during said period Hb concentration reaches an increase in the range from 1 to 8 g/dl over baseline.

In any Embodiment herein, in an example during said period Hb concentration reaches an increase in the range from 1 to 3, 2.5, 2, 1.5 or 1.25 g/dl over baseline. For example the Hb concentration reaches an increase from 1 to 2 g/dl.

12. The antagonist, combination or kit of any one of Embodiments 2 to 11, wherein the period consists of 3 or 4 consecutive weeks and at the end of said period Hb concentration reaches at least 150% of baseline.

13. The antagonist, combination or kit of any one of Embodiments 2 to 12, wherein the period consists of 3 or 4 consecutive weeks and (a) for the entire duration of said period Hb concentration is no lower than 110% of baseline Hb concentration; and during said period Hb concentration reaches at least 150% of baseline; and/or (b) for the entire duration of said period Hb concentration is increased over baseline by at least 1 g/dl and during said period Hb concentration reaches an increase in the range from 1 to 8 g/dl over baseline. For example the Hb concentration reaches an increase from 1 to 2 g/dl.

14. The antagonist, combination or kit of any one of Embodiments 2 to 13, wherein in said period the antibody or fragment is administered on $D_0$.

15. The antagonist, combination or kit of Embodiment 14, wherein the antibody or fragment is administered as a single dose on $D_0$ to the subject.

In any Embodiment herein, in an example the antibody or fragment is administered as a single dose on $D_0$ to the subject, wherein the single dose is administered in one or a plurality of aliquots to the subject.

16. The antagonist, combination or kit of any one of Embodiments 2 to 15, wherein an initial ESA dose is administered on Do or no more than 2 days thereafter.

17. The antagonist, combination or kit of any one of Embodiments 2 to 16, wherein an ESA dose is administered on the $4\text{-}9^{th}$ (eg, on the $7^{th}$) day immediately after $D_0$.

18. The antagonist, combination or kit of any one of Embodiments 2 to 17, wherein a ESA dose is administered on the $12\text{-}16^{th}$ (eg, on the $14^{th}$) day immediately after $D_0$.

19. The antagonist, combination or kit of any one of Embodiments 2 to 18, wherein a ESA dose is administered on the $19\text{-}23^{rd}$ (eg, on the $21^{st}$) day immediately after $D_0$.

In any Embodiment herein, in an example an ESA dose is administered in each of (i) the $4\text{-}9^{th}$ (eg, on the $7^{th}$) day, (ii) the $12\text{-}16^{th}$ (eg, on the $14^{th}$) day and (iii) the $19\text{-}23^{rd}$ (eg, on the $21^{st}$) day immediately after $D_0$.

20. The antagonist, combination or kit of any one of Embodiments 2 to 19, wherein an equivalent of 4 ESA doses is administered during said period.

By "equivalent" here, it is intended that a plurality of aliquots of the ESA can be administered (eg, on the same day or sequentially), wherein the aliquots amount to a total dose of the ESA. In an example, the ESA is darbepoetin alfa or Aranesp® and a dose is in the range from 15 to 100 mcg (micrograms); or from 30 to 100 mcg. In an example, the ESA is epoetin alfa and a dose is in the range from 3000 to 30000 units (ie, units refers to International Units, also known as IU, UI, IE, ME, NE in various languages).

Generally herein, a dose (eg, of antibody, fragment or ESA) can be administered in one aliquot or a plurality of aliquots (eg, on the same day, simultaneously, within a 30, 1 or 24 hour window).

21. The antagonist, combination or kit of any one of Embodiments 2 to 20, wherein ESA is administered to the subject during each of the first and second weeks after the initial ESA dose.

22. The antagonist, combination or kit of any one of Embodiments 2 to 21, wherein ESA is administered to the subject during each of the first, second and third weeks after the initial ESA dose.

23. The antagonist, combination or kit of Embodiment 21 or 22, wherein ESA is administered as a single dose at the end of each said week, optionally wherein said period consists of 3 or 4 weeks starting at $D_0$.

In an example of any of the Embodiments, said period consists of 4 weeks starting at $D_0$ and anaemia is treated in the $4^{th}$ week.

24. The antagonist, combination or kit of any one of Embodiments 2 to 23, wherein no more than 4 doses of ESA are administered to the subject during said period and optionally a single dose of said antibody or fragment.

25. The antagonist, combination or kit of any one of Embodiments 2 to 24, wherein over said period (wherein the period is a 4 consecutive week period), the total dose of the antibody and total dose of ESA are administered to said subject in a ratio of X:Y, wherein X is from 10 to $2\times10^6$ and Y=4.

In an example, a total weekly dose of ESA (eg, wherein the subject is a human) is from 10 or 15 to 80, 100, 200 or 300 mcg (micrograms). For example, the total weekly dose is from 10 to 80; from 15 to 80; or from 30 to 80 mcg. For example, the ESA comprises or consists of darbepoetin alfa, epoetin alfa or any other ESA disclosed herein. In an example, each dose of ESA (or a weekly dose) is administered to the subject in the range from 1.5 to 2 mcg/kg ESA.

In certain configurations, the method relates to reducing or sparing the administration of ESA. In this instance, for example, a total weekly dose of ESA (eg, wherein the subject is a human) is from 1 to 20 mcg, eg, from 1 up to 15 mcg. In an example where there is ESA sparing or reduction, each dose of ESA (or a weekly dose) is administered to the subject in the range from 0.01 or 0.1 to 0.3 or 1 mcg/kg ESA, eg, from 0.01 to 0.3; or from 0.1 to 0.3; or from 0.01 to 1; or from 0.1 to 1 mcg/kg.

26. The antagonist, combination or kit of any one of Embodiments 2 to 25, wherein Hb concentration at the end of said period (eg, a 3 or 4 consecutive week period) is at least 130% of Hb concentration in a control anaemia patient of the same species that has received administration of the anti-BMP6 antibody or fragment in the same dosing regimen as said subject except the patient has not received administration of an ESA during said period.

27. The antagonist, combination or kit of Embodiment 26, wherein said Hb concentration at the end of said period is significantly higher than in said control at the end of said period, as determined by a p-value of $p<0.0001$.

28. The antagonist, combination or kit of any one of Embodiments 2 to 27, wherein mean corpuscular haemoglobin (MCH) at the end of said period is at least 109% of MCH in a control anaemia patient of the same species that has received administration of the anti-BMP6 antibody or fragment in the same dosing regimen as said subject except the patient has not received administration of an ESA during said period.

The mean corpuscular haemoglobin (MCH) is the average mass of haemoglobin per red blood cell in a sample of blood.

29. The antagonist, combination or kit of any one of Embodiments 2 to 28, wherein Hb concentration at the end of said period (eg, a 3 or 4 consecutive week period) is at least 120% of Hb concentration in a control anaemia patient of the same species that has received administration of said ESA in the same dosing regimen as said subject except the patient has not received administration of an anti-BMP6 antibody or fragment during said period. Optionally, the control patient has received a control IgG4 antibody that does not specifically bind BMP6 (eg, wherein the BMP6 antibody and the control antibody are administered to the subject and control patient respectively in the same dose). Optionally, X is from 10 to $2\times10^5$, $2\times10^4$ or $2\times10^3$.

30. The antagonist, combination or kit of Embodiment 29, wherein said Hb concentration at the end of said period is significantly higher than in said control at the end of said period, as determined by a p-value of $p<0.0001$.

31. The antagonist, combination or kit of any one of Embodiments 2 to 30, wherein mean corpuscular haemoglobin (MCH) at the end of said period (eg, a 3 or 4 consecutive week period) is at least 119% of MCH in a control anaemia patient of the same species that has received administration of said ESA in the same dosing regimen as said subject except the patient has not received administration of an anti-BMP6 antibody or fragment during said period.

32. The antagonist, combination or kit of Embodiment 31, wherein said MCH at the end of said period is significantly higher than in said control at the end of said period, as determined by a p-value of $p<0.0001$.

33. The antagonist, combination or kit of any one of Embodiments 2 to 32, wherein said subject at $D_0$ suffers from anaemia of chronic disease (ACD) and optionally wherein the anaemia is associated with chronic inflammation (eg, the subject suffers from arthritis) or a bacterial infection (eg, *Streptococcus* infection), or wherein the subject is a chronic kidney disease (CKD) patient.

34. The antagonist, combination or kit of any one of Embodiments 2 to 33, wherein the anaemia in said subject at the end of said period is less severe than on $D_0$.

35. The antagonist of Embodiment 1, wherein the antagonist comprises or consists of an anti-BMP6 antibody or fragment.

36. The antagonist, combination or kit of any one of Embodiments 2 to 34, wherein the antibody or fragment competes with a reference antibody for binding BMP6, wherein the reference
   antibody is mAb507 (R&D Systems) or an antibody comprising
   a. Heavy chains each comprising or consisting of the amino acid sequence of SEQ ID NO: 1 or 2, and light chains each comprising or consisting of the amino acid sequence of SEQ ID NO: 3; or
      b. Heavy chains each comprising or consisting of the amino acid sequence of SEQ ID NO: 4 and light chains each comprising or consisting of the amino acid sequence of SEQ ID NO: 5.

Competition herein can, for example, be determined by SPR (eg, at 37 degrees C. at pH7.6 and optionally as a Fab); by ELISA; by fluorescence activated cell sorting (FACS); or in a homogenous time resolved fluorescence (HTRF) assay. SPR may be carried out using Biacore™, Proteon™ or another standard SPR technique. In one embodiment, competition is determined by ForteBio Octet® Bio-Layer Interferometry (BLI) such techniques being readily apparent to the skilled person.

In an alternative, the reference antibody is any anti-BMP6 antibody disclosed in WO2016098079 (the sequences and disclosure relating to such antibodies being incorporated herein for potential use in the present invention).

37. The antagonist, combination or kit of any one of Embodiments 2 to 36, wherein the antibody or fragment competes with said reference antibody for binding to SEQ ID NO: 6. Said SEQ ID NO: 6 can be used as a peptide perse, part of a larger peptide or part of a BMP6 protein (eg, a wild type human BMP6 or recombinantly produced BMP6).

Additionally or alternatively, the antibody or fragment competes with said reference antibody for binding to a further sequence selected from the group consisting of SEQ ID NOs: 7-19. Said further sequence can be used as a peptide perse, part of a larger peptide (eg, comprising SEQ ID NO: 6) or part of a BMP6 protein (eg, a wild type human BMP6 or recombinantly produced BMP6, eg, comprising SEQ ID NO: 6). For example, the antibody or fragment competes with said reference antibody for binding to SEQ ID NO: 7. For example, the antibody or fragment competes with said reference antibody for binding to SEQ ID NO: 8. For example, the antibody or fragment competes with said reference antibody for binding to SEQ ID NO: 9. For example, the antibody or fragment competes with said reference antibody for binding to SEQ ID NO: 10. For example, the antibody or fragment competes with said reference antibody for binding to SEQ ID NO: 11. For example, the antibody or fragment competes with said reference antibody for binding to SEQ ID NO: 12. For example, the antibody or fragment competes with said reference antibody for binding to SEQ ID NO: 13. For example, the antibody or fragment competes with said reference antibody for binding to SEQ ID NO: 14. For example, the antibody or fragment competes with said reference antibody for binding to SEQ ID NO: 15. For example, the antibody or fragment competes with said reference antibody for binding to SEQ ID NO: 16. For example, the antibody or fragment competes with said reference antibody for binding to SEQ ID NO: 17. For example, the antibody or fragment competes with said reference antibody for binding to SEQ ID NO: 18. For example, the antibody or fragment competes with said reference antibody for binding to SEQ ID NO: 19. The sequence ID numbers in this paragraph and for Embodiments herein are those disclosed in WO2017191437, the disclosure of which is incorporated herein.

38. The antagonist, combination or kit of any one of Embodiments 2 to 37, wherein the antibody or fragment competitively inhibits the binding of soluble haemojuvelin (HJV) to BMP6.

39. The antagonist, combination or kit of any one of Embodiments 1 to 38, wherein the antibody or fragment does not competitively inhibit the binding of soluble haemojuvelin (HJV) to BMP6 (eg, as determined by SPR, HTRF or ELISA).

40. The antagonist, combination or kit of any one of Embodiments 2 to 39, wherein the antibody comprises VH domains encoded by a VDJ region sequence, wherein the VDJ is derived from the recombination of a VH gene segment, D gene segment and JH gene segment, wherein the VH is a human germline (i) VH1-3, (ii) VH2-5 or (iii) VH3-15 gene segment.

41. The antagonist, combination or kit of any one of Embodiments 2 to 40, wherein the antibody comprises VL domains encoded by a VJ region sequence, wherein the VJ is derived from the recombination of a VL gene segment and JL gene segment, wherein the VL is a human germline (iv) Vκ3-20, (v) Vλ3-1, (vi) Vκ1-17 or (vii) Vλ1-40.

42. The antagonist, combination or kit of any one of Embodiments 2 to 41, wherein the antibody or fragment binds to BMP6 with a stronger affinity (lower KD determined by SPR) than binding to BMP7; and optionally binds to BMP6 with a stronger affinity than to BMP5.

Optionally the antibody or fragment binds to BMP6 with a stronger affinity than to each of BMP2, 4, 5 and 9.

43. The antagonist, combination or kit of any one of Embodiments 2 to 42, wherein the antibody or fragment binds to a human BMP6 sequence comprising SEQ ID NO: 6.

44. The antagonist, combination or kit of any one of Embodiments 2 to 43, wherein the antibody has an affinity (KD) for binding BMP6 of from 1 µM to 5 nM, optionally wherein binding is determined by SPR using a Fab of said antibody at 37° C. at pH 7.6.

In an example, the antibody (eg, as a Fab) or fragment has an affinity (KD) for binding BMP6 of
   (a) from 2, 3, 4, 5 or 10 µM to 3, 4 or 5 nM;
   (b) from 1-10 µM to 5 nM;
   (c) from 10 µM to 3, 4 or 5 nM;
   (d) from 50 or 80 µM to 200 nM;
   (e) from 50 or 80 µM to 150 nM; or
   (f) from 50 or 80 µM to 100 nM.

In an example, the KD is (or is about) 5-15 $\mu$M (eg, 10 $\mu$M). In an example, the KD is (or is about) 2-5 nM (eg, 3 nM). In an example, the KD is (or is about) 100-400 $\mu$M (eg, 140 or 390 $\mu$M).

45. The antagonist, combination or kit of any one of Embodiments 2 to 44 (eg, Embodiment 44), wherein the antibody has off-rate ($K_{off}$) for binding BMP6 of from $1\times10^{-5}$ to $1\times10^{-3}$ $S^{-1}$, optionally wherein binding is determined by SPR using a Fab of said antibody at 37° C. at pH 7.6.

In an example, the antibody (eg, as a Fab) or fragment has an off-rate ($K_{off}$) for binding BMP6 of
  (a) from $1\times10^{-5}$ to $5\times10^{-4}S^{-1}$;
  (b) from $1\times10^{-5}$ to $6\times10^{-4}S^{-1}$;
  (c) from $1\times10^{-5}$ to $7\times10^{-4}$ $S^{-1}$;
  (d) from $1\times10^{-5}$ to $8\times10^{-4}S^{-1}$;
  (e) from $2\times10^{-5}$ to $1\times10^{-3}$ $S^{-1}$;
  (f) from $2\times10^{-1}$ to $5\times10^{-4}$ $S^{-1}$;
  (g) from $2\times10^{-1}$ to $6\times10^{-4}$ $S^{-1}$;
  (h) from $2\times10^{-1}$ to $7\times10^{-4}S^{-1}$; or
  (i) from $2\times10^{-5}$ to $8\times10^{-4}S^{-1}$.

In an example, the $K_{off}$ is (or is about) $5\times10^{-4}S^{-1}$ (eg, when the KD is (or is about) from 2 nM to 400 $\mu$M; when the KD is (or is about) 2-5 nM (eg, 3 nM); or when the KD is (or is about) 100-400 $\mu$M (eg, 140 or 390 $\mu$M)). In an example, the $K_{off}$ is (or is about) $3\times10^{-5}$ $S^{-1}$ (eg, when the KD is (or is about) from 5-15 $\mu$M (eg, 10 $\mu$M)).

46. The antagonist, combination or kit of any one of Embodiments 2 to 45 (eg, Embodiment 44 and/or 45), wherein the antibody has on-rate (Kon) for binding BMP6 of from $1\times10^5$ to $1\times10^7$ $M^{-1}S^{-1}$, optionally wherein binding is determined by SPR using a Fab of said antibody at 37° C. at pH 7.6.

In an example, the antibody (eg, as a Fab) or fragment has an on-rate (Kon) for binding BMP6 of
  (a) from $1\times10^1$ to $1\times10^6$ $M^{-1}S^{-1}$;
  (b) from $1\times10^5$ to $2\times10^6$ $M^{-1}S^{-1}$;
  (c) from $1\times10^5$ to $3\times10^6$ $M^{-1}S^{-1}$;
  (d) from $1\times10^5$ to $4\times10^6$ $M^{-1}S^{-1}$;
  (e) from $1\times10^5$ to $5\times10^6$ $M^{-1}S^{-1}$;
  (f) from $2\times10^5$ to $5\times10^6$ $M^{-1}S^{-1}$;
  (g) from $3\times10^5$ to $5\times10^6$ $M^{-1}S^{-1}$;
  (h) from $4\times10^5$ to $5\times10^6$ $M^{-1}S^{-1}$;
  (i) from $5\times10^5$ to $5\times10^6$ $M^{-1}S^{-1}$; or
  (j) from $6\times10^5$ to $5\times10^6$ $M^{-1}S^{-1}$.

In an example, the $K_{on}$ is (or is about) 1 or $2\times10^{-5}$ $M^{-1}S^{-1}$ (eg, when the KD is 2-5 nM (eg, 3 nM)). In an example, the $K_{on}$ is (or is about) 1-4, 1, 2, 3 or $4\times10^{-6}$ $M^{-1}S^{-1}$ (eg, when the KD is (or is about) from 5-400 $\mu$M (eg, 140 or 390 $\mu$M) or 5-15 $\mu$M (eg, 10 $\mu$M)).

47. The antagonist, combination or kit of any one of Embodiments 2 to 46, wherein
  (a) the period consists of 3 or 4 consecutive weeks and
    (i) for the entire duration of said period Hb concentration is no lower than 110% of baseline Hb concentration; and during said period Hb concentration reaches at least 120% of baseline; and/or
    (ii) for the entire duration of said period Hb concentration is increased over baseline by at least 1 g/dl and during said period Hb concentration reaches an increase in the range from 1 to 8 g/dl over baseline;
  (b) wherein a dose of ESA is administered at least twice during the first two or three weeks of said period;
  (c) wherein the antibody or fragment binds to BMP6 with a stronger affinity (lower KD determined by SPR) than binding to BMP7; and optionally binds to BMP6 with a stronger affinity than to BMP5 (and optionally binds to BMP6 with a stronger affinity than to each of BMP2, 4, 5 and 9); and
  (d) wherein the antibody or fragment competes with a reference antibody for binding BMP6, wherein the reference antibody is mAb507 (R&D Systems) or an antibody comprising
    I. Heavy chains each comprising or consisting of the amino acid sequence of SEQ ID NO: 1 or 2, and light chains each comprising or consisting of the amino acid sequence of SEQ ID NO: 3; or
    II. Heavy chains each comprising or consisting of the amino acid sequence of SEQ ID NO: 4 and light chains each comprising or consisting of the amino acid sequence of SEQ ID NO:5.

Optionally, in part I the heavy chains consist of the amino acid sequence of SEQ ID NO:1 and the light chains consist of the amino acid sequence of SEQ ID NO:3. Optionally, in part I the heavy chains consist of the amino acid sequence of SEQ ID NO:2 and the light chains consist of the amino acid sequence of SEQ ID NO:3. Optionally, in part II the heavy chains consist of the amino acid sequence of SEQ ID NO:4 and the light chains consist of the amino acid sequence of SEQ ID NO:5.

In an example (as per the antibody used in Example 2 below), in part (d) the anti-BMP6 antibody of the invention is an antibody that competes with a reference antibody of part I or part II in an HTRF assay. For example, wherein in the HTRF assay the antibody of the invention is a labelled antibody that is pre-incubated with human BMP6 and subsequently combined with unlabelled reference antibody (according to part I or II), wherein competition between antibodies is detected by the assay. In an example, the assay uses AlexaFluor™ 647 labelled antibody of the invention. In an alternative, the human BMP6 is labelled (eg, with AlexaFluor™ 647, the test antibody is labelled with biotin for binding to Eu3+cryptate-streptavidin, and the reference antibody is unlabelled).

Optionally, the anti-BMP6 antibody of the invention (test antibody) competes in an HTRF assay with the reference antibody for binding human BMP6 (or binds the same epitope of human BMP6 as the reference antibody), wherein the assay uses a directly or indirectly labelled test antibody directly or indirectly labelled with a donor (such as for example Eu3+cryptate) or an acceptor fluorophore (such as for example AlexaFluor™ 647) and a target BMP6 labelled with either a donor or acceptor fluorophore to enable energy transfer between donor and acceptor, whereby a fluorescence signal is produced and detected. In an example, where AlexaFluor™ 647 labelling is used, competition is detected by a reduction in fluorescence signal at 665 nM of at least 20% when the test antibody is in the presence of the reference antibody versus signal without the reference antibody. Optionally, the reduction in signal at 665 nM is at least 20, 30, 40, 50, 60, 70, 80 or 90%.

Optionally, the anti-BMP6 antibody (test antibody) is one that competes in a HTRF assay with a reference antibody for binding human BMP6 (or binds the same epitope of human BMP6 as the reference antibody), wherein the reference antibody comprises heavy chains each comprising the amino acid sequence of SEQ ID NO: 1 or 2, and light chains each comprising the amino acid sequence of SEQ ID NO: 3, wherein the assay uses the test antibody directly or indirectly labelled with a donor label (such as for example Eu3+cryptate) or an acceptor fluorophore label (such as for example AlexaFluor™ 647) and a human BMP6 labelled with either an acceptor fluorophore or donor respectively to enable energy transfer between donor and acceptor, wherein said competition between the antibodies is detected by a reduction in fluorescence signal of at least 20% when the test antibody is in the presence of the reference antibody versus signal without the reference antibody. For example, the test antibody is directly or indirectly labelled with AlexaFluor™ 647 and competition is detected by a reduction in fluorescence signal at 665 nM of at least 20% when the test antibody is in the presence of the reference antibody versus signal without the reference antibody. Optionally, the reduction in signal at 665 nM is at least 20, 30, 40, 50, 60, 70, 80 or 90%.

Optionally, the anti-BMP6 antibody (test antibody) also competes in an HTRF assay with a reference antibody for binding human BMP6 (or binds the same epitope of human BMP6 as the reference antibody), wherein the reference antibody comprises heavy chains each comprising the amino acid sequence of SEQ ID NO: 4, and light chains each comprising the amino acid sequence of SEQ ID NO: 5, wherein the assay for example uses the test antibody directly or indirectly labelled with a donor label (such as for example Eu3+cryptate) or an acceptor fluorophore label (such as for example AlexaFluor™ 647) and a human BMP6 labelled with either an acceptor fluorophore or donor respectively to enable energy transfer between donor and acceptor, wherein said competition between the antibodies is detected by a reduction in fluorescence signal of at least 20% when the test antibody is in the presence of the reference antibody versus signal without the reference antibody. For example, the test antibody is directly or indirectly labelled with AlexaFluor™ 647 and competition is detected by a reduction in fluorescence signal at 665 nM of at least 20% when the test antibody is in the presence of the reference antibody versus signal without the reference antibody. Optionally, the reduction in signal at 665 nM is at least 20, 30, 40, 50, 60, 70, 80 or 90%.

For example in part (b) a dose of ESA is administered 2, 3 or 4 times during the first 3 weeks of said period, or during said period.

In an alternative, the reference antibody is any anti-BMP6 antibody disclosed in WO2016098079 (the sequences and disclosure relating to such antibodies being incorporated herein for potential use in the present invention).

48. The antagonist, combination or kit of any one of Embodiments 1 to 47 for
    a. treating ACD in the subject;
    b. treating or preventing moderate or severe anaemia in the subject;
    c. treating or preventing anaemia in the subject, wherein the subject suffers from an inflammatory disease or condition;
    d. eliminating or reducing the need to administer iron or blood transfusion to the subject;
    e. treating or preventing anaemia in the subject, wherein the subject suffers from a microbial infection; or
    f. reducing administration of ESA to the subject.
49. A method of treating anaemia in a subject, the method comprising
    (a) on an initial day ($D_0$) administering to the subject an anti-BMP6 antibody or fragment; and
    (b) in a period of at least 3 consecutive weeks, said period starting on $D_0$, administering a plurality of doses of an erythropoietin stimulating agent (ESA) wherein blood haemoglobin (Hb) concentration in said subject is elevated from a baseline concentration on $D_0$ for the entire duration of said period, such that for the entire duration of said period:—
    (i) Hb concentration is no lower than 100% of baseline Hb concentration; and during said period Hb concentration reaches at least 120% of baseline; and/or
    (ii) Hb concentration is increased over baseline by at least 1 g/dl.
50. The method of Embodiment 49, wherein the method, antibody fragment or ESA is as recited in any one of Embodiments 2 to 48.
51. The antagonist, combination, kit or method of any preceding Embodiment, wherein the anaemia is moderate or severe anaemia.
52. An anti-Bone Morphogenetic Protein 6 (BMP6) antagonist for use in a method of maintaining a blood haemoglobin (Hb) level of at least 10 g/dL in a subject, the method comprising administering an anti-BMP6 antagonist and an erythropoiesis stimulating agent (ESA) to the subject.
Any anti-BMP6 antibody or fragment of the invention can be used as the anti-Bone Morphogenetic Protein 6 (BMP6) antagonist.
53. An anti-Bone Morphogenetic Protein 6 (BMP6) antagonist for use in a method of preventing the blood haemoglobin level of a subject from decreasing to less than 10 g/dL, the method comprising administering an anti-BMP6 antagonist and an erythropoiesis stimulating agent (ESA) to the subject.
54. An anti-Bone Morphogenetic Protein 6 (BMP6) antagonist for use in a method of raising blood haemoglobin to a level of at least 10 g/dL in a subject suffering from anaemia, the method comprising administering an anti-BMP6 antagonist and an erythropoiesis stimulating agent (ESA) to the subject, wherein said anaemia is treated.
55. An anti-Bone Morphogenetic Protein 6 (BMP6) antagonist for use in a method of treating or preventing anaemia in a subject suffering from an inflammatory disease or condition, the method comprising administering an anti-BMP6 antagonist and an erythropoiesis stimulating agent (ESA) to the subject, wherein said anaemia is treated or prevented.
56. An anti-Bone Morphogenetic Protein 6 (BMP6) antagonist for use in a method of eliminating or reducing the need to administer iron or blood transfusion to a subject suffering from anaemia, the method comprising administering an anti-BMP6 antagonist and an erythropoiesis stimulating agent (ESA) to the subject, wherein said need is eliminated or reduced.
57. An anti-Bone Morphogenetic Protein 6 (BMP6) antagonist for use in a method of treating or preventing anaemia in a subject suffering from a microbial infection, the method comprising administering an anti-BMP6 antagonist and an erythropoiesis stimulating agent (ESA) to the subject.
58. An anti-Bone Morphogenetic Protein 6 (BMP6) antagonist for use in a method of reducing administration of an erythropoiesis stimulating agent (ESA) to a subject suffering from anaemia for treating anaemia, the method comprising administering an anti-BMP6 antagonist and said ESA, wherein anaemia is treated in the subject.
59. An anti-Bone Morphogenetic Protein 6 (BMP6) antagonist for use in a method of treating or reducing the risk of anaemia in a subject suffering from or at risk of anaemia, the method comprising administering an anti-BMP6 antagonist and a low dose of an erythropoiesis stimulating agent (ESA) to the subject, wherein anaemia is treated or the risk of anaemia is reduced in the subject.

60. The antagonist of any one of Embodiments 52 to 59, wherein the antagonist is according to any one of Embodiments 1 to 1, 2, 7 to 48 and 51.

61. The antagonist of any one of Embodiments 52 to 59, wherein the antagonist is according to any other of Embodiments 52 to 59.

62. The antagonist, combination, kit or method of any preceding Embodiment, wherein the ESA is
    a. Epoetin alfa and is administered at a weekly dose of less than 1000, 1500, 2500, 5000, 11000, 18000, 34000 or 90000 units, optionally wherein the subject has previously received a weekly epoetin alfa treatment of <1500, 1500 to 2499, 2500 to 4999, 5000 to 10999, 11000 to 17999, 18000 to 33999, 34000 to 89999 or >90000 units respectively;
    b. darbepoetin alfa or Aranesp® and is administered at a weekly dose of less than 6.25, 10, 12.5, 20, 25, 40, 60, 100 or 200 mcg, optionally wherein the subject has previously received a weekly darbepoetin alfa or Aranesp® treatment of 6.25, 10, 12.5, 20, 25, 40, 60, 100 or 200 mcg respectively; or
    c. darbepoetin alfa or Aranesp® and is administered at a weekly dose of less than 6.25, 10, 20, 40, 60, 100 or 200 mcg, optionally wherein the subject has previously received a weekly Epoetin alfa treatment of 1500 to 2499, 2500 to 4999, 5000 to 10999, 11000 to 17999, 18000 to 33999, 34000 to 89999 or >90,000 units respectively.

63. The antagonist, combination, kit or method of any preceding Embodiment, wherein the anti-BMP6 antagonist is an antibody and each dose is administered at a total of no more than 30 mg/kg.

64. An anti-BMP6 antagonist and/or an ESA for use in a therapeutic regimen method for treating or preventing anaemia in a subject suffering from or at risk of anaemia, the regimen comprising simultaneously or sequentially administering an anti-BMP6 antagonist and an ESA to the subject, wherein
    a. On day zero the antagonist is administered to the subject; and no later than day 7 (eg, on day 1) the ESA is administered to the subject; or
    b. On day zero the ESA is administered to the subject; and no later than day 7 (eg, on day 1) the antagonist is administered to the subject; or
    c. On day zero the antagonist and the ESA are simultaneously administered to the subject; or
    d. On day zero the subject has already received the ESA and on day zero the antagonist is administered to the subject; or
    e. On day zero the subject has already received the antagonist and on day zero the ESA is administered to the subject;
    whereby at day 14 or later the blood haemoglobin level is at least 10 g/dL in the subject,
    wherein said anaemia is treated or prevented.

65. The antagonist and/or ESA according to Embodiment 64, which is further according to any one of Embodiments 1 to 1, 2, 7 to 48 and 51.

66. The antagonist and/or ESA according to Embodiment 64 or 65, wherein the anti-BMP6 antagonist and ESA are administered to the subject no more than 7 days apart.

67. The antagonist and/or ESA according to Embodiment 64, 65 or 66, wherein the regimen maintains blood Hb level in the subject at more than 10 g/dL in the subject.

68. The antagonist and/or ESA according to any one of Embodiments 64 to 67, wherein the method maintains or raises blood haemoglobin level to at least 10 g/dL in the subject at least 13 or 14 days after the subject has received the anti-BMP6 antagonist and ESA.

69. The antagonist and/or ESA according to Embodiment 67 or 68, wherein the anti-BMP6 antagonist and ESA are administered to the subject no more than 1 day apart.

70. The antagonist and/or ESA according to any one of Embodiments 64 to 69, wherein the anti-BMP6 antagonist and ESA are administered to the subject simultaneously.

71. The antagonist and/or ESA according to any one of Embodiments 64 to 70, wherein the blood haemoglobin level of the subject is prevented from decreasing to less than 10 g/dL (eg, at day 14).

72. The antagonist and/or ESA according to any one of Embodiments 64 to 71, wherein the blood haemoglobin of the subject is raised to a level of at least 10 g/dL (eg, at day 14).

73. The antagonist and/or ESA according to any one of Embodiments 64 to 72, wherein moderate or severe anaemia is prevented in the subject (eg, at day 14).

74. The antagonist, combination, kit, ESA or method of any preceding Embodiment, wherein the subject is suffering from
    a. an inflammatory disease or condition; or
    b. an infection;
    c. kidney disease;
    d. HIV or undergoing HIV treatment; or
    e. cancer; and
      anaemia is treated or prevented in the subject.

75. The antagonist, combination, kit, ESA or method of any preceding Embodiment, wherein the subject is a mammal.

76. The antagonist, combination, kit, ESA or method of any preceding Embodiment, in combination with an anti-inflammatory agent, or wherein an anti-inflammatory agent is administered to the subject.

77. The antagonist, combination, kit, ESA or method of any preceding Embodiment, wherein the ESA is an erythropoietin.

In an example, the subject is suffering from chronic kidney disease (CKD). Reference is made to "KDIGO Clinical Practice Guideline for Anaemia in Chronic Kidney Disease", Kidney International Supplements (2012) 2, 279; doi:10.1038/kisup.2012.37. This discusses stages of chronic kidney disease (stages 1-5), diagnosis, CKD nomenclature, Hb levels and ranges in humans of various ages and ESA hyporesponsiveness. This reference discloses:—

Diagnosis of Anaemia
    Diagnose anaemia in adults and children >15 years with CKD when the Hb concentration is <13.0 g/dl in males and <12.0 g/dl in females. (Not Graded)
    Diagnose anaemia in children with CKD if Hb concentration is <11.0 g/dl in children 0.5-5 years, <11.5 g/dl in children 5-12 years, and <12.0 g/dl in children 12-15 years. (Not Graded)
Thus, in the present invention, optionally
(a) the subject is an adult or child >15 years with CKD and during said period (eg, at the beginning of the 3$^{rd}$ week from $D_0$) Hb concentration <13.0 g/dl (when the subject is male) or <12.0 g/dl (when the subject is female); or (b) the subject with CKD and during said period (eg, at the beginning of the $3^{rd}$ week from $D_0$) Hb concentration <11.0 g/dl (wherein the subject is aged 0.5-5 years), <11.5 g/dl (wherein the subject is aged 5-12 years), or <12.0 g/dl (wherein the subject is aged 12-15 years).

Optionally, the subject is a CKD patient that has a diagnosed malignancy, has suffered one or more strokes, and/or has suffered a malignancy. ESA therapy is usually to be proceeded with caution (if at all) in such patients, and thus the invention (especially ESA reducing or sparing aspects thereof) are advantageous in such subjects.

Optionally, the subject is a CKD 5D patient (eg, an human adult, eg, a male or female) with Hb concentration from 9.0 to 10.0 g/dl.

Optionally, the invention is for maintaining Hb concentration above 11.5 g/dl in an human adult patient with CKD.

Optionally, the invention is for maintaining Hb concentration from 9.0 to 13 g/dl (eg, 9.0 to 11.5 g/dl) in an adult human patient with CKD.

Optionally, the invention is for maintaining Hb concentration from 11.0 to 12 g/dl in a paediatric human patient with CKD. In an example, the patient is 15 or younger; or younger than 15; or 10 or younger.

In an example, the CKD patient is an adult male. In another example, the CKD patient is an adult female.

Optionally, the subject (eg, an adult human) is a CKD 5HD patient, a patient on hemofiltration or a patient on hemodiafiltration therapy, wherein the method comprises intravenous or subcutaneous administration of ESA.

Optionally, the subject (eg, an adult human) is a CKD ND or CKD 5PD patient, wherein the method comprises subcutaneous administration of ESA.

Optionally, before administration of the anti-BMP6 antibody of fragment, the patient is ESA hyporesponsive indicated by less than 5% increase or no increase in Hb concentration after a month ESA treatment (prior to carrying out the method of the invention).

Reference is made to WO2017191437 for general methodology and tests (eg, see the Examples therein).

Inhibiting HJV-Independent BMP Receptor Dimerisation & Signalling

The art has studied signalling involving BMP6 complexed with HJV. Latour et al, however, proposed an alternative pathway in which BMP6-mediated BMP receptor dimerisation occurs without complexing HJV with BMP6 (Hepatology. 2016 January; 63(1):126-37. doi: 10.1002/hep.28254. Epub 2015 Nov. 12, "Differing impact of the deletion of hemochromatosis-associated molecules HFE and transferrin receptor-2 on the iron phenotype of mice lacking bone morphogenetic protein 6 or hemojuvelin"). As shown in Example 8, the inventors surprisingly found that they could inhibit HJV-independent dimerisation of BMP receptors in human cells by BMP6 using anti-BMP6 antagonists, such as antibodies (eg, in IgG4 format). Thus, in one configuration, the invention relates to inhibiting formation of BMP-BMPR complexes devoid of HJV, or intracellular signalling triggered by such complexes, for the treatment or prevention of a hepcidin-mediated disease or condition in a human or animal subject.

For example, the following Concepts are provided:—

1. An antibody or fragment that specifically binds to a bone morphogenetic protein (BMP) for use in a method of treating or preventing a disease or condition caused by haemojuvelin (HJV)-deficient BMP-BMP receptor (BMPR) complexes in a human or animal subject, wherein the method comprises administering the antibody or fragment to the subject for inhibiting formation of said complexes and/or inhibiting triggering of intracellular signalling by such complexes in the subject, whereby a HJV-independent BMP-BMPR mediated disease or condition is treated or prevented.

2. An antibody or fragment that specifically binds to a bone morphogenetic protein (BMP) for use in a method of treating or preventing HJV-independent anaemia or osteoporosis in a human or animal subject, wherein the method comprises administering the antibody or fragment to the subject for inhibiting formation of haemojuvelin (HJV)-deficient BMP-BMP receptor (BMPR) complexes and/or inhibiting triggering of intracellular signalling by such complexes in the subject, whereby HJV-independent anaemia or osteoporosis is treated or prevented.

3. An antibody or fragment that specifically binds to a bone morphogenetic protein (BMP) for use in a method of treating or preventing haemojuvelin (HJV)-independent anaemia or osteoporosis in a human or animal subject, wherein the method comprises administering the antibody to the subject, whereby HJV-independent anaemia or osteoporosis is treated or prevented.

4. An antibody or fragment for treating or preventing a disease or condition in a human or non-human animal subject, wherein
   a. the disease or condition is mediated by bone morphogenetic protein (BMP) receptor multimerization in hepatic or bone cells of the subject; and
   b. the antibody or fragment is administered to said subject for inhibiting said receptor multimerization, whereby the disease or condition is treated or prevented.

5. The antibody or fragment of any preceding Concept, wherein the BMP is BMP2, 4, 5, 6, 7, or 9.

6. The antibody or fragment of any preceding Concept, wherein the BMP is BMP6.

7. The antibody or fragment of any preceding Concept, wherein the BMP and receptor are human BMP and BMPR.

8. The antibody or fragment of any preceding Concept, wherein the antibody is an anti-BMP6 selected from (i) mAb507, (ii) an antibody comprising VH domains wherein each domain comprises the amino acid sequence of SEQ ID NO: 402; and VL domains, wherein each domain comprises the amino acid sequence of SEQ ID NO: 410; (iii) an antibody comprising VH domains wherein each domain comprises the amino acid sequence of SEQ ID NO: 418; and VL domains, wherein each domain comprises the amino acid sequence of SEQ ID NO: 426, and (iv) an antibody comprising VH domains wherein each domain comprises the amino acid sequence of SEQ ID NO: 114; and VL domains, wherein each domain comprises the amino acid sequence of SEQ ID NO: 123; or wherein the antibody or fragment competes (as determined by SPR) for binding to human BMP6 with an antibody selected from (i) to (iv).

9. The antibody or fragment of any preceding Concept, wherein the antibody or fragment is in an IgG4 (eg, IgG4PE) format.

10. The antibody or fragment of any preceding Concept, wherein said multimerization or complex formation is multimerization of (i) a Type I BMP receptor with (ii) a Type II BMP receptor.

11. The antibody or fragment of Concept 10, wherein said Type I BMP receptor is SKR1, CD292 or CDw293.

12. The antibody or fragment of any preceding Concept, wherein said subject is a human whose genome comprises a SKR1 nucleotide sequence comprising SNP rs13406336 and/or rs188547477; or wherein the human expresses a SKR1 with alanine at position 15 and/or an arginine at position 160; wherein said multimerization is multimerization of (iii) said SKR1 or a SKR1 encoded by said nucleotide sequence with (iv) a BMP receptor.

13. The antibody or fragment of any preceding Concept, wherein said subject is a human whose genome comprises a CD292 nucleotide sequence comprising one, two or three SNPs selected from rs11528010, rs142454490 and rs35619497; or wherein the human expresses a CD292 comprising one, two or three amino acids selected from a proline at position 2, a threonine at position 33 and an arginine at position 443; wherein said multimerization is multimerization of (v) said CD292 or a CD292 encoded by said nucleotide sequence with (vi) a BMP receptor.

14. The antibody or fragment of any preceding Concept, wherein said subject is a human whose genome comprises a CDw293 nucleotide sequence comprising one, two or three SNPs selected from rs34231464, rs138801821, rs200035802, rs143554488, rs35973133 and rs112111860; or wherein the human expresses a CDw293 comprising one, two or three amino acids selected from an arginine at position 149, a valine at position 140, an arginine at position 31, a serine at position 175, an arginine at position 224 and an aspartate at position 297; wherein said multimerization is multimerization of (vii) said CDw293 or a CDw293 encoded by said nucleotide sequence with (viii) a BMP receptor.

15. The antibody or fragment of any one of Concepts 10 to 14, wherein said Type II BMP receptor or the receptor of (iv), (vi) or (viii) is BRK-3, ACVR2A or ACVR2B.

16. The antibody or fragment of any preceding Concept, wherein said subject is a human whose genome comprises a BRK-3 nucleotide sequence comprising one, two or three SNPs selected from rs2228545, rs112862820, rs140683387 and rs201067849; or wherein the human expresses a BRK-3 comprising one, two or three amino acids selected from a serine at position 775, an asparagine at position 29, a glutamine at position 31 and a valine at position 348; wherein said multimerization is multimerization of (ix) said BRK-3 or a BRK-3 encoded by said nucleotide sequence with (x) a BMP receptor.

The antibody or fragment of any preceding Concept, wherein said subject is a human whose genome comprises a ACVR2B nucleotide sequence comprising SNPB rs121434437; or wherein the human expresses ACVR2B comprising an arginine at position 40; wherein said multimerization is multimerization of (xi) said ACVR2B or a ACVR2B encoded by said nucleotide sequence with (xii) a BMP receptor.

17. The antibody or fragment of any preceding Concept, wherein a receptor or each receptor is a BMP6 receptor, BMP7 receptor, BMP2 receptor or BMP9 receptor.

18. The antibody or fragment of any preceding Concept, for inhibiting signalling in hepatic or bone cells of said subject, wherein the signalling is mediated by said receptor multimerization.

19. The antibody or fragment of any preceding Concept, wherein the signalling is Smad signalling.

20. The antibody or fragment of any preceding Concept, for inhibiting elevation of Smad mRNA in hepatic cells of said subject, whereby the disease or condition is treated or prevented.

21. A method of treating or preventing a disease or condition in a human or non-human animal subject, wherein
   a. the disease or condition is mediated by HJV-independent bone morphogenetic protein (BMP) receptor multimerization in hepatic or bone cells of the subject; and
   b. the method comprises administering an anti-BMP antibody or fragment to said subject for inhibiting said receptor multimerization, whereby the disease or condition is treated or prevented.

22. The method of Concept 22, wherein the antibody, fragment and/or receptor(s) are according to any one of Concepts 1 to 21.

ESA Sparing Aspects & Treating ESA-Refractory or Low Responder Subjects

In an example, the antibody or fragment is for increasing plasma haemoglobin in a human or animal subject.

In an example, the antibody or fragment is for increasing mean corpuscular haemoglobin (MCH) in a human or animal subject.

In an example, the antibody or fragment is for increasing corpuscular volume (MCV) (and also optionally mean corpuscular haemoglobin (MCH)) in a human or animal subject.

In an example, the antibody or fragment is for increasing iron availability in a human or animal subject.

In an example, the antibody or fragment is for increasing transferrin saturation in a human or animal subject.

In an example, the antibody or fragment is for increasing transferrin binding to iron in a human or animal subject.

In an example, the antibody or fragment is for reducing the total dose of ESA (eg, EPO, Darbepoetin alfa) administered over a 4 week period to a human or animal subject for treating or preventing anaemia, osteoporosis or any other disease or condition disclosed herein.

In an example, the antibody or fragment is for reducing to ½ to ⅓ the total dose required in a control subject receiving identical treatment over the 4 week period except for administration of ESA without administration of an anti-BMP6 antagonist (eg, antibody or fragment) to a human or animal subject for treating or preventing anaemia, osteoporosis or any other disease or condition disclosed herein.

In an example, the antibody or fragment is for sparing by ½ to ⅓ the administration of ESA administered to a human or animal subject over a treatment period, eg, a 4 week period, for treating or preventing anaemia, osteoporosis or any other disease or condition disclosed herein.

Optionally, the subject suffers from anaemia of chronic inflammation or CKD. Optionally, the anaemia is anaemia of chronic inflammation in the subject.

Optionally, the antibody is an IgG4 antibody.

Optionally, the dose of ESA administered to the subject is not effective when administered in the absence of an anti-BMP6 antagonist.

Optionally the dose of ESA administered to the subject is not effective when administered in the absence of an anti-BMP6 antagonist to produce in the subject one, more or all effects selected from an (a) Increase in haemoglobin;

(b) Increase in the mean corpuscular volume (MCV);

(c) Increase in mean corpuscular haemoglobin (MCH);

(d) Increase of iron availability; and/or (e) Increase of transferrin saturation with iron;

wherein the ESA and an anti-BMP6 antagonist are administered to the subject for producing said selected effect(s).

In an example, the antibody or fragment of the invention is for administration to a human or animal subject for producing in the subject one, more or all effects selected from an (a) Increase in haemoglobin;

(b) Increase in the mean corpuscular volume (MCV);

(c) Increase in mean corpuscular haemoglobin (MCH);

(d) Increase of iron availability; and/or (e) Increase of transferrin saturation with iron;

wherein the ESA and an anti-BMP6 antagonist are administered to the subject for producing said selected effect(s).

In an example, the subject herein is refractory to a dose of ESA, but is responsive for treatment of anaemia, osteoporosis or another disease or condition when administered the antibody or fragment of the invention and the ESA dose.

Thus, in an example, the antibody or fragment of the invention is for administration in combination with a dose of an ESA to a human or animal subject for treating a BMP6-related disease or condition in the subject, wherein the subject is treated with the combination, but is not treatable for the disease or condition by administration of the dose of ESA in the absence of administration of said antibody or fragment.

The disease or condition may be anaemia or any other disease or condition disclosed herein.

EXAMPLES

Example 1

Generation of a HepG2 Luciferase Reporter Cell Line for Studying Impact on Hamp Expression The aim was to generate a human hepatic cell line that expresses a reporter gene under control of the hamp regulatory elements to allow testing for BMP6 induced expression of the hepcidin-encoding (hamp) gene. The complete regulatory region of about 3 kb with response elements to pSMAD (BMP) and pSTAT (IL6) has been characterised in the literature (Casanovas et al., 2014). The genomic DNA from HepG2 Cells was isolated and PCR was performed to amplify the hamp regulatory region and add restriction sites Spe1 and Xho1 (Hep Prom SPE1 Forward= AAAAA-AACTAGTAAATGGCCCCATGTGGCCCCCGCCTTG-TCTGC SEQ ID NO: 6); Hep Prom XHO1 Reverse= TTTTTTCTCGAGCTGTCTGGCTGTCCCACTGCT-GGGTCTTGAGCTT SEQ ID NO: 7). PCR products were cloned by standard molecular biology methods into pMCS-Red Firefly Luc (ThermoFisher) plasmid vector.

The hamp regulatory region followed by the Red Firefly luc insert was re-amplified by PCR and Kpn1 and AsiS1 restriction sites introduced to allow subcloning into a PiggyBac expression vector containing a puromycin selection cassette constructed in house (Yusa et al., 2011).

HepG2 cells (ATCC) were transfected with the constructed Red Firefly Luc plasmid containing the cloned hamp regulatory region using Freestyle max transfection agents (ThermoScientific).

Confirmation of Activity of HepG2 Hamp Reporter Cell Line

Figure 2:
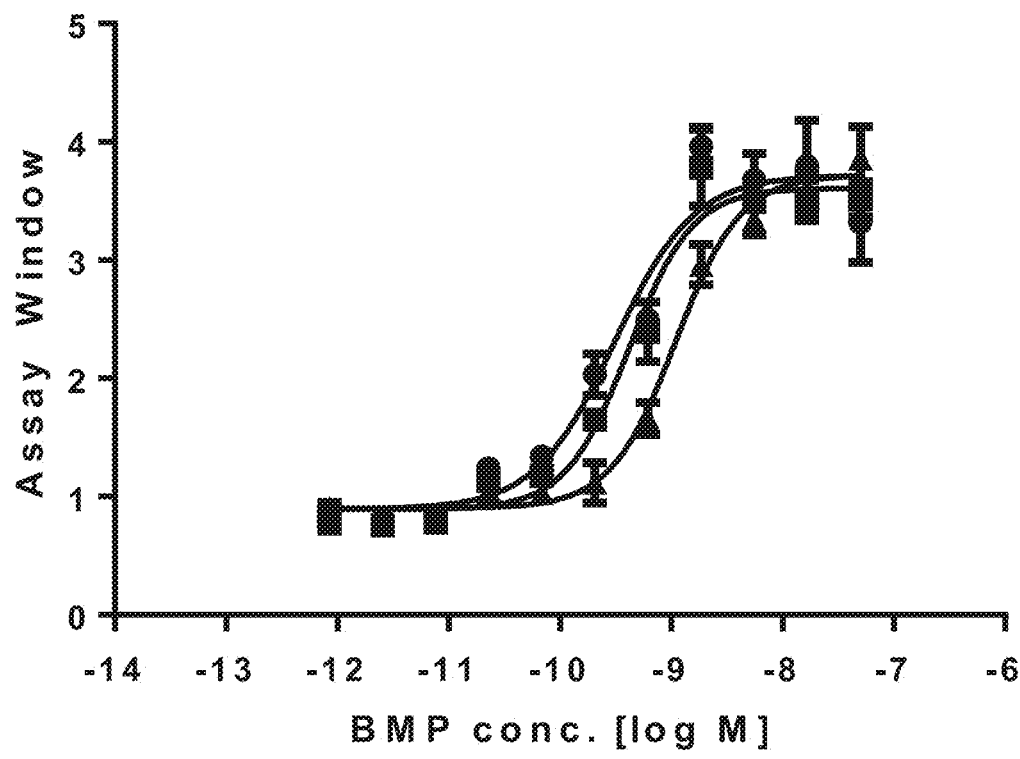
Figure 3A:
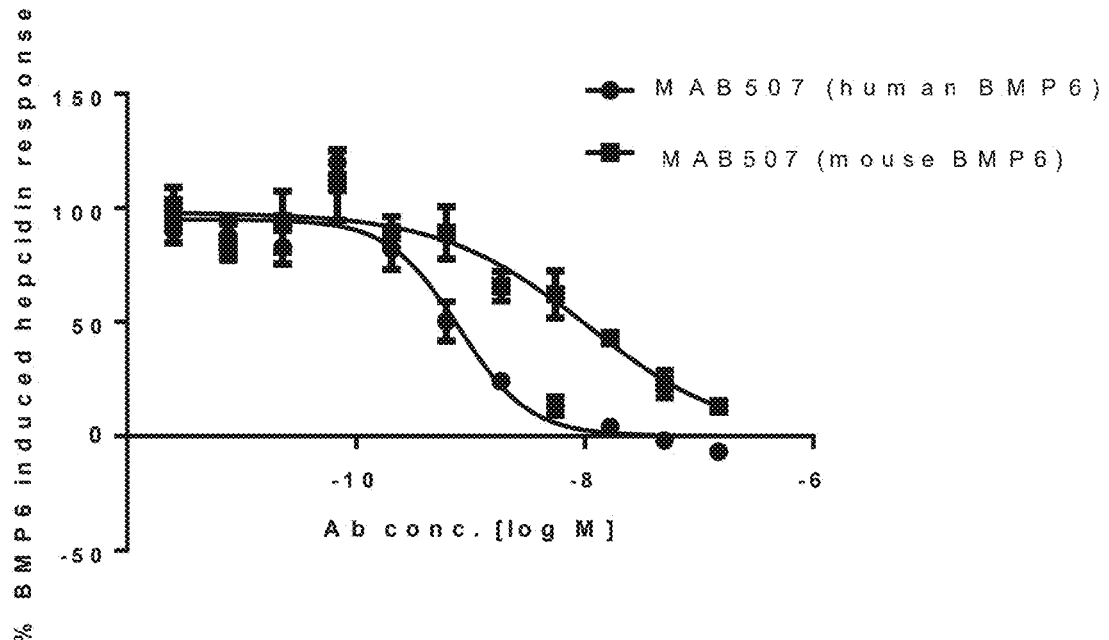
Figure 3B:
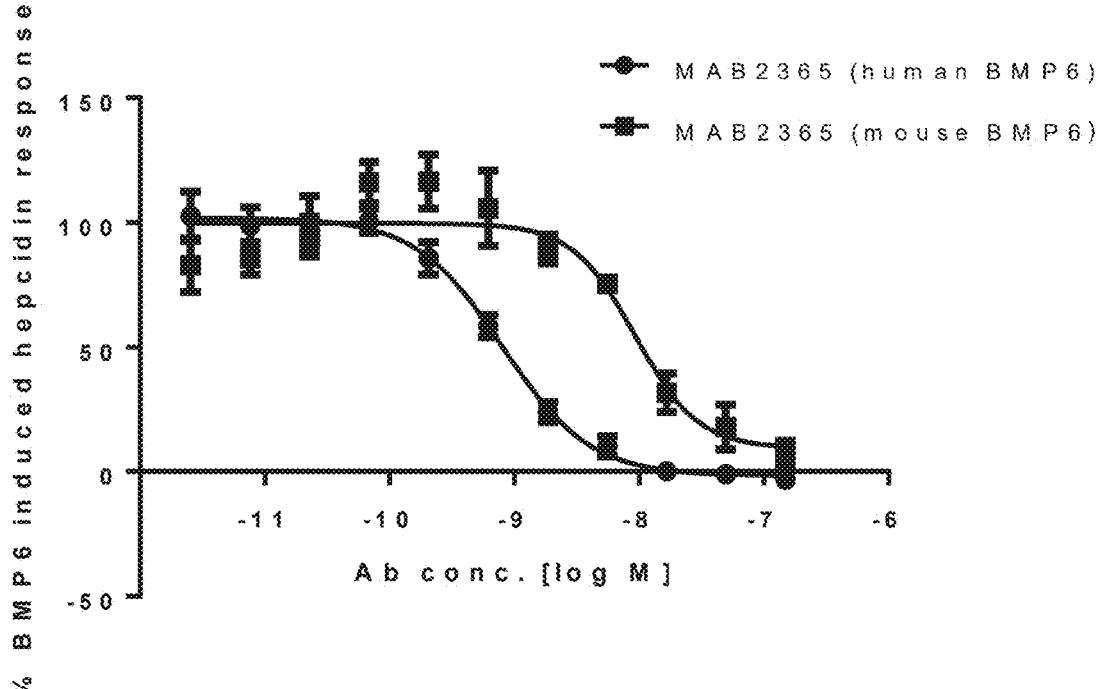

Stable cell lines carrying the Red Firefly luciferase gene under control of the entire 2.8 kB human hepcidin promoter regulatory element as described above were tested for function by stimulating the cells with various recombinant human BMP proteins known to stimulate the SMAD pathway. FIGS. 1A-1B show that human BMP2 (R&D Systems 355-BM SEQ ID NO: 493), BMP4 (R&D Systems 314-BP; SEQ ID NO: 494), BMP5 (R&D Systems 615-BMC; SEQ ID NO: 495), BMP6 (Peprotech 120-06; SEQ ID NO: 2) and BMP7 (R&D Systems 354-BP; SEQ ID NO: 496) were all able to induce the expression of the cloned luciferase reporter gene to a similar degree. BMP6 and BMP7 consistently gave the highest level of stimulation even when different media conditions were used. For some BMPs the assay window was elevated in MEM medium compared to hybridoma growth medium with 25% MEM (compare FIGS. 1A/1B)). The HepG2 luciferase reporter line was also tested with different commercially sourced batches of human and mouse BMP6 proteins (R&D Systems 507-BP; SEQ ID NO: 3, Peprotech 120-6; SEQ ID NO: 2 and R&D Systems 6325-BM; SEQ ID NO: 5) (FIG. 2). Cross-reactivity and the capacity to neutralise the activation effect of BMP6 with anti-BMP6 monoclonal antibodies MAB507 and MAB2365 (both R&D Systems) for mouse and human BMP6 respectively was also assessed using this cell line. This revealed that despite the commercially available antibodies MAB507 and MAB2365 being described by the manufacturer as human BMP6 and mouse BMP6 specific monoclonals respectively, they both were cross-reactive with BMP6 from both species albeit with slightly different potency (FIGS. 3A-3B).

Materials and Methods for Stimulation Assay

The HepG2 hamp luciferase reporter cell line was seeded into two 96 well plates, $(2 \times 10^4$ cells/well in 50 µl of MEM media (Minimum Essential Medium—#31095-029, Gibco); 1% v/v FBS). The different BMP proteins mentioned above were diluted in 25 µl of MEM containing 1% FBS and serially diluted 1:3 starting at a concentration of 50 nM. 25 µl of MEM or 25 µl Hybridoma Media (HMM) was then added to each well depending on the experiment (equivalent to 25% of final volume). 25 µl of each dilution was then added to each well containing the cells and plates incubated for 6 h at 37° C. After 24 hrs incubation, 100 µl of Firefly luciferase glow reagent (Thermo Scientific #16197) was added to each well. Cells were put on a shaker for three minutes and then incubated at room temperature in the dark for ten minutes. Luminescence was measured using an Envision™ reader (Perkin Elmer). In some cases (FIG. 2) the experiment was carried out in a total volume of 60 µl using 25% HMM or a fixed final concentration of 1 nM BMP6 and antibody dilutions prepared in HMM for a final concentration of 25% HMM (FIGS. 3A-3B).

Example 2

Immunisation and Generation of Human Anti-BMP6 Monoclonal Antibodies Using Kymouse™

Figure 4:
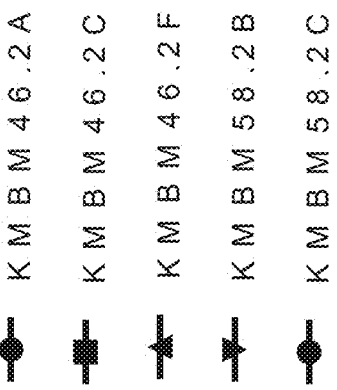
Figure 4:
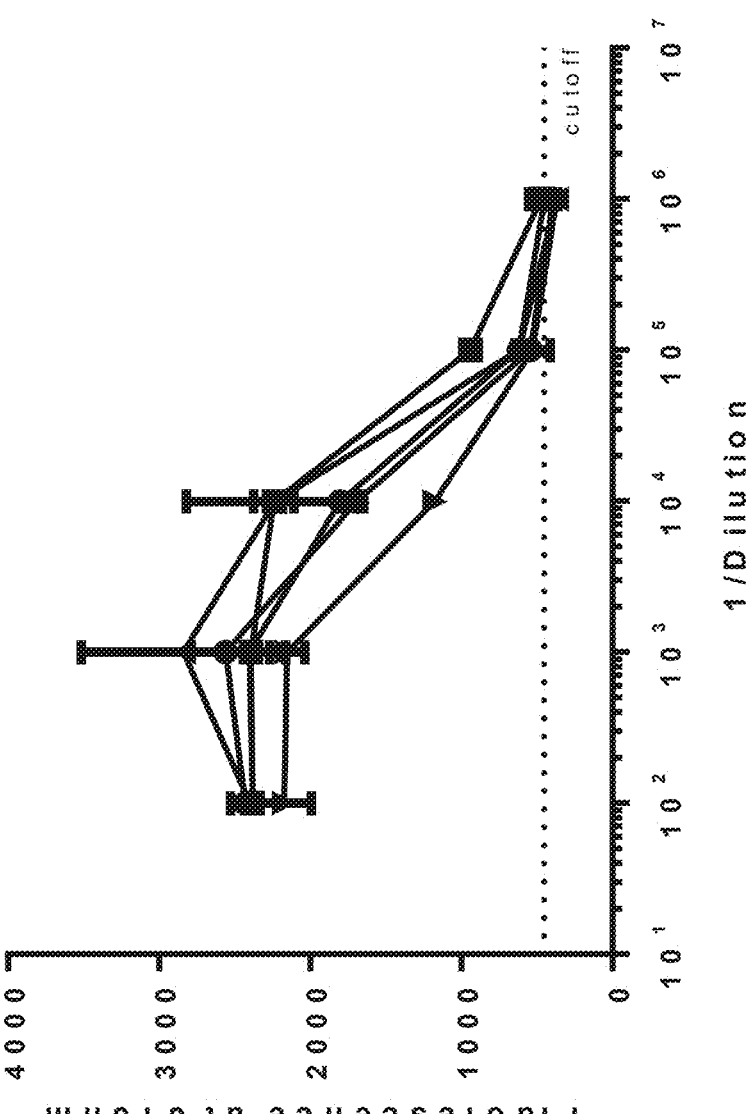

This example describes the generation of human anti-BMP6 antibodies using the Kymouse™ platform (see, e.g., WO2011/004192, WO2011/158009 and WO2013/061098). For this project, Kymouse™ HK strains containing human immunoglobulin genes producing kappa (HK) antibodies having human variable domains were generated that had the genes for murine bmp6 knocked out. These Kymouse™ HK bmp6 −/− mice were immunized with recombinant human BMP6 (Peprotech 120-06; SEQ ID NO: 2) using a prime/ boost regime (Table 1). At the end of each regime a final boost was applied and spleens and lymph nodes were removed about 6-7 days after. In some cases only spleno-cytes were used in others cells obtained from draining lymph nodes were also used (Table 2). Tissues were disaggregated into single cell suspensions for antigen-driven selection of B-cells using B-cell FACS selection technology. Where serum titres were determined during the course of the immunisation a DELFIA assay was used as outlined below. Example serum titres for anti-BMP6 IgG after 3 boosts shown for 5 animals (KM089) in FIG. 4. As evident from Table 1, KM152 was a straight repeat from KM089 and produced similar titres (data not shown).

TABLE 1

Overview Immunisation Regimes using Kymouse ™ HK bmp6 -/- mice

| Immunisation | Kymouse ™ strain | Prime/boost regime |
|---|---|---|
| KM089 | HK bmp6 -/- | Prime followed by 3-4 boosts; |
| KM152 | HK bmp6 -/- | Prime followed by 2-3 boosts; |

Determination of Serum Titres by DELFIA®:

Serum titres for anti-BMP6 antibodies were determined by a reverse DELFIA® assay (Perkin Elmer) where anti-bodies were captured via the Fc domain (goat anti-mouse IgG; Southern Biotech 1030-01), blocked with blocking buffer (PBS containing 1% w/v BSA) and then biotinylated BMP6 (Peprotech 120-06 SEQ ID NO: 2)) added to the wells. Bound BMP6 was detected using DELFIA Eu-N1 Streptavidin (Perkin Elmer) at 1:1000 dilution. Enhance-ment solution was added for 5 minutes and left at room temperature in the dark and then read at 615 nm (Perkin Elmer Envision). Plates were washed between each incuba-tion step 3× with wash buffer (PBS 0.1% v/v Tween). Anti-human BMP6 antibody (R&D systems MAB507) was used as a positive control.

Murine Tissue Isolation and Preparation:

Selected animals based on anti-BMP6 titres were given a final boost and spleens excised 6-8 days later, washed in 1×PBS and kept on ice until further processing. Tissues were prepared in buffer containing 1×PBS (Invitrogen) and 3% heat-inactivated FBS (Invitrogen). Splenocytes were dis-persed by mashing the tissue through a 40 μm strainer (BD Falcon) and rinsing with 30 ml 3% FBS/PBS buffer before centrifugation at 500 g for 10 minutes at 4° C. To remove red blood cells, the pelleted splenocytes were resuspended in 1 ml of ACK Lysis Buffer (Invitrogen). After 2 minutes of incubation at room temperature, the lysis reaction was stopped by addition of 9 ml of 3% FBS/1×PBS buffer. Cell clumps were filtered out with a 40 μm strainer. The remain-ing splenocytes were pelleted for further procedures.

BCT Sorting and Processing for Expression

For KM089 one B-cell sort was carried out using 4 animals and for KM152 two sorts were carried out with a total of 6 animals (Table 2). Splenocytes, and in some cases also lymph nodes, were prepared from selected animals and subjected to antigen specific B-cell selection and sorting. For this, biotinylated BMP6 material was generated from recombinantly produced human BMP6 (Peprotech 120-06 SEQ ID NO: 2) and the material tested for binding activity with anti-BMP6 MAB507 (R&D Systems; data not shown). Background binding of the labelled material was assessed by measuring the binding of the labelled BMP6 material to B-cells isolated from animals immunised with an unrelated immunogen. Antigen positive and B-cell marker positive single B-cells were sorted into 96 well plates and immedi-ately frozen for molecular biology processing. B-cell tech-nology (see WO2015040401 for a general description) was used to amplify V-regions from those antigen-selected B-cells. From this primary PCR product V-regions were recovered by further PCR and standard molecular biology methods used in the art and cloned into mammalian expres-sion vectors with the recovered heavy and light chain pairing as recombinant chimeric IgG or as chimeric Fab fragments in HEK cells in 96 well culture plates. After 6-8 days of culture supernatants were tested for binding or neutralisation activity as outlined below. In some cases the primary PCR product derived from antigen selected single B-cells was also subjected to NGS sequencing and V-regions generated from synthetic DNA, cloned into mammalian expression vectors and plasmid DNA prepared for transfection of mammalian cells for expression.

Example 3

Primary Screening

Primary screening was carried out by homogeneous time resolved FRET (HTRF) to establish the binding of the recovered antibody to human BMP6 (Peprotech 120-06 SEQ ID NO: 2) and in some cases also by surface plasmon resonance (SPR) using human Fab fragments binding to immobilised human BMP6. In some instances, the HepG2-based hamp luciferase reporter gene assay described in Example 1 using human BMP6 (Peprotech 120-06 SEQ ID NO: 2) was used in a primary screen setting to directly select for neutralising antibodies (Table 2). Where off-rate ranking was used as a selection criterion a threshold for the off-rate (kd) of a least 10-4 [1/s] at 37° C. was used.

TABLE 2

Summary of primary screens and outcomes carried out on culture supernatants or purified IgG or Fab fragments recovered and expressed in mammalian cells

| Immunisation Regime | Input into Ag-driven B-cell sorting | Input material | Primary screen | Hit selection criteria | Primary hits |
|---|---|---|---|---|---|
| KM089-B1 | spleens from 4 mice | 1149 supernatants produced from single B-cells cloning/expression at 3 different dilutions | HTRF binding to human BMP6 | >10% effect over background | 508 |

TABLE 2-continued

Summary of primary screens and outcomes carried out on culture supernatants or
purified IgG or Fab fragments recovered and expressed in mammalian cells

| Immunisation Regime | Input into Ag-driven B-cell sorting | Input material | Primary screen | Hit selection criteria | Primary hits |
|---|---|---|---|---|---|
| KM152-B1 | spleens from 4 mice | 117 purified clones recovered from single B-cell PCR expressed as IgG and Fab fragments | Binding to human BMP6 (HTRF) and off-rate (SPR) | >10% binding over background (HTRF; 69 hits) and off-rate $<1 \times 10^{-4}$ (SPR; 23 hits) | 23 SPR hits selected (including 14 also positive for HTRF) |
| KM152-B2 | spleens and lymph nodes from 2 mice | 76 purified clones recovered from single B-cell PCR expressed as IgG and Fab fragments | Binding to human BMP6 off-rate (SPR) and BMP6 neutralisation (HepG2 hamp luciferase reporter assay 11-point titration) | Off-rate $<1 \times 10^{-4}$ (SPR; 12 hits) and neutralisation of BMP6 induced luciferase reporter gene expression (23 hits) | 12 unique clones selected based on sequence analysis (including 5 clones positive in both screens) |

HTRF Assay for Binding to Human BMP6

Biotinylated BMP6 (Peprotech 120-06 SEQ ID NO: 2)) was detected with streptavidin D2 (Cisbio (Cat No 610SADLB) and antibodies bound to BMP6 were detected using anti-mouse IgG (Southern Biotech #1030-01) labelled with cryptate. MAB507 (R&D Systems) was used as a positive control and mouse IgG isotype as a negative control. Plates were read on an Envision plate reader (Perkin Elmer) and data was analysed using IDBS software. Positives were generally defined as >10% signal of positive control.

Screening for Functional Inhibition of Human BMP6 Induced Luciferase Expression in HepG2 Cells Under Control of the Hamp Regulatory Region In some cases the HepG2 hamp luciferase reporter gene assay described in Example 1 was used for the primary assessment of recovered IgG to assess the neutralisation capacity for BMP6. 15 ul of a known inhibitor of BMP6 signalling was used as the positive control (R&D systems MAB507; (Andriopoulos et al., 2009)) and human or mouse IgG used as the negative control. Purified antibodies were prepared in HMM 25% E Media from 150 nM, 1:3 dilution curve, 11 points) or IgG-containing supernatant samples were added to 15 ul human BMP6 (Peprotech 120-06 SEQ ID NO: 2) at 10 nM final in MEM 1% FBS and incubated 30 min at RT and then 30 ul HepG2 reporter cells added at 10 000 cells/well and incubated at 37° C. overnight. Next day 30 ul of luciferase substrate buffer (Pierce Firefly Luc One-Step Glow Assay Kit Cat Number: 16197, Perbio) was added to the whole plate and read using an Envision plate reader (Perkin Elmer).

SPR Off-Rate Ranking Analysis

Off-rate screening was performed on a ProteOn™ XPR36 system (BioRad). Biotinylated BMP-6 (Peprotech 120-06 SEQ ID NO: 2) was captured on the NLC sensor chip surface and 50 μl of purified Fab material used as analyte diluted in 200 μl HBS-EP buffer. Off-rate analysis carried out using the software inherent to the ProteOn and all assay runs were carried out at 37°. The inventors set as a decision criterion, that antibodies that displayed of-rates of <1×10-4 [1/s] or better were identified as a positive.

Example 4

Secondary Screening and Selection of Lead Panels

Table 3 summarises the secondary screening and further selection criteria devised by the inventors and applied that led to the selection of lead panels for in vivo analysis. This re-testing involved the use of the HepG2 hamp luciferase reporter gene assay using a BMP6 stimulus and/or SPR off-rate ranking where not applied already in the primary screen. In addition, all selected hits were tested for specificity for BMP6 by testing their capacity to neutralise related BMP molecules in the HepG2 reporter gene assay. In the first instance BMP5 (SEQ ID NO: 495) and BMP7 (SEQ ID NO: 496) were tested due to their higher amino acid homology to BMP6 (human BMP5 shares 81% and human BMP7 72% amino acid homology with human BMP6 in the mature protein). As outlined in Example 1, all of these BMPs are able to effectively trigger the luciferase reporter gene expression in HepG2 cells under control of the hamp regulatory element region. MAB507 was used in this assay as a control since this mAb has previously shown cross-reactivity with BMP5 and BMP7 in particular (Andriopoulos et al., 2009). The inventors set as a decision criterion, that antibodies that showed consistent neutralisation of either BMP5 (SEQ ID NO: 495) and BMP7 (SEQ ID NO: 496) or both were excluded. In the case of KM089-B1 secondary screen the HepG2 reporter gene assay was also performed with murine BMP6 (R&D Systems; SEQ ID NO: 5) to test for murine cross reactivity, however, for subsequent campaigns this screen was dropped from the secondary screens since murine cross reactivity was commonly observed across all hits presumably due to the high homology between human and mouse BMP6.

TABLE 3

Summary of secondary and further assessments of primary hits carried out on culture
supernatants or purified IgG or Fab fragments recovered and expressed in mammalian cells

| Clone pools | Secondary screen input | Secondary screen I | Outcome | Secondary screen II | Outcome |
|---|---|---|---|---|---|
| KM089-B1 PCR recovery | 508 HTRF hit supernatants containing IgG | Human and mouse BMP6 neutralisation (HepG2 hamp luciferase reporter assay (single point)) | 237 >50% neutralisation and murine cross-reactivity | 237 purified Fabs off-rate screened (SPR) with off-rate <1 × 10⁻⁴ and BMP6 neutralisation (HepG2 hamp luciferase reporter assay (11-point)) | 23 combined hits; sequence analysis, expression data and testing for specificity for BMP6 resulted in 6 antibodies selected for in vivo analysis (Table 7) |
| KM152-B1 NGS and PCR recovery | 157 new purified antibodies identified by next-generation sequencing (NGS) and network analysis | Off-rate screen (SPR) and BMP6 neutralisation (HepG2 hamp luciferase reporter assay (11-point)) | 60 hits (16 off-rate SPR and 44 HepG2 hamp luciferase reporter assay) | 60 secondary hits from NGS were combined with 23 hits recovered from single B-cell PCR primary screen (Table 2) | Sequence analysis resulted in 4 unique combined hits; 1 hit selected for in vivo assessment following expression and specificity testing for BMP6 (Table 7) |
| KM152-B2 PCR recovery | 12 selected hits (Table 2) | BMP neutralisation (HepG2 hamp luciferase reporter assay (11-point)) using BMP5, BMP6 and BMP7 | 7 selected for in vivo assessment (Table 8) | — | — |
| All campaigns NGS and network analysis | 21 purified antibodies identified with highly related amino acid sequences to CL-58838 | BMP neutralisation (HepG2 hamp luciferase reporter assay (11-point)) using BMP5, BMP6 and BMP7 | 10 antibodies identified as neutralisers of BMP6; 3 excluded due to cross-reactivity with BMP7 (Table 6) | 4 antibodies selected for expression after assessing potency for BMP6 neutralisation (HepG2 hamp luciferase reporter assay (11-point)) in comparison with CL-58838 | 3 antibodies selected for in vivo assessment following sequence comparison with previously tested clones and expression (Table 9) |

$$40$$

Selection of Lead Panels for In Vivo Testing 23 combined hits were identified from KM089 secondary screening (Table 3). 4 clones were also identified from KM152-B1 with a combination of secondary screening the primary hits from single B-cell PCR and an NGS analysis of all sorted antigen specific B-cells (Table 3). These 27 antibodies were subjected to a detailed sequence analysis to identify unique clonal sequences and sequences with no obvious developability liabilities in the judgement of the inventors. Following these gating criteria, 12 antibodies were chosen by the inventors, re-expressed and purified as fully human IgG4 (SEQ ID NO: 454). Two of the 12 antibodies showed signs of expression or post-purification quality issues and were therefore not pursued further. The remaining 10 antibodies were then tested for specificity for human BMP6 and neutralisation potency of human BMP6 using the HepG2 hamp luciferase reporter assay (Table 4).

TABLE 4

Lead selection from 10 antibodies derived from KM089 and KM152 and assessed in
secondary screen for selectivity for human BMP6; antibodies selected for in vivo analysis shown in
bold)

| Antibody ID | Origin | hBMP5 neutralisation (n = 1) | hBMP5 neutralisation (n = 2) | hBMP7 neutralisation (n = 1) | hBMP7 neutralisation (n = 2) |
|---|---|---|---|---|---|
| CL-66833 | KM152-B1 | No | No | No | No |
| CL-57890 | KM089 | Incomplete curve Max response 20% | Incomplete curve Max response 68.5% | Incomplete curve Max response 59.8% | Incomplete curve Max response 24.4% |
| CL-57931 | KM089 | No | No | No | No |
| CL-58838 | KM089 | No | No | Incomplete curve Max response 53% | No |

TABLE 4-continued

Lead selection from 10 antibodies derived from KM089 and KM152 and assessed in
secondary screen for selectivity for human BMP6; antibodies selected for in vivo analysis shown in
bold)

| Antibody ID | Origin | hBMP5 neutralisation (n = 1) | hBMP5 neutralisation (n = 2) | hBMP7 neutralisation (n = 1) | hBMP7 neutralisation (n = 2) |
|---|---|---|---|---|---|
| CL-58851 | KM089 | No | No | No | No |
| CL-58252 | KM089 | No | No | No | No |
| CL-58102 | KM089 | No | No | No | No |
| CL-57859 | KM089 | Yes, EC50 4.5 nM | Incomplete curve Max response 8% | Incomplete curve Max response 13.2% | Incomplete curve Max response 34.1% |
| CL-58832 | KM089 | Incomplete curve Max response 9% | Incomplete curve Max response 11.7% | Incomplete curve Max response 16.9% | Incomplete curve Max response 57.7% |
| CL-57945 | KM089 | No | No | Incomplete curve Max response 39.1% | No |

Following this, 7 clones with no observed cross reactivity to BMP5 (R&D Systems 615-1BMC; SEQ ID NO: 495) or BMP7 (R&D Systems 354-BP; SEQ ID NO: 496) (shown in bold Table 4) were progressed to in vivo rat studies (Example 11) and therefore re-expressed in scaled-up CHO suspension cells and purified for in vivo use.

For KM152-12 12 combined hits selected after primary neutralisation screening (Table 2) were re-expressed. This purified lead panel was further tested by comparing the potency for neutralising human BMP6 (Peprotech 120-06; SEQ ID NO: 2) in 11-dilution point curves in the HepG2 hamp luc reporter assay with the best leads from KM089 and also considering neutralisation for BMP5 (R&D Systems 615-1BMC; SEW ID NO: 495) and BMP7 (R&D Systems 354-BP; SEQ ID NO: 496). From this, 5 antibodies were excluded that did not show superior potency to previous leads from KM089 leaving 7 clones for in vivo testing (data not shown; Table 5).

TABLE 5

12 antibodies selected from KM152-B2 assessed in
secondary screen for selectivity for human BMP6;
antibodies selected for in vivo analysis shown in bold)

| Antibody ID | Origin | hBMP5 neutralisation | hBMP7 neutralisation | Selected for in vivo assessment |
|---|---|---|---|---|
| CL-75714 | KM152-B2 | No | No | Yes |
| CL-75605 | KM152-B2 | No | No | No; expression issues; no superior neutralisation |
| CL-75565 | KM152-B2 | No | No | Yes |
| CL-75539 | KM152-B2 | No | No | Yes |
| CL-75520 | KM152-B2 | No | No | Yes |
| CL-75519 | KM152-B2 | No | No | No; expression issues; no superior neutralisation |
| CL-75511 | KM152-B2 | No | No | No; expression issues; no superior neutralisation |
| CL-75506 | KM152-B2 | No | No | Yes |
| CL-75500 | KM152-B2 | No | No | Yes |
| CL-75496 | KM152-B2 | No | No | No; no superior neutralisation |

TABLE 5-continued 12 antibodies selected from KM152-B2 assessed in
secondary screen for selectivity for human BMP6;
antibodies selected for in vivo analysis shown in bold)

| Antibody ID | Origin | hBMP5 neutralisation | hBMP7 neutralisation | Selected for in vivo assessment |
|---|---|---|---|---|
| CL-75194 | KM152-B2 | No | No | No; no superior neutralisation |
| CL-75183 | KM152-B2 | No | No | Yes |

Following the analysis of the first set of 7 antibodies in vivo (Table 4) and observing superior activity for CL-58838 (see Example 11), the decision was taken to use data obtained by next generation sequencing (NGS) to potentially expand the panel of lead clones by identifying antibodies that were based on the Vh (SEQ ID NO: 114) and Vk (SEQ ID NO: 123) class sequences of this antibody. Paired Vh and Vk chains obtained from NGS on the amplified V-regions after B-cell sorting were analysed for sequences with high homology to CL-58838 with the aim of obtaining slightly mutated yet highly related antibody sequences to CL-58838. The search was driven by having identical use of human V, D and i-regions (IGHV3-11*01, IGHD6-19*01, IGHJ4*02/ IGKV3-20*01, IGKJ1*01) and identical CDRH3 sequence. A total of 21 antibodies were identified by this method, expressed, purified and assessed for function, specificity for BMP6 and potency (Table 3). The 21 antibodies were derived from 5 different immunised mice from immunisation campaigns KM089 and KM152. Ten antibodies were initially confirmed as neutralisers of BMP6 but after assessing for specificity for BMP6 over BMP5 and BMP7 and comparing potencies for neutralising human BMP6 in the HepG2 luc assay in comparison with CL-58838 7 antibodies were selected shown in Table 6. A cross-sequence comparison with antibodies tested in all previous screening campaigns excluded another 3 antibodies that were assessed before leaving four new unique antibodies that were expressed and purified for in vivo analysis. Of these four, CL-58713 did not express at sufficient quantities at this scale and was therefore also excluded. The three remaining new antibodies were progressed to an in vivo study in rats (shown in bold Table 6 and shown in Example 17) and came from two different immunised bmp6 –/– mice from immunisation KM089.

TABLE 6

| | | hBMP5 neutral-isation | hBMP7 neutral-isation | Selected for in vivo assessment (example 17) |
|---|---|---|---|---|
| Antibody ID | Origin | | | |
| CL-58722 | KM089 animal CP-230 | No | No | Yes |
| CL-58713 | KM089 animal CP-230 | No | No | No (not sufficient material available for in vivo study |
| CL-58921 | KM089 animal CP-231 | No | No | No (sequence same as CL-58838) |
| CL-58676 | KM089 animal CP-230 | No | No | No (sequence same as CL-58756) |
| CL-58835 | KM089 animal CP-231 | No | No | Yes |

TABLE 6-continued

Antibodies identified by NGS with same V-gene usage and CDRH3 length as CL-58838 and selected by functional screen

| Antibody ID | Origin | hBMP5 neutral-isation | hBMP7 neutral-isation | Selected for in vivo assessment (example 17) |
|---|---|---|---|---|
| CL-71800 | KM089 animal CP-231 | No | No | No (sequence same as CL-58838) |
| CL-58756 | KM089 animal CP-230 | No | No | Yes |

Example 5

Sequence Analysis of Lead Clones

Antibodies selected for in vivo use were analysed for the V-region gene usage and the degree of mutation introduced during the in vivo maturation process that occurs naturally during immunisation of the Kymouse™. Tables 7-9 summarise this information for the antibodies selected in Tables 4-6. All CDR definitions shown here are IMGT definitions.

TABLE 7

7 antibodies selected from KM089 and KM152-B1 for in vivo study

| Antibody ID | IGHV gene | IGHD gene | IGHJ gene | CDRH3 length (IMGT) | Mutations outside CDRH3 (IMGT) Nucleic acid | Amino acid | IGLV gene | IGLJ gene | CDRL3 length (IMGT) | Mutations outside CDRL3 (IMGT) Nucleic acid | Amino acid |
|---|---|---|---|---|---|---|---|---|---|---|---|
| CL-66833 | IGHV1-3*01 | IGHD3-10*01 | IGHJ4*02 | 11 | 17 | 12 | IGKV1-5*03 | IGKJ1*01 | 9 | 7 | 5 |
| CL-57931 | IGHV1-3*01 | IGHD3-10*01 | IGHJ3*02 | 11 | 24 | 14 | IGKV3-20*01 | IGKJ1*01 | 9 | 15 | 11 |
| CL-58838 | IGHV3-11*01 | IGHD6-19*01 | IGHJ4*02 | 10 | 5 | 3 | IGKV3-20*01 | IGKJ1*01 | 9 | 21 | 9 |
| CL-58851 | IGHV1-3*01 | IGHD7-27*02 | IGHJ4*02 | 11 | 19 | 16 | IGKV3-20*01 | IGKJ1*01 | 9 | 17 | 11 |
| CL-58252 | IGHV1-3*01 | IGHD4-23*01 | IGHJ4*02 | 11 | 12 | 9 | IGKV1-5*03 | IGKJ1*01 | 9 | 2 | 1 |
| CL-58102 | IGHV1-3*01 | IGHD5-18*01 | IGHJ4*02 | 11 | 24 | 12 | IGKV3-20*01 | IGKJ1*01 | 9 | 26 | 16 |
| CL-57945 | IGHV1-3*01 | IGHD5-18*01 | IGHJ4*02 | 11 | 21 | 12 | IGKV3-20*01 | IGKJ1*01 | 9 | 15 | 11 |

TABLE 8

KM152-B2 7 antibodies selected from KM152-B2 for in vivo study

| Antibody ID | IGHV gene | IGHD gene | IGHJ gene | CDRH3 length (IMGT) | Mutations outside CDRH3 (IMGT) Nucleic acid | Amino acid | IGLV gene | IGLJ gene | CDRL3 length (IMGT) | Mutations outside CDRL3 (IMGT) Nucleic acid | Amino acid |
|---|---|---|---|---|---|---|---|---|---|---|---|
| CL-75714 | IGHV1-3*01 | IGHD3-10*01 | IGHJ4*02 | 11 | 17 | 11 | IGKV3-15*01 | IGKJ3*01 | 9 | 8 | 8 |
| CL-75565 | IGHV1-3*01 | IGHD3-10*01 | IGHJ4*02 | 11 | 2 | 2 | IGKV3-15*01 | IGKJ3*01 | 9 | 4 | 3 |
| CL-75539 | IGHV1-3*01 | IGHD3-10*01 | IGHJ4*02 | 11 | 11 | 9 | IGKV3-15*01 | IGKJ3*01 | 9 | 5 | 3 |
| CL-75520 | IGHV1-3*01 | IGHD3-22*01 | IGHJ4*02 | 13 | 9 | 6 | IGKV3-20*01 | IGKJ3*01 | 8 | 6 | 4 |
| CL-75506 | IGHV1-3*01 | IGHD3-10*01 | IGHJ4*02 | 11 | 6 | 6 | IGKV3-15*01 | IGKJ3*01 | 9 | 5 | 4 |

TABLE 8-continued

| KM152-B2 7 antibodies selected from KM152-B2 for in vivo study | | | | | | | | | | |
|---|---|---|---|---|---|---|---|---|---|---|
| | | | | | Mutations outside CDRH3 (IMGT) | | | | Mutations outside CDRL3 (IMGT) | |
| | | | CDRH3 | | | | | CDRL3 | | |
| Antibody ID | IGHV gene | IGHD gene | IGHJ gene | length (IMGT) | Nucleic acid | Amino acid | IGLV gene | IGLJ gene | length (IMGT) | Nucleic acid | Amino acid |
| CL-75500 | IGHV1-3*01 | IGHD3-10*01 | IGHJ4*02 | 11 | 10 | 5 | IGKV3-15*01 | IGKJ3*01 | 9 | 6 | 4 |
| CL-75183 | IGHV1-3*01 | IGHD3-16*02 | IGHJ5*02 | 11 | 11 | 8 | IGKV1-5*03 | IGKJ3*01 | 8 | 5 | 4 |

TABLE 9

| CL-58838-like antibodies identified by NGS and sequence mining | | | | | | | | | | |
|---|---|---|---|---|---|---|---|---|---|---|
| | | | | | Mutations outside CDRH3 (IMGT) | | | | Mutations outside CDRL3 (IMGT) | |
| | | | CDRH3 | | | | | CDRL3 | | |
| Antibody ID | IGHV gene | IGHD gene | IGHJ gene | length (IMGT) | Nucleic acid | Amino acid | IGLV gene | IGLJ gene | length (IMGT) | Nucleic acid | Amino acid |
| CL-58835 | IGHV3-11*01 | IGHD6-19*01 | IGHJ4*02 | 10 | 6 | 4 | IGKV3-20*01 | IGKJ1*01 | 9 | 22 | 10 |
| CL-58756 | IGHV3-11*01 | IGHD6-19*01 | IGHJ4*02 | 10 | 1 | 1 | IGKV3-20*01 | IGKJ1*01 | 9 | 3 | 3 |
| CL-58722 | IGHV3-11*01 | IGHD6-19*01 | IGHJ4*02 | 10 | 3 | 2 | IGKV3-20*01 | IGKJ1*01 | 9 | 3 | 3 |

Example 6

Binding Kinetics for Antibody CL-58838 Measured by SPR

The kinetics for CL-58838 IgG4 (SEQ ID NO: 116 and SEQ ID NO: 125) binding to human BMP6 was determined by surface plasmon resonance (SPR) at 37° C. at pH 7.6. Like the other antibodies used in the Examples, the CL-58838 IgG4 antibody comprised the IgH constant region of SEQ ID NO: 454 (which we call "IgG4-PE"), which is effector function inactivated and hinge stabilised. Briefly, for this measurement biotinylated recombinant human BMP6 (Peprotech 120-06) (SEQ ID NO: 2) was immobilised on a streptavidin coated biosensor chip and binding examined using a single cycle kinetic method run at 5 different IgG concentrations. In this set-up the bivalent IgG4 antibody interacts with the dimeric BMP6 antigen which means that avidity will play a part in the overall binding kinetics measured due to potential multiple interactions occurring per molecule. The bivalent model used for the data analysis was intended to deconvolute this effect but is not as reliable as measuring true 1:1 interactions. In this set-up the KD values should therefore be referred to as "relative" affinity values. The relative KD value determined for CL-58838 by this method was 0.07 nM (Table 10).

TABLE 10

| Measurement of CL-58838 IgG4 binding kinetics to human BMP6 at 37° C. and pH 7.6 | | | |
|---|---|---|---|
| Sample | ka [1/Mx1/s] | kd [1/s] | Relative KD [nM] |
| CL-58838 IgG4 | $5.22^{06}$ | $3.69^{-04}$ | 0.07 |

In a second experimental set-up Fab fragments of CL-58838 were generated by expression in CHO cells and the interaction was measured where the Fab fragments were the analyte in the flowcell binding to immobilised biotinylated human BMP6 (Peprotech 120-06) (SEQ ID NO: 2) on a Neutravidin Biosensor chip NLC (Biorad). Since this experimental set-up involves monomeric Fab fragments that avoid bivalent interactions this represented an interaction were avidity has very limited or no contributions to the binding kinetics and therefore true KD values could be determined (Table 11). CL-58838 showed a true KD for the interaction of Fab fragment with human BMP6 at 37° C. and pH 7.6 of around 140 µM.

TABLE 11

| Representative result from two experiments measuring the binding kinetics of a CL-58838-based Fab fragment to immobilised human BMP6 at 37° C. and pH 7.6 | | | |
|---|---|---|---|
| Sample | Ka [1/Mx1/s] | Kd [1/s] | KD [nM] |
| CL-58838 Fab | $3.64^{06}$ | $4.99^{-04}$ | 0.14 |

Methods

SPR Analysis of IgG

Recombinant human BMP6 (Peprotech 120-06) (SEQ ID NO: 2) was biotinylated and immobilised on a SA Biosensor Chip (GE Healthcare) and a single cycle kinetic method was deployed running IgG at 5 different concentrations of CL-58838 (0.1, 0.5, 2.5, 12.5 and 62.5 nM) as the analyte. The binding sensorgrams were double referenced using an identical set of injections with buffer in place of the antibody. The data was fitted to the bivalent model inherent to the Biacore 8K (GE Healthcare) analysis software. The assay was run at 37° C., using HBS-EP as the running buffer at pH 7.6.

SPR Analysis of Fab Fragments

Human BMP6 (Peprotech 120-06) (SEQ ID NO: 2) was biotinylated and immobilised on a Neutravidin Biosensor chip NLC (Biorad 1765021). Fab fragments of CL-58838 were generated by expression in HEK cells and purified with protein G and size exclusion chromatography. The Fabs were used and as analyte at 64, 16, 4, 1 and 0.25 nM. The binding sensorgrams were double referenced using a buffer injection. Data was fitted to the 1:1 model inherent to the ProteOn XPR36 analysis software. The assay was run at 37° C. using HBS-EP as the running buffer at pH 7.6.

Example 7

Testing of CL-58838 for Cross-Reactivity with Other BMPs

Antibody CL-58838 IgG4 (SEQ ID NO: 116 and SEQ ID NO: 125) was assessed in more detail in respect of its lack of cross-reactivity with other BMP family members. The screening strategy already effectively excluded any effects on BMP5 and BMP7, the two most related BMP amino acid sequences (81% and 72% respectively). As outlined in Example 4, the cross-reactivity was assessed using the HepG2 reporter gene assay developed in Example 1 with an extended panel to also include less homologous members of the BMP family like BMP2 (56%), BMP4 (58%) and BMP9 (54%). Assays were run at fixed final concentrations of all BMP of 10 nM that provided adequate stimulation of the hamp driven reporter gene expression and a 11-point dilution range of CL-58838 antibody starting at a final concentration of 600 nM. For BMP2 (R&D Systems 355-BM; SEQ ID NO: 493), BMP4 (R&D Systems 314-BP; SEQ ID NO: 494) and BMP9 (Peprotech 120-7; SEQ ID NO: 497) cross-reactivity testing was carried out once whereas for BMP5 (R&D Systems 615-BMC SEQ ID NO: 495) and BMP7 (R&D Systems 354-BP; SEQ ID NO: 496) n=2. One experiment is shown in each case in FIGS. 7A-7E. Results show that there was no detectable neutralisation of CL-58838 against any of the BMP tested here. Commercial control antibodies specific for the relevant BMP tested in each assay neutralised the reporter gene expression as expected (anti-BMP2/4 R&D Systems MAB3552; anti-BMP5 R&D Systems MAB7151, anti-BMP7 R&D Systems MAB3541, anti-BMP9 R&D Systems 3209).

Method

Human BMPs were prepared at 40 nM (10 nM final assay concentration) in MEM 1% FBS. Control curves were prepared using anti-BMP2/4 (R&D Systems), anti-BMP5 (MAB7151, R&D Systems), anti-BMP7 (MAB3541, R&D Systems) and Human IgG4 isotype control (in house produced). Reference antibodies were titrated from 2.4 μM in PBS (600 nM final assay concentration) using a three-fold dilution series for the generation of 11-point curve. BMP standard curves were prepared from 800 nM in PBS (200 nM final assay concentration) using a three-fold dilution series for the generation of 11-point curve. Titrations for each molecule tested were generated by three-fold dilution, 11-points curves in PBS. 15 μL were then transferred from the dilution to the assay plates (LUC). 15 μL of PBS were added to total binding and non-specific binding wells, 15 μL of human BMPs at 40 nM were added to test wells and to total binding control well and 15 μL of MEM 1% FBS was transferred to non-specific binding control wells. Plates were left at room temperature while preparing HepG2 reporter cells. Cells were detached from flasks, pelleted and re-suspended in MEM supplemented with 1% FBS at 3.3×105 cells/ml. 30 μl of cells were added to the entire test plates at 10,000 cells/well. Plates were incubated overnight at 37° C., 5% CO2 and the next day, 30 μl of luciferase substrate (contained in Pierce Firefly Luc one step glow assay kit) was added to assay plate. Plates were incubated for 10 minutes at room temperature in the dark and read using the Envision (Perkin Elmer).

Example 8

Testing Anti-BMP6 Antibodies for Interference of Receptor Dimerization

It has been suggested in the literature that ALK2 and ALK3 are the major type I BMP receptors expressed in the liver of mice and humans (Mayeur et al., 2014; Xia et al., 2008) that enable BMP induced signalling in hepatocytes. We were therefore interested in how blocking the biological activity of BMP6 with anti-BMP6 antibodies affects the dimerization of BMPR1 and BMPR2 that has been described as a requirement to trigger phosphorylation of BMPR1 and subsequent signalling through the SMAD pathway. We investigated the impact on BMPR1A (ALK3, CD292) with BMPR2 (T-ALK) and BMPR1B (ALK6) and with BMPR2 (T-ALK) dimerisation. Dimerisation was measured using the PathHunter® eXpress dimerisation assay (DiscoverX). In this system, U20S cells are stably transfected with modified human ALK3/ALK6 and BMPR2 intracellularly tagged with inactive enzyme subunits, Pro-Link™ (PK) or Enzyme Acceptor (EA) respectively. Upon ligand-induced activation, the two receptors dimerize forcing the two enzyme components to complement creating an active enzyme that then hydrolyses a substrate to generate a chemiluminescent signal. Here we used BMP6 to trigger the dimerization event in both cases.

Initially, a BMP6 response curve was established using a range of BMP6 concentration starting at 5 μg/ml final concentration and further doubling dilutions. Eventually, a fixed concentration of 200 ng/ml BMP6 was chosen for analysing the effects of anti-BMP6 antibodies on BMP6 induced receptor dimerisation. The effect of anti-BMP6 monoclonal mouse antibody MAB507 (R&D Systems) and various other anti-BMP6 antibodies on the dimerization was studied at a range of antibody concentrations. Antibody A is an anti-BMP6 antibody comprising VH domains wherein each domain comprises SEQ ID NO: 402; and VL domains, wherein each domain comprises SEQ ID NO: 410. Antibody B is an anti-BMP6 antibody comprising VH domains wherein each domain comprises SEQ ID NO: 418; and VL domains, wherein each domain comprises SEQ ID NO: 426.

FIG. 6A shows the representative result of two experiments carried out for the dimerisation of BMPR1A (ALK3)/BMPR2. All human anti-BMP6 antibodies tested reduced ALK3/BMPR2 receptor dimerisation in a concentration dependent manner leading to a complete inhibition of dimerisation at concentrations greater than 10 nM. The IC50 values in this experiment were 2 nM for the human anti-BMP6 antibodies tested. The murine monoclonal MAB507 (R&D Systems) had a slightly lower IC50 of 3 nM. Whilst not wishing to be bound by any particular theory, the most likely interpretation of this observation is that binding of the anti-BMP6 antibodies to BMP6 prevents BMP6 from interacting with one or both BMP-receptors thus preventing a BMP6-driven dimerization of the type I and type II receptor.

However, it is also conceivable that some anti-BMP6 antibodies may bind to BMP6 in a manner that would still allow the interaction of the BMP6-antibody complex with one of those receptors molecules and where then the antibody remains bound to BMP6 on the interaction of the complex with one of the receptors. This bound receptor-antibody complex might then sterically prevent or interfere with the subsequent interaction of this receptor-antibody complex with the other paired receptor thus avoiding an effective dimerization and signal generation in this assay.

FIG. 6B shows the representative result of two experiments carried out for the dimerisation of BMPR1B (ALK6)/BMPR2. Human anti-BMP6 antibodies 1-8 were tested for their ability to impact ALK6/BMPR2 receptor dimerisation in a concentration dependent manner. All antibodies tested lead to a complete inhibition of dimerization. Some of the anti-BMP6 antibodies used here showed only full neutralisation at 100 nM or above. The murine monoclonal MAB507 (R&D Systems) had an IC50 of about 0.2 nM in this assay.

As indicated by The Human Protein Atlas (world wide web.proteinatlas.org/ENSG00000168509-HFE2/cell #rna) U2O2 cells do not express HJV (also known as haemojuvelin, hemojuvelin, HFE2A, HJV, JH and RGMC). Furthermore, we engineered the cell line to express exogenous human BMP receptors, but no engineering was performed to express exogenous HJV. The results, therefore, showed that surprisingly we could inhibit HJV-independent dimerization of BMP receptors by BMP6 using anti-BMP6 antagonists.

Method

A human ALK3+human BMPR2-expressing cell line created, and a human ALK6+human BMPR2-expressing cell line created (the ALKs were engineered with inactive enzyme subunits, ProLink™ (PK), whereas the BMPR2 was engineered with Enzyme Acceptor (EA). PathHunter® eXpress BMPR1A+BMPR2 and BMPR1B+BMPR2 transfected U20S cells (DiscoverX #93-1053C3 or #93-1063E3) were resuspended in the provided Cell Plating reagent and 100 μl of the cell suspension added to each well (1×10⁴ cells/well) of a white-walled clear bottom 96-well tissue culture plate (DiscoverX #15-073) and incubated for 24 h at 37° C. For establishing the appropriate assay window a titration of human BMP6 (Peprotech 120-06) (SEQ ID NO: 2) was prepared starting at a final concentration of 5 μg/ml and diluted 1 in 3 (×11) in Cell Plating Reagent. From the results of this dilution series a fixed final concentration of 200 ng/ml BMP6 was chosen for both experiments. Antibodies were then tested by adding 200 ng/ml hBMP6 final concentration to a serial dilution of anti-BMP6 antibodies to wells of a microtitre plate and incubating for 1 h at room temperature. Following this, 10 μl of this pre-incubated mixture was then added to U20S cells cultured plate per well and incubated at 37° C. for a further 16 h. Detection reagent was prepared by adding 1 volume Flash Cell Assay Buffer (DiscoverX #30-390) to 4 volumes Flash Substrate Reagent (DiscoverX #10-219). 110 μl of this prepared Detection Mix was added to each well and incubated for 1 h at room temperature in the dark. Plates were read and analysed using an Envision (PerkinElmer) plate reader.

Example 9

Linear Epitope Mapping Using Overlapping Peptide Arrays

Linear epitope mapping was carried out using linear peptides covering the entire sequence of mature human BMP6. The BMP6 peptides were elongated with neutral glycine-serine (GSGSGSG) linkers at the C- and N-terminus to avoid generating truncated peptides at the C- and N-terminus. The elongated BMP6 sequence was then converted into overlapping 15 amino acid peptides with an overlap of 14 amino acids. Microarray chips were printed that contained all the overlapping peptides as well as peptide variations for all locations where mouse BMP6 sequence differs from human BMP6 (PEPerPRINT GmbH). The resulting BMP6 peptide microarrays contained 232 different peptides printed in duplicate (464 peptide spots). CL-58838, Antibody A, Antibody B, mab155963 (Abcam) raised with a linear synthetic BMP6 peptide and Morph 6.1 (*Acris* BM4103) raised with a synthetic peptide of BMP6 (SEQ ID NO: 17; Schluessener et al. 1995).

Method

Antibodies were used at concentrations of 1 μg/ml, 10 μg/ml and 100 μg/ml, in incubation buffer; incubation for 16 h at 4° C. and shaking at 140 rpm. Species specific secondary antibodies were used: Staining with control antibody mouse monoclonal anti-HA (12CA5) DyLight800 (1:2000) was done simultaneously with secondary antibodies goat anti-human IgG (H+L) DyLight680 (1:5000) and sheep anti-rabbit IgG (H+L) DyLight680 (1:5000). However, to avoid any interference between secondary and control antibody, staining with the mouse control antibody was done after the staining with the secondary antibody goat anti-mouse IgG (H+L) DyLight680.Read out was via the LI-COR Odyssey Imaging System; scanning offset 0.65 mm, resolution 21 μm, scanning intensities of 7/7 (red=700 nm/green=800 nm).

A clear response was seen with Antibody A against a single epitope-like spot pattern formed by adjacent peptides with the consensus motif TLVHLMNPEYV (SEQ ID NO: 8). Equally, a clear response against a single epitope-like spot pattern formed by adjacent peptides was seen with Antibody B with the consensus motif HLMNPEY (SEQ ID NO: 9). A weaker but still clear response against four epitope-like spot patterns formed by adjacent peptides for human or mouse was seen with mab155963 identifying the consensus motifs SASDYNSSELKTA (human; SEQ ID NO: 10), ELKTACRKHELYV (human; SEQ ID NO: 11), GSSDYNGSELKTA (mouse; SEQ ID NO: 12) and ELK-TACKKHELYV (mouse/rat; SEQ ID NO: 13). All those motifs exhibited the consensus core motif ELKTA (SEQ ID NO: 14) likely to correspond to a core epitope recognised by this rabbit anti-BMP6 monoclonal and presumably part of the peptide used to generate this monoclonal. A very strong response against two pattern formed by adjacent peptides was seen with Morph6.1 with the consensus motifs QSQD-VAR (human; SEQ ID NO: 15) and QSQDVSR (mouse/rat; SEQ ID NO: 16) that only differed by one exchange of amino acids S and A seen between the human and rat/mouse set of BMP6 peptides. These motives are fully contained within the BMP6 peptide sequence used as the immunogen to generate this monoclonal (QSRNRSTQSQDVARVSS-ASDYNSSELKTAC SEQ ID NO: 17; Schluessener et al. 1995). In contrast to these results, no staining above the noise level of the assay was seen with CL-58838 IgG4 (SEQ ID NO: 116 and SEQ ID NO: 125) even upon significant increased brightness and contrast. However, all positive control linear epitopes used in the assay performed as expected. This outcome is most likely explained by the fact that CL-58838, in contrast to all the antibodies mapped above, binds to a conformationally sensitive or discontinuous epitope that could not be mimicked or represented by the linear antigen-derived peptides in the microarray.

Example 10

Western Blot Analysis of Binding to Human BMP6

Figure 5:
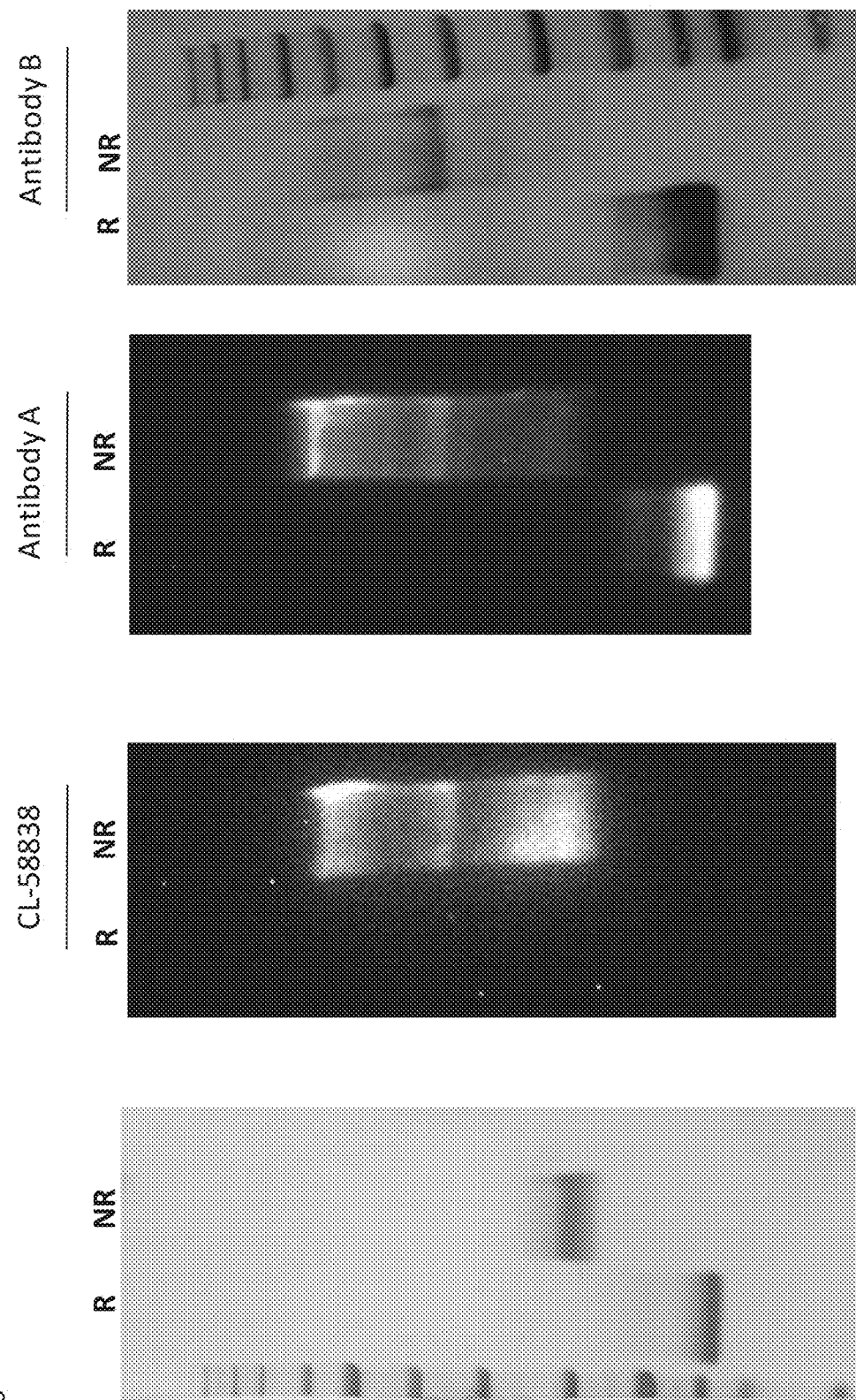

Since the peptide mapping experiment in Example 9 suggested that CL-58838 was not able to bind overlapping linear peptides generated from the BMP6 primary sequence, the antibody was subjected to Western blotting where human BMP6 was applied to SDS-PAGE under reducing and non-reducing conditions. Since BMP6 is a disulphide linked dimer the reducing condition should create monomers on the gel instead of dimers on the non-reduced gel. The presence of SDS will cause a general unfolding of the protein structure in both cases revealing potential linear epitopes but also remove or at least reduce secondary structures. From the results in Example 9 it was anticipated that CL-58838 might not recognise unfolded BMP6 presented on an SDS-PAGE whereas Antibodies A and B that clearly recognised linear parts of the BMP6 sequence might. FIG. 5 shows the results of this analysis. The Coomassie stained gel clearly shows BMP6 monomers at 18 kDa in the reduced lane and about 32 kDa dimers in the non-reduced lane confirming the formation of monomers on applying reducing conditions. CL-58838 generated a signal on the non-reduced, disulphide linked dimers but not on the reduced monomers. In contrast, Antibody A generated a signal on the dimers and a very defined signal on the BMP6 monomers indicating that the epitope sufficient for binding Antibody A does not require a particular fold or the dimerisation of BMP6. Antibody B gave very comparable results to Antibody A again emphasising the similarity of the epitope of those two antibodies.

These results also indicated that CL-58838 is still able to recognise BMP6 in the presence of SDS but requires the conformational interface of a disulphide linked BMP6 dimer to bind. This conforms with the results seen in Example 9 and may indicate that the epitope for CL-58838 encompasses residues only brought together in the BMP6 dimer and/or that crucial residues mediating binding activity are located close to an intermolecular disulphide link between BMP6 monomers.

Example 11

Assessment of Anti-BMP6 Antibodies Following a Single Intravenous Injection (iv) in Normal Rats Male Wistar rats (250-325 g, n=6/group) were given a single 1 mg/kg iv injection of fully human IgG4 anti-BMP6 antibodies. Two or three control groups were included in each study receiving a single 1 mg/kg iv dose, a hIgG4 isotype control antibody (labelled "isotype") and one or two additional human IgG anti-BMP6 antibodies (Antibody A and B).

Animals were bled pre-dose at one hour prior to dosing (−1) to give baseline measurements and then at 5 minutes, at 6 and 24 hours and on days 3, 7, 9, 14, 22, 29 and 36. Plasma transferrin saturation (TSAT) was determined for every time point.

These experiments were designed to measure the change in TSAT following a single iv injection of fully human IgG4 anti-BMP6 antibody generated by the invention. A total of 17 antibodies (Tables 4-6 and 7-9) were evaluated in three independent studies according to the experimental procedure outlined above. Tables 12-14 shows the results of these 3 experiments for TSAT.

TABLE 12

TSAT calculated from iron parameters measured in plasma following a single iv injection of
antibodies selected in Table 7. All antibodies and controls dosed at 1 mg/kg as described above

| TSAT [%] Time (Hours) | Isotype Control | Antibody B | CL-57931 | CL-58851 | CL-66833 | CL-58252 | CL-57945 | CL-58102 | CL-58838 | Antibody A |
|---|---|---|---|---|---|---|---|---|---|---|
| −1.00 | 45.52 | 45.42 | 39.08 | 44.45 | 45.75 | 45.07 | 45.72 | 43.98 | 41.45 | 38.58 |
| 0.08 | 46.52 | 44.08 | 39.82 | 42.87 | 43.83 | 43.62 | 46.50 | 44.72 | 46.42 | 41.27 |
| 6.00 | 61.95 | 63.02 | 71.73 | 60.87 | 68.30 | 61.88 | 76.03 | 53.40 | 72.45 | 62.80 |
| 24.00 | 47.88 | 94.95 | 63.72 | 84.38 | 84.43 | 86.17 | 83.95 | 60.38 | 90.47 | 81.73 |
| 72.00 | 52.84 | 86.53 | 64.18 | 83.37 | 66.90 | 76.02 | 82.32 | 50.18 | 87.00 | 78.53 |
| 168.00 | 46.92 | 90.10 | 55.50 | 78.23 | 69.73 | 76.00 | 70.25 | 53.93 | 90.90 | 79.00 |
| 216.00 | 52.68 | 92.38 | 50.47 | 76.12 | 60.35 | 71.72 | 56.55 | 48.23 | 85.85 | 81.95 |
| 336.00 | 47.73 | 89.02 | 42.57 | 50.63 | 55.87 | 50.03 | 45.80 | 47.28 | 71.77 | 79.90 |
| 528.00 | 46.72 | 57.02 | 44.77 | 42.68 | 44.15 | 54.25 | 43.43 | 36.03 | 58.07 | 59.07 |
| 696.00 | 42.17 | 43.00 | 40.85 | 40.60 | 46.03 | 44.38 | 39.07 | 36.75 | 48.50 | 35.70 |
| 864.00 | 41.62 | 34.73 | 39.92 | 36.83 | 47.00 | 43.92 | 34.83 | 36.28 | 47.82 | 33.55 |

TABLE 13

TSAT calculated from iron parameters measured in plasma following a single iv injection of
antibodies selected in Table 8. All antibodies and controls dosed at 1 mg/kg as described above

| TSAT [%] Time (Hours) | Isotype Control | CL-75183 | CL-75500 | CL-75506 | CL-75520 | CL-75539 | CL-75565 | CL-75714 | Antibody A |
|---|---|---|---|---|---|---|---|---|---|
| −1.00 | 40.07 | 42.48 | 41.72 | 46.88 | 39.13 | 46.88 | 41.07 | 44.03 | 37.92 |
| 0.08 | 40.12 | 40.53 | 40.75 | 42.00 | 38.07 | 47.58 | 41.78 | 46.07 | 36.93 |
| 6.00 | 55.57 | 67.85 | 64.60 | 60.35 | 60.13 | 61.02 | 52.45 | 65.10 | 75.82 |
| 24.00 | 40.13 | 47.13 | 52.20 | 51.23 | 49.07 | 50.97 | 45.03 | 74.17 | 98.18 |

TABLE 13-continued

TSAT calculated from iron parameters measured in plasma following a single iv injection of
antibodies selected in Table 8. All antibodies and controls dosed at 1 mg/kg as described above

| TSAT [%] Time (Hours) | Isotype Control | CL-75183 | CL-75500 | CL-75506 | CL-75520 | CL-75539 | CL-75565 | CL-75714 | Antibody A |
|---|---|---|---|---|---|---|---|---|---|
| 72.00 | 42.53 | 52.40 | 51.27 | 61.10 | 51.85 | 48.57 | 48.68 | 54.87 | 86.68 |
| 168.00 | 41.15 | 52.70 | 45.07 | 52.53 | 47.28 | 59.72 | 49.62 | 58.25 | 89.30 |
| 216.00 | 41.78 | 48.63 | 50.03 | 52.58 | 49.50 | 50.93 | 45.28 | 52.03 | 95.65 |
| 336.00 | 48.08 | 53.38 | 45.72 | 45.80 | 46.95 | 55.67 | 47.57 | 59.47 | 98.30 |
| 528.00 | 41.50 | 46.00 | 47.33 | 45.17 | 43.83 | 49.33 | 41.33 | 47.67 | 58.17 |
| 696.00 | 40.40 | 40.40 | 44.00 | 42.75 | 40.35 | 48.15 | 44.12 | 46.07 | 38.87 |
| 864.00 | 39.02 | 41.08 | 42.47 | 42.28 | 38.80 | 45.20 | 37.83 | 42.70 | 34.87 |

TABLE 14

TSAT calculated from iron parameters measured in plasma following a single iv injection of
antibodies selected in Table 9. All antibodies and controls dosed at 1 mg/kg as described above

| TSAT [%] Time (Hours) | Isotype Control | Antibody B | CL-58722 | CL-58756 | CL-58835 | Antibody A |
|---|---|---|---|---|---|---|
| −1.00 | 42.37 | 38.98 | 44.98 | 44.05 | 43.32 | 37.73 |
| 0.08 | 43.38 | 36.25 | 44.28 | 45.55 | 46.46 | 38.53 |
| 6.00 | 58.33 | 61.60 | 57.30 | 71.78 | 64.74 | 66.20 |
| 24.00 | 42.77 | 91.95 | 73.35 | 67.38 | 94.58 | 93.78 |
| 72.00 | 45.77 | 79.03 | 62.55 | 51.97 | 92.32 | 89.37 |
| 168.00 | 57.65 | 83.32 | 57.63 | 52.00 | 89.30 | 94.88 |
| 216.00 | 57.57 | 86.27 | 51.82 | 62.38 | 89.64 | 95.62 |
| 336.00 | 49.23 | 79.76 | 51.52 | 52.25 | 80.06 | 91.72 |
| 528.00 | 40.50 | 61.36 | 44.62 | 48.77 | 58.64 | 47.06 |
| 696.00 | 49.28 | 49.50 | 45.72 | 50.37 | 52.56 | 36.10 |
| 864.00 | 33.02 | 37.74 | 39.33 | 41.65 | 43.00 | 33.68 |

Figure 8A:
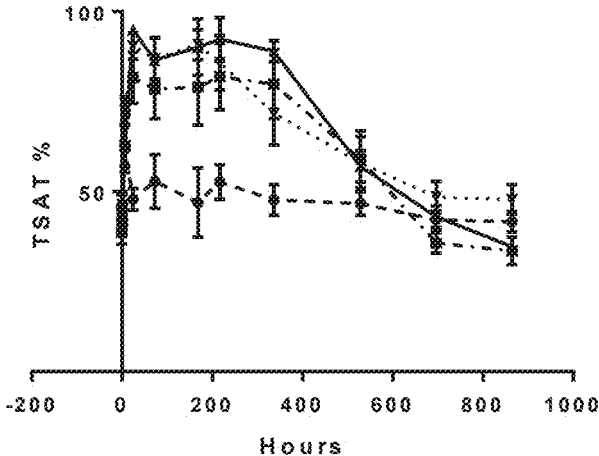
Figure 8B:
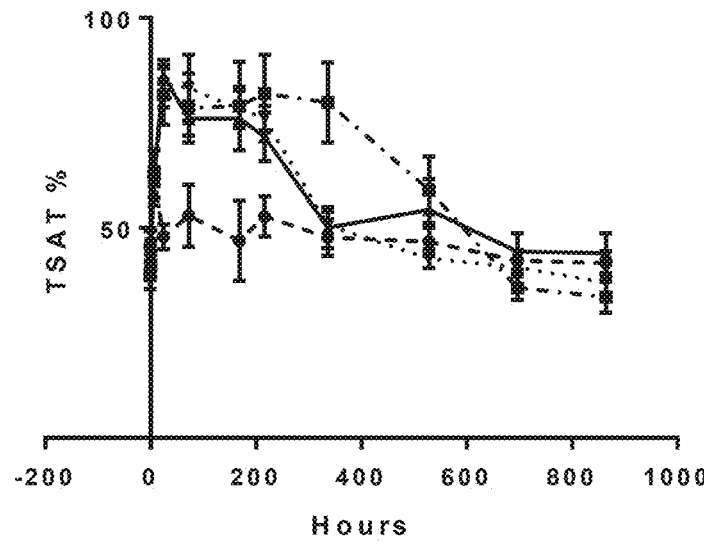
Figure 8C:
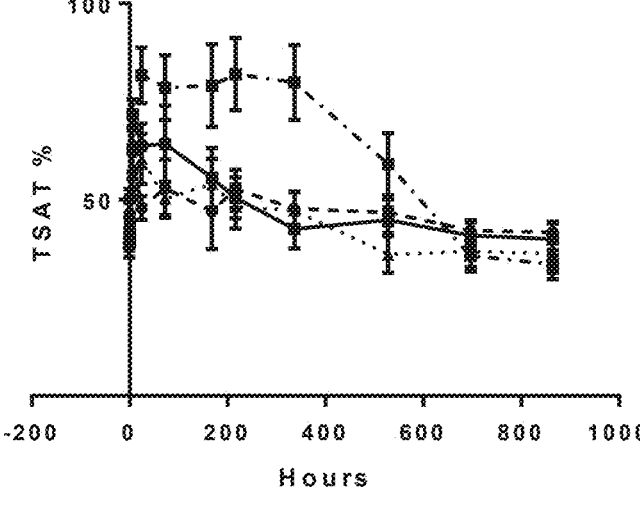
Figure 8D:
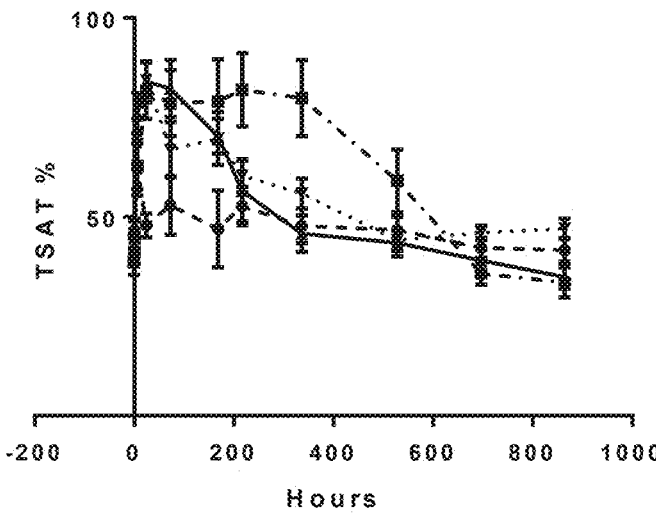
Figure 8E:
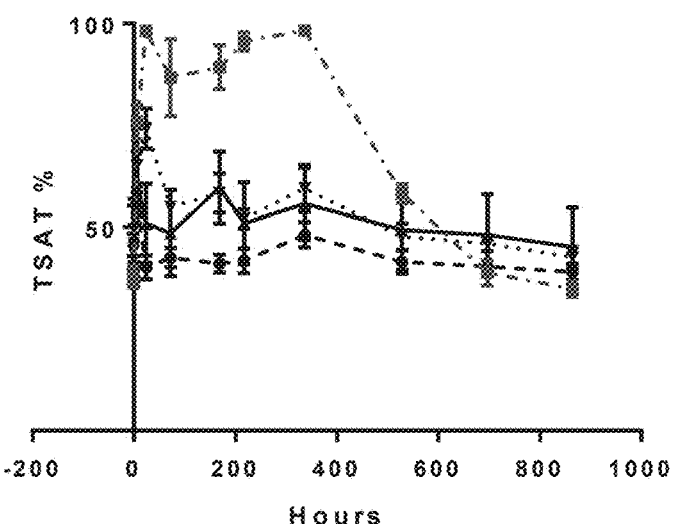
Figure 8F:
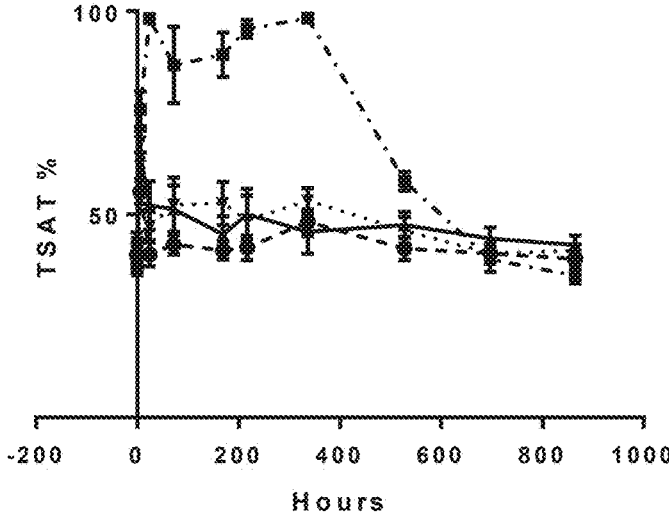
Figure 8G:
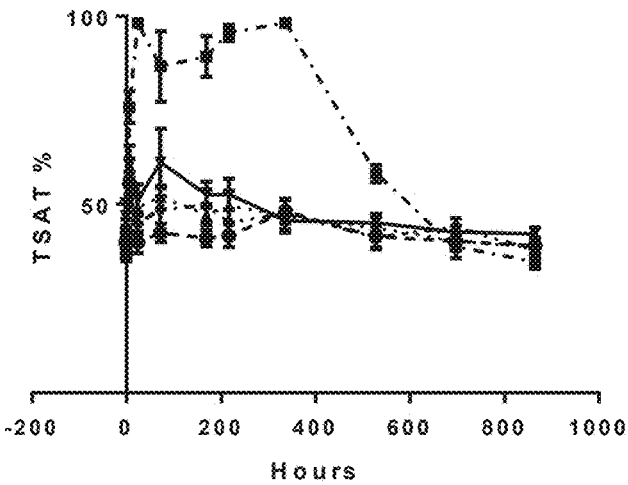
Figure 8H:
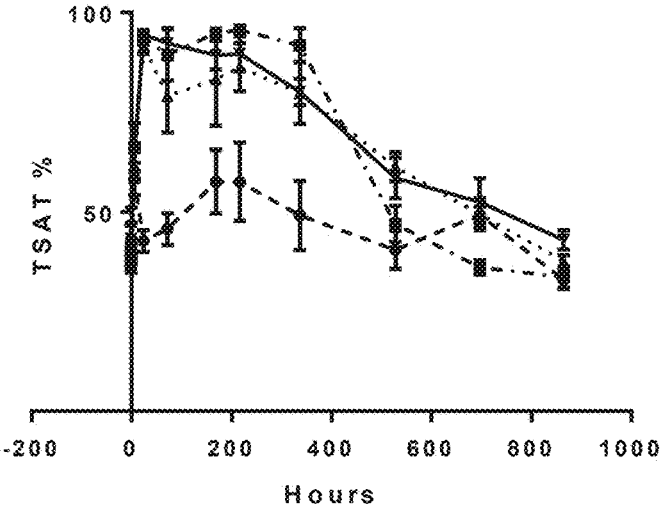
Figure 8I:
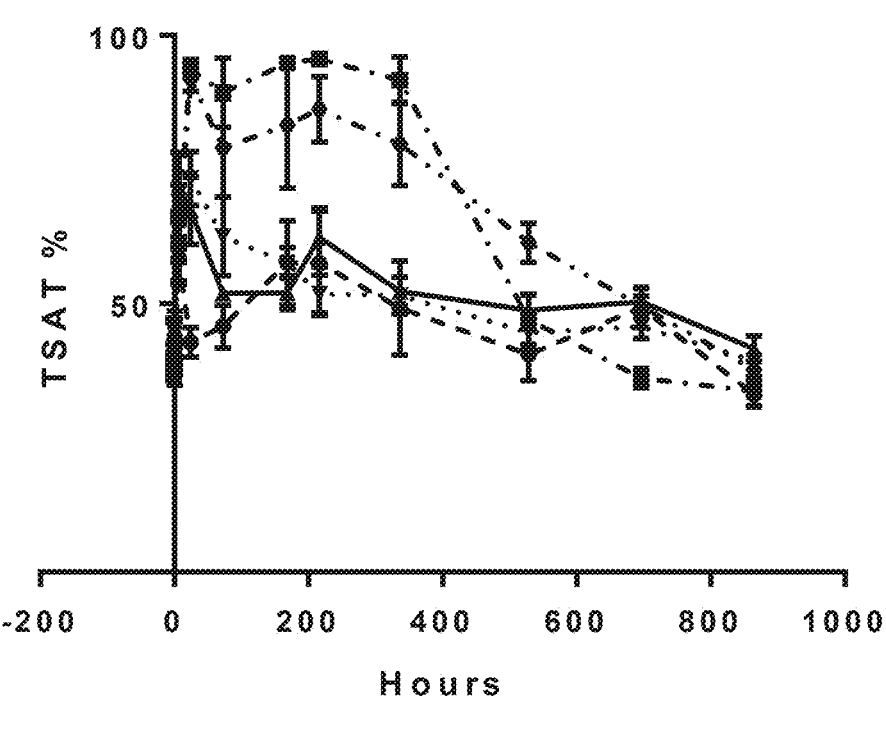

Plotted results are shown in FIGS. 8A-8D (for Table 12), FIGS. 8E-8G (for Table 13) and FIGS. 8H-8I (for Table 14). Overall, from all three experiments, the two antibodies that showed the highest effect on TSAT levels in terms of peak increase in TSAT and duration of effect were CL-58838 (FIG. 8A) and CL-58835 (FIG. 8H).

Example 12

Dose response assessment of CL-55838 following a single iv injection in normal rats Antibody CL-58838 was one of the antibodies that showed a preferable profile in Example 11 and it was therefore of interest to determine the effect on transferrin saturation and duration of effect following IV injection of CL-58838 over a range of doses. Male Wistar rats (250-325 g, n=6/group) were given a single iv injection of 0.3, 1 or 3 mg/kg of CL-58838 fully human IgG4 (SEQ ID NO: 116 and SEQ ID NO:125). hIgG4 isotype control (labelled "isotype") and Antibody A were also included receiving a single 1 mg/kg iv dose.

Animals were bleed pre-dose at one hour prior to dosing (−1) to give baseline measurements and then at 5 minutes, at 6 and 24 hours, and on days 3, 7, 9, 14, 22, 29 and 36. Plasma TSAT was determined for every time point (Table 15).

TABLE 15

TSAT calculated from iron parameters measured in plasma following
a single iv injection of antibody CL-58838 at various doses.
Isotype control and Antibody A were dosed at 1 mg/kg only

| | TSAT [%] | | | |
|---|---|---|---|---|
| Time (Hours) | Isotype Control | CL-58838 0.3 mg/kg | CL-58838 1 mg/kg | CL-58838 3 mg/kg | Antibody A 1 mg/kg |
| −1.00 | 43.13 | 42.43 | 47.72 | 51.47 | 41.35 |
| 0.08 | 40.10 | 40.17 | 43.55 | 46.45 | 43.57 |
| 6.00 | 52.70 | 66.40 | 61.05 | 65.35 | 57.75 |
| 24.00 | 42.98 | 88.18 | 90.23 | 98.30 | 96.95 |
| 72.00 | 39.43 | 73.23 | 82.83 | 96.28 | 90.27 |
| 168.00 | 43.37 | 66.63 | 84.10 | 90.98 | 98.33 |
| 216.00 | 46.45 | 63.78 | 68.23 | 94.50 | 95.97 |
| 336.00 | 46.92 | 50.98 | 84.80 | 95.92 | 96.43 |
| 528.00 | 48.58 | 41.13 | 66.92 | 96.02 | 70.05 |
| 696.00 | 41.12 | 37.47 | 56.45 | 80.48 | 39.87 |
| 864.00 | 40.72 | 34.20 | 46.90 | 67.70 | 31.52 |

FIGS. 9A-9B show the results for this experiment. There was a rapid and strong increase in TSAT with dose dependent peak levels and dose dependent duration of the modulation of TSAT following treatment with CL-58838. 3 mg/kg had the highest and longest duration of effect with TSAT elevated over isotype control for at least 864 h (FIG. 9A). CL-58838 showed a comparable increase in TSAT and duration of effect to Antibody A when compared at the same dose of 1 mg/kg although the peak levels of Antibody A appeared slightly higher but returned to isotype levels by 696 h whereas CL-58838 was still elevated over isotype at this time point (FIG. 9B).

Figure 11A:
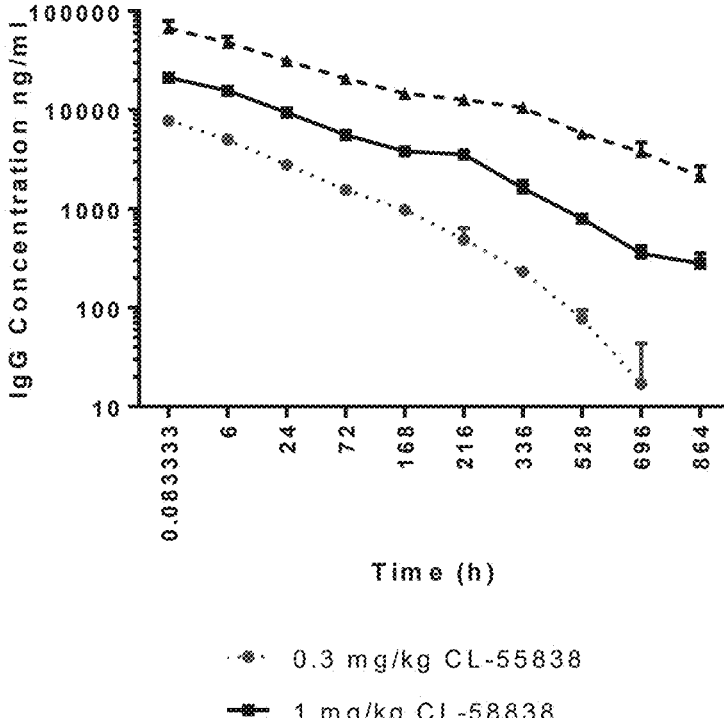
Figure 11B:
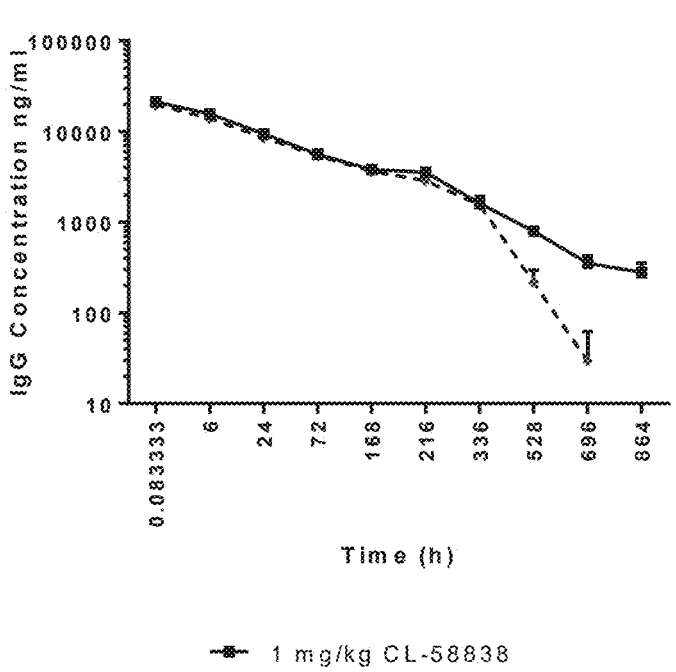

FIGS. 11A-11B show the pharmacokinetic (PK) profile of CL-58838 in this experiment (FIG. 11A) with an increase in peak concentration and duration of exposure with each escalation in dose. When comparing this PK profile to that of Antibody A at the 1 mg/kg dose, CL-58838 showed a comparable peak concentration but an increased duration of exposure (FIG. 11B).

Example 13

Dose Response Assessment of CL-55838 Following a Single Subcutaneous (Sc). Injection in Normal Rats Male Wistar rats, 250-325 g, n=6/group, were given a single sub cutaneous (sc) injection of 0.3, 1 or 3 mg/kg of CL-58838 as a fully human IgG4 anti-BMP6 antibody (SEQ ID NO: 116 and SEQ ID NO: 125). hIgG4 isotype control antibody (labelled "isotype") and anti-BMP6 Antibodies A and B were also included each receiving a single 1 mg/kg sc dose.

Animals were bleed pre-dose at one hour prior to dosing (−1) to give baseline measurements and then at 5 minutes, at 6 and 24 hours, and on days 3, 7, 9, 14, 22, 29 and 36. Plasma TSAT was determined for every time point (Table 16).

Example 14

Assessment of CL-58838 in a PG-PS Rat Model of Anaemia of Chronic Inflammation

The PG-PS rat disease model is a disease model of persistent and long lasting joint inflammation following administration of Group A streptococcal peptidoglycan-polysaccharide (PG-PS). Most of these rats also develop severe anaemia over a two to three week period and the model therefore also represents a model for the inflammation driven functional iron deficiency anaemia observed in many chronic inflammatory diseases, i.e. represents a model for anemia of chronic disease (ACD; (Theurl et al., 2011)).

6-8 week old female Lewis rats were given a single intraperitoneally (ip) injection of 15 mg/kg PG-PS at day −14. On day-1 (week 0) the animals were bled from the tail vein, plasma collected and whole blood taken and used for complete blood count (CBC) analysis. Animals which developed anaemia (haemoglobin level of less than 15 g/dl) as well as an increase in leukocyte count, entered the study. A treatment naïve group, was included in the study for baseline readings (n=5). On day 0, animals were randomised into groups to give a similar mean haemoglobin level and leucocyte count in all of the treated groups (n=6-9). Rats

TABLE 16

TSAT calculated from iron parameters measured in plasma following a single sc injection of antibody CL-58838. Isotype control and antibodies A and B were dosed at 1mg/kg only

| TSAT [%] Time (Hours) | Isotype Control IgG4 (IV) | CL-58838 0.3 mg/kg | CL-58838 1 mg/kg | CL-58838 3 mg/kg | Antibody A 1 mg/kg | Antibody B 1 mg/kg |
|---|---|---|---|---|---|---|
| −1.00 | 43.13 | 41.17 | 42.13 | 42.75 | 43.83 | 44.70 |
| 0.08 | 40.10 | 44.63 | 42.38 | 43.08 | 43.10 | 43.68 |
| 6.00 | 52.70 | 58.75 | 60.53 | 66.07 | 57.83 | 59.28 |
| 24.00 | 42.98 | 79.08 | 87.90 | 97.77 | 94.97 | 88.97 |
| 72.00 | 39.43 | 79.12 | 86.07 | 98.20 | 98.50 | 84.08 |
| 168.00 | 43.37 | 77.48 | 93.37 | 99.10 | 95.72 | 94.82 |
| 216.00 | 46.45 | 64.88 | 88.55 | 98.52 | 98.98 | 88.15 |
| 336.00 | 46.92 | 50.48 | 85.22 | 83.07 | 71.15 | 93.32 |
| 528.00 | 48.58 | 40.67 | 62.65 | 63.60 | 47.47 | 56.90 |
| 696.00 | 41.12 | 40.07 | 50.47 | 54.88 | 39.05 | 45.73 |
| 864.00 | 40.72 | 38.20 | 37.53 | 53.62 | 37.63 | 36.48 |

FIGS. 10A-10B show the results. There was a rapid and strong increase in TSAT at all doses with dose dependent peak levels at 24 to 72 h and a dose dependent duration of the modulation of TSAT following treatment with CL-58838. 3 mg/kg had the longest duration with TSAT elevated over isotype control for at least 864 h (FIG. 10A). CL-58838 showed a very comparable increase in TSAT to Antibody A and B at 1 mg/kg (FIG. 10B). The duration of effect was more similar to Antibody B in this experiment both still elevated over isotype control at 528 h.

Figure 11C:
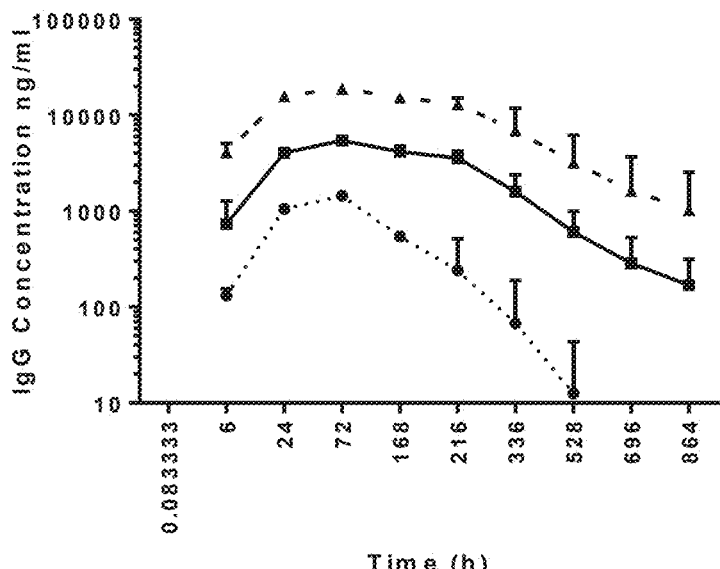
Figure 11D:
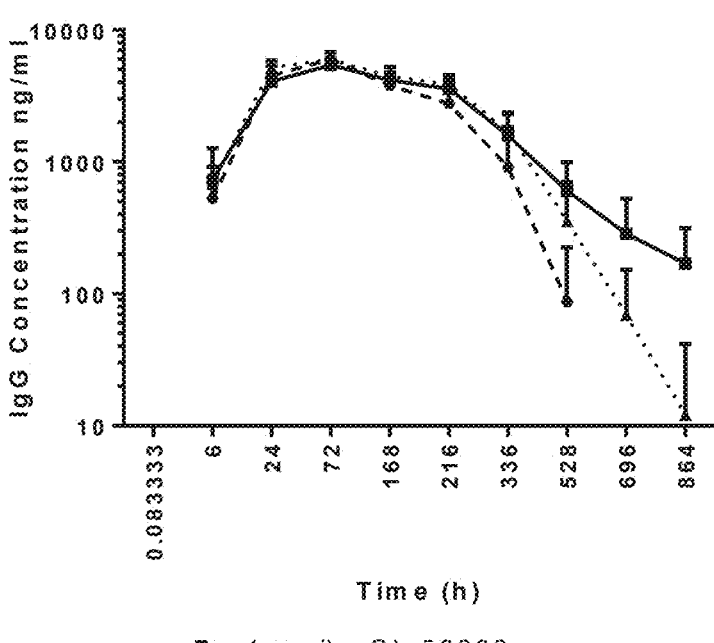

FIGS. 11C-11D show the pharmacokinetic (PK) profile of CL-58838 following a single sc dose, with an increase in peak concentration and duration of exposure with each escalation in dose (FIG. 11C). When comparing CL-58838's PK profile to that the anti-BMP-6 antibodies A and B at the 1 mg/kg dose, CL-58838 showed a comparable peak exposure with an increased duration of exposure (FIG. 11D).

were then treated with either a single sc injection of IgG4 isotype control (n=8), CL-58838 3 mg/kg (n=9), Darbepoietin alpha (EPO) 10 µg/kg (n=8) or a combination of both CL-58838 3 mg/kg and EPO 10 µg/kg (n=7). EPO administration was repeated every week in the groups receiving EPO.

Blood was taken from the tail vein on day −1 (week 0), 7 (week 1), 14 (week 2), 21 (week 3) and at cull at day 28 (week 4) to allow further analysis of iron status and anemia.

The experiment was designed to investigate whether CL-58838 was able to positively impact anaemia in the rats compared with untreated control. To determine this effects on haemoglobin, TSAT, whole blood counts and hepcidin levels were measured following a single dose of CL-58838 alone or in combination with erythropoietin (EPO) representing a common treatment option in anaemia of chronic disease.

TABLE 17

Haemoglobin (g/dl), haematocrit (haemocrit, %), mean cell volume (MCV, fL), mean cell
haemoglobin (MCH, pg) and white blood cells (WBC × $10^3/\mu L$) measured at 0, 1, 2, 3 and
4 weeks post commencement of treatment. CL-58838 and isotype control were dosed at
3 mg/kg, EPO (Darbepoietin alpha) was dosed at 10 μg/kg.

| | Naïve | | | | | Isotype Control | | | | | CL-58838 | | | | |
|---|---|---|---|---|---|---|---|---|---|---|---|---|---|---|---|
| Week | 0 | 1 | 2 | 3 | 4 | 0 | 1 | 2 | 3 | 4 | 0 | 1 | 2 | 3 | 4 |
| Haemoglobin | 15.4 | 15.8 | 15.7 | 15.2 | 15.4 | 15.6 | 14.7 | 15.8 | 12.4 | 11 | 15.9 | 13.1 | 14.9 | 13.9 | 13.6 |
| Haemocrit | 50 | 48.3 | 515 | 47.8 | 46.7 | 50.5 | 45.6 | 52.3 | 40.3 | 34.2 | 51.1 | 40 | 49.4 | 45.3 | 45.5 |
| MCV | 60 | 59 | 58.5 | 56 | 56.8 | 57.4 | 54.1 | 52.6 | 50.3 | 50.3 | 56.5 | 55.1 | 55 | 51.9 | 52.8 |
| MCH | 18.6 | 19.3 | 17,9 | 17.8 | 18.7 | 17.8 | 17.7 | 16 | 15.6 | 16.4 | 17.6 | 18.1 | 16.7 | 16 | 17 |
| WBC | 7.48 | 7.2 | 6.52 | 5.3 | 4.98 | 11.4 | 16 | 14.9 | 14.8 | 11.1 | 14.3 | 14.4 | 15 | 14 | 10.3 |

| | ESA | | | | | CL-58838 + ESA | | | | |
|---|---|---|---|---|---|---|---|---|---|---|
| Week | 0 | 1 | 2 | 3 | 4 | 0 | 1 | 2 | 3 | 4 |
| Haemoglobin | 15.7 | 13.5 | 15 | 15.4 | 14.1 | 15.8 | 18 | 18.6 | 19 | 23.8 |
| Haemocrit | 51.9 | 42.3 | 51.7 | 51.7 | 45 | 50.3 | 57.3 | 62.6 | 62.9 | 76.9 |
| MCV | 57.3 | 53.9 | 52 | 49.6 | 50.8 | 58.8 | 62.3 | 61.5 | 60.8 | 59.5 |
| MCH | 17.4 | 17.2 | 15.1 | 14.7 | 15.5 | 18.3 | 19.2 | 18 | 18 | 18.5 |
| WBC | 15.3 | 17.3 | 18.3 | 18.4 | 15.6 | 10.7 | 11 | 9.83 | 8.43 | 9.08 |

Figure 12A:
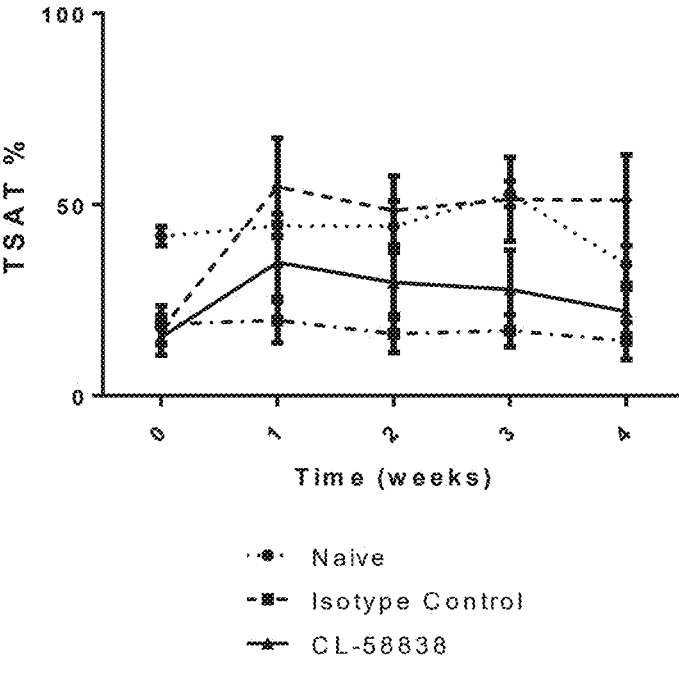
Figure 12B:
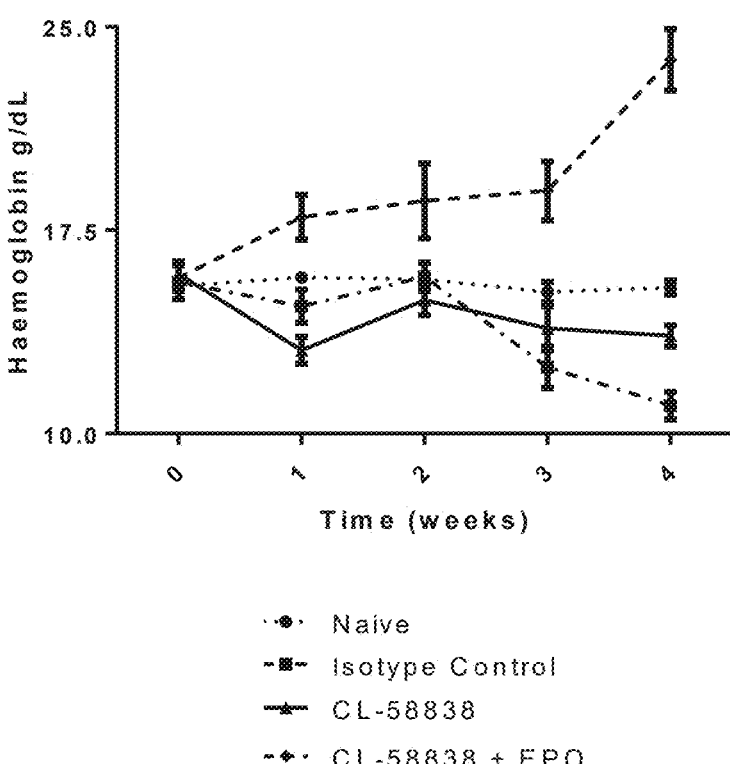
Figure 12C:
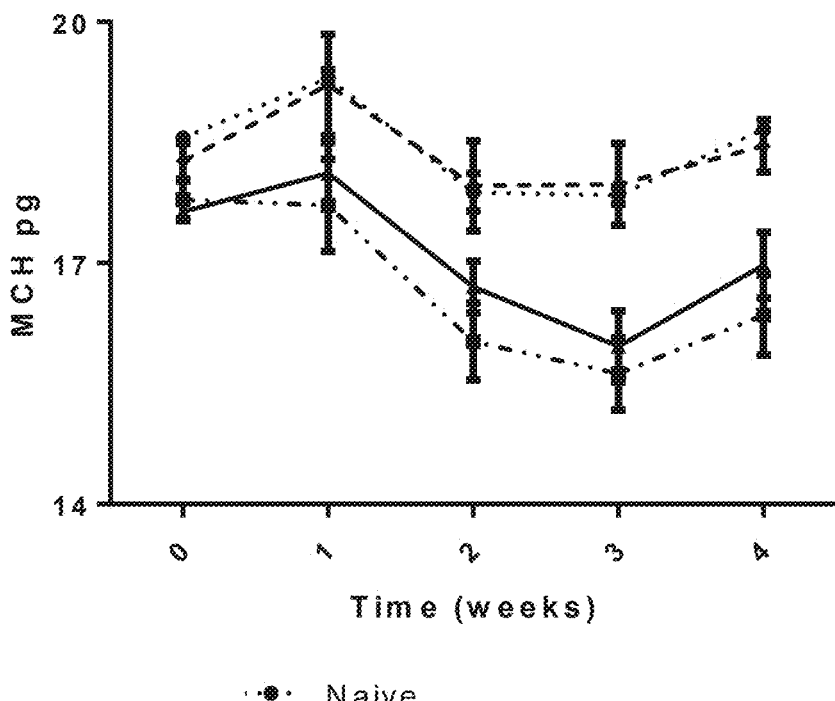
Figure 12D:
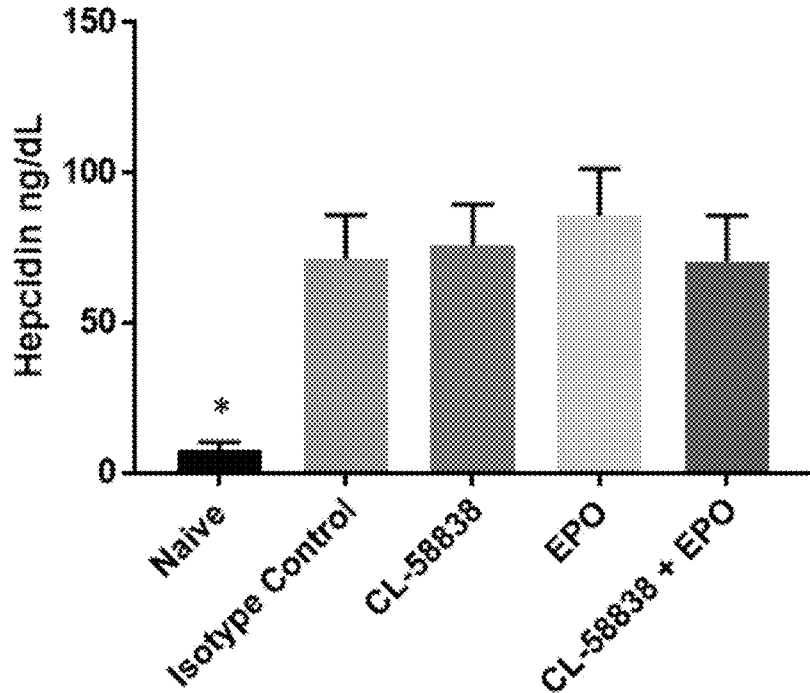
Figure 12E:
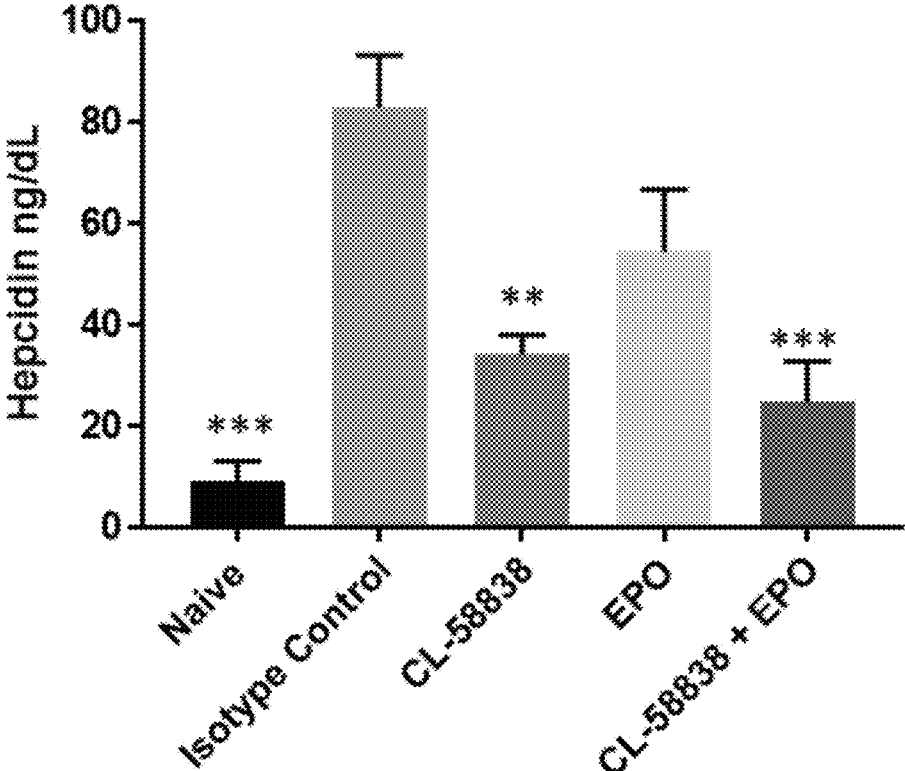
Figure 12F:
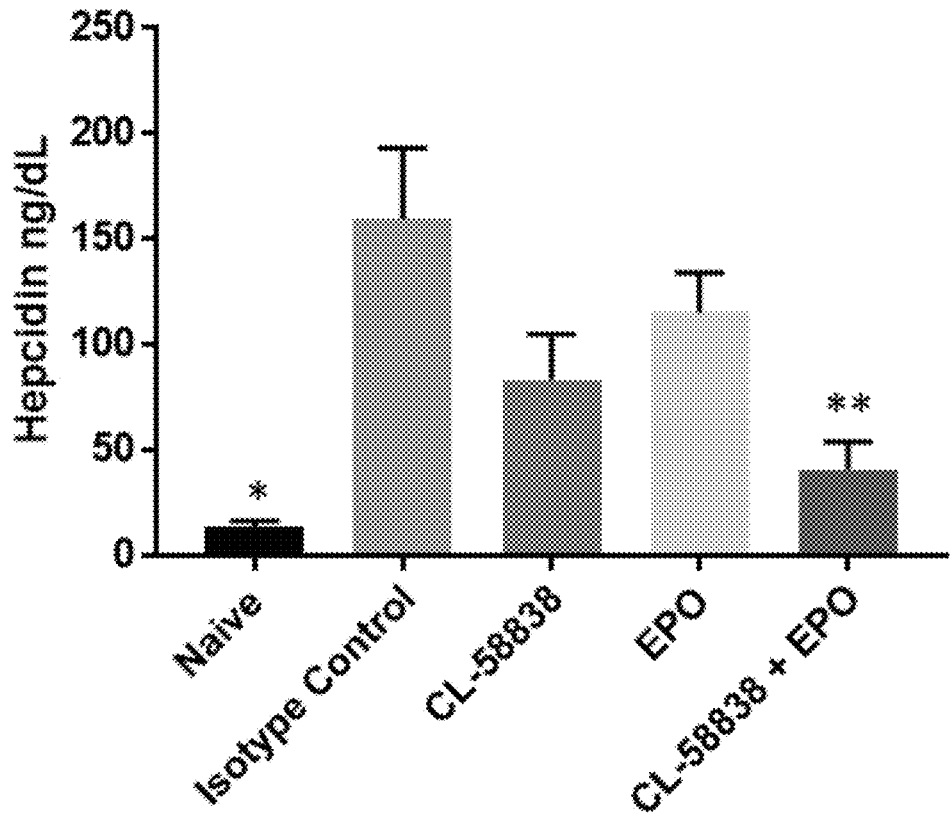

Table 17 and FIGS. 12A-12F show that treatment with CL-58838 on its own increased TSAT at all four time points compared to animals treated with isotype control (FIG. 12A). Combining CL-58838 with EPO administration elevated the TSAT much further staying elevated at over 50% for the duration of the experiment similar to the TSAT seen in naïve animals. CL-58838 also prevented the drop of haemoglobin seen for the isotype treated animals between week 3 and 4 (FIG. 12B). Combining CL-58838 with EPO administration caused a massive synergistic increase of haemoglobin way beyond the levels seen in naïve animals (FIG. 12B). Similar observations were made for MCH where co-treatment restored the MCH levels observed for naïve animals (FIG. 12C). FIGS. 12 D-12F show the results of circulating hepcidin levels at week 0 (FIG. 12D), week 1 (FIG. 12E) and week 2 (FIG. 12F). At the start of treatment (FIG. 12D) all groups already had vastly elevated hepcidin levels driven by a quick onset of inflammation over naïve animals. At weeks 1 and 2 after starting treatment isotype control animals further increased hepcidin levels presumably due to ongoing inflammation and over production of hepcidin (FIGS. 12E and 12F). Treatment with EPO alone was not able to reduce the increase of hepcidin levels and still increased over time, staying within 20-30% of the isotype control. Treatment with CL-58838 alone had a marked effect on hepcidin levels with an initial substantial decrease over isotype control treated animals and then remaining at around 50% of the hepcidin levels of isotype control treated animals. Treatment with CL-58838 and EPO administration decreased hepcidin levels initially to a similar degree as CL-58838 alone but then maintained or even further reduced hepcidin levels in comparison to isotype, CL-58838 or EPO treated animals. The addition of EPO and CL-58838 together appears to have a synergistic effect on hepcidin levels possibly through the effective stimulation of erythropoiesis in the presence of increased levels of available iron and resulting in a possible down regulation of hepcidin production (Nai et al., 2015).

Example 15

Dose Response Assessment of CL-58838 Following a Single iv Dose Injection in Cynomolgus Monkeys 15 male healthy cynomolgus monkeys weighing 2.5-4.0 kg were given a single iv injection of CL-58838 human IgG4 (SEQ ID NO: 116 and SEQ ID NO: 125) at 1, 3 and 10 mg/kg. Anti-BMP6 antibodies A and B were also included as a single iv injection 3 mg/kg.

Animals were bled pre-dose on days −6, −1 and just prior to dosing (0) to give baseline measurements, then at 6/24 hours, and on days 3, 7, 9, 14, 22, 29, 35 and 43. Plasma TSAT and hepcidin levels were measured at every time point to assess the efficacy of CL-58838 at modulating iron metabolism. The values for TSAT at all time points and all groups are shown in Table 18.

TABLE 18

TSAT calculated from iron parameters measured in plasma of
cynomolgus monkeys following a single iv injection of antibody.
Isotype control and antibodies A and B were dosed at 3 mg/kg only

| | TSAT [%] | | | | |
|---|---|---|---|---|---|
| Time (Hours) | CL-58838 1 mg/kg | CL-58838 3 mg/kg | CL-58838 10 mg/kg | Antibody A 3 mg/kg | Antibody B 3 mg/kg |
| −144 | 30.43 | 44.77 | 31.60 | 34.17 | 42.63 |
| −24 | 33.93 | 39.40 | 33.70 | 36.00 | 39.37 |
| 0 | 40.00 | 36.50 | 49.70 | 42.43 | 49.53 |
| 6 | 35.77 | 27.60 | 37.00 | 34.67 | 33.53 |
| 24 | 59.57 | 80.17 | 81.73 | 85.33 | 90.10 |
| 72 | 62.17 | 74.43 | 94.77 | 94.23 | 89.20 |
| 168 | 69.10 | 79.87 | 93.03 | 77.40 | 75.90 |
| 216 | 57.57 | 82.37 | 93.67 | 89.27 | 82.70 |
| 336 | 41.47 | 65.20 | 78.13 | 71.27 | 67.47 |
| 528 | 53.30 | 57.57 | 68.87 | 63.53 | 73.07 |
| 696 | 56.90 | 52.47 | 68.47 | 61.80 | 66.50 |
| 840 | 59.87 | 58.80 | 57.50 | 70.53 | 67.17 |
| 1032 | 56.70 | 53.97 | 54.13 | 61.03 | 64.93 |

FIGS. 13A-13D show an increase in TSAT and duration of effect following a single iv dose of 3 mg/kg of CL-58838 that was comparable to antibody A and B at the same dose (A). There was a dose dependent increase in overall effect on TSAT, TSAT peak levels and duration of the modulation of TSAT following treatment with CL-58838 at different doses (FIG. 13B). CL-58838 and antibody A and B all showed a similar decrease in plasma hepcidin levels and a comparable duration of effect at 3 mg/kg (FIG. 13C). The decrease in hepcidin following treatment with CL-58838 was maximal at 3 mg/kg and treating with 10 mg/kg showed no further decrease of hepcidin levels (FIG. 13D).

Figure 14A:
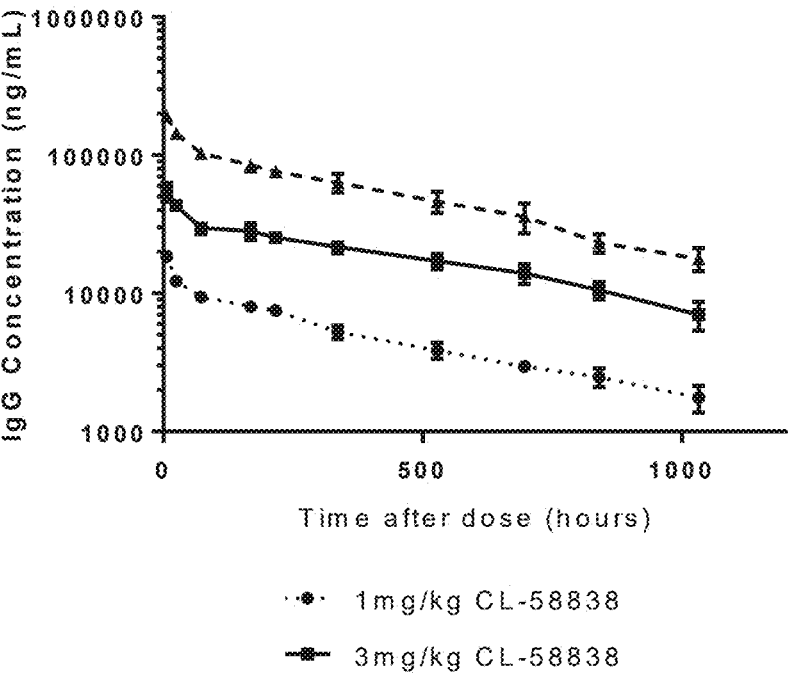
Figure 14B:
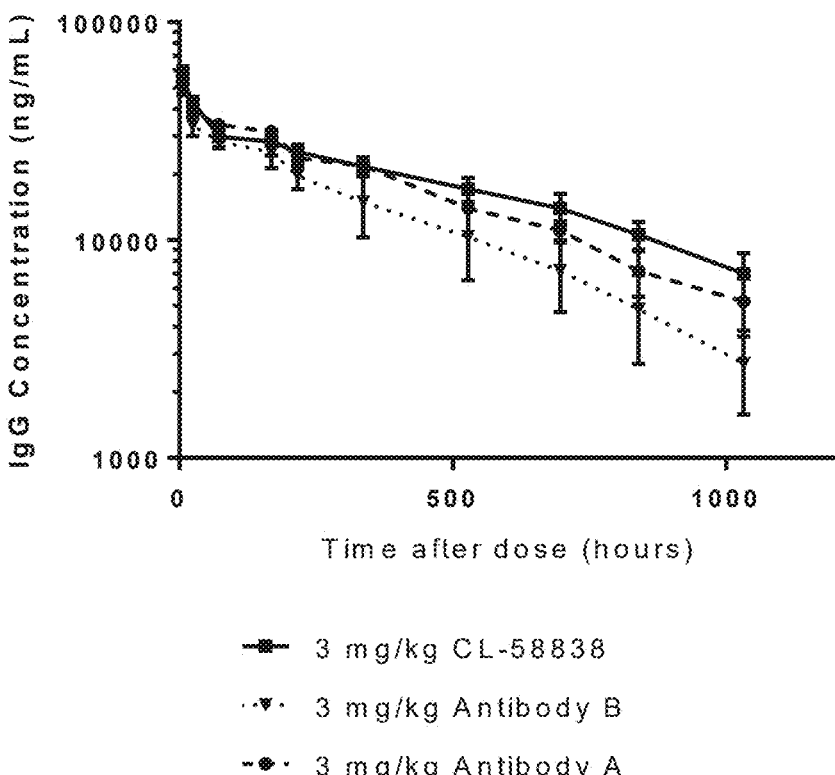

FIGS. 14A-14B show the PK profile of CL-58838 (FIG. 14A) in this experiments with an increased exposure and peak concentration and duration of exposure with each escalation in dose. When comparing the exposure profile of CL-58838 to Antibody A or B at 3 mg/kg all antibodies showed similar profiles but CL-58838 showed a trend for a possibly increased duration of exposure (FIG. 14B).

Example 16

Sequence Analysis of CL-58838 and CL-58838-Like Antibodies

Figure 15:
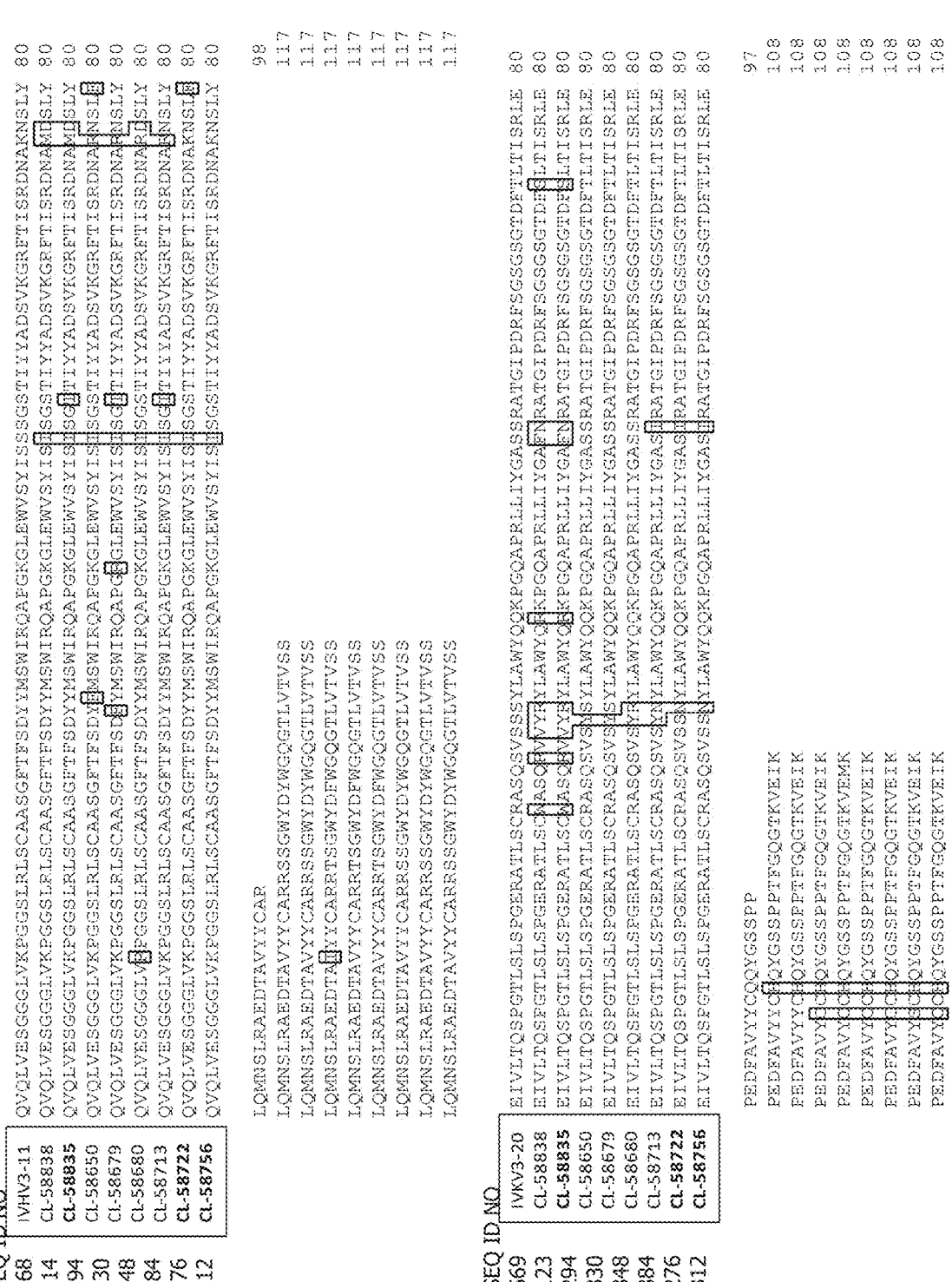

Following the results of the in vivo analysis of selected antibodies (Example 11) the sequences of antibodies that referred functional activity were analysed again and compared in light of the fact that only CL-58838 had shown very potent activity of a prolonged elevation of iron levels and TSAT. Since sequences for all antibodies recovered from the Kymouse™ were available, the sequence pool was mined for antibodies with identical VDJ-region (IGHV3-11*01, IGHD6-19*01, IGHJ4*02/IGKV3-20*01, IGKJ1*01) and identical CDRH3 sequences. Several antibodies were identified from the pool of NGS sequences across two immunisation regimes as explained in Example 5 (Table 6).. Eventually three new antibodies were selected for in vivo analysis (shown in bold Table 6 and in Table 9). However, after testing in vivo (Example 11, Table 14) neither CL-58722 or CL-58756 identified by this method showed comparable activity to CL-58838 and only CL-58835 was comparable. This was surprising given the high level of homology between the amino acid sequences in this antibody panel. FIG. 15 shows an alignment of the Vh (IGHV3-11) and Vk (IGKV3-20) regions for all unique antibodies from Table 6 and CL-58838. First to note is that CL-58838 and CL-58835 have identical light chains which are unique to those two antibodies and otherwise only differ by one amino acid in CDRH2. Antibodies that were tested in vivo but did not show comparable potency to CL-58838 or CL-58835 in vivo do not show the germ line Vh changes at residues 75 and 76 (Kabat) to M75 and D76 seen with CL-58838 or CL-58835. No other Vh tested had these mutations or other significant differences that could explain this difference. It is therefore possible that these two mutations may be the major sequence motif mediating the exceptional potency observed for those two antibodies. It cannot be excluded that the unique Vk regions also contributed to the characteristics of CL-58838 and CL-58835 although it is known in the field that the Vh region and the CDRH3 in particular are the often the main contributor to the specificity and potency of antibodies (Xu and Davis, 2000).

Another observation was made when the cross-reactivity with BMP7 was considered. Antibodies that showed a degree of cross-reactivity with BMP7 in this panel were CL-58680, CL-58679 and CL-58680. Sequence differences in the Vh domain cannot be attributed to this effect since they also occur in other clones. However, in the Vk domain position 52 and 53 (Kabat) are not changed from germline IGKV3-20 for the clones that cross-reacted with BMP7 whereas all the clones that did not cross-react with BMP7 have one or both of these residues changed.

Figure 16:
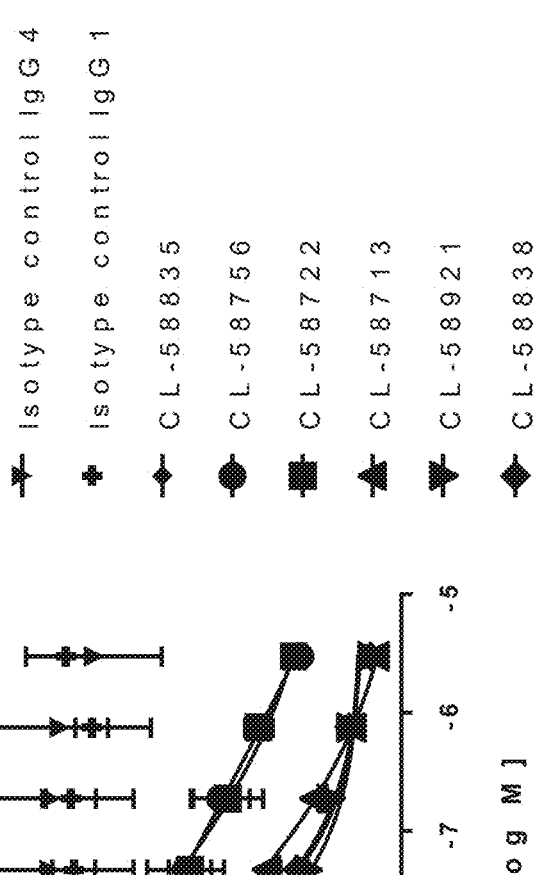

The in vitro potency of those antibodies was comparable when tested in a head to head competition experiment in a homogeneous time resolved FRET (HTRF) assay where biotinylated CL-58838 detected with streptavidin-cryptate is binding to BMP6 labelled with 647 (FIG. 16). This interaction of labelled CL-58838 with labelled human BMP6 was then competed by unlabelled antibodies tested in this experiment. CL-58838 competed fully with labelled CL-58838 as expected. CL-58722 and CL-58756 showed somewhat lower ability to compete with labelled CL-58838 possibly reflecting also some impact of the sequence changes on the affinity for BMP6. This analysis surprisingly demonstrated that although the antibodies selected for in vivo analysis from this series (with identical VDJ usage and identical CDRH3) demonstrated very comparable ability to bind and neutralise human BMP6 and all compete with CL-58838 for binding to BMP6 yet still differed significantly in their in vivo potency.

Example 17

Assessment of the ESA-Sparing Capacity of CL-58838 in a PG-PS Rat Model of Anaemia of Chronic Inflammation As detailed in Example 14, the PG-PS rat disease model is a well-established model to study the anaemia of chronic inflammation.

The aim of this study was to test if the anti-BMP-6 IgG4 antibody CL-58838 (SEQ ID NO: 116 and SEQ ID NO: 125)) in combination with Darbepoetin alpha (EPO) can reduce the EPO doses needed to effectively restore haematological parameters using this model compared to EPO monotherapy.

Method 6-8 week old female Lewis rats were given a single intraperitoneally (ip) injection of 15 mg/kg PG-PS at timepoint "W-2" and after two weeks (i.e. timepoint "W0") animals were bled from the tail vein to perform complete blood count analysis. Only if rats had an increased granulocyte count at timepoint W0, they were included in this experiment (see FIG. 17 A). An untreated naïve group was included in the study for baseline readings (Group I, see Table 19). In addition, Haemoglobin (Hgb) values of included rats were examined. If the Hgb-value was <13.5 g/dL the rat was allocated into a specific treatment group (II-IV, see Table 19). If the Hgb value was >13.5 g/dL rats were not allocated to a specific treatment group and re-analysed the next week (see FIG. 17 B). At all time points plasma was collected for further analysis. After allocation of the animals to one respective treatment group, rats in Group II were treated with a single s.c. injection of IgG4 control antibody, rats in Group III were treated with Darbepoetin alfa 10 µg/kg and rats in Group IV received a combination of CL-58838 3 mg/kg and Darbepoetin alfa 10 µg/kg (see Table 19).

TABLE 19

Treatment groups to assess the ESA-sparing capacity of CL-58838 for treatment of ACD.

| Group I | Naive control rats |
| Group II | ACD rats receiving IgG4 control antibody [3 mg/kg] s.c. |
| Group III | ACD rats receiving Darbepoetin alfa [10 µg/kg] s.c |
| Group IV | ACD rats receiving CL-58838 [3 mg/kg] and Darbepoetin alfa [10 µg/kg] |

After the initial treatment, administration of CL-58838 (Group IV) or IgG4 control (Group II), was repeated every three weeks. In contrast, any further EPO administration was dependent on the Hgb-value, which was evaluated in each individual rat every week throughout the whole study. As shown in FIG. 17 B, EPO was only administered if the Hgb-value in treatment groups III and IV was below the average Hgb value of the naïve control rats (Group I). We choose this experimental set up to mimic real life clinical setting in humans as CKD patients only receive EPO dependent on a certain pre-defined Hgb-level.

Blood was taken every week (i.e. timepoint "W0-W6") from the tail vein and at cull at "W7" to allow further analysis of iron status and anaemia.

From "W0" onwards, rats were allocated to one of the treatment groups according to the criteria described above. After Week 3 all rats were allocated to one of the treatment group and treatment could be started. Of importance, Hgb values were evenly distributed among the groups at the day of 1$^{st}$ treatment (FIG. 17 C). Details on the numbers of rats and the time point of treatment initiation is shown in Table 20.

TABLE 20

Rats listed according to their time point of inclusion in the experiment.

| Group | Treatment | Number (included in week 0/1/2/3) |
|---|---|---|
| Group I | Naïve controls | 5 (5/0/0/0) |
| Group II | ACD/IgG4 control antibody [3 mg/kg] | 7 (2/2/2/1) |
| Group III | ACD/Darbepoetin alfa [10 µg/kg] | 10 (1/5/2/1) |
| Group IV | ACD/CL-58838 [3 mg/kg] and Darbepoetin alfa [10 µg/kg] | 11 (1/5/3/2) |

Results

As outlined above, rats were allocated into a treatment group if their Hgb value was <13.5 g/dL. ACD rats treated with the isotype control antibody stayed anemic throughout the experiment. Treatment with EPO alone could restore Hgb-levels to near normal values. However, the combination of CL-58838 and EPO showed a synergistic effect on Hgb-values. Already one week after treatment initiation, Hgb-values were normalised and further increased over time (FIG. 17 C). In addition, the mean corpuscular volume (MCV) and mean corpuscular haemoglobin (MCH) as sensitive markers for iron availability were normalised in ACD rats treated with a combination of CL-58838 and EPO, while ACD control rats and rats treated with EPO only stayed microcytic and hypochromic throughout the whole experimental period (FIGS. 17 D and 17E).

In addition, to evaluate if combination therapy has an EPO-sparing effect, the amount of EPO, that was administered in rats of treatment group III and IV was monitored. The following calculations are based on the additional EPO doses, thus excluding the EPO dose that was administered for the 1$^{st}$ treatment:

In total, a maximum of 40 (ACD/Darbepoetin alfa) and 44 (ACD/Darbepoetin alfa+CL-58838) EPO administrations would have been theoretically possible after 4 weeks of treatment had all rats fallen below the defined threshold of the average Hgb value of the naïve control rats. Sticking to our criteria explained above and outlined in FIG. 17B, 21 out of 40 possible doses had to be administered to rats of Group III. In contrast, only 8 additional EPO doses had to be applied to rats of Group IV out of the 44 possible EPO administrations. In other words, while EPO-treated rats "consumed" 53% of all possible EPO doses, the combination group only needed only 18% to maintain the Hb values above the cut off (FIG. 17 F). This clearly shows that the combination therapy can correct the Hgb-value much more efficiently than EPO monotherapy. Consequently, addition of CL-58838 is capable to result in an EPO-sparing effect.

Example 18

Assessment of CL-58838 in a mouse model of chronic kidney disease Beyond the rat model described in Examples 14 and 17, the human IgG4 anti-BMP-6 antibody CL-58838 (SEQ ID NO: 116 and SEQ ID NO: 125) was also tested in a murine chronic kidney disease model (CKD). Kidney damage was induced via a special diet containing 0.2% Adenine (Akchurin et al., 2016). The aim of this study was to test the effects of CL-58838 as a monotherapy or in combination with Darbepoetin alfa (EPO) in this disease model.

Method 3-week-old male C57BL/6N mice were fed a special diet containing 0.2% adenine, 0.9% phosphate and 30 mg iron (referred to as Adenine diet). Untreated control mice (n=7) were fed a diet containing 30 mg Fe without Adenine.

At timepoint "Week 0" CKD animals were randomised into the different treatment groups (for details see Table 21). Thus, Group II was treated with a single s.c. injection of IgG4 control [3 mg/kg](n=5), Group III received CL-58838 [3 mg/kg](n=6), Group IV was treated with Darbepoetin alfa [10 µg/kg](n=6) and Group V received a combination of both CL-58838 [3 mg/kg] and Darbepoetin alfa [10 µg/kg] (n=6). An untreated naïve group, was included in the study for baseline readings (n=7). EPO treatment was repeated weekly, i.e. mice were treated 4 times with EPO. CL-58838 administration was done every second week, i.e. mice received two injections of the drug. The experiment was terminated after 4 weeks of treatment.

The experimental setup is shown in FIG. 18 A.

TABLE 21

Treatment groups to assess CL-58838 in a mouse model of chronic kidney disease

| Group I | Healthy controls |
|---|---|
| Group II | CKD mice receiving IgG4 control antibody [3 mg/kg] i.p. |
| Group III | CKD mice receiving CL-58838 [3 mg/kg] i.p. |
| Group IV | CKD mice receiving Darbepoetin alfa [10 µg/kg] i.p. |
| Group V | CKD mice receiving CL-58838 [3 mg/kg] and Darbepoetin alfa [10 µg/kg] i.p. |

Results 4 weeks after the 1$^{st}$ treatment, mice were analysed. Monotherapy with either CL-58838 or EPO could slightly improve Hgb values, however, combination therapy normalised Hgb values to baseline values (FIG. 18 B). Moreover, CL-58838 treated animals had significantly higher mean corpuscular volume (MCV) and mean corpuscular haemoglobin (MCH) values than untreated or EPO only treated mice. Of importance, MCV and MCH were completely normalised in double-treated animals, suggesting an improved supply of iron for erythroid progenitors of these treated animals (FIGS. 18 C and 18 D). As CL-58838 modulates hepcidin expression via targeting BMP6, we took a detailed look into genes, proteins and parameters related to iron metabolism in these animals. As shown in FIG. 18 E, hepatic Hamp expression levels were significantly reduced in animals receiving CL-58838 monotherapy or in combination with Darbepoetin alfa. Plasma iron levels and consequently transferrin saturation (TSAT) values were decreased in CKD control animals. EPO as well as CL-58838 monotherapy led to a slight increase of iron levels and TSAT. Again, combination therapy caused the strongest increase in plasma iron levels (FIG. 18 F). In accordance therewith, also TSAT values significantly increased in animals receiving the double treatment compared to animals treated with EPO alone (FIG. 18 G). In conclusion these data clearly show that iron is efficiently mobilized, bound to Tf, being incorporated into haemoglobin of red blood cells in the bone marrow.

Example 19

Assessment of ESA-Sparing Capacity of CL-58838 in a Mouse Model of Chronic Kidney Disease As detailed in Example 18, CKD was induced in male mice via a diet containing Adenine, causing kidney damage and leading to anaemia after 8 weeks. The aim of this study was to test if 1) combining therapy of CL-58838 and EPO (Darbepoetin alfa) could lead to a better overall response and a potential reduction of the dose of EPO.
2) an EPO dose that on its own had no effect on improving Hgb outcome could be made effective if combined with CL-58838.

Method 3-week-old male C57BL/6N mice were fed a special diet containing 0.2% adenine, 0.9% phosphate and 30 mg iron (referred to as Adenine diet). At "Week 0" CKD animals were randomised into the different treatment groups (for details see Table 22 and FIG. 18A) and treatment was started. 4 weeks after the $1^{st}$ treatment, mice were analysed.

TABLE 22

| Treatment groups to assess | | |
| --- | --- | --- |
| Treatment group | Darbepoetin alfa [µg/kg] | CL-58838 [mg/kg] |
| Group I | 0 | 0 |
| Group II | 1 | 0 |
| Group III | 1 | 0.1 |
| Group IV | 0.01 | 1 |
| Group V | 0.1 | |
| Group VI | 1 | |
| Group VII | 0.01 | 10 |
| Group VIII | 0.1 | |
| Group IX | 1 | |

Results

Treatment of mice suffering from CKD with the maximal EPO dose in this study (1 µg/kg) could not improve anaemia. However, if 1 µg/kg EPO was combined with CL-58838, irrespective of the CL-58838 dose [0.1 mg/kg, 1 mg/kg and 10 mg/kg], anaemia could be significantly ameliorated (FIG. 19A). Effects were more pronounced with the two higher doses of CL-58838. These results clearly show that an EPO dose, which has no effect on Hgb levels on its own, if combined with CL-58838, can be made effective.

Vice versa, our experimental setup allowed to evaluate if combination therapy can lead to using lower doses of EPO in a combination treatment (i.e. ESA-sparing). In this respect, a dose of 10 mg/kg CL-58838 was capable to significantly increase Hb levels if combined with 0.1 µg/kg EPO, which is 10-fold lower than the EPO dose used alone, and even 100-fold lower than the dose used in Example 18 (FIG. 19 B).

Moreover, mean corpuscular volume (MCV), being a surrogate for iron availability for erythrocytes, was dose-dependently increased (FIG. 19 C). In other words, the higher the dose of administered CL-58838, the better was the supply of erythrocytes with iron, which is reflected as higher MCV values. As it is well established that iron in the form of saturated transferrin (TSAT) represents the major iron-delivery pathway for developing erythrocytes, we also evaluated this parameter. As shown in FIG. 19D TSAT was significantly increased in mice receiving 1 µg/kg EPO in combination with 1 mg/kg and 10 mg/kg CL-58838, compared to mice receiving EPO alone.

In addition, even the lowest EPO dose (0.01 µg/kg) in combination with 1 mg/kg of CL-58838, which did not lead to a significant increase in Hb (not shown), did lead to a higher MCV values, indicating better red blood cell quality (FIG. 19 E).

Anti-BMP6 via CL-58838 treatment targets at lowering hepcidin levels. Thus, hepcidin levels (by measuring Hamp mRNA expression levels in the liver, which are known to correlate well with plasma hepcidin levels), were analysed. In general, there was a clear trend towards lower Hamp expression levels in all double-treated animals, except mice being in Group III, who received the lowest herein tested CL-58838 dose [0.1 mg/kg](FIG. 19 F). Of interest, animals receiving the same CL-58838 dose but different doses of EPO (ie. treatment groups IV-VI and VII-IX), revealed a tendency towards higher Hamp expression levels with higher EPO doses. As Hb levels also dose-dependently increased, higher Hamp expression levels must be interpreted in view of the crosstalk between iron homeostasis and erythropoiesis. For example, in case of sufficient Hb levels, Hamp expression is no longer as strongly repressed by signals generated by developing erythrocytes, such as Erfe (Kautz et al., 2014).

REFERENCES

Akchurin, O., Sureshbabu, A., Doty, S. B., Zhu, Y.-S., Patino, E., Cunningham-Rundles, S., Choi, M. E., Boskey, A., Rivella, S., 2016. Lack of hepcidin ameliorates anemia and improves growth in an adenine-induced mouse model of chronic kidney disease. Am. J. Physiol.-Ren. Physiol. 311, F877-F889.

Andriopoulos, B., Corradini, E., Xia, Y., Faasse, S. A., Chen, S., Grgurevic, L., Knutson, M. D., Pietrangelo, A., Vukicevic, S., Lin, H. Y., Babitt, J. L., 2009. BMP6 is a key endogenous regulator of hepcidin expression and iron metabolism. Nat. Genet. 41, 482-7.

Casanovas, G., Banerji, A., D'Alessio, F., Muckenthaler, M. U., Legewie, S., 2014. A Multi-Scale Model of Hepcidin Promoter Regulation Reveals Factors Controlling Systemic Iron Homeostasis. PLoS Comput. Biol. 10.

Kautz, L., Jung, G., Nemeth, E., Ganz, T., 2014. Erythroferrone contributes to recovery from anemia of inflammation. Blood 124, 2569-74.

Mayeur, C., Lohmeyer, L. K., Leyton, P., Kao, S. M., Pappas, A. E., Kolodziej, S. A., Spagnolli, E., Yu, B., Galdos, R. L., Yu, P. B., Peterson, R. T., Bloch, D. B., Bloch, K. D., Steinbicker, A. U., 2014. The type I BMP receptor Alk3 is required for the induction of hepatic hepcidin gene expression by interleukin-6. Blood 123, 2261-2268.

Nai, A., Lidonnici, M. R., Rausa, M., Mandelli, G., Pagani, A., Silvestri, L., Ferrari, G., Camaschella, C., 2015. The second transferrin receptor regulates red blood cell production in mice. Blood 125, 1170-1179.

Theurl, I., Schroll, A., Sonnweber, T., Nairz, M., Theurl, M., Willenbacher, W., Eller, K., Wolf, D., Seifert, M., Sun, C. C., Babitt, J. L., Hong, C. C., Menhall, T., Gearing, P., Lin, H. Y., Weiss, G., 2011. Pharmacologic inhibition of hepcidin expression reverses anemia of chronic inflammation in rats. Blood 118, 4977-4984.

Xia, Y., Babitt, J. L., Sidis, Y., Chung, R. T., Lin, H. Y., 2008. Hemojuvelin regulates hepcidin expression via a selective subset of BMP ligands and receptors independently of neogenin. Blood 111, 5195-5204.

Xu, J. L., Davis, M. M., 2000. Diversity in the CDR3 region of V(H) is sufficient for most antibody specificities. Immunity 13, 37-45.

Yusa, K., Zhou, L., Li, M. A., Bradley, A., Craig, N. L., 2011. A hyperactive piggyBac transposase for mammalian applications. Proc. Natl. Acad. Sci. U.S.A 108, 1531-6.

SEQUENCES:

| Seq ID No: | Description | Sequence |
| --- | --- | --- |
| 1 | Human BMP6 | Amino acid sequence Uniprot ID number: 22004 (leader sequence in *italics*; pro-peptide underlined; mature protein bold) | MPGLGRRAQWLCWWWGLLCSCCGPPPLRPPLPAAAAAAGGQLLGDGGSPGRTEQ PPPSPQSSSGFLYRRLKTQEKREMQKEILSVLGLPHRPRPLHGLQQPQPPALRQQEEQQ QQQLPRGEPPPGPGRLKSAPLFMLDLYNALSADNDEDGASEGERQQSWPHEAASSSQR RQPPPGAAHPLNRKSLLAPGSGSGGASPLTSAQDSAFLNDADMVMSFVNLVEYDKEFS PRQRHHKEFKFNLSQIPBGEVTAAEFRIYKDCVMGSFKNQTFLISIYQVLQEHQHRDSD LFLLDTRVVWASEEGWLEFDITATSNLMVVTPQHNMGLQLSVVTRDGVHVHPRAAGL VGRDGPYDKQPFMVAFFKVSEVHVRTTRSASSRRRQQSRNRSTQSQDVARVSSASDY NSSELKTACRKHELYVSFQDLGWQDWIIAPKGYAANYCDGECSFPLNAHMNATNHA IVQTLVHLMNPEYVPKPCCAPTKLNAISVLYFDDNSNVILKKYRNMVVRACGCH |
| 2 | Human BMP6 Recombinant protein | Amino acid sequence Peprotech Catalog Number: 120-06 | VSSASDYNSSELKTACRKHELYVSFQDLGWQDWIIAPKGYAANYCDGECSFPLNAHMN ATNHAIVQTLVHLMNPEYVPKPCCAPTKLNAISVLYFDDNSNVILKKYRNMV VRACGCH |
| 3 | Human BMP6 Recombinant protein | Amino acid sequence R&D Systems Catalog Number: 507-BP | QQSRNRSTQSQDVARVSSASDYNSSELKTACRKHELYVSFQDLGWQDWIIAPKGYAAN YCDGECSFPLNAHMNATNHAIVQTLVHLMNPEYVPKPCCAPTKLNAISVLYFDDNSNVI LKKYRNMVVRACGCH |
| 4 | Mouse BMP6 | Amino acid sequence Uniprot ID number: P20722 (leader sequence in *italics*; pro-peptide underlined; mature protein bold) | MPGLGRRAQWLCWWWGLLCSCGPPPLRPPLPVAAAAAGGQLLGAGGSPVRAEQPP PQSSSGFLYRRLKTHEKREMQKEILSVLGLPHRPRPLHGLQQPPVLPPQQQQQQQ QQQTAREPPPGRLKSAPLFMLDLYNALSNDDEEDGASEGVGQEPGSHGGASSQLRQ PSPGAAHSLNRKSLLAPGPGGGASPLTSAQDSAFLNDADMVMSFVNLVEYDKEFSPHQ RHHKEFKFPNLSQIPEGEAVTAAEFRVVKDCVVGSFKNQTFLISIYQVLQEHQHRDSDLFLL DTRVVWASEEGWLEFDITATSNLMVVTPQHNMGLQLSVVTRDGLHVNPRAAGLVGR DGPYDKQPFMVAFFKVSEVHVRTTRSASSRRRQQSRNRSTQSQDVSRGSGSSDYNGS ELKTACKKHELYVSFQDLGWQDWIIAPKGYAANYCDGECSFPLNAHMNATNHAIVQ TLVHLMNPEYVPKPCCAPTKLNAISVLYFDDNSNVILKKYRNMVVRACGCH |
| 5 | Mouse BMP6 Recombinant protein | Amino acid sequence R&D Systems (based on UniProt ID P20722) Catalog Number: 6325-BM | SASSRRRQQSRNRSTQSQDVSRGSGSSDYNGSELKTACKKHELYVSFQDLGWQDWIIA PKGYAANYCDGECSFPLNAHMNATNHAIVQTLVHLMNPEYVPKPCCAPTKLNAISVLYF DDNSNVILKKYRNMVVRACGCH |
| 6 | Forward primer | Nucleotide sequence | AAAAAAACTAGTAAATGGCCCCATGTGGCCCCCGCCTTGTCGC |
| 7 | Reverse primer | Nucleotide sequence | TTTTTTTCTCGAGCTGTCTGGCTGTCCCACTGCTGGGTCTTGAGCTT |
| 8 | Peptide | Amino acid sequence | TLVHLMNPEYV |
| 9 | Peptide | Amino acid sequence | HLMNPEY |
| 10 | Peptide | Amino acid sequence | SASDYNSSELKTA |
| 11 | Peptide | Amino acid sequence | ELKTACRKHELYV |

-continued

SEQUENCES:

| Seq ID No: | | Description | | Sequence |
|---|---|---|---|---|
| 12 | | Peptide | Amino acid sequence | GSSDYNGSELKTA |
| 13 | | Peptide | Amino acid sequence | ELKTACKKHELYV |
| 14 | | Peptide | Amino acid sequence | ELKTA |
| 15 | | Peptide | Amino acid sequence | QSQDVAR |
| 16 | | Peptide | Amino acid sequence | QSQDVSR |
| 17 | | Peptide | Amino acid sequence | QSRNRSTQSQDVARVSSASDYNSSELKTAC |
| 18 | CL-66833 | CDRH1 (IMGT) | Amino acid sequence of CDRH1 using IMGT | GYTFTNHA |
| 19 | CL-66833 | CDRH2 (IMGT) | Amino acid sequence of CDRH2 using IMGT | INAGNGKT |
| 20 | CL-66833 | CDRH3 (IMGT) | Amino acid sequence of CDRH3 using IMGT | TRRVYGESYDH |
| 21 | CL-66833 | CDRH1 (KABAT) | Amino acid sequence of CDRH1 using Kabat | NHAIH |
| 22 | CL-66833 | CDRH2 (KABAT) | Amino acid sequence of CDRH2 using Kabat | WINAGNGKTDYSQNFQG |
| 23 | CL-66833 | CDRH3 (KABAT) | Amino acid sequence of CDRH3 using Kabat | RVYGESYDH |
| 24 | CL-66833 | Heavy chain variable region | Amino acid sequence of $V_H$ | QVQFVQSGAEVKSPGASVKVSCKASGYTFTNHAIHWVRQAPGQRLEWMGWINAGN GKTDYSQNFQGRVIITRDTSANTAYMSLSSLTSEDTAFYYCTRRVYGESYDHWGQGTLV TVSS |
| 25 | CL-66833 | Heavy chain variable region | Nucleotide sequence of $V_H$ | CAGGTCCAGTTTGTGCAGTCTGGGGCTGAGGTGAAGAGTCCTGGGGCCTCTGTGAA GGTTTCCTGCAAGGCTTCTGGATACACCTTCACA AATCATGGA TACATTGGGT GC GCCAGGCC CCCGGACAAA GGCTTGAGTG GATGGGATGG ATCAACGCTGGCAATG GTAAAACTGATTATTCACAGAACTTCCAGGGCAGAGAGTCATCATTACCAGGGACACAT CCCGGAACAACAGCCTACATGTCCCTGAGCAGCCTGACATCTGAGGACACGGCTTTTT AATTACTGTACTAGAAGGGTCTACGGTGAATCGTATGACCA CTGGGGCCAGGGAACCCTGGTCACCGTCTC CTCA |
| 26 | CL-66833 | Full heavy chain sequence | Amino acid sequence heavy chain | QVQFVQSGAEVKSPGASVKVSCKASGYTFTNHAIHWVRQAPGQRLEWMGWINAGN GKTDYSQNFQGRVIITRDTSANTAYMSLSSLTSEDTAFYYCTRRVYGESYDHWGQGTLV TVSSASTKGPSVFPLAPCSRSTSESTAALGCLVKDYFPEPVTVSWNSGALTSGVHTFPAVL QSSGLYSLSSVVTVPSSLGTKTYTCNVDHKPSNTKVDKRVESKYGPPCPAPEFEGG |

-continued

SEQUENCES:

| Seq ID No: | | | Description | Sequence |
|---|---|---|---|---|
| | | | | PSVFLFPPKPKDTLMISRTPEVTCVVVDVSQEDPEVQFNWYVDGVEVHNAKTKPREEQ FNSTYRVVSVLTVLHQDWLNGKEYKCKVSNKGLPSSIEKTISKAKGQPREPQVYTLPPSQ EEMTKNQVSLTCLVKGFYPSDIAVEWESNGQPENNYKTTPPVLDSDGSFFLYSRLTVDKS RWQEGNVFSCSVMHEALHNHYTQKSLSLSLGK |
| 27 | CL-66833 | CDRL1 (IMGT) | Amino acid sequence of CDRL1 using IMGT | QGIRNN |
| 28 | CL-66833 | CDRL2 (IMGT) | Amino acid sequence of CDRL2 using IMGT | AAS |
| 29 | CL-66833 | CDRL3 (IMGT) | Amino acid sequence of CDRL3 using IMGT | LQHQIYPWT |
| 30 | CL-66833 | CDRL1 (KABAT) | Amino acid sequence of CDRL1 using KABAT | RASQGIRNNLG |
| 31 | CL-66833 | CDRL2 (KABAT) | Amino acid sequence of CDRL2 using KABAT | AASSLQS |
| 32 | CL-66833 | CDRL3 (KABAT) | Amino acid sequence of CDRL3 using KABAT | LQHQIYPWT |
| 33 | CL-66833 | Light chain variable region | Amino acid sequence of VL | DIQMTQSPSSLSASVGDRVTITCRASQGIRNNLGWYQQKPGKAPKRLIYAASSLQSGVP SRFSGSGSGTEFTLTISSLQPEDVAIYFCLQHQIYPWTFGQGTKVETK |
| 34 | CL-66833 | Light chain variable region | Nucleic acid sequence of VL | GACATCCAGA TGACCCAGTC TCCATCCTCC CTGTCTGCAT CTGTAGGAGA CAGAG TCACC ATCACTTGCC GGGCAAGTCA GGGCATTAGA AATAATTTAG GCTGGTATCA GCAGAAACCA GGGAAAGCCC CTAA GCGCCT GATCTATGCT GCATCCAGTT TGCAAAGTGG GGTCCCATCA AGGTTTAGCG GCAGTGGATC TGGGACAGAA TTCA CTCTCA CAATCAGCAG CCTGCAGCCT GAAGATGTTG CAATTTATTT CTGTCTACAA CATCAAATTT ACCCGTGGAC GTTCGG CCAA GGGACCAAGG TGGAAACCAA A |
| 35 | CL-66833 | Full light chain sequence | Amino acid sequence light chain | DIQMTQSPSSLSASVGDRVTITCRASQGIRNNLGWYQQKPGKAPKRLIYAASSLQSGVP SRFSGSGSGTEFTLTISSLQPEDVAIYFCLQHQIYPWTFGQGTKVETK RTVAAPSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC |
| 36 | CL-57931 | CDRH1 (IMGT) | Amino acid sequence of CDRH1 using IMGT | GYTFTSYA |
| 37 | CL-57931 | CDRH2 (IMGT) | Amino acid sequence of CDRH2 using IMGT | ISAANGNT |

-continued

SEQUENCES:

| Seq ID No: | | Description | Sequence |
|---|---|---|---|
| 38 | CL-57931 | CDRH3 (IMGT) | Amino acid sequence of CDRH3 using IMGT | ARRKLWSPFDI |
| 39 | CL-57931 | CDRH1 (KABAT) | Amino acid sequence of CDRH1 using Kabat | SYALH |
| 40 | CL-57931 | CDRH2 (KABAT) | Amino acid sequence of CDRH2 using Kabat | WISAANGNTDYSWKFQG |
| 41 | CL-57931 | CDRH3 (KABAT) | Amino acid sequence of CDRH3 using Kabat | RKLWSPFDI |
| 42 | CL-57931 | Heavy chain variable region | Amino acid sequence of $V_H$ | QVQLVQSGAEVQKPGASVKVSCKASGYTFTSYALHWVRQAPQGRLEWLGWISAANG NTDYSWKFQGRVTLTRDTSANTVYMELNSLTSEDSAVVYCARRKLWSPFDIWGQGTLV TVSS |
| 43 | CL-57931 | Heavy chain variable region | Nucleotide sequence of $V_H$ | CAGGTCCAACTTGTGCAGTCTGGGGCTGAGGTGCAGAAGCCTGGGGCCTCAGTGAA GGTTTCCTGCCAAGGCTTCTGGATACACCTTCACTTCATATGCTTTGCATTGGGTGCG CAGGCCCCGGACAAAGGCTTGAGTGGCTGGGATGGATCAGCGGCTGCCAATGGTAA CACAGATTATTCATGGAAGTTCCAGGGCAGAGTCACATTACCAGGACACATCCGC AAACACAGTCTACATGGAACTGAACAGTCTGACATCTGAGGACTCGGCTGTGTATTA CTGTGCGAGAAGGAAACTATGGTCTCCTTTTGATATCTGGGGCCAAGGGACATTGG TCACCGTCTCTTCA |
| 44 | CL-57931 | Full heavy chain sequence | Amino acid sequence heavy chain | QVQLVQSGAEVQKPGASVKVSCKASGYTFTSYALHWVRQAPQGRLEWLGWISAANG NTDYSWKFQGRVTLTRDTSANTVYMELNSLTSEDSAVVYCARRKLWSPFDIWGQGTLV TVSSASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPAPEFEGG PSVFLFPPKPKDTLMISRTPEVTCVVVDVSQEDPEVQFNWYVDGVEVHNAKTKPREEQ FNSTYRVVSVLTVLHQDWLNGKEYKCKVSNKGLPSSIEKTISKAKGQPREPQVYTLPPSQ EEMTKNQVSLTCLVKGFYPSDIAVEWESNGQPENNYKTTPPVLDSDGSFFLYSRLTVDKS RWQEGNVFSCSVMHEALHNHYTQKSLSLSLGK |
| 45 | CL-57931 | CDRL1 (IMGT) | Amino acid sequence of CDRL1 using IMGT | QSLTNSF |
| 46 | CL-57931 | CDRL2 (IMGT) | Amino acid sequence of CDRL2 using IMGT | GAF |
| 47 | CL-57931 | CDRL3 (IMGT) | Amino acid sequence of CDRL3 using IMGT | QYYGTSPWT |
| 48 | CL-57931 | CDRL1 (KABAT) | Amino acid sequence of CDRL1 using KABAT | WASQSLTNSFLA |

-continued

SEQUENCES:

| Seq ID No: | | Description | | Sequence |
|---|---|---|---|---|
| 49 | CL-57931 | CDRL2 (KABAT) | Amino acid sequence of CDRL2 using KABAT | GAFSRAT |
| 50 | CL-57931 | CDRL3 (KABAT) | Amino acid sequence of CDRL3 using KABAT | QYYGTSPWT |
| 51 | CL-57931 | Light chain variable region | Amino acid sequence of V_L | EIVLTQSPGTLSLSPGERATLSCWASQSLTNSFLAWYRQKPGQAPRLLISGAFSRATDIPD RISGSGSGTDFTLTINRLEPEDFAVYYCQYYGTSPWTFGQGTKVEIK |
| 52 | CL-57931 | Light chain variable region | Amino acid sequence of V_L | GAAATTGTGTTGACGCAGTCTCCAGGCACCCTGTCTTTGTCTCCAGGGGAAAGAGCC ACCCTCTCCTGTTGGGCCAGTCAAAGTCTTACCAACAGTTTCTTAGCCTGGTACCGGC AGAAACCTGGCCAGGCTCCCAGGCTCCTCATCTCTGGTGCATTCAGCAGGGCCACTG ACATCCCAGACAGGATCAGTGGCAGTGGATCTGGGACAGACTTCACTCTCACCATCA ACAGACTGGAGCCTGAAGATTTTGCAGTGTATTACTGTCAGTACTATGGTACCTCAC CGTGGACGTTCGGCCAAGGGACCAAGGTGGAAATCAAA |
| 53 | CL-57931 | Full light chain sequence | Amino acid sequence light chain | EIVLTQSPGTLSLSPGERATLSCWASQSLTNSFLAWYRQKPGQAPRLLISGAFSRATDIPD RISGSGSGTDFTLTINRLEPEDFAVYYCQYYGTSPWTFGQGTKVEIKRTVAAPSVFIFPPS DEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 54 | CL-57945 | CDRH1 (IMGT) | Amino acid sequence of CDRH1 using IMGT | GYTFTTFA |
| 55 | CL-57945 | CDRH2 (IMGT) | Amino acid sequence of CDRH2 using IMGT | INPGNVKT |
| 56 | CL-57945 | CDRH3 (IMGT) | Amino acid sequence of CDRH3 using IMGT | ARRQLWLPFDY |
| 57 | CL-57945 | CDRH1 (KABAT) | Amino acid sequence of CDRH1 using Kabat | TFAIH |
| 58 | CL-57945 | CDRH2 (KABAT) | Amino acid sequence of CDRH2 using Kabat | WINPGNVKTDYSQKFQG |
| 59 | CL-57945 | CDRH3 (KABAT) | Amino acid sequence of CDRH3 using Kabat | RQLWLPFDY |
| 60 | CL-57945 | Heavy chain variable region | Amino acid sequence of V_H | QVHLVQSGAEVKNPGASVKVSCKASGYTFTTFAIHWLRQAPGQRLEWMGWINPIGNV KTDYSQKFQGRVTISRDTSATTAYMELSSLRSEDTAVYYCARRQLWLPFDYWGQGTLVT VSS |
| 61 | CL-57945 | Heavy chain variable region | Nucleotide sequence of V_H | CAGGTCCACCTTGTTCAGTCAGGGCAGAGAGGTGAAGAACCCTGGGGCCTCAGTGAA GGTCTCCTGCCAAGGCTTCTGGATACACCTTCACTACCTTTGCTATTCATTGGTTGCGC CAGGCCCCCGGACAGAGAGCTTGAGTGGATGGGATGGATCAACCCTGGCAATGTTAA |

-continued

SEQUENCES:

| Seq ID No: | | Description | Sequence |
|---|---|---|---|
| | | | GACAGATTATTCGCAGAGAGTTCCAGGGCAGAGTCACCATTAGCAGGGACACATCCG CGACCACTGCCTACATGGAGCTGAGCAGCCTGAGATCTGAAGACACGGCTGTTTATT ACTGTGCGAGAAGACAATTATGGTTACCCTTTGACTACTGGGGCCAGGGAACCCTG GTCACCGTCTCCTCAG |
| 62 | CL-57945 | Full heavy chain sequence | Amino acid sequence heavy chain | QVHLVQSGAEVKNPGASVKVSCKASGYTFTTFAIHWLRQAPGQRLEWMGWINPGNV KTDYSQKFQGRVTISRDTSATTAYMELSSLRSEDTAVYYCARRQLWLPFDYWGQGLTVT VSSASTKGPSVFPLAPCSRSTSESTALGCLVKDYFPEPVTVSWNSGALTSGVHTFPAVL QSSGLYSLSSVVTVPSSSLGTKTYTCNVDHKPSNTKVDKRVESKYGPPCPAPEFEGG PSVFLFPPKPKDTLMISRTPEVTCVVVDVSQEDPEVQFNWYVDGVEVHNAKTKPREEQ FNSTYRVVSVLTVLHQDWLNGKEYKCKVSNKGLPSSIEKTISKAKGQPREPQVYTLPPSQ EEMTKNQVSLTCLVKGFYPSDIAVEWESNGQPENNYKTTPPVLDSDGSFFLYSRLTVDKS RWQEGNVFSCSVMHEALHNHYTQKSLSLGK |
| 63 | CL-57945 | CDRL1 (IMGT) | Amino acid sequence of CDRL1 using IMGT | QSISNNF |
| 64 | CL-57945 | CDRL2 (IMGT) | Amino acid sequence of CDRL2 using IMGT | GAS |
| 65 | CL-57945 | CDRL3 (IMGT) | Amino acid sequence of CDRL3 using IMGT | QHYGGSPWT |
| 66 | CL-57945 | CDRL1 (KABAT) | Amino acid sequence of CDRL1 using KABAT | RASQSISNNFLA |
| 67 | CL-57945 | CDRL2 (KABAT) | Amino acid sequence of CDRL2 using KABAT | GASSRAT |
| 68 | CL-57945 | CDRL3 (KABAT) | Amino acid sequence of CDRL3 using KABAT | QHYGGSPWT |
| 69 | CL-57945 | Light chain variable region | Amino acid sequence of $V_L$ | EIVLTQSPGTLSLSPGEGATLSCRASQSISNNFLAWYQQKPGQAPRLLIFGASSRATAIPD RFVGSGSGTDFTLTITGLEPEDFAVYHCQHYGGSPWTPGQGTKVEIK |
| 70 | CL-57945 | Light chain variable region | Amino acid sequence of $V_L$ | GAAATTGTGTTGACGCAGTCTCCAGGCACCCTGTCTTTGTCTCCAGGGGAGGGAGCC ACCCTCTCCTGCAGGGCCAGTCAGAGTATTAGCAACAACTTCTTAGCCTGGTACCAA CAGAAACCTGGCCAGGCTCCCAGACTCCTCATCTTTGGTGCATCCAGCAGGGCCACT GCCATCCCAGACAGGTTCGTTGGCAGTGGGTCTGGGACAGACTTCACTCTCACCATC ACCGGACTGGAGCCTGAAGATTTTGCAGTGTATCACTGTCAACACTATGGTGGTTCA CCTTGGACGTTCGGCCAAGGGACCAAGGTGGAAATCAAA |
| 71 | CL-57945 | Full light chain sequence | Amino acid sequence light chain | EIVLTQSPGTLSLSPGEGATLSCRASQSISNNFLAWYQQKPGQAPRLLIFGASSRATAIPD RFVGSGSGTDFTLTITGLEPEDFAVYHCQHYGGSPWTFGQGTKVEIKRTVAAPSVFIFPP SDEQLKSGTASVVCLLNNFYPREAKVQWKVDNALQSGNSQESVTEQDSKDSTYSLSSTL TLSKADYEKHKVYACEVTHQGLSSPVTKSFNRGEC |

-continued

SEQUENCES:

| Seq ID No: | | Description | Sequence |
|---|---|---|---|
| 72 | CL-58102 | CDRH1 (IMGT) | Amino acid sequence of CDRH1 using IMGT | GYSFTNYA |
| 73 | CL-58102 | CDRH2 (IMGT) | Amino acid sequence of CDRH2 using IMGT | IHAGNGKT |
| 74 | CL-58102 | CDRH3 (IMGT) | Amino acid sequence of CDRH3 using IMGT | ARRQLWLPFDY |
| 75 | CL-58102 | CDRH1 (KABAT) | Amino acid sequence of CDRH1 using Kabat | NYALH |
| 76 | CL-58102 | CDRH2 (KABAT) | Amino acid sequence of CDRH2 using Kabat | WIHAGNGKTEYAQKFQD |
| 77 | CL-58102 | CDRH3 (KABAT) | Amino acid sequence of CDRH3 using Kabat | RQLWLPFDY |
| 78 | CL-58102 | Heavy chain variable region | Amino acid sequence of V_H | QVQLVQSGAEVKKPGASVKVSCKASGYSFTNYALHWVRQAPGQRLEWMGWIHAGN GKTEYAQKFQDRVTISRDISAITVYMELSSLRSEDTAVYYCARRQLWLPFDYWGQGTLVT VSS |
| 79 | CL-58102 | Heavy chain variable region | Nucleotide sequence of V_H | CAGGTCCAGCTTGTGCAGTCTGGGGCTGAGGTGAAGAAGCCTGGGGCCTCAGTGA AGGTTTCCTGTAAGGCTTCTGGGTACAGTTTCACTAACTATGCTTTACATTGGGTGCG CCAGGCCCCGGACAAAGACTTGAGTGGATGGGATGGATCCACGCTGGTAATGGTA AGACAGAATATGCACAGAAGTTCCAGGACAGAGAGCCTGAGATCTGAAGACACGGCTGTTTAT GCGATCACAGTTTACATGGAACTGAGCAGCCTGAGATCTGAAGACACGGCTGTTTAT TATTGTGCGAGAAGACAGTTATGGTTACCCTTTGACTACTGGGGCCAGGGACCCTG GTCACCGTCTCCTCA |
| 80 | CL-58102 | Full heavy chain sequence | Amino acid sequence heavy chain | QVQLVQSGAEVKKPGASVKVSCKASGYSFTNYALHWVRQAPGQRLEWMGWIHAGN GKTEYAQKFQDRVTISRDISAITVYMELSSLRSEDTAVYYCARRQLWLPFDYWGQGTLVT VSSASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPAPEFEGG PSVFLFPPKPKDTLMISRTPEVTCVVVDVSQEDPEVQFNWYVDGVEVHNAKTKPREEQ FNSTYRVVSVLTVLHQDWLNGKEYKCKVSNKGLPSSIEKTISKAKGQPREPQVYTLPPSQ EEMTKNQVSLTCLVKGFYPSDIAVEWESNGQPENNYKTTPPVLDSDGSFFLYSRLTVDKS RWQEGNVFSCSVMHEALHNHYTQKSLSLSLGK |
| 81 | CL-58102 | CDRL1 (IMGT) | Amino acid sequence of CDRL1 using IMGT | QIIINRQ |
| 82 | CL-58102 | CDRL2 (IMGT) | Amino acid sequence of CDRL2 using IMGT | GAS |

-continued

SEQUENCES:

| Seq ID No: | | | Description | Sequence |
|---|---|---|---|---|
| 83 | CL-58102 | CDRL3 (IMGT) | Amino acid sequence of CDRL3 using IMGT | QHYGGSPWT |
| 84 | CL-58102 | CDRL1 (KABAT) | Amino acid sequence of CDRL1 using KABAT | RAGQIINRQLA |
| 85 | CL-58102 | CDRL2 (KABAT) | Amino acid sequence of CDRL2 using KABAT | GASNRVT |
| 86 | CL-58102 | CDRL3 (KABAT) | Amino acid sequence of CDRL3 using KABAT | QHYGGSPWT |
| 87 | CL-58102 | Light chain variable region | Amino acid sequence of $V_L$ | EIVLTQSPDTLSLSPGETASFSCRAGQIINRQLAWYQRRPGQAPRLLIYGASNRVTGIPDRFSGSGSGTDFTLTINRLEPEDFAVYYCQHYGGSPWTFGQGTKVEIK |
| 88 | CL-58102 | Light chain variable region | Nucleic acid sequence of $V_L$ | GAAATTGTTGACGCAGTCTCCAGACACCCTCTCTTTGTCTCCAGGGGAAACAGCCAGTTCTCCTGCAGGGGCCGGTCAAATTATTAATCAACAGACAGTTAGCCTGGTACCAGCGGAGACCTGGCCAGGCTCCCGGCTCCTCATCTATGGCGCGTCCAATAGGGTCACTGGCATCCCAGACAGGTTCAGTGGCAGTGGGTCTGGGACAGACTTCACTCTCACGATCAATAGACTGGAGCCTGAAGATTTTGCAGTGTATTACTGTCAGCACTATGGTGCTCACCTTGGACGTTCGGCCAAGGGACCAAGGTGGAAATCAAA |
| 89 | CL-58102 | Full light chain sequence | Amino acid sequence light chain | EIVLTQSPDTLSLSPGETASFSCRAGQIINRQLAWYQRRPGQAPRLLIYGASNRVTGIPDRFSGSGSGTDFTLTINRLEPEDFAVYYCQHYGGSPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 90 | CL-58252 | CDRH1 (IMGT) | Amino acid sequence of CDRH1 using IMGT | GYTFTSHA |
| 91 | CL-58252 | CDRH2 (IMGT) | Amino acid sequence of CDRH2 using IMGT | INAANGKT |
| 92 | CL-58252 | CDRH3 (IMGT) | Amino acid sequence of CDRH3 using IMGT | ARRPYGGPFDY |
| 93 | CL-58252 | CDRH1 (KABAT) | Amino acid sequence of CDRH1 using Kabat | SHAMH |
| 94 | CL-58252 | CDRH2 (KABAT) | Amino acid sequence of CDRH2 using Kabat | WINAANGKTDYSQNFQG |
| 95 | CL-58252 | CDRH3 (KABAT) | Amino acid sequence of CDRH3 using Kabat | RPYGGPFDY |

-continued

SEQUENCES:

| Seq ID No: | | Description | Sequence |
|---|---|---|---|
| 96 | CL-58252 | Heavy chain variable region | Amino acid sequence of V$_H$ | QVQFVQSGAEVKKPGASVKVSCKASGYTFTSHAMHWVRQAPGQRLEWMGWINAAN GKTDYSQNFQGRVTITRDTYANTVYMELSSLRSEDTAVYYCARRPYGGPFDYWGQGTL VTVSS |
| 97 | CL-58252 | Heavy chain variable region | Nucleotide sequence of V$_H$ | CAGGTCCAGTTTGTGCAGTCTGGGGCTGAGGTGAAGAAGCCTGGGGCCTCAGTGAA GGTTTCCTGTAAGGCTTCTGGATACACACTTCACTAGCCATGCTATGCATTGGGTGCG CCAGGCCCCCGGACAAAGGCTTGAGTGGATGGGATGGATCAACGCTGCCAATGGTA AAACAGATTATTCACAGAACTTCCAGGCAGGCAGAGTCACCATTACCAGGGACACCATACG CGAACAGCAGTCTACATGGAACTGAGCCAGCCTGAGATCTGAAGACACGGCTGTGTAT TACTGTGCGAGACGCCCTTACGGTGCCCTTTGACTACTGGGGCCAGGGACCCTG GTCACCGTCTCCTCA |
| 98 | CL-58252 | Full heavy chain sequence | Amino acid sequence heavy chain | QVQFVQSGAEVKKPGASVKVSCKASGYTFTSHAMHWVRQAPGQRLEWMGWINAAN GKTDYSQNFQGRVTITRDTYANTVYMELSSLRSEDTAVYYCARRPYGGPFDYWGQGTL VTVSSASTKGPSVFPLAPCSRSTSESTAALGCLVKDYFPEPVTVSWNSGALTSGVHTFPA VLQSSGLYSLSSVVTVPSSLGTKTYTCNVDHKPSNTKVDKRVESKYGPPCPPCPAPEFEG GPSVFLFPPKPKDTLMISRTPEVTCVVVDVSQEDPEVQFNWYVDGVEVHNAKTKPPREE QFNSTYRVVSVLTVLHQDWLNGKEYKCKVSNKGLPSSIEKTISKAKGQPREPQVYTLPPS QEEMTKNQVSLTCLVKGFYPSDIAVEWESNGQPENNYKTTPPVLDSDGSFFLYSRLTVD KSRWQEGNVFSCSVMHEALHNHYTQKSLSLSLGK |
| 99 | CL-58252 | CDRL1 (IMGT) | Amino acid sequence of CDRL1 using IMGT | QSISIW |
| 100 | CL-58252 | CDRL2 (IMGT) | Amino acid sequence of CDRL2 using IMGT | KAS |
| 101 | CL-58252 | CDRL3 (IMGT) | Amino acid sequence of CDRL3 using IMGT | QQYNLYPWT |
| 102 | CL-58252 | CDRL1 (KABAT) | Amino acid sequence of CDRL1 using KABAT | RASQSISIWLA |
| 103 | CL-58252 | CDRL2 (KABAT) | Amino acid sequence of CDRL2 using KABAT | KASSLES |
| 104 | CL-58252 | CDRL3 (KABAT) | Amino acid sequence of CDRL3 using KABAT | QQYNLYPWT |
| 105 | CL-58252 | Light chain variable region | Amino acid sequence of V$_L$ | DIQMTQSPSTLSASVGDRVTITCRASQSISIWLAWYQQKPGKAPKLLIYKASSLESGVPSR FSGSGSGTEFTLTISSLQPDDFATYYCQQYNLYPWTFGQGTKVEIK |

-continued

SEQUENCES:

| Seq ID No: | | Description | Sequence |
|---|---|---|---|
| 106 | CL-58252 | Nucleic acid sequence of V_L | GACATCCAGATGACCCAGTCTCCTTCCACCCTGTCTGCATCTGTAGGAGACAGAGTC<br>ACCATCACTTGCCGGGCCAGTCAGAGTATTAGTATCTGGTTGGCCTGGTATCAGCAG<br>AAACCAGGGAAAGCCCCTAAGCTCCTGATCTATAAGGCGTCAGTTTAGAAAGTGG<br>GGTCCCATCAAGGTTCAGCGGCAGTGGATCTGGGACAGAATTCACTCTCACCATCAG<br>CAGCCTGCAGCCTGATGATTTTGCAACTTATTACTGTCAACAGTATAATCTTTATCCG<br>TGGACGTTCGGCCAAGGGACCAAGGTGGAAATCAAA |
| 107 | CL-58252 | Amino acid sequence light chain | DIQMTQSPSTLSASVGDRVTITCRASQSISWLAWYQQKPGKAPKLLIYKASSLESGVPSR<br>FSGSGSGTEFTLTISSLQPDDFATYYCQQYNLYPWTFGQGTKVEIKRTVAAPSVFIFPPPSD<br>EQLKSGTASVVCLLNNFYPREAKVQWKVDNALQSGNSQESVTEQDSKDSTYSLSSTLTL<br>SKADYEKHKVYACEVTHQGLSSPVTKSFNRGEC |
| 108 | CL-58838 | Amino acid sequence of CDRH1 using IMGT | GFTFSDYY |
| 109 | CL-58838 | Amino acid sequence of CDRH2 using IMGT | ISISGSTI |
| 110 | CL-58838 | Amino acid sequence of CDRH3 using IMGT | ARRSSGWYDY |
| 111 | CL-58838 | Amino acid sequence of CDRH1 using Kabat | DYYMS |
| 112 | CL-58838 | Amino acid sequence of CDRH2 using Kabat | YISISGSTIYYADSVKG |
| 113 | CL-58838 | Amino acid sequence of CDRH3 using Kabat | RSSGWYDY |
| 114 | CL-58838 | Amino acid sequence of V_H | QVQLVESGGGLVKPGGSLRLSCAASGFTFSDYYMSWIRQAPGKGLEWVSYISISGSTIYY<br>ADSVKGRFTISRDNAMDSLYLQMNSLRAEDTAVYYCARRSSGWYDYWGQGTLVTVSS |
| 115 | CL-58838 | Nucleotide sequence of V_H | CAGGTGCAACTGGTGGAGTCTGGGGGAGGCTTGGTCAAGCCTGGAGGGTCCCTGA<br>GACTCTCCTGTGCAGCCTCTGGATTCACCTTCAGTGACTACTACATGAGTTGGATCCG<br>CCAGGCTCCAGGGAAGGGGCTGGAGTGGGTTTCATACATTAGTATTAGTGGTAGTA<br>CCATATACTACGCAGACTCTGTGAAGGGCCGATTCACCATCTCCAGGGACAACGCCA<br>TGGACTCACTGTATCTGCAAATGAACAGCCTGAGAGCCGAGGACACGGCCGTGTAT<br>TACTGTGCGAGACGGAGCAGTGGCTGGTACGACTACTGGGGCCAGGGAACCCTGG<br>TCACCGTCTCCTCA |
| 116 | CL-58838 | Amino acid sequence heavy chain | QVQLVESGGGLVKPGGSLRLSCAASGFTFSDYYMSWIRQAPGKGLEWVSYISISGSTIYY<br>ADSVKGRFTISRDNAMDSLYLQMNSLRAEDTAVYYCARRSSGWYDYWGQGTLVTVSS<br>ASTKGPSVFPLAPCSRSTSESTAALGCLVKDYFPEPVTVSWNSGALTSGVHTFPAVLQSS<br>GLYSLSSVVTVPSSSLGTKTYTCNVDHKPSNTKVDKRVESKYGPPCPPCPAPEFEGGPSVF<br>LFPPKPKDTLMISRTPEVTCVVVDVSQEDPEVQFNWYVDGVEVHNAKTKPREEQFNST |

-continued

SEQUENCES:

| Seq ID No: | | | Description | Sequence |
|---|---|---|---|---|
| | | | | YRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSGK |
| 117 | CL-58838 | CDRL1 (IMGT) | Amino acid sequence of CDRL1 using IMGT | QRVVYRY |
| 118 | CL-58838 | CDRL2 (IMGT) | Amino acid sequence of CDRL2 using IMGT | GAF |
| 119 | CL-58838 | CDRL3 (IMGT) | Amino acid sequence of CDRL3 using IMGT | HQYGSSPPT |
| 120 | CL-58838 | CDRL1 (KABAT) | Amino acid sequence of CDRL1 using KABAT | WASQRVVYRYLA |
| 121 | CL-58838 | CDRL2 (KABAT) | Amino acid sequence of CDRL2 using KABAT | GAFNRAT |
| 122 | CL-58838 | CDRL3 (KABAT) | Amino acid sequence of CDRL3 using KABAT | HQYGSSPPT |
| 123 | CL-58838 | Light chain variable region | Amino acid sequence of V<sub>L</sub> | EIVLTQSPGTLSLSPGERATLSCWASQRVVYRYLAWYQRKPGQAPRLLIYGAFNRATGIPDRFSGSGSGTDFSLTISRLEPEDFAVYYCHQYGSSPPTFGQGTKVEIK |
| 124 | CL-58838 | Light chain variable region | Nucleic acid sequence of V<sub>L</sub> | GAAATTGTGTTGACGCAGTCTCCAGGCACCCTGTCTTTGTCTCCAGGGGAAAGAGCCACCCTCTCTTGTTGGGCCAGTCAGAGGGTTGTTTACAGATACTTAGCCTGGTACCAGCGGAAACCTGGCCAGGCTCCCAGACTTCTCATTTATGGTGCATTCAACAGGGCCACTGGCATCCCAGACAGGTTCAGTGGCAGTGGGTCTGGGACAGACTTCAGTCTCACTATCAGTAGACTGGAGCCTGAGGATTTTGCAGTTTATTACTGTCACCAATATGGTAGTTCACCACCGACGTTCGGCCAAGGGACCAAGGTGGAAATCAAA |
| 125 | CL-58838 | Full light chain sequence | Amino acid sequence light chain | EIVLTQSPGTLSLSPGERATLSCWASQRVVYRYLAWYQRKPGQAPRLLIYGAFNRATGIPDRFSGSGSGTDFSLTISRLEPEDFAVYYCHQYGSSPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 126 | CL-58851 | CDRH1 (IMGT) | Amino acid sequence of CDRH1 using IMGT | GFTFITYA |
| 127 | CL-58851 | CDRH2 (IMGT) | Amino acid sequence of CDRH2 using IMGT | INVGNGNR |
| 128 | CL-58851 | CDRH3 (IMGT) | Amino acid sequence of CDRH3 using IMGT | ARRPLWGPFDY |

-continued

SEQUENCES:

| Seq ID No: | | Description | | Sequence |
|---|---|---|---|---|
| 129 | CL-58851 | CDRH1 (KABAT) | Amino acid sequence of CDRH1 using Kabat | TYAFH |
| 130 | CL-58851 | CDRH2 (KABAT) | Amino acid sequence of CDRH2 using Kabat | WINVGNGNREYSQKFQD |
| 131 | CL-58851 | CDRH3 (KABAT) | Amino acid sequence of CDRH3 using Kabat | RPLWGPFDY |
| 132 | CL-58851 | Heavy chain variable region | Amino acid sequence of $V_H$ | QVQLVQSGAEVKKPGASVKVSCKATGFTFITYAFHWVRQAPGQRFEWMGWINVGNG NREYSQKFQDRVTITRDTSATTVYMELNSLKSEDTAMYFCARRPLWGPFDYWGQGTLV TVSS |
| 133 | CL-58851 | Heavy chain variable region | Nucleotide sequence of $V_H$ | CAGGTCCAACTTGTGCAGTCTGGGGCTGAGGTGAAGAAGCCTGGGGCTCAGTGAA GGTTCCTGCAAGGCTACTGGATTCACCTTCATTACCTATGCTTTCCATTGGGTGCGC CAGGCCCCCGGACAAAGGTTTGAGTGGATGGCAATGGGAATCAACGTTGGCAATGGTAA CAGAGAATATTCACAGAAGTTCCAGGACAGAGTCACCATTACCAGGGACACATCCG CGACCACAGTCTACATGGAACTGAACAGCCTGAAATCTGAAGACACGGCTATGTATT TCTGTGCGAGACGCCCCCTCTGGGGTCCCTTTGACTACTGGGGCCAGGGAACCCTG GTCACCGTCTCCTCA |
| 134 | CL-58851 | Full heavy chain sequence | Amino acid sequence heavy chain | QVQLVQSGAEVKKPGASVKVSCKATGFTFITYAFHWVRQAPGQRFEWMGWINVGNG NREYSQKFQDRVTITRDTSATTVYMELNSLKSEDTAMYFCARRPLWGPFDYWGQGTLV TVSSASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPAPEFEGG PSVFLFPPKPKDTLMISRTPEVTCVVVDVSQEDPEVQFNWYVDGVEVHNAKTKPREEQ FNSTYRVVSVLTVLHQDWLNGKEYKCKVSNKGLPSSIEKTISKAKGQPREPQVYTLPPSQ EEMTKNQVSLTCLVKGFYPSDIAVEWESNGQPENNYKTTPPVLDSDGSFFLYSRLTVDKS RWQEGNVFSCSVMHEALHNHYTQKSLSLSLGK |
| 135 | CL-58851 | CDRL1 (IMGT) | Amino acid sequence of CDRL1 using IMGT | QIFSNTF |
| 136 | CL-58851 | CDRL2 (IMGT) | Amino acid sequence of CDRL2 using IMGT | GAS |
| 137 | CL-58851 | CDRL3 (IMGT) | Amino acid sequence of CDRL3 using IMGT | QHYGGSPWT |
| 138 | CL-58851 | CDRL1 (KABAT) | Amino acid sequence of CDRL1 using KABAT | RASQIFSNTFLA |
| 139 | CL-58851 | CDRL2 (KABAT) | Amino acid sequence of CDRL2 using KABAT | GASKRAT |
| 140 | CL-58851 | CDRL3 (KABAT) | Amino acid sequence of CDRL3 using KABAT | QHYGGSPWT |

-continued

SEQUENCES:

| Seq ID No: | | Description | Sequence |
|---|---|---|---|
| 141 | CL-58851 | Light chain variable region | Amino acid sequence of $V_L$ | EIVLTQSPGTLSLSPGERATLSCRASQIFSNTFLAWYQKPGQAPRLLVYGASKRATAIPD RFSGSGSGTDFILTINRLEPEDFAVYYCQHYGGSPWTFGRGTKVEIK |
| 142 | CL-58851 | Light chain variable region | Nucleic acid sequence of $V_L$ | GAAATTGTTTGACACAGTCTCCAGGCACCCTGTCTTTGTCTCCAGGGGAAAGAGCC ACCCTCTCCTGCAGGGCCAGTCAGATTTTTAGCAACACCTTCTTAGCCTGGTACCAGC AGAAACCTGGCCAGGCTCCCAGGCTCCTCGTGTATGGTGCATCCAAGAGGGCCACT GCCATCCCAGACAGGTTTAGTGGCAGTGGGTCTGGGACAGACTTCATTCTCACCATC AACAGACTGGAGCCTGAAGATTTTGCAGTATATTACTGTCAACACTATGGTGGGTCA CCGTGGACGTTCCGCCGAGGGACCAAGGTGGAAATCAAA |
| 143 | CL-58851 | Full light chain sequence | Amino acid sequence light chain | EIVLTQSPGTLSLSPGERATLSCRASQIFSNTFLAWYQKPGQAPRLLVYGASKRATAIPD RFSGSGSGTDFILTINRLEPEDFAVYYCQHYGGSPWTFGRGTKVEIKRTVAAPSVFIFPPS DEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 144 | CL-75183 | CDRH1 (IMGT) | Amino acid sequence of CDRH1 using IMGT | GYTFTSHA |
| 145 | CL-75183 | CDRH2 (IMGT) | Amino acid sequence of CDRH2 using IMGT | IHAGNGNS |
| 146 | CL-75183 | CDRH3 (IMGT) | Amino acid sequence of CDRH3 using IMGT | ARRAIMAPFDL |
| 147 | CL-75183 | CDRH1 (KABAT) | Amino acid sequence of CDRH1 using Kabat | SHAIH |
| 148 | CL-75183 | CDRH2 (KABAT) | Amino acid sequence of CDRH2 using Kabat | WIHAGNGNSKQSQNFQD |
| 149 | CL-75183 | CDRH3 (KABAT) | Amino acid sequence of CDRH3 using Kabat | RAIMAPFDL |
| 150 | CL-75183 | Heavy chain variable region | Amino acid sequence of $V_H$ | QVQLVQSGAEVKKPGASVKVSCKASGYTFTSHAIHWVRQAPGQRLEWMGWIHAGNG NSKQSQNFQDRVTITRDTSASAAYMELSSLRSEDTAVYYCARRAIMAPFDLWGQGTLV TVSS |
| 151 | CL-75183 | Heavy chain variable region | Nucleotide sequence of $V_H$ | CAGGTCCAGCTTGTGCAGTCTGGGGCTGAGGTGAAGAAGCCTGGGGCCTCAGTGA AGGTTTCCTGCAAGGCTTCTGGATACACCTTCACTAGCCATGCTATACATTGGGTGC GCCAGGCCCCCGGACAACGGCTTGAGTGGATGGGATGGATCCATGCTGGCAATGG TAACTCAAAACAGTCAACGAACTTCCAGGACAGAGTCACCATTACCAGGGACACATC CGCGAGCCAGCCTACATGGAGCTGAGCAGCCTGAGATCTGAAGACACGGCTGTAT ATTACTGTGCGAGACGGGCCATAATGGCCCCCGTTTGACCTCTGGGGCCAGGGAACC CTGGTCACCGTCTCCTCA |

-continued

SEQUENCES:

| Seq ID No: | | Description | Sequence |
|---|---|---|---|
| 152 | CL-75183 | Full heavy chain sequence | QVQLVQSGAEVKKPGASVKVSCKASGYTFTSHAIHWVRQAPGQRLEWMGWIHAGNG NSKQSQNFQDRVTITRDTSASAAYMELSSLRSEDTAVVYCARRAIMAPFDLWGQGTLV TVSSASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPAPEFEGG PSVFLFPPKPKDTLMISRTPEVTCVVVDVSQEDPEVQFNWYVDGVEVHNAKTKPREEQ FNSTYRVVSVLTVLHQDWLNGKEYKCKVSNKGLPSSIEKTISKAKGQPREPQVYTLPPSQ EEMTKNQVSLTCLVKGFYPSDIAVEWESNGQPENNYKTTPPVLDSDGSFFLYSRLTVDKS RWQEGNVFSCSVMHEALHNHYTQKSLSLSLGK |
| 153 | CL-75183 | Amino acid sequence of CDRL1 using IMGT | QSINNW |
| 154 | CL-75183 | Amino acid sequence of CDRL2 using IMGT | KAS |
| 155 | CL-75183 | Amino acid sequence of CDRL3 using IMGT | QQYYSSWT |
| 156 | CL-75183 | Amino acid sequence of CDRL1 using KABAT | RASQSINNWLA |
| 157 | CL-75183 | Amino acid sequence of CDRL2 using KABAT | KASSLES |
| 158 | CL-75183 | Amino acid sequence of CDRL3 using KABAT | QQYYSSWT |
| 159 | CL-75183 | Amino acid sequence of $V_L$ | DIQMTQSPSTLSASVGDRVTITCRASQSINNWLAWYQQKPGKAPNLLIYKASSLESGVP SRFSGSGSGTEFTLTINSLQPDDFATYYCQQYYSSWTFGQGTKVEIK |
| 160 | CL-75183 | Nucleic acid sequence of $V_L$ | GACATCCAGATGACCCAGTCTCCTTCCACCCTGTCTGCATCTGTAGGAGACAGAGTC ACCATCACTTGCCGGGCCAGTCAGAGTATTAATAACTGGTTGGCCTGGTATCAGCAG AAACCAGGGAAAGCCCCTAACCTCCTGATCTATAAGGCGTCTAGTTTAGAAAGTGG GGTCCCATCAAGGTTCAGCGGCAGTGGATCTGGGACAGAATTCACTCTCACCATCAA CAGCCTGCAGCCTGATGACTTTGCAACTTATTACTGCCAACAGTATTATAGTTCTTGG ACGTTCGGCCAAGGGACCAAGGTGGAAATCAAA |
| 161 | CL-75183 | Full light chain sequence | DIQMTQSPSTLSASVGDRVTITCRASQSINNWLAWYQQKPGKAPNLLIYKASSLESGVP SRFSGSGSGTEFTLTINSLQPDDFATYYCQQYYSSWTFGQGTKVEIKRTVAAPSVFIFPPS DEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 162 | CL-75500 | Amino acid sequence of CDRH1 using IMGT | GYTFTSYA |

-continued

SEQUENCES:

| Seq ID No: | | Description | Sequence |
|---|---|---|---|
| 163 | CL-75500 | CDRH2 (IMGT) | Amino acid sequence of CDRH2 using IMGT | INAGNGNT |
| 164 | CL-75500 | CDRH3 (IMGT) | Amino acid sequence of CDRH3 using IMGT | ARRGFGEPFDY |
| 165 | CL-75500 | CDRH1 (KABAT) | Amino acid sequence of CDRH1 using Kabat | SYAVH |
| 166 | CL-75500 | CDRH2 (KABAT) | Amino acid sequence of CDRH2 using Kabat | WINAGNGNTKFSQKFQG |
| 167 | CL-75500 | CDRH3 (KABAT) | Amino acid sequence of CDRH3 using Kabat | RGFGEPFDY |
| 168 | CL-75500 | Heavy chain variable region | Amino acid sequence of $V_H$ | QVQLVQSGAEVKKPGASVKVSCKASGYTFTSYAVHWVRQAPGQRLEWMGWINAGN GNTKFSQKFQGRITITRDTSASTTYMELNSLRSEDTAVYYCARRGFGEPFDYWGQGLTV TVSS |
| 169 | CL-75500 | Heavy chain variable region | Nucleotide sequence of $V_H$ | CAGGTCCAGCTTGTGCAGTCTGGGGCTGAGGTGAAGAAGCCTGGGGCCTCAGTGA AGGTTTCCTGCAAGGCTTCTGGATACACACCTTCACTAGCTATGCTGTCCATTGGGTGC GCCAGGCCCCCGGACAAAGGCTTGAGTGGATGGGATGGATCAACGCTGGCAATGG TAACACAAAATTTTCACAGAAGTTCCAGGGCAGAATCACCATTACCAGGGACACATC CGCGAGCACAACCTACATGGAGCTGAGCAGTCTGAGATCTGAGGACACGGCTGTGT ATTATTGTGCGAGAAGGGGGTTCGGGGAGCCATTTGACTACTGGGGCCAGGGAAC CCTGGTCACCGTCTCCTCA |
| 170 | CL-75500 | Full heavy chain sequence | Amino acid sequence heavy chain | QVQLVQSGAEVKKPGASVKVSCKASGYTFTSYAVHWVRQAPGQRLEWMGWINAGN GNTKFSQKFQGRITITRDTSASTTYMELNSLRSEDTAVYYCARRGFGEPFDYWGQGTLV TVSSASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPPCPAPEFEGG PSVFLFPPKPKDTLMISRTPEVTCVVVDVSQEDPEVQFNWYVDGVEVHNAKTKPREEQ FNSTYRVVSVLTVLHQDWLNGKEYKCKVSNKGLPSSIEKTISKAKGQPREPQVYTLPPSQ EEMTKNQVSLTCLVKGFYPSDIAVEWESNGQPENNYKTTPPVLDSDGSFFLYSRLTVDKS RWQEGNVFSCSVMHEALHNHYTQKSLSLSLGK |
| 171 | CL-75500 | CDRL1 (IMGT) | Amino acid sequence of CDRL1 using IMGT | QSISNN |
| 172 | CL-75500 | CDRL2 (IMGT) | Amino acid sequence of CDRL2 using IMGT | GTS |
| 173 | CL-75500 | CDRL3 (IMGT) | Amino acid sequence of CDRL3 using IMGT | QQYNIWPFT |
| 174 | CL-75500 | CDRL1 (KABAT) | Amino acid sequence of CDRL1 using KABAT | RASQSISNNLA |

-continued

SEQUENCES:

| Seq ID No: | | Description | Sequence |
|---|---|---|---|
| 175 | CL-75500 | Amino acid sequence of CDRL2 using KABAT | GTSTRAT |
| 176 | CL-75500 | Amino acid sequence of CDRL3 using KABAT | QQYNIWPFT |
| 177 | CL-75500 | Light chain variable region | EIVMTQSPATLSVSPGERATLSCRASQSISNNLAWYQQKPGQAPRLLIYGTSTRATGIPA RFSGSGSGTEFTLTISTLQSEDFAVYYCQQYNIWPFTFGPGTKVDIK |
| 178 | CL-75500 | Nucleic acid sequence of V_L | GAAATAGTGATGACGCAGTCTCCAGCCACCCTGTCTGTGTCTCCAGGGGAAAGAGC CACCCTCTCCTGCAGGGCCAGTCAGAGTATTAGTAACAACTTAGCCTGGTACCACA GAAACCTGGCCAGGCTCCTCATCTATGGTACATCCACCAGGGCCACTGG TATCCCAGCCAGGTTCAGTGGCAGTGGGTCTGGGACAGAGTTCACTCTCACCATCAG CACCCTGCAGTCTGAAGATTTTGCAGTTTATTACTGTCAGCAGTATAATATCTGGCCT TTCACTTTCGGCCCTGGGACCAAAGTGGATATCAAA |
| 179 | CL-75500 | Full light chain sequence | EIVMTQSPATLSVSPGERATLSCRASQSISNNLAWYQQKPGQAPRLLIYGTSTRATGIPA RFSGSGSGTEFTLTISTLQSEDFAVYYCQQYNIWPFTFGPGTKVDIKRTVAAPSVFIFPPSD EQLKSGTASVVCLLNNFYPREAKVQWKVDNALQSGNSQESVTEQDSKDSTYSLSSTLTL SKADYEKHKVYACEVTHQGLSSPVTKSFNRGEC |
| 180 | CL-75506 | Amino acid sequence of CDRH1 using IMGT | GYTFTSYA |
| 181 | CL-75506 | Amino acid sequence of CDRH2 using IMGT | INPGNGNT |
| 182 | CL-75506 | Amino acid sequence of CDRH3 using IMGT | ARRGFGEPFDY |
| 183 | CL-75506 | Amino acid sequence of CDRH1 using Kabat | SYAIH |
| 184 | CL-75506 | Amino acid sequence of CDRH2 using Kabat | WINPGNGNTKFSQKFQG |
| 185 | CL-75506 | Amino acid sequence of CDRH3 using Kabat | RGFGEPFDY |
| 186 | CL-75506 | Heavy chain variable region | QVQLVQSGAEVKKPGASVKVSCKASGYTFTSYAIHWRQAPGQRLEWMGWINPGNG NTKFSQKFQGRITITRDTSASTTYMELNSLRSEDTAVYYCARRGFGEPFDYWGQGTLVT VSS |

-continued

SEQUENCES:

| Seq ID No: | | Description | Sequence |
|---|---|---|---|
| 187 | CL-75506 | Heavy chain variable region | Nucleotide sequence of V_H | CAGGTCCAGCTTGTGCAGTCTGGGGCTGAGGTGAAGAAGCCTGGGGCCTCAGTGA<br>AGGTTTCCTGCAAGGCTTCTGGATACACCTTCACTAGCTATGCTATCCATTGGGTGCG<br>CCAGGCCCCGGACAAAGGCTTGAGTGGATGGGATGGATCAACCCTGGCAATGGTA<br>ACACAAAATTTCACAGAGTTCAGGGCAGAATCACCATTACCAGGGACACACATCCG<br>CGAGCACACCTACATGGAGCTGAACAGCCTGAGATCTGAAGACACGGCTGTGTAT<br>TACTGTGCGAGAGGGGTTCGGGAGCCATTTGACTACTGGGGCCAGGGAACCC<br>TGGTCACCGTCTCCTCA |
| 188 | CL-75506 | Full heavy chain sequence | Amino acid sequence heavy chain | QVQLVQSGAEVKKPGASVKVSCKASGYTFTSYAIHWVRQAPGQRLEWMGWINPGNG<br>NTKFSQKFQGRITITRDTSASTTYMELNSLRSEDTAVYYCARRGFGEPFDYWGQGTLVT<br>VSSASTKGPSVFPLAPCSRSTSESTAALGCLVKDYFPEPVTVSWNSGALTSGVHTFPAVL<br>QSSGLYSLSSVVTVPSSSLGTKTYTCNVDHKPSNTKVDKRVESKYGPPCPAPEFEGG<br>PSVFLFPPKPKDTLMISRTPEVTCVVVDVSQEDPEVQFNWYVDGVEVHNAKTKPREEQ<br>FNSTYRVVSVLTVLHQDWLNGKEYKCKVSNKGLPSSIEKTISKAKGQPREPQVYTLPPSQ<br>EEMTKNQVSLTCLVKGFYPSDIAVEWESNGQPENNYKTTPPVLDSDGSFFLYSRLTVDKS<br>RWQEGNVFSCSVMHEALHNHYTQKSLSLSLGK |
| 189 | CL-75506 | CDRL1 (IMGT) | Amino acid sequence of CDRL1 using IMGT | QSISSN |
| 190 | CL-75506 | CDRL2 (IMGT) | Amino acid sequence of CDRL2 using IMGT | GTS |
| 191 | CL-75506 | CDRL3 (IMGT) | Amino acid sequence of CDRL3 using IMGT | QQYNIWPFT |
| 192 | CL-75506 | CDRL1 (KABAT) | Amino acid sequence of CDRL1 using KABAT | RASQSISSNLA |
| 193 | CL-75506 | CDRL2 (KABAT) | Amino acid sequence of CDRL2 using KABAT | GTSTRAT |
| 194 | CL-75506 | CDRL3 (KABAT) | Amino acid sequence of CDRL3 using KABAT | QQYNIWPFT |
| 195 | CL-75506 | Light chain variable region | Amino acid sequence of V_L | EIVMTQSPATLSVSPGERATLSCRASQSISSNLAWYQQNPGQAPRLLIYGTSTRATGIPA<br>RFSGSGSGTEFTLTISTLQSEDFAVYYCQQYNIWPFTFGPGTKVDIK |
| 196 | CL-75506 | Light chain variable region | Nucleic acid sequence of V_L | GAAATAGTGATGACGCAGTCTCCAGCCACCCTGTCTGTCTCCAGGGGAAAGAGC<br>CACCCTCTCCTGCAGGGCCAGTCAGAGTATTAGCAGCAACTTAGCCTGGTACCAACA<br>GAACCCTGGCCAGGCTCCCAGGCTCCTCATCTATGGTACATCCACCAGGGCCACTGG<br>TATCCCAGCCAGGTTCAGTGGCAGTGGGTCTGGGACAGAGTTCACTCTCACCATCAG<br>CACCCTGCAGTCTGAAGATTTTGCAGTTTATTACTGTCAGCAGTATAATATCTGGCCT<br>TTCACTTTCGGCCCTGGGACCAAAGTGGATATCAAAC |

-continued

SEQUENCES:

| Seq ID No: | | Description | Sequence |
|---|---|---|---|
| 197 | CL-75506 | Full light chain sequence | Amino acid sequence light chain | EIVMTQSPATLSVSPGERATLSCRASQSISSNLAWYQQNPGQAPRLLIYGTSTRATGIPA RFSGSGSGTEFTLTISTLQSEDFAVYYCQQYNIWPFTFGPGTKVDIKRTVAAPSVFIFPPSD EQLKSGTASVVCLLNNFYPREAKVQWKVDNALQSGNSQESVTEQDSKDSTYSLSSTLTL SKADYEKHKVYACEVTHQGLSSPVTKSFNRGEC |
| 198 | CL-75520 | CDRH1 (IMGT) | Amino acid sequence of CDRH1 using IMGT | GYTFTSYA |
| 199 | CL-75520 | CDRH2 (IMGT) | Amino acid sequence of CDRH2 using IMGT | INAGNGYT |
| 200 | CL-75520 | CDRH3 (IMGT) | Amino acid sequence of CDRH3 using IMGT | AARDRITIIRPFDY |
| 201 | CL-75520 | CDRH1 (KABAT) | Amino acid sequence of CDRH1 using Kabat | SYAMH |
| 202 | CL-75520 | CDRH2 (KABAT) | Amino acid sequence of CDRH2 using Kabat | WINAGNGYTKYSQKFQD |
| 203 | CL-75520 | CDRH3 (KABAT) | Amino acid sequence of CDRH3 using Kabat | DRITIIRPFDY |
| 204 | CL-75520 | Heavy chain variable region | Amino acid sequence of $V_H$ | QVQLVQSGAEVKKPGASVKVSCKASGYTFTSYAMHWVRQAPGHRLEWLGWINAGNG YTKYSQKFQDRVAITRDTSASTAFMELSSLRSEDTAVYYCARDRITIIRPFDYWGQGTLVT VSS |
| 205 | CL-75520 | Heavy chain variable region | Nucleotide sequence of $V_H$ | CAGGTCCAACTTGTGCAGTCTGGGGCTGAGGTGAAGAAGCCTGGGGCCTCAGTGAA GGTTTCCTGCAAGGCTTCTGGATACACCTTCACTAGCTATGCTATGCATTGGGTGCGT CAGGCCCCCGGACACAGGCTTGAGTGGTTGGGATGGATCAACGCTGGCAATGGTTA CACAAAATATTCACAGAAATTCCAGGACGAGAGTCGCCATTACCAGGGACACATCCGC GAGCACAGCCTTCATGGAGCTGAGCAGCCTGAGATCTGAAGACACACGGCTGTGTATT ACTGTGCGAGAGATCGTATTACTATTATTCGGCCCCTTTGACTACTGGGGCCAGGGAA CCCTGGTCACCGTCTCCTCA |
| 206 | CL-75520 | Full heavy chain sequence | Amino acid sequence heavy chain | QVQLVQSGAEVKKPGASVKVSCKASGYTFTSYAMHWVRQAPGHRLEWLGWINAGNG YTKYSQKFQDRVAITRDTSASTAFMELSSLRSEDTAVYYCARDRITIIRPFDYWGQGTLVT VSSASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPPCPAPEFEGG PSVFLFPPKPKDTLMISRTPEVTCVVVDVSQEDPEVQFNWYVDGVEVHNAKTKPREEQ FNSTYRVVSVLTVLHQDWLNGKEYKCKVSNKGLPSSIEKTISKAKGQPREPQVYTLPPSQ EEMTKNQVSLTCLVKGFYPSDIAVEWESNGQPENNYKTTPPVLDSDGSFFLYSRLTVDKS RWQEGNVFSCSVMHEALHNHYTQKSLSLSLGK |
| 207 | CL-75520 | CDRL1 (IMGT) | Amino acid sequence of CDRL1 using IMGT | QSISSSY |

-continued

SEQUENCES:

| Seq ID No: | | Description | Sequence |
|---|---|---|---|
| 208 | CL-75520 | CDRL2 (IMGT) | Amino acid sequence of CDRL2 using IMGT | GAS |
| 209 | CL-75520 | CDRL3 (IMGT) | Amino acid sequence of CDRL3 using IMGT | QLYGSPFT |
| 210 | CL-75520 | CDRL1 (KABAT) | Amino acid sequence of CDRL1 using KABAT | RASQSISSSYLA |
| 211 | CL-75520 | CDRL2 (KABAT) | Amino acid sequence of CDRL2 using KABAT | GASSRAT |
| 212 | CL-75520 | CDRL3 (KABAT) | Amino acid sequence of CDRL3 using KABAT | QLYGSPFT |
| 213 | CL-75520 | Light chain variable region | Amino acid sequence of $V_L$ | EIVLTQSPGTLSLSPGERATLSCRASQSISSSYLAWFQQKPGQAPRLLIYGASSRATGIPDR FSGNGSGTDFTLTISRLEPEDFAVYYCQLYGSPFTGPGTKMDIK |
| 214 | CL-75520 | Light chain variable region | Nucleic acid sequence of $V_L$ | GAAATTGTGTTGACGCAGTCTCCAGGCACCCTGTCTTTGTCTCCAGGGGAAAGAGCC ACCCTCTCCTGCAGGGCCAGTCAGAGTATTAGCAGCAGCTACTTAGCCTGGTTCCAG CAAAAACCTGGCCAGGCTCCCAGGCTCCTCATCTATGGTGCATCCAGCAGGGCCACT GGCATCCCAGACAGGTTCAGTGGCAGTGGGTCTGGGACAGACTTCACTCTCACCATC AGCAGACTGGAGCCTGAAGATTTTGCAGTGTATTACTGTCAGCTGTATGGTAGCCCA TTCACTTTCGGCCCTGGGACCAAAATGGATATTAAAC |
| 215 | CL-75520 | Full light chain sequence | Amino acid sequence light chain | EIVLTQSPGTLSLSPGERATLSCRASQSISSSYLAWFQQKPGQAPRLLIYGASSRATGIPDR FSGNGSGTDFTLTISRLEPEDFAVYYCQLYGSPFTGPGTKMDIKRTVAAPSVFIFPPSDE QLKSGTASVVCLLNNFYPREAKVQWKVDNALQSGNSQESVTEQDSKDSTYSLSSTLTLS KADYEKHKVYACEVTHQGLSSPVTKSFNRGEC |
| 216 | CL-75539 | CDRH1 (IMGT) | Amino acid sequence of CDRH1 using IMGT | GYTFTSYA |
| 217 | CL-75539 | CDRH2 (IMGT) | Amino acid sequence of CDRH2 using IMGT | INVGNGKT |
| 218 | CL-75539 | CDRH3 (IMGT) | Amino acid sequence of CDRH3 using IMGT | ARRGFGEPFDY |
| 219 | CL-75539 | CDRH1 (KABAT) | Amino acid sequence of CDRH1 using Kabat | SYAIH |
| 220 | CL-75539 | CDRH2 (KABAT) | Amino acid sequence of CDRH2 using Kabat | WINVGNGKTKFSQKLQG |

-continued

SEQUENCES:

| Seq ID No: | | Description | Sequence |
|---|---|---|---|
| 221 | CL-75539 | CDRH3 (KABAT) | Amino acid sequence of CDRH3 using Kabat | RGFGEPFDY |
| 222 | CL-75539 | Heavy chain variable region | Amino acid sequence of V_H | QVQLVQSGAEVKKPGASVKVSCKASGYTFTSYAIHWVRQAPQRLEWMGWINVGNG KTKFSQKLQGRITITRDTSASTTYMELNSLRSEDTAVFYCARRGFGEPFDYWGQGTLVTV SS |
| 223 | CL-75539 | Heavy chain variable region | Nucleotide sequence of V_H | CAGGTCCAGCTTGTGCAGTCTGGGGCTGAGGTGAAGAAGCCTGGGGCCTCAGTGA AGGTTCCTGCCAAGGCTTCTGGATACACCTTCACTAGCTATGCTATCCATTGGGTGCG CCAGGCCCCGGACAAAGGCTTGAGTGGATGGGATGGATCAACGTTGGCAATGGTA AAACAAAATTTTCACAGAAGTTACAGGGCAGAATCACCATTACCAGGGACACACATCCG CGAGCACAACCTACATGGAGCTGAGCCTGAGACTGAAGACACCGCTGTGTTT TACTGTGCGAGAAGGGGTTCGGGAGCCATTTGACTACTGGGGCCAGGGAACCC TGGTCACCGTCTCCTCA |
| 224 | CL-75539 | Full heavy chain sequence | Amino acid sequence heavy chain | QVQLVQSGAEVKKPGASVKVSCKASGYTFTSYAIHWVRQAPQRLEWMGWINVGNG KTKFSQKLQGRITITRDTSASTTYMELNSLRSEDTAVFYCARRGFGEPFDYWGQGTLVTV SSASTKGPSVFPLAPCSRSTSESTAALGCLVKDYFPEPVTVSWNSGALTSGVHTFPAVLQS SGLYSLSSVVTVPSSSLGTKTYTCNVDHKPSNTKVDKRVESKYGPPCPPCPAPEFEGGPSV FLFPPKPKDTLMISRTPEVTCVVVDVSQEDPEVQFNWYVDGVEVHNAKTKPREEQFNS TYRVVSVLTVLHQDWLNGKEYKCKVSNKGLPSSIEKTISKAKGQPREPQVYTLPPSQEEM TKNQVSLTCLVKGFYPSDIAVEWESNGQPENNYKTTPPVLDSDGSFFLYSRLTVDKSRW QEGNVFSCSVMHEALHNHYTQKSLSLSGK |
| 225 | CL-75539 | CDRL1 (IMGT) | Amino acid sequence of CDRL1 using IMGT | QSISSN |
| 226 | CL-75539 | CDRL2 (IMGT) | Amino acid sequence of CDRL2 using IMGT | GTS |
| 227 | CL-75539 | CDRL3 (IMGT) | Amino acid sequence of CDRL3 using IMGT | QQYNIWPFT |
| 228 | CL-75539 | CDRL1 (KABAT) | Amino acid sequence of CDRL1 using KABAT | RASQSISSNLA |
| 229 | CL-75539 | CDRL2 (KABAT) | Amino acid sequence of CDRL2 using KABAT | GTSTRAT |
| 230 | CL-75539 | CDRL3 (KABAT) | Amino acid sequence of CDRL3 using KABAT | QQYNIWPFT |
| 231 | CL-75539 | Light chain variable region | Amino acid sequence of V_L | EIVMTQSPATLSVSPGERATLSCRASQSISSNLAWYQQKPGQAPRLLIYGTSTRATGIPAR FSGSGSGTEFTLTISTLQSEDFAVYYCQQYNIWPFTFGPGTKVDIK |

-continued

SEQUENCES:

| Seq ID No: | | | Description | Sequence |
|---|---|---|---|---|
| 232 | CL-75539 | Light chain variable region | Amino acid sequence of $V_L$ | GAAATAGTGATGACGCAGTCTCCAGCCACCCTGTCTGTGTCTCCAGGGGAAAGAGC CACCCTCTCCTGCAGGGCCAGTGCAGGGCCTCCAGCTCCCATCTATGGTGACAGTATTAGCAGCAACA GAAACCTGGCCAGGCTCCCAGGCTCCTCATCTATGGTGACATCCACAGGGCCACTGG TATCCCAGCCAGGTTCAGTGGCAGTGGGTCTGGGACAGAGTTCACTCTCACCATCAG CACCCTGCAGCCTGAAGATTTTGCAGTTTATTACTGTCAGCAGTATAATATCTGGCCT TTCACTTTCGGCCCTGGGACCAAAGTGGATATCAAA |
| 233 | CL-75539 | Full light chain sequence | Amino acid sequence light chain | EIVMTQSPATLSVSPGERATLSCRASQSISSNLLAWYQQKPGQAPRLLIYGTSTRATGIPAR FSGSGSGTEFTLTISTLQSEDFAVYYCQQYNIWPFTFGPGTKVDIKRTVAAPSVFIFPPSDE QLKSGTASVVCLLNNFYPREAKVQWKVDNALQSGNSQESVTEQDSKDSTYSLSSTLTLS KADYEKHKVYACEVTHQGLSSPVTKSFNRGEC |
| 234 | CL-75565 | CDRH1 (IMGT) | Amino acid sequence of CDRH1 using IMGT | GYTFTSYA |
| 235 | CL-75565 | CDRH2 (IMGT) | Amino acid sequence of CDRH2 using IMGT | INAGNGNT |
| 236 | CL-75565 | CDRH3 (IMGT) | Amino acid sequence of CDRH3 using IMGT | ARRGFGEPFDY |
| 237 | CL-75565 | CDRH1 (KABAT) | Amino acid sequence of CDRH1 using Kabat | SYAIH |
| 238 | CL-75565 | CDRH2 (KABAT) | Amino acid sequence of CDRH2 using Kabat | WINAGNGNTKYSQKFQG |
| 239 | CL-75565 | CDRH3 (KABAT) | Amino acid sequence of CDRH3 using Kabat | RGFGEPFDY |
| 240 | CL-75565 | Heavy chain variable region | Amino acid sequence of $V_H$ | QVQLVQSGAEVKKPGASVKVSCKASGYTFTSYAIHWVRQAPGQRLEWMGWINAGNG NTKYSQKFQGRITITRDTSASTAYMELSSLRSEDTAVYYCARRGFGEPFDYWGQGTLVTV SS |
| 241 | CL-75565 | Heavy chain variable region | Nucleotide sequence of $V_H$ | CAGGTCCAGCTTGTGCAGTCTGGGGCTGAGGTGAAGAAGCCTGGGGCCTCAGTGA AGGTTTCCTGCAAGGCTTCTGGATACACCTTCACTAGCTATGCTATCCATTGGGTGCG CCAGGCCCCAGGACAAAGGCTTGAGTGGATGGGATGGATCAACGCTGGCAATGGT AACACAAAATATTCACAGAAGTTCCAGGGCAGAGTCACCATTACCAGGGACACATCC GCGAGCACCGCCTACATGGAGCTGAGCAGCCTGAGATCTGAAGACACGGCTGTGTA TTACTGTGCGAGAGGGGGTTCGGGGAGCCATTTGACTACTGGGGCCAGGGAACC CTGGTCACCGTCTCCTCA |
| 242 | CL-75565 | Full heavy chain sequence | Amino acid sequence heavy chain | QVQLVQSGAEVKKPGASVKVSCKASGYTFTSYAIHWVRQAPGQRLEWMGWINAGNG NTKYSQKFQGRITITRDTSASTAYMELSSLRSEDTAVYYCARRGFGEPFDYWGQGTLVTV SSASTKGPSVFPLAPCSRSTSESTAALGCLVKDYFPEPVTVSWNSGALTSGVHTFPAVLQS SGLYSLSSVVTVPSSSLGTKTYTCNVDHKPSNTKVDKRVESKYGPPCPPCPAPEFEGGPSV FLFPPKPKDTLMISRTPEVTCVVVDVSQEDPEVQFNWYVDGVEVHNAKTKPREEQFNS |

-continued

SEQUENCES:

| Seq ID No: | | Description | Sequence |
|---|---|---|---|
| 243 | CL-75565 | Amino acid sequence of CDRL1 using IMGT | TYRVVSVLTVLHQDWLNGKEYKCKVSNKGLPSSIEKTISKAKGQPREPQVYTLPPSQEEM TKNQVSLTCLVKGFYPSDIAVEWESNGQPENNYKTTPPVLDSDGSFFLYSRLTVDKSRW QEGNVFSCSVMHEALHNHYTQKSLSLSLGK |
| 244 | CL-75565 | Amino acid sequence of CDRL1 using IMGT | QSISSN |
| 245 | CL-75565 | Amino acid sequence of CDRL2 using IMGT | GTS |
| 245 | CL-75565 | Amino acid sequence of CDRL3 using IMGT | QQYNIWPFT |
| 246 | CL-75565 | Amino acid sequence of CDRL1 using KABAT | RASQSISSNLA |
| 247 | CL-75565 | Amino acid sequence of CDRL2 using KABAT | GTSTRAT |
| 248 | CL-75565 | Amino acid sequence of CDRL3 using KABAT | QQYNIWPFT |
| 249 | CL-75565 | Amino acid sequence of V_L | EIVMTQSPATLSVSPGERATLSCRASQSISSNLAWYQQKPGQAPRLLIYGTSTRATGIPAR FSGSGSGTEFTLTISTLQSEDFAVYYCQQYNIWPFTFGPGTKVDIK |
| 250 | CL-75565 | Nucleic acid sequence of V_L | GAAATAGTGATGACGCAGTCTCCAGCCACCCTGTCTGTGTCTCCAGGGGAAAGAGC CACCCTCTCCTGCAGGGCCAGTCAGAGTATTAGCAGCAACTTAGCCTGGTACCAACA GAAACCTGGCCAGGCTCCCAGGCTCCTCATCTATGGTACATCCACCAGGGCCACTGG TATCCCAGCCAGGTTCAGTGGCAGTGGGTCTGGGACAGAGTTCACTCTCACCATCAG CACCCTGCAGTCTGAAGATTTTGCAGTTTATTACTGTCAGCAGTATAATATCTGGCCT TTCACTTTCGGCCCTGGGACCAAAGTGGATATCAAA |
| 251 | CL-75565 | Full light chain sequence | EIVMTQSPATLSVSPGERATLSCRASQSISSNLAWYQQKPGQAPRLLIYGTSTRATGIPAR FSGSGSGTEFTLTISTLQSEDFAVYYCQQYNIWPFTFGPGTKVDIKRTVAAPSVFIFPPSDE QLKSGTASVVCLLNNFYPREAKVQWKVDNALQSGNSQESVTEQDSKDSTYSLSSTLTLS KADYEKHKVYACEVTHQGLSSPVTKSFNRGEC |
| 252 | CL-75714 | Amino acid sequence of CDRH1 using IMGT | GYTFTTYA |
| 253 | CL-75714 | Amiino acid sequence of CDRH2 using IMGT | INAGNGRT |
| 254 | CL-75714 | Amino acid sequence of CDRH3 using IMGT | ARRGFGBPFDQ |

-continued

SEQUENCES:

| Seq ID No: | | Description | Sequence |
|---|---|---|---|
| 255 | CL-75714 | CDRH1 (KABAT) | Amino acid sequence of CDRH1 using Kabat | TYAIH |
| 256 | CL-75714 | CDRH2 (KABAT) | Amino acid sequence of CDRH2 using Kabat | WINAGNGRTEYSEKFQG |
| 257 | CL-75714 | CDRH3 (KABAT) | Amino acid sequence of CDRH3 using Kabat | RGFGEPFDQ |
| 258 | CL-75714 | Heavy chain variable region | Amino acid sequence of V_H | QVHLVQSGAEVKKPGASVKVSCKTSGYTFTTYAIHWVRQAPGQGLEWMGWINAGNG RTEYSEKFQGRVTITRDTSASTVYMDLSSLRSGDTAVYYCARRGFGEPFDQWGQGTLVT VSS |
| 259 | CL-75714 | Heavy chain variable region | Nucleotide sequence of V_H | CAGGTCCACCTTGTGCAGTCTGGGGCTGAAGGTGAAGAAGCCTGGGGCCTCAGTGAA GGTGTCCTGCAAGACTTCTGGATACACCTTCACCACCTATGCTATTCATTGGGTGCGC CAGGCCCCCGGACAAGGGCTTGAGTGGATGGGATGGATCAACGCTGGCAATGGTA GAACAGAATATTCAGAGAAGTTTCAGGCAGAGTCACCATTACCAGGGACACTTCC GCGAGTACAGTCTACATGGACCTGAGCAGCCTGAGATCTGGAGACACGGCTGTGTA TTACTGTGCGAGAAGGGGATTCGGGGAGCCATTTGACCCTGGGGCCCAGGGAACC CTGGTCACCGTCTCCTCA |
| 260 | CL-75714 | Full heavy chain sequence | Amino acid sequence heavy chain | QVHLVQSGAEVKKPGASVKVSCKTSGYTFTTYAIHWVRQAPGQGLEWMGWINAGNG RTEYSEKFQGRVTITRDTSASTVYMDLSSLRSGDTAVYYCARRGFGEPFDQWGQGTLVT VSSASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPAPEFEGG PSVFLFPPKPKDTLMISRTPEVTCVVVDVSQEDPEVQFNWYVDGVEVHNAKTKPREEQ FNSTYRVVSVLTVLHQDWLNGKEYKCKVSNKGLPSSIEKTISKAKGQPREPQVYTLPPSQ EEMTKNQVSLTCLVKGFYPSDIAVEWESNGQPENNYKTTPPVLDSDGSFFLYSRLTVDKS RWQEGNVFSCSVMHEALHNHYTQKSLSLSLGK |
| 261 | CL-75714 | CDRL1 (IMGT) | Amino acid sequence of CDRL1 using IMGT | QSVSSN |
| 262 | CL-75714 | CDRL2 (IMGT) | Amino acid sequence of CDRL2 using IMGT | GAS |
| 263 | CL-75714 | CDRL3 (IMGT) | Amino acid sequence of CDRL3 using IMGT | QQYNNWPFI |
| 264 | CL-75714 | CDRL1 (KABAT) | Amino acid sequence of CDRL1 using KABAT | RASQSVSSNLA |
| 265 | CL-75714 | CDRL2 (KABAT) | Amino acid sequence of CDRL2 using KABAT | GASTRAT |

-continued

SEQUENCES:

| Seq ID No: | | Description | Sequence |
|---|---|---|---|
| 266 | CL-75714 | Amino acid sequence of CDRL3 using KABAT | CDRL3 (KABAT) | QQYNNWPFI |
| 267 | CL-75714 | Amino acid sequence of V_L | Light chain variable region | EIVMTQSPATLSVSPGERATLSCRASQSVSSNLAWYQHPGQAPRLLIYGASTRATGFP PRPSGSGSGTDFTLTINSLQSEDFAVYYCQQYNNWPFIFGPGTKLDIT |
| 268 | CL-75714 | Nucleic acid sequence of V_L | Light chain variable region | GAAATAGTGATGACGCAGTCTCCAGCACCACCCTGTCTGTGTCTCCAGGGGAAAGAGC CACCCTCTCCTGCAGGGCCAGTCAGAGTGTTAGCAGCAACTTAGCCTGGTACCAGCA CCAACCTGGCCAGGCTCCCAGGCTCCTCATCTATGGTGCATCCACCAGGGCCACTGG TTTCCCACCCAGGTTCAGTGGCAGTGGGTCTGGGACAGACTTCACTCTCACCATCAA CAGCCTGCAGTCTGAAGATTTTGCAGTTTATTACTGTCAGCAGTATAATAACTGGCCT TTCATTTTCGGCCCTGGGACCAAACTGGATATCACA |
| 269 | CL-75714 | Amino acid sequence light chain | Full light chain sequence | EIVMTQSPATLSVSPGERATLSCRASQSVSSNLAWYQHPGQAPRLLIYGASTRATGFP PRPSGSGSGTDFTLTINSLQSEDFAVYYCQQYNNWPFIFGPGTKLDITRTVAAPSVFIFPP SDEQLKSGTASVVCLLNNFYPREAKVQWKVDNALQSGNSQESVTEQDSKDSTYSLSSTL TLSKADYEKHKVYACEVTHQGLSSPVTKSFNRGEC |
| 270 | CL-58722 | Amino acid sequence of CDRH1 using IMGT | CDRH1 (IMGT) | GFTFSDYY |
| 271 | CL-58722 | Amino acid sequence of CDRH2 using IMGT | CDRH2 (IMGT) | ISISGSTI |
| 272 | CL-58722 | Amino acid sequence of CDRH3 using IMGT | CDRH3 (IMGT) | ARRSSGWYDY |
| 273 | CL-58722 | Amino acid sequence of CDRH1 using Kabat | CDRH1 (KABAT) | DYYMS |
| 274 | CL-58722 | Amino acid sequence of CDRH2 using Kabat | CDRH2 (KABAT) | YISISGSTIYYADSVKG |
| 275 | CL-58722 | Amino acid sequence of CDRH3 using Kabat | CDRH3 (KABAT) | RSSGWYDY |
| 276 | CL-58722 | Amino acid sequence of V_H | Heavy chain variable region | QVQLVESGGGLVKPGGSLRLSCAASGFTFSDYYMSWIRQAPGKGLEWVSYISISGSTIYY ADSVKGRFTISRDNAKNSLFLQMNSLRAEDTAVYYCARRSSGWYDYWGQGTLVTVSS |
| 277 | CL-58722 | Nucleotide sequence of V_H | Heavy chain variable region | CAGGTGCAACTGGTGGAGTCTGGGGGAGGCTTGGTCAAGCCTGGAGGGTCCCTGA GACTCTCCTGTGCAGCCTCTGGATTCACCTTCACTGACTACTACATGAGCTGGATCCG CCAGGCTCCAGGGAAGGGGCTGGAGTGGGTTTCATACATTAGTATTAGTGGTAGTA CCATATACTACGCAGACTCTGTGAAGGGCCGATTCACCATCTCCAGGGACAACGCCA |

-continued

SEQUENCES:

| Seq ID No: | | Description | Sequence |
|---|---|---|---|
| | | | AGAACTCACTGTTTCTGCAAATGAACAGCCTGAGAGCCGAGGACACGGCCGTGTAT |
| | | | TACTGTGCGAGAGAAGCAGTGGGTACGACTACTGGGGCCAGGGAACCCTGG |
| | | | TCACCGTCTCCTCA |
| 278 | CL-58722 | Full heavy chain sequence | Amino acid sequence heavy chain |
| | | | QVQLVESGGGLVKPGGSLRLSCAASGFTFSDYMSWIRQAPGKGLEWVSYISISGSTIYY |
| | | | ADSVKGRFTISRDNAKNSLFLQMNSLRAEDTAVYYCARRSSGWYDYWGQGTLVTVSSA |
| | | | STKGPSVFPLAPCSRSTSESTAALGCLVKDYFPEPVTVSWNSGALTSGVHTFPAVLQSSGL |
| | | | YSLSSVVTVPSSSLGTKTYTCNVDHKPSNTKVDKRVESKYGPPCPCPAPEFEGGPSVFLF |
| | | | PPKPKDTLMISRTPEVTCVVVDVSQEDPEVQFNWYVDGVEVHNAKTKPREEQFNSTYR |
| | | | VVSVLTVLHQDWLNGKEYKCKVSNKGLPSSIEKTISKAKGQPREPQVYTLPPSQEEMTK |
| | | | NQVSLTCLVKGFYPSDIAVEWESNGQPENNYKT |
| | | | TPPVLDSDGSFFLYSRLTVDKSRWQEGNVFSCCSVMHEALHNHYTQKSLSLSLGK |
| 279 | CL-58722 | Amino acid sequence of CDRL1 using IMGT | QSVSSNY |
| 280 | CL-58722 | Amino acid sequence of CDRL2 using IMGT | GAS |
| 281 | CL-58722 | Amino acid sequence of CDRL3 using IMGT | HQYGSSPPT |
| 282 | CL-58722 | Amino acid sequence of CDRL1 using KABAT | RASQSVSSNYLA |
| 283 | CL-58722 | Amino acid sequence of CDRL2 using KABAT | GASIRAT |
| 284 | CL-58722 | Amino acid sequence of CDRL3 using KABAT | HQYGSSPPT |
| 285 | CL-58722 | Amino acid sequence of V$_L$ | EIVLTQSPGTLSLSPGERATLSCRASQSVSSNYLAWYQQKPGQAPRLLIYGASIRATGIPD |
| | | | RFSGSGSGTDFTLTISRLEPEDFAVYSCHQYGSSPPTFGQGTKVEIK |
| 286 | CL-58722 | Nucleic acid sequence of V$_L$ | GAAATTGTGTTGACGCAGTCTCCAGGCACCCTGTCTTTGTCTCCAGGGGAAAGAGCC |
| | | | ACCCTCTCCTGCAGGGCCAGTCAGAGTGTTAGCAGCAACTACTTAGCCTGGTACCAG |
| | | | CAGAAACCTGGCCAGGCTCCCAGGCTCCTCATCTATGGTGCATCCATCAGGGCCACT |
| | | | GGCATCCCAGACAGGTTCAGTGGCAGTGGGTCTGGGACAGACTTCACTCTCACCATC |
| | | | AGCAGACTGGAGCCTGAAGATTTTGCAGTGTATTCCTGTCACCAGTATGGTAGCTCA |
| | | | CCTCCGACGTTCGGCCAAGGGACCAAGGTGGAAATCAAAC |
| 287 | CL-58722 | Full light chain sequence | Amino acid sequence light chain |
| | | | EIVLTQSPGTLSLSPGERATLSCRASQSVSSNYLAWYQQKPGQAPRLLIYGASIRATGIPD |
| | | | RFSGSGSGTDFTLTISRLEPEDFAVYSCHQYGSSPPTFGQGTKVEIKRTVAAPSVFIFPPSD |
| | | | EQLKSGTASVVCLLNNFYPREAKVQWKVDNALQSGNSQESVTEQDSKDSTYSLSSTLTL |
| | | | SKADYEKHKVYACEVTHQGLSSPVTKSFNRGEC |

-continued

SEQUENCES:

| Seq ID No: | | Description | Sequence |
|---|---|---|---|
| 288 | CL-58835 | CDRH1 (IMGT) | Amino acid sequence of CDRH1 using IMGT | GFTFSDYY |
| 289 | CL-58835 | CDRH2 (IMGT) | Amino acid sequence of CDRH2 using IMGT | ISISGTTI |
| 290 | CL-58835 | CDRH3 (IMGT) | Amino acid sequence of CDRH3 using IMGT | ARRSSGWYDY |
| 291 | CL-58835 | CDRH1 (KABAT) | Amino acid sequence of CDRH1 using Kabat | DYYMS |
| 292 | CL-58835 | CDRH2 (KABAT) | Amino acid sequence of CDRH2 using Kabat | YISISGTTIYYADSVKG |
| 293 | CL-58835 | CDRH3 (KABAT) | Amino acid sequence of CDRH3 using Kabat | RSSGWYDY |
| 294 | CL-58835 | Heavy chain variable region | Amino acid sequence of V_H | QVQLVESGGGLVKPGGSLRLSCAASGFTFSDYYMSWIRQAPGKGLEWVSYISISGTTIYY ADSVKGRFTISRDNAMDSLYLQMNSLRAEDTAVYYCARRSSGWYDYWGQGTLVTVSS |
| 295 | CL-58835 | Heavy chain variable region | Nucleotide sequence of V_H | CAGGTGCAACTGGTGGAGTCTGGGGGAGGCTTGGTCAAGCCTGGAGGGTCCCTGA GACTCTCCTGTGCAGCCTCTGGATTCACCTTCAGTGACTACTACATGAGTTGGATCCG CCAGGCTCCAGGGAAGGGGCTGGAGTGGGTTTCATACATTAGTATTAGTGGTACTA CCATATACTACCAGACGCTGTGAAGGGCCGATTCACCATCTCCAGGGACAACGCCA TGGACTCACTGTATCTGCAAATGAACAGCCTGAGAGCCGAGGACACGGCCGTGTAT TACTGTGCGAGACGGAGCAGTGGCTGGTACGACTACTGGGGCCAGGGAACCCTGG TCACCGTCTCCTCA |
| 296 | CL-58835 | Full heavy chain sequence | Amino acid sequence heavy chain | QVQLVESGGGLVKPGGSLRLSCAASGFTFSDYYMSWIRQAPGKGLEWVSYISISGTTIYY ADSVKGRFTISRDNAMDSLYLQMNSLRAEDTAVYYCARRSSGWYDYWGQGTLVTVSS ASTKGPSVFPLAPCSRSTSESTAALGCLVKDYFPEPVTVSWNSGALTSGVHTFPAVLQSS GLYSLSSVVTVPSSSLGTKTYTCNVDHKPSNTKVDKRVESKYGPPCPPCPAPEFEGGPSVF LFPPKPKDTLMISRTPEVTCVVVDVSQEDPEVQFNWYVDGVEVHNAKTKPREQFNST YRVVSVLTVLHQDWLNGKEYKCKVSNKGLPSSIEKTISKAKGQPREPQVYTLPPSQEEMT KNQVSLTCLVKGFYPSDIAVEWESNGQPENNYKTTPPVLDSDGSFFLYSRLTVDKSRWQ EGNVFSCSVMHEALH NHYTQKSLSLSLGK |
| 297 | CL-58835 | CDRL1 (IMGT) | Amino acid sequence of CDRL1 using IMGT | QRVVYRY |
| 298 | CL-58835 | CDRL2 (IMGT) | Amino acid sequence of CDRL2 using IMGT | GAF |
| 299 | CL-58835 | CDRL3 (IMGT) | Amino acid sequence of CDRL3 using IMGT | HQYGSSPPT |

-continued

SEQUENCES:

| Seq ID No: | | Description | Sequence |
|---|---|---|---|
| 300 | CL-58835 | CDRL1 (KABAT) Amino acid sequence of CDRL1 using KABAT | WASQRVVRYLA |
| 301 | CL-58835 | CDRL2 (KABAT) Amino acid sequence of CDRL2 using KABAT | GAFNRAT |
| 302 | CL-58835 | CDRL3 (KABAT) Amino acid sequence of CDRL3 using KABAT | HQYGSSPPT |
| 303 | CL-58835 | Light chain variable region Amino acid sequence of V_L | EIVLTQSPGTLSLSPGERATLSCWASQRVVRYLAWYQRKPGQAPRLLIYGAFNRATGIP DRPSGSGSGTDFSLTISRLEPEDFAVYYCHQYGSSPPTFGQGTKVEIK |
| 304 | CL-58835 | Light chain variable region Nucleic acid sequence of V_L | GAAATTGTGTTGACGCAGTCTCCAGGCACCCTGTCTTTGTCTCCAGGGGAAAGAGCC ACCCTCTCTTGTTGGGCCAGTCAGAGGGTTGTTACAGATACTTAGCCTGGTACCAG CGGAAACCTGGCCAGGCTCCCAGACTTCTCATTTATGGTGCATTCAACAGGGCCACT GGCATCCCAGACAGGTTCAGTGGCAGTGGGTCTGGGACAGACTTCAGTCTCACTAT CAGTAGACTGGAGCCTGAGGATTTTGCAGTTTATTACTGTCACCAATATGGTAGTTC ACCACCACGTTCGGCCAAGGGACCAAGGTGGAAATCAAA |
| 305 | CL-58835 | Full light chain sequence Amino acid sequence light chain | EIVLTQSPGTLSLSPGERATLSCWASQRVVRYLAWYQRKPGQAPRLLIYGAFNRATGIP DRPSGSGSGTDFSLTISRLEPEDFAVYYCHQYGSSPPTFGQGTKVEIKRTVAAPSVFIFPPS DEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 306 | CL-58756 | CDRH1 (IMGT) Amino acid sequence of CDRH1 using IMGT | GFTFSDYY |
| 307 | CL-58756 | CDRH2 (IMGT) Amino acid sequence of CDRH2 using IMGT | ISISGSTI |
| 308 | CL-58756 | CDRH3 (IMGT) Amino acid sequence of CDRH3 using IMGT | ARRSSGWYDY |
| 309 | CL-58756 | CDRH1 (KABAT) Amino acid sequence of CDRH1 using Kabat | DYYMS |
| 310 | CL-58756 | CDRH2 (KABAT) Amino acid sequence of CDRH2 using Kabat | YISISGSTIYYADSVKG |
| 311 | CL-58756 | CDRH3 (KABAT) Amino acid sequence of CDRH3 using Kabat | RSSGWYDY |
| 312 | CL-58756 | Heavy chain variable region Amino acid sequence of V_H | QVQLVESGGGLVKPGGSLRLSCAASGFTFSDYYMSWIRQAPGKGLEWVSYISISGSTIYY ADSVKGRFTISRDNAKNSLYLQMNSLRAEDTAVYYCARRSSGWYDYWGQGTLVTVSS |

-continued

SEQUENCES:

| Seq ID No: | | Description | Sequence |
|---|---|---|---|
| 313 | CL-58756 | Heavy chain variable region | Nucleotide sequence of V_H | CAGGTGCAGCTGGTGGAGTCTGGGGGAGGCTTGGTCAAGCCTGGAGGGTCCCTGA GACTCTCCTGTGCAGCCTCTGGATTCACCTTCAGTGACTACTACATGAGCTGGATCCG CCAGGCTCCAGGGAAGGGGCTGGAGTGGGTTTCATACATTAGTATTAGTGGTAGTA CCATATACTACCAGACACTGTGAAGGGCCGATTCACCATCTCCAGGGACAACCGCCA AGAACTCACTGTATCTGCAAATGAACAGCCTGAGAGCCGAGGACACGGCCGTGTAT TACTGTGCGAGAAGAGCAGTGGCTCGTGTACGACTACTGGGGCCAGGGAACCCTGG TCACCGTCTCCTCA |
| 314 | CL-58756 | Full heavy chain sequence | Amino acid sequence heavy chain | QVQLVESGGGLVKPGGSLRLSCAASGFTFSDYYMSWIRQAPGKGLEWVSYISISGSTIYY ADSVKGRPTISRDNAKNSLYLQMNSLRAEDTAVYYCARRSSGWYDYWGQGTLVTVSSA STKGPSVFPLAPCSRSTSESTAALGCLVKDYFPEPVTVSWNSGALTSGVHTFPAVLQSSGL YSLSSVVTVPSSSLGTKTYTCNVDHKPSNTKVDKRVESKYGPPCPPCPAPEFEGGPSVFLF PPKPKDTLMISRTPEVTCVVVDVSQEDPEVQFNWYVDGVEVHNAKTKPREEQFNSTYR VVSVLTVLHQDWLNGKEYKCKVSNKGLPSSIEKTISKAKGQPREPQVYTLPPSQEEMTK NQVSLTCLVKGFYPSDIAVEWESNGQPENNYKTTPPVLDSDGSFFLYSRLTVDKSRWQE GNVFSCSVMHEALHNHYTQKSLSLSLGK |
| 315 | CL-58756 | CDRL1 (IMGT) | Amino acid sequence of CDRL1 using IMGT | QSVSSNY |
| 316 | CL-58756 | CDRL2 (IMGT) | Amino acid sequence of CDRL2 using IMGT | GAS |
| 317 | CL-58756 | CDRL3 (IMGT) | Amino acid sequence of CDRL3 using IMGT | HQYGSSPPT |
| 318 | CL-58756 | CDRL1 (KABAT) | Amino acid sequence of CDRL1 using KABAT | RASQSVSSNYLA |
| 319 | CL-58756 | CDRL2 (KABAT) | Amino acid sequence of CDRL2 using KABAT | GASIRAT |
| 320 | CL-58756 | CDRL3 (KABAT) | Amino acid sequence of CDRL3 using KABAT | HQYGSSPPT |
| 321 | CL-58756 | Light chain variable region | Amino acid sequence of V_L | EIVLTQSPGTLSLSPGERATLSCRASQSVSSNYLAWYQQKPGQAPRLLIYGASIRATGIPD RFSGSGSGTDFTLTISRLEPEDFAVYCCHQYGSSPPTFGQGTKVEIK |
| 322 | CL-58756 | Light chain variable region | Nucleic acid sequence of V_L | GAAATTGTGTTGACGCAGTCTCCAGGCACCCTGTCTTTGTCTCCAGGGGAAAGAGCC ACCCTCTCCTGCAGGGCCAGTCAGAGTGTTAGCAGCAACTACTTAGCCTGGTACCAG CAGAAACCTGGCCAGGCTCCCAGGCTCCTCATCTATGGTGCATCCATCAGGGCCACT GGCATCCCAGACAGGTTCAGTGGCAGTGGGTCTGGGACAGACTTCACTCTCACCATC AGCAGACTGGAGCCTGAAGATTTTGCAGTGTATTGCTGTCACCAGTATGGTAGCTCA CCTCCGACGTTCGGCCAAGGGACCAAGGTGGAAATCAAA |

-continued

SEQUENCES:

| Seq ID No: | | Description | Sequence |
|---|---|---|---|
| 323 | CL-58756 | Amio acid sequence light chain | Full light chain sequence | EIVLTQSPGTLSLSPGERATLSCRASQSVSSNYLAWYQQKPGQAPRLLIYGASIRATGIPD RFSGSGSGTDFTLTISRLEPEDFAVYCCHQYGSSPPTPGQGTKVEIKRTVAAPSVFIFPPSD EQLKSGTASVVCLLNNFYPREAKVQWKVDNALQSGNSQESVTEQDSKDSTYSLSSTLTL SKADYEKHKVYACEVTHQGLSSPVTKSFNRGEC |
| 324 | CL-58650 | Amino acid sequence of CDRH1 using IMGT | CDRH1 (IMGT) | GFTFSDYF |
| 325 | CL-58650 | Amino acid sequence of CDRH2 using IMGT | CDRH2 (IMGT) | ISISGSTI |
| 326 | CL-58650 | Amino acid sequence of CDRH3 using IMGT | CDRH3 (IMGT) | AARTSGWYDF |
| 327 | CL-58650 | Amino acid sequence of CDRH1 using Kabat | CDRH1 (KABAT) | DYFMS |
| 328 | CL-58650 | Amino acid sequence of CDRH2 using Kabat | CDRH2 (KABAT) | YISISGSTIYYADSVKG |
| 329 | CL-58650 | Amino acid sequence of CDRH3 using Kabat | CDRH3 (KABAT) | RTSGWYDF |
| 330 | CL-58650 | Amino acid sequence of $V_H$ | Heavy chain variable region | QVQLVESGGGLVKPGGSLRLSCAASGFTFSDYFMSWIRQAPGKGLEWVSYISISGSTIYY ADSVKGRFTISRDNARNSLFLQMNSLRAEDTAIYYCARRTSGWYDFWGQGTLVTVSS |
| 331 | CL-58650 | Nucleotide sequence of $V_H$ | Heavy chain variable region | CAGGTGCAGC TGGTGGAGTC TGGGGGAGGC TTGGTCAAGC CTGGAGGGTC CCTGCGACTC TCCTGTGCAG CCTCTGGATT CACCTTCAGT GACTACTTCA TGAGCTGGAT CCGCCAGGCT CCAGGGAAGG GGCTGGAGTG GGTTTCGTAC ATTAGTATTA GTGGTAGTAC CATATACTAC GCAGACTCTG TGAAGGGCCG ATTCACCATC TCCAGGGACA ACGCCAGGAA CTCACTGTTT CTGCAAATGA ACAGCCTGAG AGCCGAGGAC ACGGCCATCT ATTACTGTGC GAGAGAGACC AGTGGCTGGT ACGACTTCTG GGGCCAGGGA ACCCTGGTCA CCGTCTCCTC A |
| 332 | CL-58650 | Amino acid sequence heavy chain | Full heavy chain sequence | QVQLVESGGGLVKPGGSLRLSCAASGFTFSDYFMSWIRQAPGKGLEWVSYISISGSTIYY ADSVKGRFTISRDNARNSLFLQMNSLRAEDTAIYYCARRTSGWYDFWGQGTLVTVSSA STKGPSVFPLAPCSRSTSESTAALGCLVKDYFPEPVTVSWNSGALTSGVHTFPAVLQSSGL YSLSSVVTVPSSSLGTKTYTCNVDHKPSNTKVDKRVESKYGPPCPPCPAPEFEGGPSVFLF PPKPKDTLMISRTPEVTCVVVDVSQEDPEVQFNWYVDGVEVHNAKTKPREEQFNSTYR VVSVLTVLHQDWLNGKEYKCKVSNKGLPSSIEKTISKAKGQPREPQVYTLPPSQEEMTK NQVSLTCLVKGFYPSDIAVEWESNGQPENNYKTTPPVLDSDGSFFLYSRLTVDKSRWQE GNVFSCSVMHEALHNHYTQKSLSLSLGK |

-continued

SEQUENCES:

| Seq ID No: | | Description | Sequence |
|---|---|---|---|
| 333 | CL-58650 | CDRL1 (IMGT) | Amino acid sequence of CDRL1 using IMGT | QSVSYSY |
| 334 | CL-58650 | CDRL2 (IMGT) | Amino acid sequence of CDRL2 using IMGT | GAS |
| 335 | CL-58650 | CDRL3 (IMGT) | Amino acid sequence of CDRL3 using IMGT | HQYGSSPPT |
| 336 | CL-58650 | CDRL1 (KABAT) | Amino acid sequence of CDRL1 using KABAT | RASQSVSYSYLA |
| 337 | CL-58650 | CDRL2 (KABAT) | Amino acid sequence of CDRL2 using KABAT | GASSRAT |
| 338 | CL-58650 | CDRL3 (KABAT) | Amino acid sequence of CDRL3 using KABAT | HQYGSSPPT |
| 339 | CL-58650 | Light chain variable region | Amino acid sequence of V<sub>L</sub> | EIVLTQSPGTLSLSPGERATLSCRASQSVSYSYLAWYQQKPGQAPRLLIYGASSRATGIPD RFSGSGSGTDFTLTISRLEPEDFAVYCCHQYGSSPPTFGQGTKVEIK |
| 340 | CL-58650 | Light chain variable region | Nucleic acid sequence of V<sub>L</sub> | GAAATTGTTGACGCAGTCTCCAGGCACCCTGTCTTTGTCTCCAGGGGAAAGAGCC ACCCTCTCCTGCAGGGCCAGTCAGAGTGTTAGCTACAGCTACTTAGCCTGGTACCAG CAGAAACCTGGCCAGGCTCCCAGGCTCCTCATCTATGGTGCATCCAGCAGGGCCACT GGCATCCCAGACAGGTTCAGTGGCAGTGGGTCTGGGACAGACTTCACTCTCACCATC AGCAGACTGGAGCCTGAAGATTTTGCAGTGTATTGTTGTCACCAGTATGGTAGTTCA CCTCCGCACGTTCGGCCAAGGGACCAAGGTGGAAATCAAA |
| 341 | CL-58650 | Full light chain sequence | Amino acid sequence light chain | EIVLTQSPGTLSLSPGERATLSCRASQSVSYSYLAWYQQKPGQAPRLLIYGASSRATGIPD RFSGSGSGTDFTLTISRLEPEDFAVYCCHQYGSSPPTFGQGTKVEIKRTVAAPSVFIFPPSD EQLKSGTASVVCLLNNFYPREAKVQWKVDNALQSGNSQESVTEQDSKDSTYSLSSTLTL SKADYEKHKVYACEVTHQGLSSPVTKSFNRGEC |
| 342 | CL-58679 | CDRH1 (IMGT) | Amino acid sequence of CDRH1 using IMGT | GFTFSDFY |
| 343 | CL-58679 | CDRH2 (IMGT) | Amino acid sequence of CDRH2 using IMGT | ISISGTTI |
| 344 | CL-58679 | CDRH3 (IMGT) | Amino acid sequence of CDRH3 using IMGT | ARRTSGWYDF |
| 345 | CL-58679 | CDRH1 (KABAT) | Amino acid sequence of CDRH1 using Kabat | DFYMS |

-continued

SEQUENCES:

| Seq ID No: | | Description | Sequence |
|---|---|---|---|
| 346 | CL-58679 CDRH2 (KABAT) | Amino acid sequence of CDRH2 using Kabat | YISISGTTIYYADSVKG |
| 347 | CL-58679 CDRH3 (KABAT) | Amino acid sequence of CDRH3 using Kabat | RTSGWYDF |
| 348 | CL-58679 Heavy chain variable region | Amino acid sequence of $V_H$ | QVQLVESGGGLVKPGGSLRLSCAASGFTFSDFYMSWIRQAPGRGLEWVSYISISGTTIYY ADSVKGRFTISRDNARNSLYLQMNSLRAEDTAVYYCARRTSGWYDFWGQG TLVTVSS |
| 349 | CL-58679 Heavy chain variable region | Nucleotide sequence of $V_H$ | CAGGTGCAGCTGGTGGAGTCTGGGGGAGGCTTGGTCAAGCCTGGAGGGTC CCTTA GACTCTCCTGTGCAGCCTCTGGATTCACCTTCAGTGACTTCTACATGAGCTGGATCCG CCAGGCTCCAGGGAAGGGGCTGGAGTGGGTTTCGTACATTAGTATTAGTGGTACTA CCATATACTACGCAGACTCTGTGAAGGGCCGATTCACCATCTCCAGGGACAACGCCA GGAACTCACTGTATCTGCAAATGAACAGCCTGAGAGCCGAGGACACGGCCGTGTAT TACTGTGCGAGAAGAACCAGTGGCTGGTACGACTTCTGGGGCCAGGGAACCCTGGT CACCGTCTCCTCA |
| 350 | CL-58679 Full heavy chain sequence | Amino acid sequence heavy chain | QVQLVESGGGLVKPGGSLRLSCAASGFTFSDFYMSWIRQAPGRGLEWVSYISISGTTIYY ADSVKGRFTISRDNARNSLYLQMNSLRAEDTAVYYCARRTSGWYDFWGQG TLVTVSS ASTKGPSVFPLAPCSRSTSESTAALGCLVKDYFPEPVTVSWNSGALTSGVHTFPAVLQSS GLYSLSSVVTVPSSSLGTKTYTCNVDHKPSNTKVDKRVESKYGPPCPPCPAPEFEGGPSVF LFPPKPKDTLMISRTPEVTCVVVDVSQEDPEVQFNWYVDGVEVHNAKTKPREEQFNST YRVVSVLTVLHQDWLNGKEYKCKVSNKGLPSSIEKTISKAKGQPREPQVYTLPPSQEEMT KNQVSLTCLVKGFYPSDIAVEWESNGQPENNYKTTPPVLDSDGSFFLYSRLTVDKSRWQ EGNVFSCSVMHEALHNHYTQKSLSLSLGK |
| 351 | CL-58679 CDRL1 (IMGT) | Amino acid sequence of CDRL1 using IMGT | QSVSYSY |
| 352 | CL-58679 CDRL2 (IMGT) | Amino acid sequence of CDRL2 using IMGT | GAS |
| 353 | CL-58679 CDRL3 (IMGT) | Amino acid sequence of CDRL3 using IMGT | HQYGSSPPT |
| 354 | CL-58679 CDRL1 (KABAT) | Amino acid sequence of CDRL1 using KABAT | RASQSVSYSYLA |
| 355 | CL-58679 CDRL2 (KABAT) | Amino acid sequence of CDRL2 using KABAT | GASSRAT |
| 356 | CL-58679 CDRL3 (KABAT) | Amino acid sequence of CDRL3 using KABAT | HQYGSSPPT |

-continued

SEQUENCES:

| Seq ID No: | | Description | Sequence |
|---|---|---|---|
| 357 | CL-58679 | Light chain variable region | Amino acid sequence of $V_L$ | EIVLTQSPGTLSLSPGERATLSCRASQSVSYSYLAWYQQKPGQAPRLLIYGASSRATGIPD RFSGSGSGTDFTLTISRLEPEDFAVYCCHQYGSSPPTFGQGTKVEMK |
| 358 | CL-58679 | Light chain variable region | Nucleic acid sequence of $V_L$ | GAAATTGTGTTGACGCAGTCTCCAGGCACCCTGTCTTTGTCTCCAGGGGAAAGAGCC ACCCTCTCTGCAGGGCCAGTCAGAGTGTTAGCTACAGCTACTTAGCCTGGTACCAG CAGAAACCTGGCCAGGCTCCCAGGCTCCTCATCTATGGTGCATCCAGCAGGGCCACT GGCATCCCAGACAGGTTCAGTGGCAGTGGGTCTGGGACAGACTTCACTCTCACCATC AGCAGACTGGAGCCTGAAGATTTTGCAGTGTATTGCTGTCACCAGTATGGTAGTTCA CCTCCGACGTTCGGCCAAGGGACCAAGGTGGAAATGAAA |
| 359 | CL-58679 | Full light chain sequence | Amino acid sequence light chain | EIVLTQSPGTLSLSPGERATLSCRASQSVSYSYLAWYQQKPGQAPRLLIYGASSRATGIPD RFSGSGSGTDFTLTISRLEPEDFAVYCCHQYGSSPPTFGQGTKVEMKRTVAAPSVFIFPPS DEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 360 | CL-58680 | CDRH1 (IMGT) | Amino acid sequence of CDRH1 using IMGT | GFTFSDYY |
| 361 | CL-58680 | CDRH2 (IMGT) | Amino acid sequence of CDRH2 using IMGT | ISISGSTI |
| 362 | CL-58680 | CDRH3 (IMGT) | Amino acid sequence of CDRH3 using IMGT | ARRTSGWYDF |
| 363 | CL-58680 | CDRH1 (KABAT) | Amino acid sequence of CDRH1 using Kabat | DYYMS |
| 364 | CL-58680 | CDRH2 (KABAT) | Amino acid sequence of CDRH2 using Kabat | YISISGSTIYYADSVKG |
| 365 | CL-58680 | CDRH3 (KABAT) | Amino acid sequence of CDRH3 using Kabat | RTSGWYDF |
| 366 | CL-58680 | Heavy chain variable region | Amino acid sequence of $V_H$ | QVQLVESGGGLVRPGGSLRLSCAASGFTFSDYYMSWIRQAPGKGLEWVSYISISGSTIYY ADSVKGRFTISRDNARDSLYLQMNSLRAEDTAVYYCARRTSGWYDFWGQG TLVTVSS |
| 367 | CL-58680 | Heavy chain variable region | Nucleotide sequence of $V_H$ | CAGGTGCAGC TGGTGGAGTC TGGGGGAGGC TTGGTCAGGC CTGGAGGGTC CCT GAGACTC TCCTGTGCAG CCTCTGGATT CACCTTCAGT GACTACTACA TGAGCTGGAT CCGCCAGGCT CCAGGGAAGG GGCT GGAGTG GGTTTCGTAC ATTAGTATTA GTGGTAGTAC CATATACTAC GCAGACTCTG TGAAGGGCCG ATTCACCATC TCCAG GGACA ACGCCAGGGA CTCACTTTAT CTGCAAATGA ACAGCCTGAG AGCCGAGGAC ACGGCCGTGT ATTACTGTGC GAGA AGAACC AGTGGCTGGT ACGACTTCTG GGGCCAGGGA ACCCTGGTCA CCGTCTCCTCA |

-continued

SEQUENCES:

| Seq ID No: | | Description | Sequence |
|---|---|---|---|
| 368 | CL-58680 | Full heavy chain sequence | QVQLVESGGGLVRPGGSLRLSCAASGFTFSDYYMSWIRQAPGKGLEWVSYISISGTIYY ADSVKGRFTISRDNARDSLYLQMNSLRAEDTAVYYCARRTSGWYDFWGQG TLVTVSS ASTKGPSVFPLAPCSRSTSESTAALGCLVKDYFPEPVTVSWNSGALTSGVHTFPAVLQSS GLYSLSSVVTVPDSSLGTKTYTCNVDHKPSNTKVDKRVESKYGPPCPPCPAPEFEGGPSVF LFPPKPKDTLMISRTPEVTCVVVDVSQEDPEVQFNWYDGVEVHNAKTKPREQFNST YRVVSVLTVLHQDWLNGKEYKCKVSNKGLPSSIEKTISKAKGQPREPQVYTLPPSQEEMT KNQVSLTCLVKGFYPSDIAVEWESNGQPENNYKTTPPVLDSDGSFFLYSRLTVDKSRWQ EGNVFSCSVMHEALHNHYTQKSLSLSLGK |
| 369 | CL-58680 | Amino acid sequence of CDRL1 using IMGT | QSVSYRY |
| 370 | CL-58680 | Amino acid sequence of CDRL2 using IMGT | GAS |
| 371 | CL-58680 | Amino acid sequence of CDRL3 using IMGT | HQYGSSPPT |
| 372 | CL-58680 | Amino acid sequence of CDRL1 using KABAT | RASQSVSYRYLA |
| 373 | CL-58680 | Amino acid sequence of CDRL2 using KABAT | GASSRAT |
| 374 | CL-58680 | Amino acid sequence of CDRL3 using KABAT | HQYGSSPPT |
| 375 | CL-58680 | Light chain variable region | EIVLTQSPGTLSLSPGERATLSCRASQSVSYRYLAWYQQKPGQAPRLLIYGASSRATGIPD RPSGSGSGTDFTLTISRLEPEDFAVYCCHQYGSSPPTFGQGTKVEIK |
| 376 | CL-58680 | Nucleic acid sequence of V_L | GAAATTGTGT TGACGCAGTC TCCAGGCACC CTGTCTTTGT CTCCAGGGGA AAGAG CCACC CTCTCCTGTA GGGCCAGTCA GAGTGTTAGC TACAGGTACT TAGCCTGGTA CCAGCAGAAA CCTGGCCAGG CTCC CAGGCT CCTCATCTAT GGTGCATCCA GCAGGGCCAC TGGCATCCCA GACAGGTTCA GTGGCAGTGG GTCTGGGACA GACT TCACTC TCACCATCAG CAGACTGGAG CCTGAAGATT TTGCAGTGTA TTGCTGTCAC CAGTATGGTA GTTCACCTCC GACGTT CGGC CAAGGGACCA AGGTGGAAAT CAAA |
| 377 | CL-58680 | Full light chain sequence | EIVLTQSPGTLSLSPGERATLSCRASQSVSYRYLAWYQQKPGQAPRLLIYGASSRATGIPD RFSGSGSGTDFTLTISRLEPEDFAVYCCHQYGSSPPTFGQGTKVEIKRTVAAPSVFIFPPSD EQLKSGTASVVCLLNNFYPREAKVQWKVDNALQSGNSQESVTEQDSKDSTYSLSSTLTL SKADYEKHKVYACEVTHQGLSSPVTKSFNRGEC |

-continued

SEQUENCES:

| Seq ID No: | | Description | Sequence |
|---|---|---|---|
| 378 | CL-58713 | CDRH1 (IMGT) | Amino acid sequence of CDRH1 using IMGT | GFTFSDYY |
| 379 | CL-58713 | CDRH2 (IMGT) | Amino acid sequence of CDRH2 using IMGT | ISISGITI |
| 380 | CL-58713 | CDRH3 (IMGT) | Amino acid sequence of CDRH3 using IMGT | ARRSSGWYDY |
| 381 | CL-58713 | CDRH1 (KABAT) | Amino acid sequence of CDRH1 using Kabat | DYYMS |
| 382 | CL-58713 | CDRH2 (KABAT) | Amino acid sequence of CDRH2 using Kabat | YISISGITIYYADSVKG |
| 382 | CL-58713 | CDRH3 (KABAT) | Amino acid sequence of CDRH3 using Kabat | RSSGWYDY |
| 384 | CL-58713 | Heavy chain variable region | Amino acid sequence of $V_H$ | QVQLVESGGGLVKPGGSLRLSCAASGFTFSDYYMSWIRQAPGKGLEWVSYISISGITIYY ADSVKGRFTISRDNARNSLYLQMNSLRAEDTAVYYCARRSSGWYDYWGQG TLVTVSS |
| 385 | CL-58713 | Heavy chain variable region | Nucleotide sequence of $V_H$ | CAAGTTCAGTTGGTTGAGTCTGGCGGCGGACTGGTTAAGCCTGGCGGATCTCTGAG ACTGTCTTGTGCCGCCTCTGGCTTCACCTTCTCCGACTACTACATGTCCTGGATCAGA CAGGCCCCTGGCAAAGGCCTGGAATGGGTGTCTTACATCTCCATCTCCGGCATCACC ATCTACTACGCCGACTCCGTGAAGGGCAGATTCACCATCTCCAGAGACAACGCCCGG AACTCCCTGTACCTGCAGATGAACTCTCTGGAGGCCGAGGACACCGCCGTGTACTAC TGCGCCCGTAGATCCTCTGGATGGTACGACTATTGGGGCCAGGGCACCCTGGTCAC AGTTTCTAGT |
| 386 | CL-58713 | Full heavy chain sequence | Amino acid sequence heavy chain | QVQLVESGGGLVKPGGSLRLSCAASGFTFSDYYMSWIRQAPGKGLEWVSYISISGITIYY ADSVKGRFTISRDNARNSLYLQMNSLRAEDTAVYYCARRSSGWYDYWGQG TLVTVSS ASTKGPSVFPLAPCSRSTSESTAALGCLVKDYFPEPVTVSWNSGALTSGVHTFPAVLQSS GLYSLSSVVTVPSSSLGTKTYTCNVDHKPSNTKVDKRVESKYGPPCPPCPAPEFEGGPSVF LFPPKPKDTLMISRTPEVTCVVVDVSQEDPEVQFNWYVDGVEVHNAKTPREQFNST YRVVSVLTVLHQDWLNGKEYKCKVSNKGLPSSIEKTISKAKGQPREPQVYTLPPSQEEMT KNQVSLTCLVKGFYPSDIAVEWESNGQPENNYKTTPPVLDSDGSFFLYSRLTVDKSRWQ EGNVFSCSVMHEALHNHYTQKSLSLSLGK |
| 387 | CL-58713 | CDRL1 (IMGT) | Amino acid sequence of CDRL1 using IMGT | QSVSYNY |
| 388 | CL-58713 | CDRL2 (IMGT) | Amino acid sequence of CDRL2 using IMGT | GAS |
| 389 | CL-58713 | CDRL3 (IMGT) | Amino acid sequence of CDRL3 using IMGT | HQYGSSPPT |

-continued

SEQUENCES:

| Seq ID No: | | Description | Sequence |
|---|---|---|---|
| 390 | CL-58713 | CDRL1 (KABAT) | Amino acid sequence of CDRL1 using KABAT | RASQSVSYNYLA |
| 391 | CL-58713 | CDRL2 (KABAT) | Amino acid sequence of CDRL2 using KABAT | GASIRAT |
| 392 | CL-58713 | CDRL3 (KABAT) | Amino acid sequence of CDRL3 using KABAT | HQYGSSPPT |
| 393 | CL-58713 | Light chain variable region | Amino acid sequence of $V_L$ | EIVLTQSPGTLSLSPGERATLSCRASQSVSYNYLAWYQQKPGQAPRLLIYGASIRATGIPD RFSGSGSGTDFTLTISRLEPEDFAVYCCHQYGSSPPTFGQGTKVEIK |
| 394 | CL-58713 | Light chain variable region | Nucleic acid sequence of $V_L$ | GAAATTGTCTGACTCAGTCCCCTGGCACACTGTCTTTGAGCCCTGGCGAGAGAGCT ACCCTGTCCTGTAGAGCCTCTCAGTCCGTCTCTACAACTACCTGGCCTGGTATCAGC AGAAGCCCGGCCAGGCTCCTAGACTGTTGATCTACGGCGCCTCCATCAGAGCCCACA GGCATCCCTGATAGATTCTCCGGCTCTGGCTCTGGCACCGACTTCACCCTGACCATCT CCAGACTGGAACCCGAGGACTTCGCCGTGTACTGTCACCAGTACGGCTCTAGCC CTCCTACCTTTGGACAGGGCACCAAGGTGGAAATCAAA |
| 395 | CL-58713 | Full light chain sequence | Amino acid sequence light chain | EIVLTQSPGTLSLSPGERATLSCRASQSVSYNYLAWYQQKPGQAPRLLIYGASIRATGIPD RFSGSGSGTDFTLTISRLEPEDFAVYCCHQYGSSPPTFGQGTKVEIKRTVAAPSVFIFPPSD EQLKSGTASVVCLLNNFYPREAKVQWKVDNALQSGNSQESVTEQDSKDSTYSLSSTLTL SKADYEKHKVYACEVTHQGLSSPVTKSFNRGEC |
| 396 | Antibody A | CDRH1 (IMGT) | Amino acid sequence of CDRH1 using IMGT | GYTFTSYA |
| 397 | Antibody A | CDRH2 (IMGT) | Amino acid sequence of CDRH2 using IMGT | INPYNRGT |
| 398 | Antibody A | CDRH3 (IMGT) | Amino acid sequence of CDRH3 using IMGT | AARPFGNAMDI |
| 399 | Antibody A | CDRH1 (KABAT) | Amino acid sequence of CDRH1 using Kabat | SYAMH |
| 400 | Antibody A | CDRH2 (KABAT) | Amino acid sequence of CDRH2 using Kabat | YINPYNRGTKYNENFKG |
| 401 | Antibody A | CDRH3 (KABAT) | Amino acid sequence of CDRH3 using Kabat | RPFGNAMDI |
| 402 | Antibody A | Heavy chain variable region | Amino acid sequence of $V_H$ | QVQLVQSGAEVKKPGSSVKVSCKASGYTFTSYAMHWVRQAPGQGLEWMGYINPYND GTKYNENFKGRVTITADESTSTAYMELSSLRSEDTAVYYCARRPFGNAMDIWGQGTLVT VSS |

-continued

SEQUENCES:

| Seq ID No: | | Description | Sequence |
|---|---|---|---|
| 403 | Antibody A | Full heavy chain sequence | QVQLVQSGAEVKKPGSSVKVSCKASGYTFTSYAMHWVRQAPGQGLEWMGYINPYND GTKYNENFKGRVTITADESTSTAYMELSSLRSEDTAVYYCARRPFGNAMDIWGQGTLVT VSSASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPPCPAPEFEGG PSVFLFPPKPKDTLMISRTPEVTCVVVDVSQEDPEVQFNWYVDGVEVHNAKTKPREEQ FNSTYRVVSVLTVLHQDWLNGKEYKCKVSNKGLPSSIEKTISKAKGQPREPQVYTLPPSQ EEMTKNQVSLTCLVKGFYPSDIAVEWESNGQPENNYKTTPPVLDSDGSFFLYSRLTVDKS RWQEGNVFSCSVMHEALHNHYTQKSLSLSLGK |
| 404 | Antibody A | CDRL1 (IMGT) | Amino acid sequence of CDRL1 using IMGT | ENIYRN |
| 405 | Antibody A | CDRL2 (IMGT) | Amino acid sequence of CDRL2 using IMGT | AAT |
| 406 | Antibody A | CDRL3 (IMGT) | Amino acid sequence of CDRL3 using IMGT | QGIWGTPLT |
| 407 | Antibody A | CDRL1 (KABAT) | Amino acid sequence of CDRL1 using KABAT | RSSENIYRNLA |
| 408 | Antibody A | CDRL2 (KABAT) | Amino acid sequence of CDRL2 using KABAT | AATNLAD |
| 409 | Antibody A | CDRL3 (KABAT) | Amino acid sequence of CDRL3 using KABAT | QGIWGTPLT |
| 410 | Antibody A | Light chain variable region | Amino acid sequence of V_L | DIQMTQSPSSLSASVGDRVTITCRSSENIYRNLAWYQQKPGKAPKLLIYAATNLADGVPS RPSGSGSGTDFTLTISSLQPEDFATYYCQGIWGTPLTFGGGTKVEIK |
| 411 | Antibody A | Full light chain sequence | Amino acid sequence light chain of Antibody A | DIQMTQSPSSLSASVGDRVTITCRSSENIYRNLAWYQQKPGKAPKLLIYAATNLADGVPS RPSGSGSGTDFTLTISSLQPEDFATYYCQGIWGTPLTFGGGTKVEIKRTVAAPSVFIFPPSD EQLKSGTASVVCLLNNFYPREAKVQWKVDNALQSGNSQESVTEQDSKDSTYSLSSTLTL SKADYEKHKVYACEVTHQGLSSPVTKSFNRGEC |
| 412 | Antibody B | CDRH1 (IMGT) | Amino acid sequence of CDRH1 using IMGT | GFTFSSYV |
| 413 | Antibody B | CDRH2 (IMGT) | Amino acid sequence of CDRH2 using IMGT | IRLETHGYAA |
| 414 | Antibody B | CDRH3 (IMGT) | Amino acid sequence of CDRH3 using IMGT | ARVERSKSGFDN |

-continued

SEQUENCES:

| Seq ID No: | | Description | Sequence |
|---|---|---|---|
| 415 | Antibody B CDRH1 (KABAT) | Amino acid sequence of CDRH1 using Kabat | SYVVH |
| 416 | Antibody B CDRH2 (KABAT) | Amino acid sequence of CDRH2 using Kabat | RIRLETHGYAAEYAASVKG |
| 417 | Antibody B CDRH3 (KABAT) | Amino acid sequence of CDRH3 using Kabat | VERSKSGFDN |
| 418 | Antibody B Heavy chain variable region | Amino acid sequence of $V_H$ | QVQLVESGGGLVKPGGSLRLSCAASGFTFSSYVVHWVRQAPGKGLEWVGRIRLETHGY AAEYAASVKGRFTISRDDSKNTLYLQMNSLKTEDTAVYYCARVERSKSGFDNWGQGTL VTVSS |
| 419 | Antibody B Full heavy chain sequence | Amino acid sequence heavy chain of Antibody B | QVQLVESGGGLVKPGGSLRLSCAASGFTFSSYVVHWVRQAPGKGLEWVGRIRLETHGY AAEYAASVKGRFTISRDDSKNTLYLQMNSLKTEDTAVYYCARVERSKSGFDNWGQGTL VTVSSASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKRVEPKSCDKTHTCPPCPAPE LLGGPSVFLFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKGQPREPQVYTLP PSREEMTKNQVSLTCLVKGFYPSDIAVEWESNGQPENNYKTTPPVLDSDGSFFLYSKLTV DKSRWQQGNVFSCSVMHEALHNHYTQKSLSLSPGK |
| 420 | Antibody B CDRL1 (IMGT) | Amino acid sequence of CDRL1 using IMGT | SSNIGAGYS |
| 421 | Antibody B CDRL2 (IMGT) | Amino acid sequence of CDRL2 using IMGT | GQS |
| 422 | Antibody B CDRL3 (IMGT) | Amino acid sequence of CDRL3 using IMGT | QSWDSSQTLVV |
| 423 | Antibody B CDRL1 (KABAT) | Amino acid sequence of CDRL1 using KABAT | TGSSSNIGAGYSVH |
| 424 | Antibody B CDRL2 (KABAT) | Amino acid sequence of CDRL2 using KABAT | GQSERPS |
| 425 | Antibody B CDRL3 (KABAT) | Amino acid sequence of CDRL3 using KABAT | QSWDSSQTLVV |
| 426 | Antibody B Light chain variable region | Amino acid sequence of $V_L$ | QSVLTQPPSVSGAPGQRVTISCTGSSSNIGAGYSVHWYQQLPGTAPKLLIYGQSERPSGV PDRFSGSKSGTSASLAITGLQAEDEADYYCQSWDSSQTLVVFGGGTKLTVL |

-continued

SEQUENCES:

| Seq ID No: | Description | Sequence |
|---|---|---|
| 427 | Full light chain sequence Antibody B | QSVLTQPPSVSGAPGQRVTISCTGSSNIGAGYSVHWYQQLPGTAPKLLIYGQSERPSGGV<br>PDRFSGSKSGTSASLAITGLQAEDEADYCQSWDSSQTLVVFGGGTKLTVLGQPKAAPS<br>VTLFPPSSEELQANKATLVCLISDFYPGAVTVAWKADSSPVKAGVETTTPSKQSNNKYAA<br>SSYLSLTPEQWKSHRSYSCQVTHEGSTVEKTVAPTECS |
| 428 | Human IgG1 constant region<br>IGHG1*01<br>Human Heavy Chain Constant Region (IGHG1*01) Nucleotide Sequence | gcctccaccaagggcccatcggtcttccccctggcaccctcctccaagagcacctctgggggcacagcggccct<br>gggctgcctggtcaaggactacttccccgaaccggtgacggtgtcgtggaactcaggcgccctgaccagcggcg<br>gtgcacaccttcccggctgtcctacagtcctcaggactctactccctcagcagcgtggtgaccgtgccctccagc<br>agcttgggcacccagacctacatctgcaacgtgaatcacaagcccagcaacaccaaggtggacaagaaagtt<br>gagcccaaatcttgtgacaaaactcacacatgcccaccgtgcccagcacctgaactcctggggggaccgtcag<br>tcttcctcttccccccaaaacccaaggacaccctcatgatctcccggacccctgaggtcacatgcgtggtggtgg<br>acgtgagccacgaagaccctgaggtcaagttcaactggtacgtggacggcgtggaggtgcataatgccaaga<br>caaagccgcgggaggagcagtacaacagcacgtaccgtgtggtcagcgtcctcaccgtcctgcaccaggact<br>ggctgaatggcaaggagtacaagtgcaaggtctccaacaaagccctcccagcccccatcgagaaaaccatct<br>ccaaagccaaagggcagccccgagaaccacaggtgtacaccctgcccccatcccgggatgagctgaccaaga<br>accaggtcagcctgacctgcctggtcaaaggcttctatcccagcgacatcgccgtggagtgggagagcaatgg<br>gcagccggagaacaactacaagaccacgcctcccgtgctggactccgacggctccttcttcctctacagcaagc<br>tcaccgtggacaagagcaggtggcagcaggggaacgtcttctcatgctccgtgatgcatgaggctctgcacaa<br>ccactacacgcagaagagcctctccctgtctccgggtaaa |
| 429 | Human IgG1 constant region<br>Human Heavy Chain Constant Region (IGHG1*01) Protein Sequence (P01857) | ASTKGPSVFPLAPSSKSTSGGTAALGCLVKDYFPEPVTVSWNSGALTSGVHTFPAVLQSS<br>GLYSLSSVVTVPSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREPQVYTLPPSRDE<br>LTKNQVSLTCLVKGFYPSDIAVEWESNGQPENNYKTTPPVLDSDGSFFLYSKLTVDKSRW<br>QQGNVFSCSVMHEALHNHYTQKSLSLSPGK |
| 430 | Human IgG1 constant region<br>IGHG1*02 or IGHG1*05<br>Human Heavy Chain Constant Region (IGHG1*02 or IGHG1*05) Nucleotide Sequence | gcctccaccaagggcccatcggtcttccccctggcaccctcctccaagagcacctctgggggcacagcggccct<br>gggctgcctggtcaaggactacttccccgaaccggtgacggtgtcgtggaactcaggcgccctgaccagcggcg<br>gtgcacaccttcccggctgtcctacagtcctcaggactctactccctcagcagcgtggtgaccgtgccctccagc<br>agcttgggcacccagacctacatctgcaacgtgaatcacaagcccagcaacaccaaggtggacaagaaagtt<br>gagcccaaatcttgtgacaaaactcacacatgcccaccgtgcccagcacctgaactcctggggggaccgtcag<br>tcttcctcttccccccaaaacccaaggacaccctcatgatctcccggacccctgaggtcacatgcgtggtggtgg<br>acgtgagccacgaagaccctgaggtcaagttcaactggtacgtggacggcgtggaggtgcataatgccaaga<br>caaagccgcgggaggagcagtacaacagcacgtaccgtgtggtcagcgtcctcaccgtcctgcaccaggact<br>ggctgaatggcaaggagtacaagtgcaaggtctccaacaaagccctcccagcccccatcgagaaaaccatct<br>ccaaagccaaagggcagccccgagaaccacaggtgtacaccctgcccccatcccgggatgagctgaccaaga<br>accaggtcagcctgacctgcctggtcaaaggcttctatcccagcgacatcgccgtggagtgggagagcaatgg<br>gcagccggagaacaactacaagaccacgcctcccgtgctggactccgacggctccttcttcctctacagcaagc<br>tcaccgtggacaagagcaggtggcagcaggggaacgtcttctcatgctccgtgatgcatgaggctctgcacaa<br>ccactacacgcagaagagcctctccctgtctccgggtaaa |
| 431 | Human IgG1 constant region<br>Human Heavy Chain Constant Region (IGHG1*02) Protein Sequence | ASTKGPSVFPLAPSSKSTSGGTAALGCLVKDYFPEPVTVSWN<br>SGALTSGVHTFPAVLQSSGLYSLSSVVTVPSSSLGTQTYICNV<br>NHKPSNTKVDKKVEPKSCDKTHTCPPCPAPELLGGPSVFLFP<br>PKPKDTLMISRTPEVTCVVVDVSHEDPEVKFNWYVDGVEVH<br>NAKTKPREEQYNSTYRVVSVLTVLHQDWLNGKEYKCKVSNK |

-continued

SEQUENCES:

| Seq ID No: | Description | Sequence |
|---|---|---|
| 432 | Human IgG1 constant region IGHG1*03 Human Heavy Chain Constant Region (IGHG1*03) Nucleotide Sequence (Y14737) | A L P A P I E K T I S K A K G Q P R E P Q V Y T L P P S R D E L T K N Q V S L T C L V<br>K G F Y P S D I A V E W E S N G Q P E N N Y K T T P P V L D S D G S F F L Y S K L T<br>V D K S R W Q Q G N V F S C S V M H E A L H N H Y T Q K S L S L S P G K<br><br>gctccaccaagggcccatcggtcttccccctggcaccctcctccaagagcacctctgggggcacagcggccct<br>gggctgcctggtcaaggactacttccccgaaccggtgacggtgtcgtggaactcaggcgccctgaccagcggc<br>gtgcacaccttcccggctgtcctacagtcctcaggactctactccctcagcagcgtggtgaccgtgccctccagc<br>agcttgggcacccagacctacatctgcaacgtgaatcacaagcccagcaacaccaaggtggacaagagagtt<br>gagcccaaatcttgtgacaaaactcacacatgcccaccgtgcccagcacctgaactcctggggggaccgtcag<br>tcttcctcttccccccaaaacccaaggacaccctcatgatctcccggacccctgaggtcacatgcgtggtggtgg<br>acgtgagccacgaagaccctgaggtcaagttcaactggtacgtggacggcgtggaggtgcataatgccaaga<br>caaagccgcgggaggagcagtacaacagcacgtaccgtgtggtcagcgtcctcaccgtcctgcaccaggact<br>ggctgaatggcaaggagtacaagtgcaaggtctccaacaaagccctcccagcccccatcgagaaaaccatct<br>ccaaagccaaagggcagccccgagaaccacaggtgtacaccctgcccccatcccgggatgagctgaccaag<br>aaccaggtcagcctgacctgcctggtcaaaggcttctatcccagcgacatcgccgtggagtgggagagcaatg<br>ggcagccggagaacaactacaagaccacgcctcccgtgctggactccgacggctccttcttcctctatagcaag<br>ctcaccgtggacaagagcaggtggcagcaggggaacgtcttctcatgctccgtgatgcatgaggctctgcaca<br>accactacacgcagaagagcctctccctgtcccgggtaaa |
| 433 | Human IgG1 constant region IGHG1*03 Human Heavy Chain Constant Region (IGHG1*03) Protein Sequence | A S T K G P S V F P L A P S S K S T S G G T A A L G C L V K D Y F P E P V T V S W N<br>S G A L T S G V H T F P A V L Q S S G L Y S L S S V V T V P S S S L G T Q T Y I C N V<br>N H K P S N T K V D K R V E P K S C D K T H T C P P C P A P E L L G G P S V F L F P<br>P K P K D T L M I S R T P E V T C V V V D V S H E D P E V K F N W Y V D G V E V H<br>N A K T K P R E E Q Y N S T Y R V V S V L T V L H Q D W L N G K E Y K C K V S N K<br>A L P A P I E K T I S K A K G Q P R E P Q V Y T L P P S R E E M T K N Q V S L T C L V<br>K G F Y P S D I A V E W E S N G Q P E N N Y K T T P P V L D S D G S F F L Y S K L T<br>V D K S R W Q Q G N V F S C S V M H E A L H N H Y T Q K S L S L S P G K |
| 434 | Human IgG1 constant region IGHG1*04 Human Heavy Chain Constant Region (IGHG1*04) Nucleotide Sequence | gctccaccaagggcccatcggtcttccccctggcaccctcctccaagagcacctctgggggcacagcggccct<br>gggctgcctggtcaaggactacttccccgaaccggtgacggtgtcgtggaactcaggcgccctgaccagcggc<br>gtgcacaccttcccggctgtcctacagtcctcaggactctactccctcagcagcgtggtgaccgtgccctccagc<br>agcttgggcacccagacctacatctgcaacgtgaatcacaagcccagcaacaccaaggtggacaagaaagtt<br>gagcccaaatcttgtgacaaaactcacacatgcccaccgtgcccagcacctgaactcctggggggaccgtcag<br>tcttcctcttccccccaaaacccaaggacaccctcatgatctcccggacccctgaggtcacatgcgtggtggtgg<br>acgtgagccacgaagaccctgaggtcaagttcaactggtacgtggacggcgtggaggtgcataatgccaaga<br>caaagccgcgggaggagcagtacaacagcacgtaccgtgtggtcagcgtcctcaccgtcctgcaccaggact<br>ggctgaatggcaaggagtacaagtgcaaggtctccaacaaagccctcccagcccccatcgcgcgggatgagctgaccaaga<br>gcagccggagaacaactacaagacccacgcctcccgtgctggactcctgcctcttcttcctctacagcaagcagc<br>tcaccgtggacaagagcaggtggcagcaggggaacgtcttctcatgctccgtgatgcatgaggctctgcacaa<br>ccactacacgcagaagagcctctccctgtctccgggtaaa |
| 435 | Human IgG1 constant region IGHG1*04 Human Heavy Chain Constant Region (IGHG1*04) Protein Sequence | ASTKGPSVFPLAPSSKSTSGGTAALGCLVKDYFPEPVTVSWNSGALTSGVHTFPAVLQSS<br>GLYSLSSVVTVPSSSLGTQTYICNVNHKPSNTKVDKRVEPKSCDKTHTCPPCPAPELLGGP<br>SVFLFPPKPKDTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREPQVYTLPPSRDE<br>LTKNQVSLTCLVKGFYPSDIAVEWESNGQPENNYKTTPPVLDSDGSFFLYSKLTVDKSRW<br>QQGNIFSCSVMHEALHNHYTQKSLSLSPGK |

-continued

SEQUENCES:

| Seq ID No: | | Description | Sequence |
|---|---|---|---|
| 436 | Disabled Human IgG1 heavy chain constant region | Disabled human IGHG1*01 | Disabled Human IGHG1*01 Heavy Chain Constant Region Nucleotide Sequence. | Gcctccaccaagggcccatcggtcttccccctggcaccctcctccaagagcacctctgggggcacagcggcct gggctgcctggtcaaggactacttccccgaaccggtgacggtgtcgtggaactcaggcgccctgaccagcggc gtgcacaccttcccggctgtcctacagtcctcaggactctactccctcagcagcgtggtgaccgtgccctccagc agcttgggcacccagacctacatctgcaacgtgaatcacaagcccagcaacaccaaggtggacaagaaagtg gagcccaaatcttgtgacaaaactcacacatgcccaccgtgcccagcacctgaactcctggggggaccgtcag tcttcctcttccccccaaaaacccaaggacaccctcatgatctcccggacccctgaggtcacatgcgtggtggtg gacgtgagccacgaagaccctgaggtcaagttcaactggtacgtggacggcgtggaggtgcataatgccaaga caaagccgcgggaggagcagtacaacagcacgtaccgtgtggtcagcgtcctcaccgtcctgcaccaggact ggctgaatggcaaggagtacaagtgcaaggtctccaacaaagccctcccagcccccatcgagaaaaccatct ccaaagccaaaggtgggacccgtggggtgcgagggccacatgcagaggagaccagtgggcagccggagaacca accaggtcagcctgacctgcctggtcaaaggcttctatcccagcgacatcgccgtggagtgggagagcaatggg cagccggagaacaactacaagaccacgcctcccgtgctggactccgacggctccttcttcctctacagcaagcag tccacgctggccgtgaagatgagccaggaacgtgttcttccctgctccgtgatgcatgaggctctgcacaaccacta cacgcagaagagcctctccctgtctccgggtaaa |
| 437 | | | Disabled Human IGHG1*01 Heavy Chain Constant Region Amino Acid Sequence. Two residues that differ from the wild-type sequence are identified in bold. | ASTKGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPELAGA PSVFLFPPKPKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLYSKLTVDKSR WQQGNVFSCSVMHEALHNHYTQKSLSLSPGK |
| 438 | Human IgG2 constant region | IGHG2*01 or IGHG2*04 or IDHG2*5 | Human IgG2 Heavy Chain Constant Region (IGHG2*01 or IGHG2*03 or IGHG2*05) Nucleotide Sequence | gcctccaccaagggcccatcggtcttccccctggcgccctgctccaggagcacctcgagacagcacgcccct gggctgcctggtcaaggactacttccccgaaccggtgacggtgtcgtggaactcaggcgccctgaccagcggc aacttcggcacccagacctacatctgcaacgtgatcacaagcccagcaacaccaaggtggacaagacagtt gagcgcaaatgttgtgtcgagtgcccaccgtgcccagcaccacctggtggaggaccgtccttctctctcccc ccaaaaacccaaggacaccctcatgatctcccggacccctgaggtggcgtggacgtgagccacgaagacccggag gtacagttcaacagcacgtcggtggtcaccgttcgtggtgcaccaggactggctgaacggcaaggagtacaagtg caaggtctccaacaaaggcctcccagcccccatcgagaaaaccatctccaaaaccaaagg gcagccccgagaacaccaggtgtacaccctgcccccatcgcgggatgagctgaccaagaaccaggtcagcc tgacctggtgaaaggcttctatcccagcgacatcgccgtggagtgggagagcaatgggcagccggagaa agagaggctggcagggagggaacgtcttcatcgtgatgcatgaggctctgcacaaccaccactacacgca gaagagcctctccctgtctccgggtaaa | (continued / supplemental protein)

ASTKGPSVFPLAPCSRSTSESTAALGCLVKDYFPEPVTVSWNSGALTSGVHTFPAVLQSS GLYSLSSVVTVPSSNFGTQTYICNVDHKPSNTKVDKTVERKCCVECPPCPAPPVAGPSVF LFPPKPKDTLMISRTPEVTCVVVDVSHEDPEVQFNWYVDGVEVHNAKTKPREEQFNST FRVVSVLTVVHQDWLNGKEYKCKVSNKGLPAPIEKTISKTKGQPREPQVYTLPPSREMT KNQVSLTCLVKGFYPSDIAVEWESNGQPENNYKTTPPMLDSDGSFFLYSKLTVDKSRW QQGNVFSCSVMHEALHNHYTQKSLSLSPGK |
| 439 | | | Human Heavy Chain Constant Region (IGHG2*01) Protein Sequence | ASTKGPSVFPLAPCSRSTSESTAALGCLVKDYFPEPVTVSWNSGALTSGVHTFPAVLQSS GLYSLSSVVTVPSSNFGTQTYICNVDHKPSNTKVDKTVERKCCVECPPCPAPPVAGPSVF LFPPKPKDTLMISRTPEVTCVVVDVSHEDPEVQFNWYVDGVEVHNAKTKPREEQFNST FRVVSVLTVVHQDWLNGKEYKCKVSNKGLPAPIEKTISKTKGQPREPQVYTLPPSREMT KNQVSLTCLVKGFYPSDIAVEWESNGQPENNYKTTPPMLDSDGSFFLYSKLTVDKSRW QQGNVFSCSVMHEALHNHYTQKSLSLSPGK |
| 567 | Human IgG2 constant region | IGHG2*02 | Human Heavy Chain Constant Region (IGHG2*02) Nucleotide Sequence | GCCTCCACCAAGGGCCCATCGGTCTTCCCCCTGGCGCCCTGCTCCAGGAGCACCTCC GAGAGCACAGCGGCCCTGGGCTGCCTGGTCAAGGACTACTTCCCCGAACCGGTGAC GGTGTCGTGGAACTCAGGCGCCCTGACCAGCGGCGTGCACACCTTCCCGGCTCCT ACAGTCCTCAGGACTCTACTCCCTCAGCAGCGTGGTGACCGTGCCCTGACCTGACCTTCAGCAACTT |

-continued

SEQUENCES:

| Seq ID No: | Description | Sequence |
|---|---|---|
| | | CGGCACCCAGACCTACACCTGCAACGTAGATCACAAGCCCAGCAACACCAAGGTGG ACAAGACAGTTGAGCGCAAATGTTGTGTCGAGTGCCCACCGTGCCCAGCACCACCT GTGGCAGGACCGCCAGTCTTCCTCTTCCCCCCAAAACCCAAGGACACCCTCATGATCT CCCGGACCCCTGAGGTCACGTGCGTGGTGGTGGACGTGAGCCACGAAGACCCCGA GGTCCAGTTCAACTGGTACGTGGACGGCGTGGAGGTGCATAATGCCAAGACAAAGC CACGGGAGGAGCAGTTCAACAGCACGTTCCGTGTGGTCAGCGTCCTCACCGTCGTG CACCAGGACTGGCTGAACGGCAAGGAGTACAAGTGCAAGGTCTCCAACAAAGGCCT CCCAGCCCCCATCGAGAAAACCATCTCCAAAACCAAAGGGCAGCCCCGAGAACCAC AGGTGTACACCCTGCCCCCATCCCGGGAGGAGATGACCAAGAACCAGGTCAGCCTG ACCTGCCTGGTCAAAGGCTTCTACCCCAGCGACATCGCCGTGGAGTGGGAGAGCAA TGGGCAGCCGGAGAACAACTACAAGACCACACCTCCCATGCTGGACTCCGACGGCT CCTTCTTCCTCTACAGCAAGCTCACCGTGGACAAGAGCAGGTGGCAGCAGGGGAAC GTCTTCTCATGCTCCGTGATGCATGAGGCTCTGCACAACCACTACACACAGAAGAGC CTCTCCCTGTCTCCGGGTAAA |
| 440 | Human Heavy Chain Constant Region (IGHG2*02) Protein Sequence | ASTKGPSVFPLAPCSRSTSESTAALGCLVKDYFPEPVTVSWNSGALTSGVHTFPAVLQSS GLYSLSSVVTVTSSNFGTQTYTCNVDHKPSNTKVDKTVERKCCVECPPCPAPPVAGPSVF LFPPKPKDTLMISRTPEVTCVVVDVSHEDPEVQFNWYVDGMEVHNAKTKPREEQFNST FRVVSVLTVVHQDWLNGKEYKCKVSNKGLPAPIEKTISKTKGQPREPQVYTLPPSREEMT KNQVSLTCLVKGFYPSDIAVEWESNGQPENNYKTTPPMLDSDGSFFLYSKLTVDKSRW QQGNVFSCSVMHEALHNHYTQKSLSLSPGK |
| 441 Human IgG2 constant region | IGHG2*04 Human Heavy Chain Constant Region (IGHG2*04) Nucleotide Sequence | gcctccaccaagggcccatcggtcttccccctggcgccctgctccaggagcacagcggccct gggctgcctggtcaaggactacttccccgaaccggtgacggtgtcgtggaactcaggcgcggc gtgcacaccttcccggctgtcctacagtcctcaggactctactccctcagcagcgtggtgaccgtgccctccagc agcttgggcacccagacctacacctgcaacgtagatcacaagcccagcaacaccaaggtggacaagacagtt gagcgcaaatgttgtgtcgagtgcccaccgtgcccagcaccacctggcaggaccgccagtcttcctcttcccc ccaaaacccaaggacaccctcatgatctcccggacccctgaggtcacgtgcgtggtggtggacgtgagccacg aagaccccgaggtccagttcaactggtacgtggacggcgtggaggtgcataatgccaagacaaagccacggg aggagcagttcaacagcacgttccgtgtggtcagcgtcctcaccgtcgtgcaccaggactggctgaacggcaa gcacccgagaacaacaggtgtacaccctgcccccatcccgggaggagatgaccaagaaccaggtcagcct gacctgcctggtcaaaggcttctaccccagcgacatcgccgtggagtgggagagcaatgggcagccggagaa caactacaagaccacacctcccatgctggactccgacggctccttcttcctctacagcaagctcaccgtggaca agagcaggtggcagcagggaacgtcttctcatgctccgtgatgcatgaggctctgcacaaccactacacgca gaagagcctctccctgtctccgggtaa |
| 442 | Human Heavy Chain Constant Region (IGHG2*04) Protein Sequence | ASTKGPSVFPLAPCSRSTSESTAALGCLVKDYFPEPVTVSWNSGALTSGVHTFPAVLQSS GLYSLSSVVTVPSSSLGTQTYTCNVDHKPSNTKVDKTVERKCCVECPPCPAPPVAGPSVF LFPPKPKDTLMISRTPEVTCVVVDVSHEDPEVQFNWYVDGVEVHNAKTKPREEQFNST FRVVSVLTVVHQDWLNGKEYKCKVSNKGLPAPIEKTISKTKGQPREPQVYTLPPSREEMT KNQVSLTCLVKGFYPSDIAVEWESNGQPENNYKTTPPMLDSDGSFFLYSKLTVDKSRW QQGNVFSCSVMHEALHNHYTQKSLSLSPGK |
| 443 Human IgG2 constant region | IGHG2*06 Human Heavy Chain Constant Region (IGHG2*06) Nucleotide Sequence | GCCTCCACCAAGGGCCCATCGGTCTTCCCCCTGGCGCCCTGCTCCAGGAGCACCTCC GAGAGCACAGCGGCCCTGGGCTGCCTGGTCAAGGACTACTTCCCCGAACCGGTGAC GGTGTCGTGGAACTCAGGCGCTCTGACCAGCGGCGTGCACACCTTCCCGGCTGTCCT ACAGTCCTCAGGACTCTACTCCCTCAGCAGCGTGGTGACCGTGCCCTCCAGCAACTT CGGCACCCAGACCTACACCTGCAACGTAGATCACAAGCCCAGCAACACCAAGGTGG |

-continued

SEQUENCES:

| Seq ID No: | | Description | Sequence |
|---|---|---|---|

444 | | Human Heavy Chain Constant Region (IGHG2*06) Protein Sequence |

ACAGAGACAGTTGAGCGCCAAATGTTGTGTCGAGTGCCCACCCT
GTGGCAGGACCGTCAGTCTTCCTTCCCCCCAAAACCCAAGGACACACCCTCATGATCT
CCCGGACCCCTGAGGTCACGTGCGTGGTGGTGGACGTGAGCCACGAAGACCCCGA
GGTCCAGTTCAACTGGTACGTGGACGGCGTGGAGGTGCATAATGCCAAGACAAAGC
CACGGGAGGAGCAGTTCAACAGCACGTTCCGTGTGGTCAGTGTGCTCACCGTCGTG
CACCAGGACTGGCTGAACGGCAAGGAGTACAAGTGCAAGGTCTCCAACAAAGCCT
CCCAGCCCCCATCGAGAAAACCATCTCCAAAACCAAAGGGCAGCCCCGAGAACCAC
AGGTGTACACCCTGCCCCCATCCCGGGAGGAGATGACCAAGAACCAGGTCAGCCTG
ACCTGCCTGGTCAAAGGCTTCTACCCCAGCGACATCGCCGTGGAGTGGGAGAGCAA
TGGGCAGCCGGAGAACAACTACAAGACCACACCTCCTGTGCTGGACTCCGACGGCT
CCTTCTTCCTCTACAGCAAGCTCACCGTGGACAAGAGCAGGTGGCAGCAGGGGAAC
GTCTTCTCATGCTCCGTGATGCATGAGGCTCTGCACAACCACTACACACAGAAGAGC
CTCTCCCTGTCTCCGGGTAAA

445 | IGHG4*01 or IGHG4*04 | Human Heavy Chain Constant Region (IGHG4*01 or IGHG4*04) Nucleotide Sequence | gcttcccacaagggcccatccgtcttccccctggcgccctgctccaggagcacctccgagagcacagccgccct
gggctgcctggtcaaggactacttccccgaaccggtgacggtgtcgtggaactcaggcgccctgaccagcggc
gtgcacaccttcccggctgtcctacagtcctcaggactctactccctcagcagcgtggtgaccgtgccctccagc
agcttgggcacgaagacctacacctgcaacgtagatcacaagcccagcaacaccaaggtggacaagagagtt
gagtccaaatatggtccccatgcccaccatgcccagcacctgagttcctggggggaccatcagtcttcctgttc
cccccaaaacccaaggacactctcatgatctcccggacccctgaggtcacgtgcgtggtggtggacgtgagccaggaagaccccg
aggaagagccgaggtccagtgacaagccacgagccggacggtgcataatgccaagacaaagccg
cgggaggagcagttcaacagcacgtaccgtgtggtcagcgtcctcaccgtcctgcaccaggactggctgaacggc
aaggagtacaagtgcaaggtctccaacaaaggcctcccgtcctccatcgagaaaaccatctccaaagccaa
aggcagccccgagagccacaggtgtacaccctgcccccatcccgggaggagatgaccaagaaccaggtca
gcctgacctgcctggtcaaaggcttctaccccagcgacatcgccgtggagtgggagagcaatgggcagccgga
gaacaactacaagaccacgcctcccgtgctggactccgacggctccttcttcctctacagcaggctaaccgtggg
acaagagcaggtggcaggagggaatgtcttctcatgctccgtgatgcatgaggctctgcacaaccactacac
acagaagagcctctccctgtctctgggtaaa 446 | | Human Heavy Chain Constant Region (IGHG4*01) Protein Sequence (P01861) |

ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPSCPAPEFLGGPSVF
LFPPKPKDTLMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQVYTLPPSQEEMT
KNQVSLTCLVKGFYPSDIAVEWESNGQPENNYKTTPPVLDSDGSFFLYSRLTVDKSRWQ
EGNVFSCSVMHEALHNHYTQKSLSLSLGK

447 | IGHG4*02 | Human IgG4 constant region | Human Heavy Chain Constant Region (IGHG4*02) Nucleotide Sequence | gcttcccacaagggcccatccgtcttccccctggcgccctgctccaggagcacctccgagagcacagccgccct
gggctgcctggtcaaggactacttccccgaaccggtgacggtgtcgtggaactcaggcgccctgaccagcggc
gtgcacacctttccggctgtcctacagtcctcaggactctactccctcagcagcgtggtgaccgtgccctccagc
agcttgggcacgaagacctacacctgcaacgtagatcacaagcccagcaacaccaaggtggacaagagagtt
gagtccaaatatggtccccatgcccaccatgcccagcacctgagttcctggggggaccatcagtcttcctgttc
cccccaaaacccaaggacactctcatgatctcccggacccctgaggtcacgtgcgtggtggtggacgtgagcc -continued

SEQUENCES:

| Seq ID No: | Description | Sequence |
|---|---|---|
| 448 | Human Heavy Chain Constant Region (IGHG4*02) Protein Sequence | aggaagaccccgagtcagttcaactggtacgtggatggcgtggaggtgcataatgccaagacaaagccgc gggaggagcagttcaacagcacctaccgtgtggtcagcgtcctcaccgtcctgcaccaggactggctgaacg caaggagtacaagtgcaaggtctccaacaaaggcctcccgtcctccatcgagaaaaccatctccaaagccaa aggcagccccgagagccaggtgtacaccctgcccccatcccaggaggagatgaccaagaaccaggtca gcctgacctgcctggtcaaaggcttctaccccagcgacatcgccgtggagtggagagcaatgggcagccgga gacaacaactacaagaccacgcctcccgtgctggactccgacggctccttcttcctctacagcaggctaaccgtgg acaagagcaggtggcaggaggggaatgtcttctcatgctccgtgatgcatgaggctctgcacaaccactacac gcagaagagcctctccctgtctctgggtaaa<br><br>ASTKGPSVFPLAPCSRSTSESTAALGCLVKDYFPEPVTVSWNSGALTSGVHTFPAVLQSS GLYSLSSVVTVPSSSLGTKTYTCNVDHKPSNTKVDKRVESKYGPPCPSCPAPEFLGGPSVF LFPPKPKDTLMISRTPEVTCVVVDVSQEDPEVQFNWYVDGVEVHNAKTKPREEQFNST YRVVSVLTVVHQDWLNGKEYKCKVSNKGLPSSIEKTISKAKGQPREPQVYTLPPSQEEM TKNQVSLTCLVKGFYPSDIAVEWESNGQPENNYKTTPPVLDSDGSFFLYSRLTVDKSRW QEGNVFSCSVMHEALHNHYTQKSLSLGK |
| 449 | Human IgG4 constant region IGHG4*03 / Human Heavy Chain Constant Region (IGHG4*03) Nucleotide Sequence | gcttccaccaagggcccatccgtcttccccctggcgccctgctccaggagcacctccgagagcacagccgcct gggctgcctggtcaaggactacttccccgaaccggtgacggtgtcgtggaactcaggcgccctgaccagcggc gtgcacaccttcccggctgtcctacagtcctcaggactctactccctcagcagcgtggtgaccgtgccctccagc agcttgggcacgaagacctacacctgcaacgtagatcacaagcccagcaacaccaaggtggacaagagagtt gagtccaaatatggtcccccatgcccaccatgcccagcacctgagttcctggggggaccatcagtcttcctgttc ccccaaaacccaaggacactctcatgatctcccggacccctgaggtcacgtgcgtggtggtggacgtgagcc aggaagaccccgaggtccagttcaactggtacgtggatggcgtggaggtgcataatgccaagacaaagccgc gggaggagcagttcaacagcacgtaccgtgtggtcagcgtcctcaccgtcctgcaccaggactggctgaacg gcaaggagtacaagtgcaaggtctccaacaaaggcctcccgtcctccatcgagaaaaccatctccaaagccaa aggcagccccgagagccaggtgtacaccctgcccccatcccgggatgagctgaccaagaaccaggtca gcctgacctgcctggtcaaaggcttctaccccagcgacatcgccgtggagtgggagagcaatgggcagccgga gaacaactacaagaccacgcctcccgtgctggactccgacggctccttcttcctctacagcaggctaaccgtgg acaagagcaggtggcaggaggggaacgtcttctcatgctccgtgatgcatgaggctctgcacaaccactacac gcagaagagcctctccctgtctctgggtaaa<br><br>ASTKGPSVFPLAPCSRSTSESTAALGCLVKDYFPEPVTVSWNSGALTSGVHTFPAVLQSS GLYSLSSVVTVPSSSLGTKTYTCNVDHKPSNTKVDKRVESKYGPPCPSCPAPEFLGGPSVF LFPPKPKDTLMISRTPEVTCVVVDVSQEDPEVQFNWYVDGVEVHNAKTKPREEQFNST YRVVSVLTVLHQDWLNGKEYKCKVSNKGLPSSIEKTISKAKGQPREPQVYTLPPSQEEMT KNQVSLTCLVKGFYPSDIAVEWESNGQPENNYKTTPPVLDSDGSFFLYSRLTVDKSRWQ EGNVFSCSVMHEALHNHYTQKSLSLGK |
| 450 | Human Heavy Chain Constant Region (IGHG4*03) Protein Sequence | ASTKGPSVFPLAPCSRSTSESTAALGCLVKDYFPEPVTVSWNSGALTSGVHTFPAVLQSS GLYSLSSVVTVPSSSLGTKTYTCNVDHKPSNTKVDKRVESKYGPPCPSCPAPEFLGGPSVF LFPPKPKDTLMISRTPEVTCVVVDVSQEDPEVQFNWYVDGVEVHNAKTKPREEQFNST YRVVSVLTVLHQDWLNGKEYKCKVSNKGLPSSIEKTISKAKGQPREPQVYTLPPSQEEMT KNQVSLTCLVKGFYPSDIAVEWESNGQPENNYKTTPPVLDSDGSFFLYSRLTVDKSRWQ EGNVFSCSVMHEALHNHYTQKSLSLGK |
| 451 | Human IgG4-PE constant region IGHG4-PE / Human Heavy Chain Constant Region (IGHG4-PE) Nucleotide Sequence Version A | gcctccaccaagggcccatccgtcttccccctggcgccctgctccaggagcacctccgagagcacagccgcct gggctgcctggtcaaggactacttccccgaaccggtgacggtgtcgtggaactcaggcgccctgaccagcggc gtgcacaccttcccggctgtcctacagtcctcaggactctactccctcagcagcgtggtgaccgtgccctccagc agcttgggcacgaagacctacacctgcaacgtagatcacaagcccagcaacaccaaggtggacaagagagtt gagtccaaatatggtccccatgcccaccatgcccagcacctgagttcctggggggaccatcagtcttctgttc ccccaaaacccaaggacactctcatgatctcccggacccctgaggtcacgtgcgtggtggtggacgtgagcc aggaagaccccgaggtccagttcaactggtacgtggatggcgtggaggtgcataatgccaagacaaagccgc gggaggagcagttcaacagcacgtaccgtgtggtcagcgtcctcaccgtcctgcaccaggactggctgaacgg caaggagtacaagtgcaaggtctccaacaaaggcctcccgtcctccatcgagaaaaccatctccaaagccaa aggcagccccgagagccaggtgtacaccctgcccccatcccaggaggagatgaccaagaaccaggtca gcctgacctgcctggtcaaaggcttctaccccagcgacatcgccgtggagtgggagagcaatgggcagccgga |

-continued

SEQUENCES:

| Seq ID No: | Description | Sequence |
|---|---|---|
| | | gaacaactacaagaccacgcctcccgtgctggactccgacggatccttcttcctctacagcaggctaaccgtgg |
| | | acaagagcaggtggcaggaggggaatgtcttctcatgctccgtgatgcatgaggctctgcacaaccactacac |
| | | acagaagagcctctccctgtctctgggtaaa |
| 452 | Human Heavy Chain Constant Region (IGHG4-PE) Nucleotide Sequence Version B | gctcccaccaagggacctagcgtgttccctctcgccccctgttccaggtccacaagcgagtccaccgctgccctc |
| | | ggctgtctggtgaaagactacttccccgagcccgtgaccgtctctggaatagcgagcctgaggtgccccgcgt |
| | | gcacaccttcccggctgtgctgcagagcagcggcctgtacagcctgagcagcgtggtgaccgtgccagtcca |
| | | gctcggcaccaaaacctacacctgcaacgtggaccacaagcctccaacaccaaggtggacaagcgggtgg |
| | | agagcaagtacggccccccctgcccctcttgtcctgaccgacagcgaggtggagaccctgtggacctgtttcc |
| | | cccaaaccccaaggacaccctgatgatctcccggacacccgaggtcacgtgtgtggtggtggacgtgagccag |
| | | gaggaccccgaggtgcagttcaatggtacgtggacggcgtggaggtgcacaatgccaagaccaagccgagg |
| | | gaggagcagttcaattccacctacagggtggtgagcgtgctgaccgtcctgcatcaggattggctgaacggca |
| | | aggagtacaagtgcaaggtctccaacaaaggactgccagcctcatcgagaaaaccatcagcaaggctaag |
| | | ctgacccgcgagggcaggagatttctacccctccccgagagcgggagcaatggcagccagccagcgccggaga |
| | | acaactacaaaaccacctcccgtgctgcgagaacagcgacctcctacacagcaggctggtgacagtggac |
| | | aagagcaggtggcaggaggggaacgtcttctctgctccgtgatgcacgaggcctgcacaatcactacaccc |
| | | agaagagcctctccctgtctctgggtaag |
| 453 | Human Heavy Chain Constant Region (IGHG4-PE) Nucleotide Sequence Version C | gcctcccaccaagggcctctcccgtgttccctctcgcacctgcaggagcacctccacagtctcaccagcagtgcct |
| | | ggctgtctggtgaaagactacttcccgagccccgtgaccgtgacatctggcgg |
| | | tccacaccttcctgcgcctgcagtcctccggctctatccctgccgtgctggaccggtgctctagtcctcc |
| | | ctcggcaccaagaccatctacctgtggaaccacaaccctccacaccaaggtggacaaacgggtcgag |
| | | agcaagtacggccctcctgcctctgtgttcccctgagttcgaaggcggaccaccgagtgctgtcctcc |
| | | cctaagccaaggacaccctcatgatcagccggaccccagagtcctcggtgtggtggtgatgtgagcagg |
| | | agagacccctgaggtcagttcaactggtatgtggacggcgtggaggtgcacaacgccaagaccaagccccgg |
| | | aaggagcagttcaacagcacctaccgggtggtgtccgtgctgaccgtgctgcaccaggactggctgaacggcaa |
| | | ggagtacaaatgcaaggtcaagaaggtttcaacaaggtcaagaaggtggccccacctcccaaggctaaag |
| | | gccagcccgggaacctcaggttacacccctcccctcctccgacaatcgcgtggagtccaacggccagccccgaga |
| | | tgacctgcctggtgaaggattctacctcccgacagcgacgggatcctctttctgtactccaggctgaccgtgataa |
| | | gttcaggtggcaggaaggcaacgtgttcagctgctcagctgcctgatgcacgaggccctgcacaatcactacaccag |
| | | aagtccctgagcctgtcctgggaaag |
| 454 | Human Heavy Chain Constant Region (IGHG4-PE) Protein Sequence (Amino acid substitution shown in BOLD) | ASTKGPSVFPLAPCSRSTSESTAALGCLVKDYFPEPVTVSWNSGALTSGVHTFPAVLQSS GLYSLSSVVTVPSSSLGTKTYTCNVDHKPSNTKVDKRVESKYGPPCPPCPAPEFEGGPSVF LFPPKPKDTLMISRTPEVTCVVVDVSQEDPEVQFNWYVDGVEVHNAKTKPREEQFNST YRVVSVLTVLHQDWLNGKEYKCKVSNKGLPSSIEKTISKAKGQPREPQVYTLPPSQEEMT KNQVSLTCLVKGFYPSDIAVEWESNGQPENNYKTTPPVLDSDGSFFLYSRLTVDKSRWQ EGNVFSCSVMHEALHNHYTQKSLSLSLGK |
| 455 | Inactivated Human IgG4 constant region | Inactivated Human Heavy Chain Constant Region (IGHG4) Nucleotide Sequence | gctcccaccaagggcccatccgtcttccccctggcgccctgctccaggagcacctccgagagcacggccgccct |
| | | gggctgcctggtcaaggactacttccccgaaccggtgacggtgtcgtggaactcaggcgccctgaccagcggc |
| | | gtgcacaccttcccggctgtcctacagtcctcaggactctactccctcagcagcgtggtgaccgtgccctccagc |
| | | agcttgggcacgaagacctacacctgcaacgtagatcacaagcccagcaacaccaaggtggacaagagagtt |
| | | gagtccaaatatggtcccccatgcccaccatgcccagcacctgagttcgaggggggaccatcagtcttcctgttc |
| | | ccccaaaacccaaggacactctcatgatctcccggacccctgaggtcacgtgcgtggtggtggacgtgagccac |
| | | aggaagagaccccgaggtccagttcaactggtacgtggatggcgtggaggtgcataatgccaagacaaagccgc |
| | | gggaggagcagttcaacagcacgtaccgtgtggtcagcgtcctcaccgtcctgcaccaggactggctgaacggca |
| | | aggagtacaagtgcaaggtctccaacaaaggcctcccgtcctccatcgagaaaaccatctccaaagccaa |

-continued

SEQUENCES:

| Seq ID No: | Description | Sequence |
|---|---|---|
| 456 | Inactived Human Heavy Chain Constant Region (IGHG4) Protein Sequence (inactivating mutations from human IgG4 shown in bold) | agggcagcccgagagcacaggtgtacacctgcccctccatccaggaggagatgaccaagaaccaggtca gcctgacctgcctggtcaaaggcttctaccccagcgacatcgccgtggagtgggagagcaatgggcagccgga gaacaactacaagaccacgcctcccgtgctggactccgacggctccttcttcctctacagcaggctaacgtg acaagagcaggtggcagcaggggaatgtcttctcatgctccgtgatgcatgaggctctgcacaaccactacac acaagagaagcctctccctgtctctgggtaaa<br>ASTKGPSVFPLAPCSRSTSESTALGCLVKDYFPEPVTVSWNSGALTSGVHTFPAVLQSS GLYSLSSVVTVPSSSLGTKTYTCNVDHKPSNTKVDKRVESKYGPPCPPCPAPPVAGGPSV FLFPPKPKDTLMISRTPEVTCVVVDVSQEDPEVQFNWYVDGVEVHNAKTKPREEQFNS TYRVVSVLTVLHQDWLNGKEYKCKVSNKGLPSSIEKTISKAKGQPREPQVYTLPPSQEEM TKNQVSLTCLVKGFYPSDIAVEWESNGQPENNYKTTPPVLDSDGSFFLYSRLTVDKSRW QEGNVFSCSVMHEALHNHYTQKSLSLSLGK |
| 457 | Human C_K constant region | IGKC*01 | Human C_K Light Chain Constant Region (IGKC*01) Nucleotide Sequence | cgtacggtggcgctccctccgctgtatcatctcccaccttccgacgagcagcagctgaagtccggcaccgcttctgtcg tgtgcctgctgaacaacttctacccccgaggccaaggtgcagtggaaggtggacaacgccctgcagtccgg caactcccaggaatccgtgaccgagcaggacagcaccaggacagcaggacagagcaggacagctgacccgt ccaaggccgactacgagaagcacaagtgtacgtcgcgagtgaccacccagggcctgtctagcccgtga caagtctttcaacccgggagtgt |
| 458 | | C_K Light Chain Constant Region (IGKC*01) Amino Acid Sequence | RTVAAPSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC |
| 459 | Human C_K constant region | IGKC*02 | C_K Light Chain Constant Region (IGKC*02) Nucleotide Sequence | cgaactcggctgcaccatctgtctcatctcccgccatctgatgagcagttgaaactctggaactgcctctgttg tgtgcctgctgaataacttctatcccagagaggccaaagtacagtggaaggtggataacgccctccaatcgggt aactcccaggagagtgtcacagagcaggacagcaccaggacagcagcctcagcgagct gagcaaagcagactacgagaaacacaaagttacgccggcagaagtcaccatcaggggcctgagctcgcccgt caacaaagagcttcaacaggggagagtgt |
| 460 | | C_K Light Chain Constant Region (IGKC*02) Amino Acid Sequence | RTVAAPSVFIFPPSDEQLKSGTASVVCLLNNFYPREAKVQWKVDNALQSGNSQESVTEQ ESKDSTYSLSSTLTLSKADYEKHKVYAGEVTHQGLSSPVTKSFNRGEC |
| 461 | Human C_K constant region | IGKC*03 | C_K Light Chain Constant Region (IGKC*03) Nucleotide Sequence | cgaactcggctgcaccatctgtctcatctcccgccatctgatgagcagttgaaactgcctctgttg tgtgcctgctgaataacttctatcccagagaggccaaagtacagcggaaggtggataacgcccccaatcggg tactccaggagagtgtcacagagcaggacagcagcctcagcgagctcagcgagcaccctgacgct gagcaaagcagactacgagaaacacaaagttacgcctcgaagtcaccatcaggggcctgagctcgcccgt cacaaaagagcttcaacaggggagagtgt |
| 462 | | C_K Light Chain Constant Region (IGKC*03) Amino Acid Sequence | RTVAAPSVFIFPPSDEQLKSGTASVVCLLNNFYPREAKVQRKVDNALQSGNSQESVTEQ ESKDSTYSLSSTLTLSKADYEKHKVYACEVTHQGLSSPVTKSFNRGEC |
| 463 | Human C_K constant region | IGKC*04 | C_K Light Chain Constant Region (IGKC*04) Nucleotide Sequence | cgaactcggctgcaccatctgtctcatctcccgccatctgatgagcagttgaaactgcctctgttg tgtgcctgctgaataacttctatcccagagaggccaaagtacagtggaaggtggataacgcccccaatcgggt aactcccaggagagtgtcacagagcaggacagcaccaggacagcagcctcagcgagct agcaaagcagactacgagaaacacaaactctagcctcgaagtcaccatcaggggcctgagctcgcgcgt acaaaagagcttcaacaggggagagtgt |
| 464 | | C_K Light Chain Constant Region (IGKC*04) Amino Acid Sequence | RTVAAPSVFIFPPSDEQLKSGTASVVCLLNNFYPREAKVQWKVDNALQSGNSQESVTEQ DSKDSTYSLSSTLTLSKADYEKHKLYACEVTHQGLSSPVTKSFNRGEC |

-continued

SEQUENCES:

| Seq ID No: | | | Description | Sequence |
|---|---|---|---|---|
| 465 | Human Cκ constant region | IGKC*05 | Cκ Light Chain Constant Region (IGKC*05) Nucleotide Sequence | cgaactggtggctgcaccatctgtcttcatcttcccgccatctgatgagcagttgaaatctggaactgcctctgttg<br>tgtgcctgctgaataacttctatcccagagaggccaaagtacagtggaaggtggataacgcccctccaatcgggt<br>aactcccaggagagtgtcacagagcaggacagcaaggacagcacctacagcctcagcagcaccctgacgctg<br>agcaaagcagactacgagaaacacaaagtctacgcctgcgaagtcacccatcagggcctgagctcgcccgtc<br>acaaagagcttcaacaggggagagtgc |
| 466 | | | Cκ Light Chain Constant Region (IGKC*05) Amino Acid Sequence | RTVAAPSVFIFPPSDEQLKSGTASVVCLLNNFYPREAKVQWKVDNALQSGNSQESVTEQ<br>DSKDSTYSLSNTLTLSKADYEKHKVYACEVTHQGLSSPVTKSFNRGEC |
| 467 | Human Cλ constant region | IGLC1*01 | Cλ light Chain Constant Region (IGLC1*01) Nucleotide Sequence (ENST00000390321.2) | cccaaggctgcccccacggtcactctgttcccgccctcctctgaggagctccaagccaacaaggccacatagt<br>gtgtctgatcagtgacttctacccgggagctgtgacagtggcctggaaggcagatagcagccccgtcaaggcg<br>ggagtggacgacagtggaagtcccccaaacagagcaacaacaagtacgcggccagtagcctacctgagcctgac<br>gcccgagcagtggaagtcccacagaagctacagctgccaggtcacgcatgaggggagcaccgtggagaaga<br>cagtggcccctacagaatgttca |
| 468 | | | Cλ Light Chain Constant Region (IGLC1*01) Amino Acid Sequence (A0A075B6K8) | PKANPTVTLFPPSSEELQANKATLVCLISDFYPGAVTVAWKADGSPVKAGVETTKPSKQS<br>NNKYAASSYLSLTPEQWKSHRSYSCQVTHEGSTVEKTVAPTECS |
| 469 | Human Cλ constant region | IGLC1*02 | Cλ Light Chain Constant Region (IGLC1*02) Nucleotide Sequence Version A | ggtcagcccaaggccaaccccactgtcactctgttcccgccctcctctgaggagctccaagccaacaaggccac<br>actagtgtgtctgatcagtgacttctacccgggagctgtgacagtggcctggaaggcagatagcagccccgtca<br>aggcgggagtggacgacagcaccccaaacagagcaacaacaagtacgcggccagtagcctacctgagc<br>ctgacgcccgagcagtggaagtcccacagaagctacagctgccaggtcacgcatgaggggagcaccgtggag<br>aagacagtggcccctacagaatgttca |
| 470 | | | Cλ Light Chain Constant Region (IGLC1*02) Nucleotide Sequence Version B | ggtcagcccaaggccaaccccactgtcactcttgttcccgccctcctctgaggagctccaagccaacaaggccac<br>actagtgtgtctgatcagtgacttctacccgggagctgtgacagtggcctggaaggcagatagcagccccgtcca<br>aggcgggagtggacgacagcaccccaaacagagcaacaacaagtacgcggccagtagcctacctgagc<br>ctgacgcccgagcagtggaagtcccacagaagctacagctgccaggtcacgcatgaggggagcaccgtggag<br>aagacagtggcccctacagaatgttca |
| 471 | | | Cλ Light Chain Constant Region (IGLC1*02) Amino Acid Sequence | GQPKANPTVTLFPPSSEELQANKATLVCLISDFYPGAVTVAWKADGSPVKAGVETTKPS<br>KQSNNKYAASSYLSLTPEQWKSHRSYSCQVTHEGSTVEKTVAPTECS |
| 472 | Human Cλ constant region | IGLC2*01 | Cλ Light Chain Constant Region (IGLC2*01) Nucleotide Sequence Version A | ggccagcctaaggccgctcctcctgtgacctctccccatctcccgaggaactgagctaacaaggccac<br>cctcgtgcctgatcagcgacttctacccgcggcctgaaggtgcctggaaggtgatagctctcctgtgaa<br>ggcgggtgtggaaaccaaccacccctccaagcagtccaacaacaatacgccctctccacctacctgtccctga<br>ccctgacagtggagtggaagtcctacagtcctacagctgccagtgacccacgagggccctccaccgtggaaaga<br>ccgtggctcctaccgagtgctcc |
| 473 | | | Cλ Light Chain Constant Region (IGLC2*01) Nucleotide Sequence Version B | ggccagcctaaagctgccccagggtcacccctgttctcctcccagcgcgaggagctccagcccaacaaggcca<br>cctcgtgctgctgatctcgacttctatccccggctgtgaaagccgtggtggttggaaagcggccaacaaagcccctgtcca<br>aagccggcgtggagaccaccacaccctccaacaacaagtacgccctcctgagtcctcagtctatcctccct<br>gaccctgagcagtggaagtcctactcctgtcaggtcctcactctcaggtgaccgacaggggctccaccgtggaaaag<br>accgtggcccccaccgagtgctcc |
| 474 | | | Cλ Light Chain Constant Region (IGLC1*02) Amino Acid Sequence | GQPKAAPSVTLFPPSSEELQANKATLVCLISDFYPGAVTVAWKADSSPVKAGVETTTPSK<br>QSNNKYAASSYLSLTPEQWKSHRSYSCQVTHEGSTVEKTVAPTECS |

-continued

SEQUENCES:

| Seq ID No: | | Description | Sequence |
|---|---|---|---|
| 475 | Human Cλ constant region | IGLC2*02 or IGLC2*03 | Cλ Light Chain Constant Region (IGLC2*02 or IGLC2*03) Nucleotide Sequence | ggtcagcccaaggctgccccctcggtcactctgttccgccctcctctgaggagcttcaagccaacaaggccac actggtgtgtctcataagtgactgctctaccgggagccgtgacagtggcctggaaggcagtagcagcccgtca aggcgggagtggagaccaacaccctccaaacaagctacagctgcagtgacatacggggtcacccatgcagagc ctgacacgcctgagcagtggagtcccagagaagctacagctgcagtgacagcagcccgtcaagcagcctgagc aagttgcccctacggaatgtca GQPKAAPSVTLFPPSSEELQANKATLVCLISDFYPGAVTVAWKADSSPVKAGVETTTPSK QSNNKYAASSYLSLTPEQWKSHRSYSCQVTHEGSTVEKTVAPTECS |
| 476 | | Cλ Light Chain Constant Region (IGLC2*02) Amino Acid Sequence | |
| 477 | Human Cλ constant region | IGL3*01 | Cλ Light Chain Constant Region (IGLC3*01) Nucleotide Sequence | cccaaggctgccccctcggtcactctgttcccaccctctctgaggagcttcaagccaacaaggccacactggt gtgtctcataagtgactgctctaccgggagccgtgacagttgcctggaaggcagatagcagcccgtcaaggcg gggtggagaccaacaccctccaaacaagctacagctgcagtgacacaagctacacctgcagtgacagcagcctgac cctgagcagtggagtcccagagaagctacagctgcagtgacagcagcccgtcaagcagcctgagaga cagttgcccctacggaatgtca PKAAPSVTLFPPSSEELQANKATLVCLISDFYPGAVTVAWKADSSPVKAGVETTTPSSKQS NNKYAASSYLSLTPEQWKSHKSYSCQVTHEGSTVEKTVAPTECS |
| 478 | | Cλ Light Chain Constant Region (IGLC3*01) Amino Acid Sequence | |
| 479 | Human Cλ constant region | IGLC3*02 | Cλ Light Chain Constant Region (IGLC3*02) Nucleotide Sequence | ggtcagcccaaggctgccccctcggtcactctgttccccaccctctctgaggagcttcaagccaacaaggccac actggtgtgtctcataagtgactgctctaccgggccagtgacagtgcctgaagtcagtggaggcagatagcagctactgagc aggcgggtggagaccaacaccctccaaacaagctacagctgcagtgacacaagctacacctgcagtgacagcagcctgagc ctgacacgcctgagcagtggagtcccagagaagctacagctgcagtgacagcagcccgtcaagcagcctgagc aagacagtgcccctacggaatgtca GQPKAAPSVTLFPPSSEELQANKATLVCLISDFYPGAVTVAWKADSSPVKAGVETTTPSK QSNNKYAASSYLSLTPEQWKSHKSYSCQVTHEGSTVEKTVAPTECS |
| 480 | | Cλ Light Chain Constant Region (IGLC1*02) Amino Acid Sequence | |
| 481 | Human Cλ constant region | IGLC3*03 | Cλ Light Chain Constant Region (IGLC3*03) Nucleotide Sequence | ggtcagcccaaggctgccccctcggtcactctgttccccaccctctctgaggagcttcaagccaacaaggccac actggtgtgtctcataagtgactgctctaccgggagccgtgacagtgcctgaagtcagtggaggcagatagcagctactgagc aggcgggtggagaccaacaccctccaaacaagctacagctgcagtgacacaagctacacctgcagtgacagcagcctgagc ctgacacgcctgagcagtggagtcccagagaagctacagctgcgccatgaaggagcaccgtggag aagacagtggccctacagaatgtca GQPKAAPSVTLFPPSSEELQANKATLVCLISDFYPGAVTVAWKADSSPVKAGVETTTPSK QSNNKYAASSYLSLTPEQWKSHKSYSCQVTHEGSTVEKTVAPTECS |
| 482 | | Cλ Light Chain Constant Region (IGLC3*03) Amino Acid Sequence | |
| 483 | Human Cλ constant region | IGLC3*04 | Cλ Light Chain Constant Region (IGLC3*04) Nucleotide Sequence | ggtcagcccaaggctgccccctcggtcactctgttccccaccctctctgaggagcttcaagccaacaaggccac actggtgtgtctcataagtgactgctctaccgggagccgtgacagtgcctgaagtcagtggaggcagatagcagctactgagc aggcgggtggagaccaacaccctccaaacaagctacagctgcagtgacacaagctacacctgcagtgacagcagcctgagc ctgacacgcctgagcagtggagtcccagagaagctacagctgcgccatgaaggagcaccgtggag aagacagtggccctacagaatgtca GQPKAAPSVTLFPPSSEELQANKATLVCLISDFYPGAVTVAWKADSSPVKAGVETTTPSK QSNNKYAASSYLSLTPEQWKSHRSYSCQVTHEGSTVEKTVAPTECS |
| 484 | | Cλ Light Chain Constant Region (IGLC3*04) Amino Acid Sequence | |

-continued

SEQUENCES:

| Seq ID No: | | Description | Sequence |
|---|---|---|---|
| 485 | Human Cλ constant region | IGLC6*01 | Cλ Light Chain Constant Region (IGLC6*01) Nucleotide Sequence | ggtcagcccaaggctgcccatcggtcactctgttccgccctcctcttgagagcttcaagccaacaaggccac actggttgtgcctgatcagtgactctacccgggagctgaagtggctgaagtgcggctggaaggcagatggcagccccgtc aacacggagtggagaccaccaccctccaacagagcaacaacaagtacgcggccagcagctacctgag cctgacgcctgagcagtgaaagctacagctgcaggtcacgcatgaaggagcaccgtgga gaagacagtggcccctgcagaatgtca |
| | | | GQPKAAPSVTLFPPSSEELQANKATLVCLISDFYPGAVKVAWKADGSPVNTGVETTTPSK QSNNKYAASSYLSLTPEQWKSHRSYSCQVTHEGSTVEKTVAPAECS |
| 486 | | | Cλ Light Chain Constant Region (IGLC6*01) Amino Acid Sequence | |
| 487 | Human Cλ constant region | IGLC7*01 or IGLC7*02 | Cλ Light Chain Constant Region (IGLC7*01 or IGLC7*02) Nucleotide Sequence | ggtcagcccaaggctgcccatcggtcactctgttcccacccctcctgagagcttcaagccaacaaggccac actggtgtcctgtaagtgactctacccgggagctgaagtggctgaagtgcggctggaaggcagatggcagccccgtca agtggaggtggagaccaccaccctccaaacagagcaacaacaagtatcggccagcagctacctgagc ctgacgcctgagcagtgaagctacacagctgcgggtcacgcatgaaggagcaccgtggag aagacagtggcccctgcagaatgtctct |
| | | | GQPKAAPSVTLFPPSSEELQANKATLVCLVSDFYPGAVTVAWKADGSPVKVGVETTKPS KQSNNKYAASSYLSLTPEQWKSHRSYSCRVTHEGSTVEKTVAPAECS |
| 488 | | | Cλ Light Chain Constant Region (IGLC7*01) Amino Acid Sequence | |
| 489 | Human Cλ constant region | IGLC7*03 | Cλ Light Chain Constant Region (IGLC7*03) Nucleotide Sequence | GGTCAGCCCAAGGCTGCCCCTCGGTCACTCTGTTCCCACCCTCCTCTGAGGAGCTTC AAGCCAACAAGGCCACACTGGTGTGTCTGTAAGTGACTTCAACCCGGAGCCCGTG ACAGTGGCCTGGAAGGCAGATGGCAGCCCCGTCAAGGTGGGAGTGGAGACCACCA AACCCTCCAAACAAGCAACAACAAGTATGCGGCCAGCAGCTACCTGAGCCTGACG CCCGAGCAGTGGAAGTCCCACAGAAGCTACAGCTGCCGGGTCACGCATGAAGGGA GCACCGTGGAGAAGACAGTGGCCCCTGCAGAATGCTCT |
| | | | GQPKAAPSVTLFPPSSEELQANKATLVCLVSDFNPGAVTVAWKADGSPVKVGVETTKPS KQSNNKYAASSYLSLTPEQWKSHRSYSCRVTHEGSTVEKTVAPAECS |
| 490 | | | Cλ Light Chain Constant Region (IGLC7*03) Amino Acid Sequence | |
| 491 | Rat BMP6 | | Amino acid sequence Uniprot ID number: Q04906 (leader sequence in italics; pro- peptide underlined; mature protein bold) | *MPGLGRRAQWLCWWWGLLCSCCGPPPLRPPLPVAAAAAGGQLLGAGGSPVRAEQPP PQSSSSGFLYRRLKTHEKREMQKEILSVLGLPHRPRPLHGLQQPQSPVLPQQQQSQQTA* REEPPPGRLKSAPLFMLDLYNSLSKDDEEDGVSEGEGLEPESHGRASSSQLKQPSPGAAH SLNRKSLLAPGPGGSASPLTSAQDSAFLNDADMVMSFVNLVEYDKEFSPRQRHHKEFKF NLSQIPEGEAVTAAEFRVYKDCVVGSFKNQTFLISIYQVLQEHQHRDSDLFLLDTRVVWA SEEGWLEFDITATSNLWVTPQHNMGLQLSVVTRDGLHINPRAAGLVGRDGPYDKQP FMVAFFKVSEVHVRTTRSASSRRRQQSRNRSTQSQDVSRGSSASDYNSSELKTACKKH ELIVSFQDLGWQDWIIAPKGYAANYCDGECSFPLNAHMNATNHAIVQTLVHLMNP EYVPKPCCAPTKLNAISVLYFDDNSNVILKKYRNMVVRACGCH |
| 492 | Cynomolgus monkey BMP6 | | Amino acid sequence Uniprot ID number: (leader sequence in italics; pro- peptide underlined; mature protein bold) | *MPGLGRRAQWLCWWWGLLCSCCGPPRPLPAAAAAAAGGQLLGDGGSPGRTEQPP PSPQSSSGFLYRRLKTHEKREMQKEILSVLGLPHRPRPLHGLQQPQPPALPLQQQQQQQ QPPRGEPPPGRLKSAPLFMLDLYNALSADDEEDGASEGERQQPWPHEGASSSQPRQP APGAAHPLNRKSLLAPGPGSGGASPLTSAQDSAFLNDADMVMSFVNLVEYDKEFSPRQ RHHKEFKFNLSQLPEGEAVTAAEFRIYKDCVMGSFKNQTFLISIYQVLQEHQHRDSDLFLL DTRVVWASEEGWLEFDITATSNLWVVTPQHNMGLQLSVVTRDGVHIHPRAAGLVGR DGPYDKQPFMVAFFKVSEVHVRTTRSASGRRRQQSRNRSTQSQDVARVSSASDYNSS ELKTACRKHELIVSFQDLGWQDWIIAPKGYAANYCDGECSFPLNAHMNATNHAIVQ TLVHLMNPEYVPKPCCAPTKLNAISVLYFDDNSNVILKKYRNMVVRACGCH* |

-continued

SEQUENCES:

| Seq ID No: | Description | Sequence |
|---|---|---|
| 493 | Human BMP2 | Recombinant protein Amino acid sequence R&D Systems Catalog Number: 355-BM | QAKHKQRKRLKSSCKRHPLYVDFSDVGWNDWIVAPPGYHAFYCHGECPFPLADHLNST NHAIVQTLVNSVNSKIPKACCVPTELSAISMLYLDENEKVVLKNYQDMVEGCGCR |
| 494 | Human BMP4 | Recombinant protein Amino acid sequence R&D Systems Catalog Number: 314-BP | SPKHHSQRARKKNKNCRRHSLYVDFSDVGWNDWIVAPPGYQAFYCHGDCPFPLADHL NSTNHAIVQTLVNSVNSSIPKACCVPTELSAISMLYLDEYDKVVLKNYQEMVVEGCGCR |
| 495 | Human BMP5 | Recombinant protein Amino acid sequence R&D Systems Catalog Number: 615-BMC | AANKRKNQNRNKSSHQDSSRMSSVGDYNTSEQKQACKHELYVSFRDLGWQDWIIA PEGYAAFYCDGECSFPLNAHMNATNHAIVQTLVHLMFPDHVPKPCCAPTKLNAISVLYF DDSSNVILKKYRNMVVRSCGCH |
| 496 | Human BMP7 | Recombinant protein Amino acid sequence R&D Systems Catalog Number: 354-BP | STGSKQRSQNRSKTPKNQEALRMANVAENSSSDQRQACKKHELYVSFRDLGWQDWII APEGYAAYYCEGECAFPLNSYMNATNHAIVQTLVHFINPETVPKPCCAPTQLNAISVLYF DDSSNVILKKYRNMVVRACGCH |
| 497 | Human BMP9 | Recombinant protein Amino acid sequence Peprotech GDF-2/BMP9 Catalog Number: 120-7 | SAGAGSHCQKTSLRVNFEDIGWDSWIIAPKEYEAYECKGGCFFPLADDVTPTKHAIVQTL VHLKFPTKVGKACCVPTKLSPISVLYKDDMGVPTLKYHYEGMSVAECCCR |
| 498 | CL-66833 | Heavy chain Nucleotide sequence of heavy chain | CAGGTCCAGTTTGTGCAGTCTGGGGCTGAGGTGAAGAAGCCTGGGGCCTCTGTGAA GGTTTCCTGCAAGGCTTCTGGATACACCTTCACAAATCATGCTATACATTGGGTGCG CCAGGCCCCGGACAAAGGCTTGAGTGGATGGGAGTCATCATTACCAGGGACACATCC GCGAACACACGCTACATGTCCCTGAGCAGCCTGACATCTGAGGACACGGCTGTTTAT TACTGTACTAGAGGGGTTACGGTGAATCGTATGACCACTGGGGCCAGGGAACCCT GGTCACCGTCTCCTCAGCCAGCACCAAGGGCCCTCCGGTTCCCCCTGGCCCCTGC AGCAGGAGCACCTCCGAATCCACAGCTGCCCTGGGCTGTCTGGTGAAGGACTACTTT CCCGAGCCCGTGACCGTGAGCTGGAACAGCGGCGTCCTGACATCCGGCGTCCACAC CTTTCCTGCCGTCCTGCAGTCCTCCGGCCTCTACTCCCTGCTCCCGGTGACCGTG CCTAGCTCCTCCTCGGCACCAAGAACCTACACCTGTAACGTGGACCACAAACCCTCCA ACACCAAGGTGGACAAACGGGTCGAGAGCAAGTACGGCCCTCCCTGCCCTCCTTGT CCTGCCCCGAGTTGGAAGGCGGACCCAGCGTGTTCCTGTTCCCTCCTAAGCCCAAG GACACCCTCATGATCAGCCGGACCACCCGAGGTGACCTGCGTGGTGGTGGATGTGAG CCAGGAGGACCCTGAGGTCCAGTTCAACTGGTATGTGGACGGCGTGGAGGTGCACA ACGCCAAGACAAAGCCCGGGAAGAGAGCAGTTCAACTCCACTACAGGGTGGTCAGC GTGCTGACCGTGCTGCATCAGGACTGGCTGAACGGCAAGGAGTACAAGTGCAAGGT CAGCAATAAGGGACTGCCCAGCAGCATCGAGAAGACCATCTCCAAGGCTAAAGGCC AGCCCCGGGAACCTCAGGTGTACACCCTGCCTCCCAGCCAGGAGGAGATGACCAAG AACCAGGTGAGCCTGACCTGCCTGGTGAAGGGATTCTACCCTTCCGACATCGCCGTG GAGTGGGAGTCCAATGGGCAGCCCGAGAACAATTATAAGACCACCCCTCCCGTCCTC GACAGCGACGGATCCTTCTTCCTGTACTCCAGGCTGACCGTGGATAAGTCCAGGTGG CAGGAAGGCAACGTGTTCAGCTGCTCCGTGATGCACGAGGCCCTGCACAATCACTA CACCCAGAAGTCCCTGAGCCTGTCCCTGGGAAAG |

-continued

SEQUENCES:

| Seq ID No: | | Description | Sequence |
|---|---|---|---|
| 499 | CL-66833 Light chain | Nucleotide sequence of light chain | GACATCCAGATGACCCAGTCTCCATCCTCCCTGTCTGCATCTGTAGGAGACAGAGTC ACCATCACTTGCCGGGCAAGTCAGGGCATTAGAAATAATTTAGGCTGGTATCAGCA GAAACCAGGGAAAGCCCCTAAGCGCCTGATCTATGCTGCATCCAGTTTGCAAAGTG GGGTCCCATCAAGGTTTAGCGGCAGTGGATCTGGACAGAATTCACTCTCACAATCA GCAGCCTGCAGCCTGAAGATGTTGCAATTTATTTCTGTCAACAATCAAATTTACCC GTGGACGTTCGGCCAAGGGACCAAGGTGGAAACCAAGCTAGCGGAGTCCCCTCCT CCGTGTTCATCTTCCCACCTTCCGACGAGCAGCTGAAGTCCGGCACCGCTTCTGTCGT GTGCCTGCTGAACAACTTCTACCCCCGAGGCCAAGGTGCAGTGGAAGGTGGACA ACGCCCTGCAGTCCGGCAACTCCCAGGAATCCGTGACCGAGCAGGACTCCAAGGAC AGCACCTACTCCCTGTCCTCCACCCTGACCCTGTCCAAGGCCGACTACGAGAAGCAC AAGGTGTACGCCTGCGAAGTGACCCACCAGGGCCTGTCTAGCCCCGTGACCAAGTC TTTCAACCGGGGCGAGTGT |
| 500 | CL-57931 Heavy chain | Nucleotide sequence of heavy chain | CAGGTCCAACTTGTGCAGTCTGGGGCTGAGGTGCAGAAGCCTGGGGCCTCAGTGAA GGTTTCCTGCAAGGCTTCTGGATACACCTTCACTTCATATGCTTTGCATTGGGTCGC CAGGCCCCCGGACAAAGGCTTGAGTGGCTGGGATGGATCAGCGGCTGCCAATGGTAA CACAGATTATTCATGGAAGTTCAGGGCAGAGTCACCCTTACCGGGACACATCCGC AAACACAGTCTACATGGAACTATGGTCTCCTTTGATATCTGGGGCCAAGGGACCATTGG TCACCGTCTCTTCAGCCAGCACCAAGGGCCCTTCCGTTCCCCTGGTCTGTTCCCCTGCAG CAGGAGCACCTCCGAATCCACAGCTGCCTGGGCCTGTCTGGTGAAGGACTACTTTCC CGAGCCCGTGACCGTGAGCTGGAACAGCGGCGCTCTGACCATCCGGCGTCCACCT TTCCTGCCGTGCTCCTGCAGTCCTCCGGCCCTCTACTCCTCGTCCTCCGTGTGACCGTGCC TAGCTCCTCCCTGCCGACCAAGACCTACACCTGTAACGTGGACCACAAACCCTCCAA CACCAAGGTGGACAAAGGGTCGAACGGCCAAGTACGGCCCTCCCTGCCCTCCTTGTCC TGCCCCCGAGTTCGAAGGCGGACCACCAGCCGTTCCTGTTCCCTCCCTAAGCCCAAGGA CACCCTCATGATCAGCCGGACACCCGAGGTGACCTGCGTGGTGGTGGATGTGAGCC AGGAGGACCCCTGAGGTCAAGTTCAACTGGTATGTGGACGGCGTGGAGGTGCACAA CGCCAAGACAAAGCCCGGGAAGGAGCAGTTCAACTCCACCTACAGGGTGGTCAGCG TGCTGACCGTGCTGCATCAGGACTGGCTGAACGGCAAGGAGTACAAGTGCAAGGTC AGCAATAAGGCACTGCCAGCAGCAGCAATCCCCAGGACCATCTCCAAGGCTAAAGGCCA GCCCCGGGAACCTCAGGTGTACACCCTGCCTCCCTCCCGGGATGAAGGGGATTCTACCCTTCCGACATCGCCGTGG AGTGGGAGTCCAACGGCCAGCCGGAGAACAATTATAAGACCACCCCTCCCGTCCTCG ACAGCGACGGATCCTTCTTCCTGTACTCCAAGCTGACCGTGGATAAGTCCAGGTGGC AGGAAGGCAACGTGTTCAGCTGCTCCGTGATGCACGAGGCCCTGCACAATCACTAC ACCCAGAAGTCCCTGAGCCTGTCCCTGGGAAAG |
| 501 | CL-57931 Light chain | Nucleotide sequence of light chain | GAAATTGTGTTGACGCAGTCTCCAGGCACCCTGTCTTTGTCTCCAGGGGAAAGAGCC ACCCTCTCCTGTTGGGCCAGTCAGTCAAAGTCTTACCCAACAGTTTCTTAGCCTGGTACCGGC AGAAACCTGGCCAGGCTCCCAGGCTCCTCATCTCTGGTGCATTCAGCAGGGCCACTG ACATCCCAGACAGGATTCAGTGGCAGTGGATCTGGGACAGACAGACTTCACTCTCACCATCA ACAGACTGGAGCCTGAAGATTTTGCAGTGTATTACTGTCAGTACTATTGGTACCTCAC CGTGGACGTTCGGCCAAGGGACCAAGGTGGAAATCAAACGTACGGTGGCCGCTCCC TCCGTGTTCATCTTCCCACCTTCTACCCCCGGGAGTCAAGTCCGGCACCGCTTCTGTCG TGTGCCTGCTGAACAACTTCTACCCCCGAGGCCAACTCCCAGGAATCCGTGACCGAGCAGGACTCCAAGGA |

-continued

SEQUENCES:

| Seq ID No: | | Description | Sequence |
|---|---|---|---|
| | | | CAGCCACCTACTCCCTGTCCTCCACCCTGACCCTGTCCAAGGCCGACTACGAGAAGCA |
| | | | CAAGGTGTACGCCTGCGAAGTGACCCACCAGGGCCTGTCTAGCCCCGTGACCAAGT |
| | | | CTTTCAACCGGGGCGAGTGT |
| 502 | CL-57945 | Heavy chain | Nucleotide sequence of heavy chain | CAGGTGCCACCTTGTTCAGTCAGGGCCAGAGGTGAAGAACCCTGGGGCCTCAGTGAA |
| | | | GGTTCCTGCAAGGCTTCTGGATACACCTTCACTACCTTTGCTATTCATTGGTTGCGC |
| | | | CAGGCCCCCGGACAGAGGCTTGAGTGGATGGATCAACCCTGGCAATGTTAA |
| | | | GACAGATTATTCGCAGAAGTTCCAGGGCAGAGTCACCATTAGCAGGGACACATCCG |
| | | | CGACCACTGCCTACATGGAGCTGAGCAGCCTGAGATCTGAAGACACGGCTGTTTATT |
| | | | ACTGTGCGAGAAGACAATTATGTTACCCTTTGACTACTACTGGGGCCAGGGAACCCTG |
| | | | GTCACCGTCTCCTCAGCCACCAACCAAGGGCCCTCCGTCTTCCCCCTGGCCCCTTGCA |
| | | | GCAGGAGCACCTCCGAATCCACAGCTGCCCTGGGCTGCCTGGTCAAGGACTACTTTC |
| | | | CCGAGCCCGTGACCGTGAACTGAACAGCGGCGTCCTCTGACATCCGGCGTCCACACC |
| | | | TTTCCTGCCGTCCTGACAGTCCTCCGGCCTACTCCCTGGTGTCCGTGGTGACCGTGC |
| | | | CTAGCTCCTCCCTCCGGCACCAAGACCTACACCTGTAACGTGGACCACAAACCCTCCA |
| | | | ACACCAAGGTGACAAACGGGTCGAGAGCAAGTACGGCCCTCCCTGCCCTCCTTGT |
| | | | CCTGCCCCCGAGTTCGAGGGCGGACCACCCAGCCGTGTTCCTGTTCCCTCCTAAGCCCAAG |
| | | | GACACCCTCATGATCAGCCGGACACCCGAGGTGACCTGCGTGGTGGTGGATGTGAG |
| | | | CCAGGAGGACCCTGAGGTCCAGTTCAACTGGTATGTGGACGGCGTGGAGGTGCACA |
| | | | ACGCCAAGACAAAGCCCGGGAAGAGACTGGCTCAGGACTGGCAAGGAGTACAAGTGCAAGGT |
| | | | GTGCTGACCGTGCTGCATCAGGACTGGCTGAACGGCAAGGAGTACAAGTGCAAGGT |
| | | | CAGCAATAAGGACTGCCCAGCACCATCGAGAAGACCATCTCCAAGGCTAAAGGCC |
| | | | AGCCCCGGGAACCTCAGGTTCTACCCTGCCTGGTGAAGGGATTCTACCCTTCCGACATCGCGTG |
| | | | GAGTGGGAGTCCAACGGCCAGCCCGAGAACAATTATAAGACCACCCCTCCCGTCCTC |
| | | | GACAGCGACGGCTCCTTCTTCCTGTACTCCAGGCTGACCGTGGATAAGTCCAGGTGG |
| | | | CAGGAAGGCAACGTGTTCAGCTGCTCCGTGATGCACGAGGCCCTGCACAATCACTA |
| | | | CACCCAGAAGTCCCTGAGCCTGTCCCCTGGGAAAG |
| 503 | CL-57945 | Light chain | Nucleotide sequence of light chain | GAAATTGTGTTGACGCAGTCTCCAGGCACCCTGTCTTTGTCTCCAGGGGAGGAGCC |
| | | | ACCCTCTCCTGCAGGGCCAGTCAGAGTATTAGCAACAACTTCTTAGCCTGGTACCAA |
| | | | CAGAAACCTGGCCAGGCTCCCAGACTCCTCATCTTTGGTGCATCCAGCAGGGCCACT |
| | | | GCCATCCCAGACAGGTTCGTTGGCAGTGGGTCTGGGACAGACTTCACTCTCACCATC |
| | | | ACCGGACTGGAGCCTGAAGATTTTGCAGTGTATCACTGCAACACTATGGTGGTTCA |
| | | | CCTTGGACGTTCGGCCAAGGGACCAAGGTGGAAATCAAACGTACGGTGGCCGCTCC |
| | | | CTCCGTGTTCATCTTCCCACCTTCTGACGAGCAGCTGAAGTCCGGACACCGCTTCTGTC |
| | | | GTGTGCCTGCTGAACAACTTCTACCCCCGCGAGGCCAAGGTGCAGTGGAAGGTGGA |
| | | | CAACGCCCTGCAGTCCGGCAACTCCCAGGAATCCGTGACCGAGCAGGACTCCAAGG |
| | | | ACAGCACCTACTCCCTGTCCTCCACCCTGACCCTGTCCAAGGCCGACTACGAGAAGC |
| | | | ACAAGGTGTACGCCTGCGAAGTGACCCACCAGGGCCTGTCTAGCCCCGTGACCAAG |
| | | | TCTTTCAACCGGGGCGAGTGT |
| 504 | CL-57945 | Heavy chain | Nucleotide sequence of heavy chain alternative coding | CAGGTGCCACCTTGTTCAGTCAGGGCCAGAGGTGAAGAACCCTGGGGCCTCAGTGAA |
| | | | GGTTCCTGCAAGGCTTCTGGATACACCTTCACTACCTTTGCTATTCATTGGTTGCGC |
| | | | CAGGCCCCCGGACAGAGGCTTGAGTGGATGGATCAACCCTGGCAATGTTAA |
| | | | GACAGATTATTCGCAGAAGTTCCAGGGCAGAGTCACCATTAGCAGGGACACATCCG |
| | | | CGACCACTGCCTACATGGAGCTGAGCAGCCTGAGATCTGAAGACACGGCTGTTTATT |

-continued

SEQUENCES:

| Seq ID No: | | Description | Sequence |
|---|---|---|---|
| | | | ACTGTGCGGAGAAGACAATTATGTTACCCTTTGACTACTGGGCCAGGGAACCCTG |
| | | | GTCACCGTCTCCTCAGCCAGCAGGCCCCTCCGTGTTCCCCTGGCCCCCTTGCA |
| | | | GCAGGAGCACCTCCGAATCCACAGCTCGCCCTGGGCTGTCTGGTGAAGGACTACTTTC |
| | | | CCGAGCCCGTGACCGTGAGCTGGAACAGCGGCGCTCTGACATCCGGCGTCCACACC |
| | | | TTTCCTGCGCTCCTCCAGTCCTCCGGCCTCTACTCCCTGTGGTGACCGTGC |
| | | | CTAGCTCCTCCCTCGGCACCAAGACCTACACCTGTAACGTGGACCACAAACCCTCCA |
| | | | ACACCAAGGTGGACAAACGGGTCGAGAGCAAGTACGGCCCCTCCCTGCCCTCCTTGT |
| | | | CCTGCCCCCGAGTTCGAGGGCGGACCCAGCCTGTTCCTGTTCCTCCTAAGCCCAAG |
| | | | GACACCCTCATGATCAGCCGGACCACCGAGGTGACCTGCGTGGTGGTGGATGTGAG |
| | | | CCAGGAGGACCCTGAGGTCCAGTTCAACTGGTATGTGGATGGCGTGGAGGTGCACA |
| | | | ACGCCAAGACAAAGCCCCGGGAAGAGCAGTTCAACTCCACCTACAGGGTGGTCAGC |
| | | | GTGCTGACCGTGCTGCTCAGGACTGGCTGAACGGCAAGGAGTACAAGTGCAAGGT |
| | | | CAGCAATAAGGACTGCCCAGCAGCATCGAGAAGACCATCTCCAAGGCTAAAGGCC |
| | | | AGCCCCGGGAACCTCAGGTGTACACCCTGCCTCCCAGCCAGGAGGAGATGACCAAG |
| | | | AACCAGGTGAGCCTGACCTGCCTGGTCAAGGGATTCTACCCTTCCGACATCGCCGTG |
| | | | GAGTGGGAGTCCAACGGCCAGCCCGAGAACAATTATAAGACCACCCCTCCCGTCCTC |
| | | | GACAGCGACGGATCCTTCTTTCTGTACTCCAGGCTGACCGTGGATAAGTCCAGGTGG |
| | | | CAGGAAGGCAACGTGTTCAGCTGCTCCGTGATGCACGAGGCCCTGCACAATCACTA |
| | | | CACCCAGAAGTCCCTGAGCCTGTCCCTGGGAAAG |
| 505 | CL-57945 | Light chain | Nucleotide sequence of light chain alternative coding | GAAATTGTGTTGACGACGTCTCCAGGCACCCTGTCTTGTCTCCAGGGAGGGGAGCC |
| | | | ACCCTCCTGCGAGGGCCAGTCCAGTGAGTATTAGCAACAACTTCTTAGCCTGGTACCAA |
| | | | CAGAAACCTGGCCAGGCTCCCAGACTCCTCATCTTTGGTGCATCCAGCAGGGCCACT |
| | | | GCCATCCCAGACAGGTTCGTTGGCAGTGGGTCTGGGACAGACTTCACTCTCACCATC |
| | | | ACCGGACTGGAGCCTGAAGATTTTGCAGTGTATCACTGTCAACACTATGGTGTTCA |
| | | | CCTTGGACGTTCGGCCAAGGGACCAAGGTGGAAATCAAACGTAACGGTGGCCGCTCC |
| | | | CTCCGTGTTCATCTTCCCACCTTCCACCCTCCGACGAGCAGGCACGTGAAGTCCGTC |
| | | | GTGTGCCTGCTGAACAACTTCTACCCCCGGAGGCCAAGGTGCAGTGGAAGGTGGA |
| | | | CAACGCCCTGCAGTCCGGCAACTCCGGCAACTCCGTGACCGAGCAGGACTCCAAGG |
| | | | ACAGCACCTACTCCCTGTCCTCCACCCTGACCCTGTCCAAGGCCGACTACGAGAAGC |
| | | | ACAAGGTGTACGCCTGCGAAGTGACCCACCAGGGCCTGTCTAGCCCCGTGACCAAG |
| | | | TCTTTCAACCGGGGCGAGTGT |
| 506 | CL-58102 | Heavy chain | Nucleotide sequence of heavy chain | CAGGTCCAGCTTGTGCAGTCTGGGGCTGAGGTGAAGAAGCCTGGGGCCTCAGTGA |
| | | | AAGTTTCCTGTAAGGCTTCTGGGTACAGTTTCACTAACTATGCTTTACATTGGGTGCG |
| | | | CCAGGCCCCCGGACAAAGACTTGAGTGGATGGGATGGATCAACGCTGGTAATGGTA |
| | | | AGACAGAATATGCCACAGAAGTTCCAGGACAGAGTCACCATTAGTAGGGACACATATCC |
| | | | GCGATCACAGTTTACATGGAACTGAGCAGCCTGAGATCTGAAGACACGGCTGTTTAT |
| | | | TATTGTGCGAGAGAACAGTTATGGTTACCCTTTGACTACTGGGGACACGGAACCCTG |
| | | | GTCACCGTCTCCTCAGCCTCCACCAAGGGCCCCTCCGTGTTCCCCTGGCCCCCTTGCA |
| | | | GCAGGAGCACCTCCGAATCCACAGCTCGCCCTGGGCTGTCTGGTGAAGGACTACTTTC |
| | | | CCGAGCCCGTGACCGTGAGCTGGAACTCCGGCGCTCTACTCCCTGTGGTGACCGTGC |
| | | | CTAGCTCCTCCCTCGGCACCAAGACCTACACCTGTAACGTGGACCACAAACCCTCCA |
| | | | ACACCAAGGTGGACAAACGGGTCGAGAGCAAGTACGGCCCCTCCCTGCCCTCCTTGT |
| | | | CCTGCCCCCGAGTTCGAGGGCGGACCCAGCCTGTTCCTGTTCCTCCTAAGCCCAAG |
| | | | GACACCCTCATGATCAGCCGGACCACCGAGGTGACCTGCGTGGTGGTGGATGTGAG |

-continued

SEQUENCES:

| Seq ID No: | | Description | Sequence |
|---|---|---|---|
| 507 | CL-58102 | Light chain Nucleotide sequence of light chain | CCAGGAGGACCCTGAGGTCCAGTTCAACTGGTATGTGGATGGCGTGGAGGTGCACA ACGCCAAGACAAAGCCCCGGGAAGAGCAGTTCAACTCCACCTACAGGGTGGTCAGC GTGCTGACCGTGCTGCATCAGGACTGGCTGAACGGCAAGGAGTACAAGTGCAAGGT CAGCAATAAGGACTGCCCAGCAGCATCGAGAAGACCATCTCCAAGGCTAAAGGCC AGCCCCGGGAACCTCAGGTGTACACCCTGCCCCCAGCCAGGAGGAGATGACCAAG AACCAGGTGAGCCTGACCTGCCTGGTGAAGGGATTCTACCCTTCCGACATCGCCGTG GAGTGGGAGTCCAACGGCCAGCCCGAGAACAATTATAAGACCACCCCTCCCGTCCTC GACAGCGACGGATCCTTCTTTCTGTACTCCAGGCTGACCGTGGATAAGTCCAGGTGG CAGGAAGGCAACGTGTTCAGCTGCTCCGTGATGCACGAGGCCCTGCACAATCACTA CACCCAGAAGTCCCTGAGCCTGTCCCTGGGAAAG |
| 508 | CL-58252 | Heavy chain Nucleotide sequence of heavy chain | GAAATTGTGTTGACGCAGTCTCCAGACACCCTCTCTTTGTCTCCAGGGGAAACAGCC AGTTTCTCTGCAGGGCCGGTCAAATTATTATCAACAGACAGTTAGCCTGGTACCAG CGGAGACCTGGCCAGGCTCCCAGGCTCCTCATCTATGGCGCGTCCAATAGGGTCACT GGCATCCCAGACAGGTTCAGTGGCAGTGGGTCTGGGACAGACTTCACTCTCACGAT CAATAGACTGGAGCCTGAAGATTTTGCAGTGTATTACTGTCAGCACTATGGTGGCTC ACCTTGGACGTTCGGCCAAGGGACCAAGGTGGAAATCAAACGTACGGTGGCCGCTC CCTCCGTGTTCATCTTCCCACCTTCCGACGAGCAGCTGAAGTCCGGCACCGCTTCTGT CGTGTGCCTGCTGAACAACTTCTACCCCCGCGAGGCCAAGGTGCAGTGGAAGGTGG ACAACGCCCTGCAGTCCGGCAACTCCCAGGAATCCGTGACCGAGCAGGACTCCAAG GACAGCACCTACTCCCTGTCCTCCACCCTGACCCTGTCCAAGGCCGACTACGAGAAG CACAAGGTGTACGCCTGCGAAGTGACCCACCAGGGCCTGTCTAGCCCCGTGACCAA GTCTTTCAACCGGGGCGAGTGT |
| | | | CAGGTCCAGTTTGTGCAGTCTGGGGCTGAGGTGAAGAAGCCTGGGGCCTCAGTGAA GGTTTCCTGTAAGGCTTCTGGATACACCTTCACTAGCCATGCTATGCATTGGGTGCG CCAGGCCCCCGGACAAAGGCTTGAGTGGATGGGATGGATCAACGCTGCCAATGGTA AACAGATTATTCACAGAACTTCCAGGCAGAGTCACCATTACCAGGGACACACATACG CGAACACAGTCTACATGGAACTGAGCAGCCTGAGATCTGAAGACACGGCTGTGTAT TACTGTGCGAGACGCCCTTACGGTGGTCCTTTGACTACTGGGGCCAGGGAACCCTG GTCACCGTCTCCTCAGCCAGCACCAAGGGCCCCTCCGTGTTCCCCCTGGCCCCCTGCA GCAGGAGCACCTCCGAATCCACAGCTGCCCTGGGCTGCCTCGTGAAGGACTACTTTC CCGAGCCCGTGACCGTGAGCTGGAACAGCGGCGCCCTGACCATCGGCGTCCACACC TTTCCTGCCGTCCTGCAGTCCTCCGGCCTCTACTCCCTGTCCTCCGTGGTGACCGTGC CTAGCTCCTCCCTGGGCACCCAGACCTACATCTGTAACGTGAACCACAAACCCTCCA ACACCAAGGTGGACAAACGGGTCGAGACGCTGGACCTGGATGTTCCGTGCTCCCAGAAG CCTGCCCCCGAGTTCGAAGGCGGACCACACCCGAGGTGTTCCTGTTCCCTCCTAAGCCCAAG GACACCCTCATGATCAGCCGGACACCCCTGAGGTGACCTGCGTGGTGGTGGATGTGAG CCAGGAGGACCCTGAGGTCCAGTTCAACTGGTATGTGGATGGCGTGGAGGTGCACA ACGCCAAGACAAAGCCCCGGGAAGAGCAGTTCAACTCCACCTACAGGGTGGTCAGC GTGCTGACCGTGCTGCATCAGGACTGGCTGAACGGCAAGGAGTACAAGTGCAAGGT CAGCAATAAGGACTGCCCAGCAGCATCGAGAAGACCATCTCCAAGGCTAAAGGCC AGCCCCGGGAACCTCAGGTGTACACCCTGCCCCCAGCCAGGAGGAGATGACCAAG AACCAGGTGAGCCTGACCTGCCTGGTGAAGGGATTCTACCCTTCCGACATCGCCGTG |

-continued

SEQUENCES:

| Seq ID No: | Description | Sequence |
|---|---|---|
| | | GAGTGGGAGTCCAACGGCCAGCCCGAGAACAATTATAAGACCACCCCTCCCGTCCTC GACAGCGACGGATCCTTCTTCTTGTACTCCAGGCTGACCGTGGATAAGTCCAGGTGG CAGGAAGGCAACGTGTTCAGCTGCTCCGTGATGCACGAGGCCCTGCACAATCACTA CACCCAGAAGTCCCTGAGCCTGTCCCTGGGAAAG |
| 509 | Light chain Nucleotide sequence of light chain | GACATCCAGATGACCCAGTCTCCTTCCACCCTGTCTGCATCTGTAGGAGACAGAGTC ACCATCACTTGCCGGGCCAGTCAGAGTATTAGTAGTATCTGGTTGGCCTGGTATCAGCAG AAACCAGGGAAAGCCCCTAAGCTCCTGATCTATAAGGCGTCTAGTTTAGAAAGTGG GGTCCCATCAAGGTTCAGCGGCAGTGGATCTGGGACAGAATTCACTCTCACCATCAG CAGCCTGCAGCCTGATGATTTTGCAACTATTACTGTCAACAGTATAATCTTTATCCG TGGACGTTCGGCCAAGGGACCAAGGTGGAAATCAAACGTACGGTGGCCGCTCCCTC CGTGTTCATCTTCCCACCTTCCGACGAGCAGCTGAAGTCCGGCACCGCCTCTGTCGTG TGCCTGCTGAACAACTTCTACCCCCGGGAGGCCAAGGTGCAGTGGAAGGTGGACAA CGCCCTGCAGTCCGGCAACTCCCAGGAATCCGTGACCGAGCAGGACTCCAAGGACA GCACCTACTCCCTGTCCTCCACCCTGACCCTGAGCAAGGCCGACTACGAGAAGCACA AGGTGTACGCCTGCGAAGTGACCCACCAGGGCCTGTCTAGCCCCGTGACCAAGTCTT TCAACCGGGGCGAGTGT |
| 510 | Heavy chain Nucleotide sequence of heavy chain alternative coding | CAGGTCCAGTTTGTGCAGTCTGGGGCTGAGGTGAAGAAGCCTGGGGCTCAGTGAA GGTTTCTGTAAGGCTTCTGGATACACCTTCACTAGCCATGCTATGCATTGGGTGCG CCAGGCCCCCGGACAAAGGCTTGAGTGGATGGGATGGATCAACGCTGCCAATGGTA AAACAGATTATTCACAGAACTTCCAGGGCAGCAGTTCACCATTACCAGGGACACATACG CGAACACAGTCTACATGGAACTGAGCAGCCTGAGATCTGAAGACACGGCTGTGTAT TACTGTGCGAGACGTCTCCTCAGCCAGCACCAAGGGCCCTTCCGTGTTCCCCCTGGCCCCTTGCA GCAGGAGCACCTCCGAATCCACAGCTGCCCTGGGCTGCCTCGTGAAGGACTACTTTC CCGAGCCCGTGACCGTGAGCTGGAACAGCGGCGCCCTGACCAGCGGCGTCCACACC TTTCCTGCCGTCCTGCAGTCCTCCGGCCTACCACTGTGACCGTGACCGTGCCCTCTCCGTGGTGACCGTGC CTAGCTCCTCCCTCGGCACCCAGACCTACATCTGCAACGTGAATCACAAGCCCTCCA ACACCAAGGTGGACAAACGGGTCGAGAGCAAGTACGGCCCTCCCTGCCCTCCTTGT CCTGCCCCCGAGTTCGAAGGCGGACCCAGCGTGTTCCTGTTCCCTCCAAAGCCCAAG GACACCCTCATGATCAGCCGGACCCCTGAGGTGACCTGCGTGGTGGTGGATGTGAG CCAGGAGGACCCTGAGGTCCAGTTCAACTGGTATGTGGACGGCGTGGAGGTGCACA ACGCCAAGACAAAGCCCGGGAGAGGAGCAGTTCAACTCCACCTACAGGGTGGTCAGC GTGCTGACCGTGCTGCATCAGGACTGGCTGAACGGCAAGGAGTACAAGTGCAAGGT CAGCAATAAGGACCTGCCCAGCAGCATCGAGAAGACCATCTCCAAGGCTAAAGGCC AGCCCCGGGAACCTGAGGTGTACACCCTGCCTGGTGAAGGGCGATTCTACCCCTTCCGACATCGCCGTG GAGTGGGAGTCCAACGGCCAGCCCGAGAACAATTATAAGACCACCCCTCCCGTCCTC GACAGCGACGGATCCTTCTTCTTGTACTCCAGGCTGACCGTGGATAAGTCCAGGTGG CAGGAAGGCAACGTGTTCAGCTGCTCCGTGATGCACGAGGCCCTGCACAATCACTA CACCCAGAAGTCCCTGAGCCTGTCCCTGGGAAAG |
| 511 | Light chain Nucleotide sequence of light chain alternative coding | GACATCCAGATGACCCAGTCTCCTTCCACCCTGTCTGCATCTGTAGGAGACAGAGTC ACCATCACTTGCCGGGCCAGTCAGAGTATTAGTAGTATCTGGTTGGCCTGGTATCAGCAG AAACCAGGGAAAGCCCCTAAGCTCCTGATCTATAAGGCGTCTAGTTTAGAAAGTGG GGTCCCATCAAGGTTCAGCGGCAGTGGATCTGGGACAGAATTCACTCTCACCATCAG |

-continued

SEQUENCES:

| Seq ID No: | | Description | Sequence |
|---|---|---|---|
| | | | CAGCCTGCAGCCTGATGATTTTGCAACTTATTACTGTCAACAGTATAATCTTTATCCG |
| | | | TGGACGTTCGGCCAAGGGACCAAGGTGGAAATCAAAACTACGGTGGCCGCTCCCTC |
| | | | CGTGTTCATCTTCCCACCTTCCGACGAGCAGCTGAAGTCCGGCACCGCTTCTGTCGTG |
| | | | TGCCTGCTGAACAACTTCTACCCCCGCGAGGCCAAGGTGCAGTGGAAGGTGGACAA |
| | | | CGCCCTGCCAGTCCGACAACTCCCAGGAATCCGTGACAGAGCAGGACTCCAAGGACA |
| | | | GCACCTACTCCCTGTCCTCCACCCTGACCCTGTCCAAGGCCGACTACGAGAAGCACA |
| | | | AGGTGTACGCCTGCGAAGTGACCCACCAGGGCCTGTCTAGCCCCGTGACCAAGTCTT |
| | | | TCAACCGGGGCGAGTGT |
| 512 | CL-58838 | Heavy chain Nucleotide sequence of heavy chain | CAGGTGCAACTGGTGGAGTCTGGGGGAGGCTTGGTCAAGCCTGGAGGGTCCCTGA |
| | | | GACTCCTGTGCAGCCTCTGGATTCACCTTCAGTGACTACTACATGAGTTGGATCCG |
| | | | CCAGGCTCCAGGGAAGGGGCTGGAGTGGGTTTCATACATTAGTATTAGTGGTAGTA |
| | | | CCATATACTACGCAGACTCTGTGAAGGGCGATTCACCATCTCCAGGGACAACGCCA |
| | | | TGGACTCACTGTATCTGCAAATGAACAGCCTGAGAGCCGAGGACACGCCGTGTAT |
| | | | TACTGTGCGAGACGGAGCAGTGGCTGGTACGACTACTGGGGCCAGGGAACCCTGG |
| | | | TCACCGTCTCCTCAGCAGCCACCAAGGGCCCTTCCGTTCCCCTGGCCCCTTGCAG |
| | | | CAGGAGCACCTCCGAATCCACAGCTGCCCTGGGCTGTCTGGTGAAGGACTACTTTCC |
| | | | CGAGCCCGTGACCGTGAGCTGGAACAGCGGCGTCTGACATCCGGCGTCCACACCT |
| | | | TTCCTGCCGTCCTGCAGTCCTCAGGACTCTACTCCCTCAGCAGCGTGGTGACCGTGCC |
| | | | TAGCTCTCCCTGCCTCGGCACCAAGACCTACACCTGTAACGTGACCACAAACCCTCCAA |
| | | | CACCAAGGTGGACAAGCCCGGGAGGTCGAGAGCAAGTACGGCCCCTCCTCCTCGTCC |
| | | | TGCTGACCGTGCCTGCCATCAGGAACGGCGACCGCTGTTCCTGTTCCCTCCTAAGCCCAAGGA |
| | | | AGCAATAAGGGACTGCCCAGCACATCGAAGAACCATCTCCAAGGCTAAAGCCA |
| | | | GCCCCGGGAACCTCAGGTGTACACCCTGCCTGGTCAGGGGATTCTACCCTTCCGACATCGCCGTGG |
| | | | ACCAGGTGAGCCTGACCTGCCTGGTGAAGGGATTCTATGAAGACACCACCCCTCCCGTCCCTCG |
| | | | AGTGGGAGTCCAACGGCCCAGGAGAACAATTATAAGACCACCCCTCCCGTCCCTCG |
| | | | ACAGCGACGGATCCTTCTTTCTGTACTCCAAGCTGACCGTGGATAAGTCCAGGTGGC |
| | | | AGGAAGGCAACGTGTTCAGCTGCTCCGTGATGCACGAGGCCCTGCACAATCACTAC |
| | | | ACCCAGAAGTCCCTGACCCTGTCCCTGGGAAAG |
| 513 | CL-58838 | Light chain Nucleotide sequence of light chain | GAAATTGTTGTTGACGCAGTCTCCAGGCACCCTGTCTTTGTCTCCAGGGGAAAGAGCC |
| | | | ACCCTCTCTTGTTTGGGCCAGTCAGAGGGTTGTTACAGATACTTAGCCTGGTACCAG |
| | | | CGGAAACCTGGCCAGGCTCCCAGACTTCTCATTTATGGTGCATTCAACAGGGCCACT |
| | | | GGCATCCCAGACAGGTTCAGTGGCAGTGGGTCTGGGACAGACTTCAGTCTCACTAT |
| | | | CAGTAGACTGGAGCCTGAGGATTTTGCAGTTTATTACTGTCACCAATATGGTAGTTC |
| | | | ACCACCGACGTTCGGCCAAGGGACCAAGGTGGAAATCAAACTGGAAATCAAACTGTGGCCCGCTC |
| | | | CCTCCGTGTTCATCTTCCCACCTTCCGACGAGCAGCTGAAGTCCGGCACCGCTTCTGT |
| | | | CGTGTGCCTGCTGAACAACTTCTACCCCCGCGAGGCCAAGGTGCAGTGGAAGGTGG |
| | | | ACAACGCCCTGCAATCCGGCAACTCCCAGGAATCCGTGACCGAGCAGGACTCCAAG |
| | | | GACAGCACCTACTCCCTGTCCTCCACCCTGACCCTGTCCAAGGCCGACTACGAGAAG |
| | | | CACAAGGTGTACGCCTGCGAAGTGACCCACCAGGGCCTGTCTAGCCCCGTGACCAA |
| | | | GTCTTTCAACCGGGGCGAGTGT |

-continued

SEQUENCES:

| Seq ID No: | | Description | Sequence |
|---|---|---|---|
| 514 | CL-58838 | Heavy chain | Nucleotide sequence of heavy chain alternative coding | CAAGTTCAGTTGGTTGAGTCTGGCGGCGGGACTGGTTAAGCCTGGCGGATCTCTGAG<br>ACTGTCTTTGTGCCGCCCTCTGGCTTCACCTTCTCCGACTACTACATGTCCTGGATCAGA<br>CAGGCCCCTGGCAAAGGCCTGGAATGGGTGTCCTACATCTCCATCTCCGGCTCCACC<br>ATCTACTACGCGACTCCCTGAGGGCAGATTCACCATCTCCAGAGACAACGCCATG<br>GACTCCCTGACCTGCCAGATGAACTCCCTGAGAGCCGAGGACACCGCCGTGTACTAC<br>TGCGCCCGTAGATCCTCTGCAGCCACCAAGGGCCCTTCCGTTCCCCTGGCCCCTGCAGCCAG<br>AGTGTCCTTGCTGCAGCCACCAAGGGCCCTTCCGTTCCCCTGGCCCCTGCAGCAG<br>GAGCACCTCCGAATCCACAGCTGCCCTGGGCTGTCTGGTGAAGGACTACTTTCCCGA<br>GCCCGTGACCGTGAGCTGGAACAGCGGCGTCCGTCCTGACCACCTTTCC<br>TGCCGTCCCTGCAGTCTCCTGGTCTCTCCCGTGGTGACCGTGCCTAGC<br>TCCTCCCTGGCACCAAGACCTACACCTGTAAACGTGGACCACAAACCCTCCAACACC<br>AAGGTGGACAAACGGGTCGAGAGCAAGTACGGCCCTCCCTGCCCTCCTTGTCCTGC<br>CCCGAGTTCGAAGGGCGGACCCAGCGTGTTCCTGTTCCCTCCTAAGCCCAAGGACAC<br>CCTCATGATGACGCCGGACACCCGAGGTGACCTGCGTGGTGGATGTGAGCCAGG<br>AGGACCCTGAGGTCCAGTTCAACTGGTATGTGGATGGCGTGGAGGTGCACAACGCC<br>AAGACAAAGCCCGGAAGAGACAGTTCAACTCCACCTACAGGGTGGTCAGGTGCT<br>GACCGTGCTGCATCAGGACTGGCTGAACGGCAAGGAGTACAAGTGCAAGGTCAGC<br>AATAAGGAGCTGCCAGCAGCATCGAGAAGACCATCTCCAAGGCTAAAGGCCAGCC<br>CCGGGAACCTTCAGGTGTACACCCTGCCTCCCCAGCCAGGAGGATGACCAAGAACC<br>AGGTGAGCCTGACCTGCCTGGTGAAAGGGGATTCTAACCTTCCGACATGCTGGAG<br>TGGGAGTCCAACGGCCAGCCCGAGAACAATTATAAGACCACCCCTCCCGTCCTCGAC<br>AGCGACGGATCCTTCTTTCTGTACTCCAGGCTGACCGTGGATAAGTCCAGGTGGCAG<br>GAAGGCAACGTGTTCAGCTGCTCCGTGATGCACGAGGCCCTGCACAATCACTACACC<br>CAGAAGTCCCTGAGCCTGTCTCCCTGGGAAAG |
| 515 | CL-58838 | Light chain | Nucleotide sequence of light chain alternative coding | GAAATTGTGCTGACTCAGTCCCCTGGCACACTGTCTTTGAGCCCTGGCGAGAGAGCT<br>ACCCTGTCTTGTTGGGCCTCTCAGAGACGGTGTACAGATACCTGGCTTGGTATCAG<br>CGGAAGCCCGGCCAGGCTCCTAGACTGTTGATCTACGGCGCCTTCAACAGAGCCAC<br>AGGCCATCCCTGACCAGATTCTCCGGCTCTGGCTCTGGCACCGACTTCTCCCTGACTATC<br>TCTCGGCTGGAACCCGGAGGACTTCGCCGTGTACTACTGTCACCAGTACGGCCAGC<br>CCTCCTACCTTTGCCAGGGCACTAAGGTGGAAATCAAACGTACGGTGGCCGCTCCC<br>TCCGTGTTCATCTTCCCACCTTCCACCCCGCAGAGCAGCTGAAGTCCGGCACCGCTTCTGTCG<br>TGTGCCTGCTGACAACTTCTACCCCCGCAGAGCCAAGGTGCAGTGGAAGGTGGAC<br>AACGCCCTGCAGTCCGGCAACTCCCAGGAATCCGTGACCGAGCAGGACTCCAAGGA<br>CAGCACCTACTCCCTGTCCTCCACCCTGACCCTGTCCAAGGCCGACTACGAGAAGCA<br>CAAGGTGTACGCCTGCGAAGTGACCCACCAGGGCCTGTCTAGCCCCGTGACCAAGT<br>CTTTCAACCAGGGCGAGTGT |
| 516 | CL-58838 | Heavy chain | Nucleotide sequence of heavy chain alternative coding | CAGGTTCAGCTGGTTGAATCTGGCGGCGGGACTGGTTAAGCCTGGCGGATCTCTGAG<br>ACTGTCTTTGTGCCGCCCTCTGGCTTCACCTTCTCCGACTACTACATGTCCTGGATCAGA<br>CAGGCCCCTGGCAAAGGCCTGGAATGGGTGTCCTACATCTCCATCTCCGGCTCCACC<br>ATCTACTACGCGACTCCCTGAGGGCAGATTCACCATCTCCAGAGACAACGCCATG<br>GACTCCCTGACCTGCCAGATGAACTCCCTGAGAGCCGAGGACACCGCCGTGTATAC<br>TGCGCCCGTAGATCCTCTGCTTCTACCAAGGGACCCAGCGTGTTCCCTCTGGCTCCTTGCTCTCCAGA<br>AGTGTCCTCTGCTTCTTACCAAGGGACCCAGCGTGTTCCCTCTGGCTCCTTGCTCTCCAGA<br>TCCACCTCCGAGTCTACAGCTGTACAGCTGTACCTGTCAAGGACTACTTTCCTGAG<br>CCTGTGACCGTGTCCTGGAACTCTGGGCGCTCTGTCACATCTGGCGTCACCTTCCA |

-continued

SEQUENCES:

| Seq ID No: | | Description | Sequence |
|---|---|---|---|
| 517 | CL-58838 | Light chain | Nucleotide sequence of light chain alternative coding | GCTGTGTCTGCAGTCCTCCGGCCTGTACTCTCTGTCTCTCTGTGTGACCGTGCCTTCCT<br>CTAGCCTGGGCACCAAGACCTACACCTGTAATGTGGACCACAAGCCTTCCAACACCA<br>AGGTGGACAAGCGCGTGGAATCTAAGTACGGCCCTCCTTGTCCTCCATGTCCTGCTC<br>CAGAGTTTGAAGGCGGCCCCTTCGTGTTTCTGTTCCCTCCAAAGCCTAAGGACACCC<br>TGATGATCTCTCGGACCCCTGAAGTGACCTGCGTGGTGGTGGTGTCCAAGAG<br>GACCCTGAGGTGCAGTTCAATTGGTACGTGGACGGCGTGGAAGTGCACAACGCCAA<br>GACCAAGCCTAGAGAGGAACAGTTCAACTCCACCTACAGAGTGGTGTCCGTGCTGA<br>CCGTGCTGCACCAGGATTGGCTGAACGGCAAAGAATACAAGTGCAAGGTGTCCAAC<br>AAGGGCCTGCCTAGCTCCATCGAAAAGACCATCAGCAAGGCCAAGGGCCAGCCTCG<br>AGAACCCCAGGTTTACACCCTGCCTCCAAGCCAAGGAGGAAATGACCAAGAACCAGG<br>TGTCCCTGACCTGCCTCGTGAAGGGATTCTACCCTTCCGATATCGCCGTGGAATGGG<br>AGTCTAATGGCCAGCCAGAGAACAACTACAAGACAACCCCTCCTGTGCTGGACTCCG<br>ACGGCTCCTTCTTTCTGTATTCCCGCCTGACCGTGGACAAGTCCAGATGGCAAGAGG<br>GCAACGTGTTCTCCTGCAGCGTGATGCACGAGGCCCTGCACAATCACTACACCCAGA<br>AGTCCCTGTCTCTGTCCCTGGGCAAG |
| 518 | CL-58838 | Heavy chain | Nucleotide sequence of heavy chain IgG4-PE Version A | GAGATCGTGCTGACCCAGTCTCCTGGCACACTGTCTCTCTCAGGCGAGAGAGCT<br>ACCCTGTCTGTTGGGCCTCTCAGAGAGTGGTGTACAGATACCTGGCTTGGTATCAG<br>CGGAAGCCCCGGCCAGGCTCCTAGACTGTTGATCTACGGCGCCTTCAACAGAGCCAC<br>AGGCATCCTGACCAGATTCTCCGGCTCTGGCTCCGGCACCGACTTCTCCCTGACTATC<br>TCTCGGCTGGAACCCGAGGACTTCGCCGTGTACTACTGTCACCAGTACGGCCAGCAGC<br>CCTCCTACCTTTGGCCAGGGCACCAAGGTGGAAATCAAGCGTACGGTGGCCGCTCC<br>CAGCGTGTTCATCTTCCCCCAGCGACGAGCAGCTGAAGAGCGGCACCGCCAGCG<br>TGGTGTGTCTGCTGAACAACTTCTACCCCAGGGAGGCCAAGGTGCAGTGGAAGGTG<br>GACAACGCCCTGCAGAGCGGCAACAGCCAGGAGAGCGTCACCGAGCAGGACAGCA<br>AGGACTCCACCTACAGCCTGAGCAGCACCCTGACCCTGAGCAAGGCCGACTACGAG<br>AAGCACAAGGTGTACGCCTGTGAGGTGACCCACCAGGGCCTGTCCAGCCCCGTGAC<br>CAAGAGCTTCAACAGGGGCGAGTGC |
| | | | | CAGGTGCAACTGGTGGAGTCTGGGGGAGGCTTGGTCAAGCCTGGAGGGTCCCTGA<br>GACTCTCCTGTGCAGCCTCTGGATTCACCTTCAGTGACTACTACATGAGTTGGATCCG<br>CCAGGCTCCAGGGAAGGGGCTGGAGTGGGTTTCATACATTAGTAGTAGTGGTAGTA<br>CCATATACTACCGGCAGACTCTGTGAAGGGCCGATTCACCATCTCCAGGGACAACGCCA<br>TGGACTCACTGTATCTGCAAATGAACAGCCTGAGAGCCGAGGACACGGCCGTGTAT<br>TACTGTGCGACGACGAGCAGTGGCTGGTACGACTACTGGGGCCAGGGAACCCTGG<br>TCACCGTCTCCTCAGCTTCCACCAAGGGCCCATCCGTCTTCCCCCTGGCGCCCTGCTC<br>CAGGAGCACCTCCGAGAGCACAGCGGCCCTGGGCTGCCTGGTCAAGGACTACTTCC<br>CCGAACCAGTGACGGTGTCGTGGAACTCAGGCGCCCTGACCAGCGGCGTGCACACC<br>TTCCCGGCTGTCCTACAGTCTCCTCAGGACTCTACTCCCTCAGCAGCGTGGTGACCGTG<br>CCCTCCAGCAGCTTGGGCACGAAGACCTACACCTGCAACGTAGATCACAAGCCCAGC<br>AACACCAAGGTGGACAAGAGAGTTGAGTCCAAATATGGTCCCCCATGCCCACCATG<br>CCCAGCACCTCTGAATTTGAGGGGGGACCATCAGTCTTCTGTTCCCCCCAAAACCCAA<br>GGACACTCTCATGATCTCCCGGACCCCTGAGGTCACGTGCGTGGTGGTGGACGTGA<br>GCCAGGAAGACCCCGAGGTCCAGTTCAACTGGTACGTGGATGGCGTGGAGGTGCA<br>TAATGCCAAGACAAAGCCGCGGGAGGAGCAGTTCAACAGCACGTACCGTGTGGTCA<br>GCGTCCTCACCGTCCTGCACCAGGACTGGCTGAACGGCAAGGAGTACAAGTGCAAG<br>GTCTCCAACAAAGGCCTCCCGTCATCCGATCGAGAAAACCATCTCCAAAGCCAAAGGG |

-continued

SEQUENCES:

| Seq ID No: | | Description | Sequence |
|---|---|---|---|
| | | | CAGCCCCGAGAGAGCCACAGGTGTACACCCTGCCCCATCCCAGGAGGAGATGACCAA |
| | | | GAACCAGGTCAGCCTGACCTGCCTGGTCAAAGGCTTCTACCCCAGCGACATCGCCGT |
| | | | GGAGTGGGAGAGCAATGGGCAGCCGGAGAACAACTACAAGACCACGCCTCCCGTG |
| | | | CTGGACTCCGACGGATCCTTCTTCCTCTACAGCAAGCTAACCGTGGACAAGAGCAGG |
| | | | TGGCAGGAGGGGAATGTCTTCTCATGCTCCGTGATGCATGAGGCTCTGCACAACCA |
| | | | CTACACACAGAAGAGCCTCTCCCTGTCTCTGGGTAAA |
| 519 | CL-58838 | Heavy chain Nucleotide sequence of heavy chain IgG4-PE Version B | CAGGTGCAACTGGTGGAGTCTGGGGGAGGCGTTGGTCAAGCCTGGAGGGTCCCTGA |
| | | | GACTCTCCTGTGCAGCCTCTGGATTCACCTTCAGTGACTACTACATGAGTTGGATCCG |
| | | | CCAGGCTCCAGGGAAGGGGCTGGAGTTCATACATTAGTATTAGTGGTAGTA |
| | | | CCATATACTACGCAGACTCTGTGAAGGGCCGATTCACCATCTCCAGGGACAACGCCA |
| | | | TGGACTCACTGTATCTGCAAATGAACAGCCTGAGAGCCGAGGACACGGCCGTGTAT |
| | | | TACTGTGCGAGACGGAGCAGTGGTGGTACGACTACTGGGGCCAGGGAACCCTGG |
| | | | TCACCGTCTCCTCAGCTTCCACCAAGGGACCTAGCGTGTTCCCTCTGCCCCCCTGTTC |
| | | | CAGGTCCACAAGCGAGTCCACCCTGCCCTGCGTGTCTGGTGAAAGACTACTTTCC |
| | | | CGAGCCCGTGACCGTCTCCTGGAATAGCGGAGCCCTGACCTCCGGCGTGCACACATT |
| | | | TCCCGCCGTGCTGCAGAGCAGCGGACTGTATAGCCTGAGCAGCGTGGTGACCGTGC |
| | | | CCAGCTCCAGCCTGGGCACCAAAACCTACACCTGCAACGTGGACCACAAGCCCTCCA |
| | | | ACACCAAGGTGGACAAGCGGGTGGAGAGCAAGTACGGCCCCCCCTTGCCCTCCTTGT |
| | | | CCTGCCCCTGAGTTCGAGGGAGGACCCTCCGTGTTCCTGTTCCCCCCAAACCCAAG |
| | | | GACACCCTGATGATCTCCCGGACCCCAGAGGTGACCTGTGTGGTGGACGTCAG |
| | | | CCAGGAAGACCCGGAGGTCAGTTCAACTGGTATGTGGACGGCGTGGAGGTGCAC |
| | | | AATGCCAAAACCAAGCCCAGGGAGGAGCAGTTCAATTCCACCTACAGGGTGGTGAG |
| | | | CGTGCTGACCGTCCTGCATCAGGATTGGCTGAACGGCAAGGAGTACAAGTGCAAGG |
| | | | TGTCCAACAAGGACTGCCCAGCTCCATCGAGAAACATCAGCAAGGCTAAGGGC |
| | | | CAGCCGAGGGAGCCCCAGGTGTATACCCTGCCTCCTAGCCAGGAAGAGATGACCAA |
| | | | GAACCAAGTGTCCCTGACCTGCCTGGTGAAGGGATTCTACCCCTCCGACATCGCCGT |
| | | | GGAGTGGGAGAGCAATGGCCAGCTTCTTTCTTCCTACAGCAAGCTGACCGTGGACAAGAGCCGGTGC |
| | | | TCGATAGCGACGGCAGCTTCTTTCTCTACAGCCGGCTGACAGTGACCAAGAGCAGG |
| | | | TGGCAGGAGGGCAACGTGTTCTCCTGTTCCGTGATGCACGAGGCCCTGCACAATCA |
| | | | CTACACCCAGAAGAGCCTCTCCCTGTCCCTGGGCAAG |
| 520 | CL-58838 | Heavy chain variable region Nucleotide sequence of V$_H$ alternative coding | CAGGTTCAGCTGTTGGTAATCTGGCGGCGGACTGGTTAAGCCTGGCGGATCTCTGAG |
| | | | ACTGTCTTGTGCGCCCTCTGGCTTCACCTTCTCCGACTACTACATGTCCTGGATCAGA |
| | | | CAGGCCCCTGGCCAAGGGCCTGGAATGGGTGTCCTACATTCCATCTCCGGCTCCACC |
| | | | ATCTACTACGCCGACTCCGTGAAGGGCAGATTCACCATCTCCAGAGACAACGCCATG |
| | | | GACTCCCTGTACCTGCAGATGAACTCCCTGAGAGCCGAGGACACCGCCGTGTACTAC |
| | | | TGCGCCCGTAGATCCTCTGGATGGTACGACTATTGGGGCCAGGGCACCCTGGTCAC |
| | | | AGTGTCCTCT |
| 521 | CL-58838 | Heavy chain variable region Nucleotide sequence of V$_H$ alternative coding | CAGGTTCAGTTGTTGGTAGTCTGGCGGCGGACTGGTTAAGCCTGGCGGATCTCTGAG |
| | | | ACTGTCTTGTGCGCCCTCTGGCTTCACCTTCTCCGACTACTACATGTCCTGGATCAGA |
| | | | CAGGCCCCTGGCCAAGGGCCTGGAATGGGTGTCCTACATTCCATCTCCGGCTCCACC |
| | | | ATCTACTACGCCGACTCCGTGAAGGGCAGATTCACCATCTCCAGAGACAACGCCATG |
| | | | GACTCCCTGTACCTGCAGATGAACTCCCTGAGAGCCGAGGACACCGCCGTGTACTAC |
| | | | TGCGCCCGTAGATCCTCTGGATGGTACGACTATTGGGGCCAGGGCACCCTGGTCAC |
| | | | AGTGTCCTCT |

-continued

SEQUENCES:

| Seq ID No: | | Description | Sequence |
|---|---|---|---|
| 522 | CL-58838 | Light chain variable region | Nucleotide sequence of V_L alternative coding | GAGATCGTGCTGACCCAGTCTCCTGGCACACTGTCACTGTCTCCAGGCGAGAGAGCT ACCCTGTCTTGTTGGGCCTCTCAGAGAGTGGTGTACAGATACCTGGCTTGGTATCAG CGGAAGCCCGGCCAGGCTCCTAGACTGTTGATCTACGGCGCCTTCAACAGAGCCAC AGGCATCCCTGACAGATTCTCCGGCTCTGGCCTGTCTACTGTCACCAGTACGGCAGC TCTCGGCTGGAACCGAGGACTTCGCCGTGTACTACTGTCACCAGTACGGCAGCAGC CCTCCTACCTTTGGCCAGGGCACCAAGGTGGAAATCAAG |

| Seq ID No: | | Description | | Sequence |
|---|---|---|---|---|
| 522 | CL-58838 | Light chain variable region | Nucleotide sequence of V_L alternative coding | GAGATCGTGCTGACCCAGTCTCCTGGCACACTGTCACTGTCTCCAGGCGAGAGAGCT<br>ACCCTGTCTTGTTGGGCCTCTCAGAGAGTGGTGTACAGATACCTGGCTTGGTATCAG<br>CGGAAGCCCGGCCAGGCTCCTAGACTGTTGATCTACGGCGCCTTCAACAGAGCCAC<br>AGGCATCCCTGACAGATTCTCCGGCTCTGGCCTGTCTACTGTCACCAGTACGGCAGC<br>TCTCGGCTGGAACCGAGGACTTCGCCGTGTACTACTGTCACCAGTACGGCAGCAGC<br>CCTCCTACCTTTGGCCAGGGCACCAAGGTGGAAATCAAG |
| 523 | CL-58838 | Light chain variable region | Nucleotide sequence of V_L alternative coding | GAAATTGTGCTGACTCAGTCCCCTGGCACACTGTCTTTGAGCCCTGGCGAGAGAGCT<br>ACCCTGTCTTGTTGGGCCTCTCAGAGAGTGGTGTACAGATACCTGGCTTGGTATCAG<br>CGGAAGCCCGGCCAGGCTCCTAGACTGTTGATCTACGGCGCCTTCAACAGAGCCAC<br>AGGCATCCCTGACAGATTCTCCGGCTCTGGCCACCGACTTCTCCCTGACTATC<br>TCTCGGCTGGAACCGAGGACTTCGCCGTGTACTACTGTCACCAGTACGGCAGCAGC<br>CCTCCTACCTTTGGCCAGGGCACTAAGGTGGAAATCAAA |
| 524 | CL-58851 | Heavy chain | Nucleotide sequence of heavy chain | CAGGTCCAACTTGTGCAGTCTGGGGCTGAGGTGAAGAAGCCTGGGGCCTCAGTGAA<br>GGTTTCCTGCAAGGCTACTGGATTCACCTTCATTACCTATGCTTTCCATTGGGTGCGC<br>CAGGCCCCCGGACAAAGGTTTGAGTGGATGGGATGGATCAACTGGTCAATGGTAA<br>CAGAGAATATTCACAGAAGTTCCAGGACAGAGTCACCATTACCAGGGACACATCCG<br>CGACCACAGTCTACATGGAACTGAACAGCCTGAGATCTGAAATCTGAAGACACGGCTATGTATT<br>TCTGTGCGAGAACGCCCCCTCTGGGGTCCTTTGACTACTGGGGCCAGGGAACCCTG<br>GTCACCGTCTCCTCAGCCAGCACCAAGGGCCCTTCCGTGTTCCCCTGGCCCCTTGCA<br>GCAGGAGCACCTCCGAATCCACAGCTGCCCTGGGCTGTCTGGTGAAGGACTACTTTC<br>CCGAGCCCGTGACCGTGAGCTGGAACAGCGGCGCCCTCTACTCCCTGGTGCACACC<br>TTTCCTGCCGTCCTGCAGTCCTCAGGACAACTGTAACGTGGACCACAAACCCTCCA<br>ACACCAAGGTGGACAAACGGGTCGAAGGCCGACCCAGCCGTGTTCCTGTTCCCTCCAAAG<br>CCTGCCCCCGAGTTCAAGGCCGGACCACACCCGAGGTGACCTGCGTGGTGGTGGACGTGAG<br>CCAGGAGGACCCTGAGGTCAGTTCAACTGGTATGTGGACGGCGTGGAGGTGCACA<br>ACGCCAAGACAAAGCCCGGGAGGAGCAGTTCAACTCCAAGGTGGTCAGC<br>GTGCTGACCGTGCTGCATCAGGACTGGCTGAACGGCAAGGAGTACAAGTGCAAGGT<br>CAGCAATAAGGACTGCCCAGCAGCATCGAGAAGACCATCTCCAAGGCTAAAGGCC<br>AGCCCCGGGAACCTCAGGTGTACACCCTGCCCCCAGCCAGGAGGAGATGACCAAG<br>AACCAGGTGTCCCTGACCTGCCTGGTGAAGGGATTCTACCCTTCCGACATCGCCGTG<br>GAGTGGGAGTCCAACGGCCAGCCCGAGAACAATTATAAGACCACCCCTCCCGTCCTC<br>GACGACGGCAGCTTCTTCCTGTACTCCAGGCTGACCGTGGATAAGTCCAGGTGG<br>CAGGAAGGCAACGTCTTCTCATGCTCCGTGATGCACGAGGCCCTGCACAATCACTA<br>CACCCAGAAGTCCCTGAGCCTGTCCCCTGGGAAAG |
| 525 | CL-58851 | Light chain | Nucleotide sequence of light chain | GAAATTGTTTTGACACAGTCTCCAGGCACCCTGTCTTTGTCTCCAGGGGAAAGAGCC<br>ACCCTCTCCTGCAGGGCCAGTCAGATTTTTAGCAACACCTTCTTAGCCTGGTACCAGC<br>AGAAACCTGGCCAGGCTCCCAGGCTCCTCGTGTATGGTGCATCCAAGAGGGCCACT<br>GCCATCCCAGACAGGTTTAGTGGCAGTGGGTCTGGGACAGACTTCATTCTCACCATC<br>AACAGACTGGAGCCTGAAGATTTTGCAGTATATTACTGTCAACACTATGGTGGGTCA<br>CCGTGGACGTTCGGCCAGGGGACCAAGGTGGAAATCAAACGTACGGTGGCCGCTCC<br>CTCCGTGTTCATCTTCCCACCTTCCGACGAGCAGCTGAAGTCCGGCACCGCTTCTGTC |

-continued

SEQUENCES:

| Seq ID No: | | Description | Sequence |
|---|---|---|---|
| | | | GTGTGCCTGCTGAACAACTTCTACCCCGCGAGGCCAAGGTGCAGTGGAAGGTGGA |
| | | | CAACGCCCTGCAGTCCGGCAACTCCCAGGAATCCGTGACCGAGCAGGACTCCAAGG |
| | | | ACAGCACCTACTCCCTGTCCTCCACCCTGACCCTGTCCAAGGCCGACTACGAGAAGC |
| | | | ACAAGGTGTACGCCTGCGAAGTGACCCACCAGGGCCTGTCTAGCCCCGTGACCAAG |
| | | | TCTTTCAACCGGGGCGAGTGT |
| 526 | CL-58851 | Heavy chain Nucleotide sequence of heavy chain alternative coding | CAGGTCCAACTTGTGCAGTCTGGGGCTGAGGTGAAGAAGCCTGGGGCCTCAGTGAA |
| | | | GGTTTCCTGCAAGGCTACTGGATTCACCTTCATTACCTATGCTTTCCATTGGGTGCGC |
| | | | CAGGCCCCCGGACAAAGGTTTGAGTGGATGGGATGGATCAACGTTGGCAATGGTAA |
| | | | CAGAGAATATTCACAGAAGTTCCAGGACAGAGTCACCATTACCAGGGACACCATCCG |
| | | | CGACCACAGTCTACATGGAACTGAACAGCCTGAAATCTGAAGACACGGCTATGTATT |
| | | | TCTGTGCGAGACAGCCCCCTGGGGTCCTTTGACTACTGGGGCCAGGGAACCCTG |
| | | | GTCACCGTCTCCTCAGCCAGCACCAAGGGCCCTTCCGTGTTCCCCTTGGCCCCTTGCA |
| | | | GCAGGAGCACCTCCGAATCCACCAGCGTGGTGTGACTGGAACGACTACTTTC |
| | | | CCGAGCCCGTGACCGTGAGCTGGAACAGCGGCGCCCTCACATCCGGCGTCCACACC |
| | | | TTTCCTGCCGTCCTGCTGCAGTCCTCCGGCCTCTACTCCCTGTCTCCGTGGTGACCGTGC |
| | | | CTAGCTCCTCCCTCGGCACCCAGACCTACACCTGTAACGTGACCACAAACCCTCCA |
| | | | ACACCAAGGTGGACAAACGGGTCGAGAGCAAGTACGGCCCTCCCTGCCCTCCTTGT |
| | | | CCTGCCCCCGAGTTCGAAGGCGGACCCACCCAGCGTGTTCCTGTTCCCTCCCAAGCCCAAG |
| | | | GACACCCTCATGATCAGCCGGACACCCGAGGTGACCTGCGTGGTGGTGGATGTGAG |
| | | | CCAGGAGGACCCTGAGGTCCAGTTCAACTGGTATGTGGACGGCGTGGAGGTGCACA |
| | | | ACGCCAAGACAAAGCCCCGGGAGGAGCAGTTCAACTCCACCTACAGGGTGGTCAGC |
| | | | GTGCTGACCGTGCTGCATCAGGACTGGCTGAACGGCAAGGAGTACAAGTGCAAGGT |
| | | | CAGCAATAAGGAGCTGCCCAGCAGCATCGAGAAGACCATCTCCAAGGCTAAAGGCC |
| | | | AACCAGGTGGAGCCTGACCTGGCTGAAGGGATTCTACCCTTCCGACATCGCCGTG |
| | | | GAGTGGGAGTCCAACGGCCAGCCCGAGAACAATTATAAGACCACCCCTCCCGTCCTC |
| | | | GACAGCGACGGATCCTTCTTCTGTCTGTACTCCGTGATGCACGAGGCCCTGCACAAT |
| | | | CAGGAAGCAAGTGTTCAGCTGCTCCGTGATGCACGAGGCCCTGGATAAGTCCAGGTGG |
| | | | CACCCAGAAGTCCCTGAGCCTGTCCCTGGGAAAG |
| 527 | CL-58851 | Light chain Nucleotide sequence of light chain alternative coding | GAAATTGTTTTGACACAGTCTCCAGGCACCCTGTCTTTGTCTCCAGGGGAAAGAGCC |
| | | | ACCCTCTCCTGCAGGGCCAGTCAGATTTTAGCAACACCTTCTTAGCCTGGTACCAGC |
| | | | AGAAACCTGGCCAGGCTCCCAGGCTCCTCGTGTATGGTGCATCCAAGAGGGCCACT |
| | | | GCCATCCCAGCACGATTCAGTGGCAGTGGATCTGGGACAGACTTCATTCTCACCATC |
| | | | AACAGACTGGAGCCTGAAGATTTTGCAGTATATTACTGTCAACACTATGGTGGGTCA |
| | | | CCGTGGACGTTCGGCCAGGGACCAAGGTGGAAATCAAACGTACGGTGGCCGCTCC |
| | | | CTCCGTGTTCATCTTCCCACCTTCCCCGAGGACGAGCAGCTGAAGTCCGGCACCGCTTCTGTC |
| | | | GTGTGCCTGCTGAACAACTTCTACCCCGGGAGGCCAAGGTGCAGTGGAAGGTGGA |
| | | | CAACGCCCTGCAGTCCGGCAACTCCCAGGAATCCGTGACCGAGCAGGACTCCAAGG |
| | | | ACAGCACCTACTCCCTGTCCTCCACCCTGACCCTGTCCAAGGCCGACTACGAGAAGC |
| | | | ACAAGGTGTACGCCTGCGAAGTGACCCACCAGGGCCTGTCTAGCCCCGTGACCAAG |
| | | | TCTTTCAACCGGGGCGAGTGT |
| 528 | CL-75183 | Heavy chain Nucleotide sequence of heavy chain | CAGGTCCAGCTTGTGCAGTCTGGGGCTGAGGTGAAGAAGCTGGGGCCTCAGTGA |
| | | | AGGTTTCCTGCAAGGCTTCTGGATACACCTTCACTAGCTATGGTATACATTGGGTGC |
| | | | GCCAGGCCCCCGGACAACGGCTTGAGTGGATGGGATGGATCAACGCTGGCAATGG |

-continued

SEQUENCES:

| Seq ID No: | | Description | Sequence |
|---|---|---|---|
| | | | TAACTCAAAACAGTCACGAACTTCCAGGACAGAGTCACCATTACCAGGGACATC CGCGAGCGCAGCCTACATGGACGTGAGCAGCCTGAGATCTGAAGACACGGCTGTAT ATTACTGTGCAGACGAGCGGCCATAATGCCCCGTTTGACCCTGGGGCCCAGGGAACC CTGGTCACCGTCTCCTCAGCCACCAAGGGCCCTTCCGTGTTCCCCCTGGCCCCTT GCAGCAGGAGCCACCTCCGAATCCACAGCTGCCCTGGGCTGCCTGGTCAAGGACTAC TTTCCCGAGCCCGTGACCGTGAGCTGGAACAGCGGCGCGTCGACATCCCGGCGTCCA CACCTTTCCTGCCGTCCTGCAGTCCTCCGGCCTCTACTCCCTGTCCCGTGGTGACC GTGCCTAGCTCCTCCTCCGGCACCAAGACCTACACCTGTAACGTGGACCACAAACCC TCCAACACCAAGGTGGACAAACGGGTCGAGAGCAAAGTACGGCCCTCCCTGCCCTCC TTGTCCTGCCCCGAGTTCAAGGCGGACCCAGCGTGTTCCTGTTCCCTCCTAAGCCC AAGGACACCCTCATGATCAGCCGGACACCCGAGGTGACCTGCGTGGTGGTGGATGT GAGCCAGGAGGACCCTGAGGTCAGTTCAACTGGTATGTGGACGGCGTGGAGGTG CACAACGCCAAGACAAAGCCCCGGGAAGAGCAGTTCAACTCCACCTACAGGGTGGT CAGCGTGCTGACCGTGCTGCATCAGGACTGGCTGAACGGCAAGGAGTACAAGTGCA AGGTCAGCAATAAGGACACTGCCCAGCAGCATCCAGAAGACCATCTCCAAGGCTAAA GGCCAGCCCCGGGAACCTCAGGTGTACACCCTGCCTGGTGAAGGATTCTACCCTTCCGACATCGC CAAGAACCAGGTGAGTCAGCCTGACCTGCCTGGTGAAGAACAATTATAGACACCCCTCCG CGTGGAGTGGAGTCCAACGGCCAGCCCGAGAACAATTATAGACACCCCTCCG TCCTGACAGCGACGGATCCTTCTTTCTGTACTCCAGGCTGACCGTGATAAGTCCA GGTGGCAGGAAGGCAAGCTGTTCAGCTGCTCCGTGATGCACGAGGCCCTGCACAAT CACTACACCCAGAAGTCCCTGAGCCTGTCCCTGGGAAAG |
| 529 | CL-75183 | Light chain — Nucleotide sequence of light chain | GACATCCAGATGACCCAGTCTCCTTCCACCCTGTCTGCATCTGTAGGAGACAGAGTC ACCATCACTTGCCGGGCCAGTCAGAGTATTAATAACTGGTTGGCCTGGTATCAGCAG AAACCAGGGAAAGCCCCTAACCTCCTGATCTATAAGGCGTCTAGTTTAGAAAGTGG GGTCCCATCAAGGTTCAGCGGCAGTGGATCTGGGACACAGAATTCACTCTCACCATCAA CAGCCTGCAGCCTGAGGACTTTGCAACTTATTACTGCCAACAGTATTATAGTTCTTTGG ACGTTCGGCCAAGGGACCAAGGTGGAAATCAAACGTACGGTGGCCGCTCCCTCCCGT GTTCATCTTCCCACCTTCCGACGAGCAGCTGAAGTCCGGCACCGCTTCTGTCGTGTGC CTGCTGAACAACTTCTACCCCCGGAGCCAAGGTCCAGCAGGACTCCAAGGACAGCA CCTACAGTCTGAGCAGCACCCTGACCCTGTCCAAGGCCGACTACGAGAAGCACAAGG TGTACGCCTGCGAAGTGACCCACCAGGGCCTGTCTAGCCCCGTGACCAAGTCTTTCA ACCGGGGCGAGTGT |
| 530 | CL-75500 | Heavy chain — Nucleotide sequence of heavy chain | CAGGTCCAGCTTGTGCAGTCTGGGGCTGAGGTGAAGAAGCCTGGGGCCTCAGTGA AGGTTTCCTGCAAGGCTTCTGGATACACCTTCACTAGCTATGCTGTCTCATTGGGTGC GCCAGGCCCCCGGACAAAGGCTTGAGTGGATGGATGGATCAACGCTGGCAATGG TAACACAAAATTTTCACAGAAGTTCCAGGGCAGAGTCACCATTACCAGGGACACATC CGCGAGCACAACCTACATGGAGTTCGGGGAGCCATTTGACTACTGGGGCCAGGGAAC CCTGGTCACCGTCTCCTCAGCCAAGGGCCCTTCCGTGTTCCCCCTGGCCCCT TGCAGCAGGAGCACCTCCGAATCCACAGCTGCCCTGGGCTGCCTGGTCAAGGACTA CTTTCCCGAGCCAGTCCGTGACCGTGAGCTGGAACTCGGTGGTGGTCAAGGACTA ACACCTTTCCTGCCGTCCTGCAGTCCTCCGGGCACCTACTCCCTGTCTCCGTGGTGAC CGTGCCTAGCTCCTCCCTGGGCACCAAGACCTACACCTGTAACGTGGACCACAAACC CTCCAACACCAAGGTGGACAAACGGGTCGAGAGCAAAGTACGGCCCTCCCTGCCCTC |

-continued

SEQUENCES:

| Seq ID No: | | Description | Sequence |
|---|---|---|---|

|  |  |  | CTTGTCTCTGCCCCCGAGTTCGAAGGCGGACCCAGCGTGTTCTCTGTTCCTCCTAAGCC |
|  |  |  | CAAGGACACCCTCATGATCAGCCGGACACCCGAGGTGACCTGCGTGGTGGTGATG |
|  |  |  | TGAGCCAGGAGGACCCCTGAGGTCCAGTTCAACTGGTATGTGGATGGCGTGGAGGT |
|  |  |  | GCACAACGCCAAGACAAAGCCCGGGAAGAGCAGTTCAACTCACCTACAGGGTGG |
|  |  |  | TCAGCGTGCTGCTGCATCAGGACTGGCTGAACGGCAAGGAGTACAAGTGC |
|  |  |  | AAGGTCAGCAATAAGGGACTGCCCAGCAGCATCGAGAAGACCATCTCCAAGGCTAA |
|  |  |  | AGGCCAGCCCCGGGAACCTCAGGTGTACACCCTGCCTCCCAGCCAGGAGGAGATGA |
|  |  |  | CCAAGAACCAGGTGAGCCTGACCTGCCTGGTGAAGGGATTCTACCCTTCCGACATCG |
|  |  |  | CCGTGGAGTGGGAGTCCAACGGCCAGCCCGAGAACAATTATAAGACCACCCCTCCC |
|  |  |  | GTCCTGGACAGCGACGGATCCTTCTTTCTGTACTCCAGGCTGACCGTGGATAAGTCC |
|  |  |  | AGGTGGCAGGAAGGCAACGTGTTTCAGCTGCTCCGTGATGCACCGAGGCCCTGCACAA |
|  |  |  | TCACTACACCCAGAAGTCCCTGAGCCTGTCCCTGGGAAAG |

| 531 | CL-75500 | Light chain Nucleotide sequence of light chain | GAAATAGTGATGACGCAGTCTCCAGCCACCCTGTCTGTGTCTCCAGGGGAAAGAGC |
|  |  |  | CACCCTCTCCTGCAGGGCCAGTCCAGTGATTAGTAACAACTTAGCCTGGTACCAACA |
|  |  |  | GAAACCTGGCCAGGCTCCCAGGCTCCTCATCTATGGTGACATCCACAGGGCCACTGG |
|  |  |  | TATCCCAGCCAGGTTCAGTGGCAGTGGGTCTGGGACAGAGTTCACTCTCACCATCAG |
|  |  |  | CAGCCTGCAGTCTGAAGATTTTGCAGTTTATTACTGTCAGCAGTATAATATCTGCCT |
|  |  |  | TTCACTTTCGGCCCTGGGACCAAAGTGGATATCAAACGTACGGTGGCCGCTCCCTCC |
|  |  |  | GTGTTCATCTTCCCACCTTCCGACGAGCAGCTGAAGTCCGGCACCGCTTCTGTCGTGT |
|  |  |  | GCCTGCTGAACAACTTCTACCCCCGAGGCCAAGGTGCAGTGGAAGGTGGACAAC |
|  |  |  | GCCCTGCAGTCCGGCAACTCCCAGGAATCCGTGACCGAGCAGGACTCCAAGGACAG |
|  |  |  | CACCTACTCCCTGTCCTCCACCCTGACCCTGTCCAAGGCCGACTACGAGAAGCACAA |
|  |  |  | GGTGTACGCCTGCGAAGTGACCCATCAGGGCCTGTCTAGCCCCGTGACCAAGTCTTT |
|  |  |  | CAACCGGGGCGAGTGT |

| 532 | CL-75506 | Heavy chain Nucleotide sequence of heavy chain | CAGGTCCAGCTTGTGCAGTCTGGGGCTGAGGTGAAGAAGCCTGGGGCCTCAGTGA |
|  |  |  | AGGTTTCCTGCAAGGCTTCTGGATACACCTTCACTAGCTATGCTATCCATTGGGTGCG |
|  |  |  | CCAGGCCCCGGACAAAGGCTTGAGTGGATGGGATGGATCAACCTGGCCAATGGTA |
|  |  |  | ACACAAAATTTTCACGAGAGTTCCAGGGCAGAATCACCATTACCAGGGACACATCCG |
|  |  |  | CGAGCACAACCTACATGGAGCTGAACAGCCTGAGATCTGAAGACACGGCTGTGTAT |
|  |  |  | TACTGTGCGAGAGGGGGTTCGGGGAGCCATTTGACTACTGGGGCCAGGGAACCC |
|  |  |  | TGGTCACCGTCTCCTCAGCCAGCACCAAGGGCCCTTCCGTGTTCCCCTGGCCCTTG |
|  |  |  | CAGCAGGAGCACCTCCGAATCCACAGCTGCCCTGGGCTGTCTGGTGAAGGACTACT |
|  |  |  | TTCCCGAGCCCGTGACCGTGAGCTGGAACAGCGGCGTCCACACCTTCCCAGCGGTCCAC |
|  |  |  | ACCTTTCCTGCCGTCTCCCGGCACCAGACCTCCTCTACTCCGTGTAACGTGACCAGTGTGACCG |
|  |  |  | TGCCTAGCTCCTCCCTGGCACCAAGACCTACACCTGTAACGTGGACCACAAACCCTC |
|  |  |  | CAACACCAAGGTGGACAAACGGGTGGAGGCAAAGCGAGAGCAAGTGCCCCTTCCCTGCCCCTTCTT |
|  |  |  | GTCCTGCCCCCCAGTTCGAAGGCGGACCCCAGCGTGTTCCTGTTCCTCCTAAGCCCA |
|  |  |  | AGGACACCCTCATGATCAGCCGGACACCCGAGGTGACCTGCGTGGTGGTGGATGTG |
|  |  |  | AGCCAGGAGGACCCCGAGGTCCAGTTCAACTGGTATGTGGATGGCGTGGAGGTGC |
|  |  |  | ACAACGCCAAGACAAAGCCCCGGGAAGAGCAGTTCAACTCCACCTACAGGGTGGTC |
|  |  |  | AGCGTGCTGACCGTGCTGCATCAGGACTGGCTGAACGGCAAGGAGTACAAGTGCAA |
|  |  |  | GGTCAGCAATAAGGGACTGCCCAGCAGCATCGAGAAGACCATCTCCAAGGCTAAAG |
|  |  |  | GCCAGCCCCGGGAACCTCAGGTGTACACCCTGCCTCCCAGCCAGGAGGAGATGACC |
|  |  |  | AAGAACCAGGTGAGCCTGACCTGCCTGGTGAAGGGATTCTACCCTTCCGACATCGCC |
|  |  |  | GTGGAGTGGGAGTCCAACGGCCAGCCCGAGAACAATTATAAGACCACCCCTCCCGT |

-continued

SEQUENCES:

| Seq ID No: | | Description | Sequence |
|---|---|---|---|
| | | | CCTCGACAGCGACGAGCATCCTTCTTTCTGTACTCCAGGCTGACCGTGGATAAGTCCAG |
| | | | GTGGCAGGAAGGCAACGTGTTCAGCTGCTCCGTGATGCACGAGGCCCTGCACAATC |
| | | | ACTACACCCAGAAGTCCCTGAGCCTGTCCCTGGGAAAG |
| 533 | CL-75506 | Light chain | Nucleotide sequence of light chain | GAAATAGTGATGACGCAGTCTCCAGCCACCCTGTCTGTGTCTCCAGGGGAAAGAGC |
| | | | CACCCTCTCCTGCAGGGCCAGTGAGGGTATTAGCAGCAACTTAGCCTGGTACCAACA |
| | | | GAACCCTGGCCAGGCTCCCAGGCTCCTCATCTATGGTGCATCCACCAGGGCCACTGG |
| | | | TATCCCAGCCAGGTTCAGTGGCAGTGGGTCTGGGACAGAGTTCACTCTCACCATCAG |
| | | | CACCCTGCAGTCTGAAGATTTTGCAGTTTATTACTGTCAGCAGTATAATATCTGGCCT |
| | | | TTCACTTTCGGCCCTGGGACCAAAGTGGATATCAAACGTACGGTGGCCGCTCCCTCC |
| | | | GTGTTCATCTTCCCACCTTCCGACGAGCAGCTTGAAGTCCGGCCACCGCTTCTGTGTGT |
| | | | GCCTGCTGAACAACTTCTACCCCGGAGGCCAAGGTGCAGTGGAAGGTGGACAAC |
| | | | GCCCTGCAGTCCGGCAACTCCCAGGAATCCGTGACCGAGCAGGACTCCAAGGACAG |
| | | | CACCTACTCCCTGTCCACCCTGACCCTGTCCAAGGCCGACTACGAGAAGCACAA |
| | | | GGTGTACGCCTGCGAAGTGACCCACCAGGGCCTGTCTAGCCCCGTGACCAAGTCTTT |
| | | | CAACCGGGGCGAGTGT |
| 534 | CL-75520 | Heavy chain | Nucleotide sequence of heavy chain | CAGGTCCAACTTGTGCAGTCTGGGGCTGAGGTGAAGAAGCCTGGGGCCTCAGTGAA |
| | | | GGTTTCCTGCAAGGCTTCTGGATACACCTTCACTAGCTATGCTATGCATTGGGTGCGT |
| | | | CAGGCCCCCGGACAACAGGCTTGAGTGGTTGGGATGGATCAACGCTGGCAATGGTTA |
| | | | CACAAAATATTCACAGAAATTCAGGACAGAGTCGCCATTACCAGGGACACATCCGC |
| | | | GAGCACAGCCTTCATGGAGCTGAGCAGCCTGAGATCTGAAGACACGGCCGTGTATT |
| | | | ACTGTGCGAGAGATCGTATTACTATTATTATTCGGCCCTTTGACTACTGGGGCCAGGGAA |
| | | | CCCTGGTCACCGTCTCCTCAGCCAGCACCAAGGGCCCTTCCGTGTTCCCCCTGGCCCC |
| | | | TTGCAGCAGGAGCACCTCCGAATTCACAAGCTGCCCTGGGCTGTCTGGTGAAGGACT |
| | | | ACTTTCCCGAGCCCGTGAGCTGGAACAGCGGCGTCCTTGACATCCGGCGTC |
| | | | CACACCTTTCCTGCCGTCTGCGTCTTCCCGGCCTCTACTCCCTGTCCTCCGTGGTGA |
| | | | CCGTGCCTAGCTCCTCCCTGCCACCAAGAACTACACCTGTAACGTGGACCACAAAC |
| | | | CCTCCAACACCAAGGTGGACAAACGGGTGGAGGCCAAGCCAAGTACCGGCCCTCCTGCCCT |
| | | | CCTTGTCCTGCCCCCGAGTTCGAAGGGGGACCCCAGCGTGTTCCTGTTCCCTCCTAAGC |
| | | | CCAAGGACACCCTCATGATCAGCCGGACCCCGAGGTGACCTGCGTGGTGGTGGAT |
| | | | GTGAGCCAGGAGGACCCTGAGGTCCAGTTCAACTGGTATGTGGATGGCGTGGAAGG |
| | | | TGCACAACGCCAAGACAAAGCCCGGGAAGAGAGCAGTTCAACTCCACCTACAGGGTG |
| | | | GTCAGCGTGCTGACCGTGCTGCATCAGGACTGGCTGAACGGCAAGGAGTACAAGTG |
| | | | CAAGGTCAGCAATAAGGCACTCCCAGCCCCCATCGAGAAGACCATCTCCAAGGCTA |
| | | | AAGGCCAGCCCCGGGAACCTCAGGTGTACACCCTGCCTCCCAGCCAGGAGGAGATG |
| | | | ACCAAGAACCAGGTGAGCCTGACCTGCCTGGTCAAGGGATTCTACCCTTCCGACATC |
| | | | GCCGTGGAGTGGGAGTCCAACGGCCAGCCGGAGAACAATTATAAGACCACCCCTCC |
| | | | CGTCCTGGACAGCGACGGCTCCTTCTTTCTGTACTCCAGGCTGACCGTGGATAAGTC |
| | | | CAGGTGGCAGGAAGGCAACGTGTTCAGCTGCTCCGTGATGCACGAGGCCCTGCACA |
| | | | ATCACTACACCCAGAAGTCCCTGAGCCTGTCCCTGGGAAAG |
| 535 | CL-75520 | Light chain | Nucleotide sequence of light chain | GAAATTGTGTTGACGCAGTCTCCAGGCACCCTGTCTTTGTCTCCAGGGGAAAGAGCC |
| | | | ACCCTCTCGCAGGGCCAGTCAGAGTATTAGCAGCAGCTTAGCCTGGTTCCAG |
| | | | CAAAAACCTGGCCAGGCTCCCAGGCTCCTCATCTATGGTGCATCCAGCAGGGCCACT |
| | | | GGCATCCCAGACAGGTTCAGTGGCAATGGGTCTGGGACAGACTTCACTCTCACCATC |
| | | | AGCAGACTGGAGCCTGAAGATTTTGCAGTGTATTACTGTCAGCGTATTGTATGGGTAGCCA |

-continued

SEQUENCES:

| Seq ID No: | | Description | Sequence |
|---|---|---|---|
| | | | TTCACTTTCGGCCCTGGGACCAAAATGGATATTAAACGTACGGTGGCCGCTCCCTCC GTGTTCATCTTCCCACCTTCCGACGAGCAGCTGAAGTCCGGCACCGCTTCTGTCGTGT GCCTGCTGAACAACTTCTACCCCGCGAGGCCAAGGTGCAGTGGAAGGTGGACAAC GCCCTGCAGTCCGGCAACTCCCAGGAATCCGTGACCGAGCAGGACTCCAAGGACAG CACCTACTCCCTGTCCTCCACCCTGACCCTGTCCAAGGCCGACTACGAGAAGCACAA GGTGTACGCCTGCGAAGTGACCCACCAGGGCCTGTCTAGCCCCGTGACCAAGTCTTT CAACCGGGGCGAGTGT |
| 536 | Heavy chain | Nucleotide sequence of heavy chain | CAGGTCCAGCTTGTGCAGTCTGGGGCTGAGGTGAAGAAGCCTGGGGCTCAGTGA AGTTTCCTGCAAGGCTTCTGGATACACCTTCACTAGCTATGCTATCCATTGGGTGCG CCAGGCCCCCGGACAAAGGCTTGAGTGGATGGGAATCAACGTTGGCAATGGTA AAACAAAATTTTCACAGAAGTTACAGGGCAGAATCACCATTACCAGGACACACATCCG CGAGCACAACCTACATGGAGCTGAACAGCCTGACATCTGAAGACACGGCTGTGTTT TACTGTGCGAGAGAGGGGTTCGGGGAGCCATTTGACTACTGGGGCCAGGGAACCC TGGTCACCGTCTCCTCAGCCAGCACCAAGGGCCCTTCCGTGTTCCCCTGGCCCTTG CAGCAGGAGCACCTCCGAATCCACAGCTGCCTGGGCTGTCTGGTGAAGGACTACT TTCCCGAGCCCGTGACCGTGAGCTGGAACAGCGGCGTCTGCACATCCGGCGTCCAC ACCTTTCCTGCCGTCCTGCAGTCCTCCGGCTCTACTCCGTCCTCCGTGGTGACCG TGCCTAGCTCCTCCCTGGGCACCCAGACCTACACCTGTAACGTGGACCACAAACCCTC CAACACCAAGGTGGACAAACGGGTGGAGGCGAAGTGCCAGCGTGTTCCTGTTCCCTAGCCCA AGGACACCCTCATGATCAGCCGGACACCCGAGGTGACCTGCGTGGTGGTGGATGTG AGCCAGGAGGACCCTGAGGTCCAGTTCAACTGGTATGTGGATGGCGTGGAGGTGC ACAACGCCAAGACAAAGCCCCGGGAAGAGCAGTTCAACTCCACCTACCAGGTGGTC AGCGTGCTGACCGTGCTGCATCAGGAGTGGCTGAACGGCAAGGAGTACAAGTGCAA GGTCAGCAATAAGGGACTGCCCAGCAGCATCGAGAAGACCATCTCCAAGGCTAAAG GCCAGCCCCGGGAACCTCAGGTGTACACCCTGCCTCCCAGCCAGGAGGAGATGACC AAGAACCAGGTGAGCCTGACCTGCCTGGTGAAGGGATTCTACCCTTCCGACATCGCC GTGGAGTGGGAGTCAACGCGACGGATCCTTCTTTCTGTACTCCAAGCTGACCGTGGACAAGTCCAG CCTCGACAGCGACGGATCCTTCTTTCTGTACTCCAAGCTGACCGTGGATAAGTCCAG GTGGCAGGAAGGCAACGTGTTCAGCTGCTCCGTGATGCACGAGGCCCTGCACAATC ACTACACCCAGAAGTCCCTGAGCCTGTCCCTGGGAAAG |
| 537 | Light chain | Nucleotide sequence of light chain | GAAATAGTGATGACGCAGTCTCCAGCCACCCTGTCTGTGTCTCCAGGGGAAAGAGC CACCCTCTCTGCAGGGCCAGTCAGAGTATTAGTAGCAACTTAGCCTGGTACCAACA GAAACCTGGCCAGGCTCCCAGGCTCCTCATCTATGGTGCATCCACCAGGGCCACTGG TATCCCAGCCAGGTTCAGTGGCAGTGGGTCTGGGACAGAGTTCACTCTCACCATCAG CACCCTGCAGTCTGAAGATTTTGCAGTTTATTACTGTCAGCAGTATAATATCTGGCCT TTCACTTTCGGCCCTGGGACCAAAGTGGATATCAAACGTACGGTGGCCGCTCCCTCC GTGTTCATCTTCCCACCTTCCGACGAGCAGCTGAAGTCCGGCACCGCTTCTGTCGTGT GCCTGCTGAACAACTTCTACCCCGCGAGGCCAAGGTGCAGTGGAAGGTGGACAAC GCCCTGCAGTCCGGCAACTCCCAGGAATCCGTGACCGAGCAGGACTCCAAGGACAG CACCTACTCCCTGTCCTCCACCCTGACCCTGTCCAAGGCCGACTACGAGAAGCACAA GGTGTACGCCTGCGAAGTGACCCACCAGGGCCTGTCTAGCCCCGTGACCAAGTCTTTT CAACCGGGGCGAGTGT |

-continued

SEQUENCES:

| Seq ID No: | Description | Sequence |
|---|---|---|
| 538 | CL-75565 | Heavy chain | Nucleotide sequence of heavy chain | CAGGTCCAGCTTGTGCAGTCTGGGGCTGAGGTGAAGAAGCCTGGGGCTCAGTGA<br>AGGTTTCCTGCAAGGCTTCTGGATACACCTTCACTAGCTATGCTATCCATTGGGTGCG<br>CCAGGCCCCGGACAAAGGCTTGAGTGGATGGGATGGATCAACGCTGGCAATGGT<br>AACACAAAATATTCACAGAAGTTCAGGGCAGAATCACCATTACCAGGGACACATCC<br>GCGAGCACAGCCTACATGGAGCTGAGCAGCCTGAGATCTGAAGACACGGCTGTGTA<br>TTACTGTGCGAGAGGGGGTTCGGGGAGCCATTTGACTACTGGGGCCAGGGAACC<br>CTGGTCACCGTCTCCTCAGCCACCAAGGGCCCTTCCGTGTTCCCCTGGCCCCCTT<br>GCAGCAGGAGCACCTCCGAATCCACAGCTGCCCTGGGCTGTCTGGTGAAGGACTAC<br>TTTCCCGAGCCCGTGACCGTGAGCTGGAACAGCGGCGTCTGACATCCGGCGTCCA<br>CACCTTTCCTGCCGTCCCAGTCTCCTCTACTCCCTGTCCCGTGGTGACC<br>GTGCCTAGCTCCTCCCTCGGCACCAAGACCTACACCTGTAACGTGGACCACAAACCC<br>TCCAACACCAAGGTGGACAAACGGGTCGAGAGCAAGTACGGGCCCTCCTGCCCTCC<br>TTGTCCTCCCCCGAGTTCGAAGGCGGACCCCAGCGTGTTCCTGTTCCCTCCTAAGCCC<br>AAGGACACCCTCATGATCAGCCGGACCCGAGGTGACCTGCGTGGTGGTGGATGT<br>GAGCCAGGAAGACCCTGAGGTCCAGTTCAACTGGTATGTGGATGGCGTGGAGGTG<br>CACAACGCCAAGACAAAGCCCGGGAAGGAGCAGTTCAACTCACCTACAGGGTGGT<br>CAGCGTGCTGACCGTGCTGCATCAGGACTGGCTGAACGGCAAGGAGTACAAGTGCA<br>AGGTCAGCAATAAGGACCTGCCCGAGCAGCCATCCCTCCTCCAGCCAGGAGATGAC<br>GGCCAGCCCCGGGAACCTCAGGTGTACACCCTGCCTCCGGAGATGAC<br>CAAGAACCAGGTGAGCCTGACCTGCCTGGTGAAGGGATTCTACCCTTCCGACATCGC<br>CGTGGAGTGGGAGTCCAACGGCCAGCCGAGAACAATTATAAGACCACCCCTCCCG<br>TCCTGGACAGCGACGGATCCTTCTTCCTGTACTCCAGGCTGACCGTGGATAAGTCCA<br>GGTGGCAGGAAGGCAACGTGTTCAGCTGCTCCGTGATGCACGAGGCCCTGCACAAT<br>CACTACACCCAGAAGTCCCTGAGCCTGTCCCTGGGAAAG |
| 539 | CL-75565 | Light chain | Nucleotide sequence of light chain | GAAATAGTGATGACGCAGTCTCCAGCCACCCTGTCTGTCTCCAGGGGAAAGAGC<br>CACCCTCTCCTGCAGGGCCAGTCAGAGTATTAGCAGCAACTTAGCCTGGTACCAACA<br>GAAACCTGGCCAGGCTCCCAGGCTCCTCATCTATGGTGCATCCACCAGGGCCACTGG<br>TATCCCAGCCAGGTTCAGTGGCAGTGGGTCTGGGACAGAGTTCACTCTCACCATCAG<br>CAGCCTGCAGTCTGAAGATTTTGCAGTTTATTACTGTCAGCAGTATAATATCTGGCCT<br>TTCACTTTCGGCCCTGGGACCAAAGTGGATATCAAACTGTGGCCGCTCCTCC<br>GTGTTCATCTTCCCACCTTCCGACGAGCAGCTGAAGTCCGGCACCGCTTCTGTCGTGT<br>GCCTGCTGAACAACTTCTACCCCCGAGGCCAAGGTCCAGTGGAAGGTGGACAAC<br>GCCCTGCAGTCCGGCAACTCCCAGGAATCCGTGACGGAGCAGGACTCCAAGGACAG<br>CACCTACTCCCTGTCCTCCACCCTGACCCTGTCCAAGGCCGACTACGAGAAGCACAA<br>GGTGTACCCCTGCGAAGTGACCCATCAGGGCCTGTCTAGCCCCGTGACCAAGTCTTT<br>CAACCGGGGCGAGTGT |
| 540 | CL-75714 | Heavy chain | Nucleotide sequence of heavy chain | CAGGTCCACCTTGTGCAGTCTGGGGCTGAGGTGAAGAAGCCTGGGGCTCAGTGAA<br>GGTGTCCTGCAAGACTTCTGGATACACCTTCACCACCTATGCTATTCATTGGGTGCGC<br>CAGGCCCCCGGACAAGGGCTTGAGTGGATGGGATGGATCAACGCTGGCAATGGTA<br>GAACAGAATATTCAGAGAAGTTTCAGGGCAGAGTCACCATTACCAGGGACACTTCC<br>GCGAGTACAGTCTACATGGACCTGAGCAGCCTGAGATCTGAAGACACGGCTGTGTA<br>TTACTGTGCGAGAGGGGGATTCGGGGAGCCACCATTTGACCAATGGGGCCAGGGAACC<br>CTGGTCACCGTCTCCTCAGCCACCAAGGGCCCTTCCGTGTTCCCCCTGGCCCCCCTT<br>GCAGCAGGAGCACCTCCGAATCCACAGCTGCCCTGGGCTGTCTGGTGAAGGACTAC<br>TTTCCCGAGCCCGTGACCGTGAGCTGGAACAGCGGCGTCTGACATCCGGCGTCCA |

-continued

SEQUENCES:

| Seq ID No: | | Description | Sequence |
|---|---|---|---|
| | | | CACCTTTCCTGCGTCCTGCAGTCCTCCGGCCTCTACTCCTGTCCGTCCGTGGTGACC GTGGCTAGCTCCTCCCTCGGCACCAAGACCTACACCTGTAACGTGGACCACAAACCC TCCAACACCAAGTGGACAAACCGGTGCAGAGCAAGTACGGCCCTCCTGCCCTCC TTGTCCTGCCCCGAGTTCGAAGGCGACCCAGCGTGTTCCTGTTCCCTCCTAAGCCC AAGGACACCCTCATGATCAGCCGGACCCCGAGGTGACCTGCGTGGTGGTGGATGT GAGCCAGGAGGACCCTGAGGTCCAGTTCAACTGGTATGTGGATGGCGTGGAGGTG CACAACGCCAAGACAAAGCCCCGGGAGGAGCAGTTCAACTCCACCTACAGGGTGGT CAGCGTGCTGCTGCACCAGGACTGGCTGAACGGCAAGGAGTACAAGTGCA AGGTCAGCAATAAGGGCACTCCCAGCCCCCATCGAGAAGACCATCTCCAAGGCTAAA GGCCAGCCCCGGGAACCTCAGGTGTACACCCTGCCTCCCAGCCAGGAGGAGATGAC CAAGAACCAGGTCAGTCTGACCTGCCTGGTCAAGGGATTCTACCCTTCCGACATCGC CGTGGAGTGGGAGTCCAACGGCCAGCCCGAGAACAATTATAAGACCACCCCTCCCG TCCTGGACAGCGACGGATCCTTCTTTCTGTACTCCAGGCTGACCGTGGATAAGTCCA GGTGGCAGGAGGGCAACGTGTTCAGCTGCTCCGTGATGCACGAGGCCCTGCACAAT CACTACACCCAGAAGTCCCTGAGCCTGTCCCTGGGAAAG |
| 541 | CL-75714 | Light chain Nucleotide sequence of light chain | GAAATAGTGATGACGACGCAGTCTCCAGCCACCCTGTCTGTGTCTCCAGGGGAAAGAGC CACCCTCTCCTGCAGGGCCAGTCAGAGTGTTAGCAGCAACTTAGCCTGGTACCAGCA CCAACCTGGCCAGGCTCCCAGGCTCCTCATCTATGGTGCATCCATCAGGGCCACTGG TTTCCCACCCAGGTTCAGTGGCAGTGGGTCTGGGACAGACTTCACTCTCACCATCAA CAGCCTGCAGCTGAAGATTTTGCAGTTTATTACTGTCAGCAGTATAATAACTGGCCT TTCATTTTCGGCCTGGACAAACTGGAATCACACGTACCGTGGCCGCCTCCCTCC GTGTTCATCTTCCCACCTTCTGACGAGCAGCTGAAGTCGGCACCGCTTCTGTCGTGT GCCTGCTGAACAACTTCTACCCCCGAGGCCAAGGTGCAGTGGAAGGTGGACAAC GCCCTGCAGTCCGGCAACTCCCAGGAATCCGTGACCGAGCAGGACTCCAAGGACAG CACCTACTCCCTGTCCAGCACCCTGACCCTGTCCAAGGCCGACTACGAGAAGCACAA GGTGTACGCCTGCGAAGTGACCCACCAGGGCCTGTCTAGCCCCGTGACCAAGTCTTT CAACCGGGGCGAGTGT |
| 542 | CL-58722 | Heavy chain Nucleotide sequence of heavy chain | CAGGTGCAACTGGTGGAGTCTGGGGGAGGCTTGGTCAAGCCTGGAGGGTCCCTGA GACTCTCCTGTGCAGCCTCTGGATTCACCTTCAGTGACTACTACATGAGCTGGATCCG CCAGGCTCCAGGGAAGGGGCTGGAGTGGGTTTCATACATTAGTAGTAGTGGTAGTA CCATATACTACGCAGACTCTGTGAAGGGCCGATTCACCATCTCCAGGGACAACGCCA AGAACTCACTGTTTCTGCAAATGAACAGCCTGAGAGCCGAGGACACGGCCGTGTAT TACTGTGCGAGAGAAGCAGTGGTGGTACGACTACTGGGGCCAGGGAACCCTGG TCACCGTCTCCTCAGCCAGCACCAAGGGCCCATCGGTCTTCCCCCTGGCACCCTGCAG CAGGAGCACCTCCGAGAGCACAGCCGCCCTGGGCTGTCTGGTGAAGGACTACTTTCC CGAGCCCGTGACCGTGAGCTGGAACTCAGGCGCCCTGACCATCCGGCGTCCACCT TTCCTGCGCGTCCTGCCAGTCCTCCTACTCCTGGTGGTGACCGTGCC TAGCTCCTCCCTGGACAACCTCACCAGTGTAACGTGGACCACAAACCCTCCAA CACCAAGGTGGACAAGCGGGTGGAACGCGGAAGCCCAAGAGCTGTGATAAAACTCACACATGCCCA CCGCCCCCAGCACCTGAACTCCTGGGGGGACCGTCAGTCTTCCTCTTCCCCCCAAAA CACCCTCATGATCTCCCGGACCCCTGAGGTCACATGCGTGGTGGTGGAC TGCTGACCGTGCTGGCATCAGGACTGGCTGAACGGCAAGGAGTACAAGTGCAAGGTC AGCAATAAGGGCACTGCCCAGCCATCGCCAGCAGGACCATCTCCAGAAGACCGAGAGACTCGAGAAGCACCAT CACGCAGAAGAGCCTCTCCCTGTCTCCGGGTAAA |

-continued

SEQUENCES:

| Seq ID No: | | Description | Sequence |
|---|---|---|---|
| | | | GCCCGGGAACCTCAGGTGTACACCCTGCCTCCCAGCCAGGAGGAGATGACCAAGA |
| | | | ACCAGGTGAGCCTGACCTGCCTGGTGAAGGGATTCTACCCTTCCGACATCGCCGTGG |
| | | | AGTGGGAGTCCAACGGCCAGCCCGAGAACAATTATAAGACCACCCCTCCCGTCCTCG |
| | | | AGCGGCGACGGATCCTTCTTTCTGTACTCCAGGCTGACCGTGGATAAGTCCAGTGGC |
| | | | AGGAAGGCAACGTGTTCAGCTGCTCCGTGATGGCACGAGGCCCTGCACAATCACTAC |
| | | | ACCCAGAAGTCCCTGAGCCTGTCCCTGGGAAAG |
| 543 | CL-58722 | Light chain Nucleotide sequence of light chain | GAAATTGTGTTGACGCAGTCTCCAGGCACCCTGTCTTTGTCTCCAGGGGAAAGAGCC |
| | | | ACCCTCTCCTGCAGGGCCAGTCAGAGTGTTAGCAGCAACTACTTAGCCTGGTACCAG |
| | | | CAGAAACCTGGCCAGGCTCCCAGGCTCCTCATCTATGGTGCATCCAGCAGGGCCACT |
| | | | GGCATCCCAGACAGGTTCAGTGGCAGTGGGTCTGGGACAGACTTCACTCTCACCATC |
| | | | AGCAGACTGGAGCCTGAAGATTTTGCAGTGTATTCCTGTCACCAGTATGGTAGCTCA |
| | | | CCTCCGACGTTCGGCCAAGGGACCAAGGTGGAAATCAAACGTACGGTGGCCGCTCC |
| | | | CTCCGTGTTCATCTTCCCACCTTCCGACGAGCAGCTGAAGTCCGGCACCGCTTCTGTC |
| | | | GTGTGCCTGCTGAACAACTTCTACCCCCGGAGAATCCGGAGGTGCAGTGGAAGGTGGA |
| | | | CAACGCCCTGCAGTCCGGCAACTCCGGCAATCCGTGACCGAGCAGGACTCCAAGG |
| | | | ACAGCACCTACTCCCTGTCCTCCACCCTGACCCTGTCTAAGGCCGACTACGAGAAGC |
| | | | ACAAGGTGTACGCCTGCGAAGTGACCCACCAGGGCCTGTCTAGCCCCGTGACCAAG |
| | | | TCTTTCAACCGGGGCGAGTGT |
| 544 | CL-58722 | Heavy chain Nucleotide sequence of heavy chain alternative coding | CAAGTTCAGTTGGTTGAGTCTGGCGGCGGACTGGTTAAGCCTGGCGGATCTCTGAG |
| | | | ACTGTCTTGTGCCGCCTCTGGCTTCACCTTCTCCGACTACTACATGTCCTGGATCAGA |
| | | | CAGGCCCCTGGCAAAGGCCTGGAATGGGTGTCTACTATCTCTACATCTCCGGCTCCACC |
| | | | ATCTACTACGCCGACTCCGTGAAGGGCAGATTCACCATCTCCAGAGACAACGCCAAG |
| | | | AACTCCCTGTTTCTGCAGATGAACAGCCTGAGAGCCGAGGACACCGCCGTGTACTAC |
| | | | TGCGCCCGTAGATCCTCTGGATGGTACGACTATTGGGGCCAGGGCACCCTGGTCAC |
| | | | AGTTTCTAGTGCCAGCACCAAGGGCCCTTCCGTGTTCCCCTGGCCCTGTTCCCTGGCCCTTGCAGCAG |
| | | | GAGCACCTCCGAATCCACAGCTGCCCTGGGCTGTCTGTGGTGAAGGACTACTTTCCCGA |
| | | | GCCCGTGACCGTGAGCTGGAACAGCGGCGCTGCCCTGACCTCCGGCGTCCACACCTTTCC |
| | | | TGCCGTCCTGCAGTCCTCTGGACTCTCCCTGGTGACCGTGCCCTCCAGC |
| | | | TCTCCCTGGCCACCAAGACCTACACCTGTAACGTGGACCACAAACCCTCCAACACC |
| | | | AAGGTGGACAAACGGGTCGAGAGCAAGTACGGCCCTCCCTGCCCTCCTTGTCCTGC |
| | | | CCCGAGTTCGAAGGCGGACCCAGCGTGTTCCTGTTCCCTCCTAAGCCCAAGGACAC |
| | | | CCTCATGATCAGCCGGACACCCGAAGTGACCTGCGTGGTGGTGGATGTGAGCCAGG |
| | | | AGGACCCTGAGGTCCAGTTCAACTGGTATGTGGACGGCGTGGAGGTGCACAACGCC |
| | | | AAGACAAAGCCCCGGGAAGAGCAGTTCAACTCCACCTACAGGGTGGTCAGCGTGCT |
| | | | GACCGTGCTGCTCATCAGGACGACTGGCTGAATGGCAAGGAGTACAAGTGCAAGGTCAGC |
| | | | AATAAGGCCCTGCCAGCCCCCATCGAGAAGACCATCTCCAAGGCTAAAGGCCAGCC |
| | | | CCGGGAACCTCAGGTGTACACCCTGCCTCCCAGCCAGGAGGAGATGACCAAGAACC |
| | | | AGGTGAGCCTGACCTGCCTGGTGAAGGGATTCTACCCTTCCGACATCGCCGTGGAG |
| | | | GAAGGCAACGTGTTCAGCTGCTCCGTGATGCACGAGGCCCTGCACAATCACTACACC |
| | | | CAGAAGTCCCTGAGCCTGTCCCTGGGAAAG |

-continued

SEQUENCES:

| Seq ID No: | | Description | Sequence |
|---|---|---|---|
| 545 | CL-58722 Light chain | Nucleotide sequence of light chain alternative coding | GAAATTGTGCTGACTCAGTCCCCTGGCACACTGTCTTTGAGCCCTGGCGAGAGAGCT ACCCTGTCCTGTAGAGCCTCAGTCCGTGTCTCCAACTACCTGGCCTGGTATCAGC AGAAGCCTGGACAGGCTCCCCGGCTGTTGATCTACGGCGCCTTCTATCAGAGCCACA GGCATCCCTGACCGGTTCTCCGGATCTGGCTCTGGCACCGATTTCACCCTGACCATCT CTCGGCTGGAACCCGAGGATTTCGCCGTGTACTCTTGCCACCAGTACGGCCTCAGCC CTCTACCTTTGGACAGGCCACCAAGGTGGAAATCAAACGTACGGTGGCCGCTCCCT CCGTGTTCATCTTCCCACCTTCCGACGAGCAGCTGAAGTCCGGCACCGCTTCTGTCGT GTGCCTGCTGAACAACTTCTACCCCCGAGGCCAAGGTGCAGTGGAAGGTGGACA ACGCCCTGCAGTCCGGCAACTCCCAGGAATCCGTCACCGAGCAGGACTCCAAGGAC AGCACCTACTCCCTGTCCAGCACCCTGACCCTGTCCAAGGCCGACTACGAGAAGCAC AAGGTGTACGCCTGCGAAGTGACCCACCAGGGCCTGTCTAGCCCCGTGACCAAGTC TTTCAACCGGGGCGAGTGT |
| 546 | CL-58835 Heavy chain | Nucleotide sequence of heavy chain | CAGGTGCAACTGGTGGAGTCTGGGGGAGGCTTGGTCAAGCCTGGAGGGTCCCTGA GACTCTCCTGTGCAGCCTCTGGATTCACCTTCAGTGACTACTACATGAGTTGGATCCG CCAGGCTCCAGGGAAGGGGCTGGAGTGGGTTTCATACATTAGTAGTGGTACTA CCATATACTACGCAGACTCTGTGAAGGGCCGATTCACCATCTCCAGGGACAACGCCA TGGACTCACTGTATCTGCAAATGAACAGCCTGAGAGCCGAGGACACGGCCGTGTAT TACTGTGCGAGACGGAGCAGTGGCTGGTACGACTACTGGGGCCAGGGAACCCTGG TCACCGTCTCCTCAGCCAGCACCAAGGGCCCTGTCCCTGGCCCCTGCAG CAGGAGCACCTCCGAATCCACAGCTGCCCTGGGCTGTCTGGTGAAGGACTACTTTCC CGAGCCCGTGACCGTGTCCTGGAACAGCGGCGTCCACACCTTCCCAGCTGTCCCACCT TTCCTGCGCGTCCTGCAGTCCTCCGGCCTCTACTCCCTGTCCTCCGTGTGACCGTGCC TAGCTCCTCCCTGGGCAAGACCTACACCTGTAACGTGGACCACAAAACCCTCCAA GCCCCGAGTTCGAAGGCGGACCCCAGGCTGTTCCTGTTCCCTCCCTAAGCCCAAGGA CACCCTCATGATCAGCCGGACCCCTGAGGTGACCTGCGTGGTGGTGGACGTGTGAGCC AGGAGGACCCCTGAGGTCCAGTTCAACTGGTATGTGGATGGCGTGGAGGTGCACAA CGCCAAGACAAAGCCCGGGAAGGAGCAGTTCAACTCCACCTACAGGGTGGTCAGCG TGCTGACCGTGCTGCATCAGGACTGGCTGAACGGCAAGGAGTACAAGTGCAAGGTC AGCAATAAGGGACTGCCCAGCAGCATCGAGAAGACCATCTCCAAGGCTAAAGGCCA GCCCCGGGAAACCTCAGTGTACACCCTGCCTCCCAGCCCAGGAGGAGATGACCAAGA ACCAGGTGAGCCTGACCTGCCTGGTGAAGGGATTCTACCCTTCCGACATCGCCGTGG AGTGGGAGTCCAACGGCCACGGCCGGAGAACAATTATAAGACCACCCCTCCCGTCCTCG ACAGCGACGGATCCTTCTTTCTGTACTCCAAGCTGACCGTGGATAAGTCCAGGTGGC AGGAAGGCAACGTGTTCAGCTGCTCCGTGATGCACGAGGCCCTGCACAATCACTAC ACCCAGAAGTCCCTGAGCCTGTCCCTGGGAAAG |
| 547 | CL-58835 Light chain | Nucleotide sequence of light chain | GAAATTGTGTTGACGCAGTCTCCAGGCACCCTGTCTTTGTCTCCAGGGGAAAGAGCC ACCCTCTCTTGTTGGGCCAGCCAGTCAGAGGGTTGTTTACAGATACTTAGCCTGGTACCAG CGGAAACCTGGCCAGGCTCCCAGACTTCTCATTTATGGTGCATTCAACAGGGCCACT GGCATCCCAGCCAGGTTCAGTGGCAGTGGGTCTGGGACAGACTTCACTCTCACTAT CAGTAGACTGGAGCCTGAAGATTTTGCAGTTTATTACTGTCACCAATATGGTAGTTC ACCACCGACGTTCGGCCAAGGGACCAAGGTGGAAATCAAACGTGGCCGCTC CTCCGTGTTCATCTTCCCACCTTCCGACGAGCAGCTGAAGTCCGGCACCGCTTCTGT CGTGTGCCTGCTGAACAACTTCTACCCCCGGGAGGCCAAGGTGCAGTGGAAGGTGG ACAACGCCCTGCAGTCCGGCAACTCCCAGGAATCCGTGACCGAGCAGGACTCCAAG |

-continued

SEQUENCES:

| Seq ID No: | | Description | Sequence |
|---|---|---|---|

| | | | GACAGCACCTACTCCCTGTCCTCCACCCTGACCCTGTCCAAGGCCGACTACGAGAAG |
| | | | CACAAGGTGTACGCCTGCGAAGTGACCCACCAGGGCCTGTCCTAGCCCGTGACCAA |
| | | | GTCTTTCAACCGGGGCGAGTGT |

| 548 | CL-58835 | Heavy chain | Nucleotide sequence of heavy chain alternative coding |
| | | | CAAGTTCAGTTGGTTGAGTCTGGCGGCGGACTGGTTAAGCCTGGCGGATCCTGAG |
| | | | ACTGTCTTGTGCCGCCTCTGGCTTCACCTTCTCCGACTACTACATGTCTGGATCAGA |
| | | | CAGGCCCCTGGCAAAGGCCTGGAATGGGTGTCCTACATCTCCATCTCCGGCCACCACC |
| | | | ATCTACTACGCCGACTCCGTGAAGGGCAGATTCACCATCTCCAGAGACAACGCCATG |
| | | | GACTCCCTGTACCTGCAGATGAACTCCCTGAGAGCCGAGGACACCGCCGTGTACTAC |
| | | | TGCGCCCGTAGATCCTCTGGATGGTACACTATTGGGGCCAGGGCACCCTGGTCAC |
| | | | AGTTTCTAGTGCCAGCACCAAGGGCCCTTCCGTGTTCCCCCTGGCCCCTGCAGCAG |
| | | | GAGCACCTCCGAATCCACAGCTGCCCTGGGCTGTCTGGTGAAGGACTACTTTCCCGA |
| | | | GCCCGTGACCGTGAGCTGGAACAGCGGCGCTCTGACATCCGGCGTCCACACCTTTCC |
| | | | TGCCGTCCTGCAGTCCTCCGGCCTCTACTCCCTGTCCGGTGTGACCGTGCCTAGC |
| | | | TCCTCCCTGGCCACCCAAGACCTACACCTGTAACGTGGACCACAAACCCTCCAACACC |
| | | | AAGGTGGACAAACGGGTCGAGAGCAAGTACGGCCCTCCCTGCCCTCCTTGTCCTGC |
| | | | CCCGAGTTCGAAGGCGGACCACCCAGCGTGTTCCTGTTCCCCCTAAGCCCAAGGACAC |
| | | | CCTCATGATCAGCCGGACACCCGAGGTGACCTGCGTGGTGGTGGATGTGAGCCAGG |
| | | | AGGACCCTGAGGTCCAGTTCAACTGGTATGTGGACGGCGTGGAGGTGCACAACGCC |
| | | | AAGACAAAGCCCGGGAAGAGAGCAGTTCAACTCCACCTACAGGGTGGTCAGCGTGCT |
| | | | GACCGTGCTGCATCAGGACTGGCTGAACGGCAAGGAGTACAAGTGCAAGGTCAGC |
| | | | AATAAGGCCCTGCCCGCACCATCGAGAAAACCATCTCCAAGGCTAAAGGCCAGCC |
| | | | CCGGGAACCTCAGGTGTACACCCTGCCTCCCCAGCCAGGGATTCTACCCTTCCGACATCGCC |
| | | | AGTGAGCCTCAGGTGCTGGGCTGGTGAAGGGATTCTACCCTTCCGACATCGCCGTGGAG |
| | | | TGGGAGTCCAACGGCCAGCCCGAGAACAATTATAAGACCACCCCTCCCGTCCTCGAC |
| | | | AGCGACGGATCCTTCTTTCTGTACTCCAAGCTGACCGTGGATAAGTCCAGGTGGCAG |
| | | | GAAGGCAACGTGTTCAGCTGCTCCGTGATGCACGAGGCCCTGCACAATCACTACACC |
| | | | CAGAAGTCCCTGAGCCTGTCCCCTGGGAAAG |

| 549 | CL-58835 | Light chain | Nucleotide sequence of light chain alternative coding |
| | | | GAAATTGTGCTGACTCAGTCCCCTGGCACACTGTCTTTGAGCCCTGGCGAGAGAGCT |
| | | | ACCCTGTCTTGTTGTGGGCCTCTCAGAGAGTGGTGTACAGATACCTGGCTTGGTATCAG |
| | | | CGGAAGCCCGGCCAGGCTCCTAGACTGTTGATCTACGGCGCCTTCAACAGAGCCAC |
| | | | AGGCATCCCTGACAGATTCTCCGGCTCTGGCTCTGGCACCGACTTCTCCCTGACTATC |
| | | | TCTCGGCTGGAACCCGAGGACTTCGCCGTGTACTACTGTCAGCAGTACGGCAGCAGC |
| | | | CCTCCTACCTTTGGCCAGGGCACTAAGGTGGAAATCAAACGTACGGTGGCCGCTCCC |
| | | | TCCGTGTTCATCTTCCCACCTTCTGACGAGCAGCTGAAGTCCGGCACCGCTTCTGTCG |
| | | | TGTGCCTGCTGAACAACTTCTACCCCGCGAGGCCAAGGTGCAGTGGAAGGTGGAC |
| | | | AACGCCCTACCAGTCCGGCAACTCCCAGGAATCCGTGACCGAGCAGGACTCCAAGGA |
| | | | CAGCACCTACTCCCTGTCCTCCACCCTGACCCTGTCCAAGGCCGACTACGAGAAGCA |
| | | | CAAGGTGTACGCCTGCGAAGTGACCCACCAGGGCCTGTCTAGCCCCGTGACCAAGT |
| | | | CTTTCAACCGGGGCGAGTGT |

| 550 | CL-58756 | Heavy chain | Nucleotide sequence of heavy chain |
| | | | CAGGTGCAGCTGGTGGAGTCTGGGGGAGGCTTGGTCAAGCCTGGAGGGTCCCTGA |
| | | | GACTCTCCTGTGCAGCCTCTGGATTCACCTTCAGTGACTACTACATGAGCTGGATCCG |
| | | | CCAGGCTCCAGGGAAGGGGCTGGAGTGGGTTTCATACATTAGTAGTAGTGGTAGTA |
| | | | CCATATACTACGCAGACTCTGTGAAGGGCCGATTCACCATCTCCAGGGACAACGCCA |
| | | | AGAACTCACTGTATCTGCAAATGAACAGCCTGAGAGCCGAGGACACGGCCGTGTAT |

-continued

SEQUENCES:

| Seq ID No: | | Description | Sequence |
|---|---|---|---|
| | | | TACTGTGCGAGAGAAGCAGTGGTGCTGGTACGACTACTGGGGCCAGGGAACCCTGG |
| | | | TCACCGTCTCCTCAGCCAGCACCAAGGGCCCTTCCCTGTTCCCCCTGGCCCCTTGCAG |
| | | | CAGGAGCACCTCCGAATCCACAGCTGCCCTGGGCTGTCTGGTGAAGGACTACTTTCC |
| | | | CGAGCCCGTGACCGTGAGCTGGAACAGCGGCGTCCTGACCATCCGGCGTCCACACCT |
| | | | TTCCTGCCGTCCCTCCAGTCCTCACTCTACTGCCTCCTCCGTGGTGACCGTGCC |
| | | | TAGCTCCTCCTGGCCACCAAGACCTACACCTGTAACGTGGACCACAAACCCTCCAA |
| | | | CACCAAGGTGGACAAACGGGTCGAGAGCAAGTACGGCCCTCCTGCCCCTCCTTGTCC |
| | | | TGCCCCCGAGTTCGAAGGCGGACCCCAGCGTGTTCCTGTTCCCTCCTAAGCCCAAGGA |
| | | | CACCCTCATGATCAGCCGGACACCCGAGGTGACCTGCGTGGTGGTGGATGTGAGCC |
| | | | AGGAGGACCCTGAGGTCCAGTTCAACTGGTATGTGGATGGCGTGGAGGTGCACAA |
| | | | CGCCAAGACAAAGCCCCGGGAAGAGCAGTTCAACTCCACCTACAGGGTGGTCAGCG |
| | | | TGCTGACCGTGCTGCATCAGGACTGGCTGAACGGCAAGGAGTACAAGTGCAAGTC |
| | | | AGCAATAAGGGACTGCCCAGCAGCATCGAGAAGACCATCTCCAAGGCTAAAGGCCA |
| | | | GCCCGGGAACCTCAGGTGTACACCCTGCCTCCCAGCCAGGAGGAGATGACCAAGAA |
| | | | ACCAGGTGAGCCTGACCTGCCTGGTGAAGGGATTCTACCCTTCCGACATCGCCGTGG |
| | | | AGTGGGAGTCCAACGGCCAGCCCGAGAACAATTATAAGACCACCCCTCCCGTCCTCG |
| | | | ACAGCGACGGATCCTTCTTTCTGTACTCCAGGCTGACCGTGGATAAGTCCAGGTGGC |
| | | | AGGAAGGCAACGTGTTCAGCTGCTCCGTGATGCACGAGGCCCTGCACAATCACTAC |
| | | | ACCCAGAAGTCCCTGAGCCTGTCCCTGGGAAAG |
| 551 | CL-58756 | Light chain Nucleotide sequence of light chain | GAAATTGTGTTGACGACGTCTCCAGGCACCCTGTCTTTGTCTCCAGGGGAAAGAGCC |
| | | | ACCCTCTCCTGCAGGGCCAGTCAGAGTGTTAGCAGCAACTACTTAGCCTGGTACCAG |
| | | | CAGAAACCTGGCCAGGCTCCCAGGCTCCTCATCTATGGTGCATCATCAGGGCCACT |
| | | | GGCATCCCAGACAGGTTCAGTGGCAGTGGGTCTGGGACAGACTTCACTCTCACCATC |
| | | | AGCAGACTGGAGCCTGAAGATTTTGCAGTGTATTGCTGTCACCAGTATGGTAGCTCA |
| | | | CCTCCGACGTTCGGCCAAGGGACCAAGGTGGAAATCAAACGTAACGTGGCCGCCTCC |
| | | | CTCCGTGTTCATCTTCCCACCTTCCACCCCGGCAGCAGCGAGTCCGAGTCCGGCCGCTTCTGTC |
| | | | GTGTGCCTGCTGCTGAACAACTTCTACCCCCGAGGGCCAAGGTGCAGTGGAAGGTGGA |
| | | | CAACGCCCTGCAGTCCGAGTCCGGCCAACTCCGTGACCGAGCAGGACTCCAAGG |
| | | | ACAGCACCTACTCCCTGTCCTCCACCCTGACCCTGTCCAAGGCCGACTACGAGAAGC |
| | | | ACAAGGTGTACGCCTGCGAAGTGACCCACCAGGGCCTGTCTAGCCCCGTGACCAAG |
| | | | TCTTTCAACCGGGGCGAGTGT |
| 552 | CL-58756 | Heavy chain Nucleotide sequence of heavy chain alternative coding | CAAGTTCAGTTGGTTGGTGAGTCTGGCGGCGGACTGGTTAAGCCTGGCGGATCTCTGAG |
| | | | ACTGTCTTGTGCCGCCTCTGGCTTCACCTTCTCCGACTACTACATGTCCTGGATCAGA |
| | | | CAGGCCCCTGGCAAAGGCCTGGAATGGGTGTCTCACATCTCCATCTCCGGCTCCACC |
| | | | ATCTACTACGCCGACTCCGTGAAGGGCAGATTCACCATCTCCAGAGACAACGCCAAG |
| | | | AACTCCCTGTACCTGCAGATGAACAGCCTGAGAGCCGAGGACACCGCCGTGTACTA |
| | | | CTGCGCCCGTAGATCCTCTGGATGGTACGACTATTGGGGCCAGGGCACCCTGGTCA |
| | | | CAGTTTCTAGTGCCAGCACCAAGGGCCCTTCCGTGTTCCCCCTGGCCCCTTGCAGCA |
| | | | GGAGCACCTCCGAATCCACAGCTGCCCTGGGCTGTCTGGTGAAGGACTACTTTCCCG |
| | | | AGCCCGTGACCGTGAGCTGGAACTCCGGCGCCCTCACCTCCGTGGTGGTGCCTAG |
| | | | CTGCTCCTCGGCACCACCAAGACCTACACCTGTAACGTGGACCACAAACCCTCCAACACC |
| | | | AAGGTGGACAAACGGGTCGAGAGCAAGTACGGCCCTCCTGCCCCTCCTTGTCCTGC |
| | | | CCCCGAGTTCGAAGGCGGACCACCCAGCGTGTTCCTGTTCCTTCCTTAAGCCCAAGGACAC |
| | | | CCTCATGATCAGCCGGACACCCGAGGTGACCTGCGTGGTGGTGGATGTGAGCCAGG |

-continued

SEQUENCES:

| Seq ID No: | | Description | Sequence |
|---|---|---|---|
| | | | AGGACCCTGAGGTCCAGTTCAACTGGTATGTGGATGGCGTGGAGGTGCACAACGCC |
| | | | AAGACAAAGCCCCGGGAAGAGCAGTTCAACTCCACCTACAGGGTGGTCAGCGTGCT |
| | | | GACCGTGCTGCATCAGGACTGGCTGAACGGCAAGGAGTACAAGTGCAAGGTCAGC |
| | | | AATAAGGACTGCCCAGCACCATCGAGAAGACCATCTCCAAGGCTAAAGGCCAGCC |
| | | | CCGGGAACCTCAGGTGTACACCCTGCCCCCAGCCAGGAGGAGATGACCAAGAACC |
| | | | AGTGAGCCTGACCTGCCTGGTGAAGGGATTCTACCCTTCCGACATCGCCGTGGAG |
| | | | TGGGAGTCCAACGGCCAGCCCGAGAACAATTATAAGACCACCCCTCCCGTCCTCGAC |
| | | | AGCGACGGATCCTTCTTTCTGTACTCCAGGCTGACCGTGGATAAGTCCAGGTGGCAG |
| | | | GAAGGCAACGTGTTCAGCTGCTCCGTGATGCACGAGGCCCTGCACAATCACTACACC |
| | | | CAGAAGTCCCTGAGCCTGTCCCCTGGGAAAG |
| 553 | CL-58756 | Light chain Nucleotide sequence of light chain alternative coding | GAAATTGTGCTGACTCAGTCCCCTGGCACACTGTCTTTGAGCCCTGGCGAGAGAGCT |
| | | | ACCCTGTCCTGTAGAGCCTCCAGTCCGTGTCCTCCAACTACCTGGCCTGGTATCAGC |
| | | | AGAAGCCTGGACAGGCTCCCCGGCTGTTGATCTACGGCGCTTCTATCAGAGGCCACA |
| | | | GGCATCCCTGACCGGTTCTCCGGATCTGGCTCTGGCACCGATTTCACCCTGACCATCT |
| | | | CTCGGCTGGAACCCGAGGATTTCGCCGTGTACTGCTGTCACCAGTACGGCTCTAGCC |
| | | | CTCCTACCTTTGGACAGGGCACCAAGGTGGAAATCAAACGTAACTGTGGCCGTCCCT |
| | | | CCGTGTTCATCTTCCCACCTTCCGACGAGCAGCTGAAGTCCGGCACCGCTTCTGTCGT |
| | | | GTGCCTGCTGAACAACTTCTACCCCCGCGAGGCCAAGGTGCAGTGGAAGGTGGACA |
| | | | ACGCCCTGCAGTCCGGCAACTCCCAGGAATCCGTGACCGAGCAGGACTCCAAGGAC |
| | | | AAGGTGTACGCCTGCGAAGTGACCCACCAGGGCCTGTCTAGCCCCGTGACCAAGTC |
| | | | TTTCAACCGGGGCGAGTGT |
| 554 | CL-58650 | Heavy chain Nucleotide sequence of heavy chain | CAGGTGCAGCTGGTGGAGTCTGGGGGAGGCTTGGTCAAGCCTGGAGGGTCCCTGC |
| | | | GACTCCTCTGCAGCCTCTGGATTCACCTTCAGTGACTACTTCATGAGCTGGATCCG |
| | | | CCAGGCTCCAGGGAAGGGGCTGGAGTGGGTTTCAGGTACATTAGTATTAGTGGTAGTA |
| | | | CCATATACTACCAGACTCTGTGAAGGGCCGATTCACCATCTCCAGGGACAACGCCA |
| | | | GGAACTCACTGTTTCTGCAAATGAACAGCCTGAGAGCCGAGGACACGGCCATCTATT |
| | | | ACTGTGCGAGAGAAACCAGTGGCTGGTACGACTTCTGGGGCCAGGGAACCCTGGTC |
| | | | ACCGTCTCCTCAGCCAGCACCAAGGGCCCTCTTCCCCTGGCCCCCTGGCCCCTTGCCAGCA |
| | | | GGAGCACCTCCGAATCCACCAGCTGCCCTGGGCTGTCTGGTGAAGGACTACTTTCCCG |
| | | | AGCCCGTGACCGTGAGCTGGAACAGCGGCGTGCTCTGACCATCCGGCCGTCCACCTTTC |
| | | | CTGCCGTCCTGCAGTCCTCCGGCCTTCACTCCAGTGACTACTTCATGAGCTGGGATCCG |
| | | | CTCCTCCCTGGCCACCAAGAACTACACGTAACGTGACCCACAAACCCTCCAAACACC |
| | | | AAGGTGGACAAACGGGTCGAGAGCAAGTACGGCCCTCCCCGCCCTCCTTGTCCTGC |
| | | | CCCGAGTTCGAGGGCGGACCCAGCCGTGTTCCTGTTCCCTCCTAAGCCCAAGGACAC |
| | | | CCTCATGATCAGCCGGACACCCGAGGTGACGTGGTGGTGGATGTGAGCCAGG |
| | | | AGGACCCTGAGGTCCAGTTCAACTGGTATGTGGATGGCGTGGAGGTGCACAACGCC |
| | | | AAGACAAAGCCCCGGGAAGAGCAGTTCAACTCCACCTACAGGGTACAAGTGCAAGGTCAGC |
| | | | AATAAGGACTGCCCAGCACCATCGAGAAGACCATCTCCAAGGCTAAAGGCCAGCC |
| | | | CCGGGAACCTCAGGTGTACACCCTGCCCCCAGCCAGGAGGAGATGACCAAGAACC |
| | | | AGGACCCTGAGGTCCAGTTCAACTGGTATGTGGATGGCGTGGAGGTGCACAACGCC |
| | | | AATAAGGACTGCCCAGCACCATCGAGAAGACCATCTCCAAGGCTAAAGGCCAGCC |
| | | | CCGGGAACCTCAGGTGTACACCCTGCCCCCAGCCAGGAGGAGATGACCAAGAACC |
| | | | AGTGAGCCTGACCTGCCTGGTGAAGGGATTCTACCCTTCCGACATCGCCGTGGAG |
| | | | TGGGAGTCCAACGGCCAGCCCGAGAACAATTATAAGACCACCCCTCCCGTCCTCGAC |

-continued

SEQUENCES:

| Seq ID No: | | Description | Sequence |
|---|---|---|---|
| | | | AGCGACGGATCCTCTTTCTGTACTCCAGGCTGACCGTGGATAAGTCCAGGTGGCAG |
| | | | GAAGGCAACGTGTTCAGCTGCTCCGTGATGCACGAGGCCCTGCACAATCACTACACC |
| | | | CAGAAGTCCCTGAGCCTGTCCCTGGGAAAG |
| 555 | CL-58650 | Light chain Nucleotide sequence of light chain | GAAATTGTTGTGACGCAGTCTCCAGGCACCCTGTCTTTGTCTCCAGGGGAAAGAGCC |
| | | | ACCCTCTCGCAGGGCCAGTCAGAGTGTTAGTAGCTACTTAGCCTGGTACCAG |
| | | | CAGAAACCTGGCCAGGCTCCCAGGCTCCTCATCTATGGTGCATCCAGCAGGGCCACT |
| | | | GGCATCCCAGACAGGTTCAGTGGCAGTGGGTCTGGGACAGACTTCACTCTCACCATC |
| | | | AGCAGACTGGAGCCTGAAGATTTTGCAGTGTATTGTTGTCACCAGTATGGTAGTTCA |
| | | | CCTCCGACGTTCGGCCAAGGGACCAAGGTGGAAATCAAACGTACGGTGGCCGCTCC |
| | | | CTCCGTGTTCATCTTCCCACCTTCCGACGAGCAGCTGAAGTCCGGACACCGCTTCTGTC |
| | | | GTGTGCCTGCTGAATAACTTCTACCCCCGGAGGCCAAGGTCCAGTGGAAGGTGGA |
| | | | CAACGCCCTGCAGTCCGGCAACTCCCAGGAATCCGTGACCGAGCAGGACTCCAAGG |
| | | | ACAGCACCTACTCCCTGTCCAGCACCCTGACCCTGTCCAAGGCCGACTACGAGAAGC |
| | | | ACAAGGTGTACGCCTGCGAAGTGACCCACCAGGGCCTGTCTAGCCCCGTGACCAAG |
| | | | TCTTTCAACCGGGGCGAGTGT |
| 556 | CL-58679 | Heavy chain Nucleotide sequence of heavy chain | CAGGTGCAGCTGGTGGAGTCTGGGGGAGGCTTGGTCAAGCCTGGAGGGTCCCTTA |
| | | | GACTCTCCTGTGCAGCCTCTGGATTCACCTTCAGTGACTTCTACATGAGCTGGATCCG |
| | | | CCAGGCTCCAGGGAAGGGGCTGGAGTGGGTTTCGTACATTAGTAGTATTAGTGGTACTA |
| | | | CCATATACTACGCAGACTCTGTTGAAGGGCGATTCACCATCTCCAGGGACAACGCCA |
| | | | GGAACTCACTGTATCTGCAAATGAACAGCCTGAGAGCCGAGGACACGGCCGTGTAT |
| | | | TACTGTGCGAGAGAACCAGTGGCTGGTACGACTTCTGGGGCCAGGGAACCCTGGT |
| | | | CACCGTCTCCTCAGCCACCAAGGGCCCTTCCGTGTTCCCCCTGGCCCCCTGCAGC |
| | | | AGGAGCACCTCCGAATCCACAGCTGCCCTGGGCTGTCTGGTGAAGGACTACTTTCCC |
| | | | GAGCCCGTGACCGTGAGCTGGAACTCAGGCGCTCTGACCATCCGGCGTCCACACCTT |
| | | | TCCTGCGCCTCCTGCAGTCTCCGGCCTCTACTCCTGTCCTCCGTGGTGACCGTGCCT |
| | | | AGCTCCTCCCTGGGCACCCAGACCTACAGCTGCAAGGTACGGCCCTCCCTGCCCTGTCCT |
| | | | ACCAAGGTGGACAAACGGGTCGAGAGCAAGTACGGCCCTCCCTGCCCCTGTCCT |
| | | | GCCCCGAGTTCGAAGGCGGACCCAGCGTGTTCCTCCTAAGCCCAAGGAC |
| | | | ACCCTCATGATCAGCCGGACACCCGAGGTGACCTGCGTGGTGGTGGATGTGAGCCA |
| | | | GGAGGACCCTGAGGTCCAGTTCAACTGGTATGTGGACGGCGTGGAGGTGCACAAC |
| | | | GCCAAGACAAAGCCCGGGAAGAGCCAGTTCAACTCCACCTACAGGGTGGTCAGCGT |
| | | | GCTGACCGTGCTGCATCAGGACTGGCTGAACGGCAAGGAGTACAAGTGCAAGGTCA |
| | | | GCAATAAGGGACTGCCCGCACCAGCATCGAGAAGACCATCTCCAAGGCTAAAGGCCAG |
| | | | CCCCGGGAACCTCAGGTGTACACCCTGCCCCCAGCCAGGGAGGAGATGACCAAGAA |
| | | | CCAGGTGAGCCTGACCTGCCTGGTGAAGGGCAATCTACCCTTCCAGCAATCGCCGTGGA |
| | | | GTGGGAGTCCAACGGCCAGCCCGAGAACAATTATAAGACCACCCCTCCCGTCCTGGA |
| | | | CAGCGACGGATCCTCTTTCTGTACTCCAGGCTGACCGTGGATAAGTCCAGGTGGCA |
| | | | GGAAGGCAACGTGTTCAGCTGCTCCGTGATGCACGAGGCCCTGCACAATCACTACA |
| | | | CCCAGAAGTCCCTGAGCCTGTCCCTGGGAAAG |
| 557 | CL-58679 | Light chain Nucleotide sequence of light chain | GAAATTGTTGTGACGCAGTCTCCAGGCACCCTGTCTTTGTCTCCAGGGGAAAGAGCC |
| | | | ACCCTCTCGCAGGGCCAGTCAGAGTGTTAGCAGCTACTTAGCCTGGTACCAG |
| | | | CAGAAACCTGGCCAGGCTCCCAGGCTCCTCATCTATGGTGCATCCAGCAGGGCCACT |
| | | | GGCATCCCAGACAGGTTCAGTGGCAGTGGGTCTGGGACAGACTTCACTCTCACCATC |
| | | | AGCAGACTGGAGCCTGAAGATTTTGCAGTGTATTGTTGTCACCAGTATGGTAGTTCA |

-continued

SEQUENCES:

| Seq ID No: | Description | Sequence |
|---|---|---|
| 558 | Heavy chain Nucleotide sequence of heavy chain CL-58680 | CCTCCGACGTTCGGCCAAGGGACCAAGGTGGAAATGAAACGTACGGTGGCCGCTCC CTCCGTGTTCATCTTCCCACCTTCCGACGAGCAGCTGAAGTCCGGCACCGCTTCTGTC GTGTGCCTGCTGAACAACTTCTACCCCCGCGAGGCCAAGGTGCAGTGGAAGGTGGA CAACGCCCTGCAGTCCGGCAACTCCCAGGAATCCGTGACCGAGCAGGACTCCAAGG ACAGCACCTACTCCCTGTCCTCCACCCTGACCCTGTCCAAGGCCGACTACGAGAAGC ACAAGGTGTACGCCTGCGAAGTGACCCACCAGGGCCTGTCTAGCCCCGTGACCAAG TCTTTCAACCGGGGCGAGTGT |
| | | CAGGTGCAGCTGGTGGAGTCTGGGGGAGGCTTGGTCAGGCCTGGAGGGTCCCTGA GACTCTCCTGTGCAGCCTCTGGATTCACCTTCAGTGACTACTACATGAGCTGGATCCG CCAGGCTCCAGGGAAGGGGCTGGAGTGGGTTTCGTACATTAGCAGTGGTAGTA CCATATACTACCCAGACTCTGTGAAGGGCCGATTCACCATCTCCAGGGACAACGCCA GGGACTCACTTTATCTGCAAATGAACAGCCTGAGAGCCGAGGACACGGCCGTGTAT TACTGTGCGAGAGAACCAGTGGCTGGTACGACTTCTGGGGCCAGGGAACCCTGGT CACCGTCTCCTCAGCCACCAAGGGCCCTTCCGTGTTCCCCCTGGCCCCCTTGCAGC AGGAGCACCTCCGAATCCACAGCTGCCCTGGGCTGTCTGGTGAAGGACTACTTTCCC GAGCCCGTGACCGTGAGCTGGAACAGCGGCGTCCACACCTTCCCAGCCGTCCACCTT TCCTGCGCGTCCTGCAGTCCTCCGGCCTCTACTCCCTGTCCTCCGGTGACCCTGCCT AGTCCTCCCTGCGCCACCAAGACCTACACCTGTAACGTGACCACAAACCCTCCAAC ACCAAGGTGACAAACGGGTCGAGAGCAAGTACGGCCCTCCCTGCCCTCCTAAGGAC ACCCTCATGATCAGCCGACACCCGAGGTGACCTGCGTGGTGGTGATGTGAGCCA GGAGGACCCTGAGGTCCAGTTCAACTGTATGTGGATGGCGTGGAGGTGCACAAC GCCAAGACAAAGCCCCGGGAAGAGCAGTTCAACTCCACCTACCAGGTGGTCAGCGT GCTGACCGTGCTGCATCAGGACGTGGCTGAACGGCAAGGACCATCTCCAAGGCTAAAGCCAG CCCCGGGAACCTCAGGTGTACACCCTGCCTCAGCCAGGAGATGACCAAGAA CCAGGTGAGCCTGACCTGCCTGGTGAAGGGATTCTACCCTTCCGACATCGCCGTGGA GTGGGAGTCCAACGGCCAGCCCGGAGAACAATTATAAGACCACCCCTCCCGTCCTCGA CAGCGACGGATCCTTCTTCTGTACTCCAGGCTGACCGTGGATAAGTCCAGGTGGCA GGAAGGCAACGTGTTCAGCTGCTCCGTGATGCACGAGCCCTGCACAATCACTACA CCCAGAAGTCCCTGAGCCTGTCCCTGGGAAAG |
| 559 | Light chain Nucleotide sequence of light chain CL-58680 | GAAATTGTTGTGACGCAGTCTCCAGGCACCCTGTCTTTGTCTCCAGGGGAAAGAGCC ACCCTCTCTGTAGGGCCAGTCAGAGTGTTAGCTACAGGTACTAGCCTGGTACCAG CAGAAACCTGGCCAGGCTCCCAGGCTCCTCATCTATGGTGCATCCAGCAGGGCCACT GGCATCCCAGACAGGTTCAGTGGCAGTGGGTCTGGGACAGACTTCACTCTCACCATC AGCAGACTGGAGCCTGAAGATTTTGCAGTGTATTGCTGTCACCAGTATGGTAGTTCA CCTCCGACGTTCGGCCAAGGGACCAAGGTGGAAATCAAACGTACGGTGGCCGCTCC CTCCGTGTTCATCTTCCCACCTTCCGACGAGCAGCTGAAGTCCGGCACCGCTTCTGTC GTGTGCCTGCTGAACAACTTCTACCCCCGCGAGGCCAAGGTGCAGTGGAAGGTGGA CAACGCCCTGCAGTCCGGCAACTCCCAGGAATCCGTGACCGAGCAGGACTCCAAGG ACAGCACCTACTCCCTGTCCTCCACCCTGACCCTGTCCAAGGCCGACTACGAGAAGC ACAAGGTGTACGCCTGCGAAGTGACCCACCAGGGCCTGTCTAGCCCCGTGACCAAG TCTTTCAACCGGGGCGAGTGT |

-continued

SEQUENCES:

| Seq ID No: | | Description | Sequence |
|---|---|---|---|
| 560 | CL-58713 Heavy chain | Nucleotide sequence of heavy chain | CAAGTTCAGTTGGTTGAGTCTGCGGGCGGGACTGGTTAAGCCTGGCGATCTCTGAG ACTGTCTTGTGCCGCCTCTGGCTTCACCTTCTCCGACTACTACATGTCCTGGATCAGA CAGGCCCCTGGCAAAGGCCTGGAATGGGTGTCCTACATCTCCATCTCCGGCATCACC ATCTACTACGCCGACTCCGTGAAGGGCAGATTCACCATCTCCAGAGACAACGCCCGG AACTCCCTGACCTGCAGATCCTTCTGAGAGCCGAGGACACCGCCGTGTACTAC TGCGCCCGTAGATCCTCTGAGATGGTACGACTATTGGGGCCAGGGCACCCTGGTCAC AGTTTCTAGTGCCAGCACCAAGGGCCCTTCCGTGTTCCCCCTGGCCCCTTGCAGCAG GAGCACCTCCGAATCCACAGCTGCCCTGGGCTGTCTGGTGAAGGACTACTTTCCCGA GCCCGTGACCGTGAGCTGGAACAGCGGCGTCCGTGACCAGCAGCGTCCACACCTTCC TGCCGTCCTGCAGTCCTCCGGCCTCTACTCCCTGGTGGTGACCGTGCCTAGC TCCTCCCTGGCCACCAAGACCTACACCTGTAACGTGGACCACAAACCCTCCAACACC AAGGTGGACAAGCGGGTCGAGAGCAAGTACGGCCCCTCCTGCCCTCCTTGTCCTGC CCCGAGTTCGAAGGCGGACCCAGCGTGTTCCTGTTCCCTCCTAAGCCCAAGGACAC CCTCATGATCAGCCGGACACCCGAGGTGACCTGCGTGGTGGTGGATGTGAGCCAGG AGGACCCTGAGGTCCAGTTCAACTGGTATGTGGATGGCGTGGAGGTGCACAACGCC AAGACAAAGCCCCGGGAAGAGCAGTTCAACTCCACCTACAGGGTGGTCAGCGTGCT GACCGTGCTGCATCAGGACTGGCTGAACGGCAAGGAGTACAAGTGCAAGGTCAGC AATAAGGGACTGCCCAGCAGCATCGAGAAGACCATCTCCAAGGCTAAAGGCCAGCC CCGGGAACCTCAGGTGTACACCCTGCCTCCCAGCCAGGAGGAGATGACCAAGAACC AGGTGAGCCTGACCTGCCTGGTCAAGGGATTCTACCCTTCCGACATCGCCGTGGAG TGGGAGTCCAACGGCCAGCCCGAGAACAATTATAAGACCACCCCTCCCGTCCTCGAC AGCGACGGCTCCTTCTTTCTGTACTCCCAGCTGACCGTGGATAAGTCCAGGTGGCAG GAAGGCAACGTGTTCAGCTGCTCCGTGATGCACGAGGCCCTGCACAATCACTACACC CAGAAGTCCCTGAGCCTGTCCCTGGGAAAG |
| 561 | CL-58713 Light chain | Nucleotide sequence of light chain | GAAATTGTGCTGACTCAGTCCCCTGGCACACTGTCTTTGAGCCCTGGCGAGAGAGCT ACCCTGTCCTGTAGAGCCTCTCAGTCCGTGTCCTACAACTACCTGGCCTGGTATCAGC AGAAGCCCGGCCAGGCTTCCTAGACTGTTGATCTATGGCGCGCCTCCATCAGAGCCACA GGCATCCCTGATAGATTCTCCGGCTCTGGCTCTGGCACCGACTTCACCCTGACCATCT CCAGACTGGAACCCGAGGACTTCGCCGTGTACTACTGTCAACAGGTCACCAGTACGGC CTCCTACCTTTGGACAGGGCACCAAGGTGGAAATCAAACGTACGGTGGCTGCACCC CCGTGTTCATCTTCCCACCTTCCGACGAGCAGCTGAAGTCCGGCACCGCTTCTGTCGT GTGCCTGCTGAACAACTTCTACCCCCGAGGAATCCGGCCAAGGTGCAGTGGAAGGTGGACA ACGCCCTGCAGTCCGGCAACTCCCAGGAATCCGTGACCGAGCAGGACTCCAAGGAC AGCACCTACTCCCTGTCCTCCACCCTGACCCTGAGCAAGGCCGACTACGAGAAGCAC AAGGTGTACGCCTGCGAAGTGACCCACCAGGGCCTGTCTAGCCCCGTGACCAAGTC TTTCAACCGGGGCGAGTGT |
| 562 | Mature Human BMP6 | Amino acid sequence of a mature human BMP6 | SASSRRRQQSRNRSTQSQDVARVSSASDYNSSELKTACRKHELYVSFQDLGWQDWIIAP KGYAANYCDGECSFPLNAHMNATNHAIVQTLVHLMNPEYVPKPCCAPTKLNAISVLYF DDNSNVILKKYRNMVVRACGCH |
| 563 | Mature Rat BMP6 | Amino acid sequence of a mature human BMP6 | SASSRRRQQSRNRSTQSQDVSRGSSASDYNSSELKTACKHELYVSFQDLGWQDWIIAP KGYAANYCDGECSFPLNAHMNATNHAIVQTLVHLMNPEYVPKPCCAPTKLNAISVLYF DDNSNVILKKYRNMVVRACGCH |

-continued

SEQUENCES:

| Seq ID No: | Description | Sequence |
| --- | --- | --- |
| 564 | Mature Cynomolgus monkey BMP6 | Amino acid sequence of a mature Cynomolgus monkey BMP6 | SASGRRRQQSRNRSTQSQDVARVSSASDYNSSELKTACRKHELYVSFQDLGWQDWIIA PKGYAANYCDGECSFPLNAHMNATNHAIVQTLVHLMNPEYVPKPCCAPTKLNAISVLYF DDNSNVILKKYRNMVVRACGCH |
| 565 | Antibody A' Heavy chain variable region | Amino acid sequence of VH | QVQLVQSGAEVKKPGSSVKVSCKASGYTFTSYAMHWVRQAPGQGLEWMGYINPYNR GTKYNENFKGRVTITADESTSTAYMELSSLRSEDTAVYYCARRPFGNAMDIWGQGTLVT VSS |
| 566 | Antibody A' Full heavy chain sequence | Amino acid sequence heavy chain of Antibody A' | QVQLVQSGAEVKKPGSSVKVSCKASGYTFTSYAMHWVRQAPGQGLEWMGYINPYNR GTKYNENFKGRVTITADESTSTAYMELSSLRSEDTAVYYCARRPFGNAMDIWGQGTLVT VSSASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPPCPAPEFEGG PSVFLFPPKPKDTLMISRTPEVTCVVVDVSQEDPEVQFNWYVDGVEVHNAKTKPREEQ FNSTYRVVSVLTVLHQDWLNGKEYKCKVSNKGLPSSIEKTISKAKGQPREPQVYTLPPSQ EEMTKNQVSLTCLVKGFYPSDIAVEWESNGQPENNYKTTPPVLDSDGSFFLYSRLTVDKS RWQEGNVFSCSVMHEALHNHYTQKSLSLSLGK |

The invention claimed is:

1. An antibody or antigen binding fragment thereof that specifically binds to Bone Morphogenetic Protein 6 (BMP6), wherein:

(a) (i) the antibody or antigen binding fragment thereof comprises a VH domain comprising heavy-chain complementarity determining region (CDR) sequences of SEQ ID NO: 111 (CDRH1), SEQ ID NO: 112 (CDRH2), and SEQ ID NO: 113 (CDRH3); and (ii) the antibody or antigen binding fragment thereof comprises a VL domain comprising light-chain CDR sequences of SEQ ID NO: 120 (CDRL1), SEQ ID NO: 121 (CDRL2), and SEQ ID NO: 122 (CDRL3); or (b) (i) the antibody or antigen binding fragment thereof comprises a VH domain comprising heavy-chain CDR sequences of SEQ ID NO: 291 (CDRH1), SEQ ID NO: 292 (CDRH2), and SEQ ID NO: 293 (CDRH3); and (ii) the antibody or antigen binding fragment thereof comprises a VL domain comprising light-chain CDR sequences of SEQ ID NO: 300 (CDRL1), SEQ ID NO: 301 (CDRL2), and SEQ ID NO: 302 (CDRL3).

2. The antibody or antigen binding fragment thereof according to claim 1, wherein the VH domain is encoded by a nucleotide sequence that is derived from the recombination of a human VH gene segment, DH gene segment and JH gene segment, wherein:

(a) the VH gene segment is IGHV3-11;

(b) the DH gene segment is IGHD6-19; and/or (c) the JH gene segment is IGHJ4.

3. The antibody or antigen binding fragment thereof according to claim 1, wherein the antibody or antigen binding fragment thereof comprises CDR sequences of SEQ ID NOs: 111, 112, 113, 120, 121, and 122, wherein the VH domain comprises SEQ ID NO: 114 and the VL domain comprises SEQ ID NO: 123.

4. The antibody or antigen binding fragment thereof according to claim 1, wherein the antibody or antigen binding fragment thereof comprises CDR sequences of SEQ ID NOs: 111, 112, 113, 120, 121, and 122, and wherein the VH domain comprises SEQ ID NO: 114 or an amino acid sequence that is at least 85% identical thereto.

5. The antibody or antigen binding fragment thereof according to claim 1, comprising first and second copies of said VH domain, and/or first and second copies of said VL domain.

6. The antibody or antigen binding fragment thereof of claim 1, wherein the VL domain is encoded by a nucleotide sequence that is derived from the recombination of a human VL gene segment and JL gene segment, wherein (a) the VL gene segment is IGKV3-20; and/or (b) the JL gene segment is IGKJ1.

7. The antibody or antigen binding fragment thereof according to claim 1, wherein the antibody or antigen binding fragment thereof comprises CDR sequences of SEQ ID NOs: 111, 112, 113, 120, 121, and 122, and comprises a VL domain comprising SEQ ID NO: 123, or an amino acid sequence that is at least 85% identical thereto.

8. The antibody or antigen binding fragment thereof according to claim 1, wherein the antibody or antigen binding fragment thereof comprises CDR sequences of SEQ ID NOs: 111, 112, 113, 120, 121, and 122, and comprises:

(i) a heavy chain sequence comprising SEQ ID NO: 116 or an amino acid sequence that is at least 85% identical thereto; and/or (ii) a light chain sequence comprising SEQ ID NO: 125 or an amino acid that is at least 85% identical thereto.

9. The antibody or antigen binding fragment thereof according to claim 1, wherein the antibody or antigen binding fragment thereof specifically binds to (i) human BMP6 comprising SEQ ID NO: 562;

(ii) a cynomolgus BMP6 comprising SEQ ID NO: 564; and/or (iii) a rat BMP6 comprising SEQ ID NO: 563.

10. The antibody or antigen binding fragment thereof according to claim 1, wherein the antibody or antigen binding fragment thereof comprise a heavy chain and/or a light chain comprising a human constant region.

11. The antibody or antigen binding fragment thereof according to claim 10, wherein the human constant region is an IgG4-PE constant region.

12. The antibody or antigen binding fragment thereof according to claim 1, further comprising an antigen-binding site that specifically binds another target antigen.

13. A method of treating or preventing a BMP6-mediated disease or condition in a subject, the method comprising administering to said subject a therapeutically effective amount of the antibody or antigen binding fragment thereof of claim 1, wherein the BMP6-mediated disease or condition is thereby treated or prevented.

14. The method according to claim 13, wherein the BMP6-mediated disease or condition is anaemia.

15. A pharmaceutical composition comprising the antibody or antigen binding fragment thereof of claim 1 and a pharmaceutically acceptable excipient, diluent, or carrier.

16. A kit comprising the pharmaceutical composition according to claim 15 and a label or instructions for use to treat and/or prevent a BMP6-mediated disease or condition in a human.

17. A nucleic acid that encodes the VH domain and/or the VL domain of the antibody or antigen binding fragment thereof of claim 1.

18. A vector comprising the nucleic acid of claim 17.

19. A host cell comprising the nucleic acid of claim 17.

20. The antibody or antigen binding fragment thereof according to claim 1, wherein the antibody or antigen binding fragment thereof comprises CDR sequences of SEQ ID NOs: 291, 292, 293, 300, 301, and 302, wherein the VH domain comprises SEQ ID NO: 294 and the VL domain comprises SEQ ID NO: 303.

21. The antibody or antigen binding fragment thereof according to claim 1, wherein the antibody or antigen binding fragment thereof comprises CDR sequences of SEQ ID NOs: 291, 292, 293, 300, 301, and 302, wherein the VH domain comprises SEQ ID NO: 294 or an amino acid sequence that is at least 85% identical thereto.

22. The antibody or antigen binding fragment thereof according to claim 1, wherein the antibody or antigen binding fragment thereof comprises CDR sequences of SEQ ID NOs: 291, 292, 293, 300, 301, and 302, and comprises a VL domain comprising SEQ ID NO: 303, or an amino acid sequence that is at least 85% identical thereto.

23. The antibody or antigen binding fragment thereof according to claim 1, wherein the antibody or antigen binding fragment thereof comprises CDR sequences of SEQ ID NOs: 291, 292, 293, 300, 301, and 302, and comprises:

(i) a heavy chain sequence comprising SEQ ID NO: 296 or an amino acid sequence that is at least 85% identical thereto; and/or (ii) a light chain sequence comprising SEQ ID NO: 305 or an amino acid that is at least 85% identical thereto.

* * * * *